US009556446B2

(12) United States Patent
McCouch et al.

(10) Patent No.: US 9,556,446 B2
(45) Date of Patent: Jan. 31, 2017

(54) RICE COMPRISING AN RC RESPONSIVE PROMOTER DRIVING EXPRESSION OF A HETEROLOGOUS NUCLEIC ACID MOLECULE

(75) Inventors: Susan McCouch, Locke, NY (US); Megan Sweeney, Tucson, AZ (US)

(73) Assignee: Cornell University, Ithaca, NY (US)

( * ) Notice: Subject to any disclaimer, the term of this patent is extended or adjusted under 35 U.S.C. 154(b) by 1613 days.

(21) Appl. No.: 11/991,996

(22) PCT Filed: Sep. 14, 2006

(86) PCT No.: PCT/US2006/036020

§ 371 (c)(1), (2), (4) Date: Mar. 24, 2009

(87) PCT Pub. No.: WO2007/033370

PCT Pub. Date: Mar. 22, 2007

(65) Prior Publication Data

US 2009/0205082 A1 Aug. 13, 2009

Related U.S. Application Data

(60) Provisional application No. 60/717,060, filed on Sep. 14, 2005.

(51) Int. Cl.
*C12N 15/82* (2006.01)
*C07K 14/415* (2006.01)

(52) U.S. Cl.
CPC ......... *C12N 15/8222* (2013.01); *C07K 14/415* (2013.01); *C12N 15/825* (2013.01)

(58) Field of Classification Search
USPC .......................................................... 800/282
See application file for complete search history.

(56) References Cited

U.S. PATENT DOCUMENTS

| | | | | |
|---|---|---|---|---|
| 6,727,414 | B2 * | 4/2004 | Moldenhauer et al. | 800/320.2 |
| 2005/0278800 | A1 * | 12/2005 | Elton et al. | 800/278 |

OTHER PUBLICATIONS

Waterhouse et al, Virus resistance and gene silencing in plants can be induced by simultaneous expression of sense and antisence RNA, 1998, PNAS 95:13959-13964.*

Gallop et al. (Expression of the grape dihydroflavonol reductase gene and analysis of its promoter region, 53 J of Exp Bio No. 373, 1397-1409 (2002)).*

Chen (Gen Bank Accession No. AF101045.1 submitted by Chen Oct. 22, 1998).*

Nesi et al. (The TT8 Gene Encodes a Basic Helix-Loop-Helix Domain Protein Required for Expression of DFR and BAN genes in Arabidopsis Siliques, 12 Plant Cell, 1863-1878 (2000)).*

Nakai et al. (Molecular characterization of the gene for hihydroflavonol 4-reductase of Japonica rice varieties, 15 Plant Biotech No. 4, 221-225 (1998)).*

Ithal et al. Rice flavonoid pathway genes, OsDfr and OsAns, are induced by dehydration, high salt and ABA, and contain stress responsive promoter elements that interact with the transcription activator, OsC1-MYB. (2004) Plant Science; vol. 166; pp. 1505-1513.*

Nakai et al. Molecular characterization of the gene for dihydroflavonol 4-reductase of Japonica Rice Varieties. (1998) Plant Biotechnology; vol. 15; pp. 221-225.*

Singh, K. B. Transcriptional regulation in plants: the importance of combinatorial control. (1998) Plant Physiol.; vol. 118; pp. 1111-1120.*

Indian Examination Report for Indian Patent Application No. 1452/KOL NP/2008.

Spelt et al., "Anthocyanin1 of Petunia Encodes a Basic Helix-Loop-Helix Protein that Directly Activates Transcription of Structural Anthocyanin Genes," *The Plant Cell* 12: 1619-1631 (2000).

Spelt et al., GenBank Accession AF260919, published on Oct. 25, 2000, 1-2.

International Search Report for International Application No. PCT/US2006/036020, completed Jun. 8, 2008, mailed Nov. 7, 2008 (4 pages).

Lesnick et al., "Activation of the maize anthocyanin gene a2 is mediated by an element conserved in many anthocyanin promoters," Plant Physiol. 117:437-445 (1998).

Hearing Notice for Indian Patent Application No. 1452/KOLNP/2008, dated Mar. 17, 2016 (2 pages).

* cited by examiner

*Primary Examiner* — Cathy Kingdon Worley

(74) *Attorney, Agent, or Firm* — Clark & Elbing LLP

(57) ABSTRACT

The present invention relates to rice plants, seeds, and cells that include a promoter responsive to a basic helix-turn-helix red anthocyanin transcription factor operably linked to a heterologous nucleic acid molecule.

8 Claims, 142 Drawing Sheets

Figure 2. Sequence differences between Jefferson, Nipponbare and *O. rufipogon* in bHLH gene

| | | | | | | | | | | | | | | |
|---|---|---|---|---|---|---|---|---|---|---|---|---|---|---|
| NA position (Nipponbare) | 21 | 138-147 | 300-332 | 415 | 643 | 966 | 1108 | 1172 | 1210 | 1375 | 1415 | 1482 | 1557 | 1746 |
| NA position (*O.rufipogon*) | 21 | 137 | 289 | 371 | 599 | 922 | 1065 | 1167 | 1167 | 1332 | 1372 | 1439 | 1514 | 1703 |
| SEQ ID NO: 9 Nipponbare | T | full | full | G | T | T | deletion | C | T | C | A | G | C | T |
| SEQ ID NO: 6 Jefferson | T | full | full | G | T | T | deletion | C | T | C | A | G | C | T |
| SEQ ID NO: 4 *O.rufipogon* | A | deletion | deletion | T | G | A | A | T | C | T | G | A | T | C |

| | | | | | | | | | | | | |
|---|---|---|---|---|---|---|---|---|---|---|---|---|
| NA position (Nipponbare) | 1858 | 2206 | 2278 | 2448 | 2450 | 2985 | 3206 | 3304 | 3692 | 3702 | 3815 | 4038 |
| NA position (*O.rufipogon*) | 1815 | 2163 | 2235 | 2405 | 2407 | 2942 | 3205 | 3361-3362 | 3693 | 3659 | 3772 | 3995 |
| SEQ ID NO: 9 Nipponbare | A | A | A | T | A | A | A | deletion | T | T | G | T |
| SEQ ID NO: 6 Jefferson | A | A | A | T | A | A | A | deletion | T | T | G | T |
| SEQ ID NO: 4 *O. rufipogon* | C | G | G | A | G | G | deletion | GA | deletion | C | T | C |

| | | | | | | | | | |
|---|---|---|---|---|---|---|---|---|---|
| NA position (Nipponbare) | 4503 | 4967 | 5183 | 5393 | 5644 | 6260 | 6339 | 6378 | 6416-6421 |
| NA position (*O. rufipogon*) | 4460 | 4924 | 5141-5154 | 5365 | 5617 | 6234-6245 | 6324 | 6362 | 6400 |
| SEQ ID NO: 9 Nipponbare | A | G | deletion | deletion | A | deletion | T | T | AAATGC |
| SEQ ID NO: 6 Jefferson | A | G | deletion | deletion | A | deletion | T | T | AAATGC |
| SEQ ID NO: 4 *O. rufipogon* | G | A | full | A | G | CGG x4 | C | C | deletion |

Cornell University
College of Agriculture and Life Sciences
Dept of Plant Breeding & Genetics

Fine Mapping of a Pericarp Color QTL

Megan T Sweeney[1], M. J. Thomson[2] and S.R. McCouch[1]

[1] Department of Plant Breeding, Cornell University, Ithaca, NY 14853
[2] Indonesian Center for Agricultural Biotechnology and Genetic Resources Research and Development (ICABIOGRAD), Jl. Tentara Pelajar 3A, Bogor, 16111, Indonesia

Introduction

Most of the rice that is grown and consumed in the US is non-pigmented, but rice can also produce red, brown and purple grain. Red grain is ubiquitous among wild rices and in some regions of the world cultivars with red grain are preferred for their taste, texture and ceremonial or medicinal value. The ubiquitous presence of weedy red rice in farmers' fields is the most economically important pest and grain quality problem faced by US rice growers today, leading to losses of as much as $50 million per year (Gealy et al., 2002). Using classical genetic analysis, two loci associated with red grain pigmentation, Rc (brown pericarp and seed coat) and Rd (red pericarp and seed coat), have been identified. When present together, functional copies of these genes produce red color in the seed coat and pericarp (Kato and Ishikawa, 1921).

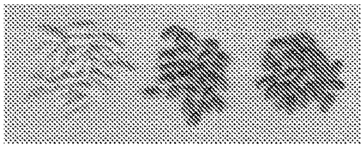

From left to right,
Jefferson, white pericarp *rc Rd* or *rc rd*
Rc mutant, brown pericarp *Rc rd*
O. rufipogon, red pericarp *Rc Rd*

Results

Previous QTL mapping in this lab has identified a single, significant QTL associated with red grain (rg 7.1) on chromosome 7. This QTL was identified in two independent populations derived from interspecific crosses between the same wild ancestor Oryza rufipogon (IRGC 105491) and O. sativa cultivars, in one case, a US tropical japonica cultivar, Jefferson, and in the other case, an indica cultivar, IR64, that is widely planted in Asia. The LOD score associated with the rg7.1 QTL peaks in both populations was very large, (LOD = 99 and 33, respectively), and the QTL was detected in multiple environments in both studies. The peaks of both QTLs corresponded roughly to the previously mapped position of the mutant, brown pericarp, Rc. Using the Jefferson/O. rufipogon population, rg7.1 encompassed an 8 cM region which represented ~ 6Mb straddling the border of the centromere. This population was used to fine map the QTL. Genetic to physical distance in the initial region is region is large, 1530kb/cM in the BC2F3 generation, but decreases in the next two generations to about 420 kb/cM, which is still higher than the rice genome average of about 240 kb/cM. The region responsible for the QTL has been narrowed to 402.4 kb.

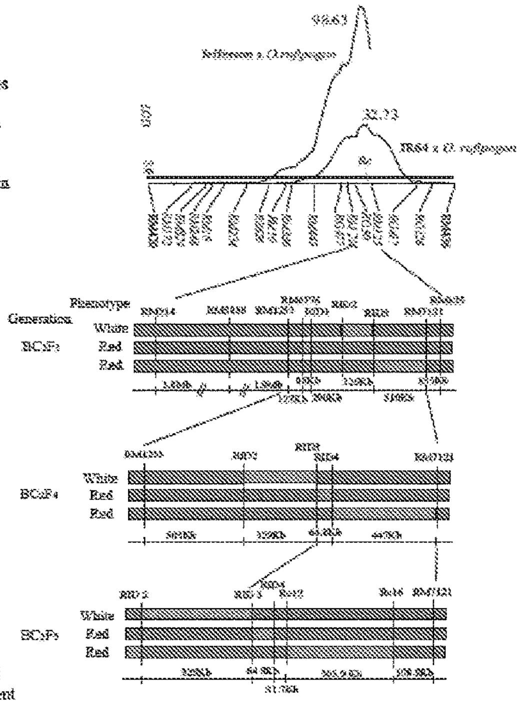

Future Work

Additional generation will be screened for recombinants and the QTL region will be examined for candidate gene relating to pigmentation.

Acknowledgements and References

This material is based upon work supported by the National Science Foundation under Grant No. 0110004.

Gealy, D. R., T. H. Tai, et al. (2002). "Identification of red rice, rice and hybrid populations using microsatellite markers." Weed Science 500: 333-339.

Kato, S. and J. Ishikawa (1921). "On the inheritance of the pigment of red rice." Japan J Genet 1: 7-7.

FIG. 4

**SEQ ID NO:1 *O. rufipogon* predicted protein sequence of Rc – functional allele causing red color in seeds 668 aa**
MAGGEAQAALQAVAQSLRWTYSLLWQLCPHQGSSLVWGEGHYNGAVKTRKST
VMQPPPAEEEDDADHAARHRSRQLRELYDWLQQAGENSSGGVQTSSTTASRRP
GAALSPEDLTETEWFFLMSASYSFPPGIGLPGRAFARRGHVWLTGANEVDSKVF
LRAILAKTVVCIPVVDGVLEIGTTEKVEEDMGLIQYARGIFMDQHGIHMKPTLSQ
HSTSNPVTHCTHQHPIQVQMQLGITSQTKFDYSDELNADEENDDTEEEGMSGSD
TNNTDTERNSGQLQLQMQDQLNMVSNDHQTMPNNAVSSELMQCEMSEVVRDG
CSNNILEDEIQMLMDCQNSNCQLNLQGPDEPCHSWHFLCEELQNDYQPATEDQV
ASPENTHYPKTLMTILHYNTLRQQEMNIKNYLPVSEKSSFSRWTTPEGSDDNKT
MISPGTTQRMLKSILMIVPSSHCSYRGAETPESRGGKGASGTRKVGAIQGDFSAN
HVLKERRRREKLNEKFIILRSLVPFMTKMDKASILGDTIEYVKQLRNRIQELESSS
SSSRAAARAPSAAAAGRRRKRSAAAATATAAEGMSSSNGRNGGEAAEVVQVSII
ESDALLELRCGCGGGGGGGGGVVLLRVMQAMQELQLEVTAVQASCAGGELL
AELRAKVVVMILICMKMQMQMQN

SEQ ID NO:2 Jefferson predicted protein sequence of Rc – mutant allele leading to white seeds 662 aa
MAGGEAHAALQAVAQSLRWTYSLLWQLCPHQGSSLVWGEGHYNGAVKTRKST
VMQPPPAEEEDDADHAARHRSRQLRELYDWLQQAGENSSGGVQTSSTTASRRP
GAALSPEDLTETEWFFLMSASYSFPPGIGLPGRAFARRGHVWLTGANEVDSKVF
LRAILAKTVVCIPVVDGVLEIGTTEKVEEDMGLIQYARGIFMDQHGIHMKPTLSQ
HSTSNPVTHCTHQHPIQVQMQLGITSQTKFDYSDELNADEENDDTEEEGMSGSD
TNNTDTERNSGQLQLQMQDQLNMVSNDHQTIPNNAVSSELMQCEMSEVVRDG
CSNNILEDEIQMLMDCQNSNCQLNLQGPDEPCHSWHFLCEELQNDYQPATEDQV
ASPENTHYPKTLMTILHYNTLRQQEMNIKNYLPVSEKSSFSRWTTPEGSDDNKT
MISPGTTQRMLKSILMIVPSSHCSYRGAETPESRGGKGASG*CHPRFQCQPCAEREE*
*KKREAQEVHNSAIFGTFHDKDGQGVDTRRHDRVREAAKEPHTRARVVVVVVTSSRPG*
*AIGGGRREAEEEIRRRRHCHGGGRDEQQQWPQWRRGGGGGAGVHHRERRAAGAPV*
*RLRRRRRRCGAAPGDAGDAGAPAGGHRRPGLVRRWRAARRAARQGRRYDPDLHENA*
*NANANAEL*

**SEQ ID NO:3 *O. rufipogon* predicted mRNA sequence of Rc – functional allele causing red color in seeds 2007**
ATGGCCGGCGGCGAGGCGCAAGCGGCGCTGCAGGCGGTGGCGCAGAGCCTC
CGGTGGACCTACAGCCTCCTCTGGCAGCTCTGCCCCCACCAAGGTAGCTCGCT
GGTGTGGGGGGAGGGGCACTACAACGGCGCCGTCAAGACGCGGAAGTCGAC
GGTGATGCAGCCGCCGCCGGCGGAGGAGGAGGACGACGCCGACCACGCGGC
GCGCCACCGGAGCCGGCAGCTGAGGGAGCTCTACGACTGGCTGCAGCAGGC
CGGGGAGAACTCCAGCGGCGGCGTGCAGACGTCGTCGACGACGGCGAGCCG
GCGGCCGGGGGCGGCGCTGTCGCCGGAGGACCTGACGGAGACGGAGTGGTT
CTTCCTCATGTCGGCATCCTACTCCTTCCCTCCCGGCATCGGGTTACCTGGAA
GGGCATTTGCAAGGAGAGGCCATGTATGGCTCACTGGAGCAAATGAAGTTGA
CAGCAAAGTATTCCTAAGAGCAATTCTTGCCAAGACAGTTGTGTGCATTCCTG
TTGTCGATGGCGTCCTGGAAATTGGAACTACGGAAAAGGTGGA

FIG. 5A

GGAAGATATGGGCCTGATTCAGTATGCAAGGGGCATCTTCATGGATCAACAT
GGCATCCACATGAAGCCTACCCTCTCACAGCACTCAACATCCAACCCAGTCA
CCCACTGTACTCATCAGCATCCAATCCAGGTTCAGATGCAACTAGGTATCACC
AGCCAAACAAAGTTTGATTATTCAGATGAGCTCAATGCAGATGAGGAGAATG
ATGACACAGAAGAAGAGGGCATGTCAGGTTCAGACACTAACAACACTGACA
CTGAAAGGAATTCAGGCCAGCTGCAACTTCAAATGCAAGACCAACTGAACAT
GGTGAGCAATGACCACCAGACAATGCCAAATAATGCAGTTTCCAGTGAGCTA
ATGCAGTGTGAGATGTCAGAAGTGGTAAGAGATGGCTGCTCAAATAATATTT
TAGAGGATGAAATCCAAATGCTGATGGATTGCCAAAACAGTAATTGTCAGTT
AAATTTGCAAGGGCCAGATGAGCCTTGTCACTCTTGGCATTTTCTCTGCGAGG
AGTTACAAAATGATTACCAGCCAGCTACTGAAGATCAAGTGGCATCACCTGA
AAATACCCATTACCCAAAAACACTCATGACAATCCTACATTACAACACGCTG
CGACAACAAGAGATGAACATCAAGAACTACTTGCCAGTTTCAGAGAAATCAT
CATTCTCCAGATGGACTACTCCTGAAGGAAGTGATGACAACAAGACCATGAT
CAGTCCAGGCACCACACAGAGAATGCTCAAGAGCATCCTGATGATTGTTCCC
AGTAGTCACTGCAGTTACAGGGGAGCAGAAACACCTGAATCAAGGGGCGGG
AAAGGCGCAAGTGGA*ACGCGAAAAGTCGG*TGCCATCCAAGGTGATTTCAGTG
CCAACCATGTGCTGAAAGAGAGGAGAAGAAGAGAGAAGCTCAATGAGAAGT
TCATAATTCTGCGATCTTTGGTACCTTTCATGACAAAGATGGACAAGGCGTCG
ATACTAGGCGACACGATCGAGTACGTGAAGCAGCTAAGGAACCGCATACAA
GAGCTCGAGTCGTCGTCGTCGTCGTCACGAGCAGCCGCCCGGGCGCCATCGG
CGGCGGCCGCCGGGAGGCGGAGGAAGAGATCCGCCGCCGCCGCCACTGCCA
CGGCGGCGGAAGGGATGAGCAGCAGCAATGGCCGCAATGGCGGCGAGGCGG
CGGAGGTGGTGCAGGTGTCCATCATCGAGAGCGACGCGCTGCTGGAGCTCCG
GTGCGGTTGCGGCGGCGGCGGCGGCGGCGGCGGCGGCGGTGTGGTGCTGCTC
CGGGTGATGCAGGCGATGCAGGAGCTCCAGCTGGAGGTCACCGCCGTCCAGG
CCTCGTGCGCCGGCGGCGAGCTGCTCGCCGAGCTGCGCGCCAAGGTCGTCGT
CATGATCCTGATCTGCATGAAAATGCAAATGCAAATGCAGAATTAA

**SEQ ID NO:4 *O. rufipogon* genomic sequence of Rc – functional allele causing red color in seeds**
6406
ATGGCCGGCGGCGAGGCGCAAGCGGCGCTGCAGGCGGTGGCGCAGAGCCTC
CGGTGGACCTACAGCCTCCTCTGGCAGCTCTGCCCCCACCAAGGGTACCTAC
CCTACCTACCTACGACACGATGCACAGTGTTCATCCATGGCGGATCGTCGTCG
TTGTCGATGATCATCGAAGGAAGCTAGAGGATATGGCTCAATACTTTGATAA
TATATATACTGATCTCTCCGTACAACAAAAATATAAAAATTCTAGCTAGTATC
GAATGAGACATATGCTATGCTAGTACTATTATTAGGATATATCACGAGTTTTT
ATATTTTGAGACGGATGTAATAATTCTGAATTTAGTTGTGATCGCATGGCATG
CAGTAGCTCGCTGGTGTGGGGGGAGGGGCACTACAACGGCGCCGTCAAGAC
GCGGAAGTCGACGGTGATGCAGCCGCCGCCGGCGGAGGAGGAGGACGACGC
CGACCACGCGGCGCGCCACCGGAGCCGGCAGCTGAGGGAGCTCTACGACTG
GCTGCAGCAGGCCGGGGAGAACTCCAGCGGCGGCGTGCAGACGTCGTCGAC
GACGGCGAGCCGGCGGCCGGGGGCGGCGCTGTCGCCGGAGGACCTGACGGA
GACGGAGTGGTTCTTCCTCATGTCGGCATCCTACTCCTTCCCTCCCGGCATCG
GGTATATAATAAAAAATATAGATATAAATATTTAAGCATGCATGCATAAATT

FIG. 5B

AAACCACACTTCTTGTTACGTGTTCTTGGCAAAATGATGAACAATTACCACTA
ATTAATTGGAGCCAGAAACCCTAAAGATTTACCCACCTGGTTAATTAATCGGT
GTGTTGATCCACGCATGCATGCATGCAGAAAATCAAGATCAGGATAGCTCCT
TTTCTTTTGCAGGTTAATTAGCTAGATCTTCACGTAAAATTAGCTAGCTAGAT
TTTAAAATATAATTTATTCAATTTGATTTATGATTTTTATTTTTTATTTCAAAT
AGATACAACTGTATACAAAATTTTATTTTGGTACATACCTCCGATCCAACTAC
ATCAGAGGTAAAAAAAAAAAATTAAACCGTTGGAATTGATTAGAACAAGATC
GTGCGGTCAAATTATATCATAACTAACTTTTTTGATTCTCTAAAGCATAGAGA
TGTATATATACATCGTACTATTAGGCTCTATATTTCCTGATTAACACTAGATG
CATATATAATTTTGATAGTCAAAATATACTTTTGATAGGCTCTAAAGAAAAAC
TTAATAACATGTACTCCCTCCATATACTTTTGATAGTCATATTTCATCTTGACA
CACAGATCAAGTATAAGTAATTTTACTTATCATCCATTTAAACACGCTACTAG
TTATTCCTCGTAAACAAGCGATTCATTAATATTTACATTTCTCGATGCTTGTGT
AGCC*AA*TATTGTGTGGAAGAATAGAATGTCATTAAGAGGATAGGTTGTTGGA
TTGAAATATGCCTATCAAAAATAAATTTTTAGATTTGAAAATATGTCTATCAA
AAGTAGATGGAGGGAGTATTAATTAATGTGAATTTCCAATCCTACTGTTGTGA
TATTAGGCTTTGTACCTTCTTGTCCAGGAGGTATATATATGGCTCTTTTAAGG
ATGGGAGAAAATATCATCTTTAATACAACTATATATGGCTTTTGTTTGATAAA
TACAACTTTTATTTTGTATGAACACAAATATATTGATAAATATCCACCATTAT
AATCCTAACCCATTAGGATCATATGGTGTATATTTTTTTAACTATTTGTTTTTT
ATAAATTAATATTAAGAGATCACAATACAAATATAGTATTATGAAAGTACTC
TTAACAACATATCCAATGATAAAATTATTATTATTACAAAATATAGTGGTCAA
ATTGTATAGAATTCAATAGCCTGATTTTATGACGTCAAGTAAATTAAATAAAG
AATGAAGGTAGTGCTAGAGTGATCAAACAATATCTCTCCTAAAATATGTCCT
ATAAGTTTTACTCCATAAATCCAAGGGTCAAAAGTTGTTGGGTTATTTTTTTA
GATAATAACATACTACCCCTTTTCAAAATGTATGATTCTATTGACTTTTTGCA
CAACATTTAACCATTTGTCATATTAAAAATTAGTATAAACATCTAAAAATATA
AGTTACGATTATATTTTATTTGATGATAAAACAACTCACAACAAAATAAATA
ATATTTATATAATCTTTTTGGAATAAGACGAATGATCAAACATTATTCAAAAA
GTCAATGGTATAGTACGTTTTGAAATTGATAGACTATGAGAGCAAAATTTTG
AGATAACATGGAAAATTATCCTCTTAGACATTGCACTGTGTAATAATTAATAA
TAATGAATGAAAGGCTAAGACTTTTCTTCCACCT
TATAAAGGTGGTTGAATATATAGCAATCACATCATTACATGATTTTGTAACCA
ACCGTCTCTATAGCTCCGATACAGTGCTAGTTTCACATCGTAATAATTAAAGA
GTATAATAATAAATCGAGGTGTACTTCTCATCGATGAAGTGATGTGCCGCTTA
GCTAAATTAAACTCGTATGCGAAAAATCAGTATATGTCCGGTTAATTTCTAAG
AGAGAGATTGAGAGAGAATAATTGCGCCCCTCCAAATCCCCCTCTTGGACGT
TAGGGAGCTATATAGACGGTATTGCTAAGTGCGATGTGTACATAACGTACCT
GTCGTAGGAACATTTCTCATCCAAATTAAGTAGTAATGCATGGCATGAAATC
CATTTTTGTATTTTGCATGGCAAAGAATGACAACAAGGAATACACTAGCTAG
CCCTGCCCTTTTTCAATTTAATTTAACATCAAACTTAGTTATTGTATTTCTTTT
GTCAGAATAGCATGCATTGCATACTCTTTAAAAATAATTAATTAGTGTATTTT
ACTAGTCTTACAAAGGTATCAAGAGAGACAACTAATTATAGTTGGGAGACAC
CAAACTTGTTTTTAATAATGACAATTAAAACCCTACCTCTACATCCAACATAG
ACGTACATAGTCCGAAGGCGCCAAATATTTGTACATTTAGCTACCAGATTTCA
GTACGAGTTCTCACATTATAATTTTGATTTTTTTATTTTTTTTATAAACAATCT

FIG. 5C

GGTACCCTTTTATGTCTGGAAGGAAAAAAAAATCTAAATTGCAACATTTTAGT
CGGTGAGAATGGTACTCTGTCCTAGCTACTTTCTACACATGAGAGAGAGAGA
GAGAGAGAGAGAGAGAGCCTTTAATTGCCCTTGCCCATGCATCTTTCTTTGCA
CACATGTATGCTTTTCACATTGTCATGAGGAGAGAACTTGTTAAGTTGCACAC
ATGTGTGCTTTGCATGTCTTCAGGTTACCTGGAAGGGCATTTGCAAGGAGAG
GCCATGTATGGCTCACTGGAGCAAATGAAGTTGACAGCAAAGTATTCCTAAG
AGCAATTCTTGCCAAGGTTCAGCCATCACCTTCTCTTACCTATTTTTCACTCTG
AATGCCAACAGTGCTTTGCACATTGTAGTCTGTTTGCAGACTGCAAATGATGA
CCATAATCAGATCAGAAAATAAAATAATATTATATACTTTTTGAGCCAGCTA
GCAAGAATATGTAACAATAATTCTCCTTTTTTTTCTTGTTCTTCTCCCTGATGT
GGTGCATAACAAATAACCAAACTGATGAATGGCAGAGTGCTGGTATCCAGGT
ATTTGCCTCTAAAAGTAGCTACACGTTTACTATGAAATTTTGTGGCTTTTTTTC
ATCTTTGGATGCAGTGGCCATTATCTAAAAACTATGAATTTCCAGACTGCAGT
TTTTATCTAATTTTGTGACTTTGTACATCAGACAGTTGTGTGCATTCCTGTTGT
CGATGGCGTCCTGGAAATTGGAACTACGGAAAAGGTGATTTCGTATATTATC
AGCTGACAATCTAATTATATGGGCCATATAATTAAGTATAAATCAAAATACC
TCATAATACATTATAAAGTATCTAATGTGATTATGTGAATATTGGCTATTTCA
ATGTAATTTGATATATGAAACTGATAATCCTCTGAAACTCCGTAAGGATCAA
ACTAATCAAAATGTATATATTTTCAAGGTGGAGGAAGATATGGGCCTGATTC
AGTATGCAAGGGGCATCTTCATGGATCAACATGGCATCCACATGAAGCCTAC
CCTCTCACAGCACTCAACATCCAACCCAGTCACCCACTGTACTCATCAGCATC
CAATCCAGGTTCAGATGCAACTAGGTATCACCAGCCAAACAAAGTTTGATTA
TTCAGATGAGCTCAATGCAGATGAGGAGAATGATGACACAGAAGAAGAGGG
CATGTCAGGTTCAGACACTAACAACACTGACACTGAAAGGAATTCAGGCCAG
CTGCAACTTCAAATGCAAGACCAACTGAACATGGTGAGCAATGACCACCAGA
CAATGCCAAATAATGCAGTTTCCAGTGAGCTAATGCAGTGTGAGATGTCAGA
AGTGGTAAGAGATGGCTGCTCAAATAATATTTTAGAGGATGAAATCCAAATG
CTGATGGATTGCCAAAACAGTAATTGTCAGTTAAATTTGCAAGGGCCAGATG
AGCCTTGTCACTCTTGGCATTTTCTCTGCGAGGAGTTACAAAATGATTACCAG
CCAGGTATTACATTTGAGAAGATAATCCTTCAAAAGCACCCTTGTTCCAAAA
ATATATATTTGTACTCTTCACACAAGCACTGCCATTTTTTTTCTTTTTTGCATA
CATCCTCAATTCTTGCATTTCTTTTCCATATATTTGATACAACTGTCTCCATTT
CCCTTCTGTCACAGCTACTGAAGATCAAGTGGCATCACCTGAAAATACCCATT
ACCCAAAAACACTCATGACAATCCTACATTACAACACGCTGCGACAACAAGA
GATGAACATCAAGAACTACTTGCCAGTTTCAGAGAAATCATCATTCTCCAGA
TGGACTACTCCTGAAGGAAGTGATGACAACAAGACCATGATCAGTCCAGGCA
CCACACAGAGAATGCTCAAGAGCATCCTGATGATTGTTCCCAGTAGTCACTG
CAGTTACAGGGGAGCAGAAACACCTGAATCAAGGGGCGGGAAAGGCGCAAG
TGGA*ACGCGAAAAGTCGG*TGCCATCCAAGGTGATTTCAGTGCCAACCATGTGC
TGAAAGAGAGGAGAAGAAGAGAGAAGCTCAATGAGAAGTTCATAATTCTGC
GATCTTTGGTACCTTTCATGACAAAGGTAATTAAGTACTCCCTCTATTTCTAT
AAAGCCGTATTTGACTAGTTATCTTATTTAGAAAGTATGTGCAAATATGTAAA
ATATAAGTCATACTTAAAAGAACTTTTAATGTTATTAAATAATAAGTCACACC
AAAAATAAAACATATATATTTTTAATAAGATAAATGATTAAATGTATATATA
AAAATTAATAGCGTCACATATTTTAAAATAGAGGGGTATTTAAGTACCCACA
GGATCATCAAAATTCAGTTATCTTTTCTTAAGCCTCTAACGAACATTGGAAGA

FIG. 5D

TCCTCACTAATGGGCAGCATGAATCTAGGGTTCACTATTTCGGAATGCAAAAT
ATGTTTTGCCGGGCATCCGATTTTTAAAAAATTCAGAATGAAGAAAATTGAA
TCTTTTTTATGGATTTGAATAAATCTTGATAAATTCGAAAAAATTTCCGAACT
TTTGGCCAGAAGTGAATCCTACCCGTATCCACCGGTAATAAACCTAAATTTTT
GGGAGTAATGAATTAATGTTATATATAATCCATGAATTATATAGTTCCAAACT
ACTCCGTAACAAATTTTCAGGAGTAGTGAAATTAATATTATTACAATCTCAGA
AAAAAATGGCAGAAACAATTAATCTGTTTTCAATTATTAATTAATTTGTTTTT
GTGTCCAGATGGACAAGGCGTCGATACTAGGCGACACGATCGAGTACGTGAA
GCAGCTAAGGAACCGCATACAAGAGCTCGAGTCGTCGTCGTCGTCGTCACGA
GCAGCCGCCCGGGCGCCATCGGCGGCGGCCGCCGGGAGGCGGAGGAAGAGA
TCCGCCGCCGCCGCCACTGCCACGGCGGCGGAAGGGATGAGCAGCAGCAAT
GGCCGCAATGGCGGCGAGGCGGCGGAGGTGGTGCAGGTGTCCATCATCGAG
AGCGACGCGCTGCTGGAGCTCCGGTGCGGTTGCGGCGGCGGCGGCGGCGGC
GGCGGCGGCGGTGTGGTGCTGCTCCGGGTGATGCAGGCGATGCAGGAGCTCC
AGCTGGAGGTCACCGCCGTCCAGGCCTCGTGCGCCGGCGGCGAGCTGCTCGC
CGAGCTGCGCGCCAAGGTCGTCGTCATGATCCTGATCTGCATGAAAATGCAA
ATGCAAATGCAGAATTAA

SEQ ID NO:5 Jefferson predicted mRNA sequence of Rc – mutant allele leading to white seeds - 1987 na

ATGGCCGGCGGCGAGGCGCATGCGGCGCTGCAGGCGGTGGCGCAGAGCCTC
CGGTGGACCTACAGCCTCCTCTGGCAGCTCTGCCCCCACCAAGGGAGCTCGC
TGGTGTGGGGGGAGGGGCACTACAACGGCGCCGTCAAGACGCGGAAGTCGA
CGGTGATGCAGCCGCCGCCGGCGGAGGAGGAGGACGACGCCGACCACGCGG
CGCGCCACCGGAGCCGGCAGCTGAGGGAGCTCTACGACTGGCTGCAGCAGG
CCGGGGAGAACTCCAGCGGCGGCGTGCAGACGTCGTCGACGACGGCGAGCC
GGCGGCCGGGGGCGGCTCTGTCGCCGGAGGACCTGACGGAGACGGAGTGGT
TCTTCCTCATGTCGGCATCCTACTCCTTCCCTCCCGGCATCGGGTTACCTGGA
AGGGCATTTGCAAGGAGAGGCCATGTATGGCTCACTGGAGCAAATGAAGTTG
ACAGCAAAGTATTCCTAAGAGCAATTCTTGCCAAGACAGTTGTGTGCATTCCT
GTTGTCGATGGCGTCCTGGAAATTGGAACTACGGAAAAGGTGGAGGAAGATA
TGGGCCTGATTCAGTATGCAAGGGGCATCTTCATGGATCAACATGGCATCCA
CATGAAGCCTACCCTCTCACAGCACTCAACATCCAACCCAGTCACCCACTGT
ACTCATCAGCATCCAATCCAGGTTCAGATGCAACTAGGTATCACCAGCCAAA
CAAAGTTTGATTATTCAGATGAGCTCAATGCAGATGAGGAGAATGATGACAC
AGAAGAAGAGGGCATGTCAGGTTCAGACACTAACAACACTGACACTGAAAG
GAATTCAGGCCAGCTGCAACTTCAAATGCAAGACCAACTGAACATGGTGAGC
AATGACCACCAGACAATACCAAATAATGCAGTTTCCAGTGAGCTAATGCAGT
GTGAGATGTCAGAAGTGGTAAGAGATGGCTGCTCAAATAATATTTTAGAGGA
TGAAATCCAAATGCTGATGGATTGCCAAAACAGTAATTGTCAGTTAAATTTG
CAAGGGCCAGATGAGCCTTGTCACTCTTGGCATTTTCTCTGCGAGGAGTTACA
AAATGATTACCAGCCAGCTACTGAAGATCAAGTGGCATCACCTGAAAATACC
CATTACCCAAAAACACTCATGACAATCCTACATTACAACACGCTGCGACAGC
AAGAGATGAACATCAAGAACTACTTGCCAGTTTCAGAGAAATCATCATTCTC
CAGATGGACTACTCCTGAAGGAAGTGATGACAACAAGACCATGATCAGTCCA
GGCACCACACAGAGAATGCTCAAGAGCATCCTGATGATTGTTCCCAGTAGTC

FIG. 5E

ACTGCAGTTACAGGGGAGCAGAAACACCTGAATCAAGGGGCGGG<u>AAAGGCG</u>
<u>CAAGTGGA*TGC*</u>CATCCAAGGTGATTTCAGTGCCAACCATGTGCTGAAAGAGA
GGAGAAGAAGAGAGAAGCTCAATGAGAAGTTCATAATTCTGCGATCTTTGGT
ACCTTTCATGACAAAGATGGACAAGGCGTCGATACTAGGCGACACGATCGAG
TACGTGAAGCAGCTAAGGAACCGCATACAAGAGCTCGAGTCGTCGTCGTCGT
CGTCACGAGCAGCCGCCCGGGCGCCATCGGCGGCGGCCGCCGGGAGGCGGA
GGAAGAGATCCGCCGCCGCCGCCACTGCCACGGCGGCGGAAGGGATGAGCA
GCAGCAATGGCCGCAATGGCGGCGAGGCGGCGGAGGTGGTGCAGGTGTCCA
TCATCGAGAGCGACGCGCTGCTGGAGCTCCGGTGCGGTTGCGGCGGCGGCGG
CGGCGGTGTGGTGCTGCTCCGGGTGATGCAGGCGATGCAGGAGCTCCAGCTG
GAGGTCACCGCCGTCCAGGCCTCGTGCGCCGGTGGCGAGCTGCTCGCCGAGC
TGCGCGCCAAGGTCGTCGTTATGATCCTGATCTGCATGAAAATGCAAATGCA
AATGCAAATGCAGAATTAA

SEQ ID NO:6 Jefferson genomic sequence of Rc – mutant allele leading to white seeds – 6429 na ATGGCCGGCGGCGAGGCGCATGCGGCGCTGCAGGCGGTGGCGCAGAGCCTC
CGGTGGACCTACAGCCTCCTCTGGCAGCTCTGCCCCCACCAAGGGTACCTAC
CCTACCTACCTACGACACGATGCACAGTGTTCATCCATGGCCGGCCATGGCG
GATCGTCGTCGTTGTCGATGATCATCGAAGGAAGCTAGAGGATATGGCTCAA
TACTTTGATAATATATATACTGATCTCTCCGTACAACAAAAATATAAAAATTC
TAGCTAGTATCGAATGAGACATATGCTATGCTAGTACTACGAATCTAAAAAG
ATGTACATATTTTGATTCGTATTATTAGGATATATCACGAGTTTTTATATTTTG
AGACGGATGTAATAATTCTGAATTTAGTTGTGATCGCATGGCATGCAGGAGC
TCGCTGGTGTGGGGGGAGGGGCACTACAACGGCGCCGTCAAGACGCGGAAG
TCGACGGTGATGCAGCCGCCGCCGGCGGAGGAGGAGGACGACGCCGACCAC
GCGGCGCGCCACCGGAGCCGGCAGCTGAGGGAGCTCTACGACTGGCTGCAG
CAGGCCGGGGAGAACTCCAGCGGCGGCGTGCAGACGTCGTCGACGACGGCG
AGCCGGCGGCCGGGGGCGGCTCTGTCGCCGGAGGACCTGACGGAGACGGAG
TGGTTCTTCCTCATGTCGGCATCCTACTCCTTCCCTCCCGGCATCGGGTATATA
ATAAAAAATATAGATATAAATATTTAAGCATGCATGCATAAATTAAACCACA
CTTCTTGTTACGTGTTCTTGGCAAAATGATGAACAATTACCACTAATTAATTG
GAGCCAGAAACCCTAAAGATTTACCCACCTGGTTAATTAATCGGTGTGTTGAT
CCACGCATGCATGCATGCAGAAAATCAAGATCAGGATAGCTCCTTTTCTTTTG
CAGGTTAATTAGCTAGATCTTCACGTATAATTAGCTAGCTAGATTTTAAAATA
TAATTTATTCAATTTGATTTATGATTTTTATTTTTTATTTCAAATAGATACAAC
TGTATACAAAATTTTATTTTGGTACATACCTCCGATCCAACTACATCAGAGGT
AAAAAAAAAATTAAACCGTTGGAATTGATTAGAACAAGATCGTGCGGTCAAA
TTATATCATAACTAACTTTTCTGATTCTCTAAAGCATAGAGATGTATATATAC
ATCGTATTATTAGGCTCTATATTTCCTGATTAACACTAGATGCATATATAATTT
TGATAGTCAAAATATACTTTTGATAGGCTCTAAAGAAAAACTTAATAACATG
TACTCCCTCCATATACTTTTGATAGTCATATTTCATCTTGACACACAGATCAA
GTATAAGTAATTCTACTTATCATCCATTTAAACACGCTACTAGTTATTCCTCAT
AAACAAGCGATTCATTAATATTTACATTTCTCGATGCTTGTGTAGCCAATATT
GTGTGGAAGAATGGAATGTCATTAAGAGGATAGGTTGTTGGATTGAAATATG
CCTATCAAAAATAAATTTTTAGATTTGAAAATATGCCTATCAAAAGTAGATG

FIG. 5F

GAGGGAGTATTAATTAATGTGAATTTCCAATCCTACTGTTGTGATATTAGGCT
TTGTACCTTCTTGTCCAGGAGGTATATATATGGCTCTTTTAAGGATGGGAGAA
AATATCATCTTTAATACAACTATATATGGCTTTTGTTTGATAAATACAACTTTT
ATTTTGTATGAATACAAATATATTGATAAATATCCACCATTATAATCCTAACC
CATTAGGATCATATGGTGTATATTTTTTTAACTATTTGTTTTTTATAAATTAAT
ATTAAGAGATCACAATAAAAATATAGTATTATGAAAGTACTCTTAACAACAT
ATCCAATGATAAAATTATTATTATTACAAAATATAGTGGTCAAATTGTATAGA
ATTCAATAGCCTGATTTTATGACGTCAAGTAAATTAAATAAAGAATGAAGGT
AGTGCTAGAGTGATCAAACAATATCTCTCCTAAAATATGTCCTATAAGTTTTA
CTCCATAAATCCAAGGGTCAAAAGTTGTTGGGTTATTTTTTTAGATAATAACA
TACTACCCCTTTTCAAAATGTATGATTCTATTGACTTTTTGCACAACATTTAAC
CATTTGTCATATTAAAAATTAGTATAAACATCTAAAAATATAAGTTACAATTA
TATTTTATTTGATGATAAAACAACTCACAACAAAATAAATAATATTTATATAA
TCTTTTTGGAATAAAACGAATGATCAAACATTATTCAAAAAGTCAATGGTAT
AGTACGTTTTGAAATTGATAGACTATGAGAGCAAAATTTTGAGATAACATGG
AAAATTATCCTCTTAGACATTGCACTGTGTAATAATTAATAATAATGAATGAA
AGGCTAAGACTTTTCTTCCACCTTATATAAGTGGTTGAATATATAGCAATCAC
ATCATTACATGATTTTGTAACCAACCGTCTCTATAGCTCCGATACAGTGCTAG
TTTCACATCGTAATAATTAAAGAGTATAATAATAAATCGAGGTGTACTTCTCA
TCGATGAAGTGATGTGCCGCTTAGCTAAATTAAACTCGTATGCGAAAAATCA
GTATATGTCCGGTTAATTTCTAAGAGAGAGATTGAGAGAGAATAATTGCGCC
CCTCCAAATCCCCCTCTTGGACGTTAGGGAGCTATATAGACGGTATTGCTAAG
TGCGATGTGTACATAACGTACCTGTCGTAGGAACATTTCTCATCCAAATTAAG
TAGTAATGCATGGCATGAAATCCATTTTTGTATTTTGCATGGCAAAGAATGAC
AACAAGGAATACACTAGCTAGCCCTGCCCTTTTTCAATTTAATTTAACATCAA
ACTTAGTTATTGTATTTCTTTTGTCAGAATAGCATGCATTGCATACTCTTTAAA
AATAATTAATTAGTGTATTTTACTAGTCTTACAAAAGTATCAAGAGAGACAA
CTAATTATAGTTGGGAGACACCAAACTTGTTTTTAATAATGACAATTAAAACC
CTACCTCTACATCCAACATAGACGTACATAGTCCGAAGGCGCCAAATATTTGT
ACATTTAGCTACCAGATTTCAGTACGAGTTCTCACATTATAATTTTGATTTTTT
TATTTTTTTTATAAACAATCTGGTACCCTTTTATGTCTGGAAGGAAAAAAAAA
ATCTAAATTGCAACATTTTAGTCGGTGAGAATGGTACTCTGTCCTAGCTACTT
TCTACACATGAGAGAGAGAGAGAGAGAGAGAGAGAGAGAGCCTTTAATTGCCC
TTGCCCATGCATCTTTCTTTGCACACATGTATGCTTTTCACATTGTCATGAGGA
GAGAACTTGTTAAGTTGCACACATGTGTGCTTTGCATGTCTTCAGGTTACCTG
GAAGGGCATTTGCAAGGAGAGGCCATGTATGGCTCACTGGAGCAAATGAAGT
TGACAGCAAAGTATTCCTAAGAGCAATTCTTGCCAAGGTTCAGCCATCACCTT
CTCTTACCTATTTTTCACTCTGAATGCCAACAGTGCTTTGCACATTGTAGTCTG
TTTGCAGACTGCAAATGATGACCATAATCAGATCAGAAAATAAAATAATATT
ATATACTTTTTGAGCCAGCTAGCAAGAATATGTAACAATAATTCTCCTTTTTT
TTTCTTGTTCTTTTCCCTGATGTGGTGCATAACAAATAACCAAACTGATGAAT
GGCAGAGTGCTGGTATCCAGGTATTTGCCTCTAAAAGTAGCTACACGTTTACT
ATGAAATTTTGTGGCTTTTGTTCATCTTTGGATGCAGTGGCCATTATCTAAAA
ACTATGAATTTCCAGACTGCAGTTTTTATCTAATTTTGTGACTTTGTACATCAG
ACAGTTGTGTGCATTCCTGTTGTCGATGGCGTCCTGGAAATTGGAACTACGGA
AAAGGTGATTTCGTATATTATCAGCTGACAATCTAATTATATGGGCCATATAA

FIG. 5G

TTAAGTATAAATCAAAATACCTCATAATATATTATAAAGTATCTAATGTGATT
ATGTGAATATTGGCTATTTCAATGTAATTTGATATATGAAACTGATAATCCTC
TGAAACTCCGTAAGGATCAAACTAATCAAAATGTATATATTTTCAAGGTGGA
GGAAGATATGGGCCTGATTCAGTATGCAAGGGGCATCTTCATGGATCAACAT
GGCATCCACATGAAGCCTACCCTCTCACAGCACTCAACATCCAACCCAGTCA
CCCACTGTACTCATCAGCATCCAATCCAGGTTCAGATGCAACTAGGTATCACC
AGCCAAACAAAGTTTGATTATTCAGATGAGCTCAATGCAGATGAGGAGAATG
ATGACACAGAAGAAGAGGGCATGTCAGGTTCAGACACTAACAACACTGACA
CTGAAAGGAATTCAGGCCAGCTGCAACTTCAAATGCAAGACCAACTGAACAT
GGTGAGCAATGACCACCAGACAATACCAAATAATGCAGTTTCCAGTGAGCTA
ATGCAGTGTGAGATGTCAGAAGTGGTAAGAGATGGCTGCTCAAATAATATTT
TAGAGGATGAAATCCAAATGCTGATGGATTGCCAAAACAGTAATTGTCAGTT
AAATTTGCAAGGGCCAGATGAGCCTTGTCACTCTTGGCATTTTCTCTGCGAGG
AGTTACAAAATGATTACCAGCCAGGTATTACATTTGAGAAGATAATCCTTCA
AAAGCACCCTTGTTCCAAAAATATATATTTGTACTCTTCACACAAGCACTGCC
ATTTTTTTTCTTTTTTGCATACATCCTCAATTCTTGCATTTCTTTTCCATATATT
TGATACAACTGTCTCCATTTCCCTTCTGTCACAGCTACTGAAGATCAAGTGGC
ATCACCTGAAAATACCCATTACCCAAAAACACTCATGACAATCCTACATTAC
AACACGCTGCGACAGCAAGAGATGAACATCAAGAACTACTTGCCAGTTTCAG
AGAAATCATCATTCTCCAGATGGACTACTCCTGAAGGAAGTGATGACAACAA
GACCATGATCAGTCCAGGCACCACACAGAGAATGCTCAAGAGCATCCTGATG
ATTGTTCCCAGTAGTCACTGCAGTTACAGGGGAGCAGAAACACCTGAATCAA
GGGGCGGGAAAGGCGCAAGTGGA*TGC*CATCCAAGGTGATTTCAGTGCCAACC
ATGTGCTGAAAGAGAGGAGAAGAAGAGAGAAGCTCAATGAGAAGTTCATAA
TTCTGCGATCTTTGGTACCTTTCATGACAAAGGTAATTAAGTACTCCCTCTATT
TCTATAAAGCCGTATTTGACTAGTTATCTTATTTAGAAAGTATGTGCAAATAT
GTAAAATATAAGTCATACTTAAAGAACTTTTAATGTTATTAAATAATAAGTCA
CACCAAAAATAAAACATATATATTTTTAATAAGATAAATGATTAAATGTATA
TATAAAAATTAATAGCGTCACATATTTTAAAATAGAGGGGTATTTAAGTACC
CACAGGATCATCAAAATTCAGTTATCTTTTCTTAAGCCTCTAACGAACATTGG
AAGATCCTCACTAATGGCAGCATGAATCTAGGGTTCACTATTTCGGAATGCA
AAATATGTTTTACCGGGCATCCGATTTTTAAAAAATTCAGAATGAAGAAAAT
TGAATCTTTTTTATGGATTTGAATAAATCTTGATAAATTCGAAAAAATTTCCG
AACTTTTGGCCAGAAGTGAATCCTACCCGTATCCACCGGTAATAAACCTAAA
TTTTTGGGAGTAATGAATTAATGTTATATATAATCCATGAATTATATAGTTCC
AAACTACTCCGTAACAAATTTTCAGGAGTAGTGAAATTAATATTATTACAATC
TCAGAAAAAAATGGCAGAAACAATTAATCTGTTTTCAATTATTAATTAATTTG
TTTTTGTGTCCAGATGGACAAGGCGTCGATACTAGGCGACACGATCGAGTAC
GTGAAGCAGCTAAGGAACCGCATACAAGAGCTCGAGTCGTCGTCGTCGTCGT
CACGAGCAGCCGCCCGGGCGCCATCGGCGGCGGCCGCCGGGAGGCGGAGGA
AGAGATCCGCCGCCGCCGCCACTGCCACGGCGGCGGAAGGGATGAGCAGCA
GCAATGGCCGCAATGGCGGCGAGGCGGCGGAGGTGGTGCAGGTGTCCATCAT
CGAGAGCGACGCGCTGCTGGAGCTCCGGTGCGGTTGCGGCGGCGGCGGCGG
CGGTGTGGTGCTGCTCCGGGTGATGCAGGCGATGCAGGAGCTCCAGCTGGAG
GTCACCGCCGTCCAGGCCTCGTGCGCCGGTGGCGAGCTGCTCGCCGAGCTGC

FIG. 5H

GCGCCAAGGTCGTCGTTATGATCCTGATCTGCATGAAAATGCAAATGCAAAT
GCAAATGCAGAATTAA

SEQ ID NO:7 BAC83694 putative intensifier [Oryza sativa (japonica cultivar-group) cultivar="Nipponbare"
MAGGEAHAALQAVAQSLRWTYSLLWQLCPHQGSSLVWGEGHYNGAVKTRKST
VMQPPPAEEEDDADHAARHRSRQLRELYDWLQQAGENSSGGVQTSSTTASRRP
GAALSPEDLTETEWFFLMSASYSFPPGIGLPGRAFARRGHVWLTGANEVDSKVF
LRAILAKTVVCIPVVDGVLEIGTTEKVEEDMGLIQYARGIFMDQHGIHMKPTLSQ
HSTSNPVTHCTHQHPIQVQMQLGITSQTKFDYSDELNADEENDDTEEEGMSGSD
TNNTDTERNSGQLQLQMQDQLNMVSNDHQTIPNNAVSSELMQCEMSEVVRDG
CSNNILEDEIQMLMDCQNSNCQLNLQGPDEPCHSWHFLCEELQNDYQPATEDQV
ASPENTHYPKTLMTILHYNTLRQQEMNIKNYLPVSEKSSFSRWTTPEGREQKHLN
QGAGKAQVDAIQGDFSANHVLKERRRREKLNEKFIILRSLVPFMTKMDKASILG
DTIEYVKQLRNRIQELESSSSSSRAAARAPSAAAAGRRRKRSAAAATATAAEGM
SSSNGRNGGEAAEVVQVSIIESDALLELRCGCGGGGGGVVLLRVMQAMQELQLE
VTAVQASCAGGELLAELRAKVVVMILICMKMQMQMQMQN

SEQ ID NO:8 mRNA for putative intensifier [Oryza sativa (japonica cultivar-group) cultivar="Nipponbare" NP1112028 (TGR Rice) (XM_477136 GenBank)
ATGGCCGGCGGCGAGGCGCATGCGGCGCTGCAGGCGGTGGCGCAGAGCCTC
CGGTGGACCTACAGCCTCCTCTGGCAGCTCTGCCCCCACCAAGGGAGCTCGC
TGGTGTGGGGGGAGGGGCACTACAACGGCGCCGTCAAGACGCGGAAGTCGA
CGGTGATGCAGCCGCCGCCGGCGGAGGAGGAGGACGACGCCGACCACGCGG
CGCGCCACCGGAGCCGGCAGCTGAGGGAGCTCTACGACTGGCTGCAGCAGG
CCGGGGAGAACTCCAGCGGCGGCGTGCAGACGTCGTCGACGACGGCGAGCC
GGCGGCCGGGGGCGGCTCTGTCGCCGGAGGACCTGACGGAGACGGAGTGGT
TCTTCCTCATGTCGGCATCCTACTCCTTCCCTCCCGGCATCGGGTTACCTGGA
AGGGCATTTGCAAGGAGAGGCCATGTATGGCTCACTGGAGCAAATGAAGTTG
ACAGCAAAGTATTCCTAAGAGCAATTCTTGCCAAGACAGTTGTGTGCATTCCT
GTTGTCGATGGCGTCCTGGAAATTGGAACTACGGAAAAGGTGGAGGAAGATA
TGGGCCTGATTCAGTATGCAAGGGGCATCTTCATGGATCAACATGGCATCCA
CATGAAGCCTACCCTCTCACAGCACTCAACATCCAACCCAGTCACCCACTGT
ACTCATCAGCATCCAATCCAGGTTCAGATGCAACTAGGTATCACCAGCCAAA
CAAAGTTTGATTATTCAGATGAGCTCAATGCAGATGAGGAGAATGATGACAC
AGAAGAAGAGGGCATGTCAGGTTCAGACACTAACAACACTGACACTGAAAG
GAATTCAGGCCAGCTGCAACTTCAAATGCAAGACCAACTGAACATGGTGAGC
AATGACCACCAGACAATACCAAATAATGCAGTTTCCAGTGAGCTAATGCAGT
GTGAGATGTCAGAAGTGGTAAGAGATGGCTGCTCAAATAATATTTTAGAGGA
TGAAATCCAAATGCTGATGGATTGCCAAAACAGTAATTGTCAGTTAAATTTG
CAAGGGCCAGATGAGCCTTGTCACTCTTGGCATTTTCTCTGCGAGGAGTTACA
AAATGATTACCAGCCAGCTACTGAAGATCAAGTGGCATCACCTGAAAATACC
CATTACCCAAAAACACTCATGACAATCCTACATTACAACACGCTGCGACAGC
AAGAGATGAACATCAAGAACTACTTGCCAGTTTCAGAGAAATCATCATTCTC
CAGATGGACTACTCCTGAAGGAAGGGAGCAGAAACACCTGAATCAAGGGGC

FIG. 5I

GGGAAAGGCGCAAGTGGA*TGC*CATCCAAGGTGATTTCAGTGCCAACCATGTG
CTGAAAGAGAGGAGAAGAAGAGAGAAGCTCAATGAGAAGTTCATAATTCTG
CGATCTTTGGTACCTTTCATGACAAAGATGGACAAGGCGTCGATACTAGGCG
ACACGATCGAGTACGTGAAGCAGCTAAGGAACCGCATACAAGAGCTCGAGT
CGTCGTCGTCGTCGTCACGAGCAGCCGCCCGGGCGCCATCGGCGGCGGCCGC
CGGGAGGCGGAGGAAGAGATCCGCCGCCGCCGCCACTGCCACGGCGGCGGA
AGGGATGAGCAGCAGCAATGGCCGCAATGGCGGCGAGGCGGCGGAGGTGGT
GCAGGTGTCCATCATCGAGAGCGACGCGCTGCTGGAGCTCCGGTGCGGTTGC
GGCGGCGGCGGCGGCGGTGTGGTGCTGCTCCGGGTGATGCAGGCGATGCAGG
AGCTCCAGCTGGAGGTCACCGCCGTCCAGGCCTCGTGCGCCGGTGGCGAGCT
GCTCGCCGAGCTGCGCGCCAAGGTCGTCGTTATGATCCTGATCTGCATGAAA
ATGCAAATGCAAATGCAAATGCAGAATTAA

SEQ ID NO:9 AP005098 Oryza sativa (japonica cultivar-group) genomic DNA, chromosome 7 provides mRNA XM_477136 and product XP_477136 putative intensifier [Oryza sativa (japonica cultivar-group)]

CACTCAGATCTACACAGGAGTTCTTGCAATTTCTCAACATCAACCTCATTAGGGCATAAAAAG
ATGTCATGACAGTATCCAAGCTTCTCTAGAACGTTCCTTGAAATTCCTTCAACATCTCTAGTAC
GGAGCGACCTTTTCAATTTCCTGTTTTCTCTCAGAATTTCACTATTCATTGACCTGACCTCATCC
AGCTGCTGTCTAGCACATTCCAACTCGTGGACAAGGTATTCTTTCTCGTCTAGAACCTCTTTCA
AGCGAATCCTATAAAAATACAGGTCGATATCCTCATCTGATTTGGTTGGCTGAAAACATAGGT
CTCAATTAGTTAGAAAAAACCACATGGACCCTTCAATTTGTTAGGGAAAGAAAACTACAACA
GGAGCTTCTACTGTGATAGGTTTTTAATGACTGATATGACTATATTTCAAAATTGAGCATCAA
AGCCACTACATCCAAACCAATCAGAGTCTGGGCACATTGAAGATCCAACATTTTCAAGATGTG
CTTTAATTTGCCGACCATGCCAAAGCAGTTAGAAGTTTTAACAGAATTGAATATAGAAAGTTA
ACACAGACCATAACCGAACAAACAATAGAACTTACAACACTGAATAATACCTGTTTTTCACGT
GGCCTATCAGAAGAACAACTTTCTTGGAATGTTGGTCTTGAATCAGAGTCAGCTGCATAGGAA
AAAGTATTTCTCAAGAAATGATAAAAGATGAAGTATTTACAACTTAACAACACAAACACATA
TATAAAAAATCCTAGGACAAACTTAAATGCAACAAAAAGTATTACTTATTAACACCCATATTT
GGCATCTTAAGTGAAAATAGCAAGATATGGTCAAATTTGTAGAGGACCCGGCTTGCTGCGCG
AGGCCGGTCTGACCGCCGCCATAGGGCCGATCAGACCAACGGTGTGGGGCCAGTTTGACTGG
CGGTATGTAGCCGATAAGACCGGCAGGGTCCAGTTCTGAGTCTAGTTTCATCGGTTCTCGGGA
TTTTTTTGCTTGGGTTGAGGTTTTTCGAGTCCTAATTGGTTTCTACACCTAGTGGGACGTGGAG
AGGGTCCTGTGGAGGGCCTGACCAACCCCTTTATAAGGGTCATGGCTGGTTCAATTGAGATAC
ACAATGTACAACAACGCAATTTGCTAATTGAATCGTTCTTTCAATAAAGCATCTACTTTTTGCC
TAGCTTTTAGCCTAGTTTGTCTATCTTCGTTGGTTTGTGCTTGTTGGAGAAACGGGAACCAGGG
TCCCCTTTTCCCCAGGATCATGAGACACAGGGGCCCACAAAAATCACTTTCTACCACATACAT
ATATGTATCTATAATTCGTTGCCAGGTCAGAAACCACGGAAGTGGAGGACAACAGTTGGCGA
GGAATGGGGACCTGGGCCCTTATCCAAATAGGGCCCGGGGCACCGACACTTTTGAAAGTTTTC
ATTTATTCGTCTTCGCCGCAAGAGTGCAAGTACTCTTTGTAGGTTAGTCCTGAAAACGTTCCGC
TCCACCCATGATATGGGTTTTTCTCCCTATTCGTCTAAATCGGCTCCGCTAATTGGTTTTGATCT
CTAAACCCGTCTTGACCAGGGGGTTTCTCAAGGTTGAGGTGGTTGGCGACTCCATGCACCACA
AAGCCTTTTCTAGTTCATATTGGGTACTAAGTTCACTTAATTGGACTGGAATAGGTCGATGGGT
ACCAGATTGACCCCCAGTCCGCTCTCATCCCTACTAAATATTTATATGTACACTTGGTTAAGAT
CATTTTAATGTAAACTGAAATAGCTTATTTGCTCTGATAAAAAAGAGAAAACATATCAAAATT
TATCATAGTGGTTTACCTCGGACTAATAGGGGCAGGGGATCATTTCTCAAGCTTTCTTCTACTT
TTTCATGGCACACAGTACGGATTTCCTCTTCACATCTGTCATCATAAGCAGCAAAAAATGATG
AGGTTGATTCCCTAATAAAATATTAAACAAAAAGTATACCGGTGTTATAATCAGACCCAACAA
AAAATTTCTGATGGATAGGAGTTTAGCAGACTGTAATAAAATGAACAAAAAGTAACTTCAAA
GAGACAATTATCTATACTCTATAGGGTGTAGCTTCTGGCAGAAACTAAGCCTTCAGTTATAGC
ATCTACAGATTAAGAAAAATTCAACACAATAATCACAACATACATCTTTCCAAAGCTGTTCTG

FIG. 5J

GGAACACTCATTTGTTTTGTAGCCAGGATAGATGAGCAGAGATCCTGATTGCTGGTCCTGGAG
AAACAAAAGTGTCTTAGCAGAAAAACAAAATAAACCATCAAAAGAATTAGTCATTTTGTTTCC
TGCAACTAAAATCCAAAAATCACATATCAATCATCTGGTTCTAGTCTTCTATCATGAATGTGA
GATTGACACGTTGCTTAAATTCTAAAATTAAATTGAATTTATTGAATGGAAATCCATATTAAC
AAGAGTGCTCCATTGTTACAAGCATTTACTTTATAATCAGTTCATTAAGAGTGCTCCATTGTTA
CAAGCATTTACTTTATAATCAGTTCATTAAACATATCTTTGTAAGAGCAACTAAATGAGGTAA
TATAAAACACATTAAGAGCTAATAAGTAATAACTAAAAAAGAACAGTACGCAAATTCAATGT
GTCAAAAGAGAAAGGTGAGATGCAATAAAGTTCAGTTTTGGGGATTTTTTCTGGTGTGTTGTT
CACAGCCACACACACACTATTTCACTTAGCTACATATGCAAGCAGGTCCCCAATACAAGAGCA
TATTACATCAACACTCCCCCTCAAGATGGGCAAAAGATATCAATCATGCCCATCTTGTTACAC
ATTGACTCACTCTCACTAGGACCTAATCCCTTGGTTAAACAATCAGCTAGCTGCTCAGAAGAT
TTAATGTATTGTAGTCTAAGAGCCCCACTATCGATCTTCTCTTTGATGAAGAACCTATCAATTT
CGATATGTTTGGTGCGGTCATGTTGAACTGGATTGTTTGCAATGTTGATAGCAGATTTGTTGTC
ACAATGAAGCACCACAGTATTATTTCTGAACAACCGTAGCTCCAACAATAGATTCTTCACCCA
CAACATCTCACTTAAACTCAATGCCATGGCTCTATACTCAGCTTCCGCGGTAGATCGAGCCAC
TACCGCCTGCTTCTTGCTTCGCCAACAGACAACATTGCCACCCACAAATACACAATATCCTGA
TGTAGATCTTCTATCATCCACACTGCTTGCCCAATCAGCATCACAATATCCTTCCACATCCAAG
TGTTGGTTCTTTCTAAACCACAACCCCTTACCAGGAGTTCCTTTCAAGTACCTCAAGATCCTAT
GAACCACCTCTAGATGAGTTGTTCTAGGATCATGCATATACCTACTAACCACACTCACCGCAT
AAGAGATATCTGGTCTAGTGTGGCATAGATATATCAAACGTCCAACCAACCTCTGATAAGTTT
CCCTATCAACTGGATCACCTGACTGTGCACTCAATTGGTGATTCCTATCAATGGGAGTAGCAC
TTGTACGACATCCAAGCATTCCGGTTTCTTTTAACAAATTAAGGACATACTTTCTTTGAGAGAG
AACTATCCCCTTTGATGATCGAGCAACCTCAATCCCAAGAAAGTATCGAAGAGGTCCAAGATC
CTTCACCTCAAAGGCCTCTCCTAATCGCTGCTTTAAGCATTTGATCTCTTCTACATCATCTCCA
GTGATCACTATATCATCAACATAAACAGCCAAGATAGTGATGTGTGCCCCCCTATGTCTATAG
AAAACTGTGTGATCTCCATTACATTGTGAATATCCCATATTGCACAATGCACGCCTAAACCTG
TCAAACCATGCACGTGGGGATTGTTTCAAACCGTACAAGGACTTCTTGAGCCTACATACCTTC
CCAACAGTCTGGCTATTTCCAAATCCAGGGGGAATCTCCATATATACCTCCTCTTGTAAATCAC
CATGTAGAAAAGCATTCTTGACATCTAACTGATGAAGAGGCCATCCAAAGTTAACTGCACATG
ATATCAAAATCCTCACCGTACTCATCTTAGCCACAGGTGCAAATGTTTCATCATAGTCAATTCC
ATATGTTTGACTATAACCTTTTGCAACTAATCTTGCTTTATATCTATCCACTTTCCCTTCAGGGG
TTTGCTTCACTGTAAATACCCATTTACATCCCACTGCTCTTTTCCCCATTGGTAGTTTCACAAGT
TCCCATGTCTTATTCTTTTCAAGGGCACGCAACTCCTCCTTCATTGCATCCTTCCATCTTGGATC
TTGTTTTGCACATCTCTAGTCCTTTGGAATAGGCACTATTTGCAATGATGCAATGAATGCTTTA
TATGCAGGTGAAATATGAGAGTATGAGATATAGTTTGCAATGTCATGTCTAGAACTAAGGTGT
TCAAAACCAAGGCGTATAGGAGGTCTTCCAGCATTAGATCTAGTTTCTCTACGTTGTGCAAGA
GGTAACTCTACTTGTTCAAAGGTAGGAGAAATGTTACCACTTGTCTCAAGGAGGGAGGAACTT
GTTGGAGAGAGGCTAGAGGAGGAATCTGGGACTGCGTACTCAAACTGTTGCAGCTGTTGTGA
CTCCTTGTCTTGCTCTTGCATAGGCTCACCACTTCTCTCCCCCTGATTCTGAATTTGGCTCCTCT
GGTGCACTTGCTCCTTCCCTGTCACCTTATCAACTTGGTTCTTGTTCCTTCTTTGATATACTCTC
ATTTCAGTTTGTTGTACTTCCACACGCTCCAGAGGACATGGGATTGTCCCGACAACTACCCCCT
CATCCTTGTCACAACTAATGTCTACTACCTTCTCACCAATGTCCACAACCTTCTCAATAGTATC
ACCAACAAAACTCGGAATTGACCCAATAACCACATCCTCATCACCTTGCTTATGTGCATCAAC
CTCAACTATCTCCCCCTCTCGACTGTCGATCTCGATGACAGTTGAGAACTCCTCTAGAAATTGA
TCAAGGTCTCCTCGACTCCTGTAATAAGGTTCAAACTCTCGAAATGTTACATCCATACTAACA
AATAACCTCTTCCCAATAGGGTCCCAACACTTATAACCTTTCTGGTTAGATGCATAGCCAACA
AAGACACATTTTACTGCATGAGGATCCAACTTGCCAACAAAAGGTCGATGATCTCTCACAAAA
CAAACACAACCAAATACCTTTGGGGGAACTTTAAATTCTCGCTTCCCAAGTAAAAGTTCAGCT
GGTGATTTCATACCAAGTATCCTGGATGGCATGCGGTTGATAAGGTATGCGGCTGTCATCACT
GCCTCACTCCACAGATACTTAGGTACGTTCATTTGAAACATTAATGACCGAGCCACCTCTAGC
AAATGCCGATTCTTCCTCTCAGCTACACCATTTTGAGGGGGGGCTCCAGGACAAGTGGTTTGA
TGAATAATTCCATGATCTGAGACATATGACACAAACTCACTATTAATATACTCCGTCCCATTGT
CAGTTCGAATAATCCGAACCCTTGCATCAAACTGATTGGTAACCAATTTGTGGAAGTCTTGAA
AGCAACGAAGGACCTCATTCTTATGTCTAAGCATGTAAATCCAAGTCATACGAGTATAACAAT
CAATAAAGGTAACAAACCATTTGAATCCACTCACAGAAGTAACTGGGCATGGTCCCCAAACA
TCAGAATGTATTAATATAAAAGGTTCACAACTACGAAGACCAATTCCAGCATATGTAGACCGT

FIG. 5K

GTATGTTTGCCAAACTCACAAGCATCACAAACAAGTCTACTCTTGTCCACTTTGGTAAAGAGG
TCAGGATACAGCTTACTCAAACTCTCGAAAGATGGATGTCCTAATTGACAATGAAGCAAAATA
ATCTCCTTCTCAGTATCTCCCACTACTACAGCCAATCCCATCTCCTCTTGATTGATGTACCACA
GCCCATTACGCCTGACTCCAGTCCCAATCCTCCTCCCAGGCAGTAGCCAAAAAACAAGCAAAA
ACAAGAGACGTACCACCTCCTTCCTAGTTCCTGCAGCAAACAATCCTCCTATGTCACCAAGTC
TGCAGCCAAGCCACCATCCTCCTTTTCCCTTAGCTGAGCTCCTCACATTTCCTGCGTGAGCAGC
AGGTTACAACACACGCGCTGCGCCCGCGCGGCCGCGCGCAGCGCGCGCTCACCAGCCCCTCA
ACGTGGCTGTGTGTAGAGGCTGGTCAGGCCGGATGAGAGCAGGGGCGACGTGCGACGACGGC
AGCGGCGACGGCGGCGGCGATGGACGGCGGCGGCGGCGACAGCAAGCTAGGGTTAGGGCTC
TGATACCATAAAGTTCAGTTTTGGGGATTTTTTCTGGTGTGTTGTTCACAGCCACACACACACT
ATTTCACTTAGCTACATATGCAAGAAGGTCCCCAATACAAGAGCATATTACATCAACATGCAA
AACATCCATCAAGTCAAATAATCTGAAATTACTTCTGCAATTATAATGCTGACAACATGCTAA
CGCATCCAACAGTTAAAAGTGTGCAGGAACTAATACCACTCAATTTAGTAATTCATTACAGCC
ACGCTTGATGGAAACAGAGAGAAATTAAGCAATGGTTTATTGGAAATTAGCCGTGCCTAGAG
AAGAGGATGGACGCCTCACTGCCGCAAGGCCATTAACTGATCAGGATCAAACTATGACTGCC
AAAAACATCTCCAACTAACCATCTCAATTCTTACAAGTTACAACTATGAACCAGATGATGAGA
AGTTGAGAACCCACGCAATTCCAAAACGATCATAGAGCATCGACGCGCGGGTTAGGAACACA
CTTGCATTGCCATAACACGATCAAAAACAACAAGCGATCGAATGATACGGGGGAGTCGAGTA
CGCACCACCACCTCCTGATCGGGCTTCTCCTTGTCAAACTTGGAGCACGAGGACTTGTTGATG
ATGTCGCTGGCCATCTTGTCGTGCGGAGAGGAGAGTTTATCACCATCTGCGCCGTGCTCGGCC
GCCGCCGAGGACGACGCCGAGGTCGCGGAGGCGCAGTCCATGGCCGTGGGCACCCCCACCTG
CGGTGCCCCAGACAGCGTCGTGCCGTGGGTGGTCATCATCTCGACGCCCCCGGAGGACTCGGC
GGGACGGGGCGACGACGCCGGGGTGGAGGAGGAAGCCGCCGCGGCGTCCATGGCGCCCTTG
GGCTCTTCCGCTTCAGTAGTTAAGTCCCGCTTGCCCTGCAATCGAGAGAGACATCAGGAACAC
ACACCCGTGAGTCGTGAGCGTAGTTGGTGCCGGAGAAGGAGAAACGAGGGACGGCGTACGA
GGTCGTGGCGGGGAGGCATTGGGCGGCGGCGCCGCCGCGGCGGAGGAGCAGCCCGACACGG
CGGATTCTGGAAGGTTCGGCGTGGGGAGGAAGACGGCTTCGCGGGGAAATGACCAGCCGCTC
CGCTTTTTTTTTTTCCTTTCCCGTTTTTTCAGGAGAGAGAGAGATGGGTTTGGGTTTCGTCGGG
TCGGGTGGGTTTGGGTTTTGGAGCCTCTGAAGTTGGACATGGGTTTCGTTGCATTCCACGTCGT
GCGGGTTGGGGATTTGGATTGGGCCCACAGGGCGTACGTGGCCCCGCGTCGTGCGGGTTAGAT
TCTTCGCTTGAGCTAATAAGTTCAATCGGGACTGTATGTTTATTTGTCGGGTGATTTCCAAAAA
AGGAAAATCATCTAGATTTTTTTTACCTTTAGATTTACATCCAACAGACTACAAAAGAATATA
ACAAATACATATTTATTTATATATTATTTTTATCAAAATTACAGTATACTTACATGTCACATCA
ACTGAATTTACAAATGTAATTTTAGTTATATAGGCCTATAACTTTATATTTCACGACGACGATG
ATGAGAGAGGCGGTATCGCTCGCCGAACAGCTTTGGCCGTACTGCCGGCGGCCAGCTCGATC
AGAGGCCACCCTGGCACCGTGCTTCTCCAACATCGCGCGCGGGCGTACGTACCAGCCGGCCG
GCGAGCTTCATGCAACGTTCGATGCCGTTCACATTGCAAGCTGCATGGATGCTAAAACGTATC
AAATGCCAGAAAAAAAATCACACGAGAGATGGATAGCAAAACCGAGTTCGATGGGAGTAGA
CTCAACTTCGGCTGTGTCTCGTGTTTTTTTAGTAAGTTTACCTGACGTCTCTCAATTATCCACAG
AGCAGCCCAACAAATCAGGAAAGACATTCAAGAAAATAACTTCGTTTTTCAGCCTCCTTGATG
ATCTCATTTTCTTCCTCTTCTCCTCCCCTATTGTTGTCCCCTCTCTATCGTTATTTCTATTTCCTA
AGAATGTCGCTTCATATCTCCGGTAACAGTTCACTTGTAAGCTCTATGTAACCTACTAATTTCA
CCCCCTCTAATGTATTCGGCAATAATCTTGCCGCTTTCACCTAAAAAAACTATACGCTGAGTAT
ATCTGAGATCCCCTAACTGCAATATCAAAAATGTGCACCACGGACTATGTAAAACAGTTCAAA
AAAGGTCCCAGATTATAGATGGCCAAACGGGCCACCCGGCCCGACACAACCCAGATACAACC
GGTACGGCACGACCTACATGTCGGGTCGTGTCGTGTCAGCCCGCGAGCTGCACACACAGCCCA
GGCACGATCCAATAAGACTTGGGCCATGCCAGGCCGGTCCGAAGGCATGACAACCCATCATG
TTTCTCTATAAAATAAGTCTATTTTTCCTCCCTCGACTCTTTGGGTTGTGTCTTATATGGCTAAA
AAATAAGTCTATTTTGTATTCCTCTTCTCTTTGGGCCTTGTCATATATGGTTAATTAAGTCTATT
TTAGATCCCTCTACTATTTTCTTCCACCGTGCCGGGCCGGGCCAGCCCACCGTGCCAAGGCATC
AGCCTTGGCACGACCCAACTGTCGAGCCGTGCAAGCACAGGCCCGACAAATAGTCGGGCCAT
GCAATGCTTGGGCTGGGCGATCGGGCCTTAGGCCTTATGGCCATCTATAGTATAGATACCTGG
TTTCGCTGACGTGGCATCCTAGTCAGAAAAAAATAAAAAAAATGTAAGGCCCACATGTAAGT
GAGAAGGAAAATGTGGGCCCCACGTGTCAGCATCATCTTCTTCCTTTCGCTGACGTGACATCC
TAGTCAGAAAAAATTTAAAAAAAAGTAAGTGGGGCCCACATGGAAGTGACAAAAATTATAGG
CAAAATTTGCTACAGGACACTGAAATATTGCGGTCTTTGCTGTGAGACACCCGAAGATCGTGT

FIG. 5L

ATTTGCTGGTGGACATTGTAAAGAAGTGGTAATTAGCTGCTGGACACTCCTCCCATTATTTTAT
TATTTCCGGTCAAAATGGAGAGAGAAAGAGTTGTGTAAGTACTAAAATGCCCCTGGACACGT
ACTGTTCTTCCTCTCTCTCTCCTTTTCTTTTCCCAATTCTTCCTCGCGACGGCGGCCGGCCCGAG
CCGGGATGGCTCGGCCACGGCGGGGCGGCGGCGGCGGCGCATCACCGGGGTTCACCGCCGAC
GGCGATGACGCACGGCGGTGGCCCGGCGCACAAATGAGGTCGGCAAAGCTTGGTTGTCGACG
ATGGCTCGCGAAATGTTTCGGCGGCGGCGCTTCACCTTGGATGAACGGCGATGGCTCAATTTC
TTCAAAGGATTGTCATGCATGCATGTCTTTCGTGTTAGAGAGGTCCATGCGAGGCTACCATGG
CAAGGAATCGGATTGGGACTCACCGGAGAGGGAGAAATCAAAGATGGAGCTCAGCGACCGG
AGTTGGAGAAAGATGATGCCGATCTCTAAGATCGCTGCGCGACTGGATAGGGTACTTGGGGG
TAAATAGAGAGGAGGTCGAGGTGAAGCTGATGGCGTGGTGGCTCGGCCTACAACGATCCACT
GCACCCGGAACGGTGACGACGTCGAGGCGGCGACGCGCAGAGCGCGCTCCAAGGCCGGCGAT
GACACGATGGCGTTCCCGTCGATCCGCTGCACGAGAGAGGATGGAATCAAAATGAAAAATCT
TCGGCATGTTAAGGTAAGTATGGAACGGTGGTGAGGCAGACATGGAGATAGCTCTACAGTGA
CAGCGGGCGTTTTCTTCTTCATGGCCGGCGAGGGATTTGAGGACGGCGAAGAGATTGAGGGCT
TCCTCTCTCAGTTTGGTCGACACTAGAGCTGGGGTTCACCGCCGACGGCGACGACGCACGACG
GCTCAGCCATGGTGGAGCTCGGCGGCGGCGCAATGAGAAAGAGACGAACAGAGAGAGAGGA
AGAAGAAGAACAGAGAGAGAGAGAGATTGACAAGTGGGCCCATGGGCAAACTTGTCTTTAACCA
AAGTTTCTCTCTCCATTTTGATCGGAAATAATAAAATAATAGAAGGAGTGTCCAGCAGCTAAT
TACCACTTCTTGCAGTGTCCACCAGCAAATACACGATCTTGGGGTGTCTCACAGCAAAGGCCG
TAATCTTTCGGTGTCCTGTAGCAAATTTTGCCAAAATTATAGGGTCCACATCTTTTTCCCTTCT
CTTTTCTTTTTTCTTTTATTCTCTTCTCTTCTCCTTCAGCCGAACGGCGGTGGCAGGTGGCGACG
GGCGACGTACGAGAGCGGCGGCGGCGACAGATGCCTCTTTCCCCCTCCCGCCGACGCGGCCG
ACATCCTCACCCCCTCTCCTGTCGGCCTCATCTCCCCTCACTCGGTCGGCCTCCACTCCCCCTCT
CCCGTCGGTCGCTTGGCGAAGGTGGCTCGTGGGCCTCTTCCGAGGCTCGGCGGGTAGGCGGCT
GTAGACCCCCGATTTTAGAAATCGGAAATCTTCTGTGTTTATCCGTACCAATCCCTGGATCAGT
AGTTGGTACACACATATATAGTTGGATCACAACATATCACGAATGAATTTAGGCTAAAAGAGT
TAAATACTTACATTAGGGCCAGGTAGGCCAACAACTATCAGAGAACAACAGCGGAAGACAAA
ATAATATAAGGGCCCGGTTAACATGCCACAGGCAGTCGACTAGGGAACGAGACCTAGAACAA
GACCGCACTCCGATCATCTTGTTGGATACGCAAGCGTACCGACAAGGGCTTCTCTTCAACACT
CTCCTAAAAGATATATGAATAGCAAGGGTGAGTACCAACCGTACTCAGCAAGCCACCACAAC
AACAATGCATATGATAGAGGGTATTTCAAGGAATGGCTTCAGGTTCTTTTGCATAAAGCTAAT
TTTACAATTCTTTTCACAAGCCTAAAACCTAGCATAGACTGATCAAATTTTAGTACCAGTGTTC
ACTTTAAACAACGACGGTTCTGTCCACCATCCATTGTGATCCCAAGGATAGCTTCCCGCCATT
GAATCGTCATGGTTTTCTGAGGATGTCCACCTTCCCTCCTATCGGGAAGTGGCTCCATCAGCAT
AAAATTCATCATGCAATAACCCATCCCCCACAAGTTAAGAATTTAGAGTCTAGCCAAGTGTAA
TACATGTCCCGGTGCTCAATAACCGCGAGCACGGCTATTCGAATAGATTTGGTTTACTCACAC
TGCAGTGGATGTACACTTTACCCGCACTCCGCGACTGCCCAACACATGAGCCTCGTCCCAACA
CATGAAACGCGTCACGGCAAAGCTTTTCGATAACCTCGCATTGGCAGTACCCGCTCCATGAAC
TTTTCATCCTCATGCACTCTAGGCGTACACGGTTTCTAGCAGTGAGAGGAGTTCTGGCGCACC
CGGGAAGGGAAGACTCACACATGCATTAAGTTATAATTATGTTTTAGATTCTCACATGGCAGT
CCTACCGATGGCGACACCACTGTAGACACCCGCCTCGCGGTCCTACCAATGGCTGCCCCACCG
TAGAGCCCCTGCCTCACACATCAAGAAACCACTATGCATGGATACTGCCTCCGCTCAGCTATC
TACTCCGCTAGGTCTATACCCATACGAGAAGTGCGGTTGTACGGGGGTCGTTTCCTGCTTAAC
TTCATGGCTCGGTCCTTAATTGACCAGGGACGGCACTAGCCTTTTCCGGACACCACCCAAGTC
CTCCAGCCGCCCTAGTCGAAAACAGTTGTTTTACTTTATTTTCCTTTCACAAATCATGTCATCA
ATATCATGGCAATGTGGCGCTCATGTCTCCACATGCCGTATCTCAATTACCTTCCCAAAGGTA
ATTGCCCAAGCATATAGCATTTGATAAATATGAGTATGCATGAATCTAAAATAGCATTTCTAA
GCAAGTGTCATAGTTGACTAGGGACTCGTACGTATCTATGGTTACAAAGATTTAAAGGTGAAC
AATAATCAAGGCATGGTATAATCACAAGTAGGATGTTCATAATTGCATGCAATTTTATTTGTA
AACAAAACAATTTCGCAATTGGGATCAACATGTTCAAGGAATAGTGATGACTTGCCTTGCTCA
GGATAATCCTTATTACTGATATAATCTTGATCAACCTTCACCTCCTGGAAGTTGCAGACGTTGC
CTCACGTCTAACCGATACACAAGGTCTATAATACGCGAGAAAAACCAATATTCAAACAACAA
TCAAATACGCGCAACAAAATGTACTATTCATGTCTGCTAATGGATTCCAATCACGCTAGGGGC
TAAGGTTTCTTAATCTTTCTATTGTCAACGTGGCCTATTTAGGAGTTAACCAACATAGCATTTA
TGGGATACATATATATTTGGCTAATCGGTGGTTTAGTCTATCAAATGGCTTATGGAAGGATTA
TGGCTAAGCATGCATCTATCTAAATAGGACGGTCATATACTAGAGGTTCTATTGTTAGATGGA

FIG. 5M

TTTAGGATCAATCAAATAATTATAGTGAATCATTTGTATTATTTATTTTATTGATGGAAGCTTT
ACTTTAATTATGAACATATTTTACTTGTCACAATAAATTATAAAAGGTTAATAATTATCCATGC
TCTATATGTTAAGTTCGGGAAGTTTATAATATTATAGTTACAGATTATCTCTTAATGAACAATC
CGGAGTTACAATCGAACTATGAACATATGAGGTCAAGATTTATAATTAGGACTTATCTACTAT
TCATGTTTGTTATATACTCCCCAGTTTGATATATGAAAAAGATAAATTAATTGTGTAACTATAA
TGGGATGTACAATATATGTGTGCAACAAGGTATAAGGTTTTGGTCGCCTACTATACATGAGCT
TATTTAGAAAGTGTACTACCCAATGCTCCAAGTGATTCCTGAATATATTGTAGTTTAATTATAC
ATTAGCTAGTTTCTATGAGTGATATTGTATATGTGATGCGACAAGTTTAAGCACTGGTTCTATT
GGGTTACTAATAAGTGGTAATCAATTTAGGCATATATAAGCTATTCTATATGGTATTGCATCG
ATTATTTTACTTAGTGATTCCTCCACATCTAGCTCTATTATTATTCTCCTAAACAGGTTAAAGA
TTCATCTATGTGTGTTCATATTTTAGTTGCATAATCATAAGGCTACACTTGATTTAAATAACCT
ATAAGCCATGGATTTAATTATATGGCCATCGAAATTTTCCTATACATCCATTCATTTGATACAT
CACATAAAATTAGTTTGTGTGGTTGTTACAGTGGCAAGACATGTTAGAGACAAATATTATTAT
ATCTACTCTACTGTACAATACTAATTTTATTTATTAACATATTTTTTTAAGTTGACTATTATGC
ATCATCTTGATATTAATTATTTAATGTTTATAAATATATTTTATCAAATAGTGAATTATATATC
ATTGGAAAGCTTATGAATTTAGATGAATTTGGGTTCAAGTTTCACTCAAATCGGAGCTAAATA
TCGAACGAAATCCTAGAAATATTATATGATTTAATTTAGTCTATGACTAAATGATTAAATATA
ATACACGGCTAAAATCCCTAGTAATTAAATCTGAATTTCTACCGTGAATCGATTACTTATAGG
GTTTACCCAAAAATAATCTATAATAATCTATAAGAATTCATCTATTTGTTTAGTTATTAATTAC
GTCTAAATTACTACCGCGAATTGATTTCTTATAGAAATTACCAAGAATAATCCATAATTTATAT
TAAATTTTGCAATTCTATGACTATAATTAATCTATAATTAAATTCTAATTATTTTAAATTTTCTA
AACTTCCCTAATCTCCCTCTAATTTCCTATTTACTTCCTTTTCCTTTTTCTCCCTTTTCTCTCTTTT
CCTTTTCTTTTCTTTCTCTCCTCTCTTTCCCTCTCTTTCTTTTTCTCTCCTTTTTTTCTCTCCTCCTT
TTCTTTTCTTTTTCCTTCTCTCTCTCCCTCCCGGCTTCTTTCTCTCTTCCTCGGCTTCTCCCTTTCT
CTCTCTCTCTCTCGGCTTCTTCTCCCTGGTGACGACGACCGAGCAAGGGGAGGAGGCGGCGGC
TTACCGACGACGGCGGCGGCGACGGCGGCACGACGACCGAGCAAGGGGAGGAGGCGGCGGC
TTACCGACGACGGCGGCGGCGACGGCGGCACAACGACGGCGCACGGCGCGGCGGCACGAAG
GCGGCGGTGCGGCGGCGCGAGGGCGGCGCCACGACGGCGCACGGCGCGGCGGCGGCGGTGC
AGGCGGCGCGGTGGCTCAAAGCGGCGGTGCGGCGGCGTGGAGGCGGGAGGCGCAGTGGAGT
GAGTAGAGGAGAGGAGGTGAGAATGGGGGAAAATGGGTGTGGGGTGGGGAAGAGGAGGGG
GCCGGGGTTTTTATAGGGGCGAGCGGCCTCATGACGCGACGGGCGGCGCGGCGCGGGGCTCG
GCGCGGCTCGGTATGACGGCGACGGCGACGCGGCGCGGCAGCGGCGCGGGGTGCGAGGCGG
CGACGCGACGGGCGAGCGGCGCACGGGGCGCGAGGCGTGGGCGCGCTGCGCGAGGCGGCGC
GCGACGTTGGCGCGGCGCGGCAACGGTGACGCGAGGTGCGCGGCGCGGTGACGAGACGACG
CGGCAGCGGCGGTGCGCGGCGCGAGGCGTGGGGCGTGGGCGCGGCGACGCGACGGCGGCGT
GACAGGCGCGCGGCGGGCCAGGGGCGCGGGGACGACGGGACCGGTTCGCGGCGACGGGACG
GCCGACGGCGACGGCGCGGCAGCGGCGACGCAACGCGGGCGGCGTGGCGCGGGGAGCGAGG
CAGCCAGGCGCGCGCGGCTGAGGGGGAAAATAGAGCCAGGGACCACGTCGAGCACCTAGAG
TGCAATGAACAGTGACTTTTCCTATTTATCCCGATTTTAGTGTATTTTCCATATAAATTTGATTC
CACAATTCCTAGTTTTACATATATGCATTTTACTCAATATTTGTGTTATCTTAACTAATGAATTC
ACCCTAGATTAATATTATCCATATTTATTTATTTATCGCACAAATGAATTCTTTTTAGATTAATT
TGAGTTATTGGCCCTAAGGTGAACTTATATATTTTTGAAGACTTTGGGGTACTATTAAATTTAA
TATAACGACTTGTCATGATTAATACATTAGCAGATTGGTCAAGTTTAGTTGTATAGCAATATAT
TTTACACGGATAGGTTTAATCTATTTATTCTATAAATAGTAAATTAAGACTCGGTACAACATTA
ATCTAATTTTAAACACTCACATATTCTTGTTTATATATAAGGATTAATTTATTTATATGACCATT
ATTTTATATGAGTGATTTTCATGTCATGAGTAACTCGGCGACATGTTGCAAGTATCAATCTATA
TATTCCGGTGAATTACTTATTTATAAACACGATCACTATAATGGTGATCATCATTTCATGTGTT
CTTATATTTCATGTGAGATTCGATTCAAATGAATTAGATTTAATCTTACTATTTCTTTAGCTAAT
TGTGACATCAAGCTATCAATCATGGTTCGAATATTTAATACCTGATTTGTAATTTGTAATAGAA
ATTAATATTTGACTTAACTATCTTGTGCATAATTATTTGTAGGATTAACAATATTATATTCTCG
TAAATTTACCTATTACTTAAATTTTTAGATCCTTACTTTACTTTCTTTGTGATCATTTACGGTTT
GGCAAGCAATTGCAATCATAACAACCAGCATGATGAAAAAGTTTTGAAAAGTTCGAAATTTT
AGTGATTTTTATTGTTGGGAATTTTCAGGATGTTACAGCGGCGCAGGAGGGGTGGAGCCGCGT
CGTGACCCTCTTGCGAGCGTCTCCACTACTGTGTCGCCGTACTCTACGAGTTTGTTCTAGGCGC
GGCGGTGTCCCTCATGACGCCGAGCGTGCGATGCCGACAGGTGGTTCTCGGGGCGTGGCGCA
CCCTTGTCGGCTTCTTCCTTGCCGAGCACGACCGCGAGCTCGAAGCGGTCGTGCGTGATCTCG

FIG. 5N

CACGCCGTCTCCCGCGTGTGCGCCTTAGATCTCCGCCACGCTCATCTGTCGCCGCCCTCGCTCC
GCTCCGTCGGGCGCTTCGCCCCTACTCCGCTCCGCTGCCACCTCCTCACCGCCTAGCCGCCGAC
GCTGCCTCCTCACTGGCCCTAGTCGGCATTGTTTCCTCGCCGGCCCAAGCTATCGACCATCATT
AGCTCGTCGTTGCCGTGAGCCTTAGCCGACGCCCCCACGCCACCTCATCGCCGCCCGGGCTGT
AACGGCCGCTGCCACCGTCACCTCGGCGAGGGAGGAGAGACCAAGAGTAGGGTAGAGAGAG
TGGGAGAGAGCAGGAGAAGAGATAAGGTGGAGAATAAGGATGACAGGTGGGTCCTACATTTT
TTTTCCCACATAAGCGTCTAGTCAGCATGAGTGGACCGGGTCAAATTGCCACGTCAGCAAAAC
CAGGTGTCTATTCTGCTATAGGACCTAGACTGGACGGTTTTGTATAGTTTAGGGGTAAAGATA
TCTGGTATTGAGAATAAGGGATGTCAAGGTATAAAATTGAGGGACGACAGTGAATGTATAGT
TAATTAAGTACTAGCTTCATTTCATATTATTCGTTTGACTTTTTTTCTTTAGTTAAACTTCTTTA
GGTTTGACTAAATTTTATAAGAAAAAAATAGTAACATCTACATCACCAAATTAGTTTCATTAA
ATCTAACATTTGATATATTTTGATAATATGCTTATTTTGTATTGAAAATGTTAGTATATTTTTCT
ATAAACTTGGTTAAATTTAAAGAAGTTTGGTTGAGAAAAAAGTCAAACGACTTATAATATGAA
ACAAAGGGAGTATTAGGCTTAAAAAAACTTGAAAATTTGATTAATATGATTTCACGACAACT
TTTCTATAGAAATTTTTTATAAAAAAATACCGTTTAGTAGTTTTCGAAGCGTACGCGCGGTAA
ACGAGGGAGTAAGGTTGGGAACCTCAAATTGAGAGCACAGCATCATCATTTTTGGATGGGCTT
GGTGCGCATGGTTGGATGAACTACGAATGAGTTTACTTGGAAATTTTTTCATCTCGACGTCGA
GTTTGAATCGTGTTGACAAACCGTAATACCATATACAATAGATTCTTAACTTGTAATACTGGA
GTACTTGAGATCCTATAGCAGTATTGTGCTTGGTTTCAACTAATGTGGCGAGTTGAATGTGGTC
AACCTGGCCGAGTTTTGCGTGGGATCCACATGGGCCCCACTTGTTAGGGCCCATTCTCTCTCTA
CCTATCTCTATTTTTTTTCTCTTTCGCTCTTCATTTGTAGGCTGGCGCCGCCCAACATCATGTGG
TCGAGCTAGAGGAGTTGCTTTGGCAGGTGGCCACAGCGGCAGTGGCACTCCCCCTCTCTCTTT
CGCCCTTTGCTCGATGATGGTTGCGTAGGGCAGCGGTGGTGCTTCCCCTTCCCCGACTAGGTC
GGGCTTGCAACGACGACAACCTTCTCCCCGTCGAGCTCCTCACCCATCACTGTAGTTGGTGAG
CTATAGGGTAAGATAGACTTAAACCTAGGGCCTTATCACTTTACAGTTAAAATTAACCGTACA
AAGTTTTGGTTTTCTCAAAATTTGGGGAGGTAACAATCCAAACATTGCCAAAAATTGCTCCAC
TATCAAAGTTTGGCAATTTTAGAATCTTCCTCTCACAAAAAATTTAAAAAAAAACAAACTAAA
CATAGCCTACACTTGTTAACTTTACCAAATATTGATAAATTTGGTACTGTCAAAATTTGGCAAT
GTTGATATTTAGGCATCAAAAAGTGAACAACCCGTTCCGATGCCACAAGCCCACAACCCACCT
CACCCTGCCGACCATGTCAAACCAAGCAGAAGCTTCCAGAGCAAGGTGCCCGCGGCCCACGT
AGCCCACGCCGCCGAACAGCACACAGCCGCAACTCGCACGAACCCCCGGGCATGCCTGACCT
TGTGCGGCGGCGACCATGGCTGCCCCCTCGCCGGAGCGGAGCCCTCGTCGCCGGGGACCGAC
TCCCCGGTGCTCTGCGTGCGAATCGTATCCCTCGACTACCACATGGCGCCGCCCCTCCCCGGC
CGGATTCGACTTCTCCTACAGCCACTTCCACGGTGCGTTTCCCTCCCCGCCCCCTTTCTCCACC
CGCCTCTCTCGAGCCCCCGTTTCGCCCCCCTTGTGCTATGCCTCTGCACCGCGCCCACGTCACG
TCAAGCGGTTGATGAGTTTGATGTGTGGTGGATTTAGGTGAAGGAGGTGATCAGGCTCCACTC
CTTACTTGCCTCCACATCCATCTGGTGCGTAGCAGCTTCTCTGATGAGTGCTTTTTTTTTCTCT
CTGTTGATATTACGGATGAGCTAGTTTTGGTCGTCATGTTTGGTTGCAGCTTCAAGCTTTCAAC
CGAGTGCGTCGCGTCCTTTCAAGTGTTTTGAGTGTGAGTTACGCTGTGAGGGTATAATACATTT
GTGTTTGCTGTTAGGTAGCCATGCGCAGCAACTAATCCTCCTCATGTATTACACGGTATCTATG
CCCAACAATTGATGCCCATGGAGGGAATGTGGCAATGTGCTCTTTGTTGATACTGTACGCGCA
CCAAATTCGAAGTTTGGAGATCCAACTTCACTTTCGAAGTTCACTAAATTTGAAGCCCTCTTAT
CCTGCATGGGCTTAACATTATTTTCTATACACTTGGTGTTTGCTTGTAATATATGCAATATTTA
CTTCTGTGTGCACTTGATTTTTGTTTTTTTTTTGTTTTGGTTGAGTTTGGACATGCATATGATGA
TTAGCTCTATTATATTTTGAATTCATGTTTTTGAATGAATACAGATATACTTCAATTTTTTTTAT
ATCGCTTCTCTATGGAAAGTTGCTCACACTATTCCATTCATCATTAGTTGTGCCAACTAGTTTG
TAAACGTTTGCTGTTTTTTGTATCTCCTTCAATTTCTGTCTGTGCCTTGCACAGAGGACCTTCTT
CATAACATTGAAAAAGGTAATTCATTATTTGTAGTTATGCAACCCTGATGTATCATGTATATGC
TATTACTGTTACTTTTGCAATTTGTTACATGGATTGTTCTATTTTGAATTGTACTGCTGATTTTC
TATCTACATTACCTGAAAACTTTTTGCTGATGATTTTCATATCTACATCACCTGAAACTTGAAA
TTGATTGTTATTTATTCATATTCTAACTGAGCCTTACTGCTATCTCACAAACTTTTTAGACACTA
ATTCCTCTTGTATATGGCAGTTGCACACCGCTGTTGCAATTTTATTGACTTAATTAATTAATTC
GTGATTTGAAAGGTCACTTCTTCATCTGTCGAAAGCTTGCCTTGTATGCATCTGCAACACATTT
AGATAACTTAAACAGTAGGCTGAACCCTTTGTATGTGCATGTGGCTCGGTAAGCATCTCTTAG
ATTTGTACTGGTGAAAAGGGCACCTGTGTCTAGAAATAAGTGGCCGTTACTTTTTCTTAACCA
AATAGCCTAAATGTGTTATTCTCTGCAAATGGTAGAACTGAATACTGATGCTCCCTGATTAAC

FIG. 5O

TGTTGCTTGTAATGTCAAGAACATCGCTTGATGACAAGGAGAAATTGATATGTCTCTTTCCTGC
CCTTTCTCTAGGTAATTCATATATAATTGGGGTCTATCAAGTGACCTTGAGAAAGCTTTGCAGG
TATTTGTGATGTCCAGTTATGTATCCATAACTTTATTGTTTTCTAAAAAGTATTTTGGCTGCTAT
GGATGTTTGAACCAGTTCTAGATTACCTGTTCTTTCCTTCACACCTAGTGTTTCCATGAACATA
TTCCATATGATTAATTATAAATCAAAACCAAACAAAGTATTTACTGAAATCTTCACAAAAGAT
ATACTGAGTTGTGGAACACAGTAACTGCATCCTCGCTGTTTCCTTTGCTGTGCAATTTCTGCCT
ATCAGTGTTCATCCTGAAAGATTATATTAGGTTCTCCTTTAATTAATTAATTTTGATTTATTTCT
GTATTTTTTTCCTTCAGAACTAATTCTTGATTTCTTAGCATTAACTCCTATTTTATATTTATTGTC
TAGCTTCTCCTTGTCAATATTGAAACTGTTGTACTCACTATATGTTTCTGTTTCAGTGTCCTAAT
AGTTTATCAGTAAATATACTGACCATTTATTACTGGCTCAATGCTTGGTGTGAGTATCTAAGTT
CTGATGTCTTATGATTGTTGCTTCCACCTAGAGTTTGCAACCATGATATATTATTCCAATTCTG
GACTTCAAGGTAGTCTATGTAAAATGGTAAAAATGCAAAACTTCCTTCATTTGTTCTGTGTTGG
AGTTATCATGAGAAAAATCTACTGATTTGTTTTGTAGCTAATTGGCTATACATAATTGCCTATG
CATATATTCTTGACAAGCATTAAATAAGTCAGTGGGAATTTTATTGGTGTTCCGTGATATCCTT
AATATTTGTTGATATTGAATCCAACTATTGAATACCATGTTGCTTGTTTAAACCACAATTTCAT
GAGAAATCATCTACTGCACAAGTGCACATTCTGCTGCAGCCCAGCTATTGGTCTGTTGACCCC
TTCTGCTTAATTTATGACCTTGGTATTTTCCAAATTTCCAGTAGCTAAACATGTCTGACAGGAG
GAATATAGCTGTTATACTTCTAGATTTTTTTTCTTTCACTATTTTTTGGCAATGGTACTTTGTT
TTATTATCCCCTCTATTTCTTCTTAATTGTTACTAGTATTGTTTATATTTCACTGTCTCGGAGTT
ACAATTTGGACCTTCTCTGCTATAGTTTAACATCAAGGTATATCAATAAAACTATAATATTACA
GCAGTATGTTCAGCAAGGAATCTATTGATATAATATCTATATAGCCAATCTATCTAGTTGTTGA
CATATTAATGGTCAAACTTTGCAGAATTTTATGGCTAGTTCTGACACTGGAAGGAGTATTTATT
GAAAGAGAGAGTTGTAATAGATATTTCAATATTATTATTTGCTTTTGTTCATTGCGTATGTTTC
CTTTCAGCTTTACATTAATAATGACTACACTTGTCTGCTGTAGGAAACTAGTATTTTTACGTGA
AAGATTTGATTTCAAACGCCTTCTGTTGCATGCCATTTCACTTGAAAAATGTGCATTGTGTCTC
AGTGTTGCATGTGTATGTTGCTTTATTTTCATGATGTGAAGCTGTGGATTCATTCTCCTAGCAA
CATGAAACTTGGCCTCTAGACAGTTATGCCATCTAGGATCGAGTCTGTTCTCTGTACAGACTAT
CATATGTTATAGTAATTTGAAATTGTTCAGTTTATCTTGTGATCTTCCTTGTAAATACACTTTAC
TCTTCTCGAATGGGAGTATTTTAAACTATTTCCTGTGGTTCCTGATTTTGAGATGCTTGGTTTCA
GGATGGTGCTGTTCTTAATAGAGTATTCCAACCTTATGAGTCTCACATTCCCTATCTTCTTCAC
TTTTTGGTAAGAGCAACACTTAGTTTCTTTTCATAGTTGTTGTGAACTGCAAGAACAGTATTTC
ATTTTGTCTCTTATGCAGTCTTAACATAATAAATACCACAGTCTAGCTTTTATGATATATAGTA
TATTGATATTTGAGCGGCTGGAGTGCCAGGATATTAATGATTGAATTGAACCTGTGAATGGAG
AAGAACAACCAAATGATCAAATATCTTACCGCAGTTCTGTAAGGCTCGATGAGAGTAGTTCGC
TGAGCAATAATATTCCTCAGCTTGATGGGTCATCTGATGAAAACCAGGAAGTTCCACAAGAAG
ATGGTAAGTATAAAATCAACAGGAAAAGTGCAGGATTGCCTAGTTACTCATCTCCTCAAAGTA
GTTGAACTTCTCTGGTGCTCTTTGCCACCTCCCATTAAAAAGAGGTCAGATGTAAATGTTGATG
GTCATGTTAAAACCTCTCCAGACGGTGCGATGCCAACTGAGAAGGAACCAAGTGTTTCTTTCA
TGAGTAGAACTGGAAAGAACTCCCATGCTACCACAGATAAGACTGGCAGGGAATCTTTTAGT
CGATCAGGTGAACATGACCCATTGTGTGATTCTGTGAGGGTCTGAGAGACTTGATGATGAGGA
GGAGGATATCTTTTCAGTCTGAACAATCAGAAGTTGGCAAGTCTGGAGATGCAATATACATCA
TTTGTAAAGAGAATGAAATTGTGAATTCCGAGGGACTAGAATGGCCTGATTCATCCAGTGGCC
TTTCGAATTCATAAATGTGTTTTTCTGGCAGTGAATATTAGCAGATGACCTTTGCACAGAAGCC
TCCAATGAAGAATGAAGTATTATGTTGTTTGGAGGGCTCTTCAGCAGGTAGTGAGCTGCCTCA
GTTTAAGTTAAAGTGGTATTTATTTATCATGGTCAATGTAAGTTCCACAAGTGATCTTTATTTT
ATCATGGTGAATGCAATTCATTTGATGTATACTGTAGTTGTTGCTCATGTAAATTTTGTAGTAG
TTTTGATGTTGTTGTTAACGATCTAATATATAAATAATTGTATTAGTGCCTACGTATGATTATG
TAACAGATGTTCATTGTTTTCTTTCAGTTTTTCTAGCATTAGGCTTTTAGGTCCTTTGCCATTTA
CATAGCTTAGCATGTATGCAAAAATAGTACTCCCTCCGTTTCACAATGTAAGACTTTCTAGCAT
TGCCCACATATATATAGATGTTAATGAATCTAAACACATTCATTTAGATGCTAATGAATCTAG
ACATATGTATGTGGTTAGATTCATTAACATCTATATATATATATATATGGGCAATGCTAAAAA
GTCTTACATTGTGAAACGGAGAAAGCATTATTTATTTGTTTGTTATCATTTGCCATTTACACAG
CTTATCATTATTTATTATTGTTTTCCCTCTAGAACAGTTTGGACTATCAACCAAATGAAATAGT
ATACCACTATAACTTACTATAAGTACAGTGCTATTCTGTTAAAACTTAATCTTTCTTGAATTTT
CCGGTATCATCATTCACTTCATATCATTTAAAACACATTATATTTTCTCTGTTAATCCACATTCG
CTCTTCTGCTATTTTTCAACTTCTAAACTGGGATTTATCGATATCCCTCTGTTTTTCAATCAGAA

FIG. 5P

TGCTGAAGCGAATAAGCAGAATGAATCATTTCAACACATGGAAAGTAGCGAGTTTTCATTGG
ATACATGGGGTGTTCCAACTCATTTCCAAAATGATTGGTCAGCCCTATATTTGCTAACACATGC
ATTTTTGCCACCCCGTGGGCCAGTGGCTAACCTAACAATCTTGTTCCATTAGTGTCTCCGGTAT
AGATTATTTCCTGCACAGTCAATTTAATGACCATGTATCGATGTTGTCACACACTGTTATCTTA
GGCCATTTCAACTGTAGTGAGAGAGTGTCTGTTGATCAGGAACGAGCAAACAATTCTACTCTT
TCACCATACTAGCAAATTACCCATGCCATGCTATGCCATGGGATAAAAAATGAAACTGCTTTG
CTGTGTTATTACTACGCAGCATTTGGGTGTTTTTCCCCCTTTTTTTTGTTTTTTCCTAATTGGCG
GTTTTCTGGAGAAACTGTTTGGTTTTTTCTAGAGGGGGTGGAGCACAGAATTGGTTGGGTGGA
GAGGAGGAGGACGATGACTCCCTTTTAGTGTAGTAGAGATATGGGAGGTCCTACTTTGATGGA
CGATTCTCTTGCATCCAAATTGGCTTTGGAGCATAGCCCTACAACCTTTCCTAATGGTACAGTT
ATGATGGAACCAGATCTTTCCAACCAAGTAATGAAAAATCTACTCCCTCCGTTTCAAATTATA
AGTCGTTTTGACTTTGGTCAAAGTCAATCTACTTTAAGTTTGACCAAGTTTTAGAAAAAAGGT
AGTAACATTTTCAATCCAAGATAAATATATTATGAAAATGTATTCAATTATCGATTAAATGAA
ACTAATTTTGTGCTGTAAATATTACTATATTTGTCTACAAACTTAATCAAACTTGAATTAGTTT
GACTTTGATCAAAGTCAAAACGACTAATAATCTGAAACGGAAGGAGTAGCTGATTGGCATGA
GTTTTCCCAGATCTTAGGAAGAGATGAGAAGGATAAACTAACACCTCTCAGTCAAATTGGATT
CCGTGGTCCTACTAGCACTGGTAGTGGATTACAATTGACTATAAGTAGCATAGTGGTTGTACC
ACATTCTTTTTTCTTTTGTTCCTGACGTACATATGTTTCTTTTTGTTAATTCTTCATACAATGTAG
GTGCTAATTTACTGTTCGTGGAAAAATCTATGTCTGCAACCAGCAGTTCTTTTTTGTTATTATT
AATCATGTCAGTTTGACTTGCTCTATCCAGTGAAAAGAAAATGCAAAGTTGAATTACCAGTTT
ATCACATGACATTTATTTCATTAATACATGTATTAACAGAAAGCAGAGGAGAGCTGCATCCTG
ATCCACGATTTCGTGTCATCAACGCTGTATCGCTGGCTGTTGAGGATGATGCTGACAACACTA
CTGAAATCATGTGCTTTATACGTGGAAACAATGACAGTTCACACAGGAGGAGGTTGTGTGAA
ATCACTCAAATCTTGGAATTGTTTGTTGTTTTACTTTTCCGTTTCTTCTTGTTTTGGCACTAACC
AGTCATCTTTTCCTTTTTAATCAAAATTCCATTCTGTTTAATTTTGTTTTTCTCAAGCAACATAT
ATCTTAATGAGTCTACAGAATCTCAAGGAATTGAACTGTCCTAATCAGAAGAGTTGTGTGCTT
GTGTTAAATGTGAAATTTAGTACATTAGTATGTGAGTCATAATCCTAGTTCAACAAGAGAAGT
CTGCATGGACATCGAGTGACTATGGTGGTGACTGCTACAGTGCAGTAGCAACTGATGTCATTT
GACGAGAGTACTTTGGATCATTACTTTTATTTATGGGTCTGTTAAGGATTTGATATGGTACCAT
CAAAAACACATTTGTTGCTTCCATGTGATGGGCCTTTCATATGTGCTGAACATATCCTATGCTT
CTGGACTTGAAGAACACCATATAACTTCGGGTTCTTTTATTTAGAATTTGTTGGATCATAAACC
ACAGTTTTACTGTTTTAGAGTTACACTCTCATGTAGCCATAATTGTTTGTTTTCAGCTAAGGAA
CTTGTTTGATTCTTTTTTAAGGGCTGTAAGAGTTCAACCTGTTGTATTGAGATGTCTTTATTGTC
CTTTTTCTTGTAACTGCAGAAACCTGGATAGAGTTGCCGGTTGCGACATAAACGTATTTCCTTG
AGAGACAGAAACTTTTAAACCATCTTATTAATGAAATATGTTCAATCGATCCAGATATTATAG
TTGGATGGGAGATTCAGTTGGGATCTTTAGGATTTTTTGCTGAAGGAGCTGGTATAGGCTTAC
TGAAAAGAATTTCAAGGACACCACCAAATCAGATGAAACATCCACCTATGAACCCAGTGGAG
GAATCTTGTCAGGAGTTTCCTGGAGCATCTTCAGCTGATGATGTTATTGATGATGCTAGTGAG
AGCAATTGGAGTCATACTCATGCTAGTGGTATACATGTTGATGGAAGAATCATTCTGAACTTA
TGGCGTCTCATGCGTGCAGAAATTAAGCTTAATAATTACTCCCTTGAGGCTGTAGCTGATGAA
GTCTTGAGGAAGGTACCATTAGTACCAACCAAGATATTGAATCGATGGTTTGCAACAGGTCCT
GGACGAGGAAGATACCGGTGCATAGAATATGTTAACAATTGATCTTCTCTCAACCTTGAAATA
TTAAATATACTTGACCTGGTAAATGGAATCCCCCACATTTATCGTGCTGGTACATCATCAAGA
TATTGCTATTTGAGATTTCCTTTGTATTTCTAGTTGAAAACTTTTATCAATTTTGCATCTTCTCC
TTAACAATCTCCTAGCCACGATTTATCACACAGAAATGCAGTTGGTTTTGTTGACATTTCTTGC
ACAAGCTACTTCTAAATGTTGTTCTTCTATAGCCATTTTTTTCCGACAAATATTACCTGACCAT
GCAGGTAAAGAGGACATCTGTACTTGCCTGTGTATTTAGTATTGATTTCTTCTCTGTTCTTTCA
CGAAGTTCTCTGTATCGTGTTGAATCTATCTATGCTCTTGAGATTGGCCCATACACAAAACTAC
CTTGCAATTTCCCCAGGAAATTAACAGGTGAAATCACTCCCTAACATATTAAGATCTCTTCAG
ATATATAGTTTCTCGTTCACATTTACCACAAATTCTGGAACATGTCCTAGAGATGATGTTATGG
ATTCTACTGGCAGGTAACAGGCTTGTATTGTATACATGATTTCTTTGTGCCAAAGATGGCCTTT
TGCCCATTTGGTCAGCAGGGATCCAAAAGAAGTTACTACCTCCGTTTTATATTATAAGTCATTT
TGACTTTTTTACTAATCAAACCTTTTAAGTTTGATTAAGTTTATAGAAAAATATAGCAACGTCT
TTAACACAAAACAAGCATGTTATTAAAATGTAATCAATATTATATTCAATAAAACTAAATTGG
TGTTATCGATGTTGCTAAATTTTTATATAAATTTGTTCAAACCTAAAGAAGCTTTACTAAGAAA
AAAAAGTCAAAGTGCAAGGAAAAAAAATATTTAGGACACTTTTCAAGATTTTGATGGGAGTG

FIG. 5Q

CTATTTTAAGCACCATGAAAACTTAACTTTACCTGTGCATAGAAACAAAAAAAAAAAGGGAC
TCCCCCTGCGTCGCTCTCGCGCGGGCGGCTCGGGGGGCGAAAAACCCTAGCCGCCCGCGCCTC
CTCTCAATCCCCTACCTCGCCACTGCTGGAGCTTGTCGGCGCGAAGCCGGTAGCTAGCAGGGA
AGGTGGCAGCGAGGACTTCTCTTCGTGGCGCGAAGTGGACGGACGAAGACGACGAAGCTCC
CCGCCGGCGCGGTCCGAGGAGGCCACGACAGCAAGGTGGGGTGAGGCGGCGGATCCGGCCTT
CCCTCGCCTAGATCTGTGCGGCGGCAGCGGGAGGAGGCTTGGGGCAGCGTGGCGGCGGGCTG
CTGCGGCTCGGCCGGCCTGGCTCGGCAGCTGCGCGGCGGACGGCCACGGCAGGCCACGCGGA
GGCGGCGGACAGCGCAGCCTGCCCAGGGCGGCTCACTCGCTTGCCCTGGCCGCCCAGCGGCA
GCCCAAGACGCAGCGACCGCCCCTTGGGCGCGGTGGGTCTCCTCGGCGTCCAGGCCTCGGTGG
CGGCTCGGCGTGGTGACCGGACAGTCGGGATGCCGCCGCGATGGCCAGGTGAGATGCGGCGG
CCGAAGAACAGGGGCACCGGCGGGTGGCGCCGATCCGGAGCGGCTGCGCCACTAGCGGCCAG
ATGGCAGTGCAAAGGGAGCTGGCAGTGGTGGGTCGTCTTCCTCATTGCCGGTCGGCACCCTCG
CCCTTCCCGGAGCTCCTCCTCTTCTTTGCAGGGAGTTTCTAGGTTGGATTGAGGTGGCCGCTCG
TCAACGGGGGAAGCTCATGCTGCCGAAGCAATGTCACCTAGTCCCGGGTTCTCCTAAAGCCAA
AACTGACGAGGCGGCCGGTGGGTGGTGGAATAGAGGGGTCCTGGGCCAACTCTCAGGGGTGG
TGGTTAGCTGAAGTCGGCCGACGGAGGGGCGTTGGTGCGGTGTGGTGGATGCTATGTACTGCC
ATTTGTCTGTGTGGTAGTTCTGAGTTGGTGGATGGCGATCTGCAGTCAAGGTTATAGGGTACC
AGGCGAAAGCCTAGTTCGGTGGTTCACCGGGCCAGCAGCGGCTACGTCTTCGGGCGTCGTAAC
CTCCTTGGGCGTTGTCAAGGGTTACCATCTTCCTTTCTCGACGAGCTTCTTTAGGTGAAAACTG
TTAGAATAGGTGTCGAATATACTTCCTATTTGGTTACAGTTGGACTTAGAGTTGTAATAGGTGT
TAGGGGATGGAGTTAGAGTCAGACTCTGTAACCCATCATCTCTCTTAAATAGAGAGGGAGGC
ACCACAATGTAACCATGGCGACTGCAATGTAGCGTAGACACGCAGGGAGATGATGACGGCGT
GGCCATGAACTCGTAGCGGCTAGGAGCTATATTGGTTGGGGAGGAGCGCCCATAATCAGAGC
CCCGGGGATGTAGGCTTTGGGTGAACCTCGTTAACAAATATCGTGTGTTCTTGTGTCATCATCT
GGCATGTCTTGGGTGATCAATGACTGAAGCGATCGGGAAGGTTAGTCGTCGTTCCGCTATATC
GACTAACTTTTATAACAAAAACCACATCTTTTTAGATGGGTGATGGCGGCATCCTGTATGTCG
TGACCACCGTGGTGGCATCGTTTTCGGAGCGTCATCTATGTGGTACAAAAACCACATCTTTTTA
GATGGGTGATGGCGGCATCCTGTATGTCGTGACACCGTGGTGGCATCGTTTTCGGAGCGTCAT
CTATGTGGTGTTACCATAAGCCTAGCGGTGTTCGGCCATACTTAGCGGGGGTCGTTTAGTGCT
AGGTTTCACCCTCAGCAGTTTGTGCTTGGGTGTTAGTGCGTGGTGTGTGGCAATGCACCTTGGT
ACATTTTAATGTTTTTTCTTATAACTTTTACTCCTTAATATACTCGGTTAGCCTCCTTCGGTCCT
TCCGGCGAAAAAAAAAACTTTCATGCCGGGCATCATTTTATCCATCTGTCTATCTTCTGGTTTG
TTACTCACATAAAGTTAGAAAATTGGATCTGTTCTTTGCTACAATTTAATTAAATATGAATGCC
TAAAAATATAGATTCCAGTATTTTAAGTGTTCTGTGCAACTTCGCAGGTTGCTTCTCAGCCAGT
CATGGAATGCTTGCCACTATGGAACCAGAGTCAGGTTTCTGCTCTGACCCATTGAATCCTTTTA
TCCCTCCATGATAATAAGCATATACTTGGGTAAAGTTTTTTCCGTCATAGTCAAGGGTACTTGG
TGTCAGCTCATATTCAGCCAGATCCACACGGAAGATTGCTGACTCCAAAATGGTTCCTTTACG
TGCAACCTGAGGTAATGCTTTTCTTGGGTGAGCTAAATTGTTTTCAAACATTACAGTTACTAGA
TAAAACCACGCGCATTGCTACAGGAATTTAAACAATAAAAAAATAACATGTAAGATAGGTAG
ATAACATTATATTAAGTAAATTGATATGGTTTATGATAATTTAAATTTAAATAGTACGTAGAA
TGATGATTCAAATGTAAAAAGTAAGATGATATGATTTTATGGAAGAAAAAAAGTAGGGAGAT
AATTTGAACTGTAGATTAATCTTCTAAGGGCTAAAAACAATTGATGTGATATGACTTAATTAA
AGGGAAAAAGAAGAAAGATAATTTAGACCATAGATTAATCATTTAAGCACTACCTAAGTGAG
GATGAACTATATAAATATATAGGATATCATAAAATATAACAAAGATATACATTGAAACATTAT
GTGAATTATGTTGGATAATAATTTAACATGTTTGTATATGAAAAGCTCCTAATTTATAAAACTA
TAAAGATATAGCATGTTTGCATGATGTTTAAATGTGATGATTATTAGTGGATGATGATGTGGC
ATCTTGTTAATTAGTATATGAAGATGTGACATCTTGTTAGTGGATGATGATGTGTCATCTTTGC
ATGTTTAGGTTAAGGAGTTTGTTAGAGGAAAAAAAGGAGAAAGATAATTTGGACCATAGATT
AATCATTTAAGCACTAAGTGAGGATGAACTATATAAGTATGTAGGATATCATAAAACATAAA
GATATACATTGAAACATTATATAAATTATGCGGAATGATAATTTAACATGCTTGTATTTTAAA
AGCTCTTAAATTATAAAAACTATAAAATTATAGGTAATATAACATGTTTGCATGATGTTTAAA
TGTGATAATTAGTGGATGATGATGTGGCATCTTTGCATGTTAAATTTAAGGAGTTAGTGGGGG
ATAACTTTATAGTAAGATACTAGGTTAGGATTACATGGTTTTTTATTTACTTTGTTATAGGGCA
TGCCTAGCATCATATCTGTAGACTGTAGCTCATATTCAGCGGTGGGTGAAGTGACCGAAAATC
TTGGGAAAAAGTACATTGAAGGTCCCTCAACTTGTCATCGAGTTACAAAATCGTCCCCCAACC
ACATTTATTTGATCATTTGATTTGATGTCGATTCTTCTCCACTTTATGGTTATTCTCTGCAAAAG

FIG. 5R

ATTAGTAATCCTAATACTAGTGAAAAGTTATTATTCTAACTTAAATATGCATTGCAAGTATAA
CTAGTTTTCCTCTATTTTGGTAATATTAACGGTCGAAACTGATTGCGAACGATCGTCAATAAGG
TCGAACACCCGAGCGGTGGAGTGGCCGTTGCCGGAGGTGCGAGCGGAGTCGGCAACTTGACC
CAATGGCTCGTCTTGTGGCCGCCGAGCGCTTGGTAGAAGCTAAAGGACTTGCCGTATACGGAG
CACTTGAACTCCGCACCTACCGGTGCTGGCCCCGTCGTCGAGAGAGGAGGCGGCGCCTGGAC
ACGGTGGTGGCCCCCGCGGGCGAGCATGAGGAGGCAGAGCGCGAGGTTCTCCTCCGATCGCT
GGCGGCGCGACCTCTTCCGCTTCACCCACCCCTGCGGCAGGTGCCCGCCCTCCTCCCCGCTTGT
GGCGCTGCTGCTTGTCACGACCGCTGCCTCCTCCATCTCGTGCTGCTGCTCCTCCTCCTTAAGC
ACCGCGGCGTGGAGCGCTTCCGTCTCGCCATTCGCGACAGGCCGCCGCCGTCGCCTCCTCCTC
TCCTGCCTCGCCTCGATGGCCTCCGCCCCAGCTGCCGCCCGACTTGCCGAGAAGAGTGAGAGA
GAGAGGAGGAAGAGAGAGGGTGCTGACGTGGCCACGCGGACCTACGTGGGTCCCACGCTGAC
TCAGCCATCACATAGGACGAAACCGGGTTCGAAACCATCAAAGAACATAAAGTGAATGGTTT
TTGTAAGTTGAGGGATGGCTCTATATCTGGTTTTGTGGTTGGATGATGATTTGTAACTCAGAT
GACAAGTTGAGGTGCCTTCGGTGTACCTTTTCCAAAATCTTGTGCTAGTAAATGGGCCAAAAG
GGTATTCGTAACAGGACGGCCCGGCCCATATGCAGGAAGAGGAATCGTCTTGATGTCTCCTCA
GTCCTCAACCTAAGGATACATTTCCCCGTCTCCTCGAGACCTTCGACTGCGGCCCCAAGCGCC
GCCGATCCCCATCCCATCCCATCCATCCCGCCTTCGCCGCGCCGGAGGCCGCTGGTGTTCGTCC
ACCTATTCCCGCCGTATCGCATCCATTTCTGGTGAGCGTCCAATCCTCTTTCTCATCTCTATTTC
TCTCTCACACGCACATTTGCTCGCGTTAACCCTTGTTTCTCTCTTCTAGTAGAGCATTGCCTGTG
GGGGACAAAAGTTTCTTTTTTGTTTAAGGTATTCGGAATCAAATCAGTCTCCGGTTCGTAAAC
GGATTAGCGGTGCGTATTCCGATTCGATTCCGATTCTTAGACGGAGTTTTTTTAGTTTAGGCTT
TATATATCCAGCAAATTGGATGTAGGCTTTCCCCAGCTCATGTTAAACCTTGAGGTTGTCGCTG
TGCAGATACAAAAAGAGTGAAGGGAGGGAGGGGCAGATCCAGATCGAGAGGAAGCAAATGT
CATCAGAAATAATAATGTCGTCCAAGAGGCTATGCAGAGAGTCAGATGACGAAGACGAACGC
CATTGCAGCAGCAGCACGAACACGAAGAAGAGGGCGTGCAGAGAGTCAGAGGAGGAAGACG
AACGCCATTGCAGCAGCAACAGCAGTACGAAGAAGAAGAGCCTGAAGCTGGGTTTGGTTCCC
TTCAGCTCTCACAACCACAACCACAAGCAGCGGCACCTGTACCTGGTGCTGGACGACTGGGA
GGCAGGATACAGCATCCACAAGGTTGTCGACGACGACTTCGGCGCCCGCCCTGCCGCCGCCG
CCGCCAAGCACAACCCGCTCATCCGCATCCAGGCGCAGCACGCCTACTCAAGGTTCTTCGCTG
CCCACGGCACCAAGATCATTGCCATGCATCCCGCCAGCTTCAGCCCTGGCATCCCTGTGTTCG
ACACCCGGACCCTCGAGATGGCGGTGTACCCTCCCCCTAAGAGCAGATCCATCATCTGTCCAC
CCGTGTATGCCTCCGTCGGCGACAGGCTCGTCACATTCGTCCACCAATATCTCGAGGTGCTGG
GGCCCCATCCACCACGCTCCGCCGCCGTCGACGACGACGATGAGCCAGAGCCGCCACCGTGG
TCCTGGACCACCGTGGAGCCACTCCCGCAATTCCACTCCGGCCTCGTCACCGGCTACGCCTTG
CACCCGGATGGGCGCACCATCTTCATTTCCATCGAGGATTGCGTTACGTTTGGCACGCGTAAA
TCCACCTTCAGCTTCGACGCGGGGCGCCTCGAGTGGACCCGCGTCGGCGACTGGATGCTGCCG
TTCGAGGGCCAAGCTCACTACGACCGTGAGCTGGACGCCTGGGTCGGGATCTGCCGCTACGGT
GAAGGAACCGGGCATCTCTGTTGCTGCGACGTCCCTCCTTCGCCCGCCGCCGATGCTGCTTGT
ACCACCACCTTGCCTGCCTGGAAGTTTTGCAAGGAGGTGATGTTCAAGAAGGGCTTCACCGGG
TACTGGGGGGCTACGCTCGTGTACATGGGCGACAGCAGGTTCTGCCTGGTGGATTGCCGGGTG
CCTGATGACTGTGACGTCCGCACCACCCTCCGTGTGCTCACCATCACCTCCTTTGGTCTCAAGT
ATGATAAGGCCGGTGAACTGGTCACCACTCGGTACCGTGCTTACGCATCGATCTCATACCAGA
TTGCTGGCAAATTTAAGAGACTCGAGGATCCTATAGCATTCTGGATGTAATTTATTTATGATCA
TGCAAAACTAGTTAGTAGTATCAGGTGTTATTGTCCTACTCAGTTTTATTATATATATATGTGA
GCATGCAATTTTGGCATAACCTGTTTTATATATGGTCGCCTTGTCAATTTGGTCCATCTTTGTC
AGCACTGTGTTTTGCTGTAAACTGCTTTTCCCTCTTGTAGCACAATGCTTAAAAAACTGGGGGA
AATGAATCCCTATAACTTTACAAAGTGAGTTATGTCTGATGCCTAATCAGTACATTTTGCCCAA
GCTTGGCTTTGATTGTGTGATGTTGCTCCCTTTGGTACACAATTTATTTGCTGAATAAGCTGGG
TTTTTGTACAGCATGTTTTTGTACCAGTGCGTAGTTTTGTGTTTATCTCATAAGTTTCTGCTCCG
AGTACATTATTGAAATTTTAGACTTGAATCAAAATTCGTATTAATGATTTTTTTTTCTTCACTA
CAAATTATGACGAAATGTCACATCCTCAAAATTAACCCTAAAATTTTTTTGACTGCATTATGA
AGGAATTTTAGTTGAATTTTGAAAAGCTTAGGAACATATATAATGACTTAACTACAATTTTATT
TCTTTGAGTTTTATTCTTTAACTAATTCTAATTTTGGTACAAATCAATCCAAAGCTATATCCTAC
ACTTATTATTTGCTCAGACACCAAAGTGAACTCATTTTCTTCTTCAATATAATTCTTCCTCTAG
GTTATATCCATTTAAATTTAAATCTATTTCAAATTTCAAACCAGAGAAAATTTCCTTGAGATTC
CTACAATAGTAGATATCTCTATTCTTGAACACTTGTCATTTTAACGCCCACTATTCTCTCTATTT

FIG. 5S

AGGCCCCATTTGGTATGGCTCCAAACTCCAACTCTCAACTCTAAACTTCAACTTCAGTGAGAG
CTAGCTCCTATAGAAACTGAAGTGGGTATGAAAGTGTTTGGCTAGATTGGTTAGCTCCACGCC
ACCACGTACCTAGTTGGCATCTCATCGAACACCTGGTTGGCATTGCCCTACCATCGCCGCCGC
CACTGCCACACGCGCATCGTCCTTGGTTGTCGCCGTTGCCGACTCTGCGCCTGCGCCCGCGCA
CCGCCGACCCCGTGCCTCCCGCACACCACCAACCCCGCGCCTCCCGCGCACCACCTGCCGCCG
CCGCCGCCCGTACCCCTTGTGCGCCGCGCCGCGCAACCCACCCGCCGCAACCGACGCCCGTCA
CCACCGCCCGTCGCCGCTGCCACCAGCGATTGCTGCTGTAAAGGAGGAAGATGGGAAGGAGA
GAGAACGGGAGGAGAGGGGGTGTGAAAGGGACAGTTTAGTGGCATATCGTGTAAATATATGA
AAAATTTAAAGGGTAGTGGGCCTTTTGGGGTGGAGTGGAGCTGTGGAGCAGCAAAAACCTAG
CTCTACCCTCATAGTACAAACTTGTAGAGCAACTCTGCTAATTCCGCTCCAAAAAATAGCGAA
TCTACACCGTTTGGCGCAGCTCCAGCTCTAGGTAAGTTAGAGTTGGGAGCTAGAGCTGTGCCA
AACGGGGCCTTAAATCCTTCAATTGCTGGAAAAATTTGAAGGTTACTGTTCATAGCACAGAAG
ATGTTTGACGAAATGCACCCACCAATCCATTTTGGCCCATCTTCTAGAAACCTTGTCTTTGATT
CTCTATAAGCCCAACCCAACCGAAGTATGCCCCTAGCAGCCCCAACATGACACCGCTGAACA
AGTGGGTGTGCCAGCGCGGTCGGCTTCACCGGATGTGTTTGGTTTGTGGTCAAAATTGAATAG
AATATGATCATTTATATTTGTGGAAAAATGGTGGCCTGTGTTTTTTTTGGTTGGATGCATATGA
TCATCTAATTATTTGTTTGGTTGCATGAATGAAAAGAAATAAAATGAAAAGATAATATATTGA
GTAATGATAAAATATGTTATTTATCATTAATATAGCTATAATCTATACTAATTAAAAACAATAT
AGATTACTTATATCTAATCAACACTAATTTTGATAAGTTGATTGTACTAATTAACAATAAAATA
CATTAATGATGGATAATCAATTACTAATGATTGAGATTAGCAAATGTGGATATACTCATCTAG
GATCTTTGTGAAATATTCCTTTCCAGACCACTCTAACCTTTGTCTACCAACCAAACAGACTAAA
ACTGAATCATCATCTCCTATTCGACATATCCTTCCAAGCAAACACACCGCAAGTCACACATGC
CGTCATGTGGCCTCCATGCCATGAAATAGGGAAAATCTCTCACATAGTCTCTTATTGGGGCAA
CCACGTTAACGAGAATCCACCCTACCATCGCACATGTGTCACCCTCCATGCTACCGAAGCCTA
GTGCTAGGGTTCACAATTAAGTGGAATCTGGTTCGGATTTCGCATATTCTGGATATTTGGATTT
CAGTTTTCCGGATTCAAACTTAATTTTAAAATTTTTACAAAATTTATCTAGATTTCATCGAGTT
TTGTTAGTTTTTAATGGATTTCACGAAATCCAATGAGACAAGGAAGTATAAAGAGCTAATACA
CATATATGTCCAAATTCATAGTAGTAACATGTCTAATATAGTGATATAGTATTAGATTGCTATA
TTTTGGTCAGAAGGACTACTCCTTCCGGGTTAATAATATTTATCGTTTTGGACAAGGGCACGGT
CTCCAAAAAACAACTTTGACCATTATTTTTCATTATAATATGTATAAAAATATTAATAAATATA
TGATTTTATTAAAGTACTTTTTAAGACTAATTTATACATGTAGTCACCATATTTAAAAGACAAA
TATTTTAAAAATAATTCATAATCAAAGATTCTAAAGTTTGATCTCACCCTTGTTTAAAACAAAG
TATTATGAGCCCGGAGGGAGTATTACTTTTAGGGTATATTTTAGGGAAATTCTGTTTTGAAAC
GAATGAGTAGCGGCGCATGCTTAATATTCACATTCTCACTATTACATCATTCGGCCCCAAAAA
AGTTATTTTCTCCATTCCATAAGATAAGACACAGTTTCATGATATAATGCATGCATGAATTCAT
GCCATTAACTAACACTTATTTTTCTCTAAATTATTTTTTTAGGCCTTCATTCTCAATCTCTTTAA
TTCTATTGGGTGCATGTATATGAGGTGATAATAACTATTTCTTGGTATTTAGGTTGAGGGTAAT
TGAGCCTTATATTTTGAAACGGAGAAAGTAATATAGTATGAGACGTGACATATTTTAGTATTA
CGAATTTTAATGTCAAATTTAGATTACAGTAGTCCTAAAATATATTATATCTTATACTAAATTA
ACTGTTAATTGCGAGGAAGAAAGTATTTCATAGCCTCATAGGTGTATTTAGACCATCCATTTG
CACCTTCCACTTGCCGGTAAACTGACACGGTAATAATGAGAGTTAGGGTTTACATTATCGGTT
GACCACTAAATTTCGAGCTTCATCGATATCACGGTTTTCGATAAATTTCGATCGTTTTTTTGAT
AAATTTCGACCAAATCTACTGTTTAACCTTCGAAATTCTAATCGAAACTTAATTCCGAGCCATG
TCGAAACATCGAAATTTCGTGGAATTCCACCGGTTTTTATCGGAGCTGTGAACTGTATTAGGG
TGTGTTTGGATGGTGGTCAAGGATGGATAGAATATGGCCATCCATATTTTCAGGGATATGGCC
ATCCAATTTTTTGTTTGGTTCGACGGATAGGATGAGCCAAGTTTATGTTTGGTTGGAAGGAAA
AGAGGTGGATATGGTGAGCCAATTTTTTGTTTGGTAGGATGGATGGGTGTTGTGATCACCTTTT
GGATGAAATGGTGAGAATACCTCCTTCTCCTTATAGATGGCCTAACTATCTTTTTTTTGTCTGA
TTTTACAATATAATGTAAGCAAATAAGTTGTATTAATGTTATAGAGCAGATTTTCATCGGACA
ATTCAAAGACAAGCACCTGTACTACATATCCGATGTTGCAATGCACTCCTCTCTGTGAATGAC
ATTTTGTGCCATTTCTAGTTATTTTTGGAAGTTTCGTTATCAGCACCTGTTTCATCTCATAGCTT
AATCATTTTACTGGTTTTCAAGTTGAATGAAAAATCCTGCGGAAAGTTCTGATGGAACTCTTTT
CAGGTTGTTGAGGTACTACACAGGCAGCACAGCTATACTTGTGTTTCAACAAACTGAACTGAC
GAATCTGAATCTAAATCCACAAACCAATGAGTTTTGCTGTTGTGTCTCTGTGCATTGCTTGGTT
GACCATCAAGAAGAACATCAAATACCATTTGCCGCTCCTGAACTGCCGGACACCGCCTACCGC
CGCCGCCACTGCAAGCCGCCGCTGAACGCCGCCCACCGCCTCCACCTGTGTGTCTGCCGCTCC

FIG. 5T

CCTGCGCCTCCTCCCACGACCCTGCGCCTCCTCCCACGCAGCCCTTCGTGCCGGTGCTTGAGAC
CGTTGGTGCCTCCGGCTGCGCCACCAGGGGAGACGAAGGGGAAATGAAGGGAGAAAAGCTA
GGGTTCAGACTTGAGAGCTCCAGAGACTCAGACCGGTGAGAAAGAAAGAAAAGAAGAGGAG
AGGAAGAGAAAACGAGGGGGAAGGAGGAGCGAATGCCACTTTTTTCTTTCACGTGCGCTCGC
CCGTCCCTGGATCGCCCCGTCCGCCCCATTCGGCTGGATGCATCTGTCCGGTATTTACTGCGAA
TATTCCTTAGGGGGTGGCTATATCCCATACTAGCCCAGCAACCAAACACCTAAAAAAATCTGG
CGGCCATCTCCTATCCAAGCAAAACCCACCATCCAAACACATCCTCAATGACTAGAGTTCAAC
GTGAGCTTCTAAAGAAAAGAGAGAAGTTCAACGTGAGCTGCTCCTGTTCACGGGTCCCACGCC
CCCACGTCATCACGCGGGCAGGATAAAAAAAACCGACAGCGAAAGTGCGCGATGACGTCACG
ACAGCGACGCACCACGCATGCTCATCCCCCTACAGTCCCCTCGGCCCACTCATCCCGGCCCAA
ATAAAAAGCCCATCCGCCGCCTCGCTGTACAGTACCGCGGGGCCCACGCCCCGCACTACGCAC
GGATCCCGCCGCGCGTCCGACTCAGCGCCCACGCCACGTCCGCACCCACCGCATCTCCACCCA
CACCCACTGACCTATGGGCCCCACCACCCCACCCCACCCACCGGGCAACACCTGTACCCGCAC
CGAACAGCGTACTAGTGTACTACTACTACTTGGACCCATCAGACCGACACGTGGGCCCCACAG
CAACCGCGCCGTCCACGTGTCACCCTACATGCGCGACGGACCAATGGAAGGGCGCCACGTGG
GAGTGTGAACCGTTAGGCGTACACGGCGGTGTGTACACGAGGGGGAGGAGGGGGGTCACCGA
TTCACCAAACCCTAGGGCCTCCTTTTTTTTTTTTTTTCGCTGCTTCGCTTTTTTGCTGCTGCT
GCTGCTGCTGCTTCGTCGCACCGCCCCGGTAGCCTCACCGCCGGCGAACGCGCAGCGCGCGAC
CACCGTTGCTTGGAGCTAGCTCGCGGGGATCTGCAGATCTCGCCCATGGCGTCCTCGTCGGAC
GAGCAGCCGAAGCCGCCGGAGCCGCCCGCGGCGGCGGCGGTGGCGGGGACGGCCGTGGCCA
CCGCCGCCGCGGCGGTGCCGACGCACGCCGAGTGGGCGGCTTCGCTGCAGGCGTACTACGCC
GCCGCGGGGCACCCCTACGCGTGGCCCGCGCAGGTAGGATTCCGCGGAATTCCGGGTTGGGG
TGGGGGGGGGGGGAAGGTTTGGTGGTTGGTTTTCGGGTTCTGACTAGGGTTTGGTTTTGCTTCT
CTCGGATGCAGCATCTGATGGCGGCGGCGGCTGCGGGGGCGCCGTACGGCGCGCCGGTGCCG
TTCCCGATGTACCACCCGGGCGCCGCCGCGGCGTACTACGCGCACGCGTCCATGGCCGCGGTG
AGACCCTCTCGCCTCTGCTCGTTTTGATTGCCAATTGGGCTTGGATTTGGGTCTGAAATCGTTG
CTCCTGCGTAGGGTGTTCCTTACCCGACAGCTGAAGCCATGGCGGCGGCGGCGGCGGCGGCG
GCGGGGGCGGTGCCGGAAGGGAAGGGGAAGGGGAAGGGCGCCGCCGCGTCGCCTGAGAAGG
GAAGCTCCGCGGCGCCCTCTGGGGATGATGCATCCCGGAGGTACAGTTTCGTGTCCCTGCACT
TCATCGAGTGTATTTTTGGTCTCCTTTTTTTCTCTTTTATGTTTGAATTTAAGTTTTGAGTTTTGT
TGCGTGCGCAGTGGTGACAGTGGCAGCGAGGAGTCGTCTGATACTAGAGATGATGACACTGA
CCACAAGGTACCAAAGCAACCTGGTTTGACGCGAAGGGCCGTTTAAAATTTGGCTTTGCTTTA
CTGTAATAACTATGCTGATGGCCTTGTGTGGTTGAAATTTGATTTCTTCAGGATTCGTCTGCAC
CTAAGAAAAGGAAATCTGGTAATACATCGGCAGAAGGTGGGTTGTTGGAATGCTTAACTATG
TGTTTTTTTGGACTGAGTTGTTTTTATTTTTGAGGGGAATGTGTGGATGATTAGAGACTGGTGT
TTGCCAGGTGAGCCGTCTCAAGCTACGCTTGTGCCCTATGCTGCTGTCGAGTCACCGTATCCGT
TGAAGGGGAGGTCTGCGTCGAAGCTTCCAGTTTCTGCACCAGGGCGGGCGGCACTTCCTAATG
CCACACCTAATTTGAACATAGGGATAGATCTTTGGAGTACTCCCCCAGCCTTAGCTGTGCCCG
CAGGGCAGGGGGAAGCAAGTCCTGGGTTGGCACTTGCTCGACGTGATGGTGTTGCTCACCTGG
TATGTATGGCGTCATGAGAGAGATTTTTTACAGTGTGTCTTAGCCTATGTGGAATGTCTCATGA
ATGACTGATGACATGAGCTTTTGTCTTCTTACACATAATTATCATATTTATGGCTATATCGTTA
TTCGTCTAAATCCACCTTTTGGTATATTCTTACCTTTTCAGGATGAGCGTGAATTGAAGAGGGA
GAGGCGCAAACAATCTAACAGAGAGTCTGCCAGGAGATCAAGGTTGCGCAAGCAGGTATTTC
TGGAACATTACATTCTTATTTCCTGCGAAATGTCACATTGAGAAATAAACCATGCCTGGTTTTA
ATTTGGTGATTCTGCTCGCATTATTGTAGTACTAGTGAACCTGGTAAGATCTGCTTTGATGACC
CTACAAAACAAGACAAGTGGACAACACAAATCATATGGCAGTTATGAGCCAATTTAGGCAGA
AATTGATGTGCACATGTTACTTTCCTATTGGTATCACATCGGTTACTAAACGATATTTCAAATG
AAGCATCTTTGGTTAGTTGATGTTAACATAGTTAAAACAAAACTAACTTAGTAATGCGGTACC
TAGCTGGAGTTGTTTGTTTGAAGCGATGCTACTAAAGTCCATCGGTTTTATCAAAGACCCTACC
ATGTTTGTTTTTATTGGTTTTGCAAATTACACATCACCATACGTAGAGCAACATACTGAAGTAT
GATAAACTGATACTAGAAACAATAACTGCTGTTTCATTTTTCTCATTTATACGTGAGTCAGTAG
TATTGATTTCAGTAACATTTAGAATTTGCCACATGACTCCTCACATGATACGGACATATGGCTT
ATTAGGTTTTGTATCGTTTCATTATGCTCAGTATTTTCTAGAACCAGTTTCGACGTACTGCCTTC
TGAATTCAGTAAGCTGCATGACGCAAAAGAAAAAAAAACATTTGGTTCAACATTCACTTAAA
AGAATGCATAAAAAGTCGCAAGGAAGATCAGAAAGACATGGGATATATTCATTGTTTAAGAT
CACTGTCAAAGAAGAGATCTAATACATCTAATTTCAGTAGGTTGGATACCTCTATGGGTCTGG

FIG. 5U

CAGTAGATGGCAGACCTGGAAAGAAACACTTATTCTGCTTGGTGCTGCCATATTTCTGGCAGG
AGGAATAGAGTGCATGCTAGATGCCGGGAGAGGCATTTGGTATGATGTCAGCACTTCACCAG
ATGTTGGCTTGTCTGCACACGGGCAATATGCACAACAAGCCATGCTCCAAGAAACTGACAAA
CAGCATGCTCCCAGGCCTTAACGGATCTTGTACTTAAAAGTCTTAGGTCCCAAATAAAAATGC
AACATCTATAACATATGATTGGTACTTTCCTTTTCCAATATGGTCCGTTAGGACTTAGGAGCTG
ATGTGAAATAACTGACACAAACCCTTTTACCAAACTGAGCATGCAAACACCAAGTAATAGTAT
TGGAACCGGAGAATAATGGACCTCTAGTACAGAAAACTGTTTGCTATAGAACCAAATTTTCCT
TGCCTACAATGAATTTGTTGCCAGTGCTGATGTCCAATTGAAATGGCCACGCTGAAACATATC
CTTTATTTCGTAAACATGGCCAGCTGGTGGTTGATGCTTTGCCTCTGGCCATCTTATAAAAATC
GAAGGTACCAAATGCCTATCTGTAGTTGTGAGATGGCATTTGTTAGTTTTCTTGTCAAAAATCA
AATATCATCAGAACAAAAATTTTTCTTCTGGCAACCACACCAGCTAGTTGACATTTATTTTTTA
GCCAACCATGTGAGCATATATCTCAAGTTCCATTAGGCGGCATGAAAAGTTTATTTCGTGGTT
TCCTTACTTTCCATTTTTTTTCTGATGGGGTGTGGATCTAACCAACGGATGGCTACCTGAAATG
TATAGAAGATGCAAGAAAAAATGTAGATGCTAAAATTACAATGTCTATGACTTGAGTTTACAA
CATCTGGTTTTGTAAACAAATTGACCTGTCCATCTTGTCAGCTACTTGGCTCTTGAGCTCCCTA
GCTTTTTTATTCGGTATTTTCAACAGGAGATTTTAATGTTAGAACATTTGTTTCACGTCTGACA
CATTTCAATCTACCACTGTTTATCAGCAAGAGTGTGAGGAACTAGCTCGGAAGGTTGCTGAAC
TGACAACTGAGAACAGTGCCCTTCGGTCAGAGCTTGATCAGCTTAAGAAGGCCTGTGAGGAT
ATGGAAGCAGAGAATACACGACTGATGGTGAGCACATGGCACTCCACCCATACTTTGCCATTA
GTTGAGACAGGAAATGCTACTTCTTTCCACATTACCCAATTCTTATGGATAATTTTAAACTTTA
TGAAGGGTGATAAGGCTCAATACAAGGGACCAACTGTGACAACCACTCTGGGTATGAGCATC
GACTCATCGAAGACGCAACACCATGACGACGAGGGCCAGCTTCACAAGAACACTAATAATAA
CAGCAACGGGAACTATGTAGGTGGCAGCCACAAACCAGAGGCTAACTCTAGGTGAGAGAGAA
TCATGAGGAAGTGACGACAAAGATGAGATGAGGTGTTCTTCTTATCTAACCACAACACCCATC
ATCAAACCAGTGTGTGTTCTTTTTTAGCAAAAAGCTGTTGTTTTAGTTCTTCTCACAACTCACC
GGGGCCCTGTAGAGCTGCCCCCAAATCGCAGCCATATGTATTATTTATGGCTCGTTGCCGAGA
AGAAATGAGTTTGTGTTTTGTGTTTGTGTGGTGTGTGTTTTGTAAACCGATTGATGTAGCTATT
GTAACAAACCTAGCGCTTAGAATTTTTATGTTTGCTAACATTTGATGAGGGAATGTAACCGGC
CAATTCGGTGGCCTGATCGGTTTTATGATGAAATGCGTAACAAATAGCATTTATATTTTCTATG
TCTGGTTGCTGGCATGATTATGGAGGATCTTATGCTCAGGAGGTGGTCGGATTGAATGTCTTG
TATCGCTCCTTAATTTTCTTGCCCAATGTCACTCTGTATACATGGTATGGTAAGAACAGTGAGA
TACTACTATTTTTCAAACTGAGACAGTGAGATAATATCAGTGGCTGGATGATTTTTTGCCATAT
ACTCCATCTTGTCGTAAATATTTGACCAATAGTTTTTCAAACTTTTGAACTTTGACTACCAATT
AGGGAGTAACTTCATAAAATCGTAAATACACCCACCTCGTTTTCACTTCTGAAGTACTTAGTTT
AAAACATACTATCGGTAGATTGGCCTTGATATATCATATACTACAAACTTCATGCATTTTATGT
TCCTACTTATTCACCCCTCTCTTATATTATACTCCTGACCATGCAACCGCCTTTTGGTGCTAGCT
CGGGAAGATGGGGGTGCGGTGGAGGATGAGCGGTGGCGGCGCAATAGGTATGAGAGGGAAG
GAGGGTGATGGCATTAAAGCTGGCATGAGGTGCGAATGGCCGGGCCGGCGCCCGTGTGAGAA
GAGCAAAGGGGAATGGGGACAAGGGGATGTTCGGAGGTGGAAGGATATTTTGTGAAAGCAC
CCGAAAATTATTAGGGTTAATTAGATTCATGCCATTATAAATTCTTAGTTTTGAAATATGCCAT
TACTATTTATCAATTCGTAGTAATGCTATTACAACTTTTCAAGTATTGGAAATATACCATGAAG
CACCCTTTCAAGGCATATATCAAAATTTTGAGACCAAATTGCCCCCATCTTCTTCCTTTCTCCT
CTCAGCTCTCTTTTGTTCATCTTCTCTCTTTCTTCCAACTCCTAGATCTGGGTCTTCCCATCTCCT
CTCTCCCATTTTTCAGTGAATCTCAGCCACGATGAACCTCGAATCCCAATGAGGTGGAGATGG
TCGGACCAGTACCACAGCTCGACTCGAGCTCGACCACAGCAGCAAGAGGTCTCTTGAGGTGA
CAACTAAGGGAAGCGGAGGCCGCAGCGACGGCAACGGCCGGGGAGGCACTTGAAGGACTGC
ACGCGCGAAGATGGCCTCCACGGAGAGGGAACGGGGTCGCGGTTGTCACGCGGGGCCAGGCG
CTGCAGTAGCCGGGGTACGCGCGTGGGGTTGAGATGAAGTGCAGGAGGACGGAGTGGCTGCT
GCTCGAATCATCCACGGCCACCGCGCCATACAGGTTGTTGTCATCCCAGCCGTCGTGGGAAAT
TGGGAGTCTCAAGAAAGACCATGTTGTGTAGCTCAACAATGCTGGGAAGCGTGGGCATGACG
ACGGATTTAGAAGGGGAGGAAAGAGGAAGAAGATGAACAGAAGAAAGCTGAGGGAAGAAA
GGAAGAAGATGAGGGCAATTTAGTCTCAAAATTTTGATAAATGCATTGAAAGGGTGTATAGC
GGCATATTTCCGATATCTGGTATAGTTATGAATTGATGAATAACAGTGGCATATTTCAAAACT
AGAAAATTTATAATGGCATGGATCCAATTAACCCAAATTATAATGTCTAGAGCGATACCTTTA
GAAGCATATTTTTTTTCTATCTTCATGTTGTATCTTGTGTAGACGAGGTTATCTTTTTTTAAGAA
AAAAACACATAGGGATATCAAACGATGCGAGGGCCTATGCGAGATACATACATATACGAGTT

FIG. 5V

TCTTTTCAAAGCAGCCGGCCACGTGACAATTTCTCCGAGGAGCCAAAAACAATTGCGAAAAAT
GAAAAAAAGAACATAGTGGCAAGGGGTTTTACTAAAGGAGGATATACTCTACACTCTCTGCT
AATGAACTATGGTACTCCATTCTTATTTAGTTCATGATATTTATGATAATATTTTGGCCGAAC
TTTTAAAATTTGGACAATCAATTATCTATTAAAACAAGTTTATAAAATCTAATAGTTTACGGTA
GCAAGATGATATTTTTAAGATGAATCTACACATGCCATTTATATTGTTTTAAAATTAAGCATAT
GAGAAAAAACTGATGGTTCATTTTGACGAAATCTTTTCTAATCATCGTATATTAAAACAAGGA
GGGACCAGTATTTTTTAATCCATTTCTTAGCACTTATCCTAGGTGCTAATGATCACAATTTCGC
TTCATATGATAGCGTCGACTACAATAAAAACAAAACAGATTGCTCACCATCAGATGCTAAACT
TGGCATGGATGATTGGATGCTAAGCATTTTAGCTTTAGCATCTGACCCGTCCTAGTTCTTTCTC
TCCCTCTAACATTCTTGGCAACTCATTATCTAAAAAAACATTCTTGGCAACTAAATAAGTAAA
TATGCACAATTGCACATCCTCTTAGAGTGAGAACTAAAATTGTGGCCTTGTGGATTTCACCCA
CTAGTATTTAAATTCTGGTGTTGCAACTACAAGCATGCATGGTCAAGACTTTTATATATAGAGT
ACGTGCGTGATGTACTTTATATAGTTGAAATGTTGATGGAGGTTATATTTGTTATGATTTTTTT
TCCTTAATTAAAATTTGAGTTTGATAAAATCATTCAGATTTTTTGATGGAACCAAATATATCCA
CATCGGTGTTTGGAATTCATGAAACTCGGACCGGGTTCCAACAGAAATGTAACCTTGAGCACA
GGTATAAAATCTGGCTCAAATGCAATTAGCGTAAGCTAAGCATTTGAGAAATTATTGATGCCG
AAAGTTTTAAAAGTATTAACCAAATTTGTAAACATCAAATAATATTTATGATGAGGGAAGGGG
GGAGGGGGTAGGGTTGTCAACGAGAATGAATGCAAGGCAACCCCTTCCTCTTCACGGCATCC
AATCCTGGTAACGCATTCTGTCTTTAGGTCAACCAAAATGGCCTCGTTAGATGAAAATGGGGG
CTACCGCTAGGAAACGAATTCTTATCCTCGATGGGATTTACCCTCATGTACATTTTTCTACCAA
ATTTAATAAAAAAAAGTTGTTCCAAAAACTGAAAGAAATTAACAATGTGTAGAGTACAGTGA
CACCTATCACTTCACCAAAAATCTAAGTTTAAATTTGGCCTACACATTGAGAAAAAGAAAACA
AAATCAGGTATTGATAGCATCACCACTATTAATACCTTAAATTTGTCTTTTTTATATCTTAATG
TGTGAGTTGAGTTTAGACCTACGATTTTGTGGACTGGAATATGTTTGTTGTATAAATGCTGTCA
AACTTTTTGAGAAGTTTTCATAACTATTTGGATGATTTTTAAAAAACAAAGGGACATTCTTTCA
AGGGATCAAAAACAGTTTCCCTACTGTCGGCTCTCCCTCTCAATGCTAGATCCGAAAGAAATG
GTGGAGGATAAAAAAAACCACTACTTCCTCCATCCACAAAAGTTAAACATATTTCACATTTGA
GTTTTTCCAAATAAGTTGTTCCTATTTGTAGTTTTTATGCATCCAAGACTTAAATGAAGAGATA
AATTAAATGTTTGATTAGAATCTAAGGAGTCATCTAAATACTCATTGGTTGCATGCTTGTATTC
ACTCATTGATTTTGTAACATGCAAGATGATTTAATATCTTCTTGGTCATCTAGACTAATATAAA
AAGTACAAGTTCATCAAACACCTGTCTTTCCTAACCCTTAGATCTATTCATCCAATGGCTTATA
TCAAAAGTTGGATCACCCCAGCAATTAGCGATCCGTGTCCTCCCGCTCCACTTCGCGTAAAAT
TAGCGTCGGTTAACAAAAAGGGAAAAAGAACAAAGCTTTTCTCCACCCCGACTGCTCCCAAC
GAGACCTCCACTACGTCTCTCGCCGCCGTCGACGGCCTCCACCGTACCGCTGCCATTTTCTCCC
TCTTCACCGCTCGCCCTACCCTTTGTCCTGCCTCCTCGCGTGCTTGCGCTGCCGACATCAGAGG
CCGGAGAGCGTGGGGTCGCCGTTGGCCACTTCCCCGCTCTTCCCCTTCGTCGCTGCATCACCGT
CCACCCATCACCGTGCAGGCGGAGATCAACCTCGCCGCCCTCCCTAGACCTCTCTCCGGCGAG
GTGCATGGACTCATTGATAGGGTTCTCTATTGGATCACCTAGGTTTAGATCTAGTTGGGTGGTT
CTATTTTCGATGGATGGTTGAACAACAATAGAGATTAAGGGAAAAGGGTTTAGGGATGTGAC
TGGTTGACGCGTTGGATGAGGAGGAAGTCCCGGCCATCGCCGTTGACGTTGCTCTGCTTGTCG
AGGATGGCGGCGACGATGTGCTTGACGGCGACGGTGGTTGTAGTAGTGGGAGTCGTGGTCGA
CGATAAGGCGTGGGGCGGCGGTGGCGCGTTCCCGTCACTGGCTGCGCCCCCTCTCGATCGGAT
TAGGGTTTGTGGGGTGGAGTGGTGGTGGCGATGAACCTTGTTTCTTGTGCCGTCCCGTCCTCCA
CCCCTCTTTATATGGCACAGTGTGACGGGGGCCCACCAGCCATTGGGCTGGGCGCCCCCGATC
AAGGCGCGGGTCAAGGCCCCCTTGAGCCGTTGGGCTCAAGGGGAGGGAGATCTATCTAACAT
TCTCCCCCTTGATCTCACTATTTCTTTTAGCTTTTTCTATTCCATCACAGATTTACATATACAGC
ATGTTTCATCATCACAGTTAATTACCGCTGGATTCGACAGCCACTATACACATCTCTATTCAGA
AATAGATACTTTAACTTTTGGGCCCTATAGTCCAGGATTCATAAGGCTTCCCTTAAACCCATGC
ATGCTACATGTTCCTTGAACATGTTGGGAGGTAGGCCTTTCATGAGCGGATCCGCGAGCATCC
TTTCTGTTCTTATGTGCTCGAGACTGATTGTTTGATCCCAGACTTTGTCTTTCACAACATAGTAC
TTTATGTCAATGTGTTTGGCAGCACCACTTGGCTGATTGTTGTGAGAGAACATTACTGTGGGTT
TGCTATCGCAGTATAACTTTAGTGGTTTCTCAATACTGTCAACCACCTTTAAAACTGGGTATGA
ACTTCTTTAGCCAGTTCACCTGCCCTGGATCCTCATAGCATGCTATAAACTCGGCGTACATAGT
AGACCCTGTAGTGATGGTCTGTTTTGAGCTTTTCCATGAAATAGCTCCTACTGCCAGGGTAAA
CACGTATCCCGATGTTGACTTTATATTATCTTTTGCAAAGTCAGAATCTGAATACCCCACTGTC
TGGAGCGATTCTGATTTTCTGTAAGACAGCATGAGGCCTTTTGTTCCTTGCAAATAACGCAAG

FIG. 5W

```
ACTTTCTTTTCCAATATCCAGTGCTCTGGGCCTGGATTACTCTGAAATCTGCCAAGTAACCAGG
TAACAAATGCCAAGTCAGGTCGTATGCACACTTGAGCGTACTGTAGGCTTCCTACAGCTGATG
CATTTGGCTTTGTTTTCATTTCATTGAGCTCATACTGATTTCTGGGACATTGCGATGCCCCATA
CTTTTCGCCTTTCACTATAGGAGCAGGTGTAGCACTGCATCTGTACATGTTGAATTTCTTCAAC
ACCTTTTCTATATATGCATTTGAGAAAATCCCAATGCATACTTTGTTCTATCTCGGTGAATCTC
TATGCCCAAAACATATGAAGCCTCACCGAGGTCTTTCATGTCAAAGTTTGAGGATAAGAATTT
CTTTGTTTCCTGCAGTAGACTGACATCACTACTAGCCAGTAGAATGTCATCTACATACAGAATT
AGGAAAATGAATCTCCCATTCTTAACTTTGAATCAATACAGTTGTCCTCGACATTCTCTTGAAA
ACCCAAAATTTCTTTATTGTCCCATCAAACTTCAAGTACCATTGTCTCGAAGCGTGTTCTCATC
CATAAATGCATCTATTTTGACGACATCCCATATTTTGTTTCCTTTCATGACAAAACCTTTCGG
TTGTGCCATGTGTACTTTTTTCCTCCAAATCTCCATTTAGGAATGTCGTTTTTACATCTATCTGA
TGTAATTCCAAATCATAATGTGCCACTAGTGCCATTATAATTCTGAAGGAATCTTTACAAGAG
ACTGGAGAAAATGTCTCATTGTAATCAATCCCTTCTCTTTGCGTGAAGCCTTTTGCCACAAGTA
ACGCTTTAAACTTTTCTATATTCCCTCTGGAGTCATATTTGGTTTTGTAGACCCATTTACAGCCT
ACTGTTTTGACTCCTTTAGGAATTTCTTCTAAATCCCAGACACCATTTAATTTCATTGATTTCAT
TTCATCTTTCATGGCTTCCAACCATTCAGATGAGCGAGCGCTTCTCATGGCCTCTTCATATGAG
GTGGGATCATCCCCCATATGTGACTCTTCTATATTATAAACATGATAGTCATCACGGATAGCC
GATCTTCTGACTCTTTCAGACCTTATAGGAGCCTCCTCATTTGGCACATTATCTATATGAGACT
GTTGCAGTTCCTCCTCTGGTGTGGCAATAATTTCTGTTGAATCCTGTAGAACAGGTTCCTCATT
TTCATTCATTGTTGCCACAGGAGAAATAACAACAGGTGTTGGTACCGCAACGTCATGCATTGC
TGGCACAACATCAGCAGGTAGAGAGAAGAAAGGTTCCTAAGTAGACGGAGTGGGTACAGAC
ACCCGCCTCTCCTCAAGATCAATTTCTCGAACTACCGAGCTCCCCCTAATCATTTCGTCTTCCA
AGAAGACGGCGTGTTTCGTTTCTACAAACTTTGCACAACTATTTGGGTAGTAGAAACGATAAC
CCTTTGATATTTCAGAATAGCCAATAAAATGGCAGCTTACTGTTTTGGGATCCAATTTCCCAAG
ATTTGGGTTAAATACTTTATTCTTTGCAAGACTCTCCCACACACGGAGGATCCATAGCTCATAC
GGTGTTTTGGGCACCGATGCATTCTATGCATTGTATGCATTGTTCTAAAATTGAGAACTCCAAT
GGAGGAAGAATTACATTCTTAAACAGTCTCTCAATTCTCCCCCTCGAAATATGGCCTAAACGA
CAGTGCCATAATTTCGATGAGACATCAGGAGTTCGCTTTCTTTTCTTTTGTCAACGAGGACACA
ACATTCACATTCTCAGAAAGAGATAACAAATAAAGCTGATTTTGCAATAGAGCAAGACCAAC
ACATGCATTATTATACCATAGTTCACATTTGCCATTTCCAAAATGGCAATCATATCTATCAAAA
TCCAATTTGGATACACTTATTAAGTTTCTTTGCAAAGAAGAGACATAAAAACATCTCGAAGTA
AAAGTATTAAGCCATTCGCGAGCTCTAGGCAAAGATCTCCAACAGCTTCAACTTTTGCTTCAA
CTCCATTGGCAACTCTAATGGATCTTTCACTTCTTTGCGTAGTCCTCATTGAACAGAATCCCTT
TAAACAATTAAACACATGAATAGTTGCTCCAGAATCAATCCACCATGTGGATCTAGAATAACT
AATGATAATGAGATTCACTTACAAATGCAATAATGTTCTCACCTTTCTTTGCTATGATCACTGT
TAGGAAGTCAGGACGATCTTTCTTGGAATGTCTTGTCTTCTTGCAGTGGATATACTGATCCTGT
CTCAATTGTGAACTGTTGTTCCTGAGGCAGATGCTGAGGCTGTTTTGCTTTTGAGGAGGATGA
CCTGTGGCTCTTTTCCATGTTATCTTTAACAAGGTTAATGGAGTCACCATTGGTCTCTTTGATTC
TTTCCTCCTCTTGCACACAATTAGAGATGAGCTCTGATACCATTGATAGGGTTCTCTATTGGAT
CACCTAGGTTTAGGTCTAGTTGGGTGGTTCTATTTGCGATGGATGGTTGAACAACAATAGAGA
TTAAGGGAAAAGGGTTTAGGGATGTGACCGGTTGACGCGTTGGATGAGGAGGAAGTCCCGGC
CATCGTCGTTGACATTGCTCTGCTTGTCGAGGACGGCGGTGACGATGTGCTTGACTGTGACGG
TGGTCGTAGCAGTGGGAGTCGTGGTTGACGATGAGGCGTGGCGCATTCCCGTCACTGGCTGCG
CCCCCTCTCGATCGGATTAGGGTTTGTGGGGTGGAGTGGTTGCGGCGATGAACCTCGTTTCTT
GTGCCGTCCCGTCCTCCACCCCTCTTTATATGGCACAGTATGACGGGGGCCCACTAGCCATTG
GGCTGGGAGCGGGTCAAGGCCCCCTTGAGCCGTTGAGCTCAAGGGGAGGGAGATCTATCTAA
CACTCATCGCTCATCCCGGCTCTCCCTGAGCTGTGGAATCGTCGTCAGTCCGCCACGCCCGAC
GACTTCCCGGTCACCGCCACGAGGGACCTCCATATCTAGCATTTGGAAACAGCGGTTCGTTCA
ATTTCTACTATTCGGTTTACTCCTTTTCTTGGTTCTATTTGATTGTGACTTGAACAATCAACCAA
TGAAGTAAATTCTTTTCTGTACATACGTGTGAAGAATCTACTATGATTGTATTGTGCCCTGCGG
GGTGTTGATGAATTGCCGTTGAGGGAGGGATGGTCTAAGATAATCAGTTCACACCCTTTAGTT
TGGTTGTTCACTTGCTTTCAGGTGACATAAAGCTACTGACATTGTGGCCTATTTGCATGTCCCA
TTTTTCAGGTATTTAGAATTCACCATAGATGTAAAGTATTTAAGGGGACATCACGAATGTAGG
CGGTATGCTCTTCTTCCATGGAGAGATCTTCAATTATCGAGCTGAAGATGCAGATGGATATGT
TCAAGATCAAGGGCAGCTACTTCAATAAATCATGCATCTTCTCTCTTAGCAACTTAAACACTA
CCATATCTTAGCTAAGGTAAGTACCTGAATCAGCTAAGATTTCGAAAAATCATATATATGGCA
```

FIG. 5X

GTTCCTTCATATTTATCATCCCTTTTTTTTGTTTTTGTGGAATATTGTTCTTTGATTACCCTGCTT
TCGAAGGAAATGATGTTTGCTAATATTATAATTTCATTTTTAAAAATGGCTATTGAAGAAATT
AAAAAAAAATGTGTACTTATACTACTCAATTTCTTCTCTGGTCTTTAACCTTGCCAATTTGGCA
TGTGTAATTTTTTTTACAAAATCAGTCTTGCATAGCTACATCTGTGTCTAACGTAAGACTGAC
TAGGAAATTATTCATGTCTTCAGGCATGTTATCAACAGTGAATATATATTGATGAAACAAGTT
GATCTGCAGATCAAGGTGAAGGAGAGGGTACTCTTTTAATTGAGGCAAAAACATTGTTTGGTT
GTTCAGTTAGGTCCCAGATGAATTTGAGACGATATCGTCTCTTTTCAGTTCATTCTTTAGTTTA
CATTCTTTGAGAATTGCACTGTGAATAATTTTGGTTTTCTATATATGCTGCATTACAGTTTCAT
GCGGTGGGATCTGAGATGATATGAATATGCACAACATCTTTTGACTTGCTGACTGGTACAACT
TAAATTGCAATTGGAATGAATGAATAGTCCAAACACTATTGCCTTTCTGACAAGAGTCCTCTT
TTGCTCCTAGATTTTTTTTCTTCCTTGGATTGGATTGCTGCCAGAATTTTTTTTACCTTGGATGG
ACTCATCACAACCCCAAGCTGGATTCTGCATGCTGTCCTTCATAAGTTGGACAAAGTGCTACA
ATGCGTGCTGTAAACTGTGAAAAAATCTCATATTTCTTTATGTTCTCCCTATACCTAGCTGCT
TGCTTCCGTATTTTGTCATGTTTACAAACTACTGTCTTTGTACATGATGAAACACAAATTCTTA
GCCATTTCCATGTATTTATTCTTAACCACTTTTGATATTACTCATGTTTACAAACTGCTGCTATC
TTAACTTATTATTAGACCATGTTCCGTCAGCACTATTACCACCAAAACTCCATAGTTTTAGACT
GGTAGCTTCAAAATTTGCCTTCAAAAACTCGATTGTTTCTTGCCGCGACATTGTAAAGTTAGCA
CAATCTGTGAAATTGTTCATGTCAACTGACATCCTGTTTAGACGATAGTAATTTTGAAATGCGT
TTGACTATACAATCTGCATTATATTTTTGCATCATATTGGTGTTTTCAAATCCTATGAATTCTAG
AGCTCTGTATCTAGAACCCAGGCAATGTGAATTCTAGACCTCTATTCGAAAAGTTGGCAAAAT
TTGAAATCCAACTTCTCCTGTAGTTTAGTACATACTCTACACATTAGCAAAGTGTGATCTACAG
CTACCCATGGAATTCACCTGCAGTCAGCACACATATGCCTATAACAGTTAACATGAGATTAAT
TGCCATGCTTCAAATTATTTTCCTTCAATTGAAAATAATTGAAATGTTATATGTGTTTATGTTCT
CCTTCTAATGCTCGGCCTGCACCATGGTTCTCTCCTTTCATTCTTTTGTACAACAGCGTGGCTAT
TGTTTGTTTGTTAAAAAGCTCACCATATATTTGTTGAGATGCTCTATGAATATTTGCTCCAAAC
AGCCGTTGCTTCACCACCAGGCACCTACAATGGACATCACTATTAGGGCCTCCACACCAATAT
CATCAACAAGCTCGGCTAAATTGTCTTGCTGCTGATGTCAACAAAGAGGTGTTGTATTTCTAC
CTGTTGTAGCTTTTATCTTACATTAACATGACATGTTCCCATACTTTTATGTATGTTTGAACAAC
CTTTGTAATATTACTAATTTGAGCGCGCATCTATTAAATAGTGCAGAATGCAGTCCCTTTTCCT
CTTTCTTTTTTTTCCCATTGAAGAAATCTGTTCTCTGAAATATGAAGTTTCAGGAAACCTCCAA
GGTGAAATTGTCCAATCTCCACATCCAACAATTATGCATGAAGTTCAAACCACTGTTTTTCTAG
CATCAGGATGAGAAAAATGATTACTCCCATTCACCAAAAGACGCACAAGCATTCATTCAGTG
AGTAACCACTTTTAATAGTGAACTACCTAATGGGCACATCACCGACCGGTTAGCCTAACATAC
TTTATTATTTGAGACGGTTTTATTACATAATTCGTAGCACAAATGAACACCATCAACTGGTCAT
GGTCTTGATGTGTGGCTGGCATCAAGTAAATTGGTTATCAGTTATATCGTGTTTGGCATTTTGG
AAAAAGTTGATAATTGATGTTATTAGTTACATTCTTCACATTCACATTAGTTCCTCGACATTTT
ACATCTGTAAGATCCTTTTTGGTGTCCTTGGTTTTTGTCTAGAAATTAAATTGACATTGTTCTTC
TGTCCATTATGTATTCTGGACGCTTTTAGGTGGTAGATAGCTAGATACTAAACAGAAACACAA
GAAAGGTATTTTTACCAAGGAATGTAGAACATGCATTAAGTATATATGTTGCATATGCACTTA
GCCCTTTTCATGGTGGCTCCCATCACGTATCTTGCTGATAATAGGTATTAAGAACGCATTTTTT
GCAATACCGTAGTCAATATGGTAGTTTTTTCTCCATTTTATTTTGATCTAAAACTCAAAACTCA
GTCGTATGAATCCAAACTCTCCTATGATACTTTTCCGACTTACATTTCAGTCTAACTTGTAATG
ATTACTGTAATTCAAAACTAAGAGATCAAGGCATCGAGCTGTCTTTTGTTCGTGTAGATGAAG
GATGTTTGATGATTTGTATTATTTTCCAAGGCTCATCGTTTGTATTTGTATTAGACTGATGAAG
ACATGACTAGCTAAATGTGTTCTCATCCTGAACCAGAAAGTTTAATGTGTTGTGATGATGATTT
TGACAAGCAAGTAAAGGCACATATAACTTGATAGATTTCTTGATAACTTTTGTTGCTCCCTGTA
CCTGTGGTGATCAGCCTCCATGAGGAACTCCAAGTATTTAGCTTTTAATGAACACAAAATGCA
TTTTTTTGAAAGTCTTTTAACTTTCTTTGATACAACTGATTGTCACTCTACTTAGTTCTACTGGT
TATTTGTGAGTAACAATTGATAGTGCAATACATGAGTAAATCAAGTGTACACGTAAATCATTC
GCAACATATATTCGCTTCCATATCATAGGCATTGTCTGATATGTGCTTGAGACATAAATTATCA
TTAGTAAACAAGAGTTGTGCCTGTGCTTTAGCATAGGCATATTACGGTGGTTATGTTTTGCTTT
GGATACTTGAAATTTATGAAATAACATAACTCAAATGAATTTTGATTGATTATGTTCTTCAATT
TAATCCTTCAATATATGTCAACGTGCCTTGCACGTGCACACTCACTAGTGGCGATAAAAGTAA
TAGGTTTAACTTTTGTGGATGGAGAGAGTACTACTGTCTAGACTAGTAGGTAGGGGTGAAAAG
AGAAAGGGTATTTCCCGCCTGCTCACCCGACACTAGGCTCAAGGGAAAGAAAGACATGTGAG
AGAAAAATTGAGTTTTTCTTAGGGTACAGACATGGGTGCAGGGTACAGACATGCTACTTTTTT

FIG. 5Y

TAGGGATTGCTACTTACTGTAAACAGTGGGCAACATGTAGTGTAGTAGTTTCCGAAATCCTAT
TACAATGTTACTAAAAATAAATAAAATTATTTTTTAAGAAATGCGTTATAATCTTTTCCTATA
GGGAATACTGACCCTAACTTGATATGTACATGCTTATCTATTTAGATTTAATTTTTTTAGTATT
ACGAAGTTCAAGGGTTAAACTACCAAATTAATAATGAGAATAAGTGGTAGGCAAATTCACTT
ACCCCATCATTACCTTCTTGCTTAAAAAAGTATAGATTCGTGTCCTGCTGCTCGACTGTTGTCC
CCATTGTCTTCACACTGGCAGATCGGTCTGAGCATTGACATTGTTGTTGAATTGTACTCCATGT
TTCAACAGTTAAACGACCATGTTTCATGTACGAGAAGGAAAATGTTTTTGTAACTTGACCATG
TTGCACATTTAAGATTTTGGTTCTATGAATTTTTGGTGTCTCACTGAAATTCAATATTTATATGT
GGAAGCAAAATGCTTCGAGTCAAATGGATTTGAAAGTTTCGCTTTTTTTTTTTTACTTATTTCC
TGACATTGCACTCCACTTCTTAATATTGCTTCGCGGTGCATTTTTTTTATGTATTTTCTTTGAAA
TGTTTTGATGACTTTTTTCCCAGAACATATAACCTGACGGTTTTGGCTGATGGTCACCTGAAAC
ATCTTGTTTTAACCGCCCGATGCTATTCTTGTCAAGATTTAAATGCTTGTGTGTGAAGTCATTC
ACACGTAACTCCACCATCAGTCCATCACACACACTAAAAGCACCCGCAATAGTAAAATAAGG
TGCTCTCTATAAAACATATACATCTCAATAATAGACTCGATTAATAGTAAACCACCTTAATAG
TATGTCTACATTGGTATCTATAGCTCTCTCCTGCATTGCCTCGTTTTTCTCTATAGCCTATCTCT
AAGTTAGTACATAGCTTTGCTCTCTCTCTCTTTATTTAATACATTCTAAGTAGGAAAATATGCT
GACATGGATCTCTTGTAGAGAGCCTATAGATAACTATTGTGGGTGCCCTAATGTATATGGGGT
TAGAAACTGATCATTTTCCTCGTAAAACGGAGTAATTCGTTAATGTATGATTAATTAAGTATTA
ATTTTTTTTAAAAAAGATTATTTGGCTTTTAAAAAAGCAACTTTCATATATAATTTTTTAAAAA
AACATATCGTTTAGCAGTTTGAAAAGCGTACGCGCAAAAAATGAAAGGGGTTGGTTGGGAAA
GGAAGGAAACAAACTCAGGCCTTGTTTAGTTCCAAACTTTTTCTTCAAACTTCCAACTTTTTCA
TCACATCAAAACTTTTCTACACACATAAACTTCCAACTTTTCCATCACATCGTTCCAATTTCAA
CCAAACTTCCAATTTTGACGTGAACTAAACACACCCTCAGTCAAAGTAATATGTAAAGTAATA
TATAGATGTAAGTCAAAAATAAAACAAGAAACACAATAGAATACAAACGCATTATGTAGCTT
AACATGCAAAGGAGTAGTTTTTATAGCTCATTAAAGACATATTAAAGCATGATGTTAAAGATT
ACCGTGCCCTTTATTAACATATATAATTAATATAATAGAGAGAACACGAGGAGGGGCGAGGA
ATTATTATTGGTTCAATCGCTTAAAAATGAGTAGAAGAAAAATAAAATATTATTAAAGATGTC
TAGCAAATCAGATCACAATCTCATTTTCCCATCATGCTCGAGCATAGGATGAGATTGAAGCAG
CATTAGGCAGATCGATCGAGCCCATGAGTCAATGCCACGTCTTGTCTTAGCTTATCCTCGTCTC
ACTGGCTTCTTTTAGTTTCTGTCCATCAGAAGCAGCAGCAAGCGGAGGCAACAAATTTGAGGG
CTGGAGTTAATTTGGGATTGCTCCTGTTCGAAGATACACCTACAAGGTTTCATTCTGGCATTAT
TTATTTCTCCCTCTCTTTTTTAATACGTTGTTGACGATTTTAGATATGAATGAGGTGGGACATG
CAGGATCCAGAGGTAAGCCCCCTCCTATTCGAAGCCGGGTGGCTAAGCCATTCCCATCTCAAG
TGGTGGCCCGATTCGGTAATTTCGGTAAGACTTTTTAAAATATATTTGACTATTAGTTTTATTT
GAAAATTTTATATAATTATCATTTATTTTATTATGATTTGATTTATCGTCAAATGTTCTAGAAG
CATGACTTAAACTTTTTTTTATATTCATAAAAGAATTTTAAACAAGACGAATAGTCAAACATTT
GTCAAAAAATCAACGGTGTCGTATATTATAAAACGGAGGTGGAGGTAATACCATGCTGGAGT
AAGATGGTGTTTGGATTTAGGGACTAAATTTTAGTTCCTGTTACATCGGATGTTTGTACACTAA
TTAGAAGTATTAAAAGTAGACTAATAATAAAATTAATTGCATAAATGAGAACTAATTCGTGAG
ACAAAATTCTTTAAATCTAATTAATACATAATTAGCACATGTTTACTGTAGCATCATATAGGCT
AATCATGGATTAATTAGGCTCAATAGATTCGTCTCACGAATTAATCTAAGGTTATGAAATGGG
TTTTATTATTAGTCTACGTTTAATACTTCTAATTAGTTTCAAACATCCGATTTAAATTTAGTCCC
TGGATCTAAACATGGTCTAAATATGTACGTACCATGATGGTATCATTTTTTTCTTTTTGGCTAG
AATGGGCATTGATTGATGATGACCATGCCGGCAGTAGGAGGGCAAGAAGGTGCCCAGTGCGA
CTCGCTAGAGTTGGACGATGCGGAGTCAGAACTTAGAACTTATACCATATAGCATACCATAAC
ATCTTTTTTTTATAATGGAATAACAATTCGGCCTTTGCTCAACGAGCTACACCAATTATTACAA
AATCCACACAAAAACAAATTCAGCACACACTGATTGATATAAAGAAAACACAAACTAAAAGA
CACCAACACAAGATAAAAGAATCCTAAATTGCTGAATTCTATTCGATAATCTCCATCCGAAGT
TGACAAGAAGTTGACAAAAAGGTACATGATTGTCGACTCAAGTTTACGACATGCATCATTTGT
TAGCTCGATATCATCATTTTTAACTTAATATCATAACATCATACAACAGTAAGGTGATTTTTGT
AAATTTCAGTGGACTTGCATTGTAAAAAAAAGTGATTCACAAGGTGTTTGAGAAAAGCTGTGG
GGTTAGCTGATCCCACGGTATTGTACATGGCTCTATCATTGACGGTGACGACTGCATATGTTA
AGGGGAAGGGGCAAAAAGCTAGCCCAATGTATAACATAAGGCAAAAATCCCTGGTCTAAGGT
GAAAAGTTGGATATGGTCCTAGACCAAAATAAAACTTTATGGTAATTATAAGGTGAAATTCAG
TCGTTAAACATAATTTTTAAGCTAAAATTATATTCGACCTATATTCCATTTGGAACAGAGGCA
GTACATGCAATCCTCAAAGTCAAACAACGACATCGACATGGATAGCAACCAATACGGCAACA

FIG. 5Z

TTATCTACATTGAAAAGGACCCTAAAAAAGAATCTACTTTTTGAAAAAAATGATCCATATAAT
AGGTTAATGCTTAGAGATCACCATCATGTTCCAACATCAAATTAAAGCCCAGCTCTTTTCTGAT
TTAGATATAATTTTTACGTCGGTTTTCGTCGTCACGTTTTTCTAAGGGATACCCAATACATTTC
GTGTAATAACTTTCTATTAAAAAACTATTTTAAAATATCAAATAAATTTACCTTTTAAAATTAT
AACAATTACTCCCTCCGTTTCATATTATAAGACTTTCTAGCATTGTTTATATTCATTTATTAACA
TCTATATCTATATGAATATGAGCAAAATCTTATAATATGAAACGGAGGAATTAAAACTTATCA
ATCATGCGTTTTCTTGTTTTCGTGGATCATCATCAACCTCAATAGAAACGTAAACGTAAGCGC
ACCACACGGCCGAGAATGCTCGTGAGCAGCGCCTGCGCCTGGCATGGACGTGCCGCTGGTGC
CAGTGCCAACGACGGCGGCCGACGACGACGCGGCGGCGGGGTCGCCGTCGCCGTCGCCGGAG
ATGGAGATGGAAGAAGACGGCGGCGGCGGCAAGGTGGTGTACGTGGCGGTCAGCGGCAACA
GGAACAAGGCGCTGCCGACGCTGCGGTGGGCGCTGCGTCGCCACGCCCCGGCGCCGGAGGGG
AGGAAGAAGACCGCGCTGCTGGTGCTCGTGTATGTGCACCGGCCAGCCACCATGATCCCAATC
TTCAGTGAGGCTTCCCATTGTTTAATTTCTCTTGTTTTTTTTTTCTTTCAAGGAAATGGTGATGA
TTCAGTGCATATAAGTTTCCTGTGTCGTAATGAGGGTTTTGAATTTTGAAACATGGGTTTTTGC
CGGTGGGGACCGAAAGAACCGAAATTTTGTTTTTTTAAAAGAATTTTAACATATTTTAACTGA
ATTTAAATAAATTTTAATCAAATTTACAAATATTTGATAAAAACAAGTAATTTTGGGGAGATT
TTTGCTTGCCAGTGGGGGCCGAAATTACCAAAATTTTCGAACCGAAATTTCAACCCATGGTCG
TAAAACACCTTGTAGAAAAGAAAAAAAACCTTTCGTAAATAGCGTACCATGAACTCAGGACT
TTAGGGTGCTAGTCAGGTCACTTAAACCACTAGCCTATATAGCTTTTCGCAAGGCGTCTTTGTT
GTGATGTTGGTGGGTGGTGGCCGAATTTGTGGGGAGAAAAAAAAAGAGATACTTGAGATTAA
GATCCTCCCAATTTTGTATTCCAGCAGGAGCAAAGGTGCCTTCAATTGTTCTCAAGGATGAAA
TAGTCACTTCTTACCGGCAGCAAGAGAGGAGGATTACTGAAAAATTTCTCCAACAATACCTGG
ACATCTGCACATCTGAAAAGGTGGAAAATCAAGCTCATTATACATATCACTGAATAAAATTCC
TTCTTCTGTTGGTTGTTGGTGTCTCTGCAATCTGCATTTCCCTCTAGCTTTTGTGTACAGAATGT
CTCTAGAGAACCACCTCACCACCTCATTTTGTCGATATTTTGCTACAGAGAATGTCTCTAGCAA
ACCACCTCATTTTGCCGATATTTCATTACAGGTTCAAGCTGAGGCATTCATGATTGCGAATGAC
AACATTGCGCATGGCCTCATAGGGGCAATTCAAGAGCATAAGATCAGCACACTCATCATGGG
AGCTGGCATATATGGGTATCCAGCCCTCCCAAAGTTATTTATTTTTATCACTTCAATTTCCATT
TCTAACAAAATTCTCCGAACTGATCGGTGCTCTTGTAACAATGTGATGCATTATTGCACCTTTT
CTTCTTGGCAGGAAAACAAGCACCCAAAGGACAAAGCTAGCAATCACCATGGAGAAGGAAGC
TGATCCATCTTGTAAGATTTTGTTTGTCCACAAGGGAAATCTATTCTCCATCAGGTAGTTGTTC
TTTGAGGAGCACTCAGTATTCATGGCTTCTTTTCTTTCTAAGACAATACAAGAAAAATTCTGGC
ATCTACACCTGTAGATAGACATAACAGTTACATTACATAAATGCGACAATCTGCCAAATCTTT
ATCTATTATATACTATAAAAGTCCATTAAACATCCTACAAACGCTCTTAAGCCGCCACGTGGT
ACTCCTACAAATACTCCTATAACGCCTCGTGGCACTCTAATATATTAAAGAAATTGCTATAAA
TTGTAAGAATAAAGTAAAACATCTAGCCTTCAGTTTTCATTTAATTCGGCGGGCCTGTTATTTT
GATCCATCAGATCAAATCACATGCTAATCTCCATGGCCCCACCCCTAGCCTGTATGTAATCCA
GTTTGTGCTTCCGCATCACGTATGCATACTCCCGTCCGCTCCTTCACGCCCTCCAATTTCCTTTC
AATTCCCAATTTATGTTAGTTAGAAAACATAATTTATAATAAAAATTAAAAACATCTAAATCA
TAGAGATAATTTTTCATCTGCTTATGTATCACTAATTTACATGGTAAAAACTCATATTTAATTA
TATTTTAACTTGCAAAAAAGAAATTTGTTAGCGTTGGGTTGTAACAATTATAAGAAAATATGA
AAATAATAATTGTATAGTAGTAGATTTTAGAGATTACCATCGTACATCACCTCATAATAATTA
AATTAGATCTATAATTGTAAAAATAAAAATGAACCTAGTTATGAGTGATATTCTAAAAAACTA
TTCCCTCCATTATGAAATTATTACAAGTCAAAATAACATTATTGTATTTATCATGAAAACTACT
TTCATATGGATGCATACTTTTCATATTTACACTAATACATTTTTAATATGTTTCCTACTCTCTCC
ATCCCAAAATATAAGGGATTTTGGATGGATGTGACACATCCTAGTACTATGAATCTGAACATG
ATATGTCACATCCACCTAAAATACCTTATAGTTTGGGATGGAGGGAGTAGGAAAAATACCTTA
CTTTTAATTTACGCTTAATTTTTTTAGTCATTGTTTTAAATAAACAATTTCCTATAGGGATGAAT
TAAATATTTTATAATATAAAGGTAACAAATAGCTTAGAAAAATTATCTAAGCAATTCTAGTAA
ATAAAATTTATGGAGAAATAGTATACTTTTAAAGCGTGGTAGATATCCTCCGGTTGATGGTCC
ACATTTATAAGTTCTTTAAACATAGCCTACGACCCTATGCTCGCGTATTTGGGCGGGCTACCTT
GTTGATAAAATGAATGTATAACTAGCTACAGCAACTCAATAATTCCAACCATGTTCATGGTTT
TTTGCCTTGTACTTTTTAAAATGGAAAATGCTGTCAACAACCAGAGATGCAATGTTTTGCAGG
CCCAGGACTACAAGCATCCCCATCTCTGTGAATAGTGATGTTCCTACTATGGCAGGTTCTCAC
ATACCTTGGTTCAGCTTCATTCCTCCTTGGCACCATGATGACCGCAGCAGCGTCACATCTTCTT
CCTTCCTCACCGACTCGCAAACCATGACCGACAATGGGCTTGATCCAGAAAATCTAGACCACC

FIG. 5AA

AATTCTTCGAAAATGCGATGCCCATGTTCGATTATGACAGCTTCAGCCTTATCAGACATGAAT
CCCTCCATGGCCTAAATGAGATAGCTAGCCAGATCATACTGTCTGGCCATTCACAGTACTTGC
GCCAGTTGAATTTCGATGTAAGCTGCAATGAGGAAGTAAGAAACCGCCAGTTCATTCACGGTA
TCGACTCGATCCTCGGAGTCGATTCGATGAACCTTGAGGAGGTGTACTGGAAGGCCTACATGG
AGGACAAGACAATCAAGTGGATTTATCTACTGGAGTACATCCATAAGATTGTATCAGTCTCAC
TGAAGCAAATCCAGGAGCAGCATGATGGTGCCTCTAGTGGCCTGACACTTGAAGGCCTCTCAG
ATGCTGCAACCAAGCCTATCAATCGATTGCTCACATTTGCGTCGACGGTCAGTAAGGTGAATG
GTTCGCCGGAGAAGCTCTTCCATACGTTGCAGATGCACAAGGCATTGTCAGAAGCTTCTCCGA
TGATCCAACAAGCCCTCTTGGGAGAACAGAAAGAGTTCTTCGTCAGAGAGCTTCACAGAATTC
TTGACACGCTGGAGGACTCTGCAAGGGAAATACTTGGTAAGCTGAAAGTCCAGATTCAATCA
CATGATTCACCGATCATACCAGGAGGCAGTGTACACTTGGTTACAACATACCTCATGAGATAT
ATCACATTGTTGGCACATAACACCAGCTCACTGAACACCATTCTAGGTCATGATCATAGTGAC
CATCTGTTGGCAGCTGACGGAATCAACTTGCTGTTGCCAAGCCACCTAATTTCTGGCTTGATAT
TCGATCTTGGCTCGATGCTTCAGAAGCAGTCTAAGCTGTACAAACCTGAAGGATTGCAGTACC
TGTTCCTTATGAACAATGAGCATTTTATTCTTCAGCACTTTGAGCGGGAAGACATAAAACTTAT
GATAGGAACTGAGTGGATTCAAAAGTACTGTCATAACATCAACCGATACAAAGTGAAATATA
TAGAAGCAACATGGGCTACTGTGGTATCTTGTTTGGACAAGAAGATCAGCATTTCACTAAATT
TTCTGCAACCTTCACCCTTGAAAGAATTTATTTCCTCTTTCGAAACAGAGTATAGACTCCAGAT
GCACTGGAAGGTCCCTGATCCAAAGCTCCGTATTGAGCTGAGACAAACTGTCTGTGACTATGT
TCTGCCAGCCTATTGTGAATTCATGGAGAAGCATCCAAATTTAGAGAAATCAGGGGACAATCT
TGAAGATATCAGGAACAAATTAAATGAACTGTTTGAAGGATGAGTTGATACTTTTATGATTAC
AAAAACAAATTCTTACTTGTTCTCTTGTTCCTTCAATTCATGCAAGGAAAATTGTAACACATAC
TAATTCAATGATTGTTAAATTAACTTTTCATTATGCAACATTACTTGCCAGTAATTGCGTATTT
TGATGCGTAAGTTGAGTTGACAGTAATGTTGGATAAAATCATAAAATACTTTTTTATTTCACAT
TATGTCAAAGTGTAATGTTTGGAGTACGCACACATCTCTGCACCAACTAGGGATTAGCTAATC
GCCAACTCAACTTACCAAAAGGTTTAAGCCAAAAATGGCATGGCACAGAAAAAACATGAGTG
AAGAGGTAACTGCTTCAGAAGCAAAAGTAGCGAAGCAAAGAAATGTCAAATGTTGTTTTCTA
GATGATTCTGATGCAGAGGCTTCTTAAATCACTTGCATTTTGGGGGGAAAAAACAGGGAAAG
AACATAGTAAAATATTTCGCCATCCTGAACACGAATACAAGAGTACACAAGAGGAAAGTGCA
TTACCAGAAATTTCACACTGGTTCTGATTGTACAAATAATCAAAAACTGTTGTAGTGAGCATT
AACAGGGGTTTGATTCTGGTTCTATATATAATCTAACTTTTGCAGCAAGCAGTCTACCCTTCGA
ATAACTCCATCAGCTTATTCTCAATTTCCTGGGGGATATACTTATGGAGCTTCATACCCTTCTT
CTGCAAGTGTGCCTGATAACATTGGACGACATGGGATGAAACAGCTTTCCTCACATTGTTCCG
AAGTTTCGGATCCTCAATTCTCCAGTTCTGTTGCTCTGCACAAGTGCTCTCCAGCATCTCGTAA
AACCTAGTCGTCAGGGGTAGATGAAAGCAAGGGAACAGTGCTTGCGTCGGTGTATGAGCATC
CAAGCAAGACATGACGGGTAGCCATGAGAGCTCAAGGTATCTTGTGATCTGGTGCTTGACCTG
GTTCTCGTACCTGAGAATCCAATCCTGCTGCAGTGCAGACTTCACCTCTAGCTTGCGAAGCCG
GTTCAATATGAAATGGGCATTGTTCAGCAAGGAAATGCATTCCAGCCCCATCATCGATTCATG
CCTCGCCATCCTCTCGAGCAAGGCGTCGAGGCGTCCGATGAAGTGCTGCACAAAGGAATCCA
CCTGCGTCCATTCCTCACCGTTCTCGCTCTCCCCATCAGCTTGATAAGCAATAATATTGTTGAT
CACGCTGTCATGTTCCCACAAAAACTTGACGTAGTTCATCACGTACAGAGTGATCTTGTGAAC
GCCACCTCTCTGCGCTACATGGTACAGGCCACTTTGAGTTTGAGATAGTGAACATACCCGTCG
CAAGATCTTCCTTACACACTTCCTGAGCTCTTTGGTGATGCCGTTTAGCTGGTCGATCGGGAAA
GTCCCGAGCGTCGCGTACAGACGCAGTATGACAGGCAACAGATCAGGCGAGGTTGGCAGCAT
GGTAATCACGACAGCTAGCTTCAGCAGGCGACGCATTTCAGATGCTCCTCGAGCTTGGCCGTG
CTCGCGGTTGATTTCTTGAATGCTTCGATCAATCAATGCCACCAATTCTTTCCCAAACAGTTGG
AGCATCTGCAAGTCTGCCCTCTGAATCCAGGTGCCGATATCTGTTGGATCGTGTGCATCTTCAG
GGATGTCCTCCAGAAGTTGTATTTAGTGGGAGACATTACCGGGTTCATCAGAGAAGCTGTGGC
TATCGTACGAAGAGGATTCTGTGGTTGCAAAGCGAATAGACAAATCTGTTGAAGATGTGAAA
CTTGGCATCCTTGTTCCAGATAGAAAAATATCAAAGATTCAGAAAGGAGGAATACTATCAAC
GTATGAAGTGGCAAGAAACAATTCTGATGAACTATTATATGATGAGAGGAGTTGTTGGGAAA
ACGAGTGAGGACTCATGAAAGGAAGTTTCCTGCAGCTAATCAAGGTCATCTCTGTTCTGTTTT
TTTTTTCTTTTTCACTATTAAAGAAATGATGGAATTTTCTGCAGCGAGTCAAGGTGGATGCTTT
TTCCTTGCACTGGAGTACACATCTCTTCCCCCTAGCCTTCAAGATTAGAAAAATGGCTACCCAC
GGAAGTTTTTTTTTTTAGAACAACTACCCACACAAGTTGACATGGGCTAAAAGATTCAACAA
CCATAGCATAAATTTGTGTAGGAACACTCACTCAAAATTTGAAGAAAAATGCGCATCGCTTCC

FIG. 5BB

CACTGATCCAGTCAAAATGAATCCCCTTTTCTTCCAGAGAAGGGATTTTTTTTTTTTCTATATA
GATAAGGGTACATTACCAAACGGGCTAAGACCCAAGTTGTTGTCGCTTTTGCAATATTGCTCA
TCCAGATGAGATGATCCACAACCATATGGAGCAGATCCCCTTCGCCTCCAGTTGCGCAAGACC
TAGCCGCAACTACCTCCAGATCGGCTCGGCCAAGAAATTCTTGGATCCACATACCTGCGCAAC
AGTGGATTGGAACTCGAAATTAGTCCCAACTGAAATGGGGAATTCCTTTCTCTCTCTCATCAA
AAGAAAAAGAGAGCAAAAGAATCTGGGAAATCGAGAGAGCAAACCCTCATCCCCATGATTCC
GTCTGGATTTGGCAACCGCAGTTTGGAGCAAGTTCAATAGTATAGCTTTGGTTATTAGAGTGG
TTACAGTACCAGGCTATAAACTAGCTATAAACATATTTTAAAAAGATAAATAAAGAGAGAAG
AGCAGTGACTCTAAGATGTAATCTGTGTATAACAGGCGGGACTAGGTATTAATAGTATAGTAA
GCAACTATTGTATGAATTGGCTATAGATAATTTGGAGCTAGTAGTGGGTTGCACCATTAAGGG
CCTGTTTGGCACAGCTCCAGCTCCAGCTCCACCCCTTCTGGAGCTGGAGCTCAGCCAAATAGT
TTCAGCTCCACCAGAACTGGGAGTAGAGTTGGGTGGAGCTCTCTCACAAAATATACTACAGTT
GTGGAGCTGGGTTTAGGCAGCTCCACAACTCCACTCCAGACTCAACTCCTGGAGTTATATTTA
GGAGTTAGAGCTGTACCAAACAGGCCCTAAGTTTGCTCTTACCTTACAGGAAGTCTGACATTA
AATGAAAGAGTGCGAATGAATGATTATGATTTAAAGTTGTTTTTGGTGGTGAGTGGGAAATCA
TTTTCCTATCCAATTAGCCAAACACCACCTATTTCTCTCGTATAAATTTAATTTAAATGTTTTAG
AGCAAGTGTATTAGTTAATTTTTACATGAGTGTCAACAATCCTTACTTTTTTTTATTTCTTTTTT
CACGTAAGTTTACAGTTGGTGAGTCTATTATTATCCTTGCTTAATGCCACGTGAGTGTTGTCCA
TGATCTCGAACACAGGAGCGGCGACGCTGGGCTTCTAGCAAGCGAAGGTGAGCATGGTGCCG
AGCAGGAGGTAAGTGGCGAGGATAAAGGGTAAATAGCATATTTAGCACTTATTTGAACCGCT
ATTATGAAATTGCTATAAAAATATAATTGTATATTTGAATTGGATACTAAACAGTTGGAAACC
ATAATACATGCCACTTACAACTTAGACTAACACCATTAGAGCAAGGTTAATACTTAATAGTGT
ATAGCCAACTGGTGGCTCTAATTATTTTGATGTTATTTTACAGTTGATTCTAGAGCTAACTACT
ACTCTCTTCGGGCTGATAATATTAGTTGTTTTGGATAAGGTTTGGATAAGGGTAAAGTCAAAC
TTTAAAATCTTTGACTACAAATAATTTCTAAAATATTTATCTTAAAAATATAAAAATCACATGT
GTAGATTAGTCTTAAAAAGTACTTCAATAAAATCATATATTTGTTGAAATTTCTATATATTTTA
TAATAGAAAATAGTTGTCAAAGTTACATTTTTGAAGACCGTGCCCTTGTCCAAAACAACAAGT
ATTATCAACCCGAAGGGAGTAGTCCAATAAGTTGGCTATTGTGGTGGCTACACTTCATTTATT
AAATAATTAATTATATATGCACACATCACTATGTAGGATGAGACAAACTTTTTCTTCAACCTTC
CAATTTTTCCATCACATCAAAACTTTCCGACACATACAAACTTTCAACTTTTTCATCACATCGT
TCCAATTTCAATCAAATTTTCAACTTTGGCGTGAACTAAACACACCAGAAGTGAACTCAGGCT
ATGTTCTTCCGCCACCTCTCCCAACTACATCTTTTGTTTTTCACGCACACGCTTTCCAAACTACT
AAATGGTGCGTATTTTGTAAAAGAGTTCTATAGAAAGTTGCTTTAAAATTATATTAATATATTT
TTCAAGTTTATTTTAGCTAATACTTAAGCTGTGTTTAGATCCAAAGGTATAAAGTTTTGGCGTG
TCACATCAGATATACGGACACACGTCTTAAGTATTAAACGTAGACTAAAAACAAAATAAATT
ACAGAATCCACATGTAAACAGCGAGACGAATTTATTAAGCCTAATTAATTTGTCATTAGTAAA
TGCTTAATGTAGCACCATATTGTCAGATCATGGAGCAATTAGGTTTAAAAGATTCGTCTCGCA
ATTTTACACGCCAATGTAATTAGTTATTTTTTCCATTTATATTTAATACTCCATACATGCATCAA
ATATTCGATGTGACAAGATGAAAAATTTTGCCAGGAGATCTAAACAGGGCCTTAATAAATTAC
TAACCTCCGCTCTATTTTGTGTGTTGGGAGCGAGGGTTCCTGTCTGTTACTAGCAAACGAAAG
GAGGACCTCCGTAGATGGCAGAATTCACAACGCGAAATATCATGCGGAACCAAAACATCGAT
CGAATATTACAACTCGTACAGTATTCCGCGAGGAAGAGTTTATAATATACACAAAGCAAATTG
TTTTGACTCAAGTACTCAACACTTCAATCCAGTTTCATCAAATTCAAACGCAGCGACCTAGAA
ATTTACCTACTGATCCCCTTCCTTATACTACCTCTTTTAAAAATATATGACGCCCTTAATTTTTC
ATTCATTTTATTTGAAAAAATTAATATAAATATAATATTTTTTACTTCTTTTACCATCAAATAA
AATATAATCTTAATTTATACTTTTACATATTTATATTAAATTTTTAATAAAATGAATAGTCAAA
ATGTTTAAAAAGGAGTATATAATAACTTGATAAGTGTGGCCCGCCTATCGGTCCATCTTCCTTT
TCTATTTTCTTCCTCCTCCACTTTAATGGTGGTGTTTTTCTCCTGAAGATAAGGATGAAGATGA
AGATGAAGATGAATGTTTTTTACACAAAACGAGATGTTATTAATGTATGATTGATTGAGTTTT
AATTATTATAAACTTAAAAAATAGATTAATATGATATTTTAGAGTAACTTATATATATATAAAGT
TTCCACACGAAACACATCGTTTAACAGTTTGAAAAGCTTTGCCACGAAAATTTTTATCTTCATA
CAACTCTTGTTGGAGAAGAGAAATGAATGGGACCATTTTCTCTCTGTCTCCCCTTCTCCTGCAC
GGCTGCATGACTAGTTGGTGGCGCCATGAATCGGGGCCGGTAGCGGACGATCCAGCTCACAA
CGGCCGGCGACAGTGCAAATCGGGCGTTGGCGGTGGGCGACCTCACGAGGACTAGCGCGGCA
TGAATCAATCCTTTGGCAATGAGCTCGAGACAGCCGGAGGCGGCGTAAAACAAGGCTCCGGG
AGGCGCGAATGGAGCCGGTGGTGGACGAGCGAGTGACAACGCCATGGGCGCGAATCGGGGC

FIG. 5CC

TCGCGCGGCGTAGCGGACGAACTCGCGACGGCTGCCAGCGCGACGCAATTCGGGGTCCGGCG
TCTGCGTGAATCAAGCCGGTGGAGGAGGAACTTAGCGATAGGTTTGCGTTGGATCGACAAGC
TTGCGGCGACCGCCGGCGGAGGAGGAACTAGCGACAGGCCTACAGTGGATGAGCTCTGAGGC
CGGCAGCAGCGCGAATTGGTGCGGCAGCGAATGAGCTCGGGGGGTCGGTGATGCCAAACGAG
CTCGCGACAGACGAGCTTGGGGGTTGCCGGCGGTGGCAGATGAGCTCACAACGGTGAGGACA
GTTCACCAGCCTGCGTGAATTCCTATGATCGACGGATTGGGAGGAGTCGTTGGTCTTCCCAAC
ATGTGGAGATCGAGAATGACGGAGTTGGGATTTCCAATTTTTTGATATTGATTGGAGGTTTGT
TGGATCCATTTTTTTTTTCTATAAAACTCCAAAAAGTTTTAGGATTGGGAGTAGTATTGGGCAT
TTCTTGTGCATGCTCTAAGCCCATACAACCCAATAAATAGTACTCCCTCCATTTACTCTTGATA
GTCATATTTCCAAATCTGAAAATTTTATTTTTGATAGGCATATTTCAATTCAACAACCTATCCT
CTTAATGACTTTCTTGGATTTAATGCGTGACTCTCTATTCTTCCACACATGATTGGCTATATGG
GCACTGAGAAATGTAAATATTAATGAATCGCTTGTTTACGAGGAATGAGTAGTACCATATTTA
AATGGATGATAAGTAGAATTACTTATTCTTGGTCTGTGTGCTAAGATGAAAATATGACTATCA
AAAATAGATGGAGGGAGTATCATATAAAAATAATGCCTCGGCCTTTTAACCACTGCTATCAAT
TTTTGATAGGGGACAAAACCCAACAAGTTACAAGTGGTATGAAGTTGCACGCTCTAACAAGT
AGTATCATCCTCCATCTTTGATCCACTCGACTCTGAATCTCCCGCTTCACCATATGTAACAGCT
TGCCCTCCAAAATCACACAGTCCAGTCTATATATCTTATGAATGGACCCACTTGCACATACCA
CCCCACTTACACTTTCGTAATTACTTCGTGTAAAAGGGTTAACCTAAAGTATTATAATTAGAG
GGACAAGCCGTTATAAATTAATTCCACTCTTGCTCAACACTAGCAAGGTGTTACTAATCAAGT
ACTCATATCACTGGTGGAGAAATGCTCTTTACTCCCGGTTTAAAACCTTTGTAGTCCCGGTTTT
CCAACCGGGACTACGAATCCGAGACTAGAGATCGCTATCTTTAGTCCCGGTTCAAATAACCGG
GACTAAAGATTGATCTTTAGTCCCGGTTGGTAACACCAACCGGGAGTAATGGGGAAGCGACA
GTTCCTCAAGATCTTTTTTTATTATTTTATTGTTGCTAATAGCTAGTGTTAATCCATGTATTTTC
TCTCGAATCGAATGGGATGCACATCCCAAATATTAAGTTACTTATACACACAGATCCTACACA
CAGATCAAATACATCACAAATCCTAAAAAACTACACACAAATTAAATACATCACAGATTATA
CAAGATTATACATCTCAGATCCATGCGATGCAATGAATCACAAAATCTAAAAAGTTATACATC
CAGTGAAACACAAATTATAAAAAAAAAGAAAGGAAAGCAAACGAGCCGGCGCCTTGCCGCC
TGCCCGCGCGCGGCCGCGCCGCCGCCCGCCTCCACGCGCGCGCCGCCTGCCTCCCCGCCCGCG
GTCGAGCTGTGGCCGCCCGCCGCAGTGCGCCGCTGCCTCCCCCCGTGCGGCCGCGCCGCCGTC
GCCCGCCGCCGGCCGGCTGATGGAAGAGGGAGTAGAGGGGAGGAGGAGGAAGGGCCGGCTG
ATGGGAGGGAGGAGAGGGGAGGAGGAGAGGAAGAGGAGGAGGGGAGGAGGAAGGGATTGG
ATCTGAGAAGAGAAAGAGAGGGGATGTTCTAATCTTATCTAAATATCTATCTGGGACTTAACC
GATCAGATGTGGGAGAGAAATATTTACTCCTGGTTGATAACTCCAACCGGGACTAAAGATCCC
GGTTGGTAGTATCAATCGGGACTAAAGATCCTCGGCCCGCTGACATACATCTGACAGGGGATG
AACCGGGACTAAATATCATCTTTAGTCCCAGGACTAAAGATCAAAAATTTTTTAACCGGGACT
AAAAATCAGTTTTAGTCCCGGTTTTTAATGGAACCGGGACTATTGTGGAATTTGATCGACCGA
CCAAATATGGTTTCTCCACCAGTGTATACTACACTGTAATTAGGACTAATCAACTACACATAT
ACCACACTCTGATTAGGACTAATCAAGTACACATATACCACATTCAAATTAGGCTGGGATGTC
ATACAACCCACCCTTCTAACCCTAGAGAATTCTACGTCCCCGTCAATCTAACCACACAAGCAT
ATAAGCAAATTTCCAGAAACACGCGTCCTCTTAGTGCACGTCTATATGTGCAGTGGCACTTAT
GGGTCATGTAGACCACATCTTAATTAATAGGGTCAGGACGTGACATGCATACCAGTCCCGCTC
CTCCCTCAAAGGACCCAACGTCCACATTGGTCCAACTTACACAAAATAACCAAATAGGTATAT
AGACCAACTTTCATGAAATAGCTGTGAGGGTCGACTCTGATATCACCCTCTGGTACCATTTGT
AATAGCCAGCCCTCCAAAACTACGTGTCCCAACTATCTGATAGGAGGGTCCAGTTACACATAC
TGTTATAAGTTGATTATACTCTACTTATAATTTCATTCTCACATCATGTAAAAGGATCAATCCG
AAAGTGATATGATTGAAAGGACAAACTCTTATAAGTTGATTATACTCTTATTCAACTATAGTA
AGGTGATAATAAATAATCAAGTGTACACAACACTCATTACACAAATCGCATACTAATTGGACA
AGGATATCACACCATCCTTAAGTGGCGTAGCCAGGAATTTTTTCTTAGGTAGTCCTAGTTTACA
AGTTCACATCACATACTAAAATTTTATAATACTATAAATACGATATATATATATAGGACACTC
ATATGGGGCATCATGGTGCCCGGGCACCATGGTTTCAAATACACAAAATCACTTAAATTTTTC
AAAATTTTCAAATTGTGAGTATATACCTAGTTATAAGAATTCGATTCATACCTATACCTATCAA
CAAAACAACTCAAATTTAACTTTATTTCACAATCCATGATTACATACCTAACTAATTATATGTA
TGGATGCTATATACCTAGAATCAAAATCTAACAAAAACAAGTTCAAATTCAGTTCAAACTTGC
TTTCAACTAGTTAGTAAAGTAGTTAATATTAATACCTAAATAATTGAAAAAGTTTCATGCTCAT
TTGAATTGGGTATATACTCAATTTCAACAATGGTGCCCGGGCACCATGGAGCACCAAACAAAT
TTACTATATATATATATATATATATATATATAAGTACAAAATTAGTGAAAATGCAATAGAAATGT

FIG. 5DD

AATAATAATATCATATAGCATAAAGAACATGCTTCTCAGTTCCAATAAATTTTAATAGAAAGC
TCACCTGTTTTTAGGCCTCCAACTCTATCCTCTTCCCTCATATATCATCAATAAAAGTATCAAT
TTAGAACTCAAATCTTCTCAAGTCCGAGCTTTAAATGTCATTGGGATAAAAGTTGGCAACTAA
TCACAAATCGATTTTTGAAGCCATTATCTACAAAGGCAAAGAACTAGTCAGCTAGAGGAAAG
AGAGTAGAAGCAAGCAAGCAGTTGTTCATTACCTGCAGACTGCGGGAGGCCATTCCATATTTT
CGTTCAATCGGAGTCGAAGCGAAGGCTGGAGGCTGTGAGGATGCCGACCTACGGTAGCAGGC
GACCGCCGAGCGCCGAAGCGGGAGGCCGGCTGGTCACTTGGCCGGGAGCACCAGAGCGGAG
ACGGTGGGTCGGTGCCGCCGCGGCGGCACGAGGAATCAGCGTCCCCCGTCCAGCAGTACGGC
GCCACGAAGAGTGGCGCAGCGCAGCGCGGTGCGGAGGGCGGACCCACGGCGGCATGGCGCA
CGGGCCTCGCCTTGGCGGCGACTCAGCGGCGGCACGTGGCTTGGGCGTCGGGCGAATCCGAA
GGGAGACAGGGAGTAGTAGCTGCTCGTCCTCTCAACTCAACCCTAGTTGTTTGGTTCCCTTAG
AGCAAGTTCAATAGTATAGCCCACTGGTAGCTTCAATTCATGTATAGCCAATCTAATAGCCAA
TTCATACAATAGTAGTTTACTATACTATTAATATATGGTCCCACTTGTCATACACACATTGCGT
CTTGGAGTCTGTGCTGCAGCTGGCTATAAATCTGTAGCCTGCTACTCTTCTCTTATCGTCTATC
TCATTAAAATATGTTTATAGCTGGCTAATAGCTTACTATTGTACCTGCTCTTAGCCTTGGGTTG
TTGATATTTGTTTGGGCCATTGGATTTCGTTATTTGGGTCTGATTTTTTAATGGGGTAGGGGGT
CTCTGCCTCTCTGGGTTAAAATCGGGGGTAGTCCCGCGCCCACCAGGACTACCCCTGGCTACG
CCCCTGCCATCCTTCTCCATTTGCAGTCATCACGTCCCACCCATGACTTAACCACTCCCTTTCTC
CATGCCCTAGCCTCCCACTTGCATTCCCCACCATCCTTGCCTCCCTCTTAAGGGTGCAATCGTT
TCAGTGATGGCGGTGGACAGTTTAGCCGCACACAAAACACGAGAAATGTGATTAGCATATGA
TTAATTAAGTATTAATATATATATATTTTTTTATGAATAAATTTGTTGGATTTTTTTAACAACTTTT
TATAGAAAGTTTCCATACAAAATATACTGTTTAGCAGTTTGAAAAATGTGCTAACGAAAAGCG
AGGAGAATCTAACCCTATAAGCTGAAAAGAGCGCACCCTAAGTCCTCTGAAGTAGAACTTCA
CTTCCGTAGCACACAGCTCGAAACTTGAGTAGTCACTAGGATCATTAGAGCTTGTGTGGCCTC
TCACAAATCAAAAGGTCAGCGTCTGTCAGGTTTTATCCTAATTCTCATATAATCCAGATTTGTT
GTACTAGGATACGATATCCAGTTCTAGATTTTTTTATGCGAAGGAATGAGATATATATATAG
TAGCAAACCCATGCTTTTAATATGCATCATATCCAACGTTGAGAAATGGCGAATCCACCCAAA
GTAGTGAAAATGAAGCGCATGCATATTCTATCATGGTAGCAGCTGAAACGAGAAAAGAATAT
GTATTCATTATGCGTTGTCAAAAGCCACAGGTAATTTCCTACTGATACCTTGATCGATCGATCG
ATGAATATTCTGCGAGCGACGCCGCCGCCGTCTAGCTCATGATCTGCACGCGGCCGGCCGGCT
CCGGAATCAACGGATGCATCCTATACAAATCTCCGCCATGTGCCCGGCCATCCACACACAAAT
TAAGTCAGACGCCAGCAACTACCGATAGCTAGCTGAGCTCCCGCTCCCGCTCCCAGCCAGATC
AAGTTGACCAGCGACGGCGGCGGCGGTGGCGGCGGCGGCTGATGAGATGGCCGGAGAAGGA
GGAGCAGAGGAGGAGAAGGTGTACGTGGCGGTCGGAGGCGAGCCGGAGAGGTGCTTGCCGA
CGCTGAGGTGGGCGCTGAGCTACACGCCGGCCGGGAGCACGCTCGTCCTCCTCTACGTCCACC
GCCCCGACGCCATGATCCCCATCTTCAGTGAGCGATCCACCGATTTATATATATCCATCTGAC
ATTTTCCGTCGTCCCGCTCTTTCATGATCCAAATCTTTTCCGTCATCCCGTGATTCACGCTACGA
AACTAGCATATTAGGATGTGTTTTATTCAACTAAAACTCTTTATATTTTAGGACAGAGAAAAT
ATCTTTTAGTTTGCTTTAGCCACATCTTAATTTACATCCTGAATTTGCCACGGCTCCCGACATTT
TCTTTAGCCCCATCTTAACTTACATCTGAATTCGCCACGGTTCCCAACATACGGGTCCTTTCCT
TTTTTTTCGAGATACTCCCTTTATCCACAAAAGTTACACCTATTTCACATTTGAGGTTTTCCAA
ATAAGTTGTTCCTATTTGTAGTTTTTATGCATTCAAAACTTAAATGAAGAGATAAATTAAATAT
TTTTATTAGAACCCAATAAGTCATCTAAATACTTATTGGTTGCATGCTTGCATTCACTCCTTAA
TTTTGTAATATTCAATATAATTTAATTTCTCCTTGGTCTTAGTATTAAAAGTAATATATGTAACT
TTTATGGATGAAGGGAGTAATAGATCTCGCTTCATTAATTTCATCACATAATGAAAGTGTATA
TTTTAAAAGTTAGTGAACATTAGCGTTAAGTCTAGCGCATATATGAATTAATCCTACTAGTCTA
GTGGGCTGAGAGTGAAGACCACAGTACCTATATCTAGATATGTGTAGCCATGGCAAGCTCTCC
CTCGTACGTGAAAGTTTCTTCGTTTAAGGTCATAATATGTTTTGAGTTAAAGTTAAACTGCTTT
AAGTTTAACTAAGTTTATAGATAAATATAATAATATTTATATTACCAAATTATTTTTATTAAAT
TAATAATTAAATATATTTTTATAATGAATTTATTTTGGATCGGAAATATTACTATTTTTTTTCTA
TAAACTTGATCAAACTTAAAGCAGTTTGATTTTAACTATTTTATAGTCTAAAACAGAGGGAGT
AGTAATTAAGACTAATTATTTTTTTCTCCAATGCACTCAGAGTTTAATGAGAGTACTTTTCGAA
AGTAAAATAGATCAAAACAAGGACTTTACAACCAACTCCATATCATATGTACACAGTTTAATG
AGGTTGGCTACATCTCCCATACTCGCGACAATAGCTCTATATCGATTCGTCAAATGACGATAT
ATATATATATATATATATAGAGAGAGAGAGAGAGAGAGAGAGAGAGAGAGAGAGAGAGACACA
CTTGCCGTTGGGGGCAGAGGTAAGCTTAGATCAGTTAGGGTTTGAACTCTAAGCCTAGCTACC

FIG. 5EE

TCCAAAATCATGATTTAATTTTAGTATTATCTCAAAATAAGGCAGCAACAAATGTAACTATAA
TATGAATACACTGTAATTGCTATATAATTACGGTGTAATTAAGATGTAATTTTAGTTTTAGTTC
AAAACCTGCTGATTGCTCACTTGGTTAAAGCGTGATGTTATCGACCAGTTAGTCAGTCCCCCC
AGCCCCACCCCCTGATTTCTCTAGCTACACAACTAGCACATGGACCGAAAATTGAAATATATA
TATATATAAACGTCGACAAATTTATAGCCTTTCTGTTATTTATTTTTGTTAAATCACCATGTAC
GTTTCTTACAAATCTAACATCTCATTAGTTAAGACCTATCTTAGCCCTAGTCTTTATTTCTCTAG
ACAACTAGCACAAATCTTAACACAAAATCAATAGACCAGAAATGAAAACATACCAAGAGAAA
AATTGTTGATAGATTTATAGCCTTTCCGTTATTATTTGTTAAATCACCATGCATATAAGTTTCA
TAGAAATCTAACATCTCATTAGTTGAGACCTATCTTAGCCTTAGTCTTTAGCAATTTGTGGCTT
CGCTAGCGCCGCCATGCATGTTTTCATTTACTAACTCATGACGATCACAGTTATATATTCAAGC
TAAATATTATAGTTAGAGGAAAATTGACCGTTTCTATAGTTGAAAATATATGTCTCGCATCAA
AATTTGACTATTGCAGTTGAAAATACGTCGTCGCATCATGTATAGAAGCACCCTTATATAAAT
TCGTCTCTTTTACTATGCATACGGTATCATCTTCTTTCGGTGCTATATGTATATATGCAGCTGG
AGCAAGGGTACCTGTGTGTGTTCTTAAGGATGAAGTCATCAACGTTCACAGGCAGAAGGAGA
GGAGCATTGTCCAGGAGAGGCTAAGAATATTCACTGCCGAATGCGAGTCTAAACAGGTACTT
ATGTAAGGGTGTGTTTGGTTCAGGGTCATACATGGATGAATTTTAAGCCTGACCAAACACACC
ATAAGTGCATTATCAAGCACAGCGTAAAAATTTTTAAGCCTGACCAAACACACCATAAGTGC
ATTATCAAGCACAGCGTTTTTATGGTACAACTTATTTTTAGCCTAACACTTATTAATGGCAAAA
AAAATAATTTATAAGTAAAATTTTATATTTATATATGTTCTTAATGATTTAATCTGAAAAATAA
ACTATGATAAAAAAATAAAATACCAAGTTTTGAGTGCGATATGTGCGCACGCGCCTCTAGAG
ATGGATTCCAACGGACGATTATAGGCTGTATATTTTTCGACGTGTGATGTATTCATACCAAAC
ATTTGACATTATAAACCAAGTCATGCTTTTCATTTCCAGGTTCATACTGAGGTTATCATAGCTG
AGAACGACAGCATAGGACTTGGCATTGTGAAGTTAATTGAAGAACATAAGATCGGCACACTC
ATCATGGGAGCTGGATATTATGGGTACGTATCATCTTAATTATGTAATATACTACTGTGTCTCA
AAAACAGTTTTTGCAAACGGATCAAAACGATTTTTCCAGACGAAGCTCCACCTCACCTGTACA
TGAAGACCTGCAAAATTAGATGACTTTTACATACGGACATTAGCCCCGCCTATGAGAATTATT
TTTGCAGGCGGACTTCTACATATTCGCAGGCGCTACATTCACCCACCTGCGAAAACCACCTCA
CCGAATAAAATAAAAACCCCTGCCACCACCCTGACCCCTCACCGCCCTTCCCGCCGGTCCCTC
CTCCTCCGGCCAGATCTAGAAGGAGGAAGGGAAGGGAGCGCCGCCTCCGCCGCTGCCGGCCA
GCTCCCTCCTCTGGCCAGATCTGGGAGGGAGGGAGGGAGGGGAGGAAGCGCTGCTTACACCC
TGCCGCCAGCACTCCTCCTCCGTCCACCGCCGATGTTGGCCGGCTCCCCTCCTCCAGCCGGATC
TGGGAGGGAGGAAGGGAGGGGAGCGCTGCCGGCTCTCCTCCTAGTCGCCACGCACCTCCACG
TCACTAGTGGCTGCCGCCTCTGCCCTTCGCCGGAGGAGTGAGGGAGTGAAGGGGGAGGGGAG
GGGATCTGGGGGGGAGGAATGAGGGAGTCAAGGGGAAAGGAGGGGAAGGTGAGGGATAGA
GATAAGGGGTGGGTGGCGTGGGTGGTGGATATTACTAAGTCGATTGGTGTGGCAAGCGAAGA
CCTAAGGTGCCGCTTGCGAAAATCGATTTTCGCAGGCGTCATGCAAAAATAATCCTTATTTTTT
TTATTTTTACAGGCAGACCTCTTAAGGCTATGCATGTGAAAATTAATTTTCGCAGACGGGACT
AGATTTATGATATTTTGAGCTTTTTTTTTTTTGTAAACGGTGATTTTATAATCCGCCTGAAAAAA
TAAAATTGTAACGTTGGGAAAAACCATTTTTTCTAGTAGAGAGATCATCAATTTTCTTATGATA
TATCATAATATACTACAGAATTAACACGGGAAATTCAGTGGTGTACCACTAATGAGACAAGA
AATTTATGCGTAGTTAGTTTAATTTAGTCAAAAAGTTATGAATGTTGATTTTCTTTCCCTAAAA
ACTGCATGCCTTATATTTTATTTTAGGGCTGTTTTGTGTCTGTAATTCTTGTTCACTATACATTA
TTCAATATAAGCACGTGATCGATATGCATGTTTTCCCCCAAATCAACCATAGTGAGATAATAA
TTTAGAAAAATTAATAACCAATTAAATATCATCTAATTTAGCATGTATACGTGTCTTAGGAGA
CGAAAAAAAAACAAGATTTCGTCTGTCTATTGGCTAGGCACAATGTGGTACGAAATAAACTAT
AAGTGCAATGCGTGCAGGCACTACTACGAGAAAGATTTTCGCGTGCGGTCAAAACCGGTTTTC
GCGAGCAGGTGGGTGGCCCTCACGCACCTAGGGGTCTGCAAAAATTGCGGATGGCGCACCCG
CACGCAGAAATTGGTGCTTATGTTGCCCGCACGGAAAAACAACAATTCGAAGAAAAGAAATA
AAAGTTCAAAAAAAATGAAAACCCTAAAATCGGCGGCAGCGCTGCCGCTCCCGGCTATCGCC
ACCTCCTCCTCCTCCTCGTTGGCCGAGGACATCGCTCCTGCCCTCGTCGTCGTCGTCGGCCGAG
GACGCTGCTCCCGCCCTCATCGGCGACCTCCACGCTGCCCGCCGCCGGATCTGCGCTCCTCTCT
GGCCGCACCGCCGCCGACGCCCCTCCCCTCCGCCAGATCTAGGGAGGGAAGGAAGGGGAGGG
GAGGGGATCAGGATCCCTCGCGGGGGGAGGGCGGCTGTCCGCTAGATCAGTGCAGGGACGGC
CGCCGCCACCTAATCCGTGCGGGAGTTGGTCACCGCACACCGGATCCCGTGCCTCCACCGCCG
CAGCGTGGAGGAGGCCGTTGTGCGCGTGGAAGAGGCCGCTGCGTGCCGCCGGCGCCTACGCC
CGCCGCTGCCATCGGGAGGAGAGGAGAGGAGAGAGGAGTGAGAAGAGGAGAGGCACCGCGC

FIG. 5FF

GAAGAGAGAGGAGTGAGGAGAAAAAGAGATAGAGAGAAGTGAGGAGAAAAAGAGATAGAG
AGGAGAGGAGAGGAGAGAAAGAGGGGAAAATTTAAAGTGGGTAAGAGGGAAAAGAGTAAG
GGTATTTTTGCATGCGGCCCTCTTAATAGGTTCGCACGCAAAAATAAGCCTATTTCTCATATA
CGACCAGTTATGGTCCGTCTGCAATATAAATGGGTCCATGTATAGGAAAATCGTTTTTTAGTA
GTGAGGCATTCATGTTTTTTTGGAGTTTACAAACAAATTAAATGGATCCACTTGAACCAACTA
TTTTTAGATGACTCGCGAAGTTCATATTGATATAGAAGAAAAAAATTACAAGATTATAACCTT
GAGAGGTTGTAACCAGGAAAAACAAAAGAAAACATGCACGCCGCCAGCGAGAGCTGGCAGC
TCCTCGCACCACACCCTGGAGAAGACACTAGAACCAAGTCGACCGCTGTGAAGCGTGATCAA
TTGCCACTAGGCCAACCAGGAGGTTACAAATGCTCCGCCAAACACTGACTCAACATATAGAA
GGACGTCAAAAAGCTCTCGGTTATCCTCACATAGAAGGATTGAGGAGAGTGAGAGGGCGAGA
GAGAAGGAGATCCACTCGTCCCTCGCTCCAACCTGATGAAGACAATCAAGAACTGCCAGCGA
CCAAACTGAGAGAACACAGCGAAGGTAAGGAACAAGACCTCCTAGACAATGTCTCCAGGAAG
GCCATGGTGTCTTAGACGTCACCATTACCCGTCCCATTGGACTCAGTTTTCACCTGGAGGGTCT
GCTAAGGGTGAAATGGTGGCCGCTCGACAAAGCCCCAAAGGGGGAACGTGGTGCTTGAAAAT
GTCGCCGTTGCCAGCTTGGGAAGTTCCGAAATAGGTTTTTACCTGTAAACCTCCACACCACAC
CTGCTACCGCCACCCCCGAGCACCGCCACTTGCACAACCTCCGCCAACTCAAACTCAACCGCA
CCAGCACCCCACCGCCAGCCAGCCCTGCCACGGTCTCCCGCACGTCCATGCCACCTCCTGCAG
CTCCCTAGCTCCCTTGCTGATGGCGCAGCTGACCACCGCATGCTACCTCCTGCTGTCAACGCG
AAACGGTCACTGCAGCCAAACACGTCCGCCTCTCGCGGTCACAGGCTGCGACGGCCTCCCTGC
CATCGCCCGGGCTGCATCTCGCATTCGCAGGCCACGACGGCGTCCCTGTTGTTGCCCACGCTG
GCCTCTGCCGCCATCAGATGCGCCAGTCTGGCCGCCGACCGCGTCGTGCAGCCGTTGCTTGTG
CCATCCTCCTTCTCCATCATCAGCCACGTCTTGCAGCCCCATCCGCCGGCCACGACAATGCTCT
CCTCGTGCCAGCCTGAGCCTTCAAAGCCGCCCTCTCCCGATCTAGTCCGGGGGGGGGGGGGGA
AGGGGGGCAGATCCACCTCCAGGGAGGGGTGGATCCGCCGCACCAACTACTCCGACCACCAG
TCCCCGCACTCGACACGTGCCGCTCCGCCTCTCGCGCCGAGGAGGACTTTCCTTGGGGTTGTTT
TCCCCGCTTTGAACCTTCCCTGCTAGCTAGCCGCTCAGTTTCTAGTGGCGGTGAGGTGGCGAG
GAAGGGTGAGGGTGATGGCGAGGATTTTGCAACCCCTCCCCACCACCTCCCCCGGGCATCTGT
GCAAGAACGACGCAGGAAGAATATATGAATTACCATTAGCCAATTTCTACATATCCTCAAACA
ATACTTGGGCAATTTCAACATTTGTCTACAATATTAAGTACCACATATTTGTCTGGCATGTGCG
GACTTAAACTCATATGTCATAGATATATATATACATGTATATATACTTATATAGGCTTTCAAAT
TCTGAAATGGCACCATCAGTGTAAAGTTACCTAATGAGGCAGCACAGTATTCCTGATAATTAA
GCTTGGATGTTTCATGAGCAGGCCGAAATCAAGCACAGGTGAGTTCAAGGTGAGGACAAAGC
TTGCGACTATTGTGGAGGAACAAGCTCATCCATCATGTAAGATCTTGTTTGTGCACGGTGGAA
AGGAGCTGTCCACAAGGTACGTATAAATTTGTTAATTTCCTATAAATTTTTCAATCCGACAAA
AATCATATTTTCTAACATTAAAATCAGTACCAGATCAACACGTCAGAAATATATCCCTCTATTT
TATATAATAAATCACTTTGACATTTTATATAGTCAAACTTCTTAAGTTCTACCAAATTTATAGA
AAAATCTAATAATATTTTCAACACAAAACAAGCATATTGTCAAATAGATTAATTCAATGTTAT
ATTTAATTCAACTAGTTTTAATGTCGTAAATGTTACTATATTTTTCTATAAATTTGATCAAATGT
AAAGAAGTCTAAGTAGTAAAAAAAACAAAGAAACTTATAATATTATAATATAAAATGGATGA
ATAATGAATAATATACAGGTCTTTCTAGGATTTTCGCTGATATTTATTATAGTTGGTAACGCGC
TTTACGATGATACATTTAAATTAGATGATTGTCTCCATCCATAAGACCTTGTCGGTTAATCCTT
ATGCGAGAGGGATATAGTATATATAGAATTTATTCCACACGTATTGTAGTATAGAATTATTCC
CCCTCAATCGCCTCCAATACTTTTCAATCCCCTTTAAACTAAACAAGCCCTGAATGGGAAATA
CTTTTAATCATCATCAGGAGGACCGGGTGACTGATAAATAGCAAAATTATATGTATATAACTG
TAAATTTGCAGACCAAGACTAATCAACATCAGGGCGGCGAGGAACGAGAACGGCGAGATTCC
TCGTGCAGCATGGCGTCTGGATGATGAGGAAGTGGAAGAAGAGTGCAGATGCAGCGCATTAT
CTTCTTCCTCCTCGAGCACCGCCAGCTATGGTGCTCTCAAGCTCGAGAAGCTAGACAATCCCG
TCATAGAGAAGTTGGAGTCGTCGTCGCCGTCCTCCGCTGACCATGGCAGCTTGTTAACCCTCA
TGGCCCCTGCCTCGCTCGTCGCCCTAAACGAGATGGTGAACGAGATGATCCTCGCCGGCATGT
CGCCGGAGCTGCGGCGGGCTCCGTTCGGCGCCGGCTGCGACGACGACGGCCAGGTGAGGAGG
TCGTTGCACGCCATCATCGGCATCGACGCCGCGCTGGGGCTGGAATGGAGGAACCTCGAGGA
GGTGCACTGGAGGGGATACATGGAGTACAAGACCACCAGGTGGCTCCACACGCTGGAGTACG
TCCGCTGCGTCGCCGCCGTCATGCACCGCGGTGGCCAGGCCCGCGCCCGGGCGCTCTCGGCGG
CGGCGGAGAAGCCCGTCGAGACGCTGCTCGAGTTCGCCACGGCCGTCAGCAGGGTGAGCGGC
TCGCCGGAGAAGCTCTTCCACATGCTGCACATGCACAAGGCTCTCGCGCACGCGGCGCCGCTC
CTCCTCGCCGCCTTCATCGGGGACGCCAAGGAGCGGTTCGCCGGCGAGCTCGAGCGAACCCTA

FIG. 5GG

GCGTCGCTGGGCGTCGCCGTGCGCGGGATACTCAGCAAGACGAAGGCCCTGATCCACTCGTA
CGGTGGCTCGCCTGGACAGAACGTCGTCGTCGTCGTCGTCGTCCCCGACGGCGGCGGCATACA
CGTGGTCACCAGCTACCTCGCGAGGTACGTCGAGCTGCTGGCTCAGCACGCCGCCTCGCTTAA
CGTCATTCTGGCCGGCGACGTCGACGTCGACGACGACGACGGTAGCCAGAGCCAGATGATGT
CACCGCTCGGCCGCCTCGTCGCCGGCGTGATCGGCAGCCTCGGCGTGATGCTCCGGAGAACGG
CGGAGCTGTACGAAACAGAAGGAGGTGAAGGTCTCCGGCACCTCTTCCTGCTGAACAACGAG
CACGCCATCCTCCAAGCCATCGAGACGACGACGCTGCTACCCCTAGCAGCCGAGTGGACGCA
GGCGTACCGCCATGGGATCGAGCAGCACAAGCAGGGGTACATACAAACATGGGCCGCCGTGG
CTACTTCCTGTCTACCACGAGATGATCCTCCTCCTCCTCCGACGTCGGCGAAGAAAGCCGGCT
TCCTACGCCGCCGCCGTCGCTCGCCGCCGTTGAGAGAATTCGCGGCGTCTCTGGAGGAGACCA
GCGTTGAGCAGATGCAGTGGAAGGCGGCCAGTCCGCATCTCCGCGACGAGCTGCGAAGAGCC
GTCAAGGAGTGCGTCGCGCAGGCCTACTCCGAGTTCATGGACAAGCATCCTACCTCCAATGCT
GGCGAGGAGTTCGCTACCGTCGATGATTTGATTCTACGCTGCCAGATAGATCAAATCCTTGAA
GGGTGATGATGATCGTACGTCGTCAGTATATTATATATTAATTGCAGCAGATATGATGTAATT
TAGGACTCCTTCCGTTTCATATACATTCGTTTGACCCTTTTTTTTTTATCAAACGTTGTTAAGTT
TGTCCAAATTTATAAAAAATGTTTAAGAACACGTAAAATATCAAATTAGTTTTACTAAATCTA
ACACTAAATATATTTTGATAATATGTTTGTTTTAGGTTGAAAATATTATTATATTTTTTTATAAA
CTTGGTCAAATTTAAAAACTTAGGAAAAAAATCAAACGACATATAATATGAAACAGAAACAG
AGTACTAGCAAGCCTTTTCTGATCATCGTGTGTATTGGTTAGTGTGTTTTTTGTTCGAGTTAGA
ACTGTTAAAACAAAGGGTTGCCCATTTGTCGATTTTGTTTTCCTCCATCGATCATTTTTTTAAC
ACTATGTCAACAATCAATCAACAACTTATACTTTTTTCCTTCTTATATATTTTTGTTAAGGGTAT
GGATAATACATACCTCATATCCTTGGCGTTATGAAGTATACAAATACGATATATCCTCAAATA
TATGGGAAGGTTACCTTCATATTAAGGAATTAGGCCAATGCATAAGGAAGCAGACTCCCCGA
ATATCTCATATGCATAAGGTTCTCTCTAAGTTCTACCTGTAAGCCAAGGCAGTTTGAGGTATA
AATACAAGACCCCCCCCCGGACACCCCCAAGGAGGTACGGGATCATCAAAATCATAGCATAG
CCACCACCCATAGCAGAAGCAATCCAGAGGACTCGAAGCTAACTCGTCGGTTTGATCTCGCCG
AGTCGTTCTCGACAGGGGTCTAGTCGGTAACTCGCTAGTTCTGTTGTTCTCTACTATAATCTCT
ATGGTTCTCATCATAATCCCATATAAACTCGATTACATCTATTACCTTTACAAGGGACTTGAAA
GAGTATAATCCTTATCTTCTATGTGTTTGATGTCGCTTCGTGTAGATTCTTGTTTCCAACTTACC
CTAATACCCTCTGGATACGGTCTATGGGTATCACCCATCGACAGTGACGTGCCGGGTAGGGAT
ACTTGATGCTCAAGGTTTCGTTGAGATGGCTTCAAGCTCAAGGCCTTCCAACAAAAATGCCTA
CAATCGTTTTGGCTTGGGAGATCCTACCCAGCCGACGTTTGCATGGACTCGAGTTGGATCCAT
CATCTTTCCCATATTCACCGCAATTCCAACCTCGCCTTCCCTAATGCTAGCTGGGGTTGAGATT
GCCACCGCAAGGATGATGGAAAACAACCCTCAGCCAGCTGCTCCTCGCATTGAGTCAAAAAA
GAGGGCGTCAATGACTTCAACTCCCTAGAGAACTCCTAAAGTGGCCAAACCCAAGACATCTCT
TAGGGCCCCTTTGATTCAAAAAAAATTCATAGGAATTTTAGGGCCCCTTTGATTCGCAGGATA
GGAAAAACACAGGAATAGAAAAAACACAGGAATAGGAAGTAGTATGATTCTTCAATCCCGCA
GGAATCAAAAACATAGGAAAAAATGAAAGGTGCCCTTTGATAGTGCTATAGGAAAAATACAA
GATTTCTCTTCCGGTTTGAATTTGAACAGATAGCCGTTGGCGTTCAAAGCAAGTACTAGCCGTT
GCATGTCCTTATATATATTGCTGTAGCTGCAACTGGACATCAACAAAACTAGCTCACCTCACC
TTCGATTGTATCGGCCAAGCATGACAAGAGCTCAAACGTGGCAATTCATTTGGTAAGTCATAA
ATGATTTTTTTCTTTTTGGTATGTATGTAAGGATTAGCAACTTATTTGCTTGCTTCTGCTCTCC
TATATATATTGGTAGACCAAACCATCAGATTTATTATTTGTTGTTGATTTCCCCTGTGATTGTC
ATGGATCCAAGTTATCGACGACGGTCACAGAATGAAGATGAGTTCATGCTTTTTGTTCTCCCT
ACCATCGAAGGAGATTCGTCACAACCATCATCTAGTAGGAAACCGATGCACACATCAAAACT
TTCAGGGGCTTGTCGTGTTAATGAAATCTTAACAGGTCATCAGAGCCTAAGCAAAAGGAATTT
TCGCATGGAAGTTAATGTTTTTCGAGCTTTAGTCGATAAGTTGCGTGAGAAACAACTACTTGC
TGATGCAAGAGATGTCTCAGTAGAAGAACAAGTTGCTATATTCTTGTATGCACTAGCAAAAAA
TGCAAGTAATGAGACCTTGCAAGATCAGTTTCAACACAGCGGGCAAACAATAAGCAAGTATT
TTGGGGTTGTGCTTGATGCAGTTACACAACTTACATGTGTATATATACGGCCACCTTTCCTACA
CCCCCATCATATCTTGAGAAGACCAAAATTTCACCCCTTTTTTGAGGTATGAACAGATTCATGT
TTTGATTTTTTTTTACTTTGAGTTAAACCAATCATTGTACATAAAAAGACTTAATCAAGGTTAT
ATTTGTATTTGTATAGAATTGTGTTGGCTCTATTGACGGGACACATGTACCAATGATACTTCCA
CTAGACCAGCAAGAACCATACCGGAATAGAAAGCAAACAATTTCTCAGAATGTTATGGTAGC
TTGCGACTTCGATCTGAAATTTGTACATGTACATGCCGGCTGGGAGGGATCAGCTTCAGACGC
AAGAGTTCTTCAAGATGCACTAAACCATGGTTTTGAAGTACCTCCTGGTAAATTTTTTCTTGTA

FIG. 5HH

GATGCTGGTTATGCAAATACAACACAGTTTCTAGCACCGTATCGTGGGACAAGATATCATTTA
AAGGAACAGGGCAGAGCTAATCAAAAGCCACAAAATTATAAGGAGTTATTCAATCTTCGGCA
TGCACAACTCAGAAACCATATAGAGAGAGCAATTGGTGTATTAAAAATGAGATTTCCTATACT
AAAGACCGGCTCACACCACCCAACTCGTAAACAAGTTGATATTTCGGTTGCCTGTTGTGTTCT
ACACAACTTCATACGCCTGCATAATGGAGATATGGTGTGGCCAAGTAATTGTCGTTTGGAGAT
TGATCCAGATCATATTGTTGATGTGCCAAATGGAGACGAGAACTATAATGGTGATGTACAAGA
ATTTAACAACTCTAGAGAAGCTGGGAATAGAAAACGAGATGACATGGCACAACGGATGTGGA
ACCATTACGTAGCACGAAGGAAATAATATATTGCATTTGACCACCATGGCATTCAAGGTCAAT
TACTAGTCTTGTACTCCAAGTTTGTCACATTCTACTTAATGAAGTAACTACTTGCATGCACTCC
CTCTAAGCAAAAGTACATCCTACTACTATCTGCTTCACAAAAGTACCCCCTTTGTTTCACAAAA
GTACTATCCTTCTATTTGCATGCCATCTATTTCACAAAAGTACTATCCTACTACTTGCATGCCA
TATGTTACACAAAAGTACTCACTCTAATGCTGCGATTTCCTTTCTAATCCAAGCCAGGCGTAAT
GCATCACTTGAAAAGGACAAGAAAACTTCCCTATTATCCTTACCTTTGAAGATATCAGCTGCC
ACCAATATATCTCCTATTTGTAGACCATGTAAACCTTCAAGCACTGTGATACACTTGTTGATGC
TGTAAGGATCCTCCAATTTCTTCTCCTCAATTGCAGCAAATCGATCTATTTCTTCTTTTTTAAGT
TTTAGGTATCTCTCATGAAATCCATCATCAGGACTAACAGATTTGATCTTTTGTTTCTTCCCAG
GTCGAGATTCAGGAACCTCTGAAGGTGTTTGTGCCGAGCTAGGTGGGACTTTTGTGAGATGGA
CAGGGGTAGGTGAATGCTATGAAAAGTCCAAATTGGCTGTCTCAACCTCTTCACCAAAAGGA
AATTGCAAACCTGATTCACCTGGAGCATTTGAATTAGGGGATGGTGACTGATATGTATCAACC
GCATTTGCTTCTTGTGTTGAATGAGCTGGTGCATTCTTTGTCTTCCTTGCATAATGGTCCATACC
ATGGCGAGTTCTCCCTTCAGCATAACGACCTGCACAATTATATTCTCCTCACGATCAGCATAA
CTTGCCTAAAACATTTCAACAAAACAAACAAACCACTGATAAAAAAAATATAAAGCTCACCA
TCATAAAGTGGAGCTAAATCATCAAAATATGGGAACGACTTATCTCGCCAATGAATTGCATCT
TTGTTCTTGCGATCAGCAAAAGTGTCCCAAACACTTTGTGGTGCACTCACCATCATTCTGTCAC
TATCCCACCCAAAACCACTTTGATCCAACAAATCTTTAACACTGCGATAATCTTTCTTCAAATC
CTGCTCCTTTTGCTTGACTTGGTTGGTCGTAAATGATGTACCGAATTTTGTATTCAGGCGGCAA
ACAATATTTGTCCATGCTTCCTTACTCCAAGCATTTTGTGTTCGAAAACCTGGCACGTCATGAT
CTGTTAGGAGCTCAATAAGGAACATCTTCATCTGGTGACTCCATCTGGCTCTCTTTGTCGTCCC
TAAATTTGACAAACATTTAACAATTTCAATTTCAGCAGTAATATGAAACAAAAAAGGTTTGAT
GCAAACAACAAGTGAAACTGAATTTGCAAATATTACCTATTTCTTGACGCTCTGCAGTCCCAT
GCTCACTGTCAACATCAACATAAACCTGTGATAGAGGTTGCTGGGCTCGTCGATCGGACAAAT
TGCGTTGATTTGTCATGGTCATCTGAGAAGAGCCTTTCGATGGCATTGCTTTCCTAACTCCCAA
AAAAAAAGAAAGAAAAAAGAAATACACAATCCTTATCAGAGAGGGATTTACACCTACAGTGC
CAATGAAACAAACTAGTTCCAAGTAGTCAGCTTAAAAATTCACTAATCCATAGATCCAAAGTA
CAGAAGCACTAATAAGTCAATAATAAGTCAAGTATGAAAGCTCAAAAGTGCAGACAAATACC
AAATCGATGGCCCTGGCTGCTGCCCTCGATGGCGGACCTGCCGCACGCCTCCGCCTAGCGGAG
CCCAACCTGCGCGCCAGATGGATGCTGTGCTTGGTTGCTGCGTGCTGCTAGTTGTTGGGCCGG
CGTCCCCAGCGGAAGCCACATACGCGACTGAGCCGGCGAGCCTTGCCTCCGCCTTGCACCCCC
AGCGGCCGGCTCAAGCTGCTGTCTATCTCTATCACAGTTGGCTTTCTTGGCTGCTAATATGTGG
TCCTCGGTGTTCTCGTTCCCATCTTTCTCTCTCTCTCTCTTTTCTGGAAGAAGCGCGAAGGGCC
ACGGTTTACCGCCAAACACACAAAAGTGGCGCCAACGACGACGTGCGCACGCGTGGGCGCGC
CCTTCTTTCGCGCCAGGAAAGTTTCCAAAGAGGTCAGACCTCTTTCTTATTTTCCTGTGAAAAT
GAACTAAAGGAATGCAATCCTAAGGAATGTTTCCTTTCATTTCCTATGAATCAAAGACATACA
TAGGAAAAAAATCCATAGGATTGTAAATCCTACAAAAGTCCTATGCCAATCCTTTGAATCAAAG
GAGCCCTTAGAGGATTTCATTCCTATAGAAATTTTTCCTATATAGCCCTTTGAATCAAAGGAAT
GGATCCTATGAAATTCCTATGGAATGACTCTTCCCATGCAAGTTTTAGAGGAAATTTAATATG
AGGTAGAACCTCATGGAAAGAATCCTTTGAGTCTTTATCTCTCCTCAAATTCCTGTATTTTTCC
TGTGGCCCAATCAAACAGTCATTCCTATGTTTTTCCTGTGTTTTGCAATCCTCTGTTTTACACTT
GCATTCCTGTCAGAATCCTATGTTTTTCCTATTCCTCCGTTTTTTCATTCCTATGATTCAAATGG
GCCCTTAAGGGTCAGGTGCCAATAAGGAAATCTCCGCCAAACCACCACACCTGGTGTTCGAAT
CACAAGACATCCCATCACTCTTTGGTCGAATGTCGGGTGATACTTCACATGAAGATTGAACTC
GATGCTTGCAAAGATCAAGCTATCCAGCGCACATCTCCACACAAGGCATGGTGCCCAACCAC
AAATCGAAAAGTCACCCCCTTACTGGCTGCAAGATCTTCTTGGAGATTGCCGGATCTAAGATC
CGCGCCCCCTGCTGTCTGATGCACCACCACCGAGATCAACCTCGAGACATATGTGTGGATGAT
AGCAAGATGGGAACTCCAGATCGCCTGGTCGGATTCATCGACATCGATCCTCGTGAACCCTCT
GTCCTTCACAGCTTGGATGATCAGGAATCTTCAGGATCCAATTCCCCGCACGAAGTGAATGTG

FIG. 5II

ATCGAAGGCATCGTCGAGGAAGTACACGAAGAGGGCGAGATTCGTCCACGAGAAGAACCCCG
AGCTCCTATTCCACCACATCCACGCTAAAAAGAAATTTAAGAAGCATGGATCCCACACGTTTG
CCATAATTTTATTTTGTCTTCCTCTTTTTTTGAGGGACATTTCTTTTATTTTTGAAAACATTTTTT
TATTGTTCACCAAATTTTCATTTAAACAAAACTCATAAGGACTGAGGTAAATTTGCATGAACA
AGGTAAATGAGAATTTAGCAATATACGCACCGTGCACCTTGAGAGGTGATATGTTTCTCCTTT
CAATGTTAGCAATTGATTTTTTTCCCGGCCCTAACCTACCTCCAGTGTGACTTGAACTTAAGGA
CTCACCCGTCAATTTGAAAAAATTCCTGCATGGGTTAGTCCATAAAGGATATACATCCGAAGT
CCATGAAAGTACCTGCTCTACAGTTCATTAATCTAACTTGATACCATGTCAAATTTGATTAAAG
CAGGCTATTTAACCTAAGCATCATGCTTAATTTAAAAAGCCTATGAATGCCTACAGCACACCC
AAACCAGAGCATACGAAAATAGACAAAGGAAACATAACCATATATGATCAAGTCAAACTCAA
CTGGAGATAAGTATGAGTAAAAGAATGGTGAACCCCTTTTTCTATCAGCAAGATAGGACTAAC
ACCAACTTTAAACCAAGATGGCCTTGGTTGATGTAACTTGTCATGACAAGCACGTTGACCACC
CCCCTCCCCACACACACACACACACACACTTGGACTTTCGTGTCGCAAGACATCAAAAACCAATT
GTGTGATGTTGGAGTCTCCTATAAGGTGTGTTCCAACACCAAGGATCACCTAATTGTTTAGTTG
ATGTAGCTATTGTGTTCTTAGGCATCATATGACCCTCGTTGTTAATCTCAACCTGAAATGGTTA
ACGATCAAGAATACCTGAAGATGCATACTATTCTAAAAAAATGGTTCATGCTTTTATTGGAAT
GGAACTTACCATGATAATCCGGGTTATCTCCCGGTAATGCTTTGTTTATGGTCTCAAGGTCGAC
CATGGGGACATCGTTATGCAAGATTAGTGCCACAAACAAATACAAGATTTGCAATATTTATGA
TGAATATAAGCATCCACAACCACACTTCTAAACATGCTAGAAATTAGGGCCGTAAGGTGGAT
GTGGTCCTCGCACAAGGAAGCGACATTAACCAGACATGACTCAGGGGATTCTTTAAGTGAGC
ATGAATCCTTTGGAACTTTGAGAGAAAAACTTTCATGCTCATTTGTGGAATTCTCATCCTTCAG
AGTTGATGTCTCAAGCTTGTCCATAGCCTGCAAGTTCTCTTTCTCAAGAGATGCATCGTGCAAG
AATGGGGTTGTTTCTTGATGACTAAAAATTTTCTGAGGGCCAGAGAAACAAGGTTTTTGCTTG
ATTGGAGGTTGTGATGGTGGTTCGGCGGAGGGCAATTTAAGGGTCTCGCCAGAATCTTCATTT
TGAATGAAATAATGAGCGTCCTGTTCTAGAAGAGATTCAGGGGACTCGTGAGACAGAGCCAC
CATCACTTCCTTTATTGGTGCATCGTAGAATTTCAAGGAGCTTTGATGGTTGCTAGATGAATTA
TCCTCAAATTGGAAAGGGGACTTCGGAGGCTGAATTTCTTCTCCCTTTGATGTTCCTGGTTCGG
GTGAGGGCTCTAGAGTTGAATCTACGGGTTCATGGAGATTGCCATAATGTCGTTAAACTCCTA
AGCAAGATTTATGGGTGGCGAATAATCACAAAGCTGGCAATTATGTATTATAATTCTTTCTTG
TAAATATTCCTTCTTTAATTTTAAACGAAAAACCCATTCTTCCTATCGATGCATTGGTCACACT
TCTACATATAAAAAAAATGTCATTGAAACTCATTGCACTTATAGCTCAATTTTATGCATGATCA
AGTAGTCTAAGACTTTTTACTGGCACTTGAAGAAATAAGGATAGGTGCAAATATTACTTAACC
ATGGTTAGTACAGATAAACTTATTTCTCCCTCCCTCCGCTGCCTATCCAAGCATACGCCCCCGC
CACCAATGTTGATGATTTAATTACAATGCTGCAACCGTGCAGTGCCTACTGATGCAAATAAAG
TAGGATCAGAATGAAGCATCCTAATATGTGCCGATGTTGACCAAAACTGCATGTTGCGTGAGT
TCATTCTTTTGTTCAACAATTAGGGCTATTCCTATATCAACATATGCTACTGAACTTTCTACTG
CAGGCGCAGGGAAAAATAATTTCAGTCGAGATGTCTTCAGTAACGTCGATATAAATAACTTCT
AGAAAAATAAACTGAATAATAGGAGCCAGGGAGGCTCCTATTATCGCTTTGTGGTAGGGTAC
TTTGTTCAATTAGGATAAGAAACCAAGTTGCTTGTTTTGTTTGTCTAGAATCCAACGGGCATTA
TCGCTTCAAATGCGTAGAGAGAGTAAAATTGGAGTTAAGATTTCTCAAAACTAACATACAAAC
AGATCCAATAACCTATCAAGAAACAAATTTTGACTAACTAATACTCTGTGATGCAAAACGGTT
AAACTAAATATTTTTTAGTTTCATTTGCCGTTTGATCAATCTGAAAAATTATCCTTTCTAATAG
TATTTCTATCTAATTACAGTACCGATTTAGTGCACATAACTTAGCAAGATAAAAGTGTATATAT
TATTGCAGCCCTTAGAAAAGCGCATTATGTAATCTGCTGAAATCCTTTCCATGAACAAATAAT
TTTTAATTCAGTCATAAATGAAGATAGTGATCCACTCTCCATGAACAGATTATTAGTGTAATTA
AGCATTGGTGGCTTGAGCTGTATATGCATCTGTGAGTCAGATTTGCTCCTAGGATCATTCCTGT
AAATTAAGACTAGCTAACTACAATGGATTTACATGAGTCTTTAATTGTCTGGTCCCTCTGAAGT
TGTGGCTGGAATTTTTCTTTTGGTGTATTTGGTTGTGATTCATGAAATATTTAGATATAATTCAT
CATCTGTTGTGCAAGCATTAGAGAATCATTTACTTGAGTAGAAAGTAAACAGATCTACATTCT
ACAAACTATTTTAATTTGCTAATACTTGCAGTGATCTACGCTCATTTGTCTCAAACTTGATTTT
GTCAATTGTGATTATAGCTAATCTCTCTTATAACGAATTCAGGGCACGTTCACGGCCGGACAA
CCCCGCCACGTGGCATCGCGCAATTGATGGAATTGGCTCTCACCCGCATCCGTTGGATAAGAA
AACAACGGTATAGACGAAGGAACAATGGACCTAACTGTAATTTTAGATTTCCCAGGGGGTTA
AACAGAAAAATTGGCATCACTCTTCCTTGCAAGTCGCGATTCGTCTCCAGCGCCGGCCACCGC
CACTCCGCATCAGTGCCGGACCTCGCCGATTCATCCAGTGCCGCCAAACCCTATCCCACAGCG
CCGCCCTCACTTTACCGCCTCCTCCGTCCGTCTGCCTCCTTCCTTGCCGATGCGCTCGACCCGG

FIG. 5JJ

CAGGCCAGCGGTTGCGGTTGAGCTTGGCAGCTTCCGTGGGGCTCGGTGGTATCGTATGGATCT
GGTGGTGGAGGTGTTGCAGTTTATTTGAAGCCACCGCCTGTGGCATGACGGCACTAAACATGC
TTATAACATACAACAGATCTGGATATTAGGAGTATCTGTTGGAATTTGAAAGTCTACAAGAAG
AAGAAATTCGCATTGATGGATCAAAACATTCCAATAACGATAATAAGAAGGAATCCTTCTGA
GGTACAAGTATATCGATCTTAGTCGTTGTAGTCTAGCTGTACTTATGTAGCTGCTTAGCTAGCT
CTAGTTCAATCTGCCGTTCTGACAGGTAGCTAATTGCCAGATTATGGAGTATGATATCCTTATT
TAGGTAAACATATTGTGGTATGATATGGAGAATTATGCCGCTTATGCTTTGCTGATTAGTGATT
AGAGCCAAGTTTTAGCTGTCGACTTGTATAATTTCGAACCCCCTTTGCTCCTTGGCTCTTAAAT
CTTTGCATTTCAAACCAACCGAAGCTTGTAGTCTTAGCAATCTACTAATGTCTATTTTACAGAT
CTAAGTATTTTAATATAAGTATGAATGAGTCTAAAACTATGATGTGCTATGTAATATTGCAGA
ACTCTTGGGCTAGAACTTATTATTACCTATCTATATAACTAATTTATTTATTTATTTAAAATTGA
CAAGTCAAAGATATTATTCGATAATAGGTTCCTTGGTAATAAGTAGTGATTCCCTTGATATATC
TAGGTACCTATACATACTACAACAAGATTATGATTATGTCAGAGTGTGTAGACTAAATCCCAA
AGAGACGCTTCTATTTACCTTAATCCTATTTTAGAACGAAGTTATATGATGTTCATATAAAGTC
AAAATTTGATTGCAGAGTAATGTAACAAAATCTTAGCTTTTGTTCTAAATAATTTTGTTGGAAG
TTACAGCGGCAAGGCATGATACTAAAATCGATCTGTCAGCTTGACATAATTACATAAGATTTC
GTGTGCTATATGCATGTATGGAGTCCAGGAGTTGTCTATAAATGATGTGCTAATATGCCTTGA
TTTTGCATAACCCCCCAGTTTCTATCTTTGTTTCTATGAATATTTACTATCATAAAAATGGTAG
GTGTCTTAACTATGTGAGCTCTTGCTTTCAGTGCTTTATAGTAAACACATAATGTTCATTTAAA
TGTTTGGGTATCAATAACCTTTATTTAACTTCCAGCTGTTATTATTACAGCAAAATGATGAAGA
AAACACTGAACATTTTTGGTTCAAGCAAAGGGTATAACAGCTCCATTAATGTGCATGGAGAAA
AGAAACAGTTCACTTCATATATCTGTTCAAGAGTACTTTTGGTGTATATATATAATAGCTCCAT
TATATATGTATGGACAAAAAAAACCACTGGTCCAGTAACTAGACCCATAAGTATGTCTGTGTA
ATTCAGATGGAGCTCTATCAAAAGCTCTGAAGGTATGAACTACTGTCCTATTTCCAAATATGA
GCAGCAATATTCGCTAAATTGATAAATTTTCACATTAACCTTTCTATTTGTCAATTGGTCCATA
CCATCATGGAGCACCATGGTTTCAAGATACCGAAAAGTTGAAATAGGATTGCCTGGATCAAA
ATCTGAATATTCATAAATTGATAATTCCAAGTTCAGTGAAGTTCTCTGATTCTTCACTTATGTG
TGAAGTGAACAACAGATTAGTAGTATTATTCAGCCATATTTGGGTAAATGACATGTTTCAGTT
TATAAGTGTTGAATGTGATAGTTGATCTAATGCACTTGCAGTAATTCAGATATTGAGAGTTTTA
TATTCCAATCTCGATCGATATGCAAATCACATCCGCTCGATAGATCCATGGCAAAGCCGCGCG
GGTACTTTCTAGTCATGGAACCTAAATTGATACAATTTTTGGGCTTATGAAATAAAGGCTAAT
CAAGTTAATTAATAATGGAATTTATAACGTGCATACATATAATACAAATCAATATAGTAGTAT
TTGAAAGGCTAACATGCTATCAACAGTCAAGAAAGGAAGATTGAGAAGGAAGCAGAGAATG
AGGAACAGAGAGTGACCTTGACTATTCTGCCCTGGATGCCGATCTGGTGGAATAGGTGTGTGG
AGGCAGCTCCTGCGGATACCCTCCTCCTCGCCGTCGCTATGCATCTGTCATCCCTTTTCCCCTC
TACTTCAAGGCTACGGGGGACTAGAGGTGGATGTGATGCGCCGACGCCAGTGGGGTATACGG
CGGCGGCAGGATCGGGATGAAGCCGCGGTGATGAGAGCAAGTTTAATAGTATAGCCAACTAC
TAGCTTAAAATCATCTATAGTCAATTTAATAGTCAATTCATACAATAGTTACGTACTACACTAT
TAATATCCGGTCACACTTATTATACACACATTACGTTTTAGAGTCCGCGCTAGAGCTAGCTAC
AAATCTATAGCCCGCTGCTCTTCTCTTTCCTCTTTTATCTCATTAAAATATGTTTATAGCTGGCT
TATAGCATACTATTGTATCTGCCCTGAGGGGGGAGATAGCGCCAGCGATGGAGATGGAGAGG
ACTAGAGGGGGAGGCAATGGCAGTGTGGAAGATGAGGCGGCGCGGCGGCTGGGCCTCGAGA
GCGGAGGCGGCGTGAAGATGAGAAGAGTCATGTTCTTTTTTTTTCTTTTACCTCAGGGACGTG
GAAAGACCTCATTGTGAAAGGAATTTCTCGAAGAACCAAGAAGATATTTTGCTGATCATATGA
TCTGCCGGCCTGAAACTGCAGGAATAGAAATCGGACAGTCCATGTTTAGTTGATAACGTGGCT
TATTATTGTTTTGAGAAAGGTCACTACTTTAGATTTAGATAGATTGTATGAGTTATGCACAAAT
TGTCTGAATATGCCATAGAAAGTTTATATAGGCAGCAACAGTCTAAACTAGAAGACTCATATC
TTCTCATACTGTTTGTGTGCCTTCCCTCATACAATAAGGGATTTATAAACATATCAATGTTCCC
ATAATCCCATCTATCTATTATATACTAAAAGTCCATTAATCTCCCTACAAACGCTCCTAAATCG
CCACATGGCAATTTTCAATCTAACCGTTAAGTTTCACTTAAATTGGTGGGCCTATTATTTTACA
CCATTAGATTAGATCTACTTGAAAAGTCATTGCTACACCCATAACGTATAAGCTTTATACATG
AGAAAGTTTTACGAGAAAAATTAAAGTATATTCTGATCGGATATAAACCCATACGTACTGCTC
GCTTAAAAAAAAAAACAAACAAACATACGTGCAGCTATAAAACCAAAAAAAAGTACTACATT
ATACATTGAAGCCGTATATACCGGAAAATCATGTCCATACGAGTGAAACCGCTCAAATCTACG
TACGTACGCACAATTAAAAAAAACAAAAACTTTAGGTACTTTTATTTAAAAAAAACGAACGT
ACATACGCGTAGACAAAACCAAGAAAAAAAAATGTACGTATGCGTAGACAAAAAAAACAGA

FIG. 5KK

TAGTTTTTTAAAATAGTATTTTCTATAGTAGAAAAACAAAACTTATTACTTCACAAATATGGTA
AAAAAACGTACAATAAAAAATATATGATTTGAAAATATATGTTTTCAGCTACGCGGGCATTCT
TTAAAAAGTTGATCTAACAATATATACAGTGACTGACTTTATTTATACATGCAAGTGAAGTGG
TACTGGAAGAAATAATATATAGTCACTTTTCTTTTATAATTTTTCATATACGTTTGAATGACAT
GCATAGGATAGTAAATGGAACATGGAAGAATATACATGTATAGGATAGTAAATAGAACATGG
AAGAATATACATTTTATGAGTGAAGTAGATAACTTAAGTATGAATTCTAATTGTGATTTTTATC
ATAAATAACACAATGGTCCAAATAGATAAAAAAAATGAAGGTATGATTTAAAAGTTAAAAAT
TATAATGAGTTAAAATATATTGTTACAAATAAATATATAATTCAGAAGGTTGTGGTTATTTAA
AAATTATTGTTGCAAATATTTTCATAAAGAGAAAAAGGGAGAAAATGTAATCAAGAGGATAA
ACTTCCTACAAACGCTTCTAATCCGGACATAGTACCCTATAAATGCTCATAGACCACCATGTG
GTACTCTAATAAATCATAGAAATTGTATAAAATAAGAAAAAATCTCGACCAATCGGTTTTCAT
TTAATTTGGTGGACCCATTATTTTCAACTATTAGATCTATCTTAAAACTACAAAATAAATTTAT
TTGTAAAAAGGCCCATGTCGTATTGGCACGACCGGCAAAAATACATGCACGTAGGTATGTAG
GTATTCCTTCTTAAGAAAAGTACGTACCTACGTAGAGTATGTACACAGCTATTCCTATGAACA
GTGCGTATACACACCGCGTCCCACATCCTTATTTTTTTTCTTCTCATCATTTGGATTAGATGGA
AAACCAAACTAATAATTTAAACTAATATCAACTATGCTTTGAGTTGTAAAAATATATGCTATT
TCGAGTTGTATTCAAATTAGGCGCATGTCATCGAAACACCCATAAAAAATATAAATAAATTGA
AAGTATAGATTATGTGATAGTTAAATTAGACTTACATTTTCCAAAATAAAAACAACTTCAAGT
GTGTGTAGAATTTCAAAAATTACTCACTCTCTCTTGTAAAAAATACTGATATGGAAAATGATG
TTATAAATTTATCAGAAATATTTTTTTATGTATTATGTGTTTACTCTATTCATATATTATTAGAA
AATTAAAGATCAAATATATTCATTTGACACCACGTCAATATCTTTTTTCTCCTACTTAGCCTTC
GTTCGATCTAGCTCATTGACTTAGCGTATCCAGGGCACACGAAAAGTCACAAGTCATTAGCAC
AAGATTAATCGAGTATTAAATATTAAAAGCTTGAAAATGGATTTATTTGTATTTTTAGAAAAC
TTCTATAATAAAAAATATTTTGTAAAATATGCACCGTTTAACAATTCGGTAAATATGGTCATG
ATAAATAATGAAGTAGCCACTCCGATAAGCACTTTAGAACTTAACCATAAATTTATTAATTAT
GCACTAAAACTAAATATGTAGTGTATAATATACTTTGTGAATCTAGAATAGTATAATATAACA
ATCGTATGTCCCCGATAAATTCTATGTAATAAGTTCTATATACAAACCAGTGTCAACAATCGT
CAAGTTATATTGTTTATAATACATCCATGCACAATGCACTTAATAATTAGTTGACATCCAATAA
GCACGTGCGTCATCAAGCACTGAAGATATATGATGATACTTAGTGGTAACCCATTAATAAAAA
AAATAATAGATAAGTAGAGGATGACACAAAATCACAACAAACAATAGTTGACTACAAGTAGA
CTAAGAGTTTAAGCAATAGCGTTCCTATACTTCTACAAACACCTGTGAGATGTCATGTGATGC
TCTAATAAATAGGAGGAAATTTAAGAAAAAAATATAAGGAGAAAACAAAACATCTACCCATC
GATTTACACTTAAACCGATGAATCCATTATTTTCAACCATTAAATTAGATTTATTCAGATAAGC
CCTTGCTTCTATAAACTAGCTAATCCCTCTCTATGCACGTACATATACAAGAGATGACAAAAA
TAAAAAAAAAAGAAGTGCGTGTATATATGCACGTACATATACGAGATGTCAAAAATAAAAAA
GAAGTATGTGTATATGGTCCACCACGTCTAGTAGTTTTCAATTTCTTTCTTTGTAGCCCTAAAG
TTCTTCTCAAATTATACATATATGTAGCGACCACTCTTTACGAGGTTGTCGAAGAAGCCACGCT
GCCATGGCGCCGCTTCATGTCACCCTCGCCAATTTTCTTGAAAATATTTTTTTGACCAACGATA
TAAAACGCAATCATAGGCGGTTGTTTAAACGTGTGCACACCCACCCTATGAATACACATACGC
ACACCCTACCTCCTATGAGAGAGAAATATTTGTCAAAAAAAACATGAAAAAGAACGAACATA
CGAGAGACTACCATTCGGGAAAAAAAAACTTACGTACATACGTACAATAAAAAATGTCATAT
GGAATCATATTTTATCCCTTTTAATTATGTCGTTCTCATATAAATTGTGTTAACAATTAGTACA
AATAATTTTGACAATATAGAGTATTTCTTTGTACATTACCCATGAACATGCGCAAGTGAATTA
GATGTATAATAAAAGAAAAAAAACATCAAAACTCATATTATGTTTGCAAAGGATGATGATAG
GTAAGTTTACATATAACCAAAACAAAGTGATTTTTTGTTTGAATATGATAGACACTATCATTTA
CCTTATCAAATTCACGGTATAAATATTTCCTTCTTTTATGGAAAGGTTACGAGGTAATCTACTG
TTCTTATAGTTAATATGATGATATATGACTTTTTTCAGATTTTTTTATATAAACATAAAATAAA
TTGCCCGCGTATCTGCACGGGCTACCTTCCTAGTTAAACAAAAAAGAGGCTGCTTTTTTTAATA
GTAAAACTATAAGTTCATAACCCCTGGCCTCTGCGCCAACCAGAGATTAGCTAATCGGTTATT
ACAACTAAAAAGCTAAAACCAACTAGTGTTCTTCCCTCAAGATTCCGAACCTCACATCTCTTG
TTTTCCGCATACACACTTCCCAAACTACTAAACAGTGTGTTTTTTTGTCAGAAAAGTTTCTATA
CAAAACTTGCCGTGAAAATCATATTAATCCATTTTTCATTTTTTTTAAGATAATACTTAATTGA
TCATGTGTTAATTTGTCGCTCCATTTCACGTATGAATTGGAGTTCCCAACCCTTTCAAAAGAAC
ACAGCCGACTTCGTTAGAAACTGCTTTCGGGATTAGATTCCCTGTAGAACGCGAAACGAGACG
TTGCATTAGCACATGATTAATAACAAGGGAGTAGCCAACCCAAGAAGCACTTTAGAAATCAG
CCAAAGGAATAATGTAGTCCTCAGGGCATCTAAAAAACTATGAATAAAGAGCTAATTGATTC

FIG. 5LL

AGAAGCCAAAAATAACAAAACAAAGAAATGTCAAATGTTGCTTTTCAGATGATTGTGATGCA
AGATCTGCTTACATTGTTACTGAAAATGATTTCCTGGTAGCTGCATACATTTCTGAAGAAATA
GGGTAAGAACACAATAAAATATTTAGCCAAACTGAAAACCACTACGGCAGATTGCATAATTC
ATGCAAAATAGGGATAAGTGCATCATATGTATGACATAGAAAAAAAATGCCATTTGCCGTAT
GGAACTTGTACCTACAGGATTAAATACCAGGACGACCACAGATCGAGTTTGCTTCATTCAGAT
AGTCATATGAGTGATGAAGCATGCATACTTGTTTTTTATTTAAATCATTAAAATAATTGGTAT
GGGATAGGCATAAAAGGACAGTTATATTCTGTCAAGCAGCGATCACGCTTATTTATCCAGGCA
GTAACGCCACTTGATCGATAAATATAACCAATAAGCAAAAAAGCAAGTTCTGATGAACCTCA
ATATATAATTCATCATTTGGGTCAAGCTAACACTACTCCAAATGATCCATAAGTTTCTGTGACA
TCACATGTTTCAAAAATATTAGCAGCAACCCAAAAATCCTCAAATAATCAACCAATCATTTCC
TTGGCCTAAATGGCTAAACCTGTGAAAATGAAATCATACACCCCTCAATGCATATAGCATTAC
TTAACATTATTTGGACTAACAAATCCCTAAGTAAAAACGTTCCAAGATTACAGCTTGAAGTTC
TACCATCTGAATCTTCCATCCGCAGCACCCAGAAACCCCTCAAAGTACTACTGCTGTTATGAA
CTCAGTATTTTTAGCCAAAATATTAATTATTGATTATATATTCTAGAAGCTGAAGCAAAAACCT
ATTCTTATATACACCGGTCCATATTTTTCTTTTATTTAATTCGAAACCCAAGGACAACAGCTCA
GCCCCAGAGTGAACCAACCCACTAGTTTGACCTGATGCAGAGTTGAATTTCCTGTTGTATATA
AAATATAGCAGCGAAAAAAAAAATAATAAAAAAAAAACTAGCAACATGCTGATGCAGATATCC
TAGTTCCAGACTTGGTGTATATATATTTCATACTCGCATTTGCAAATAAGTACACAGATAGATC
ATGCAATGATGGCGCAAAAGATGATAGAAGATGATTGCGAGAAGGTTTATGTGGCAATTAGC
CCCATCCAAAGCTTGTGCCCGCCAATGCTGCTGTGGACGTTGCGCAACACCCCACCGGGGAAG
ACGGTGATAGTGCTCCTCCGCATCTACCGACCAGCCAGAACCAACCTGATTCCTAGTATGCAT
CCTCCCTCTCTGTGAATTGTGTGATTGTTGTAGTGTGTTCTTTGACAGTACAGTTGCTGCTCAG
CACAAACAAGACTACCTGCTGGTTTTTATACGCAAGAGGCGAGAACTGGTGAGAAAATGCTA
AGAGATTACCTGCATGTCTGCGAGTCTCAGAAGGTGAAGTTTAATTGCTTCCAGTGTATGTAT
TCAATTGTGAGAAATGTATCCAGACAATTTCACAGACATGTTACATCTCTTCTTCTCCAGTTCC
ATGCTGAGGTGTTAACAGCTGAGAAGGAGAATGTTGAACTTGGTCTAGTAGAGCTAGTTTCAG
AGCTCAAGATCACAACACTCATCATGGGAGGTGGCCTCTATAGGTATACTCATGAGGTTGCCG
ACTTACTCAGAATCACATATGTTTCTAATGCCAAACTGCCCTGGTTTCTGTAGAATTGTATCAA
ATTTTCATTGTGACAACTCTTGATTCAAAATCATCAGACTCCACTTTTTAATGACCAGGAAGGA
GGCATGAAAAATATGATGCTCACAGATCGCACGATCACCGTGTTGGAAAAGGCTGATCCATC
ATGCAAGATCTTTGTTCTCAATAGAGGAAACCTATTCTTCATCAGGTACCTGTTTCCCAGAAGC
AGCACTAGATCAATCTTTTTTACGCGTAATCTTATTTGAGTTGCTCTCCAAATGTGTCGATGGC
AATGAAAGATACATAACGCAGGGAAAGGCGTATCACCATCTCCACATCCACGAAAAATGGGT
TTGCTCCTGTGGAAGTTTCTGATTTCCCCACTAGCAGCTACCATTTTTTAGGATGGCATCCGAA
TGATTATGCCAGTCGCAGCAGCATATCTTTGTCACTCCTCTCAGAAACTCAGAGCATGACAGA
CGACGGATGCGACTCAGAACAACTTGATCTAATGCTGGAGTACTTGCATCCGGGCTTCGATAA
TGACAGCTTCAGAATTGTCAGCAAAGAATCCCTCATATACCTTGACAAGATAGCAAACCAATC
AACACAATCTGGCCATGCACAGGACTTGCACCAGGCTCCATTTGATGATCGTTGTCACTGCCA
CTTCATTCCTGATATGGACCGGATTCTTGGCATTCAATCAAGGAACGATGACGAGGCACGATG
GAGGAACTGCATCAAACATAAGATGACTGAGTGGCTTCATGAACTGCGGTATGTCTGCACAAT
AGTGTTATCTGCACACAAGCAACTCATGCAGTGGCATCTTGCTGTCCATGATAGCCTGGCACT
TGACAAACTATCAAAAGCAGTAAAAGAACCCATCACTCAATTACTCACCTTTGCATCTACAGT
TAGTAAGATGCATGGTTCACCAGAGAAGTTCTTTCACATGCTGCACATGCACCAGGCTCTGAC
AGAAGCGTATCCAGTTCTACAGGAAGTGTTCTCAGGAGAGCTCAAGGAATCCTTTACTGGTGA
GCTTCACAAAATTCTTCACACCCTAAAAGATGGTACAAAAGAAACACTTGATCAGTTAAGAGT
CCAAATTCAGTCATATAGTTCAGAAGACATGCCAGAGGGAGGCGGCATACATTTGGTCACAA
CTTACCTCATCAGATATATCATGTCACTAACACAAAACACAGGTTCACTGGATGCAATTCTTG
CTCACAGTTACGAAGACCATGCATTAGCAGAAGAGAGGATGATGAACACATCAGGTCACCTG
ATATCTATGCTGATATCTGATCTTACATCCATGCTCTACAGGCTGTCTAAGTTGTACATGTCTA
AATCTGAAGGTTTACAATGGTTATTCCTTCTGAACAATGAGCATTTCATACTTCGGAAAATTG
AAGAAGCAGATATAAGGTCGATGCTACCAGCTGATTGGATTCAAAATTACCAGCACAGAGTC
GAGCAGAACAAAGTGAATTATATAGAAGCAACATGGGCTCTGACCCTGTCTTATCTGAAGAA
AGGACCAAAAGTCCCTTCAATTTCCTTCATCCTTCAACCATGAAAGAGTTCACTTCATCATTTG
AAACAACTTGCAATGCACAGGCACATTGGAAGGTCCCTGATCCAAAGCTCCGTGTTGAGCTGA
GACAAACTGTTTGTGACTATGTTCTACCTGCTTATTATGCATTCATGGAGAATCATCCAAATTT
AGAGAAGTCATCTGGACGTAGTCTGGAAGACATTAGAAACAAATTGAGTTGTTTGAAGGATG

FIG. 5MM

AATTAATACTATTGCCTGTCCAGGCAAAAAATAATTCACTCTGTTTGTTCCCTTCTTTTTCCTTT
TCTTTTTTACAGAGGACTTAGCATAGACCATAACAGTGCAACTTGGAATTTCATTTGCAGTCTA
ACACTTGTAAGCTTCACTAACAATGAATGTAATGACAGGAATGGTTGCATACAATATTTTTGT
AATCTCATATGGGACTATCTAGACCTAATTTCACTACTATTTTTTTGAGGGGAAATTTCACAAT
TTCAAATTATCTAAGCAACGAAAAAACTGCTAAATCATGTAGGCCTACCTGTTGATTTTTCCTC
TCCATCTGCAGCCCAGTGTGCTAAGACTAGCAGCCCACAAAAGCTGATGCACAAATCTTAAGG
TGTATTGAACAGTCAAGAATTTGACTGATACTAGCTCTCATCAAATGTCAACATATCTATAGA
AAAACTGATATTCTTGAGAATTCTTACAAAGCTATTTAATGACAAGTATGATGTTTAGAGTGT
TGTTTTATTTTCTCACGGTACACATGCTTGTGACTCAACCTACAACTGATAACTTCACTTTATA
GCAATGAAAAAGAGAGAAAATGAAATGTTATCAAAAGCAAGTATGAAGATATCTTTTTAAAA
ATTGGGTTTCAATGTCAGATCTATACCTGCAATTCAGTAAAGACTTCATATGAAGTCATGGAC
CATGAATGTACAAGTCAGTCACCATCACATGACTAATTTGTATGGAACTTAAAATCAGAATCA
GTTAGTTGTCCAAGGGAAAGGCACTTTATATTATCTAGTGCTTACAGCATGTGAGGTTATACT
AATCAGACAATATACTTTGTGGCCACATCAACCGACAAAATAGAGCTTCATACGGATTAGGA
AGAAACTGATATGGAGGGTTAACTGGAGAGTTTGAACAAGTAAGAAATTGAAAATTCAGTAG
GTGTCTTCTGCAAATGTAAATGTAGGTACAGAGTAAATTCCAGACTAATTATAACAAAAAAAC
ATAGTTGGATTTGGCATCATAGGTTGATTTAGAAATGAATTTGCATCCAGTAATTTAGCAGAA
ACACTTCAATATAAACTCCATATTAACTGACAGAATTGTCCCAGGAGCTTAACTGCTAAATTT
GCCTAATAGAGAAATTTTGAATGTGTCTGTTCGGTTGTTTCTAGAACTTCTTTAGCAACGAATT
ATTACTGCAACTGTTTAGGCACTAGCTGCTTGTAAATTAAAGCTTAGAAAGGTTTGCGCTCCC
ATATCTCAACAAATTAGTAGTTCTAGGACAAGAAAAAAATGCTACTCCCTAGAAATTACCACA
CAGTAGATGGTTGTAATACCACGCAATAGGAGCAACATTCAACCAAGAAACTAGTATGACAA
ATCCTCTGAGGTGTAGTGTGCACGCTTCTGATTCTTAACACTCCTTCCCAGGTATGCTTGATAA
CATTGAGTGACTCGGGATGATATGGTTTTTCTCACCACTTGCCGAAGTTTGGGGTCTTCAATTT
TCCAGTACTTTTGCACTGCACAATTGTTGTTCAACATTGTGTAAAATTCAGTTAAAGGAGGCA
GATGAAAGCAAGGAAAAAGTATGTTCTTCCTTGCAACCAGGCGTGACAGGATTGGTTCCCATG
AGTGCTCAAGGTATCTCGCTATCTGATACTCGACCTGGTTGTGGTGCCTCGTAATCCAGCTTTG
TTGCAGCGCTGACTTCATGTCTAATTTCTCGAGTATCTCCAATATGAAATGAGCATTGTTTAGT
AAGAAAATGCATTGAAACTCTGTTGACTGATACTTTGATATCGTCTCAAGCAAGGAGTCTAGG
TATCCGATCAAGGACTGCACAAAATAATCCAGTCGCGTCCATTTCCCATCGTGTAAGGGATTC
TCGCTCTCCCCGTCATCTTGAGCGAGAATAACGTTAAGCAAGCTATCATGTTCCCACATATATT
TGATATAGTTCATCATATATGAAGTAATATTGTGGATGCCGCCTCCCCGCGGCACACTGTAAA
TGCCATTTAGAGCTAGTGAACACTGCCCCTGAAAAATCTCCCTTACACACCTCTTGAGCTCACT
GGCAATGCCGTTTACCTGGTTGACAGGGAAGATTTCAAGGGTCACGTATAGACGCAAAATAG
CAGGGAGCAGATCAGATGACGGTGACAACATAGTCATTACGCCTGCAAGCTTCAGCAGGCGA
TGCATATCAGATTCTTGTTCTTGCCCATGCTTGCTGTTGATTTCTTGAATGCTCTGATCAATCAT
TGCCACCAATTCTTCCTTGAACAGTTCGAGCATCCGCGAGTCTGCCCTCTGAATCCAGATACG
GATATTTGAGAGATCGAGTCCATCTTCAGGGATGTCCCCCAGAAGTTGCTTATAGATGCGAAT
ACCGGCTTCATAAGAGCACTGCTGATACTGGGAAATAGCAGCTTCCTCAGAGGAGCTTTGGAT
ATCATACGAAGAGGCCAATTCTGTTGTGCTTGTGAGGACAAAAGACATATTTGTTGATGAAGA
TGTGGAAGCTGGCATCTTGTACCAGGTATCTACCAAGGACAACTCTATAGAACAATATCAAGA
TTCAGAAAGGAGGAATACTATGAAGTGGCAAGAAACAGTTCTGATGAACTATTATATGATGA
GAGGAGGGAAGACACGGAGTTAGTTGGGAAAACGAGTGAAGACTCAGGAAGAGTAGTCAAT
AAGTCAAACCAATGCACCTCCAATTAAAGAGAATGCATTTTTCTGCAGCTAGTCAAGGTCTTC
ATATGATTTTTCCTCGTTGCACCCTTCTGTGCAGAAAGATCAACATGCGGAAAATAAAACAAT
TTTTTCCTACAATTCCTAATCTAATGGACTAGAAAATGGCCACCTCATTCTTTTACTGAACAAT
AAACAGATTATTATTCTTTGCCTTAGATTATACGATCGATTATTTCCAAACTACGATTTCTTCA
AAAACTTTCTACATCAGCATTGCTGAAATAACTTAACCTGAGCTATTTATTAGCTTTATTACAT
ATAATATTTAATTTATCCCTCACTAATCCACCATCCATCATCTTTGCTCCACATTTCATTCATGA
ACACCCAGAAGTTCAAATGTGCCGAAATAGGCAAAACATGAAACATGGCAGAAGTTTCTGTA
GCATTTCTATAGCACCCAGAATATATGAAAAAATAAAACGCACCTTATTTCTCACTGTTCCAT
GCATCTGTGTTTCATTCCAGAAAAGAGTTCTTCATATTATTCAACAATGGCAGCCGGACATAT
CCAGAAGGATATATATATTACCTACCACCCCCATCGCCTCCGGTTGCGCAAAGACCTATCTGC
GACTGCAGAATCCAGATCCGCCGATTTCTTGGATCCATCCCTGCGGAACAGTAGGGCAAGAG
GAGGATTGGAAGTTTGGAACTCGAAAATTGTTTCAAACTGGAATAGGGAATTAATTCCCCTCT
CAACAAAAGGGGAAAAAGGAAATGGGGAATACAGATAGAAAACCCTACGAGATTTCGTCTTG

FIG. 5NN

ATTTCACAGCCGCGGGTACTCTTGCTTCCTGCCTTCCTGGCGATTGAGCTCGCTCGAGAGGATG
GAGTTGGGAGACAGAAAGAGGAGAAATTTTGATAATTACAATATTTTTTTATTCCCATCACT
TAGGTCTGTTCAGATTGGTGTAAAAATGAACTATACTTAAAATTTTAGTAATATTACTAATTTG
TCAAAATTTTAGCATTGACAATTTTTTGATGTGATTAGCTTAAAATTCTATACACATTGCCAAT
ATTTAATAACAAACTAAACCTAGCCACATAATTATCAATTTTATCAAATAATGGTATGGTTGA
AAATGTCATTAATCTGAATAGGCCCTTAGACCCTGTTTACATGGGACTAAAACTTTTTAGTCCC
TATCACATCGGATGTTTGGACACTAATTATAAATATTACACATAGACTATTAATAAAACCCAT
TCTATAACCCTGGACTAATTCGCGAGACAAATTCTTTAAGCCTAATTAATCCATGATTAGCCTA
TGTGATGCTACAGTAAACATGCGTTAATTATGGATTAATTAGGCTTAAAAAAATTATCACGCG
AATTAGATCTCATTTATGTAATTAGTTTTATAAGTAGTCTATGTTTAATACTCTAAATTCATCC
GATATAACAGGGACTAAAGTTTAGTCCCTACACCCTCTTAGTCTGAGTTCCTTAGTTTACTTTC
CACACGCACGTTTTTCAAACTACTAAAAGATACTATATCTTTTGCAAACAAATTTCTAAACAA
AAGTTGTTTTAAAATTCATATTAATTCATTTTTTTAAAAAAATAACTAATACCAATTAATCATG
TGCCAATAATTTGCTTCATTTTACGTGCGCGGAGTATTAGTTTCCAACCCCCGAAGCCAAACGT
AAGTAGTAAGCCTTACTTGCTCCGTCTCAAAAGGAGTATATTTCTAGAGTTTAAAATATATTTC
TCACTTCAGAGCAGTGGTTGCCCTATTGGTTATCTTCCATCCAAATTTCTTTTCATCCGGTCTTA
ATCATCCTCCTACTTGGATTAAAATAAACGGAAATATAGAGCTTGTTTAGTTTAGTGTTCTACA
AAGTTTTAGCGCTATCAGTATTTTGGTAGGCGTAGCATATAATTGATTAGTTTTGTATTGAAAT
CAATTGGAACCAAATTTCATGATATAGAGAAGAAAGTTACAGAACTGACCAAAATTAAGTAT
GGGCATTACCATCTACTTCTATTTGATTTCAAACCAAACCATCATACTTACTATTCAAACTACC
AAAAAAATTGATAGAGCATATTTTTGTCATCAATTCAAAATGACCCACAATCTCTTTCTCATAT
CTTAATTTGTGCTAAACTATTTAGAATGATAAGTATAGGATGGGGTTATTAGTATTAGAGGTA
GGATTATCTGAGTCTACTGCAGTGACCCATGATTTTCAAATACGATAAATTCACAAATACGAA
TAATTTCCGTGGAAAAAAAACGTGCACTTGGGAATTAATTTTGTAACACACTACTTCTACGAT
TAGAGGAAATGTGGGCCGCTAGCAGTTAGAGGACACTACTTAGAGAAGGATTGTCATCTTTGT
TGCAGGGATCAGATAAAATATCACTTCTTGCTGTAAGTACTTTTAAAAATATTATATTTCTGTA
TATTTCCTTGTCTGATTTCTTTTCATTTTTAATGTCTCAAGCCCATTTTAATTTAATTTCCACTTT
TTTCCCTACATGATACACTAAATAAGCAAACTACCAATATATGAGCATGTTCTCATAAAAAAA
CAATATATGAGAACATTATGTTATATTTTTTTAGGGACATAATAATAGACCGTTTCCACTTAAC
TACATGGCATATATTTACAAGACTAACGCACTTGATGATAAATTTACAAGTAAAAATAAATTT
TGTCACAAGGAATGTACATTTAGGGAAACAATTAATTAAGAGAAAGTACTCTGTAACACACT
ACTTCCACGATTGAGACATGGGACAAAGAGGTTATAGACAAGTGGAATAAGTTCACCGGAGG
TCCCTCAACTTAATAGCGAGATTTTTTGAGGTCCCTCAACCAGTAAACCAGAAATGTTCGCCC
CTAAACTCATTCAAACCGTTTACTGGAGGTCCCTTGGTAGTATTTTTGCCCGGTTTTACTGACG
TGGCATCCTAGTCAGAAAAAAAATTAAAAAAAAATCGTGGGGCCTATATGTAAGTGAGAAAA
AATATGGGTTCAACCATTCTAGTCAGCAATCTTCTCTCTTTTCCTTTTTCTCTTCTTCTCTTTCG
GCGTGTGCGCACCGCGGCGACCTTAGGCTGGGCGGCGGCATGCGCCTCGACCCACGCAAGAG
CATCAGCGGCGGCAGAGGGCGGCGGCGCGTGGCCAGAGCAGATAGAGGGGTGGCATCAACG
GCTGCAGTCGGCGGGCGAGCTCGGCCACAGAGAGCGAGCGGTGGCGGCGCGCGGCTAGAGC
AGCCAAAGGGGTGCGTCGGCGGCCGCAGAGGGCGAGCGGCGGCGTGCGGCCGGAGCAGGCA
GAGGGGCGGAGGACACGGGGTGCGCGGTGGCGCAGATAGGGAGCGGCAACGGCACGCGGCT
GGAGGCAGGCGGAGCAGCGGCAGGCGAGCGCGGCTGCGGAGCATCGGCGTCGGCGGGCGAG
CGACGGAGGGCGGAGCAGGCAGGCGGCGACGGGCGAGCGCGGAGGGAGACAAGGTCATTGC
CGCCGCTCGGAGAGAGGCGAGGTCGTCGCCTTGGGTGCCTCTCGTCCACCCCCGACAACAACG
ATTACGAGCCCCCCGCGCCGCCGCCCCCGCCCGGGAACAACGATGACGCCTCCGACCGCCTGC
CGCCACCTCCTTCTTCTCCCGGTCTCGCCCGCCGTCCGCTCTGCCCGCAGCCTGCCGCCGCTCT
GCTGCCTCCTCCTTCCTCTCCCAGTCTCGCCCGCCGTCCGCTCCGCCCGTAGCCCGCCGCCGTC
GTGCTGCCACCGCCTCCTTCCTCTCCAGGTCTCACCCACCGTCCGTTCCGCTCCGCTCCGCCCG
CCGCCGCTCCGCTGCCTCCGCTCGTCCGCCGTCCGCTCCGCCGCCGCGCTCGTCCGCCGTCCGC
TTCGCCTGCAGCCCGCCGTCGCTCTGCTGCCGTGCTCGCCCGCCACCCGCATCCACGCTCGCCA
TCGCGGTTGTGCCCGCCTCCGGCCTGAAGAAGAGAAGAGAGAGGAGAGAAAAGAGAAGGGA
AGGAGAAGAAAAGAGAAGAAAAAAGATGTGTCACTTACATGTGGGCCCCATGAATTTTTTTT
AATTTTTTTTGCTGACTAGGATGTCGCGTCAGCAAAACCAGGCAAAAATACTACCAAGGGACC
TCCGGCGAACAGTTTGAATGAGTTTAGGGGTGAACATTTCTGGTTTTGTGATGAGGGACCTCA
AAAAATCCCGTTGTTAAGTTGAGGGACCTGCGGTGAACTTATTCCTAGACAAGTCCCAAGACT
GTTACTTCTCTTGTTGGGCTTTCTCATGCAAATTCCTCATCGAAATTCTCATGTATTTGCGCGCA

FIG. 5OO

AAGTTTGCATGAACATGGGCATGACATGCCGACATTTCTTTATATTAAATTGTTGAATGACCG
TATAAGTTCTATATATATGCCCGTATGTAGCCATCTTTAATTCTTTTCCCTATATACCGTTTTAC
AGCTTTATACTAAAGGTTGAATTACTGACAAGTAACAATATAGAAGGGTGAGTTCTATAGAGA
AGTTGAGATGGGTTACTTTATCATTTTTACTACGTTTTTTAAACTACTAATCTGTGTTAACTAA
AAAATATTTATATGAAAGTTTCTTAATTAAAAAATCAAACAAATTCACTTTTTAAATTTACAAT
AGCTAGTACAGTACTTAATTAATCATGAACAGGGTGTTCGTTTCAAATTATGATACAAATTTT
ATCTCAGTTTTCGTTACAACGTATTTTTTTCAAACTGCTAAATAGTTTTTTTTCAAAAGTTTTTA
TATAGAAGTTGCCTTAAAATATCAGATAAATTTATTTTTTTAATAAATTAATTAAAACTCAATT
AGCCTCGTGCTAATAACTTTTTTTGTTTGATATGCTCGTACTTAATCCTCATCCATCGCAGCTTC
GAACATGGTTAGTAATAACTCTTCTCGTTTTACATGCCAAAAATCTCTCTTTTAAAATCAGCCT
TCATGCGTAGCATGTGGCTCGAAGGGGAGCAGTATGTATAATAAGCTCAAGCTCCAGCACGA
TTATTATGCCCAGATTTGCTTGTCATCAGATATTCGGATCCAATCCAATCGAATCACACAACCG
CCAGCCGGGATACGATATCGTTCCACAGCAAAGTTAATTAGTACGTCATGCTATGATTGTATA
CTCGACGATCAGTCCAAATCCCAATATGGGAAATTATTTTGTTCTATTGAGAGAATGTTCCCAT
GTTTGTTTACAAATTATCTAAAGGTTATGAAAATATTCGAAATATTTGAAAACACTCACGCAA
CATGTATGTGCCACTCCAAAAAATTTTAGATCCAAACTCAACTCACATATCGAGATATCAAAA
GATAAATTCAAGCCCTGTTTAGTTCCTCCAAAATAGCAAAAGTACTTTTTGCTAAAATAGATC
TAAACACTACTAGCAAAAGTTAGCAATTTGGCATTTGTCATTTGGGAGTCTAGAGTAGCAAAT
TTTATCAAAAAATGTGTTGGGAGCCGTGCTCTCTCTGCCTTTACTAGTAAAATGGCAAAACTTT
ACCATGCATCTATCCACTAACTAGCAAAATTTCAATACCAAATCTTTTACCACCAAAACTTTTG
CAAAAAAATTTTGCTAAGCACGCCCTCAACGTATACAGCAAATTTATCCTTTTTTTTATTATTT
CATTGTTTAGGTGGAATTTAAACTTCATTTTTTTGGTAGATGGATTGATGTCACTATACTGTAC
ATTGTAATTGTTATTCATAAACTTTCACAACTATTTACGTTGGATTTAGAAGAAAAAAAGTTAT
ATGAGAGAATATCGAATTCTCAATGGATTATAATCTATTCCATCGAAATATTTCTCTTTAGTTG
GAGAGAGGAGGTTGGTGAGACAAGTTGGGGTTTTGGTTTGGTTACCTTAAATGAGTAAAGTG
GTGCTGGTAGCCTGGTACTACTAGTAAACCGACGATAAGAACACATGCCAACAAATGACAGT
TAGCTAGCAGCAGCAGCACAGCACACAAACGACACGACAACCCAACAACACTCGCGCAGATG
AGAGTGAGACTAGTCTGACCAACCACCCTCCTCTCCAGCTCTCCTCCACGAGTGGTTGGTTCG
TTGAGGGTGACGCGCGCCAGACGCCATCATCATCCTCCCTATCGGAGAGGATGTTTGGACACT
AATATTAAATATAGACTAATAATAAAACTTATTCCATAACTCTGACTAATTCACGAAACGAAA
TAATTAATCCATGATTAGCCTATGTGATACTATTGTAAACATGTGCTAATTATGGATTAATTAA
GATTAAAAAATTTATCTCGCGAATTAGCTCTCATTTATGCAATTAGTTTTAATACTCTAAATTA
GTGTCCAAACATCCGATATGACAGGGACTAATGTTTAGTCTCCGGATCCAAACGTCTCAACTC
TCAGGACAAAGCTTGTCCCGTACTAGGAATCAGTGGCACAGAAGGTGTCGAATTATAAAAGG
AAAAAATACGAATTACCCCCTAAACTATTGGGTGAGTACGAATTACCCCTCTAGACATGAAAA
CCGGACGTTTTTTTACCCTCAACTATCGATACTGAATGTCCCCCCCACCCCACCCCCCCCGCGAA
CAGTTTTGCAAGCGATTTTGGTCTACGTGGCTGTCCAGTCAGCAATTCATTTTTTTTAAATCAG
CGAGCCCCACCTGTCAGTCTCCCACCCTCTCGTTTTCCCTCACCTCTCCATCTCTCTCCAAAATC
CACTCTCTTCTCCCTCCCTCACCTCGAGGACGGCGGGCAGAGCTCGGGGCGACGAAGGGGACC
GCGGAGCTTGGGACGGTGGCAGGAAGAGGTCGGGACGATGGCGGGTGGAGTGGGCTGTGGA
GGGGACGGCGGCGGGTAGAGCTCGGGGCGGCGGAGCTTGGGACGGCAGCGTGAGGAGGGGT
GGCGGAGGGGACGGCAGAGGACAGAGCTCGAGACGACGGCGAACGGAGCTGGGGGCCGAGG
GGGCGACAGAACTCGGGGCGGCGGATGGCGGAGCTTGGGGCGACAGAGGGGGCGCTTGCAG
CCACCGGCGCTGGGGACGACGGCGGGCGGAGCTTGATGCAAAGGGGGCGACGGAGCTCGGG
GTGGCGTAGGGGTGCCCGCAGCCACCGGCGCGCGGCTCGTCGAGGTAGCGGAGGGGACGCCC
GCAGCCAGTGGTGCTCGGGGAGTTGGAGGGGGCGGCGGAGGAAGCTCCCGCAGCCACCGCTG
CGCGGCTCGTTGAGGCGACGGAAGGGGCGTCCACTGCTGTCGGTGTTCGAGCTGCAGCCACC
AGCATTTGAGAGAGAGAGGGTGGGTGAGAGCGAAAGAGATAGAGTGGAGAAATATCTGACA
AGTGGGCCCCATCATTTTTATAATAAAAAAATTGCAGCTGCCATACCATACCACAAGAGAGGG
TCCGCCACTAGACATGGCGCATCCTAATACATCAAATCAGGGGCTTGTCCAGATTCGTTGTAA
TGTGTCTCATTTTGTACTAGGTTTGTTTTTTTATGGTTTGGAGGGAGTAAATACCATACATAAC
TATTTGCTAGAGTCTGTAAATAGCTTGGAAAAAACTAATTAATTGTCCTTCAGCTGTTTATTTT
TTTCTTCCATGTAGCAAGCATTTTAGCTATCAAACTGAAAATTAATACAAATATTTAATATTAA
AACTATAGGTTCTAGCTAAGAATCTGGACATAACTAAAAATTCATTTTTTTATAGATTTGGCA
GGCAGTAGGGGCTACTCAGGCCAGCTGCTCAGCTCAGGCTCACCTTCTCCCCCGCTAGGATCG
CCACGGCTACGAATAGTATTGTTACACCATAATAAGCACGTTACCAAATGTACGATCACATTC

FIG. 5PP

GGTGTAACCACGAGTTGGAAGATTATCATCACCATGTAGCTAATCTAGCCCTATTACGTACCA
AGGTTGTCGTTGGAAATTTGGTCATAAATCGACATATTTTAATTCAGAAAATTAAGATACTAA
GCATTACAGGTACATAGTTGAATGATCTAGTGAATGTATATTAAACATGAGCATGCTTTTGAA
AATATAAGCATAAACATCAAGTATATTCACATATGATTGGCATGATGATAAACATGAATATAC
TAACAGGAACTATGGTATCTAACAGCAAGTTTAAAACGAGGATGAATATATCCGGAGAATGC
TCCAGTACTAGTTGAGACATTGTTGGTGTTGTTGCCTCCGTTGGTATTGCCGTTCTTACCTTCTC
CAGTACTGGTGCGGGTGTTGGTGTCGGTGTTGACGGTCGACATGGCGTTGCAGAGGAAGGAG
AGCCTGACAAAGAGGATGCAGCGTAGTCAAAGCAGAACAGGAGCAGTCCGCCGAGACGCTCC
CCAAAAACTTGTTCGTTTTACCTACCCGTGTAGATTCTCAAGCAGACAGCGTTTCGGAGGCAC
CTTCTCATCCCGTGTACCTGTGTGCATAGGTGAATAGGACCAGGGAAGCGGTGGCTAGCGCAG
GAATAGAGGCACAAAGAGTTTCCGAGGAAGAGTAAGCGAGAGAAAGGAAGACACAGAGCAG
CTGAGGTGTGTCAGCTGTCTGTCCCGGTGGCGGCCTTTTATAGTGCGTGAGAAGGAGAGAAGA
ATCAATACGTTACTGCAGTAACAACGGAATCAATCTGATTTAAGTCAGGATTGATTCATTCGT
TATAGGAGTAATCGCACCCATATTGAAATCGTATCAATTGCGATTTAAGTCGGGTAATCGTGC
ACGTATTGAAATGGTATCAATTGCGATTTAAGTCGGGATTGATTCATCCGTTATAGGAGTAAT
CAAGCCCATATTGAAATCGTATCAATTGTGCTGAATGAATTGGATTCAATTCTTGTCCGTTGCA
AAATTTACAAGAGAGAGAAGCAGTCGCCGCCTTCCTCGCCACGGCCCAGCCCAGCTCGTGCA
AGCGCGTGCGGCAATCCCACCACCATCTCAACCGGTTAACAGGGGCTCTCTGATAGCTTCCTG
TTTAAGTTGAGATCTTCCCCACTTAAATTTCTAAGGTGATATTAATCCCTATAGTAGGGTCTAG
CCTATTTATTCCATCAGTTGTCATCATTTTTAAAAGTAGATAGTTATGTCCAAATTTGTATCTGT
TTTTTTTTTTACGGAGAGAGAGTACTATACTACTCCTACTTCCCTTCTAAATAGGTATGTCCAC
ATTCATATTTGGAAGTGAAGTTGAGTGCATTGTAACTGAAAGGATCGAGCCAACAAACCACA
ACCGATATAAAGTACAGTTAGCAGCAGCACCACCACAAACCAAACGACAGCACAACAGACTC
GATGGTAAGACTATTCTATGTCCAACTCACTTTCCCTCTCCCTCATCGAGTCATCGTCGCGTCG
GTTTAATTTTGCTTCCTTGAGAGTGACGCATGGCCGACGCCATCTACTTCGTCAGGTCTCTGTC
TCTCTCTCTGCCTGCTTGCCACTGCCTTTCGGTGGTTCGTGGTAGGTGACAGACATGGCCGCGC
CGCAGCAAGCAGCACGAGCACGAGCAAGCACCAACGCGCGCCACACTCCGGCTATTCGAAAT
TTGATATCATAGGGTTTGAAATTGTGCGAGTAAAACTTTATAGTGAACTTAACGTTTATTCTAC
AGAATTGCTAACCTTTATTCGGGAGAAATTTGAGATGAATTATATTTATGTCAGATCCTCCTGT
TGGAATCGTGTCATGATTCGTGCTGCACTTCTTTTTCGCCGGCTCGGTGCGATGGTGAGAACTC
CGATGAGATAAAGGCGGCCCGACCAGCTAGAGTGCTGAGTTGAGGTAAGAGTGGAAAGGGGT
CAGGGAAAGGGGAAGAGGGTTGCAAGCTTAGAGAGTGATGGTTGTGGAACACGGCGGAACG
GGCGAGCGGTGAGGTGGATGCTACCGAAACCACAGGGTCGACAGCATGCGTGGATCAATGTT
GACATCAGGGGCAAAGCAAAGTGAGTAGTTAAGAAGTGGGAGAAACGGTGGCATCTCCGGC
GGTGGGAATCCACCAAAAACAGGGAAGAAGGGGTAGGGGCACCGTCACCAGCTTAAGGAGG
AGAGGCGAAAAGGGGTGAGGGGGAAGTGCGATGGAATGTATGGCAAGCCCTGTCGGTATGGT
TGCTTCTTTTCTGACGCCGATGAGGCCAGGTGGCAGTGCAGTAGGGGCGATGATAGCTGGGAT
CGGGCATAGGGAGTGTACTCGATTGGTCAAGATTGGGTGGCACAGTCGTGGTAACATGAGGC
GGAGAAAGAGAGTTAGGGTTTAACAGATGCATGGATCTTAAAACAAATTTAACGATCCAAAA
AATATCAAATGTGGGATGAAATTTTCTGTCACATAGTAGTATTAAATCAGCAATACCTTTTATT
TAAGACATGTTTAATTTATTGACACTTTCAACTTCGCTAAATTTCGGTAGGACAACAAACTAC
ACACATTTCAACCATTACTACCTTACAAAATTTTGGCAGTTATTAGAAGCTTTCTCTCGTAACA
CTCTAACCGAATTTAGCAATGTCATCGAAGCAAACGAAATCAACACCGCCAAAATTTTGTAGT
GTCAAAATATGTACAAATCTCGCATTATCAAAATATGCTATGGTTGATTTGGGAAACAAAATA
AACCAGCCCTTAATCCTGCCACTGTTGAAGCAAACTTTAGGGAGTTTTCAACGCAAATAAGCG
CAGTTCTCAAAAGAAAAAAGAAATGCAAATAAGCCCGTACTCCCAGTCCCACGGTCCCACCG
CGGCTGTCGCCGTGGGGCCCGCTATCCGACTCTTTTCTTTCGCTTTCTCGCTGCCGGCCGGGGA
GACCTCGTCCACACACGCCAACGGCCGGCAGAGGGGTGGGGGGTGTGGGGCCCACCATGTCA
GTGGGCGCTGGGCCGCGTGGTTGTGTGCTCCGTTTGTCGTGCTCCGCGGTGCAACGTCGTTTG
AGGTGGGCCCCGCACCGCCGGGATCCGCTGCGCCTGGAGGGAACAGACCCACTTTGTTGCTCA
GGTGCACGCGTGCAGCCGCACACCGCCGGACAGAAGGAACTACTCCGTCAAAAAAAAAAAA
AACTTATATATGTCCAAATTCAAACTCAGTATTAGATTTTTTTGACAGAGGGAGTACTCTGCTA
AGTTCATTTCCAAGCTTTCTCAACTCACCCCTCTTTTTTAGCGCGCATATTTTTAAAACTATTAA
ACAATACTCTCTCTGTCCTAAATTATAAAGACATATTTTTTACATGGTCTTCAATAACATATCT
TGACTAGTATTTTATTACATTCTATGATCCCAATAAATATGAAATTAGCATCACATGAAAGTA
CTTCAAAATATGAATTTAATGACATAACATGTATAATATTTACTATAGATATAGTTAGGCTGT

FIG. 5QQ

GTTTTTACCTTTAAGTTCCCAACCCCTCTCACTCATTTTCCGCGCGCACTTTTTTAAACTGTTAA
ATGATGCGGTTTTTTAAAAAGTTTCTATATATAAGTTGCTTTAAAAAATCAAATTAATATATTT
TTTTAAAAAAAATTAGCTAATACTTAATTAATCATGCAATAATGCATGCTTCGTTTTGCGTGCCG
GGGAGGAGTGGTTCCCAACCCTCCTCCCGAACATCAAGGTTCCCAACTTCTCCTCCTCGTTTTC
CGCGCGCACGCTTTTCAAACTGTTAAACAATGATTTTTTTGCAAAAAAGTTTCTATACGAAAG
TTGTTTAAAAAATCATATTGATCCATTTTTGAAAAAAAAAATTAACTAACACTTAATTAATCA
CACATTAATGGACTACTCCATTTTCCGTGCGAGAGGGTAGGGTTCCCAACCACTGGGAACGAG
CACAGCCTTAGTATGGTTATTAGTCAAAAGTTACCGAGTTTGATTTTCCTTAAAAATGGGGCA
CTATATAATTTGGGACGGAAGGATTATGTTTTTCGTAAAAATTTAATATAGAAAAGTTGCTTT
AAAAATCATATTAATCTATTTTAAAAAATAGATTAATACTCAATTAATCATACACTAATAAAT
TGCTCCGTTTTACGTGCGTGAGGGATTAGTTTCTATCCCCAAGTGCCCTTAAGCACCGTACTTT
TAAGTTTTTAAATAAAGCTCTTGTACTACCTTCGTCCTATGATATAGCAACCTAATATCGGACG
AGACATATCCTAATACTACAAATCTAGCCATGTTTGCTTGTCCAGATTAATAATATTAGGATGT
CTCGTCTAGTATGTACTAGGTTGCTATATTTTGAAACGGAGATAGTAGTATACTCCCTCCTTCC
TAAATTGATCATCATATAATGGAATTCAAAATTTCTTAAATTGATCATTATATAACCGCATGA
ACACTGATTTTATCATAATACAATTAATACAGCATGGGAGAATGTGTGCATGGTGTCTTGATT
AATGTGATTTAAATTATCCTTGGTCTTGGTGCATAAACATATATGATGATCATTTTTGGAAAGA
AGGGAGTATTATTTAGTATCAGATGAGACACATTCTAATTTTACGAATCTGAACAGAGTCTA
TTCATGTTCATAATACTATGATGTGGCAAATTCGGTGCTATATTGTTATATTCTGGATAAAGGT
AGTATAAGTCATATAACAATATCAAAAATATATTTTATGCTACGAGTATAGGCACGAGAAGAC
CGCTTCACGCGGAGAGCTATCGCAAAGCCGATAGCGGTAAAAAATTTCCCCTCTTCCCTCTAG
CCTCTCTTCCTACTCAAATATGGCGGTTCACCACAGGTAAAGGGAGGGGGAGAAGTCAGTCTA
CCTTCTCTGCTAGGTAGTAGTAGGTATAATCGGGCTTTTCCTATTTTCTAGTCCAACCCATTTCT
TTTGTGCAGTGCAAGAAGGTCGTCGGTGTTCGGCCTCCCTTATCCCAAGAACTCTAGAACTTG
TTGGGCTCCTCTCAAACAAGGTCTTCTATATGGGAATCATTGGGTCTCTCCAAGACGTCAAAA
ACTGAAGGAGCAATAGATCTTCTCGGGTTGGTGGTTTCACCCTCAATCACAACATCAACCAGG
TAGCGCTGACCCACTTCTCCTTCTCCGGCGATCTTCTAATTCTGTCTTTGGTTCTCTTATTTTTC
TCTAGCGACGGTCTCAAAGCGGCAGCAAAGTTTTCCCATGATGCCAAGGCAGCTGTAACCTCC
ATCTTCAAGAGGCCCCATCCGGGTCTACTACTTGGCAATTTGCAGCTTGCCATAATTTTTGCGA
ATTTGCAGTCTTTGCCGTCATCGATCAAGGTACAGATGCAGAGGAAGAAGCAAGATTATGGAT
GTCATGGTTATGGATACCACGTACCTAATAGTAGTTGACTAAGCTCGGCAGGGCCCATTATGT
ACCAAGTCTTATACGGAATCATACCTCGTATATAGAAGGAGTTCCGGATAAGGAAGGATGAA
TAGAGTTCTATATGGAAATGACAAGGACTACCCGGATTGTATCCATATTGGTCTCTCTAGTTCT
ACTTGGACAAGGGGACATCTATGGGTATAAGTGCGGATTCGATGAGGAAGACTACCCTGTCA
TCGACTACGTGTTGGTTATCCATGCCGCCAAGTCGACGACAGCTAGATAGGTTATCCAAATCA
TTGTACTTGTGTGATTCAGATGAATAAAGAGCAACACTGGCTTCGGCCAACAGGAGTAGGGCT
ATTACCTGGCAGATAAGGGGTCCGAACCTGTATAAAAATCCTTGTCTTCATCTCTTTTACCTCA
ATCTCGCATATACTTTGGTGCCAACGATCCCCATACTATACAAAATACCGTAGTCGTGATATC
AAACATCGACAATGGACATGATTGCTTTTTCCTTATCTTTTGAAGTCCTTGTGTGCTTAATTCG
TGCTCAAGTTGTAATTTGCCCTTTTCTTTAGGGCCTCATGTGTAAATCTATCTATCCTCTCAAGT
CTCGACTAGCCTTTTAATAAATACGCCTTAGCTGATGTTTTCTAAAAAATACGAGTATAGAAT
GAAGGAAATGAGATATATGTATAGCCATTTGCAGTGTCATAGTAATATCTCAATTGGAATCTT
CTATATTACTAGTAGATTCTGCTTATATACATTCATATTCATAACATTAGCAACCGCTAAATAA
TTCATCCTAAACATGCGGAATATATCAATAGTAAACAACCTACTCTAGTATCACTTACTGTGA
CCGCATCTGACAAAGGTTCTCTTCAGAGGACTAGAGGAGTTTATATCAACTGCAGCTTGATCT
AAATTCATAGTTAAATTTTAATAATATATAGTTGTAGAATATAGAAAATAAATAAGAAATTAA
ATAGAAGTACAGGAAAACTACATTTTACATGTTTTCATGAGGTACTGCTAGTAGCTACTCAAC
GGTTGCTTAGGCTTGATTCGTTTATCTGGGTTGGGAACCTTTCATCGAACACGCTAAATGGAGT
GGTAGATTTACACATGATTAATTAAGTATTAGCTAAAAGTATACACATGGAAAATGATAGGGT
ATAAGTTGGAAAAGCTTGCTGTGTTCTTTGTTCAGAGTTCCCAACCCCTCTACCTCGTGTTCCG
TGCGCACGCTTTTCAAACTTCTAAACGGTGTATTTTTTAAAAAAAGTTTCTATATAAAAGTTAC
TTAAAAAATAAATTAATCTATTTTTGAAAAAAAGCTAATACTTAATTAATCACGCGCTAATGG
ACTGCTCTGTTTTCTGTGCGTACTGTTCCGGTTGGGAATCAGAGATACCGAACACATCCTAAA
AGAACACGACTTTGATATTCCTTAGGGGAATGCTAGGAATCGGTCGCTCAGGGGAGGGAGAA
AAATCGGGCGCTCCCTCCTCCCACGACGCGCACTGCCCTGGGCCCCACCACGTCTCTACCCCC
ACCTGCCACTTATCTCTATCACATACTCCATTGCAACAAATCACCTATATATTTGGAAACACT

FIG. 5RR

CTATTAAGGGAATACATTTCATTTTTTTCCACGAAGAATGTTTTACCTTTTATACCCACAATAT
TCCACTGTGTATAGATCTAATGTCGCAGTGAACTGAAACATTCTTTCACTATTTGCTGAAACAT
TATTTTTATATAAGGTGAAACAACGCCCGACTTAAACTATTGAAACATTTTCGATCTCTTAGTG
AAAAAATTCCGATATACTTGGTAGAATATCGTGCAACATTTTAAAATAATTCAATAATAAGCT
AAATTTTTTTTCATCGGAATATATCTATGTGTGTGATCTTGTTTTGAAGATTTAATTGCAACGA
ATTTAATGGTGAAATCATGATTTGGATAAATAATTTAAGAGAAAAATTAGTTTAAAGTAGTTT
TGCACGCATGCGTCATACTGATGTCAGCGTCCGATTTTTCTCCAAACCCATCGGTCGCCCGAC
GCGTAGGCTCCTCTTATTCCTTGAATTAGAATAGGTATGGCTACACGCCTACACGCACACAAG
ATAGATGAGGTGGGTGAGGCGGAGCAGAGGATCCGGCGGGCTGGGACCACCTCGTGTTGGTG
CCTGGTGGTGATGCAGTGGGCGAAGTGGTTACACCAACGCGCACCACCACCACCATCTCTCTC
TCTCTCTCTCTCTTCCTCCTTCCCACCAAACAAACATCCCACGCTTCGTCCCTCCCACTCCAC
TCCCCACCCCCGCGACGCCTGCGGCGACGACGACGGCGACGGCGAGGAAGGCTGGCCACGGC
ACGCGGCGGCGAGTAGTCCAGCATGGCGGCGCCCTCGGCGGCGGCGGCGTGGGTGGACTGGG
CCGCGGAGTACACCAAGGCGGCCCAGGCGGAGTCGCGCCCGCCCGCGGAGTGGGCCGCGCGG
GTGGCCTCCGTCGTCGCCGCCGCCGGGGACGCGCCGTGGTCGCCCGGGCTCGCCGAGATGCTC
GCCCGCGCGCTGCTGTATGGCGGTGGCGGCGCGGCGTGGAAGTACGCCGAGGCAGCGCTCGC
CGCGGGCCTCGCGTCGCCGGCGCTGCTCCTCGCGATCCTCTCCACCAGGTACGGACGGCGCGG
CGCCCCCGCTCCCATCCATTGCCCTCCCCCCACGCGCGCGCAGTGGCGTTTGTGCGCGCGCGC
GGGGAGAGACGAATTTGCGTGCGTGGTATCTGACATGGGCTCCTGCTCACGTGGGGTGTACTG
TCTGATGGAATCCGCGCAATCGCGATCGGATCAGGCTACTAGTTTCGATCTATGAGATTTCCC
TCGCAACCAGATTACCACAAATGCAAGTTGTTCTACAGCGTGGCCTGTACATGATCATAAACA
ATCTGATGTTTTGGGCCCTGTAAATTTGAGAAGGAAAAGGGATGGTGGCGTGCTTACTGTGCG
TAATACCCATAAATTTGAGAAGTATATGAATGGCAGTGTATGTAGAGTACTCGAGTGTGCAGT
GTAATGCAGATCAATTTAATACATGTATAGCAGCAGAATACTCTGTTTCATTTTTTTCACTTTT
TTTCTTCTCTCTAGAGTCTAGATCATGCTAGTTGGAATAACAAGTGCAGTTTGAAATGTGCTTT
TCAGCAGTAATCGTATAACCAACTGGCGAAATCCGTGCACATTTTCAATATCTGCTATGCTGC
TGTGGAATGTTCTATAAAATAGAATATAAGACTGATTGCAAATATTCCGTTGATGGTTTCTCTC
CATTCAGGGTCATTCCTCACCGGTTCACAAGGCCAACTGCATATAGACTTTATCTGGAGCTCTT
GCGGAGACATGGATTCAATTTTGCTTTTCAGATGAAAGCGGCGAATTTCAAAAAGTGAGGTTT
CCTTCTATGAGGTGTTCCCAGTAGTTTCATAATGCACGCATTCTATGTTCAGAGGTTTCGAAAT
ATACATCACAGGAACATGTACATCATTCTGAACGATTCAGTACTGTTCAAAAGAATTATATAA
GACGGGAATTTTAATACGATATGCTGACAATTAGAGTTTTGGGTGTCTACCACAATACATCTA
GACCACCTTATTGCATCTGCATACTGGACATATCAAGATCTGTTCCAAAGAGCAACAATTTGC
AAAGGAAGAATTTCACCTGGTTGAAAGGGCCAGTTCTGCAGTGATACATAATATTTTCGGTTG
AATTGGTTAAGGTGTCACTTTATATGTTTTCAACTCGCATATAGTTCTTTCATGTTAGTTTTTAA
AGAGTTTGTTTCTTGTGACATGTCTGTTCTGTTAGCATCCTATGTTTATGCCTTGTGTAGGTATC
TGTCATTCTGTCTGCAACTTATCATTCCTTTAGTTGTCTTCTAAATGCAAAGTTTCATGACACCT
TCTCATATTTCCGCAGGATCATGCAATTAATAGATGATAACCTTGGTCTCTCAAAGATATTTGG
CTTTTCAACATGCGAACCAGGGGTTTTTGTTGTTGAATTTACCCTTTGCATGTTATGGCAGTTG
GTTGATGCTGCATTAGATGACGAAGGCCTGTTAGAGTTGATACCGGATAAGAAAGCTCATTGG
CCAACTAGATCAGATGATGTGAGTGCATTTGATGGAACTTTCTCTGAACAAAGAATAGACAAA
ATTGACAAGTTACAGAAGATGAATAATGTGATAACTATAGAGCTCATTGGGCATCTTCTTCAT
GACAAAGTAATTACTCATATCCTCTCATTGGCACGCGAAAACATGTATGGCTTTTCAACTTCAT
GTACTGCTTTACTGAGTTATTCCAGCTCTTTCTTCCTATCACTAAAAACAGTGAATTTATCCCTT
TGTTATTATATCAATTGATAGCAACTTAATTTTATTTTAGTGAGTTAATGTATGGCTTAAATAT
CTCTGTGTTCCATATGCACCATATAATTGAAAACATTCTCTCTATTGGCTTAAGGTTCTCAAGT
CAAGCTTCTGTGTCTTCTGAGTATACAGGGTATTGCCAATATTTTTCTGGAATATATCAGATTC
ATTGTATTTATGGAATGGCTGTACACTTTTATAAAACAACTGTCGACCGCAATGCTAAAATGT
GAACTAATAGTACTCTAGAAGGACTACTGGTTGTATGAACAAGCAAGCTTGATTGGTTGCAAC
TGTAATGTTCAAATGATTTTCTCTACTACTTTATAACCAAGAAGGATCACTGATAGAATCATA
GAAACTCTGGCCATGGGGGACAAGCTCTGATATACTCATGCCAATATTGTCTGATATTGCTGT
TTGTGTTCATAACTGTACTAGAATCGTACACAAATGAACTATTGGGATAACAGTACATTGGTA
GAAGGCATTCGTTTAAACTTCCAAAGTGGGGATCAAGGGCATCCTTAAGACACCACAACTGA
ATTCACTTACTGTTTTTATTTTTTATTTTTTTGAAAAAGTATGCTACTTTAATTTGTTATTATTAC
CACCAGTACTAACGAGTCTTGATGATTCAGGCAATCTCAGTGGGCAGCATTCACTAATCGGTT
ACAATTGCTTATTACAAAGTCATCTACCTTACAAACTTCAACAGTAGCCTTGGAAGCATTTCA

FIG. 5SS

ACAGTTGAATCTTGATGTCTGCAATATATTCAGAGAAAATAAACATTGGTTGCGTAGAAAATT
CCACCCCATAGTGACTTCTAACCCTCTATCTTCTCCAAATGGACGGTGCCTTGGAGCTAGCTAT
TCTGCACAATGGATTCCTATTGATATGTATCTTGAGGATTGTCTCGATGGCTCAATTGCTGCAA
CGAATTCCATTGAGACTTTAAGTGGTAATTTTTTCCCATCAACAGAATCATATCTTTTGGTTTG
CATTGAAGCATCTTTTTCCTTGTATCATTGCTTTCTGCTATTGTTTCTGTAACTAAATGGGAGCT
TGTGCTCTTCGCAGGATTGATCAAGGCCCTCCAAGCAGTTAATAGAGCCACCTGGCATGATGC
TTTCTTGGCCCTTTGGATAGCATCACTTCGCCTTGTACAAAGGGTGAGTCTTCACGCTTCATTG
CATTTATTCAAACTTAAAACTGTCTTTAAGATCCTCATCTTGGATCTTATAAAACAAGCAGGA
AAGAGAACCAATAGAAGGTCCTGTGCCTCATCTAGACACACGGGTATGCATGCTTTTGTCTAT
CACAACACTTGCGATTGTTGACATAATCGAGGAATCAGATTCAGAGATGAACAGTAACTGGA
AAGAAAAGAGAACGAGTGATGATCTGCGCAAGGAATTGATGCTAAGTTTACAGACACTTGGT
GATTATGAAAGTTTGCTTGTCCCTCCTCCATGTATCATCTCGGTAGCTAATCAGGCTGCTTCCA
AAGCTGCAATGTTTGTTTCAAGAACCAACATTAGCAGTGGATACATGGAAAATGTCAATGACA
GGACAACAAATTATTGTAAGTGTCTGCTCTTTATCTTAGAAATACATACATAATTAGTGATCTC
ATTGACCTTTTTTTTTTTTTGCTTCAGAGTAGTATACATAAACTTGAATATCAATCTTCCTTTAA
TTTTGAGCAGCTGGAAACATGTGGCATTTGATTGTGGAGTCATGTATCTCAAGGAACTTGTTG
GAAACATCAGTTTACTATTGGCCTGGTTATATTAATGGTCATGTCAATTCCATAACTCATGCAC
TCCCAAGCCAACTTGCTGCATGGTCATCTTTCATGAAGCGTGCGCCATTAACTCAGTCATTGGT
TAATGTGTTGGTTGCAACTCCTGCACCAAGGTGTGTATCTTTTTCCCTAGGAAACAAGTGATGT
TAGTTTACCATATTAATTTGGAATGGGCATTTCTCATGAGAAGTCATCAGTTACTTAAAAGAG
AAAACTACATTATGTTCCTTATCATGATCATCATTTGTATGCCTGTCCAAGTGTCCATGTGCTT
TGGGGAAAAAAGTCAAATTAAGCTGCCAGTCAGATACAATGTCAATGGCTGCGTTGTTTAGAT
GTGCTATGCCATAGCTTATGTTTGCTGTAAATTTATTCTCTGAGATGTGGTTAGTTTCTATGGC
TGTGTATATCTGAATCATAGCATATGCATTATTTAATGCTCATACAATGTTCCTGTTAATAAAT
CACTGAATGAAGCTCATAAACATGGAAGCTTAGCAGAGGTTCAGAAGTTGTATGAAGTTGCA
GTCGATGGGTCAGATGAGGACAAGGTTTCTGCTGCCACTATTCTATGTGGTGCCACTTTGCTG
CGGGGCTGGAATTTTCAGGTTAGTGTTGTGTAGCTTGCATATTATGAAATGTTTCTGTTGGTCC
TAGTCATATGATTTATTCGAAGGGAAAATTCTTCTTTTTTTTTTGCAGAAGAAAGAACGTATAT
TCTTGTACCGCTCCAAAATGACTACTCTCTTTTGCCATGTGGCATTTTCCTTTTTATTCTTTCTT
GCCACTAGCAACTCTTGGGTCATTGAAAAAATAATCAGGAAATCCAAGAACTCAACTTAGGA
AACTGTAGTAAATTAAAAAAAATACAGATAGAGAACTGGAAAACACCAAAAATGAAATTAA
ATATTTGAAAGTTTTGGGAAAATAATTTTATGATGTTAAATTTATCTATAATACAAACTTTAAG
TTTTAAGTTCAAAATTCATCCTTGAACTTGTTTTAATTTCTGTGATTTCAAAATACCATTATTGG
TTTCTGAAAATTCTACTGTTGGTGGCGTGGGAAATTTGGAAGCAGAGGAATGACTTGTGTTTT
CAATGGCTCTATTCCGAGTGTGTCAATGGTGCTTCAATCAGTAGCACATGAAGGCACACTTCG
GTTTTTAGCCAGAGCTTCAAAGCTCCGAGAGGTGGTGGCGAGGTCAATAGCCCTTGCGGCTTA
AGTGGTCTTGTTGGTGTTTTTTTTTTCTTTTTGTAACTGTAATAGTGTTTAGTGTGGGGAGTTTC
CGGATTACCATCCCGGTGTATCTTCTTCTTATTATTATTAATGAAATGATGCACAGATCTCCTG
CGCATTCGAAAAAAAGGAAGAAATTTCTACTGTTTTCTTCAGTCAATGGGAGCTGACCTAATA
GTAGTGACAAATAGAGAAGTGCTATATTTTATTGGTAGAAGAGAAAATGGAAATTCCTTGGTA
GTAAAAAGAAAAGTTCCTCTTGTTGATTTCTATGTAAAAGCAGCATGCATCTTCATTTTTTAAT
ATCATAATGAGGTAAATTAACATCTGCTTGTCTTGAAGTTATTAATATTAAGACCTTTTGCTCT
CTTATCTTGCAGGAGCATACAGTTCGGTTAGTTGTCAAACTACTCTCAAGTTCTGATCCAATCG
ATTTTTCTGGAGGAGAGAGCCAGTTAGTAAAGCATGGCCCAATGCTCAATGTTATTGTCACTG
GAATATCACCTGTTGACTATGTTCCAATCTTCTCATTCCATGGCCTAGTATGGTTCATATGCTA
GCCTATCTTTACTTCTATTTGATGGTTTATATTTACCATCTTATTCTGAATTATATGGTTTTGCT
TTTTAAAAAATGAACAGATTCCAGAGCTGGCTGCTGCACTCATGGCAATATGTGAAGTTTTTG
GGTCCCTGTCCCCAAGTGTTTCCTGGTCTCCGAGAACAGGAGAGGAAATATCTGCTCACACAG
TCTTTTCAAATGCATTCATTCTACTATTGAGGCTCTGGAAGTTTAACCATCCACCACTTGAATA
TTGTGTAATGGGAGATGGTGCTCCAGTTGGTTCTCAGCTTACTCCTGAGTATCTTCTGTTATTG
CGAAATTCCCAAGTTGTATCTATCAGAAGTTCAGCAAAAAACAGAAATACCCAGAAACAGTT
GCCAGTTACTTCAAACCCATCGTCTGAGCATCCTATTTTCATGGATTCATTTCCAAAGTTGAAG
TTATGGTACCGACAACACCAAGCTTGTCTGGCCTCAACTCTCTCGGGATTTGCTCATGGCACA
CCAGTACATAAGAATGTAGACAGCCTTCTCAATTTGATGTTCAGAAAGGCCAACAAAGAAAG
CACTTCTATTGGTTCTTTGTCTGGGAGTAGCAGCATAAGTAATTCTTCGGGTCCTGGTGTTGAT
GATTCACATCTTTGGCCTCAGTTACCTGCTTGGGAGATACTGGAAGCTGTTCCATTTGTGGTGG

FIG. 5TT

ATGCTGCTCTAACTGCCTGTTCCCATGGAAGACTGTTTCCACGAGAACTGGCTACAGGTTTGTT
TTTGCCGATTCTTTTTTTTTTTTTTTGACGTAAAATTTTGCCGATTCTTGTTTGAAAATTAAGA
TGATTGAAGAGTGAACCTTATTATTTAACCATTACTATGTTCTATGTGATCATCAGTGTTTGAT
ACTACCTTTTCCATTCCAGGTCTCAAAGATCTGACTGATTTTCTCCCTGCATCTCTTGCGACAA
TAGTAAGTTACTTTTCAGCCGAAGTAACACGAGGTGTTTGGAAACCGGCATTCATGAATGGAA
CAGATTGGCCTAGCCCTGCTGCCAATCTATCTATGGTTGAAGAGCATATAAAAAAAATTGTAG
CTGCCACTGGCGTTGATGTTCCGAGGCTTGTCACAGGTGCTTATTTGTGCTACCATTTAGTCCA
TTGTACAAGCGATTAGCGCATTTATGCTTTACTATCATTAGTCCTGCCAGCAATTTTGCTCTTA
TTATCTTTTCACCTGCCGTGAATAAAATGCATTTTTTTTCCAACACTAATCTAGTTCTGTATCCC
ACAGGAGGAAGTACTTTGGGTACACTTCCATTGCCATTGGCTGCTTTTGTGAGCCTAACCATT
ACATACAAACTTGACAAGGCATCAGAGCGTTTCCTTAACCTTGCCGGGCCAGCTTTAGAGAAC
CTTGCTGCAAGCTGCCCATGGCCAAGCATGCCAATCGTCGCGGCACTGTGGACTCAGAAGGTG
AAGCGGTGGAGTGATTTCCTAGTGTTCTCGGCTTCACGCACGGTGTTCCACCATAACAACGAC
GCAGTTTTCCAGCTCCTCCGAAGCTGCTTCACCGCCACCCTTGGAATGTCGTCTACCACATCAG
TATGCAGCTGCGGTGGCATTGCCAGCCTTCTTGGTCACGGCTTCGGCTCTCATTGCTCCGGTGG
CCTCTCCCCAGTCGCGCCGGGAATCCTCTATCTCCGGATATTCCGGTGCATCAAGGACTGCTCC
ATACTCGCGGAAGATATACTGCGCCTCCTCATGCTCTCGGTGAAAGACATAGCCGAAACAACG
GTGTCGAGGCACCGATCCGACAAGGTCAGGAAGACCAAGTACGTGATGAGACATGGCCAGGT
ATCCCTCTCTTCCGCCATGACGCAGGTGAAGGTGGCGGCGTCGCTCGGCGCGACGCTGGTGTG
GCTCTCCGGCGGCACGGCGCTCGTCCAGTCCCTGTTCCAGGAGATGCTGCCGTCGTGGTTCCT
GTCCGTGCAGGACCTGGGGCGAGGCGGCGCGGCGAGCGGGGGCACGGTGTACAAGCTGGGC
GGCCACGCGCTGGCCTACCTCGCCGTCTACGCCGGCATGTTCGCCTGGAGGATCGACCCGACG
CCGGTGTCGCGGCGGCGGGAGCGGGTGATGTGGTCGCACTTCGAGTTCCTGGCGAGCGCGCT
GGACGGCAAGATCTCCCTCGGCTGCGACCTCTCGCTGTGGCGCGCCTACGTCTCCGGGTTCCT
GGGCCTGGTGGTGGAGTGCACGCCGTGCTGGGCGCACGAGGTGGACCTGAGGGTGCTCAGGA
GGCTCAGCGCCGGCCTCCGGCAGTGGAAGGAGGACGAGCTCGCCGTCGCGCTCCTCCGCCGT
GCCGGCCCGGAGGCCATGGCCGCCGCCGCCGAGCTCATCATCGGCGGCGACTGGTGACACTA
CGCCGGCGATCTGTACATAACTATTGCCATGTGCATGCGTGTGTAGTTGATTTCGATATTGTGG
TAGTAATTGATGACTTTGCTGATCGATCGCTAGGCTCGTTGCTCTCTTTCGCTAATGCTAGTGT
CCACTTATTAGTATATCTTGGAAGGAAGGAAACTGCTCAATATATGTGTGTTAAAAATGGTGT
TCTTGAAGAAGCCACCCGTCTCTATAGGTTATCGCTGTATCTAACATGTGTGTCGTGTGTTGCT
ATAGTGCAATTAATTGATGTGGATGGCGTGGTAGATGTAATTAGGCAAATTTTGCAATAGGAC
ACTTGTTACGTGTGGTTTTAGCCCTAGGACACTGCCCAAACTCACTTTTGGGGAAAAACACTC
CATAAACATGGTAATTTGCCAGTGGATACCGCGCCGATTAAATAATATTTTCTGGTTGAGGAG
GAAAGAGAAATCGTGTGAAATGTCAAAAATGCTCTTGGGCCCACATGTCAGCTCTATCTCCTA
TCTCTCTCCTCATCTCTCTCTTTTCTCTCTCAGAGTGCGCTCGCACGGGGTGGTGTCGGTCGCG
GCGGAGATGGCGAGGACGGTGGCCGGCGGAGTGGAGTGGGGCGGCGGCGGTGGTGGTCATG
TTGCTTGGCCACGTTGTCGTGGGGGGTGCGACACGATCGATTATGGGGATTTCTTCGCATGTG
GCAGTAGTGCTCGGCGAGCTCCTCTCCTCGCGCGCCGCTGCCGACGACTCCTTCCCCCACGCG
CAGCCGGCCGGCATTCCCCTTCCAGCGCGTTGCAGCCAGCCAGGTCCTCCCCTGTCTTGCTCGC
GCGGCCGCCGACGAGCTTCTCCTCCGCAGCCAGCCATCCTCTCGCCTGTTTGTCCCTCCCCTGC
ATCTTGCTCGCGCGGCCGCCAATGAGCTTCTTCTCCGCAGCCGGCCCACCTCCCGCCCGTCGTT
CCTTCCCTTGCCTCGTGCTCACTCGGCTTCACGTCGTCCTCCCCGAAACTCACCGGCTCTACAT
CGCGTCCCCCTCACCCCGCCGTGGCGGCGGCGCCCCTTTCTGCTGCGGGCACGGGCACGACGA
GGGGTGGCTCCGGCGGCCGTGCACTCGTCCACCGCCGCCGCCGCCCTGCTCCACTCCGCCGGC
CGCCGTCCTCGCCATCTGCGAGAGAAAAGAGAGAGAGAAAAGAGAGAGATGTGGAGAGAGA
TAGGAGATATAGCTGACATGTGGGCCCAAAGGCATTTTTGACATTTCACGCGATTTCTCTCTCC
TCCCCAACTGAAAAGTATTATTTTAATCGGCGTGGTGTCCACTAGCAAATTACCACGTTTATG
GAGTGTTTTTCTCTAAAAGTGAGTTTGGGCAGTGTCCTAGGGCTAAAACCACACATAACAAGT
GTGCTATAGTAAAATTTGCCATGTAATTAAGGGGCTAGGTTTGGTATTCTATCTTTGTCCGTTT
ATCTCTTTGTCCTCTCGCTTTGCTAAATCGTTGCGTTGGCCGAGATTTCGTTCTGTCGAATAGG
ATGTCATGTTAGGATTTCTAATAATACGATAAGAAACTAATAAAGTGAGAGATGGAATGGATT
TGCTATATCTATACAGTTTTCAATACAGGTTGTCTTTTGCATGTATTTCCTGTAAAACAACAAA
TATAAAATAATATGATATTGTATGAGCTATTTCAATCATCAAATAAATACAACGTTTCTTATAT
CCCTCATAAACATAAAAATGATACTATCTTCTATTGGAAATTGGCAAAATGCCTTATACTTTGT
ATTTCTTATTTTCACTTCATGAGAAGGGGAAGATGGTAAACTAGTCATCAATCTGAAAATGTC

FIG. 5UU

GATTGAATTGCACTTCAGAGGGAGATCTAATTAAACGTTGGAGTCACGTGGCTCCTCTTAATT
AATCCCGTATGCGTATGTTGCTTCCCTCTCCCTACTTTATGTCTCGTTACTTTATCCGCATCATC
ATTCCCCCAAAGATTCTGGCGTTACCTCACTACTTGGCGGATTAACCGATGAAAATCATCGAT
TAGTAAATCGGTCACGGCCATCAGGAATAATATTGTTGCTACATCGGCACTATCAGATGTGGA
GAAGAAACTATCCGATGTGGAGAAAAACTATCCCATTAAATAAGTTCGGAGGGGATTTTAGG
CATGTGAAATAAAATAAGCCATTAAACTTGAAAATTGAATTTATTTATTTTGGGGAAAAACTT
TTGTGTAGAAAACTTTTATACAAAATGTATTGTAGAAAACATGATCATATATTCCAATAGTTG
TTTAAGAAACAATATAATTAGCTGGTGAAAATCTAGTTAGTTTATAGTTTATAAATGTTAGAA
ATATATGAAATTCATTATTTTCATGGTGAAGAATAAAGTAGAGACTAAATTTATAAATATTGA
ATGTCCTATACATACTCACTACACACATGCACGTCACATCCTAATCAACATCACTTCATAAAA
TTATCATTTTCAAGTTATTTTGGTCCTCGTTTACATGAACTAGACAAATTCATATACTGAAATG
AGTATTTTACAAGTTTACTAAATTGCACCCACCTAACAAGTTTGTGTACCACTAATGTAATTTA
CTCATTCTATAAATAATAGTTGCATAATCTTTTGAAATCTGGATTGTTTGGAGTTAGAGATTCT
GTGACTAGCCGCGGTTGTTAGAAGCTGCACAAAGAAAATCCAAGACAATGATACTGGGGAGG
AATACATGCACGGTAAGCACTGATCAACGTGGAGAAGAGTTGTCATGAACATGGATGAAAAG
GTGATGTAGGGTTGTGTAGGATGATGAGATCGAGGAGTGCGGTAACGTGAAAATCTTAATCA
GTGAAATTGCATGCTTGCGACAATGAGCATATGGCATGAAGTTATTCATCAGTTGAGTTATTA
TGGTAGTAGTGTAGGAGTATCTACTAGTGAATTTAGTAGGCGGTGCACATCTCCAGCCTGATT
TGGAATTGGTAACCAGGTTGACGAAGGGAAGAGAAAGAGAGGGTGGTAGGTAGGACGAAAT
GAGATACCACTCTGATATATAGTTCCTTATGCTTCAGTGTGAACTTAGACCCTTTACACTACTG
TGTTGCTATAGTATTTTTGTTTGCCTTGTATAGTGTTCTAATAGACAAACAATTATATTGTGTTA
AACAACAATTGTTCATGTGGCTGCTAGATGATATAATACCGGTTCATATATAGTAACTACCAT
ATATATATATATATATATATATATATATATATATATATATATATGAAAATGGTTCTATAAACCCAG
GTGTATGTACTCCCTCTCCCATCTACCGTCCATCTCAACCAGCCTCGATGAAGCTCCTTAACGG
ATCAACGAGCGGACCCGTTTGATTACCCAGGTGTATGTACACCCCTTTCTTATTTCTTATTGG
ATATCCATATACTAAATAATTGGATTAATAAGAAAATTTTTAAAGAGAATACCGTTCCCTTTA
TTTTTCAAATTCCTGCATGTGCATGCACTCCGGCCGGCCGGTACAAGGTCAGGATCAAAAATT
TGTAGCATGCAATTGGGTGGCATCCAGTATATACTAAATCCCTCGCTAGATTTGAGCAGTATA
TACTTTCTTGTAGGATCCTCATGGTACTGGTGATTTACTAGAACATGCATGCTAATAATTAACG
ATAGATGTATATACTGGTTCATCAGTGCTTCATTCGTCTGGTTTGTTGGTTTGCTCCATCCGGA
ATCACATTCATCGCCAGCGTGTACAGCTACCGTTGGATCAAATTAATATACAATCATTCAGAT
GATAATTTTTTAAAGGTAGTATATACTGTTCTTGAAGTAAGGAGTAGTATGCATGTACTGTTTT
TTAAATTTAGTAGCAGTATATACTGTTTTTTAAGTTAGTAGCAGTACATACTGTTTTTTTAGTA
GCAGTACATACCTGTTTTTAAGTTAGTTGCAGTACATACTTTAGTATATACTGTTTTTAGTAGT
AGTTAGTAGAAGTATATACTTTTTGTTAGCTAGTAGCAGTATGTACTGTTTTTAGTTAGTAGCA
GTATATACTTTTCGTTAGTTCGTAGCAGTATATACTGTCATCCTATAAGTTCAGTATATATGTG
AAAAATGCAGTAAATACTGTCATCCTATAAAATTCAGTATATATGTGAAAAATGGAGTATATA
TTGTCATCTTACAAAGTTCAGTATATATGTGGAAAATGCAGTCTATACTGTCATCTTACAAAGT
TCAAAGTTCAGTATATATGTGAAAAATGCAGTTTATACTGTCATCTTACAAAGTTCAGTATGA
ACCCCTTCATAGAAATTCAGTGTATAGCATCATCTAAATAGTTCAGTGCGTACCACTCCGTAG
GCAAAAAAAAAAAAAAACAGTATAAACCTCTCTATAGAGAAATGCAGTATCTACAAAGTTCA
AAACATACTACTGACAATCAAAAAATCAGCTTATACTTCTCTATGTAGAATTGCAGTATATAC
TTCTGCTTAACAAAGGACAGCTTACAAAGTTCAGTACGTACCCCTCCATAAAAAAGTTCAGTA
TATACCAATCCAAAAAAATGCAGTATGTACTACCATCTTAAAAAGATTAAGTACATACCCCTC
CAAAGAAAAATTCAGTATATACAAATGCATAGAAATGCAGTATATGCAAAACCCCTCTCTATA
CAGAACTGAGATCGTGCATGAACCATACTATGCAGAACCCCTGTCTATAGGCATCAAGATTTC
CATTTCTGGTGACATACCTTGGACTGTGGTGACACACTGATTTTCTTGTGACCCTGCAAACAAG
AAAATTTAAGGCATCGAGCATCGATCTCGTCGTAGAAAAAAAACCAATACTAACCTACTGCTT
TGGATGACCTCCACTACTGAGACCCGTCGATTTTGCCACGGCTGCTCTGCTCCTGCATTCAGGC
GACTCCAAATCGATGACCTCTACTCCTGGAACACCAACGAGTGGCAGGTTCTCCAGGTCGATT
ATCTCTGTCTCCGATTGGTGAAGGAGGAGCCATCACTGGAGCAAGGAACGAGCAGATTCAAA
GATCAGAAAAGATCGCTTCTATGATCCTCCACCAGCCACCCAGCCGCCGCTGAATCGTCGCGG
AGTCAATCCGAGGAGGTGTCGTCGCTGCCTCCACCTCGCGTCAAACCGCAAATGTAGCGAGA
GCTGTTCGATTGGCTGAGTACTAACTGTTGTGATTTAGATAATTAAGCGCTAATTAAGGATCC
AGATTATTTTACAAAAGGAAAATCAAAACAGGTCCGCTCGTTGATCCATTAAGGAGCTTCATC
GAGGCTGGTTGAGATGGACGGTAGATGGGAGAGGGAGTACATACATCTGGGTATATAGAACC

FIG. 5VV

ATTTTCCTCTATATATATATATATATATATATATATATACACACACATACATACTATTGAACTGTG
TATATGGATATTGGGTTCACTAATTAGGCTATTGACACAACCGATGTAGGCAATAAGAGATTG
TTGACGTGTCACTTTAATCTACCGATTACCCTAAAGATATAGTTGACGCATCCAACTAGAGAT
AACAGACATGTCACTATTGGAGACATTCACTATTGGTATATGATTGGGTACATTGGGTATGCG
TCCAACTTGAGAACTAGATATATTGAGCATGTCACTATCAACATATGGTTCACTTGCCATACG
TTTGAGTAGAGACAGTGGGCATGTCGCTACTGCTTTAGATAGGTACACTAAGCAGCATGGAGA
GAAAGCCATTATCTTCGACTAGAGATAGCAGGTATATCACTACTCCTTTAGATTCATCCGAAT
TTTATCCGCCAGCCAACGTAGTGATGCGGTCGACGTGTCAAACTTGACAAGACATGTATGTCA
CTGCTGCTACTTTAGGATGGAAGCATAAGCCAACCTAGTGATATAATTGACGTGTCCAACCAA
GATAGTTGTCATGCCACTACTACTTTAGAATGGTTTCACTGGCTAGCTTATTTATGTAACCGAG
GCATGAGGCATCTGAACAAAAAATAGCAGACATGTCACTATTGCTTTAGGATGGTAATTCTAA
GCAGCATAGTCATGCACCCCGAAGGCGATGCGTCCAAACAAAAATAGTATGTATGTCACTAT
AGCCATATGTTGAGTCCCTTGCCCGTTTACTAATGTAACCGACGAGTAATGTTAGTACAACTA
TAGAATTGGGTTGATAGCTGGCTAGAGATAGTGGGCACGTCACTGTAGCCGTAGCTTAGATCC
ATCAATTGTGGCTAGTCTCTTGGCAGACCTGTCATAGCTAATATGGCCAACTAGAGACTATAG
ATGTTACCAATATGGCCAATTGGAGTTTTCTCATAATCATTTATTCGTAACACAACATGACCTA
TGAGTAATGCACCATGAATAAATAAATTTTACAAACCTTTGGTTATTATTAAACTAGAAAACT
TTCGGTGCTTTTTAAGCTAAACCATTAAATTAAAAAAACAAAACAAAGGAAGTTATATCATAT
TAGGGGCATTTCTCATAGACAATTGTCATGGCAGCTATTTGCTTAACCATAATGCATACGGTG
AAGATGCACACAATGTTCTATTTTCTCATGTATCAACTTGTCGTCGCGAATAAAATTATTTAAC
GAATGCTATGTAATATATTCATTATTTTTTTCCTTATTTTGTATGGCAATCGTTTTTTCCTTAAT
ACTTGAATTCTAGATATAACCTTTCAATAGAACGTAAAAAAATCCATGTTTCCTCATGCATGC
AACAACAAATAATTAAAGTTAACTAAAATACAGCACTATATAATATTATATAGTAACAATCTT
ATATCTTTCTCGACTAATATATAGCTTCTTTTTTTTTCCAACTATGATTCTATTATTATCGTATA
TCAGCACACACATTCAACGTTAAAACCATGAACAACATTGATGTGAAAGCTAGAGAAAAAAA
AAGAAAAAAAAAGGGAGAAAGGAAAAAAAACTCTTTTCTTTCTTTCAAGAGCTACACCGCA
AGCTCGTCTCGCAATTGACACCGAATTCACGTTGCCCCCGAAAATAGGGGTTGAGAGAGAGG
AAAAAAAAGTAAAAATCCCACGGACGCTAAAAAACGCACGCGCGGCGCACGCGAGAAAGAG
AGAGAAAAAAAAAAATGGCGATGGCGACGCAGCCGTCGTCCTAGGCAAGCTTCCCCCCTCCAC
CACCACCCCCTCCATGGCCGCGCCGCCCCTCCCCCTCGTCCTCGCCGCCGCCGCCATAGCCTCC
CTCGTCATTCTCGTCCTCGTCGTCTTCGCCTGCCGGCGATGGCGGCGCGCGGTGGTAGCGGCG
GCGCCGCAGCCGCCGCCGCGGGCGGCGGCGGATGTCGTCGCCGCATCTCCGGTCCGCAGCCA
GGTTAAAGATCCGAGCTCCCCTCCTCCCTCGCTTTGATCCGCACCCGCGTCGACGGAATCGAA
CGTTTCGTCGGATTAATCTGTTATTATTGTTGTTACTATTATTATTGCTACGAACATTTGGGGCT
GGCCGCCGTGGAGCGAGCTTGTTCTTGCGAATTTTCGCTGTTTGTTCGTCGTTTCTTTCGGATA
TGGCCTATCGTTCGCTGTTCCCTCGTCTGGTTGCTGAGGAATCCGTGGAAATGGGGGGCGATT
TGGTAAACCCTTGATGGAGACGAACATGTGTATATGCTGATTTTGGTTGTTTCACTAATGGTTG
CAAATCTGGGGTCGGATTATGCGCATTAGGGAGACGTAGCCATGCTTAAAGATACAGTACATT
AATGCATTACTACTTGCTACAGATCAATTAAATTAGTATGGGTATAAAAACAAGCATTGGGTT
CGTGGACATTAAGGCTGCTTTATTGTTGCTATGATTATAGTATACCAAGCGCATTGATGTATTC
ATTAGGAAAATGCGGAAATAAATGTACGGCGTTACACGATATTCTGTGGACCATGTTTTTTCT
AAAATGGAAATTCAGAAATTGTCGGAGTAATCTGAGGAAGCGTATGGTTAGAGTCACATTTG
AAGCTTGGTTCTGAACGGTGGATATCGGGTTTGCGCTAACTTTGTTTATGTGTGCTTCCATGTT
GGACAGCGGGAAATATCATGCAATTTAATGGCTATTCATAATTCTTTGCTTCATAAATTTTGTA
AATCAAATCTTTACACTTTACAGTAGCAAAATACTGTGGAATGAACACAAGTTGTTGCTTCCT
TCAATTGAAAATTAGGAAGAATTTTCTGTTCTTTTTTTATTTTTGGAAAATTTTAGAAAGAACA
CATGGAGACAAGGAAAAGAATAAAACGGCATGCAAAAAGTGGGGGAAAAAGAGGGAGGAT
GAGTTGGCCGTCTTCCCCGCACCGCTACCCCGTCACGAGATAGGCACTCCGTCACCCTCCCCC
CGTGTCCATCTGCTGCTTATATCTTGCATCCATCTTCTCCCATCAACAGATTCCATCCATAAGC
ACTGCTGCTGCTCTCTTCTATATGCAGCACATCTTTCCTACGTACTAACTGAAATCTGATCAGT
TACTTCTTGGTGGTATTTGATCCCCTCACGATCCGTTCTTCATCTCTGTGTGGAATGCTCATGG
AAGCATTCCACAAATCAAAGAAGATGGAGCAAAAACCGGTGAGCTGGATACAGCACCCCCTG
ATATGTTGTCCTTTTCTTTTTCTCTCCAAATCGTGATTTTTCCAAAGGAAAAAAAGTTTTTTTCC
TTGTCCCTCAACTCTTGGTTTGGTTTGGTTTGTATTTCTCGTCTCCAAAACTGATAAAACTCGTC
CGTCAACTCTCAAAACTGTTTAGATCTCACCTCTCACTCGTTTATAAGTGGTTTTTGACCTACT
TGGTGTAGATATGGGATCTGAGGTTGCTCTAGCTCACTTGTCAGAGAGGTTTTGGCGTCCATG

FIG. 5WW

TAAGATCTACGGTGGCAGCGGCGGGGCCTGCTTGTCATAGAATCCTCATGACAGCGGGCCCTA
CATAGACATATGATCCCGACACCACGTGGGTGAAAACCACTATTAGACAGGTTGAGGGACGA
TTGCTATGTGGTTTTAAGAGTTGAGGGATGATATTTATCCAGTTTTGATGCTGAGGGACGGAA
ATTAAATTGAGTGAAGAATTGAGGGACAAGAAATAGACGTTTTTCTTTCAAAATGATGAGCCA
GTTAGGTGTCTAGTGGCACAAATACAACATCTAAAATATGAGATACCAGAACCAAAATTTGG
AAGGCTAACTCGTTGTTCCTCTTGTAGTTTGTCTTTGTTGTATATTAGAGTCAAGGTGTGATGA
AATTTGTAAGTACTGTAGTTCCATTTATTCTCTGATTCAACCCTGGCGTGTTTTTTTTTGTCAT
TAGTGATACGAAGTTACTGCAAGTATGTTAGAGATATTTCAGAAGATTTACAGTGTGTCCCAT
GCTCAATAATATATTGAGTTTCACAGTTGTATCTTGCATTTTTGGACAGTAAGTTAGATGATTT
ATTCAATTTCATGAACCTTCCAGATTCACTCACTTAAGCATTTCGTTTTGATGGGAACTTGCTC
AAGTTATTGTCTAAGCTGACAAAACTCCATGGAGTATGTTTCTTGCATGCAAGATGTTTGAGA
GGATGAAGTTTCACATTTTGTTTTATCTTCTAAAACCTTTTCTTATAAAATCTGACTGCACTCTT
AATTATTTCTTGAAAAATTCCCACCACATGATCTACATCAATCTCTTCCTTCCATTGATTGCAG
CGTGGAAATCCATGTATTTTTTGTTTGATGATTTGCGCTCTGCATTTGCAGAATGAGGATTTAA
ATAAGCCTCTCCTTGAAATTCTGGATGATCACTCTAGCCAGAGTAACACTTTTCCTGGAAATGT
TGTTGGAGAATCTTCAAAAGTTCAAACAAGCAGGAGTGATACTTCACCAAGAAGTCATGGAA
TAAGTGATTCTGGCAGGACTTATCCTGCTGATTCCTGCACTCCGCAAGGTATGTATAATGATG
CCCAAACCTTTAGTAGCCTCCTGACATAAAAATCAACTTTCTTCAATTTCTCTCGTCTTTGTTG
CGTTGATCATCTCAGTTGAATATTGAGTGTTTACCAATGTCAACTCTTGAGTAACAGAAATTGC
TATGAATTTTGTAGGAGAAACTCATGTGATCGATGTTACAGATGATACATCTGAAGAGTTCCA
TTTGGGAAGCACACTGAAGTGTACAAAACAGACAAGTTGGTCAAGGCCTGATAAAAAACACA
AAAGATGGGGTTCTGGAGAGGATAATAAGAATGGAAGCATTTCTCTAAAAGATAATACATAT
CGTACGATATCCCTCAAACCTGATTAGAATGTTTCAGTAGCTATGCCTTGCAAAGGTTTGAATT
TGTATACGCATCTAACCCAATCTTTTGCTAGAAATGCAGGAAGCAACCTAGACGTAGAGGTCA
TTGCTGGCCCATCTCACGGAATAAGTTGTTCCCGACAGTCAACTAGTCCTACAATCCCGATAA
CTCTTGGAAGGGTCCCCCCAAGTGATTTGGTGTTGAAGGACTCTGAGGTGTCAGGGAAACATG
CTCGAATAAATTGGAATGCAAAGGTAAGTTGTTCAGGAACTATTTATTCATTTCTTGTGCCTTC
GATTTAGTGCTATTTATCTAGTTGTTTCCCCAGCCTTGTAACTAAACTGGAATAGTGATGTTTG
TAATGAAACTTAACATTACCATTTTGTTTGATTTGTTTGGTCAAATATGTGCTTTTGTTCAATA
GTAAGATGCACCTTTTGTTCAATTAGAGCCCAGGACTCAGCTGACTGATCAAAATGTTGAGAA
TTGAGATGCTAGGGTGGTATGATGGACACATACTCCTGACCTAATGCCACAAGATCCTGAACT
CACGCTTTTAGAGAAAACTATTTTTTAGTTTTTGTTCATACAGGAACTCAATAAACATTTTCAT
CCATTTCTAAAGAGAAACTGTTTCTGCCAGAAAGGTTTGCATGCTACATTTTCTTTCAGCATCT
CTTTACTGTTAGCTAGTTATTAACGAGCAGAAGCTTATTTCCTTGGCTGTAACTATGAAAAATT
ATCTTTGAGCACAGGATATGTGTGCACAAGAAGGCTTGTGCGCACAAGATATGTTCCCTTATC
TTTGAGCATTTAACGAGTAGAAAATTGTACAATGGAAGGCTAACTAGTATTATAGCTATATGC
TGTAAGCAAATATACCAATCTTGCATTGGTTTACATAAAATGAAGTGCTTGTTCATATGCAGA
CATTGAAATGGGAAATTGTGGACATGGGCAGCTTGAATGGGACATTTGTGAACTCTCGGGCA
GTTCACCATCCAAATGTTGGGTCCAGGCACTGGGGTGAGCCAGCTGAACTAGCAGATGGTGA
CATTATAACTCTAGGAACTTCATCAAAACTATCTGTAAGTTTTTTATATGCTTTCAGCATCTCT
TCTTGTTTCTCTCATGTTTGCTGAAATATTTGCTTAACTCCCATTTTCTTTCTTGCGGGGCATAA
TTGGACTAGTGTACTAACTTCCTTCATTCATAGGTTTTATACTAGTCTGACATGAAGCTTCCAG
AATTGTTAAACAGGCATGCCTTATAGAATTCGTCTCAGCAATTGTGAACCCTACACATGTTAA
TTCCTAGTTATCCATAATCTGAAACCATTAGTATTTCTTTAAGATAAATAAAGCTAGTAACTGT
GCTTTGAATGAAAAGATATTTATTTCAATCATTGTTCAGTCTTGTGTACTGAAGATACTTATT
TTCATTTTTATCAGTATTCCCTTCTGTTCTAAGCCTGTCTGCTGTCAGCCCATTCCAAGAATAAT
TTCCTTATGTTTGATCCAATTTAAGTTGAAAAAGAATGTGCTTCCTGAACACAACTCGGATAA
ATATCTGCTAAAATGGTTTGGTTGGAGATGAGGGAATTGTGCAACTTTGTATCATCAATTTATT
ACCAACAAACTAGTTGCTCTATTCGGTAGAGCTACATTGATTTACTGCACTAAGATAAGTATG
CAACTAACACGACCAAGTCTCCTTATCCTGTTAATTGGTTATCCTTGCTGACTATTTGATTGCT
CCAGTCCCTAATTTAAAAATTCATTCAACATTCTTCCTGAAAATAAAATATGCTGACTCACCA
AGACGCTGCTCTTATTTTGAATTTCAATCAAACCATGTTCTGGAAATTAGGATTTTGGAATACT
CCAGCTATCACAAACCGTTTTTTCTTTCCTGGCCAAGTACTCTAATTCATAAGCTGAAGTTTCT
TCATTGTATTGGTAATCACATTCATCATTCAAGTTGCTCTGCGACATATTTGAAGTTCTATGGC
GCATTTTCTTTAACCTATTCTTTGGTAGCATTCTTATGTTCCATTTTATAATTTGCGTTGCTATG
TCACTGAAGGTCCAGATCTCACTGCAAAATCAGCGAGTCCCTGCTGGGATTGGTATGGCATCT

FIG. 5XX

GATCCAATGGTGGGCCGTCGAAGTGGAAAGAAGCTTGCAATGGAGGATATAAGCTTTTGCCA
GTGCCCTCTGCAGGGTGTTGAACAGGTGCTGACCATTTAACTATGATAAATTTATATGCCTGTT
TTTGATACCAACTGGTTTTGCAGTTTGGACTCTTTGGAATTTTTGATGGACATGGTGGTGATGG
AGCTGCCAGAGCTGTCAGCAAGTTAGTCTTTCATTCCCACCTGATATTCAATATATATCATGGA
TATATTTTATTCTAACATATGAGGATTCATGTACTAACTTATATCTAATGGAACTTACTCTTTC
ATTAGTAATCTGATTATTTATCATCATAGCCACATGAAAAACTGATGTTTTCTCCCCCTCCTGA
TTTCTAGGATTTTTCCAGAAAATGTGGCAACTCTTTTGTCTCACCATGAGACAAAAGAAAAGG
TTCTTTCATACTCTGATGCTTCTGACGTTCTTAGATATGCTTTTACTATGACAGAAGCTGCAAT
CGATCATGAGTATGAGGTTGGTTCTCCTATTCTCTGATCTGATTATTTTTGTTGTATGGCTTGA
AATTGCCAAAGTAGGTTTTGGTTTAAACTTCTTTGCCCCTACTATGGTGATTTAATTTGTACTC
CATGGGTGGTTCAAATGCTTGCATTAAATTTAAAGTAAATTTCACAAAACTACATGTACTTTG
CCCAAACTATCACAAAACTACAGATTTAAGATGATATATCACAAAACTACAAATTTAGAACCA
AATTTATCAAAGAACAACAGATTTAAGATGGAGTATCATAAAATTACATGTTTAGTAATAAAA
TTATTACAAAATTACATGTTTTGCACCAAGTTAAGTACAAAACTACAACATTTATAACTCTAA
CATAATAGTACTTGTAGGAATTTAAACTTGTAAAATATATGTAGTTTTGTGATAATTTGAGTAT
TAAATCTGTAGTTTTGCGATAATTCGATCAAAGTACTTGTAGTTTTGTGAAATTTACTCTTTAA
ATGTTTAGCTTTTTTAACCATCCTTTACCTTTACTATCATTATTTTTGTTGTTGTTAAACTGTTCA
CTACTGAGATAGATTTGTCATTACCAACACTAAAAAAATTACATTAGCTGAGACCTGTTTCTT
ATCATATATCTAGTTCCATAAATGAAACAGTCAAGTCCTGTTCTGAATGAAGTACAGTCATGT
CCTATTCTATGATTTGAGCTTTGCCGTGAACTTGCATTAGCATAGTTTAACTAAATTTTCTATG
CTTGGTACGTGGTAACAAGAATCCCGAAGTTCCAATGTGGTTGCCTATTGCAACTTAGTAAAT
TCATTTATGGATGTTCCTAGCTGTCGTCCATTTCAAGGTTCTGACATGTCACTAGCTGAATCAT
GAAAACAGTCATTACCTGTGATAACTTTTTATTAAACACTTTGGGGGTGCCTAAAAATGGTTTT
GGGAAGCATCCATATGATTTCTGAACCACTTTATGTAGTGCCCTGCTGACTAAAAGTTCAGGT
ATTCCACATTTTACAAACAGTAAGGCGAAGAATAAAAGATATCCTGTCCCACACTGTGCAAAT
CATAGGTCTGCATCTAGTTAATTTAAATCCATCTTTGATCGGAACAACAATGATATGCTTTAGT
TAGTTCCTGCTAGTAGTTGCAAGTTGCATACTCCCTCCATCCCATAATATAAGGGATTTTGGAG
GGATGTGACATATCCTAGGACTACGAATCTGGATAGGCACCTGTCCAGATTTGTAGTCATAGG
ATATGTCACATCCCTCCAAAATCCCTTATATCATGGGACGGAGGGAGTACTCAACTAGCCGTT
GGTGAGCAGTATGCATAACTGCTAATATCATCACTGATTCCATCCACAGGATTCGGATTTAGA
AAGTTTTTCTCCAAAACATTAGATCTTGTTGCGAAAGTTTTTCTCCTGAACATTTAGATCTGGT
TGTGAACTTCATCTGGATATGGTTGATACTAACTTTATTGATTTGCTGCTAGTTGTTGCAGACC
TAGGCAGTCATTTATAGAGCAGTACTTTTATTTGCTAAATCTATATTTTCTGATCCGACCCCCA
TGATTTGAATTATAAGTGTTTTCATCCATTATAGATTTTGTTGCAAATATTATCCACAAATGTA
TATACTAGGTACTTCATTAGCTTACAATGCCAAAAATACTTCATGAGCTCTTTTTTGGGTTGAA
ACCTAGAGGTAGCAACAATTGTTTCTTTTCCTGGGATTCTGCAGTCTGGCCTGTTTTTCATTAT
CAGTAGCTTCCACATTATTGATACCATTTTAGCCATCAATAGTTTTGTGCCTTTTCTCTTCAATT
ATTTTTACACGATAACAACTGCTGTGGTTTATGATATTTGTGTGTACTATTTCAGGGGTGCACA
GCAACAGTCCTGCTGATTTGGTTTGATCAAAAGAAAGACTGTTTTGCCCAATGTGCTAATCTA
GGTGATTCAGCTTGTGTTATGAGGTAAAAAGTACCTTTTTACTTTATTTTCTGAAGTTTAGCCG
TTTGTCTGTTGACTGTAACCTCCAGTTTTTTATGTATAACATCTGCTTTTGTCAGTGTCAATGGA
AAGATGATTGAAATGACTGAAGATCATCGAGTAGCTAGTGTAACTGAACGAGCTAGGATAGC
AAGAGCTGGACAGGCCCTGAAAGCTGGCGAAGTCCGGATTAATGGTTTGCTCTTTGCCCGTTT
CAAGTTTGAGTGCAAGTCTGAGATTACCATAAATGGTGAAAGCTATATTGTTATTTTTTATTT
CTCCAGGACTTAATCTCGCCAGGATGTTCGGAGATAAGTTTCTAAAAGAGCAAGATTCACGCT
TCAGCTCAGAACCATATGTGAGCCAAGCTGTTCACATTACAAAAGCATGCACAGCTTTTGCAG
TTATTGCTAGGTAACATGATTTCTCAGTGCTGCGAAGGTAATGCTTACTGATGTAATGTGTCAA
TCATGACGTTCCGGTGATTGTTTGCATGTGTGCAGCGATGGGCTCTGGGATGTTATTAGTACTA
AAAGGGCAGTTCAGCTTGTTGTTGAGGTGAACGAGCACGCTGTTTTTTCGTGTTAGTTGCATTG
TTCTTTTAATTGTTGTCTCATGCTGGTCATATGTTGCAGGGTAGGGAGAGAAACAGTGGTGAT
AGTGCCTCGGCGGACAAAGTAGCCAATCGTATACTAAGTGAAGCTAGGAATTTGCGAACCAA
GGACAATACATCCGTAATATTTGTAGATTTTGACATCTTGAGAACAGACCATTGTATTGCCAA
ATGATTTTGACTATTTTTGGGACACCATATTCCAAGAAATCATTTGCCTGGCTGTTGCTCGTCG
CTTCCATAATTTTGCTTCAGCTATGGTGTCAAAGATGCTGCAATGTCATGAAGTGTTGCCTACC
TATCCTGTGACTGTAAATTATGTGGACTTTTAAGTTAGCTTATTATTGGATCTGATAGACTGAT
GTAACCAGTGTCATTGCCTTCATACACTGCCTCATCATTTGATTAGGTGGTTATCTTTCAGTAG

FIG. 5YY

ATTTAACTTCAAATTTCTTGATGAAAACTCAAGCATAAAGTGCATATGCTTGATGTTCATCAG
AAACCTTTTACCATGTCACAGAATATACTACAGTAAGCCCTCCAAGGACATCCTGCCAAGTGA
AAACTGCTGTGATTTCCCAACAACTCCAAAGTTCCAAACTCCATCACTGGTCAGGTTGTAAAT
GCATTGTATTGCCTTGCATTGTCTGTCTCTTTCAATCATTTTTGCACAAAGGTCAGGCTTCAGA
AGCCTCCAGTTGTTTCCCTGACAGAAATGGAATACTGTGGAATCTGCCAAGGGCTAGAATCTA
GTGGTGTAACTCTGAAATTCTCTGTCCTAATCCAGCAAGATGCATGAGGAAGGCTAGTAAATG
CTGTCCCTTTTACTCTTCTCTGCAGATTTGGCACAAATCATTCAATTCCTTTCTCTGCTACTTAG
GGCACTGCAAGTTGTTAGAGCTCTTTGCCTTAATTTGTGAGCTTTGTAGCTGAAAATCTTGGGT
GTCAAATGCTTTGCATGCTTCTCCAAACATGCAAGTTGTTTCTAGATCTGTTTGACAAAACTTT
GACTAACAGTAGTATGTGCACAAGTGACTGCTGAAAAGGAGGGAAGAGTTATAGTGTAAATA
TTTTTCCTTACTAATCAAAACGATATAAGATTTGAAAATTACCAGTTTGAATTTACGTAAAGTT
CACCGTCCCCCCCTCCACCCCAAAAAAGAAAAAAGCTGCTGCCAAAACTTCAAATTATCAAAT
TTAATTTTGAAGGTAGAGTATTTTCAACGTTTTCTTTATCAGCATTGTCTTTTGTGAATAAAAG
CTTTATTCACAAATTATTTCTTAATTGCTAATTAGCCATTTTGGCTTATAGTTAGCCTAGTCTTT
CAAGTCGCTAAGTGCATATGCTTGATGTTCATCAGAAACCTTTTACCATGTCATAGAATATACT
ACAGTAAACTTCAAATTATTTCTTAATCGCTAATTAGTCATTTTGGCTTATAGTTAGCTCTTGG
CTAACCATGCATCGGCATAATGTAACAAGGGAGGTATTAACTACTACCTACCTTATGGGTCAA
TTTCGACAACACAGGCATTGGCATATTGTAACAAGTGAGGTGTTAACTACTACTCCTACCTTA
TGGGTCAATTTGGCCAACACACTATATTGTTGAAATTAATTAAATAATTTCCCCCCGCTCGCTC
TCTCTCACCCTACAGTCTCACAAACAAGACAAACAGTACAGAGGTACTAGTAAGAAAATAGA
CACAAACATGCGTATATATTGGACGGCATCTTGTTTGGTTCCTCTGTTCACTCGTACAGAAACT
CCAAAGCTACGTACTTGAATAAAAACGCTAATGACCTACTGGCCAATAGTTAATCAACAGGC
ATTCTGCCTATATACGGCCTCTAATTAAGACACACCCTATCTACTGACCGTATATATATGCACG
TACGTAGTACGTATACAGTATCACGCATTGCAACAGCTAAACTAACTGTCTGACAATACGCTC
ACAGAAGCACGTTTTGATGGCTAGCTAACTACACCATGCTAACACTAAGATGTACACATTACA
ATATTAATTGCTTCCAACACATATGGAGAAAAAGGATCAATATATAACTGAGGGTATATATTC
TGTGTAGAATAAAAATTCCAAACCAATCAAACTCGGTTGAGATGAGAAAGTGCCGGTGGTTG
TTAGATGCATAATTAACTGCACTCATCAGGGTTTAAGTTGCTCGGTGTTTGTTAGTTGATCGGT
GTGTGCATATTGATGTGCGTGCTTGTTCATCTTCCATGTAATAAGAAAACCTACTACTCCCTCC
GTCCTATAATATAAGAGATTTTGAGTTTTTGCTTTTAACGTTTGACCACTTGTCTTATTCAAAA
TTTTTTAAAATTATTATTTGTGACTTGCTTTATTATCTACTGTACTTTAAGCACAATTTTTCGTT
TTTTATATTTGAAATTTTTTTAAAATAAGACGAGTGGTCAAACGTTGCAAGCAAAAACTAAAA
ATCCCTTATATTGTGGGACGGAGGGAGTAGTTGTTATGATCCTCTTAGATACTTCCTCCGTCCC
AAAATAAGTGCAGTTTTGCACTATTCACGCTCAACGTTTGACCGTTCGTCTTATTTGAAATTTT
TTTAATTTGTATATGAACAGTAAATACTGATATGTTTTTTTAATAAAAAAGATCATCTTTCAGC
TTTCACAACATTATAATTCCTTTTACTGAAAATACTACTAGTCTTACCCAGTGGTTAGATTATA
TTAAAGAAAATATTTAACTACCGACGTTGTAACTAGGTAAAAAGCCAAGAACTAAGAACTTC
ACTCATCATCTAAATATATGCGCAGAGAATAATTAATTTCATTTCTGAAGCAAATTCCAAAAT
TCCAAAATTTATCAGTTTAAATTTACAAATATTTTGTACCAACATAAAAAAAGAATAAAAACC
GTGCTGACGTCGAAAACGACATGTATGAACCGTTTTTTTTTTCCTTTGTCGACACATGTGGAGG
CCGGGGAGTAGTACGCATAGTAGCTCCTATAGTCCACGTGACCGACCTCGGCATGAGCCGTCG
TGTGCAGCCACCAGTCAAACCCCACCACCTTCAAATCAATTCTTCCATCCCCAACTATCAGAC
CATCTCCCTACCTAAGCTCCCTCACTCACTCGCCTTTACTTATCGATCTCGATCATCCACGAGC
TAGCTAGCAGTGCTCGCCATGGCCGGCGGCGAGGCGCATGCGGCGCTGCAGGCGGTGGCGCA
GAGCCTCCGGTGGACCTACAGCCTCCTCTGGCAGCTCTGCCCCCACCAAGGGTACCTACCCTA
CCTACCTACGACACGATGCACAGTGTTCATCCATGGCCGGCCATGGCGGATCGTCGTCGTTGT
CGATGATCATCGAAGGAAGCTAGAGGATATGGCTCAATACTTTGATAATATATATATACTGATCT
CTCCGTACAACAAAAATATAAAAATTCTAGCTAGTATCGAATGAGACATATGCTATGCTAGTA
CTACGAATCTAAAAAGATGTACATATTTTGATTCGTATTATTAGGATATATCACGAGTTTTTAT
ATTTTGAGACGGATGTAATAATTCTGAATTTAGTTGTGATCGCATGGCATGCAGGAGCTCGCT
GGTGTGGGGGGAGGGGCACTACAACGGCGCCGTCAAGACGCGGAAGTCGACGGTGATGCAG
CCGCCGCCGGCGGAGGAGGAGGACGACGCCGACCACGCGGCGCGCCACCGGAGCCGGCAGC
TGAGGGAGCTCTACGACTGGCTGCAGCAGGCCGGGGAGAACTCCAGCGGCGGCGTGCAGACG
TCGTCGACGACGGCGAGCCGGCGGCCGGGGGCGGCTCTGTCGCCGGAGGACCTGACGGAGAC
GGAGTGGTTCTTCCTCATGTCGGCATCCTACTCCTTCCCTCCCGGCATCGGGTATATAATAAAA
AATATAGATATAAATATTTAAGCATGCATGCATAAATTAAACCACACTTCTTGTTACGTGTTCT

FIG. 5ZZ

TGGCAAAATGATGAACAATTACCACTAATTAATTGGAGCCAGAAACCCTAAAGATTTACCCAC
CTGGTTAATTAATCGGTGTGTTGATCCACGCATGCATGCATGCAGAAAATCAAGATCAGGATA
GCTCCTTTTCTTTTGCAGGTTAATTAGCTAGATCTTCACGTATAATTAGCTAGCTAGATTTTAA
AATATAATTTATTCAATTTGATTTATGATTTTTATTTTTTATTTCAAATAGATACAACTGTATAC
AAAATTTTATTTTGGTACATACCTCCGATCCAACTACATCAGAGGTAAAAAAAAAATTAAACC
GTTGGAATTGATTAGAACAAGATCGTGCGGTCAAATTATATCATAACTAACTTTTCTGATTCTC
TAAAGCATAGAGATGTATATATACATCGTATTATTAGGCTCTATATTTCCTGATTAACACTAGA
TGCATATATAATTTTGATAGTCAAAATATACTTTTGATAGGCTCTAAAGAAAAACTTAATAAC
ATGTACTCCCTCCATATACTTTTGATAGTCATATTTCATCTTGACACACAGATCAAGTATAAGT
AATTCTACTTATCATCCATTTAAACACGCTACTAGTTATTCCTCATAAACAAGCGATTCATTAA
TATTTACATTTCTCGATGCTTGTGTAGCCAATATTGTGTGGAAGAATGGAATGTCATTAAGAG
GATAGGTTGTTGGATTGAAATATGCCTATCAAAAATAAATTTTTAGATTTGAAAATATGCCTA
TCAAAAGTAGATGGAGGGAGTATTAATTAATGTGAATTTCCAATCCTACTGTTGTGATATTAG
GCTTTGTACCTTCTTGTCCAGGAGGTATATATATGGCTCTTTTAAGGATGGGAGAAAATATCAT
CTTTAATACAACTATATATGGCTTTTGTTTGATAAATACAACTTTTATTTTGTATGAATACAAA
TATATTGATAAATATCCACCATTATAATCCTAACCCATTAGGATCATATGGTGTATATTTTTTT
AACTATTTGTTTTTTATAAATTAATATTAAGAGATCACAATAAAAATATAGTATTATGAAAGT
ACTCTTAACAACATATCCAATGATAAAATTATTATTATTACAAAATATAGTGGTCAAATTGTA
TAGAATTCAATAGCCTGATTTTATGACGTCAAGTAAATTAAATAAAGAATGAAGGTAGTGCTA
GAGTGATCAAACAATATCTCTCCTAAAATATGTCCTATAAGTTTTACTCCATAAATCCAAGGG
TCAAAAGTTGTTGGGTTATTTTTTTAGATAATAACATACTACCCCTTTTCAAAATGTATGATTC
TATTGACTTTTTGCACAACATTTAACCATTTGTCATATTAAAAATTAGTATAAACATCTAAAAA
TATAAGTTACAATTATATTTTATTTGATGATAAAACAACTCACAACAAAATAAATAATATTTA
TATAATCTTTTTGGAATAAAACGAATGATCAAACATTATTCAAAAAGTCAATGGTATAGTACG
TTTTGAAATTGATAGACTATGAGAGCAAAATTTTGAGATAACATGGAAAATTATCCTCTTAGA
CATTGCACTGTGTAATAATTAATAATAATGAATGAAAGGCTAAGACTTTTCTTCCACCTTATAT
AAGTGGTTGAATATATAGCAATCACATCATTACATGATTTGTAACCAACCGTCTCTATAGCTC
CGATACAGTGCTAGTTTCACATCGTAATAATTAAAGAGTATAATAATAAATCGAGGTGTACTT
CTCATCGATGAAGTGATGTGCCGCTTAGCTAAATTAAACTCGTATGCGAAAAATCAGTATATG
TCCGGTTAATTTCTAAGAGAGAGAGATTGAGAGAGAATAATTGCGCCCCTCCAAATCCCCCTCTT
GGACGTTAGGGAGCTATATAGACGGTATTGCTAAGTGCGATGTGTACATAACGTACCTGTCGT
AGGAACATTTCTCATCCAAATTAAGTAGTAATGCATGGCATGAAATCCATTTTTGTATTTTGCA
TGGCAAAGAATGACAACAAGGAATACACTAGCTAGCCCTGCCCTTTTTCAATTTAATTTAACA
TCAAACTTAGTTATTGTATTTCTTTTGTCAGAATAGCATGCATTGCATACTCTTTAAAAATAAT
TAATTAGTGTATTTTACTAGTCTTACAAAAGTATCAAGAGAGACAACTAATTATAGTTGGGAG
ACACCAAACTTGTTTTTAATAATGACAATTAAAACCCTACCTCTACATCCAACATAGACGTAC
ATAGTCCGAAGGCGCCAAATATTTGTACATTTAGCTACCAGATTTCAGTACGAGTTCTCACAT
TATAATTTTGATTTTTTTATTTTTTTTATAAACAATCTGGTACCCTTTTATGTCTGGAAGGAAAA
AAAAAATCTAAATTGCAACATTTTAGTCGGTGAGAATGGTACTCTGTCCTAGCTACTTTCTAC
ACATGAGAGAGAGAGAGAGAGAGAGAGAGAGAGAGCCTTTAATTGCCCTTGCCCATGCATCTTT
CTTTGCACACATGTATGCTTTTCACATTGTCATGAGGAGAGAACTTGTTAAGTTGCACACATGT
GTGCTTTGCATGTCTTCAGGTTACCTGGAAGGGCATTTGCAAGGAGAGGCCATGTATGGCTCA
CTGGAGCAAATGAAGTTGACAGCAAAGTATTCCTAAGAGCAATTCTTGCCAAGGTTCAGCCAT
CACCTTCTCTTACCTATTTTTCACTCTGAATGCCAACAGTGCTTTGCACATTGTAGTCTGTTTGC
AGACTGCAAATGATGACCATAATCAGATCAGAAAATAAAATAATATTATATACTTTTTGAGCC
AGCTAGCAAGAATATGTAACAATAATTCTCCTTTTTTTTTCTTGTTCTTTTCCCTGATGTGGTGC
ATAACAAATAACCAAACTGATGAATGGCAGAGTGCTGGTATCCAGGTATTTGCCTCTAAAAGT
AGCTACACGTTTACTATGAAATTTTGTGGCTTTTGTTCATCTTTGGATGCAGTGGCCATTATCT
AAAAACTATGAATTTCCAGACTGCAGTTTTTATCTAATTTTGTGACTTTGTACATCAGACAGTT
GTGTGCATTCCTGTTGTCGATGGCGTCCTGGAAATTGGAACTACGGAAAAGGTGATTTCGTAT
ATTATCAGCTGACAATCTAATTATATGGGCCATATAATTAAGTATAAATCAAAATACCTCATA
ATATATTATAAAGTATCTAATGTGATTATGTGAATATTGGCTATTTCAATGTAATTTGATATAT
GAAACTGATAATCCTCTGAAACTCCGTAAGGATCAAACTAATCAAAATGTATATATTTTCAAG
GTGGAGGAAGATATGGGCCTGATTCAGTATGCAAGGGGCATCTTCATGGATCAACATGGCAT
CCACATGAAGCCTACCCTCTCACAGCACTCAACATCCAACCCAGTCACCCACTGTACTCATCA
GCATCCAATCCAGGTTCAGATGCAACTAGGTATCACCAGCCAAACAAAGTTTGATTATTCAGA

FIG. 5AAA

TGAGCTCAATGCAGATGAGGAGAATGATGACACAGAAGAAGAGGGCATGTCAGGTTCAGACA
CTAACAACACTGACACTGAAAGGAATTCAGGCCAGCTGCAACTTCAAATGCAAGACCAACTG
AACATGGTGAGCAATGACCACCAGACAATACCAAATAATGCAGTTTCCAGTGAGCTAATGCA
GTGTGAGATGTCAGAAGTGGTAAGAGATGGCTGCTCAAATAATATTTAGAGGATGAAATCC
AAATGCTGATGGATTGCCAAAACAGTAATTGTCAGTTAAATTTGCAAGGGCCAGATGAGCCTT
GTCACTCTTGGCATTTTCTCTGCGAGGAGTTACAAAATGATTACCAGCCAGGTATTACATTTGA
GAAGATAATCCTTCAAAAGCACCCTTGTTCCAAAAATATATATTTGTACTCTTCACACAAGCA
CTGCCATTTTTTTTCTTTTTTGCATACATCCTCAATTCTTGCATTTCTTTTCCATATATTTGATAC
AACTGTCTCCATTTCCCTTCTGTCACAGCTACTGAAGATCAAGTGGCATCACCTGAAAATACC
CATTACCCAAAAACACTCATGACAATCCTACATTACAACACGCTGCGACAGCAAGAGATGAA
CATCAAGAACTACTTGCCAGTTTCAGAGAAATCATCATTCTCCAGATGGACTACTCCTGAAGG
AAGTGATGACAACAAGACCATGATCAGTCCAGGCACCACACAGAGAATGCTCAAGAGCATCC
TGATGATTGTTCCCAGTAGTCACTGCAGTTACAGGGGAGCAGAAACACCTGAATCAAGGGGC
GGGAAAGGCGCAAGTGGATGCCATCCAAGGTGATTTCAGTGCCAACCATGTGCTGAAAGAGA
GGAGAAGAAGAGAGAAGCTCAATGAGAAGTTCATAATTCTGCGATCTTTGGTACCTTTCATGA
CAAAGGTAATTAAGTACTCCCTCTATTTCTATAAAGCCGTATTTGACTAGTTATCTTATTTAGA
AAGTATGTGCAAATATGTAAAATATAAGTCATACTTAAAGAACTTTTAATGTTATTAAATAAT
AAGTCACACCAAAAATAAAACATATATATTTTTAATAAGATAAATGATTAAATGTATATATAA
AAATTAATAGCGTCACATATTTTAAAATAGAGGGGTATTTAAGTACCCACAGGATCATCAAAA
TTCAGTTATCTTTTCTTAAGCCTCTAACGAACATTGGAAGATCCTCACTAATGGCAGCATGAAT
CTAGGGTTCACTATTTCGGAATGCAAAATATGTTTTACCGGGCATCCGATTTTTAAAAAATTCA
GAATGAAGAAAATTGAATCTTTTTTATGGATTTGAATAAATCTTGATAAATTCGAAAAAATTT
CCGAACTTTTGGCCAGAAGTGAATCCTACCCGTATCCACCGGTAATAAACCTAAATTTTTGGG
AGTAATGAATTAATGTTATATATAATCCATGAATTATATAGTTCCAAACTACTCCGTAACAAA
TTTTCAGGAGTAGTGAAATTAATATTATTACAATCTCAGAAAAAAATGGCAGAAACAATTAAT
CTGTTTTCAATTATTAATTAATTTGTTTTTGTGTCCAGATGGACAAGGCGTCGATACTAGGCGA
CACGATCGAGTACGTGAAGCAGCTAAGGAACCGCATACAAGAGCTCGAGTCGTCGTCGTCGT
CGTCACGAGCAGCCGCCCGGGCGCCATCGGCGGCGGCCGCCGGGAGGCGGAGGAAGAGATC
CGCCGCCGCCGCCACTGCCACGGCGGCGGAAGGGATGAGCAGCAGCAATGGCCGCAATGGCG
GCGAGGCGGCGGAGGTGGTGCAGGTGTCCATCATCGAGAGCGACGCGCTGCTGGAGCTCCGG
TGCGGTTGCGGCGGCGGCGGCGGCGGTGTGGTGCTGCTCCGGGTGATGCAGGCGATGCAGGA
GCTCCAGCTGGAGGTCACCGCCGTCCAGGCCTCGTGCGCCGGTGGCGAGCTGCTCGCCGAGCT
GCGCGCCAAGGTCGTCGTTATGATCCTGATCTGCATGAAAATGCAAATGCAAATGCAAATGCA
GAATTAAGCTTTCATTCTTGCTCCTCTGAATTCTGAATTTATATATTCACCCTTCTTTCGATCTG
CTCGTACGTTCGTTTCGCCTAAATTATGTACAAATTAACTGAATCTTTGAACTGAAAATAACTG
AATCTTTTTTGTGTGTTTTTGTGTGGGTGAATTGGTTGGCGCAGGTGAAGGGGAGGAGGAGGA
GCAGCATCGCTCAGGTGAAGAGGGCCATCCATCTCGTCCTCTCCTCCTCATCGATATCACCCT
GAATTAATTAATAATTAATCTAGCTTCGTGCATGAATGCATGCCACAAATATATACAAATTTA
CCATATCAATATGTGAGAGAGTAATAATCATATAATTGCAATCAAGCACCTGTGCTGCATGCA
TATATATATTCTGATTGCAATTCATTTGCAAATGTTAAAACTAGATATGTATGTACATATATCA
TATATGTGGAGTACATTAACATTAGATTAATTAGAACCATCTATATATCTAACCATCGTGGCA
AATTGGTTAGATCAGGGAAGTGAAAAAACTCTAGTAATAATAATAGTAATGTAATGCCATTTT
AT

FIG. 5BBB

| my names | primer name | new name | SEQ ID NO:XX | forward primer sequence | SEQ ID NO:XX | reverse primer sequence | bp position along chr 7 | use |
|---|---|---|---|---|---|---|---|---|
| | AF1 | | SEQ ID NO. 10 | tcaattcttccatccccaac | SEQ ID NO. 11 | atgccatgcgatcacaacta | 6,061,079 - 6,061,598 | sequence |
| | AF2 | | SEQ ID NO. 12 | ctgatctctccgtacaacaaaa | SEQ ID NO. 13 | tgccaagaacacgtaacaag | 6,061,415 - 6,061,990 | sequence |
| | AF3 | | SEQ ID NO. 14 | gagggagctctacgactgg | SEQ ID NO. 15 | ccgcacgatcttgttctaat | 6,061,735 - 6,062,333 | sequence |
| | AF4 | | SEQ ID NO. 16 | caggatagctccttttcttttgc | SEQ ID NO. 17 | ggcatatttcaatccaacaacc | 6,062,105 - 6,062,712 | sequence |
| | AF5 | | SEQ ID NO. 18 | tcgatgcttgtgtagccaat | SEQ ID NO. 19 | tttgatcactctagcactaccttca | 6,062,635 - 6,063,203 | sequence |
| | AF6 | | SEQ ID NO. 20 | gcctgattttatgacgtcaagt | SEQ ID NO. 21 | gcactgtatcggagctatagaga | 6,063,142 - 6,063,711 | sequence |
| | AF7 | | SEQ ID NO. 22 | ggctaagacttttcttccacctt | SEQ ID NO. 23 | tgcaatgcatgctattctga | 6,063,610 - 6,064,126 | sequence |
| | AF8 | | SEQ ID NO. 24 | tttgcatggcaaagaatgac | SEQ ID NO. 25 | cctgaagacatgcaaagcac | 6,064,011 - 6,064,606 | sequence |
| | AF9 | | SEQ ID NO. 26 | cttgcccatgcatctttctt | SEQ ID NO. 27 | ccactgcatccaaagatgaac | 6,064,506 - 6,065,023 | sequence |
| | AF10 | | SEQ ID NO. 28 | ttccctgatgtggtgcataa | SEQ ID NO. 29 | gagggtaggcttcatgtgga | 6,064,890 - 6,065,430 | sequence |
| | AF11 | | SEQ ID NO. 30 | atgggcctgattcagtatgc | SEQ ID NO. 31 | ggaacaagggtgcttttgaa | 6,065,362 - 6,065,943 | sequence |
| | AF12 | | SEQ ID NO. 32 | gccttgtcactcttggcatt | SEQ ID NO. 33 | ggttggcactgaaatcacct | 6,065,844 - 6,066,400 | sequence, mRNA |
| | AF13 | | SEQ ID NO. 34 | caccacacagagaatgctcaa | SEQ ID NO. 35 | catgctgccattagtgagga | 6,066,263 - 6,066,792 | sequence |
| | AF14 | | SEQ ID NO. 36 | agcctctaacgaacattggaa | SEQ ID NO. 37 | cagaggagcaagaatgaaagc | 6,066,750 - 6,067,638 | sequence |
| | AF15 | | SEQ ID NO. 38 | gcgacagcaagagatgaaca | SEQ ID NO. 39 | acgggtaggattcacttctgg | 6,066,149 - 6,066,955 | sequence |
| | AF16 | | SEQ ID NO. 40 | tgcgatctttggtacctttca | SEQ ID NO. 41 | gctctcgatgatggacacct | 6,066,455 - 6,067,401 | sequence |
| | AF17 | | SEQ ID NO. 42 | agcagctaaggaaccgcata | SEQ ID NO. 43 | ttcagggtgatatcgatgagg | 6,067,193 - 6,067,868 | sequence |
| Up560 | RID7 | | SEQ ID NO. 44 | tcaacgtttgaccgttcatc | SEQ ID NO. 45 | cacatgtgtcgacaaaggaaa | 6,060,277 - 6,060,976 | polymorphism detection |
| Up112 | RID6 | | SEQ ID NO. 46 | cgtcgaaaacgacatgtatga | SEQ ID NO. 47 | gttggggatggaagaattga | 6,060,924 - 6,061,098 | polymorphism detection |
| AFex1d | RID5 | RID13 | SEQ ID NO. 48 | acctacgacacgatgcacag | SEQ ID NO. 49 | atgccatgcgatcacaacta | 6,061,299 - 6,061,598 | polymorphism detection |
| Afga | RM21197 | | SEQ ID NO. 50 | ttgcaacattttagtcggtgag | SEQ ID NO. 51 | ccatacatggcctctccttg | 6,064,410 - 6,064,645 | polymorphism detection |
| AFex5d | RID4 | RID12 | SEQ ID NO. 52 | tacaggggagcagaaacacc | SEQ ID NO. 53 | aaaggtaccaaagatcgcagaa | 6,066,321 - 6,066,473 | polymorphism detection |
| AFex7d | RM631 | RM651 | SEQ ID NO. 54 | caggtgtccatcatcgagag | SEQ ID NO. 55 | aggatcataacgacgacctt | 6,067,381 - 6,067,574 | polymorphism detection |
| Afend | RM632 | RM652 | SEQ ID NO. 56 | gccaaggtcgtcgttatgat | SEQ ID NO. 57 | ccaaccaattcacccacac | 6,067,552 - 6,067,778 | polymorphism detection |
| Rc16 | RM21177 | | SEQ ID NO. 58 | ggagggttgccgatatatga | SEQ ID NO. 59 | atgcagcgggagtttttatg | 5,728,266 - 5,728,494 | fine mapping |
| Rc12 | RM21194 | | SEQ ID NO. 60 | tatggctacacgcctacacg | SEQ ID NO. 61 | gaagcgtgggatgtttgttt | 6,034,075 - 6,034,276 | fine mapping |
| 5779_31 | RM633 | RM653 | SEQ ID NO. 62 | tactcccccattcctctcct | SEQ ID NO. 63 | agccctgctcactgttcatt | 6,139,018 - 6,138,808 | fine mapping |
| 11060_7s | RID8 | | SEQ ID NO. 64 | aactcttagtggggtcttagtcct | SEQ ID NO. 65 | caaagggagtgatacctacacatt | 6,108,072 - 6,107,956 | fine mapping |
| 6168.14-3 | RID3 | RID11 | SEQ ID NO. 66 | ggagtggttcttcgacagtaaaa | SEQ ID NO. 67 | ggagacgcagttgaagatcc | 6,133,359 - 6,133,934 | fine mapping |
| 5087.2 L | RID2 | RID10 | SEQ ID NO. 68 | aggggcagttttcagtcaga | SEQ ID NO. 69 | ctattgccccctgtggtcta | 6,411,490 - 6,412,048 | fine mapping |
| 4715.11-3/ | RID1 | RID9 | SEQ ID NO. 70 | atcatatctggggtcggatagaa | SEQ ID NO. 71 | gtacatgcagtaccgcgaca | 6,747,632 - 6,747,880 | fine mapping |
| dsid11 | | RID14 | SEQ ID NO. 72 | tgcatgcttaattacgtggtc | SEQ ID NO. 73 | tgggacggagggagtagtag | 6,068,728 - 6,068,850 | fine mapping |
| dsid2 | | RID15 | SEQ ID NO. 74 | ACGCAAGGCTTAGCTG' | SEQ ID NO. 75 | AAATGAAAGCGATGCGA | 6,083,097 - 6,083,206 | fine mapping |
| | AFin6 | | SEQ ID NO. 76 | caggcaccacacagagaatg | SEQ ID NO. 77 | ctcctctctttcagcacatgg | 6,066,259 - 6,066,419 | mRNA |

FIG. 6

| novel? | marker type |
|---|---|
| yes | |
| yes | |
| yes | |
| yes | |
| yes | |
| yes | |
| yes | |
| yes | |
| yes | |
| yes | |
| yes | |
| yes | |
| yes | |
| yes | |
| yes | |
| yes | |
| yes | |
| yes | indel |
| yes | indel |
| yes | indel |
| yes | SSR |
| yes | indel |
| yes | SSR |
| yes | SSR |
| yes | SSR |
| yes | SSR |
| yes | SSR |
| yes | indel |
| yes | indel |
| yes | indel |
| yes | indel |
| yes | indel |
| yes | indel |
| yes | indel |

FIG. 6 CONT.

| species | subspecies | Subpopulation | Phenotype | name | Cornell Reference | 21 | 96 | 316 | 324 | 601 | 660 | 897 | 1023 | 1191 | 1353 | 1390 | 1408-1421 | 1833-1844 | 1923 | 1962 | 1982-1987 | |
|---|---|---|---|---|---|---|---|---|---|---|---|---|---|---|---|---|---|---|---|---|---|---|
| O. sativa | japonica | tropical japonica | white | Jefferson | RA5699 | T | G | G | T | A | A | A | T | G | C | G | del | 12bp del | T | T | AAATGC | SEQ ID NO:78 |
| O. sativa | japonica | temperate japonica | white | Nipponbare | RA5698 | T | G | G | T | A | A | A | T | G | C | G | del | 12bp del | T | T | AAATGC | SEQ ID NO:79 |
| O. sativa | japonica | aromatic | white | Cuba - 65 | RA5015 | T | G | G | T | A | A | A | T | G | C | G | del | 12bp del | T | T | AAATGC | SEQ ID NO:80 |
| O. sativa | japonica | aromatic | white | Basmati 217 | RA4993 | A | G | G | G | A | G | G | T | A | A | G | full | 6bp del | C | C | deletion | SEQ ID NO:81 |
| O. sativa | japonica | temperate japonica | red | Gangdodo | KG2 | T | G | G | T | A | A | A | T | G | C | G | full | 12bp del | T | T | AAATGC | SEQ ID NO:82 |
| O. sativa | japonica | temperate japonica | brown | Rc | Rc | T | G | G | T | A | A | A | T | G | C | G | full | 12bp del | T | T | AAATGC | SEQ ID NO:83 |
| O. sativa | indica | aus | white | Arc 10352 | RA4981 | T | G | G | T | A | A | A | T | G | C | G | del | 12bp del | T | T | AAATGC | SEQ ID NO:84 |
| O. sativa | indica | aus | white | Dhala Shaitta | RA5361 | T | G | A | T | A | A | A | T | G | C | G | del | 12bp del | T | T | AAATGC | SEQ ID NO:85 |
| O. sativa | indica | aus | white | Kalamkati | RA4963 | A | G | G | G | A | G | G | T | A | A | G | full | 6bp del | C | C | deletion | SEQ ID NO:86 |
| O. sativa | indica | aus | white | T1 | RA4893 | A | G | G | G | A | G | G | T | A | A | G | full | 6bp del | C | C | deletion | SEQ ID NO:87 |
| O. sativa | indica | aus | light red | Jhona-349 | RA4979 | A | G | G | G | A | G | G | T | A | A | G | full | 6bp del | C | C | deletion | SEQ ID NO:88 |
| O. sativa | indica | aus | red | Kasalath | RA5339 | A | T | G | G | A | A | G | T | A | C | G | full | full | C | C | deletion | SEQ ID NO:89 |
| O. rufipogon | indica | aus | red | IRGC 105491 | RA5718 | A | T | G | G | A | A | G | T | A | C | G | full | full | C | C | deletion | SEQ ID NO:90 |
| O. sativa | indica | indica | white | IR64 | RA5133 | A | G | G | T | A | A | A | T | G | C | G | del | 12bp del | T | T | AAATGC | SEQ ID NO:91 |
| O. sativa | indica | indica | white | 93-11 | RA5700 | A | G | G | T | A | A | A | T | G | C | G | del | 12bp del | T | T | AAATGC | SEQ ID NO:92 |
| O. sativa | indica | indica | red | Pocheonjangmangmebyeo | KG37 | A | G | G | G | A | G | G | T | A | C | G | full | 6bp del | C | C | deletion | SEQ ID NO:93 |
| O. sativa | indica | indica | red | Mudgo | RA5282 | A | G | G | G | A | G | G | T | A | C | G | full | 6bp del | C | C | deletion | SEQ ID NO:94 |
| O. rufipogon | | O. rufi II | red | IRGC 106262 | RA2662 | A | G | G | G | A | A | G | T | A | C | G | full | 12bp del | C | C | deletion | SEQ ID NO:95 |
| O. rufipogon | | O. rufi I | red | IRGC 105726 | RA2755 | A | G | G | G | T | A | G | C | A | C | A | full | 12bp del | T | C | deletion | SEQ ID NO:96 |

FIG. 7A

**SEQ ID NO: 97 *Oryza sativa* ssp *japonica*, subpopulation: tropical japonica, variety: Jefferson, color: white, RA5699** atggccggcggcgaggcgcatgcggcgctgcaggcggtggcgcagagcctccggtggacctacagcctcctctggcagctctgcccccaccaaggga
gctcgctggtgtgggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgggggcggctctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcacccactgtactcatcagcatccaatccag
gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
ataccaaataatgcagtttccagtgagctaatgcagtgtgagatgtcagaagtggtaagagatggctgctcaaataatatttagaggatgaaatccaaatgct
gatggattgccaaaacagtaattgtcagttaaatttgcaagggccagatgagccttgtcactcttggcatttctctgcgaggagttacaaaatgattaccagcc
agctactgaagatcaagtggcatcacctgaaaatacccattacccaaaaacactcatgacaatcctacattacaacacgctgcgacagcaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
ga/TGCCATCCAAGGTGAtttcagtgccaaccatgtgctgaaagagaggagaagaagagagaagctcaatgagaagttcataattctgcgat
ctttggtacctttcatgacaaagatggacaaggcgtcgatactaggcgacacgatcgagtacgtgaagcagctaaggaaccgcatacaagagctcgagtc
gtcgtcgtcgtcgtcacgagcagccgcccgggcgccatcggcggcggccgccgggaggcggaggaagagatccgccgccgccgccactgccacg
gcggcggaagggatgagcagcagcaatggccgcaatggcggcgaggcggcggaggtggtgcaggtgtccatcatcgagagcgacgcgctgctgga
gctccggtgcggttgcggcggcggcggcggcggtgtggtgctgctccgggtgatgcaggcgatgcaggagctccagctggaggtcaccgccgtccag
gcctcgtgcgccggtggcgagctgctcgccgagctgcgcgccaaggtcgtcgttatgatcctgatctgcatgaaaatgcaaatgcaaatgcaaatgcagaa
ttaa

**SEQ ID NO:98 *Oryza sativa* ssp *japonica*, subpopulation: temperate japonica, variety: Nipponbare, color: white, RA5698** atggccggcggcgaggcgcatgcggcgctgcaggcggtggcgcagagcctccggtggacctacagcctcctctggcagctctgcccccaccaaggga
gctcgctggtgtgggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgggggcggctctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcacccactgtactcatcagcatccaatccag
gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
ataccaaataatgcagtttccagtgagctaatgcagtgtgagatgtcagaagtggtaagagatggctgctcaaataatatttagaggatgaaatccaaatgct
gatggattgccaaaacagtaattgtcagttaaatttgcaagggccagatgagccttgtcactcttggcatttctctgcgaggagttacaaaatgattaccagcc
agctactgaagatcaagtggcatcacctgaaaatacccattacccaaaaacactcatgacaatcctacattacaacacgctgcgacagcaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
gatgccatccaaggtgatttcagtgccaaccatgtgctgaaagagaggagaagaagagagaagctcaatgagaagttcataattctgcgatctttggtacctt
tcatgacaaagatggacaaggcgtcgatactaggcgacacgatcgagtacgtgaagcagctaaggaaccgcatacaagagctcgagtcgtcgtcgtcgt
cgtcacgagcagccgcccgggcgccatcggcggcggccgccgggaggcggaggaagagatccgccgccgccgccactgccacggcggcggaag
ggatgagcagcagcaatggccgcaatggcggcgaggcggcggaggtggtgcaggtgtccatcatcgagagcgacgcgctgctggagctccggtgcg
gttgcggcggcggcggcggcggtgtggtgctgctccgggtgatgcaggcgatgcaggagctccagctggaggtcaccgccgtccaggcctcgtgcgc
cggtggcgagctgctcgccgagctgcgcgccaaggtcgtcgttatgatcctgatctgcatgaaaatgcaaatgcaaatgcaaatgcagaattaa

**SEQ ID NO:99 *Oryza sativa* ssp *japonica*, subpopulation: aromatic japonica, variety: Cuba - 65, color: white, RA5015** atggccggcggcgaggcgcatgcggcgctgcaggcggtggcgcagagcctccggtggacctacagcctcctctggcagctctgcccccaccaaggga
gctcgctggtgtgggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgggggcggctctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcacccactgtactcatcagcatccaatccag

FIG. 7B gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
ataccaaataatgcagtttccagtgagctaatgcagtgtgagatgtcagaagtggtaagagatggctgctcaaataatatttagaggatgaaatccaaatgct
gatggattgccaaaacagtaattgtcagttaaatttgcaagggccagatgagccttgtcactcttggcatttctctgcgaggagttacaaaatgattaccagcc
agctactgaagatcaagtggcatcacctgaaaataccattacccaaaaacactcatgacaatcctacattacaacacgctgcgacagcaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
gatgccatccaaggtgatttcagtgccaaccatgtgctgaaagagaggagaagaagagagaagctcaatgagaagttcataattctgcgatctttggtacctt
tcatgacaaagatggacaaggcgtcgatactaggcgacacgatcgagtacgtgaagcagctaaggaaccgcatacaagagctcgagtcgtcgtcgtcgt
cgtcacgagcagccgcccgggcgccatcggcggcggccgccgggaggcggaggaagagatccgccgccgccgccactgccacggcggcggaag
ggatgagcagcagcaatggccgcaatggcggcgaggcggcggaggtggtgcaggtgtccatcatcgagagcgacgcgctgctggagctccggtgcg
gttgcggcggcggcggcggcggtgtggtgctgctccgggtgatgcaggcgatgcaggagctccagctggaggtcaccgccgtccaggcctcgtgcgc
cggtggcgagctgctcgccgagctgcgcgccaaggtcgtcgttatgatcctgatctgcatgaaaatgcaaatgcaaatgcaaatgcagaattaa.

**SEQ ID NO:100 *Oryza sativa* ssp *japonica*, subpopulation: aromatic, variety: Basmati 217 color: white, RA4993** atggccggcggcgaggcgcaagcggcgctgcaggcggtggcgcagagcctccggtggacctacagcctcctctggcagctctgccccccaccaagggagctcgctg
gtgtgggggggagggg cactacaacggcgccgtcaagacgcggaagtcgacggtgatgcagccgccgccggcggaggaggaggacgacgccgaccacgcggcg
cgcccaccggagccggcagctgagggagctctacgactggctgcagcaggccggggagaactccagcggcggcgtgcagacgtcgtcgacgacggcgagccggc
ggccgggggggcggcgctgtcgccggaggacctgacggagacggagtggttcttcctcatgtcggcatcctactccttccctcccggcatcgggttacctggaagggcatt
tgcaaggagaggccatgtatggctcactggagcaaatgaagttgacagcaaagtattcctaagagcaattcttgccaaggtggaggaagatatgggcctgattcagtatg
caaggggcatcttcatggatcaacatggcatccacatgaagcctaccctctcacagcactcaacatccaacccggtcacccactgtactcatcagcatccaatccaggttc
agatgcaactaggtatcaccagccaaacaaagtttgattattcagatgagctcaatgcagatgaggagaatgatgacacagaagaagagggcatgtcaggttcagacact
aacaacactgacactgaaaggaattcaggccagctgcaacttcaaatgcaagaccaactgaacatggtgagcaatgaccaccagacaatgccaaataatgcagtttcca
gtgagctaatgcagtgtgagatgtcagaagtgggccagatgagccttgtcactcttggcatttctctgcgaggagttacaaaatgattaccagccagagaaatcatcattct
ccagatggactactcctgaaggaagtgatgacaacaagaccatgatcagtccaggcaccacacagagaatgctcaagagcatcctgatgattgttcccagtagtcactga
agttacaggggagcagaaacacctgaatcaaggggcgggaaaggcgcaagtggaacgcgaaaagtcggtgccatccaaggtgatttcagtgccaaccatgtgctga
aagagaggagaagaagagagaagctcaatgagaagttcataattctgcgatctttggtacctttcatgacaaagatggacaaggcgtcgatactaggcgacacgatcga
gtacgtgaagcagctaaggaaccgcatacaagagctcgagtcgtcgtcgtcggtcgTcacgagcagccgcccgggcgccatcggcggcggccgccgggaggcgg
aggaagagATCCGCCGCCGCcgccactgccacggcggcggaagggatgagcagcagcaatggccgcaatggcggcgaggcggcggaggtggtgca
ggtgtccatcatcgagagcgacgcgctgctggagctccggtgcggttgcggcggcggcggcggcggcggcggtgtggtgctgctccgggtgatgcaggcgatgca
ggagctccagctggaggtcaccgccgtccaggcctcgtgcgccggcggcgagctgctcgccgagctgcgcgccaaggtcgtcgtcatgatcctgatctgcatgaaaa
tgcaaatgcnaatgcagaattaa

**SEQ ID NO:101 *Oryza sativa* ssp *japonica*, subpopulation: temperate japonica, variety: Gangdodo, color: red, KG2** atggccggcggcgaggcgcatgcggcgctgcaggcggtggcgcagagcctccggtggacctacagcctcctctggcagctctgccccccaccaaggga
gctcgctggtgtgggggggaggggcactacaacggcgccgtcaagacgcggaagtcgacggtgatgcagccgccgccggcggaggaggaggacgac
gccgaccacgcggcgcgcccaccggagccggcagctgagggagctctacgactggctgcagcaggccggggagaactccagcggcggcgtgcagac
gtcgtcgacgacggcgagccggcggccgggggggcggctctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcacccactgtactcatcagcatccaatccag
gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
ataccaaataatgcagtttccagtgagctaatgcagtgtgagatgtcagaagtggtaagagatggctgctcaaataatatttagaggatgaaatccaaatgct
gatggattgccaaaacagtaattgtcagttaaatttgcaagggccagatgagccttgtcactcttggcatttctctgcgaggagttacaaaatgattaccagcc
agctactgaagatcaagtggcatcacctgaaaataccattacccaaaaacactcatgacaatcctacattacaacacgctgcgacagcaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
gaAcgcgaaaagtcggtgccatccaaggtgatttcagtgccaaccatgtgctgaaagagaggagaagaagagagaagctcaatgagaagttcataattct
gcgatctttggtacctttcatgacaaagatggacaaggcgtcgatactaggcgacacgatcgagtacgtgaagcagctaaggaaccgcatacaagagctc
gagtcgtcgtcgtcgtcgtcacgagcagccgcccgggcgccatcggcggcggccgccgggaggcggaggaagagatccgccgccgccgccactgc
cacggcggcggaagggatgagcagcagcaatggccgcaatggcggcgaggcggcggaggtggtgcaggtgtccatcatcgagagcgacgcgctgct
ggagctccggtgcggttgcggcggcggcggcggcggtgtggtgctgctccgggtgatgcaggcgatgcaggagctccagctggaggtcaccgccgtc

FIG. 7C caggcctcgtgcgccggtggcgagctgctcgccgagctgcgcgccaaggtcgtcgttatgatcctgatctgcatgaaaatgcaaatgcaaatgcaaa
gaattaa

**SEQ ID NO:102 *Oryza sativa* ssp *japonica*, subpopulation: temperate japonica, variety: Rc color: brown** atggccggcggcgaggcgcatgcggcgctgcaggcggtggcgcagagcctccggtggacctacagcctcctctggcagctctgcccccaccaagggagctcgctg
gtgtggggggaggggcactacaacggcgccgtcaagacgcggaagtcgacggtgatgcagccgccgccggcggaggaggaggacgacgccgaccacgcggcg
cgccaccggagccggcagctgagggagctctacgactggctgcagcaggccggggagaactccagcggcggcgtgcagacgtcgtcgacgacggcgagccggc
ggccgggggcggctctgtcgccggaggacctgacggagacggagtggttcttcctcatgtcggcatcctactccttccctcccggcatcgggttacctggaagggcattt
gcaaggagaggccatgtatggctcactggagcaaatgaagttgacagcaaagtattcctaagagcaattcttgccaagacagttgtgtgcattcctgttgtcgatggcgtc
ctggaaattggaactacggaaaaggtggaggaagatatgggcctgattcagtatgcaaggggcatcttcatggatcaacatggcatccacatgaagcctaccctctcaca
gcactcaacatccaacccagtcacccactgtactcatcagcatccaatccaggttcagatgcaactaggtatcaccagccaaacaaagtttgattattcagatgagctcaat
gcagatgaggagaatgatgacacagaagaagagggcatgtcaggttcagacactaacaacactgacactgaaaggaattcaggccagctgcaacttcaaatgcaaga
ccaactgaacatggtgagcaatgaccaccagacaataccaaataatgcagtttccagtgagctaatgcagtgtgagatgtcagaagtggtaagagatggctgctcaaata
atattttagaggatgaaatccaaatgctgatggattgccaaaacagtaattgtcagttaaatttgcaagggccagatgagccttgtcactcttggcattttctctgcgaggagtt
acaaaatgattaccagccagctactgaagatcaagtggcatcacctgaaaatacccattacccaaaaacactcatgacaatcctacattacaacacgctgcgacagcaag
agatgaacatcaagaactacttgccagtttcagagaaatcatcattctccagatggactactcctgaaggaagtgatgacaacaagaccatgatcagtccaggcaccacac
agagaatgctcaagagcatcctgatgattgttcccagtagtcactgCagttacaggggagcagaaacacctgaatcaaggggcgggaaaggcgcaagtggaacgc
gaaaagtcggtgccatccaaggtgatttcagtgccaaccatgtgctgaaagagaggagaagaagagagaagctcaatgagaagttcataattctgcgatctttggtacctt
tcatgacaaagatggacaaggcgtcgatactaggcgacacgatcgagtacgtgaagcagctaaggaaccgcatacaagagctcgagtcgtcgtcgtcgtcgtcacga
gcagccgcccgggcgccatcggcggcggccgccgggaggcggaggaagagatccgccgccgccgccactgccacggcggcggaagggatgagcagcagcaa
tggccgcaatggcggcgaggcggcggaggtggtgcaggtgtccatcatcgagagcgacgcgctgctggagctccggtgcggttgcggcggcggcggcggcggtg
tggtgctgctccgggtgatgcaggcgatgcaggagctccagctggaggtcaccgccgtccaggcctcgtgcgccggtggcgagctgctcgccgagctgcgcgccaa
ggtcgtcgttatgatcctgatctgcatgaaaatgcaaatgcaaatgcaaatgcagaattaa

**SEQ ID NO:103 *Oryza sativa* ssp *indica*, subpopulation: aus, variety: Arc 10352, color: white, RA4981** atggccggcggcgaggcgcatgcggcgctgcaggcggtggcgcagagcctccggtggacctacagcctcctctggcagctctgcccccaccaaggga
gctcgctggtgtggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgggggcggctctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcacccactgtactcatcagcatccaatccag
gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
ataccaaataatgcagtttccagtgagctaatgcagtgtgagatgtcagaagtggtaagagatggctgctcaaataatattttagaggatgaaatccaaatgct
gatggattgccaaaacagtaattgtcagttaaatttgcaagggccagatgagccttgtcactcttggcattttctctgcgaggagttacaaaatgattaccagcc
agctactgaagatcaagtggcatcacctgaaaatacccattacccaaaaacactcatgacaatcctacattacaacacgctgcgacagcaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
gatgccatccaaggtgatttcagtgccaaccatgtgctgaaagagaggagaagaagagagaagctcaatgagaagttcataattctgcgatctttggtacctt
tcatgacaaagatggacaaggcgtcgatactaggcgacacgatcgagtacgtgaagcagctaaggaaccgcatacaagagctcgagtcgtcgtcgtcgt
cgtcacgagcagccgcccgggcgccatcggcggcggccgccgggaggcggaggaagagatccgccgccgccgccactgccacggcggcggaag
ggatgagcagcagcaatggccgcaatggcggcgaggcggcggaggtggtgcaggtgtccatcatcgagagcgacgcgctgctggagctccggtgcg
gttgcggcggcggcggcggcggtgtggtgctgctccgggtgatgcaggcgatgcaggagctccagctggaggtcaccgccgtccaggcctcgtgcgc
cggtggcgagctgctcgccgagctgcgcgccaaggtcgtcgttatgatcctgatctgcatgaaaatgcaaatgcaaatgcaaatgcagaattaa

**SEQ ID NO:104 *Oryza sativa* ssp *indica*, subpopulation: aus, variety: Dhala Shaitta, color: white, RA5361** atggccggcggcgaggcgcatgcggcgctgcaggcggtggcgcagagcctccggtggacctacagcctcctctggcagctctgcccccaccaaggga
gctcgctggtgtggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgagggcggctctgtcgccggaggacctgacggagacggagtggttcttcctcatgtcggcatcctactcctt

FIG. 7D ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcaccccactgtactcatcagcatccaatccag
gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
atgccaaataatgcagtttccagtgagctaatgcagtgtgagatgtcagaagtggtaagagatggctgctcaaataatattttagaggatgaaatccaaatgct
gatggattgccaaaacagtaattgtcagttaaatttgcaagggccagatgagccttgtcactcttggcattttctctgcgaggagttacaaaatgattaccagcc
agctactgaagatcaagtggcatcacctgaaaatacccattacccaaaaacactcatgacaatcctacattacaacacgctgcgacagcaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
gatgccatccaaggtgatttcagtgccaaccatgtgctgaaagagaggagaagaagagagaagctcaatgagaagttcataattctgcgatctttggtacctt
tcatgacaaagatggacaaggcgtcgatactaggcgacacgatcgagtacgtgaagcagctaaggaaccgcatacaagagctcgagtcgtcgtcgtcgt
cgtcacgagcagccgcccgggcgccatcggcggcggccgccgggaggcggaggaagagatccgccgccgccgccactgccacggcggcggaag
ggatgagcagcagcaatggccgcaatggcggcgaggcggcggaggtggtgcaggtgtccatcatcgagagcgacgcgctgctggagctccggtgcg
gttgcggcggcggcggcggcggtgtggtgctgctccgggtgatgcaggcgatgcaggagctccagctggaggtcaccgccgtccaggcctcgtgcgc
cggtggcgagctgctcgccgagctgcgcgccaaggtcgtcgttatgatcctgatctgcatgaaaatgcaaatgcaaatgcaaatgcagaattaa

**SEQ ID NO:105 *Oryza sativa* ssp *indica*, subpopulation: aus, variety: Kalamkati, color: white, RA4963** atggccggcggcgaggcgcaagcggcgctgcaggcggtggcgcagagcctccggtggacctacagcctcctctggcagctctgcccccaccaagggagctcgctg
gtgtgggggggaggggcactacaacggcgccgtcaagacgcggaagtcgacggtgatgcagccgccgccggcggaggaggaggacgacgccgaccacgcggcg
cgccaccggagccggcagctgagggagctctacgactggctgcagcaggccggggagaactccagcggcggcgtgcagacgtcgtcgacgacggcgagccggc
ggccgggggcggcgctgtcgccggaggacctgacggagacggagtggttcttcctcatgtcggcatcctactccttccctcccggcatcgggttacctggaagggcatt
tgcaaggagaggccatgtatggctcactggagcaaatgaagttgacagcaaagtattcctaagagcaattcttgccaagacagttgtgtgcattcctgttgtcgatggcgtc
ctggaaattggaactacggaaaaggtggaggaagatatgggcctgattcagtatgcaaggggcatcttcatggatcaacatggcatccacatgaagcctaccctctcaca
gcactcaacatccaacccggtcaccccactgtactcatcagcatccaatccaggttcagatgcaactaggtatcaccagccaaacaaagtttgattattcagatgagctcaat
gcagatgaggagaatgatgacacagaagaagagggcatgtcaggttcagacactaacaacactgacactgaaaggaattcaggccagctgcaacttcaaatgcaaga
ccaactgaacatggtgagcaatgaccaccagacaatgccaaataatgcagtttccagtgagctaatgcagtgtgagatgtcagaagtggtaagagatggctgctcaaata
atattttagaggatgaaatccaaatgctgatggattgccaaaacagtaattgtcagttaaatttgcaagggccagatgagccttgtcactcttggcattttctctgcgaggagtt
acaaaatgattaccagccagctactgaagatcaagtggcatcacctgaaaatacccattacccaaaaacactcatgacaatcctacattacaacacgctgcgacaacaag
agatgaacatcaagaactacttgccagtttcagagaaatcatcattctccagatggactactcctgaaggaagtgatgacaacaagaccatgatcagtccaggcaccacac
agagaatgctcaagagcatcctgatgattgttcccagtagtcactgAagttacaggggagcagaaacacctgaatcaaggggcgggaaaggcgcaagtggaacgc
gaaaagtcggtgccatccaaggtgatttcagtgccaaccatgtgctgaaagagaggagaagaagagagaagctcaatgagaagttcataattctgcgatctttggtacctt
tcatgacaaagatggacaaggcgtcgatactaggcgacacgatcgagtacgtgaagcagctaaggaaccgcatacaagagctcgagtcgtcgtcgtcgtcgtcacga
gcagccgcccgggcgccatcggcggcggccgccgggaggcggaggaagagatccgccgccgccgccactgccacggcggcggaagggatgagcagcagcaa
tggccgcaatggcggcgaggcggcggaggtggtgcaggtgtccatcatcgagagcgacgcgctgctggagctccggtgcggttgcggcggcggcggcggcggcg
gcggtgtggtgctgctccgggtgatgcaggcgatgcaggagctccagctggaggtcaccgccgtccaggcctcgtgcgccggcggcgagctgctcgccgagctgcg
cgccaaggtcgtcgtcatgatcctgatctgcatgaaaatgcaaatgcaaatgcagaattaa

**SEQ ID NO:106 *Oryza sativa* ssp *indica*, subpopulation: aus, variety: T1, color: white, RA4893** tggccggcggcgaggcgcaagcggcgctgcaggcggtggcgcagagcctccggtggacctacagcctcctctggcagctctgcccccaccaaggga
gctcgctggtgtgggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgggggcggcgctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccggtcaccccactgtactcatcagcatccaatcca
ggttcagatgcaactaggtatcaccagccaaacaaagtttgattattcagatgagctcaatgcagatgaggagaatgatgacacagaagaagagggcatgt
caggttcagacactaacaacactgacactgaaaggaattcaggccagctgcaacttcaaatgcaagaccaactgaacatggtgagcaatgaccaccagac
aatgccaaataatgcagtttccagtgagctaatgcagtgtgagatgtcagaagtggtaagagatggctgctcaaataatattttagaggatgaaatccaaatgc
tgatggattgccaaaacagtaattgtcagttaaatttgcaagggccagatgagccttgtcactcttggcattttctctgcgaggagttacaaaatgattaccagc
cagctactgaagatcaagtggcatcacctgaaaatacccattacccaaaaacactcatgacaatcctacattacaacacgctgcgacaacaagagatgaac
atcaagaactacttgccagtttcagagaaatcatcattctccagatggactactcctgaaggaagtgatgacaacaagaccatgatcagtccaggcaccaca
cagagaatgctcaagagcatcctgatgattgttcccagtagtcactgAagttacaggggagcagaaacacctgaatcaaggggcgggaaaggcgcaa

FIG. 7E gtggaacgcgaaaagtcggtgccatccaaggtgatttcagtgccaaccatgtgctgaaagagaggagaagaagagagaagctcaatgagaagttcataat
tctgcgatctttggtacctttcatgacaaagatggacaaggcgtcgatactaggcgacacgatcgagtacgtgaagcagctaaggaaccgcatacaagagc
tcgagtcgtcgtcgtcgtcgtcacgagcagccgcccgggcgccatcggcggcggccgccgggaggcggaggaagagatccgccgccgccgccact
gccacggcggcggaagggatgagcagcagcaatggccgcaatggcggcgaggcggcggaggtggtgcaggtgtccatcatcgagagcgacgcgct
gctggagctccggtgcggttgcggcggcggcggcggcggcggtgtggtgctgctccgggtgatgcaggcgatgcaggagctccagctggaggtc
accgccgtccaggcctcgtgcgccggcggcgagctgctcgccgagctgcgcgccaaggtcgtcgtcatgatcctgatctgcatgaaaatgcaaatgcaa
atgcagaattaa

**SEQ ID NO:107 *Oryza sativa* ssp *indica*, subpopulation: aus, variety: Jhona-349, color: light red, RA4979** atggccggcggcgaggcgcaagcggcgctgcaggcggtggcgcagagcctccggtggacctacagcctcctctggcagctctgcccccaccaagggagctcgctg
gtgtggggggaggggcactacaacggcgccgtcaagacgcggaagtcgacggtgatgcagccgccgccggcggaggaggaggacgacgccgaccacgcggcg
cgccaccggagccggcagctgagggagctctacgactggctgcagcaggccggggagaactccagcggcggcgtgcagacgtcgtcgacgacggcgagccggc
ggccgggggcggcgctgtcgccggaggacctgacggagacggagtggttcttcctcatgtcggcatcctactccttccctcccggcatcgggttacctggaagggcatt
tgcaaggagaggccatgtatggctcactggagcaaatgaagttgacagcaaagtattcctaagagcaattcttgccaagacagttgtgtgcattcctgttgtcgatggcgtc
ctggaaattggaactacggaaaaggtggaggaagatatgggcctgattcagtatgcaaggggcatcttcatggatcaacatggcatccacatgaagcctaccctctcaca
gcactcaacatccaacccggtcacccactgtactcatcagcatccaatccaggttcagatgcaactaggtatcaccagccaaacaaagtttgattattcagatgagctcaat
gcagatgaggagaatgatgacacagaagaagagggcatgtcaggttcagacactaacaacactgacactgaaaggaattcaggccagctgcaacttcaaatgcaaga
ccaactgaacatggtgagcaatgaccaccagacaatgccaaataatgcagtttccagtgagctaatgcagtgtgagatgtcagaagtggtaagagatggctgctcaaata
atattttagaggatgaaatccaaatgctgatggattgccaaaacagtaattgtcagttaaatttgcaagggccagatgagccttgtcactcttggcattttctctgcgaggagtt
acaaaatgattaccagccagctactgaagatcaagtggcatcacctgaaaatacccattacccaaaaacactcatgacaatcctacattacaacacgctgcgacaacaag
agatgaacatcaagaactacttgccagtttcagagaaatcatcattctccagatggactactcctgaaggaagtgatgacaacaagaccatgatcagtccaggcaccacac
agagaatgctcaagagcatcctgatgattgttcccagtagtcactgAagttacaggggagcagaaacacctgaatcaaggggcgggaaaggcgcaagtggaacgc
gaaaagtcggtgccatccaaggtgatttcagtgccaaccatgtgctgaaagagaggagaagaagagagaagctcaatgagaagttcataattctgcgatctttggtacctt
tcatgacaaagatggacaaggcgtcgatactaggcgacacgatcgagtacgtgaagcagctaaggaaccgcatacaagagctcgagtcgtcgtcgtcgtcgtcacga
gcagccgcccgggcgccatcggcggcggccgccgggaggcggaggaagagatccgccgcccgccactgccacggcggcggaagggatgagcagcagcaa
tggccgcaatggcggcgaggcggcggaggtggtgcaggtgtccatcatcgagagcgacgcgctgctggagctccggtgcggttgcggcggcggcggcggcggcg
gcggtgtggtgctgctccgggtgatgcaggcgatgcaggagctccagctggaggtcaccgccgtccaggcctcgtgcgccggcggcgagctgctcgccgagctgcg
cgccaaggtcgtcgtcatgatcctgatctgcatgaaaatgcaaatgcaaatgcagaattaa

**SEQ ID NO:108 *Oryza sativa* ssp *indica*, subpopulation: aus, variety: Kasalath, color: red, RA5339** atggccggcggcgaggcgcaagcggcgctgcaggcggtggcgcagagcctccggtggacctacagcctcctctggcagctctgcccccaccaaggta
gctcgctggtgtggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgggggcggcgctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcacccactgtactcatcagcatccaatccag
gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
atgccaaataatgcagtttccagtgagctaatgcagtgtgagatgtcagaagtggtaagagatggctgctcaaataatattttagaggatgaaatccaaatgct
gatggattgccaaaacagtaattgtcagttaaatttgcaagggccagatgagccttgtcactcttggcattttctctgcgaggagttacaaaatgattaccagcc
agctactgaagatcaagtggcatcacctgaaaatacccattacccaaaaacactcatgacaatcctacattacaacacgctgcgacaacaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
gaacgcgaaaagtcggtgccatccaaggtgatttcagtgccaaccatgtgctgaaagagaggagaagaagagagaagctcaatgagaagttcataattct
gcgatctttggtacctttcatgacaaagatggacaaggcgtcgatactaggcgacacgatcgagtacgtgaagcagctaaggaaccgcatacaagagctc
gagtcgtcgtcgtcgtcgtcacgagcagccgcccgggcgccatcggcggcggccgccgggaggcggaggaagagatccgccgccgccgccactgc
cacggcggcggaagggatgagcagcagcaatggccgcaatggcggcgaggcggcggaggtggtgcaggtgtccatcatcgagagcgacgcgctgct
ggagctccggtgcggttgcggcggcggcggcggcggcggcggcggtgtggtgctgctccgggtgatgcaggcgatgcaggagctccagctgga
ggtcaccgccgtccaggcctcgtgcgccggcggcgagctgctcgccgagctgcgcgccaaggtcgtcgtcatgatcctgatctgcatgaaaatgcaaatg
caaatgcagaattaa

**SEQ ID NO:109 *Oryza rufipogon*, accession: IRGC 105491, color:red, RA5718**

FIG. 7F atggccggcggcgaggcgcaagcggcgctgcaggcggtggcgcagagcctccggtggacctacagcctcctctggcagctctgcccccaccaaggta
gctcgctggtgtgggggggaggggcactacaacggcgccgtcaagacgcggaagtcgacggtgatgcagccgccgccggcggaggaggaggacgac
gccgaccacgcggcgcgccaccggagccggcagctgagggagctctacgactggctgcagcaggccggggagaactccagcggcggcgtgcagac
gtcgtcgacgacggcgagccggcggccgggggcggcgctgtcgccggaggacctgacggagacggagtggttcttcctcatgtcggcatcctactcctt
ccctcccggcatcgggttacctggaagggcatttgcaaggagaggccatgtatggctcactggagcaaatgaagttgacagcaaagtattcctaagagcaa
ttcttgccaagacagttgtgtgcattcctgttgtcgatggcgtcctggaaattggaactacggaaaaggtggaggaagatatgggcctgattcagtatgcaag
gggcatcttcatggatcaacatggcatccacatgaagcctaccctctcacagcactcaacatccaacccagtcacccactgtactcatcagcatccaatccag
gttcagatgcaactaggtatcaccagccaaacaaagtttgattattcagatgagctcaatgcagatgaggagaatgatgacacagaagaagagggcatgtc
aggttcagacactaacaacactgacactgaaaggaattcaggccagctgcaacttcaaatgcaagaccaactgaacatggtgagcaatgaccaccagaca
atgccaaataatgcagtttccagtgagctaatgcagtgtgagatgtcagaagtggtaagagatggctgctcaaataatattttagaggatgaaatccaaatgct
gatggattgccaaaacagtaattgtcagttaaatttgcaagggccagatgagccttgtcactcttggcattttctctgcgaggagttacaaaatgattaccagcc
agctactgaagatcaagtggcatcacctgaaaatacccattacccaaaaacactcatgacaatcctacattacaacacgctgcgacaacaagagatgaacat
caagaactacttgccagtttcagagaaatcatcattctccagatggactactcctgaaggaagtgatgacaacaagaccatgatcagtccaggcaccacaca
gagaatgctcaagagcatcctgatgattgttcccagtagtcactgCagttacaggggagcagaaacacctgaatcaaggggcgggaaaggcgcaagtg
gaacgcgaaaagtcggtgccatccaaggtgatttcagtgccaaccatgtgctgaaagagaggagaagaagagagaagctcaatgagaagttcataattct
gcgatctttggtacctttcatgacaaagatggacaaggcgtcgatactaggcgacacgatcgagtacgtgaagcagctaaggaaccgcatacaagagctc
gagtcgtcgtcgtcgtcgtcacgagcagccgcccgggcgccatcggcggcggccgccgggaggcggaggaagagatccgccgccgccgccactgc
cacggcggcggaagggatgagcagcagcaatggccgcaatggcggcgaggcggcggaggtggtgcaggtgtccatcatcgagagcgacgcgctgct
ggagctccggtgcggttgcggcggcggcggcggcggcggcggcggtgtggtgctgctccgggtgatgcaggcgatgcaggagctccagctgga
ggtcaccgccgtccaggcctcgtgcgccggcggcgagctgctcgccgagctgcgcgccaaggtcgtcgtcatgatcctgatctgcatgaaaatgcaaatg
caaatgcagaattaa

SEQ ID NO:110 *Oryza sativa* ssp *indica*, subpopulation: indica, variety: IR64, color: white, RA5133
atggccggcggcgaggcgcaagcggcgctgcaggcggtggcgcagagcctccggtggacctacagcctcctctggcagctctgcccccaccaaggg
agctcgctggtgtgggggggaggggcactacaacggcgccgtcaagacgcggaagtcgacggtgatgcagccgccgccggcggaggaggaggacga
cgccgaccacgcggcgcgccaccggagccggcagctgagggagctctacgactggctgcagcaggccggggagaactccagcggcggcgtgcaga
cgtcgtcgacgacggcgagccggcggccgggggcggctctgtcgccggaggacctgacggagacggagtggttcttcctcatgtcggcatcctactcct
tccctcccggcatcgggttacctggaagggcatttgcaaggagaggccatgtatggctcactggagcaaatgaagttgacagcaaagtattcctaagagca
attcttgccaagacagttgtgtgcattcctgttgtcgatggcgtcctggaaattggaactacggaaaaggtggaggaagatatgggcctgattcagtatgcaa
ggggcatcttcatggatcaacatggcatccacatgaagcctaccctctcacagcactcaacatccaacccagtcacccactgtactcatcagcatccaatcca
ggttcagatgcaactaggtatcaccagccaaacaaagtttgattattcagatgagctcaatgcagatgaggagaatgatgacacagaagaagagggcatgt
caggttcagacactaacaacactgacactgaaaggaattcaggccagctgcaacttcaaatgcaagaccaactgaacatggtgagcaatgaccaccagac
aataccaaataatgcagtttccagtgagctaatgcagtgtgagatgtcagaagtggtaagagatggctgctcaaataatattttagaggatgaaatccaaatgc
tgatggattgccaaaacagtaattgtcagttaaatttgcaagggccagatgagccttgtcactcttggcattttctctgcgaggagttacaaaatgattaccagc
cagctactgaagatcaagtggcatcacctgaaaatacccattacccaaaaacactcatgacaatcctacattacaacacgctgcgacagcaagagatgaac
atcaagaactacttgccagtttcagagaaatcatcattctccagatggactactcctgaaggaagtgatgacaacaagaccatgatcagtccaggcaccaca
cagagaatgctcaagagcatcctgatgattgttcccagtagtcactgCagttacaggggagcagaaacacctgaatcaaggggcgggaaaggcgcaa
gtggatgccatccaaggtgatttcagtgccaaccatgtgctgaaagagaggagaagaagagagaagctcaatgagaagttcataattctgcgatctttggta
cctttcatgacaaagatggacaaggcgtcgatactaggcgacacgatcgagtacgtgaagcagctaaggaaccgcatacaagagctcgagtcgtcgtcgt
cgtcgtcacgagcagccgcccgggcgccatcggcggcggccgccgggaggcggaggaagagatccgccgccgccgccactgccacggcggcgg
aagggatgagcagcagcaatggccgcaatggcggcgaggcggcggaggtggtgcaggtgtccatcatcgagagcgacgcgctgctggagctccggt
gcggttgcggcggcggcggcggcggtgtggtgctgctccgggtgatgcaggcgatgcaggagctccagctggaggtcaccgccgtccaggcctcgtg
cgccggtggcgagctgctcgccgagctgcgcgccaaggtcgtcgttatgatcctgatctgcatgaaaatgcaaatgcaaatgcaaatgcagaattaa

SEQ ID NO:111 *Oryza sativa* ssp *indica*, subpopulation: indica, variety: 93-11, color: white, RA5700
atggccggcggcgaggcgcaagcggcgctgcaggcggtggcgcagagcctccggtggacctacagcctcctctggcagctctgcccccaccaaggg
agctcgctggtgtgggggggaggggcactacaacggcgccgtcaagacgcggaagtcgacggtgatgcagccgccgccggcggaggaggaggacga
cgccgaccacgcggcgcgccaccggagccggcagctgagggagctctacgactggctgcagcaggccggggagaactccagcggcggcgtgcaga
cgtcgtcgacgacggcgagccggcggccgggggcggctctgtcgccggaggacctgacggagacggagtggttcttcctcatgtcggcatcctactcct
tccctcccggcatcgggttacctggaagggcatttgcaaggagaggccatgtatggctcactggagcaaatgaagttgacagcaaagtattcctaagagca
attcttgccaagacagttgtgtgcattcctgttgtcgatggcgtcctggaaattggaactacggaaaaggtggaggaagatatgggcctgattcagtatgcaa
ggggcatcttcatggatcaacatggcatccacatgaagcctaccctctcacagcactcaacatccaacccagtcacccactgtactcatcagcatccaatcca
ggttcagatgcaactaggtatcaccagccaaacaaagtttgattattcagatgagctcaatgcagatgaggagaatgatgacacagaagaagagggcatgt
caggttcagacactaacaacactgacactgaaaggaattcaggccagctgcaacttcaaatgcaagaccaactgaacatggtgagcaatgaccaccagac
aataccaaataatgcagtttccagtgagctaatgcagtgtgagatgtcagaagtggtaagagatggctgctcaaataatattttagaggatgaaatccaaatgc
tgatggattgccaaaacagtaattgtcagttaaatttgcaagggccagatgagccttgtcactcttggcattttctctgcgaggagttacaaaatgattaccagc

FIG. 7G cagctactgaagatcaagtggcatcacctgaaaatacccattacccaaaaacactcatgacaatcctacattacaacacgctgcgacagcaagagatgaac
atcaagaactacttgccagtttcagagaaatcatcattctccagatggactactcctgaaggaagtgatgacaacaagaccatgatcagtccaggcaccaca
cagagaatgctcaagagcatcctgatgattgttcccagtagtcactgCagttacaggggagcagaaacacctgaatcaaggggcgggaaaggcgcaa
gtggatgccatccaaggtgatttcagtgccaaccatgtgctgaaagagaggagaagaagagagaagctcaatgagaagttcataattctgcgatctttggta
cctttcatgacaaagatggacaaggcgtcgatactaggcgacacgatcgagtacgtgaagcagctaaggaaccgcatacaagagctcgagtcgtcgtcgt
cgtcgtcacgagcagccgcccgggcgccatcggcggcggccgccgggaggcggaggaagagatccgccgccgccgccactgccacggcggcgg
aagggatgagcagcagcaatggccgcaatggcggcgaggcggcggaggtggtgcaggtgtccatcatcgagagcgacgcgctgctggagctccggt
gcggttgcggcggcggcggcggcggtgtggtgctgctccgggtgatgcaggcgatgcaggagctccagctggaggtcaccgccgtccaggcctcgtg
cgccggtggcgagctgctcgccgagctgcgcgccaaggtcgtcgttatgatcctgatctgcatgaaaatgcaaatgcaaatgcaaatgcagaattaa

SEQ ID NO:112 *Oryza sativa* ssp *indica*, subpopulation: indica, variety: Pocheonjangmangmebyeo, color: red, KG37 atggccggcggcgaggcgcaagcggcgctgcaggcggtggcgcagagcctccggtggacctacagcctcctctggcagctctgcccccaccaaggg
agctcgctggtgtgggggagggcactacaacggcgccgtcaagacgcggaagtcgacggtgatgcagccgccgccggcggaggaggaggacga
cgccgaccacgcggcgcgccaccggagccggcagctgagggagctctacgactggctgcagcaggccggggagaactccagcggcggcgtgcaga
cgtcgtcgacgacggcgagccggcggccgggggcggcgctgtcgccggaggacctgacggagacggagtggttcttcctcatgtcggcatcctactcc
ttccctcccggcatcgggttacctggaagggcatttgcaaggagaggccatgtatggctcactggagcaaatgaagttgacagcaaagtattcctaagagc
aattcttgccaagacagttgtgtgcattcctgttgtcgatggcgtcctggaaattggaactacggaaaaggtggaggaagatatgggcctgattcagtatgca
aggggcatcttcatggatcaacatggcatccacatgaagcctaccctctcacagcactcaacatccaacccggtcacccactgtactcatcagcatccaatc
caggttcagatgcaactaggtatcaccagccaaacaaagtttgattattcagatgagctcaatgcagatgaggagaatgatgacacagaagaagagggcat
gtcaggttcagacactaacaacactgacactgaaaggaattcaggccagctgcaacttcaaatgcaagaccaactgaacatggtgagcaatgaccaccag
acaatgccaaataatgcagtttccagtgagctaatgcagtgtgagatgtcagaagtggtaagagatggctgctcaaataatattttagaggatgaaatccaaat
gctgatggattgccaaaacagtaattgtcagttaaatttgcaagggccagatgagccttgtcactcttggcattttctctgcgaggagttacaaaatgattacca
gccagctactgaagatcaagtggcatcacctgaaaatacccattacccaaaaacactcatgacaatcctacattacaacacgctgcgacaacaagagatga
acatcaagaactacttgccagtttcagagaaatcatcattctccagatggactactcctgaaggaagtgatgacaacaagaccatgatcagtccaggcacca
cacagagaatgctcaagagcatcctgatgattgttcccagtagtcactgCagttacaggggagcagaaacacctgaatcaaggggcgggaaaggcgca
agtggaacgcgaaaagtcggtgccatccaaggtgatttcagtgccaaccatgtgctgaaagagaggagaagaagagagaagctcaatgagaagttcata
attctgcgatctttggtacctttcatgacaaagatggacaaggcgtcgatactaggcgacacgatcgagtacgtgaagcagctaaggaaccgcatacaaga
gctcgagtcgtcgccgtcgtcgtcacgagcagccgcccgggcgccatcggcggcggccgccgggaggcggaggaagagatccgccgccgccgcc
actgccacggcggcggaagggatgagcagcagcaatggccgcaatggcggcgaggcggcggaggtggtgcaggtgtccatcatcgagagcgacgc
gctgctggagctccggtgcggttgcggcggcggcggcggcggcggcggtgtggtgctgctccgggtgatgcaggcgatgcaggagctccagctggag
gtcaccgccgtccaggcctcgtgcgccggcggcgagctgctcgccgagctgcgcgccaaggtcgtcgtcatgatcctgatctgcatgaaaatgcaaatgc
aaatgcagaattaa

SEQ ID NO:113 *Oryza sativa* ssp *indica*, subpopulation: indica, variety: Mudgo, color: red, RA5282 atggccggcggcgaggcgcaagcggcgctgcaggcggtggcgcagagcctccggtggacctacagcctcctctggcagctctgcccccaccaaggg
agctcgctggtgtgggggagggcactacaacggcgccgtcaagacgcggaagtcgacggtgatgcagccgccgccggcggaggaggaggacga
cgccgaccacgcggcgcgccaccggagccggcagctgagggagctctacgactggctgcagcaggccggggagaactccagcggcggcgtgcaga
cgtcgtcgacgacggcgagccggcggccgggggcggcgctgtcgccggaggacctgacggagacggagtggttcttcctcatgtcggcatcctactcc
ttccctcccggcatcgggttacctggaagggcatttgcaaggagaggccatgtatggctcactggagcaaatgaagttgacagcaaagtattcctaagagc
aattcttgccaagacagttgtgtgcattcctgttgtcgatggcgtcctggaaattggaactacggaaaaggtggaggaagatatgggcctgattcagtatgca
aggggcatcttcatggatcaacatggcatccacatgaagcctaccctctcacagcactcaacatccaacccggtcacccactgtactcatcagcatccaatc
caggttcagatgcaactaggtatcaccagccaaacaaagtttgattattcagatgagctcaatgcagatgaggagaatgatgacacagaagaagagggcat
gtcaggttcagacactaacaacactgacactgaaaggaattcaggccagctgcaacttcaaatgcaagaccaactgaacatggtgagcaatgaccaccag
acaatgccaaataatgcagtttccagtgagctaatgcagtgtgagatgtcagaagtggtaagagatggctgctcaaataatattttagaggatgaaatccaaat
gctgatggattgccaaaacagtaattgtcagttaaatttgcaagggccagatgagccttgtcactcttggcattttctctgcgaggagttacaaaatgattacca
gccagctactgaagatcaagtggcatcacctgaaaatacccattacccaaaaacactcatgacaatcctacattacaacacgctgcgacaacaagagatga
acatcaagaactacttgccagtttcagagaaatcatcattctccagatggactactcctgaaggaagtgatgacaacaagaccatgatcagtccaggcacca
cacagagaatgctcaagagcatcctgatgattgttcccagtagtcactgCagttacaggggagcagaaacacctgaatcaaggggcgggaaaggcgca
agtggaacgcgaaaagtcggtgccatccaaggtgatttcagtgccaaccatgtgctgaaagagaggagaagaagagagaagctcaatgagaagttcata
attctgcgatctttggtacctttcatgacaaagatggacaaggcgtcgatactaggcgacacgatcgagtacgtgaagcagctaaggaaccgcatacaaga
gctcgagtcgtcgtcgtcgtcgtcacgagcagccgcccgggcgccatcggcggcggccgccgggaggcggaggaagagatccgccgccgccgcca
ctgccacggcggcggaagggatgagcagcagcaatggccgcaatggcggcgaggcggcggaggtggtgcaggtgtccatcatcgagagcgacgcg
ctgctggagctccggtgcggttgcggcggcggcggcggcggcggcggtgtggtgctgctccgggtgatgcaggcgatgcaggagctccagctggagg
tcaccgccgtccaggcctcgtgcgccggcggcgagctgctcgccgagctgcgcgccaaggtcgtcgtcatgatcctgatctgcatgaaaatgcaaatgca
aatgcagaattaa

FIG. 7H

SEQ ID NO:114 *Oryza rufipogon*, accession: IRGC 106262, color:red, RA2662
atggccggcggcgaggcgcaagcggcgctgcaggcggtggcgcagagcctccggtggacctacagcctcctctggcagctctgcccccaccaaggg
agctcgctggtgtgggggggaggggcactacaacggcgccgtcaagacgcggaagtcgacggtgatgcagccgccgccggcggaggaggaggacga
cgccgaccacgcggcgcgccaccggagccggcagctgagggagctctacgactggctgcagcaggccggggagaactccagcggcggcgtgcaga
cgtcgtcgacgacggcgagccggcggccgggggcggcgctgtcgccggaggacctgacggagacggagtggttcttcctcatgtcggcatcctactcc
ttccctcccggcatcgggttacctggaagggcatttgcaaggagaggccatgtatggctcactggagcaaatgaagttgacagcaaagtattcctaagagc
aattcttgccaagacagttgtgtgcattcctgttgtcgatggcgtcctggaaattggaactacggaaaaggtggaggaagatatgggcctgattcagtatgca
aggggcatcttcatggatcaacatggcatccacatgaagcctaccctctcacagcactcaacatccaacccagtcacccactgtactcatcagcatccaatcc
aggttcagatgcaactaggtatcaccagccaaacaaagtttgattattcagatgagctcaatgcagatgaggagaatgatgacacagaagaagagggcatg
tcaggttcagacactaacaacactgacactgaaaggaattcaggccagctgcaacttcaaatgcaagaccaactgaacatggtgagcaatgaccaccaga
caatgccaaataatgcagtttccagtgagctaatgcagtgtgagatgtcagaagtggtaagagatggctgctcaaataatattttagaggatgaaatccaaatg
ctgatggattgccaaaacagtaattgtcagttaaatttgcaagggccagatgagccttgtcactcttggcattttctctgcgaggagttacaaaatgattaccag
ccagctactgaagatcaagtggcatcacctgaaaatacccattacccaaaaacactcatgacaatcctacattacaacacgctgcgacaacaagagatgaa
catcaagaactacttgccagtttcagagaaatcatcattctccagatggactactcctgaaggaagtgatgacaacaagaccatgatcagtccaggcaccac
acagagaatgctcaagagcatcctgatgattgttcccagtagtcactgCagttacaggggagcagaaacacctgaatcaaggggcgggaaaggcgcaa
gtggaacgcgaaaagtcggtgccatccaaggtgatttcagtgccaaccatgtgctgaaagagaggagaagaagagagaagctcaatgagaagttcataat
tctgcgatctttggtacctttcatgacaaagatggacaaggcgtcgatactaggcgacacgatcgagtacgtgaagcagctaaggaaccgcatacaagagc
tcgagtcgtcgtcgtcgtcgtcacgagcagccgcccgggcgccatcggcggcggccgccgggaggcggaggaagagatccgccgccgccgccact
gccacggcggcggaagggatgagcagcagcaatggccgcaatggcggcgaggcggcggaggtggtgcaggtgtccatcatcgagagcgacgcgct
gctggagctccggtgcggttgcggcggcggcggcggcggtgtggtgctgctccgggtgatgcaggcgatgcaggagctccagctggaggtcaccgcc
gtccaggcctcgtgcgccggcggcgagctgctcgccgagctgcgcgccaaggtcgtcgtcatgatcctgatctgcatgaaaatgcaaatgcaaatgcaga
attaa

SEQ ID NO:115 *Oryza rufipogon*, accession: IRGC 105726, color:red, RA2755
atggccggcggcgaggcgcaagcggcgctgcaggcggtggcgcagagcctccggtggacctacagcctcctctggcagctctgcccccaccaaggg
agctcgctggtgtgggggggaggggcactacaacggcgccgtcaagacgcggaagtcgacggtgatgcagccgccgccggcggaggaggaggacga
cgccgaccacgcggcgcgccaccggagccggcagctgagggagctctacgactggctgcagcaggccggggagaactccagcggcggcgtgcaga
cgtcgtcgacgacggcgagccggcggccgggggcggcgctgtcgccggaggacctgacggagacggagtggttcttcctcatgtcggcatcctactcc
ttccctcccggcatcgggttacctggaagggcatttgcaaggagaggccatgtatggctcactggagcaaatgaagttgacagcaaagtattcctaagagc
aattcttgccaagacagttgtgtgcattcctgttgtcgatggcgtcctggaaattggaactacggaaaaggtggaggaagatatgggcctgattcagtatgca
aggggcatcttcttggatcaacatggcatccacatgaagcctaccctctcacagcactcaacatccaacccagtcacccactgtactcatcagcatccaatcc
aggttcagatgcaactaggtatcaccagccaaacaaagtttgattattcagatgagctcaatgcagatgaggagaatgatgacacagaagaagagggcatg
tcaggttcagacactaacaacactgacactgaaaggaattcaggccagctgcaacttcaaatgcaagaccaactgaacatggtgagcaatgaccaccaga
caatgccaaataatgcagtttccagtgagctaatgcagtgtgagatgtcagaagtggtaagagatggctgctcaaataatattttagaggatgaaatccaaatg
ctgatggattgccaaaacagtaattgccagttaaatttgcaagggccagatgagccttgtcactcttggcattttctctgcgaggagttacaaaatgattaccag
ccagctactgaagatcaagtggcatcacctgaaaatacccattacccaaaaacactcatgacaatcctacattacaacacgctgcgacaacaagagatgaa
catcaagaactacttgccagtttcagagaaatcatcattctccagatggactactcctgaaggaagtgatgacaacaagaccatgatcagtccaggcaccac
acagagaatgctcaagagcatcctgatgattgttcccagtagtcactgCagttacaggggagcagaaacacctgaatcaaggggcaggaaaggcgcaa
gtggaacgcgaaaagtcggtgccatccaaggtgatttcagtgccaaccatgtgctgaaagagaggagaagaagagagaagctcaatgagaagttcataat
tctgcgatctttggtacctttcatgacaaagatggacaaggcgtcgatactaggcgacacgatcgagtacgtgaagcagctaaggaaccgcatacaagagc
tcgagtcgtcgtcgtcgtcgtcacgagcagccgcccgggcgccatcggcggcggccgccgggaggcggaggaagagatccgccgccgccgccact
gccacggcggcggaagggatgagcagcagcaatggccgcaatggcggcgaggcggcggaggtggtgcaggtgtccatcatcgagagcgacgcgct
gctggagctccggtgcggttgcggcggcggcggcggcggtgtggtgctgctccgggtgatgcaggcgatgcaggagctccagctggaggtcaccgcc
gtccaggcctcgtgcgccggtggcgagctgctcgccgagctgcgcgccaaggtcgtcgtcatgatcctgatctgcatgaaaatgcaaatgcaaatgcaga
attaa

FIG. 7I

SEQ ID NO:116 **Corn - *Zea mays* Intensifier1 (IN1) protein sequence, NCBI accession #:AAB03841.1**

MAAGGRGEAAQKALQSVAQSTGWTYSLLWRLCPRQGALVWAEGYYNGAIRTRKTTMTTVRQP
AGAEDAGDEETAPRRSRQLKELYDSLAAGEAAYDGGGGVGGPQQQQQAAVVPPPRRPAAALAP
EDLTETEWFYLMCASYCFPPAVGLPGEAFVRRAHVWLCGANKADSKVFSRAILARSAGIQTVACI
PVDDGVLEIGTTEKVEEDIFLIQHVRNIFVDQHGAHIMPTTLSGYSTSTPTTQLNHQPFQTKTGISLN
LGDERNSEMEDDDDDGRIDLENNTENDSTRRHLPQDASAGNELETLNAESSGPMLIANLTAQDEY
GQLHRFLSVDLSSKYLQSPGAEDQAAVAENAHYIETVLRILRFNACRQTQAASSNIAKTYLALSKN
SPFSRWNWKRKGISSMMIAEGTPQRMLKSVLLGAPSSSSHRSHRGEVQSSSPEPRGDDGEGTSRSR
RGPVPSQTELSASHVLKERRRREKLNEGFAMLRSLVPFVTKMDRASILGDTIEYVKQLRRRIQELES
RRRLVGSNQKTTMAQQPPPPAASTEERGRRQTSGGYLARAAGTGSRAAEASGNSNLGEEPPAAA
ASDTDTEVQVSIIGSDALLELRCPHREGLLLRVMQALHQELRLEITSVQASSAGDVLLAKLRAKVK
EVHGRRSSITEVKRAIHLIVSSDWICEKNPCLA

SEQ ID NO:117 **Petunia - *Petunia hybrida* Anthocyanin 1 (AN1) protein sequence, NCBI accession #: AAG25928.1**

MQLQTMLRNAVQSVQWTYSLFWQLCPQQGVLVWRDGYYNGAIKTRKTVQPMEVSAEEASLHR
SQQLRELYESLSAGESNQPTRRPSAALSPEDLTESEWFYLMCVSFSFPAGIGLPGKAYSKKHHIWIT
GANEVESKVFCRAILAKSARVQTVVCIPLLDGVVELGTTQRIQEDIGFINHVKTFFIEQQPPLPPKPA
LSEHSTSNPTTFSELNFYSSNTPPSAGTTPADEHGGVAGDEDEEDEDEEDEDEEQEDDEEAELDSD
KIAAQVGPADVIAAAEASELMQLDMSEAIRFGSPDDGSNTNMDSDFHMVGVSQAENPADYQRQA
ESFKADTSISWAHFQDLPHLPGGPSYDELSQEDTHYSQTVSTILEHLSNQSSKFSSTIMGCISQTTQS
AFTRWPSPSTTVSSPFLDGGATSGQWLLKSILFSVPFLHTKYQTAAEVSPKSRDATTVDSSTASRFR
KGCSITQEEPSGNHVLAERRRREKLNERFIILRSLVPFVTKMDKASILGDTIEYVKQLRKKVQDLEA
RANQTEATLQTKDTGTVKVLQGRGKRRMKIVEGSVGGGQAKITASSPSTTHEEEIVQVEVSIIESD
ALVELRCPYKEGLLLDVMQMLRELKVEVVTIQSSLNNGSFFAELRAKVKENIYGRKASILEVKKSI
HQLIPRV

SEQ ID NO:118 **Arabidopsis – *Arabidopsis thaliana* TRANSPARENT TESTA 8 (TT8) protein, NCBI accession #: Q9FT81, Basic helix-loop-helix protein 42,AtbHLH042**

MDESSIIPAEKVAGAEKKELQGLLKTAVQSVDWTYSVFWQFCPQQRVLVWGNGYYNGAIKTRKT
TQPAEVTAEEAALERSQQLRELYETLLAGESTSEARACTALSPEDLTETEWFYLMCVSFSFPPPSG
MPGKAYARRKHVWLSGANEVDSKTFSRAILAKSAKIQTVVCIPMLDGVVELGTTKKVREDVEFV
ELTKSFFYDHCKTNPKPALSEHSTYEVHEEAEDEEEVEEEMTMSEEMRLGSPDDEDVSNQNLHSD
LHIESTHTLDTHMDMMNLMEEGGNYSQTVTTLLMSHPTSLLSDSVSTSSYIQSSFATWRVENGKE
HQQVKTAPSSQWVLKQMIFRVPFLHDNTKDKRLPREDLSHVVAERRRREKLNEKFITLRSMVPFV
TKMDKVSILGDTIAYVNHLRKRVHELENTHHEQQHKRTRTCKRKTSEEVEVSIIENDVLLEMRCE
YRDGLLLDILQVLHELGIETTAVHTSVNDHDFEAEIRAKVRGKKASIAEVKRAIHQVIIHDTNL

FIG. 8

| Name | Species | Subpopulation | Afex5d | Seed Color |
|---|---|---|---|---|
| Ade | Oryza sativa | Indica | deletion | white |
| AENGMI | Oryza sativa | Indica | full | red |
| Ai Chiao Hong | Oryza sativa | Indica | deletion | white |
| Aluh Kuranji | Oryza sativa | Indica | deletion | white |
| Anambar | Oryza sativa | Indica | deletion | white |
| Apel | Oryza sativa | Indica | deletion | white |
| Arai Pinang | Oryza sativa | Indica | deletion | white |
| Arc 10177 | Oryza sativa | Aus | full | red |
| ARC-13829 | Oryza sativa | Aromatic | deletion | white |
| Ardas | Oryza sativa | Indica | deletion | white |
| Arias | Oryza sativa | Indica | deletion | white |
| Ase Bakacung | Oryza sativa | Tropical Japonica | deletion | white |
| Ase Dangan | Oryza sativa | Tropical Japonica | deletion | white |
| Ase pulut Jawa | Oryza sativa | Indica | deletion | white |
| Asemadsi | Oryza sativa | Tropical Japonica | deletion | white |
| Ausha Boro | Oryza sativa | Aus | full | red |
| Badali | Oryza sativa | Aus | full | red |
| Badkalamakti | Oryza sativa | Indica | deletion | white |
| BADOLBYEO | Oryza sativa | Temperate Japonica | deletion | white |
| BAEKGOKNA | Oryza sativa | Temperate Japonica | deletion | white |
| BAEKJANGGUN | Oryza sativa | Temperate Japonica | deletion | white |
| BAEKSEOK | Oryza sativa | Temperate Japonica | deletion | white |
| Bali | Oryza sativa | Indica | deletion | white |
| Baliman Putih | Oryza sativa | Indica | full | red |
| Bandang Si Gadis | Oryza sativa | Indica | deletion | white |
| Banjar | Oryza sativa | Indica | full | red |
| Baro | Oryza sativa | Indica | deletion | white |
| BASMATI | Oryza sativa | Aromatic | deletion | white |
| Basmati -1 | Oryza sativa | Aus | full | red |
| Battiboro | Oryza sativa | Aus | full | red |
| Baur | Oryza sativa | Tropical Japonica | deletion | white |
| Bengawan | Oryza sativa | Indica | deletion | white |
| Bengkongang | Oryza sativa | Indica | full | red |
| Beon-gok | Oryza sativa | Tropical Japonica | deletion | white |
| Beras merah | Oryza sativa | Indica | full | red |
| Betonan | Oryza sativa | Indica | deletion | white |
| Bho | Oryza sativa | Indica | full | red |
| Biduin | Oryza sativa | Indica | full | red |
| Bindang Jambi | Oryza sativa | Indica | deletion | white |
| Binulawan | Oryza sativa | Indica | deletion | white |
| BJ-1 | Oryza sativa | Aus | full | red |

FIG. 9A

| | | | | |
|---|---|---|---|---|
| Black Gora (NCS12) | Oryza sativa | Aus | full | red |
| Bluebonnet | Oryza sativa | Tropical Japonica | deletion | white |
| Brontok | Oryza sativa | Indica | full | red |
| Buleng | Oryza sativa | Tropical Japonica | full | red |
| Burimural | Oryza sativa | Aus | full | red |
| Burung Saniha | Oryza sativa | Tropical Japonica | deletion | white |
| Caloro | Oryza sativa | Temperate Japonica | deletion | white |
| Capli | Oryza sativa | Indica | deletion | white |
| Cempa Hulut | Oryza sativa | Tropical Japonica | deletion | white |
| Cempaka | Oryza sativa | Tropical Japonica | deletion | white |
| Cempo kunci | Oryza sativa | Indica | deletion | white |
| Cere Gelas | Oryza sativa | Indica | deletion | white |
| CHALBYEO | Oryza sativa | Temperate Japonica | deletion | white |
| CHEONGGUNBYEO | Oryza sativa | Temperate Japonica | deletion | white |
| CHEONJUDO | Oryza sativa | Temperate Japonica | deletion | white |
| CHIMABYEO | Oryza sativa | Temperate Japonica | deletion | white |
| CHINDADACHIGI | Oryza sativa | Temperate Japonica | deletion | white |
| CHOEBUJI | Oryza sativa | Temperate Japonica | deletion | white |
| Cicih Bondol | Oryza sativa | Indica | deletion | white |
| Cicih Buleleng | Oryza sativa | Indica | deletion | white |
| Ciherang | Oryza sativa | Varieties | deletion | white |
| Cinta Kasih | Oryza sativa | Indica | deletion | white |
| Cisadane | Oryza sativa | Varieties | deletion | white |
| CS-M2 | Oryza sativa | Temperate Japonica | deletion | white |
| CUBA-65 | Oryza sativa | Aromatic | deletion | white |
| DA-13 | Oryza sativa | Aromatic | deletion | white |
| DAEGOLDO | Oryza sativa | Temperate Japonica | deletion | white |
| DAEGUNA | Oryza sativa | Temperate Japonica | deletion | white |
| Dhala Shaitta | Oryza sativa | Aus | deletion | white |
| Dholai Momi | Oryza sativa | Aus | full | red |
| Dholio Boro | Oryza sativa | Aus | full | red |
| DNJ142 | Oryza sativa | Aus | full | red |
| DOAJI | Oryza sativa | Temperate Japonica | deletion | white |
| DOM-SOFID | Oryza sativa | Aromatic | deletion | white |
| Dupa | Oryza sativa | Tropical Japonica | deletion | white |
| DV32 | Oryza sativa | Aus | full | red |
| DV85 | Oryza sativa | Aus | full | red |
| DV85 | Oryza sativa | Aus | full | red |
| Early Wateribune | Oryza sativa | Temperate Japonica | deletion | white |
| Empat Bulan | Oryza sativa | Tropical Japonica | deletion | white |
| Engkoran | Oryza sativa | Indica | deletion | white |
| FIROOZ | Oryza sativa | Aromatic | deletion | white |

FIG. 9B

| | | | | |
|---|---|---|---|---|
| Fortuna | Oryza sativa | Tropical Japonica | deletion | white |
| FR-13A | Oryza sativa | Aus | full | red |
| Gadis Putih | Oryza sativa | Indica | deletion | white |
| GAKSIJEOMJO | Oryza sativa | Temperate Japonica | deletion | white |
| GANGDODO | Oryza sativa | Temperate Japonica | full | red |
| Ganggoi | Oryza sativa | Tropical Japonica | deletion | white |
| GANGREUNGDO | Oryza sativa | Temperate Japonica | deletion | white |
| Gangweondo | Oryza sativa | Tropical Japonica | deletion | white |
| Garia | Oryza sativa | Aus | full | red |
| Garu | Oryza sativa | Tropical Japonica | deletion | white |
| Genjah Rawe | Oryza sativa | Tropical Japonica | deletion | white |
| GHARIB | Oryza sativa | Aromatic | deletion | white |
| Gion Halus | Oryza sativa | Indica | deletion | white |
| Gondak Kiah | Oryza sativa | Indica | deletion | white |
| Goter | Oryza sativa | Indica | deletion | white |
| Guan Yin Tsan | Oryza sativa | Indica | deletion | white |
| Gundil | Oryza sativa | Tropical Japonica | deletion | white |
| HAENGPUNG | Oryza sativa | Temperate Japonica | deletion | white |
| HANYANGJO | Oryza sativa | Indica | full | red |
| HEUKGAENG | Oryza sativa | Temperate Japonica | deletion | white |
| Hoing | Oryza sativa | Indica | full | red |
| HONGDO | Oryza sativa | Indica | deletion | white |
| HONGNA | Oryza sativa | Temperate Japonica | deletion | white |
| Huma gadog | Oryza sativa | Tropical Japonica | full | black |
| Humbang Inai | Oryza sativa | Indica | deletion | white |
| HWADO | Oryza sativa | Temperate Japonica | deletion | white |
| HWANGJO | Oryza sativa | Temperate Japonica | deletion | white |
| HWANGTOJO | Oryza sativa | Temperate Japonica | deletion | white |
| HYOSEONGJAERAEJONG | Oryza sativa | Indica | deletion | white |
| Idi | Oryza sativa | Indica | deletion | white |
| INBUJIDO | Oryza sativa | Temperate Japonica | deletion | white |
| INBUJINADO | Oryza sativa | Temperate Japonica | deletion | white |
| Ingsa Bondol | Oryza sativa | Tropical Japonica | deletion | white |
| Ingsa Cendana | Oryza sativa | Indica | deletion | white |
| IR64 | Oryza sativa | Indica | deletion | white |
| IR-64 (60) | Oryza sativa | Indica | deletion | white |
| IRAKDO | Oryza sativa | Temperate Japonica | deletion | white |
| Irian | Oryza sativa | Indica | deletion | white |
| Jamudin | Oryza sativa | Tropical Japonica | full | red |
| JC1 | Oryza sativa | Aroma | deletion | white |
| JC1 | Oryza sativa | Aromatic | deletion | white |
| JC149 | Oryza sativa | Aromatic | deletion | white |

FIG. 9C

| | | | | |
|---|---|---|---|---|
| JC157 | Oryza sativa | Aromatic | deletion | white |
| JC73-4 | Oryza sativa | Aromatic | deletion | white |
| Jefferson | Oryza sativa | Tropical Japonica | deletion | white |
| JEOKBAKNA | Oryza sativa | Temperate Japonica | deletion | white |
| JEONGDALDO | Oryza sativa | Temperate Japonica | deletion | white |
| JEONGGEUMJO | Oryza sativa | Temperate Japonica | deletion | white |
| Jjok-je-bi-chal | Oryza sativa | Tropical Japonica | deletion | white |
| JODO | Oryza sativa | Temperate Japonica | deletion | white |
| Jonoko | Oryza sativa | Indica | full | red |
| Joseokjo | Oryza sativa | Tropical Japonica | deletion | white |
| Joseon | Oryza sativa | Tropical Japonica | deletion | white |
| Jula-Juli | Oryza sativa | Indica | deletion | white |
| Jula-Juli | Oryza sativa | Indica | deletion | white |
| Kail | Oryza sativa | Indica | deletion | white |
| Kal Shomi | Oryza sativa | Aus | full | red |
| Kalukantha | Oryza sativa | Indica | full | red |
| Kantul | Oryza sativa | Indica | deletion | white |
| Karang Dukuh | Oryza sativa | Indica | full | red |
| Karya | Oryza sativa | Indica | deletion | white |
| Kasalath | Oryza sativa | Aus | full | red |
| Kasur | Oryza sativa | Indica | deletion | white |
| Kayowa | Oryza sativa | Tropical Japonica | deletion | white |
| Keakubi | Oryza sativa | Indica | full | red |
| Kembang Ading | Oryza sativa | Tropical Japonica | deletion | white |
| Kembang Singkan | Oryza sativa | Indica | deletion | white |
| Keser A | Oryza sativa | Tropical Japonica | deletion | white |
| Keser B | Oryza sativa | Tropical Japonica | deletion | white |
| Ketan Adang | Oryza sativa | Indica | deletion | black |
| Ketan Beranakan | Oryza sativa | Tropical Japonica | full | red |
| Ketan hitam | Oryza sativa | Tropical Japonica | deletion | white |
| Ketan putih | Oryza sativa | Indica | deletion | white |
| Ketan Siam | Oryza sativa | Tropical Japonica | deletion | white |
| Keton Jalumpang | Oryza sativa | Indica | deletion | white |
| Ketumping | Oryza sativa | Indica | deletion | white |
| KITRANA-508 | Oryza sativa | Aromatic | deletion | white |
| Klara super | Oryza sativa | Indica | deletion | white |
| Klepon Putih | Oryza sativa | Indica | deletion | white |
| Koshihikari | Oryza sativa | Temperate Japonica | deletion | white |
| Koyak | Oryza sativa | Tropical Japonica | deletion | white |
| Kuala Deli | Oryza sativa | Indica | deletion | white |
| Kulit Bawang | Oryza sativa | Tropical Japonica | deletion | white |
| Kuning | Oryza sativa | Indica | deletion | white |

FIG. 9D

| | | | | |
|---|---|---|---|---|
| Kuning Biaro | Oryza sativa | Indica | deletion | white |
| Kuning Padang | Oryza sativa | Indica | deletion | white |
| Kwatik Tinggi | Oryza sativa | Indica | deletion | white |
| L-201 | Oryza sativa | Temperate Japonica | deletion | white |
| L-205 | Oryza sativa | Temperate Japonica | deletion | white |
| Lagrue | Oryza sativa | Tropical Japonica | deletion | white |
| Laka | Oryza sativa | Tropical Japonica | full | red |
| Laka Tesam | Oryza sativa | Tropical Japonica | deletion | black |
| Lakhi Jhota | Oryza sativa | Aus | full | red |
| Laksmilota | Oryza sativa | Aus | full | red |
| Lal Aman | Oryza sativa | Indica | deletion | white |
| Lambow putih | Oryza sativa | Tropical Japonica | deletion | white |
| Lemo | Oryza sativa | Indica | deletion | white |
| Lemont | Oryza sativa | Tropical Japonica | deletion | white |
| Lemunyau | Oryza sativa | Tropical Japonica | deletion | white |
| Leukat Camprung | Oryza sativa | Indica | deletion | white |
| Leukat Kapola (KP) | Oryza sativa | Indica | deletion | white |
| Leukat Kepala (K) | Oryza sativa | Indica | deletion | white |
| Leukat Medan (K) | Oryza sativa | Indica | full | red |
| Limar | Oryza sativa | Tropical Japonica | full | red |
| Lokal Buntu Sangala 1 | Oryza sativa | Indica | full | red |
| Lokal buntu Sangala 2 | Oryza sativa | Indica | deletion | white |
| Lokal Tulem | Oryza sativa | Tropical Japonica | full | red |
| Loneng | Oryza sativa | Indica | deletion | white |
| Longandobu | Oryza sativa | Indica | deletion | white |
| Lubuk Kenari | Oryza sativa | Indica | deletion | white |
| Lumaik Hitam | Oryza sativa | Indica | deletion | white |
| Lumut | Oryza sativa | Indica | deletion | white |
| M-204 | Oryza sativa | Temperate Japonica | deletion | white |
| MAEKDO | Oryza sativa | Temperate Japonica | deletion | white |
| Maintmolotsy 1226 | Oryza sativa | tropical japonica | deletion | white |
| Makmur | Oryza sativa | Indica | deletion | white |
| Mama | Oryza sativa | Tropical Japonica | deletion | white |
| Mama Laka | Oryza sativa | Indica | deletion | white |
| Marinah | Oryza sativa | Indica | deletion | white |
| Markoti | Oryza sativa | Indica | deletion | white |
| Maru | Oryza sativa | Indica | deletion | white |
| Mayor | Oryza sativa | Indica | deletion | white |
| Mesir | Oryza sativa | Indica | deletion | white |
| MOJO | Oryza sativa | Temperate Japonica | deletion | white |
| MONAJO | Oryza sativa | Temperate Japonica | deletion | white |
| Moroborekan | Oryza sativa | tropical japonica | deletion | white |

FIG. 9E

| | | | | |
|---|---|---|---|---|
| Nangka Bosok | Oryza sativa | Indica | deletion | white |
| Ndangan Cantik 1 | Oryza sativa | Tropical Japonica | deletion | white |
| Ndangan Cantik 2 | Oryza sativa | Tropical Japonica | deletion | white |
| Neulbyeo | Oryza sativa | Temperate Japonica | deletion | white |
| Nggondo | Oryza sativa | Tropical Japonica | deletion | white |
| NOINDO | Oryza sativa | Temperate Japonica | full | red |
| NOINJO | Oryza sativa | Temperate Japonica | deletion | white |
| Nurdin | Oryza sativa | Indica | deletion | white |
| O. alta | Oryza alta | Wild | full | red |
| O. australiansis | Oryza australiansis | Wild | full | red |
| O. glaberrima | Oryza glaberrima | Wild | full | red |
| O. grandiglumis | Oryza grandiglumis | Wild | full | red |
| O. latifolia | Oryza latifolia | Wild | full | red |
| O. malampuzhaensis | Oryza malampuzhaensis | Wild | full | red |
| O. minuta | Oryza minuta | Wild | full | red |
| O. minuta | Oryza minuta | Wild | full | red |
| O. nivara | Oryza nivara | Wild | deletion | white |
| O. nivara | Oryza nivara | Wild | full | red |
| O. nivara | Oryza nivara | Wild | full | red |
| O. officinalis | Oryza officinalis | Wild | full | red |
| O. officinalis | Oryza officinalis | Wild | full | red |
| O. punctata | Oryza punctata | Wild | full | red |
| O. punctata | Oryza punctata | Wild | full | red |
| O. rhizomatis | Oryza rhizomatis | Wild | full | red |
| O. rufipogon | Oryza rufipogon | Wild | full | red |
| O. rufipogon | Oryza rufipogon | Wild | full | red |
| O. rufipogon | Oryza rufipogon | Wild | full | red |
| O. rufipogon | Oryza rufipogon | Wild | full | red |
| OLWAEDU | Oryza sativa | Temperate Japonica | deletion | white |
| P. Gogo | Oryza sativa | Tropical Japonica | deletion | white |
| P. Pasir | Oryza sativa | Tropical Japonica | deletion | white |
| Pa Tou Hung | Oryza sativa | Indica | deletion | white |
| Padi AA/Sri gudang | Oryza sativa | Indica | full | red |
| Padi Ana-Ana | Oryza sativa | Indica | deletion | white |
| Padi Book | Oryza sativa | Indica | deletion | white |
| Padi Bugis | Oryza sativa | Indica | deletion | white |
| Padi Burung | Oryza sativa | Indica | deletion | white |
| Padi Cina | Oryza sativa | Indica | deletion | white |
| Padi Erna | Oryza sativa | Indica | deletion | white |
| Padi Jawa | Oryza sativa | Tropical Japonica | deletion | white |
| Padi Kuda | Oryza sativa | Indica | deletion | white |
| Padi Lumut/Rogu | Oryza sativa | Indica | deletion | white |

FIG. 9F

| | | | | |
|---|---|---|---|---|
| Padi Melayu | Oryza sativa | Indica | deletion | white |
| Padi Merah | Oryza sativa | Tropical Japonica | deletion | white |
| Padi Rantau | Oryza sativa | Indica | deletion | white |
| Padi Rantau Undik | Oryza sativa | Indica | deletion | white |
| Padi Sudara | Oryza sativa | Indica | deletion | white |
| Pae Biyu Anggolopua | Oryza sativa | Tropical Japonica | full | red |
| Pae Daya Indolobye | Oryza sativa | Tropical Japonica | full | red |
| Pae Daye Ule-Ule | Oryza sativa | Tropical Japonica | full | red |
| Pae Laguh | Oryza sativa | Indica | full | red |
| Pae Wita | Oryza sativa | Tropical Japonica | full | red |
| Pako I | Oryza sativa | Tropical Japonica | deletion | white |
| Pako II | Oryza sativa | Tropical Japonica | deletion | white |
| Pandak Semarang | Oryza sativa | Indica | deletion | white |
| PANKHARI-203 | Oryza sativa | Aromatic | deletion | white |
| Pankhiraj | Oryza sativa | Aus | full | red |
| Pare bulan | Oryza sativa | Tropical Japonica | deletion | white |
| Pare Dangang A | Oryza sativa | Indica | deletion | white |
| Pare Dangang B | Oryza sativa | Indica | deletion | white |
| Pare Dara Muda Putih | Oryza sativa | Indica | deletion | white |
| Pare Eja-3 | Oryza sativa | Tropical Japonica | full | red |
| Pare leleng | Oryza sativa | Tropical Japonica | deletion | black |
| Pare Palunglia | Oryza sativa | Tropical Japonica | deletion | white |
| Pare Pulung Cina | Oryza sativa | Tropical Japonica | deletion | white |
| Pare pulut Bampo | Oryza sativa | Tropical Japonica | full | red |
| Pare Pulut Bolong | Oryza sativa | Tropical Japonica | deletion | black |
| Pare tambong | Oryza sativa | Tropical Japonica | deletion | white |
| Pelita 1.1 | Oryza sativa | Indica | deletion | white |
| Pilihan Merah | Oryza sativa | Indica | deletion | white |
| Pilihan Putih I | Oryza sativa | Indica | deletion | white |
| Pilihan Putih II | Oryza sativa | Indica | deletion | white |
| Pimpin | Oryza sativa | Indica | deletion | white |
| Pingkan | Oryza sativa | Indica | deletion | white |
| Pirukat | Oryza sativa | Indica | deletion | white |
| POCHEONJANGMANGMEBYEO | Oryza sativa | Temperate Japonica | deletion | white |
| Pokal Gambrong | Oryza sativa | Indica | full | red |
| Popot | Oryza sativa | Indica | deletion | white |
| POPOT-165 | Oryza sativa | Indica | deletion | white |
| Porosi-A | Oryza sativa | Tropical Japonica | deletion | white |
| Porosi-B | Oryza sativa | Tropical Japonica | deletion | white |
| Protel | Oryza sativa | Indica | deletion | white |
| Pulut Hitam | Oryza sativa | Indica | deletion | black |
| Pulut Laut | Oryza sativa | Tropical Japonica | deletion | white |
| Pulut Mute | Oryza sativa | Indica | deletion | white |

FIG. 9G

| | | | | |
|---|---|---|---|---|
| Pulut Putih | Oryza sativa | Indica | full | red |
| Pulut putih | Oryza sativa | Indica | full | red |
| Pulut Unggul | Oryza sativa | Indica | deletion | white |
| Putih Ampat Angkek | Oryza sativa | Indica | deletion | white |
| Putih Panjah | Oryza sativa | Indica | deletion | white |
| Putri Manis | Oryza sativa | Indica | deletion | white |
| Raden Pulatar | Oryza sativa | Indica | deletion | white |
| Raden Rata | Oryza sativa | Indica | full | red |
| Ramos Batu | Oryza sativa | Indica | deletion | white |
| Ramos Dewi | Oryza sativa | Indica | deletion | white |
| Ramos Merah | Oryza sativa | Indica | full | red |
| Randah Padang | Oryza sativa | Indica | deletion | white |
| Rangkat | Oryza sativa | Tropical Japonica | deletion | white |
| Rangkoh | Oryza sativa | Indica | deletion | white |
| Rathuwee | Oryza sativa | Indica | deletion | white |
| Reko | Oryza sativa | Tropical Japonica | deletion | white |
| Reli | Oryza sativa | Indica | deletion | white |
| Rencong | Oryza sativa | Indica | deletion | white |
| Rendah Sasak | Oryza sativa | Indica | deletion | white |
| Rexoro | Oryza sativa | Tropical Japonica | deletion | white |
| Rijah | Oryza sativa | Indica | deletion | white |
| Rufipogon | Oryza rufipogon | Wild | full | red |
| Rumbai ayam | Oryza sativa | Indica | deletion | white |
| Rumbay | Oryza sativa | Tropical Japonica | deletion | white |
| SADUCHO | Oryza sativa | Indica | deletion | white |
| Sampit | Oryza sativa | Indica | deletion | white |
| SANDADAGIDO | Oryza sativa | Temperate Japonica | deletion | white |
| Sara Kasa | Oryza sativa | Indica | full | red |
| Sarman | Oryza sativa | Indica | deletion | white |
| Sasak Jalan | Oryza sativa | Tropical Japonica | full | red |
| Saturn | Oryza sativa | Tropical Japonica | deletion | white |
| Sawah Duku | Oryza sativa | Tropical Japonica | deletion | white |
| Sehan | Oryza sativa | Indica | deletion | white |
| Selasih | Oryza sativa | Tropical Japonica | deletion | white |
| Seng Kumang | Oryza sativa | Indica | deletion | white |
| Sentral | Oryza sativa | Indica | deletion | white |
| SEOKSANNA | Oryza sativa | Temperate Japonica | deletion | white |
| Sera | Oryza sativa | Indica | full | red |
| Serai | Oryza sativa | Indica | deletion | white |
| Sereh | Oryza sativa | Tropical Japonica | deletion | white |
| Shoemed | Oryza sativa | Temperate Japonica | deletion | white |
| Si Anak Bogor | Oryza sativa | Indica | deletion | white |
| Si Angkat | Oryza sativa | Indica | deletion | white |
| Si Gudang Baru | Oryza sativa | Indica | deletion | white |

FIG. 9H

| | | | | |
|---|---|---|---|---|
| Si Kapal | Oryza sativa | Indica | deletion | white |
| Si Lotik | Oryza sativa | Indica | full | red |
| Si Motung | Oryza sativa | Indica | full | red |
| Si Pulo Angkola | Oryza sativa | Indica | deletion | white |
| Si Pulo Manda iling | Oryza sativa | Indica | deletion | white |
| Si Pulut | Oryza sativa | Indica | deletion | white |
| Si Randah Darik | Oryza sativa | Indica | deletion | white |
| Si Reguek | Oryza sativa | Indica | deletion | white |
| Si Rendah | Oryza sativa | Indica | deletion | white |
| Siak Simpur | Oryza sativa | Indica | deletion | white |
| Siam Parapuk | Oryza sativa | Indica | full | red |
| Siam Putih | Oryza sativa | Tropical Japonica | deletion | white |
| Sinampaga selection | Oryza sativa | tropical japonica | deletion | white |
| Slereng | Oryza sativa | Indica | deletion | white |
| Snitanur | Oryza sativa | Varieties | deletion | white |
| Sokan Dhan | Oryza sativa | Aus | full | red |
| Sukamandi | Oryza sativa | Indica | deletion | white |
| SUKNA | Oryza sativa | Temperate Japonica | deletion | white |
| Sunting Beringin | Oryza sativa | Indica | deletion | white |
| Super Win | Oryza sativa | Indica | deletion | white |
| Surya | Oryza sativa | Indica | deletion | white |
| Syair | Oryza sativa | Indica | deletion | white |
| Tagalo-B | Oryza sativa | Tropical Japonica | deletion | white |
| Talum Putih | Oryza sativa | Tropical Japonica | deletion | white |
| Talum Ungu | Oryza sativa | Tropical Japonica | full | red |
| Taring Menjangan | Oryza sativa | Tropical Japonica | deletion | white |
| TCHAMPA | Oryza sativa | Aromatic | deletion | white |
| Tepi Boro | Oryza sativa | Aus | full | red |
| Toliwang II | Oryza sativa | Tropical Japonica | deletion | white |
| Toliwang IV | Oryza sativa | Tropical Japonica | deletion | white |
| Tomat | Oryza sativa | Indica | deletion | white |
| Toraja | Oryza sativa | Tropical Japonica | deletion | white |
| TREMBESE | Oryza sativa | tropical japonica | deletion | white |
| Tromas | Oryza sativa | Indica | deletion | white |
| Umbang Kencana | Oryza sativa | Indica | deletion | white |
| Untup | Oryza sativa | Indica | deletion | white |
| Untup Rajab | Oryza sativa | Indica | deletion | white |
| Uyun | Oryza sativa | Tropical Japonica | deletion | white |

FIG. 9I

| | | | | |
|---|---|---|---|---|
| Wajo Kuning | Oryza sativa | Indica | full | red |
| Widas | Oryza sativa | Indica | deletion | white |
| Wulu Mata | Oryza sativa | Indica | deletion | white |
| Yenti | Oryza sativa | Indica | deletion | white |
| Yoing | Oryza sativa | Indica | deletion | white |
| YUKWEOLJO | Oryza sativa | Temperate Japonica | deletion | white |

FIG. 9J pANDA vector

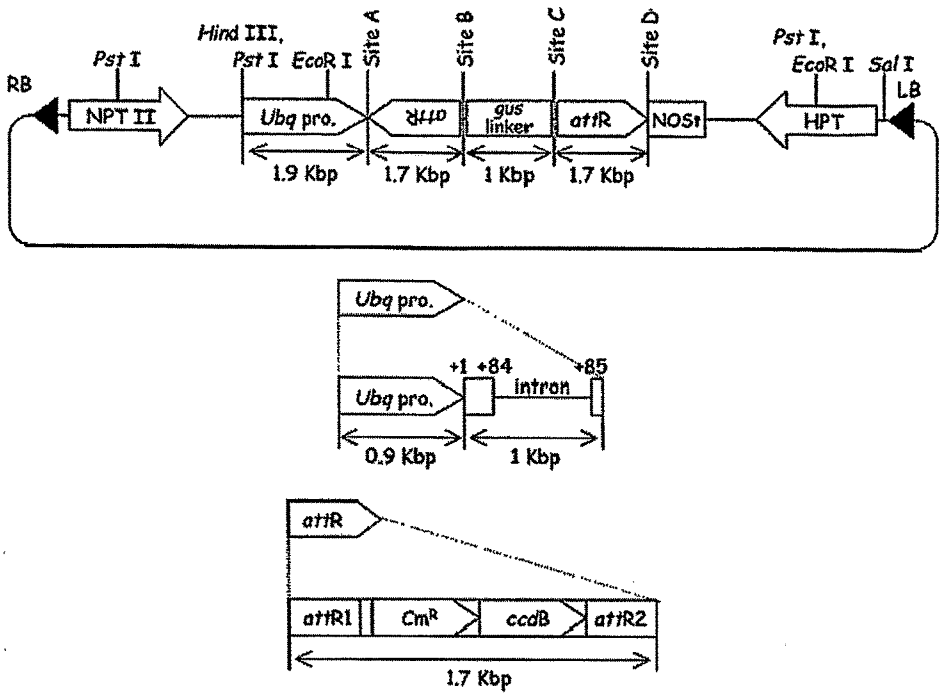

LB: left border
RB: right border
NPT II: Kanamycin resistance gene
HPT: Hygromycin resistance gene
*Ubq* pro.: Maize *ubiquitin1* promoter + 1st intron & splicing acceptor site
*att*R: LR clonase recombination cassette (Invitrogen, Cat. No. 11828-019, rfA)
*att*R1 & *att*R2: LR clonase recombination sites
CmR: Chloramphenicol resistance gene
*ccd*B: *ccd* B gene
NOSt: NOS terminator
Vector size: about 20 Kbp
Back bone: pBI101
Host *E. coli* strain: DB 3.1
*Kpn* I and *Sac* I are unique restriction enzyme sites, others are not unique.

FIG. 12A

Site A
RB---*Bam*H I, *Sma* I, *Kpn* I, *Apa* I, *Xho* I ---LB
Site B
RB---*Cla* I, *Hin*d III, *Eco*R V ---LB
Site C
RB---*Eco*R I, *Pst* I, *Sma* I, *Bam*H I, *Xho* I, *Not* I, *Eco*R V, *Pst* I, *Eco*R I ---LB
Site D
RB---*Eco*R I, *Spe* I, *Bam*H I, *Sac* I ---LB

FIG. 12A CONT.

SEQ ID NO: 119 Promoter of putative dihydroflavonol-4-reductase DFR1, *Oryza sativa, ssp japonica*
133161 bp - 138201 bp AP004797 chr6 about the gene:
note="contains full-length cDNA(s): AK067955"
protein_id="BAD45907.1"
db_xref="GI:52076894"
5040 na
ctgtactaccagctagatctggctcgcgcgctgcgcacgtgctgtcaaaggctgtgtgcactgtgcagcac
aggttgccgacttcccgttgttttcgtgaccttgatgggttgcatcttcgtctcatgggatctggacaggt
gtcaggtttccctcgcggagcaaaacgcaagcagaaaactgtggtttgcttacgatcacctggatttgata
tttgcgtgccatatctgctatgttgattctcagccgtcagcacgagctcttgagctttcatgttatcaatg
gcaaatcagatttgtttttttcctttttctgactataatcttttagcactatatatttgtatttttttttcct
actatatcaatagaaacatcgctatcttttagcactatatatttgtatttttttcctactatatcaataga
aacatcgctgcgggttgtttcaaaaaaaaaattgctaagcttgtttcttttatgatactcctatcttacta
ctccttaaaaaaaagaacttatcaatcattcatgggttttatatgtacatctcatctatatttctatatgg
aaatggaccaaattagtcaatggttgcgaataatagctcaggacaggggacagcaacaacattacaaaatc
atttgtatgagcgaatgtagctgaaccattctagtagctggttaacaagccaagcatgtcattggatacaa
aaaaatgttggcaactgtatagaaatttacaagactctgaaatctgaatctagaaaagcatcaactcattt
gggcatacaaaaagtgcagttcagaaaatgtgcaggactcccatgctaccatgatcactccgaacttcctt
ccttgaacaccttgacccaattctcagcactgtcaattatttcaccagtcttgaccaggtaccgaaccttc
gttccatcctcaaggaatttgtgtccaaccctactcgccacattcttttcctttgagtagagcatcacatt
tgagctgtgaatggggccttcaatctgatcaaagaaaacaccaacaaccataggttaacgatcaggcatct
gaaactatatatacgacactagctagaagcagcacagaaagaagtttcaagagaaacaatgctgaccatga
cgatttcacccggttcatcttctgttcctttcttgtgcttggacttcaagttcaagtccttcactattaca
gtgctgttgtgcttaaaagccgcgtaacttctccaactttacctttctcacggcctgcaatgacttgtac
tgtatcgccaatcctaacatgcatcttgtgcaggacaggaagactgtttggtttacacttcttcctctccc
atcgcttaagctgcattggaaaaagggaaatttcagacatttgagtaaatagcaagctgcagaccaaaaaa
gaattgaaacttaccctcatttgaattgggcatgtcttgatcataaatttaacctgcatataaaaatttat
gcatatcttgtcagagtttcttatgaaaatgacataaaatgtaataatcagctgcttttgagatatgacat
gaatcatgctcacgatgtttcttaggcaagaatatctaggataatcatatgatcttttagtacgagtttct
tcatataagtgcagattttagtacagttcatcatataagtgccatatatagctcagtcactccattcaaga
gcaattattcggccttattttctctcatcaccactttccaggtaagtaattagtcgtgagtgagtctcatt
ctgaggacgaagtgcagtagactatctagaagagctaaggaacgccaaaaagaatatacaaaagatagaac
aagttcagtctgataagtataccgagtgtgccaatcatttgctacaggctatccccgagtgaaatgagttt
ccatcattttcccatggaagtcttctgtgaaatttctactgttgagtaatttaaagttcaaaggcaaaatt
gtttctagccagcgaaatgtgatctatacagcaggttagaacaagaaatggtctgtctcactagagggcac
atctttcagaaaaataatcctctgcttgaaaggctgaatattgggtatccatcgcttataccaccatagga
aaaaaataatattcaagtttaaactgaaacataacaggccacatcccatggtagacaacacaatttctaac
ttctgaattcactcagttgatatactcaaacttgagatttcaagcattcattaattcatataaaccctcct
tatactagccaactaggttcaactataccacaaaatccttgagaccttttctctaaaaaaaatataccaca
aaattttgacacaacgttggttgttggctagttgaggtcctgagcctgaactcctgaaggcaacaacagta
cagtgaggcgatgtagacatcaccattgcaatgccacgctgttggtgagctctaaaatcctaaatctcagt
gcaagctggcatttctacttttccagcgaatcataagagcagagcaaacataaaggaatgcgaaaaatgag
aatcagggttgggagtcggcacaaaccccagccggcgcggcggcgaaggtggagagcgggtggccccagaa
gctgctggtgctcgccgcccccggcgcagagatggagagggacgccatcgcgccctgcaacgccgccaccc
cggccatcttcgtctcctcccctcctcttcctccctcgctcgctcaaaccgcagagaagcagcagaggata
acgaacgccttcgtgtgctcgcggacaggataatggcgagcgcttttctacatgacaaatgggcctctagg
ccgaatggattggcccacttgtaagactcataaaggcctaatgaaaggcctatcgtaatccagcccaacta
caacggaccttacggcccaagtcagccgcgatcccgttcaggctcaaatatagcgggcctcacgtaagccg
caatcccgtctcgacccaacaagaacaggtcgcacctacacagataaaatctattgtacatttctcatctc
tgctcctgattgaattacctccctcaaccgcaaaatggaggaaaatcggtcttattgtttggttatgctta
tatttatgagccaaaatttgaatttgagaacttagttttgaatttgctttttttgtttttttaaaatgctta
tattttacaacatttgctttaagttattatggacatatataaacattttactcataaataaatttttattt
gctaataaacgattcgaataagcgaaaaccgtagcagatcaacccttagatggtttgtagggtggttcctg
ttgacgtggcaggctgactcgcagagaacatgagggaggcaaaatagacttactatcacgcacgtcagcaa

FIG. 13A tccggttaaggcccaaatgtcgtgggccgctcgtcgtccgcaatcccgtttgtggtcaagtaacgtgggcc
gaacgtcctgggttgatatgggccgacacccgttttcggataaggcccagcccagcatacgctcgtcgtct
tcctcgttgcgttgcgtggcttcgtctccacacgcatcatcaccacgccacgcgccgcgagatgctgcttc
ggcgggggcgcccaggcgtggcgcctcccggattccggcggcttcgacgtcgccggcgacgcgcgcaagcc
aagcgacagttgcggaggcaagcaacccccccaagttccgtcccttttgcgcttttctgggacccatttcct
ctctcttttgggggcgctttcgcggtgacgacgctgccgatgcgcgtacgcctgaggagttcttccccat
cacgccgcgtgggggatcgggacgtcgccatttccgctgccgttttcttctctttgggggttgcaatctc
gcgtttcatttgatagggttgggcgtgggcggtggggaatggggatgggtaggtagatggcaccgatgtga
atcggacgacttcgaatcgaagccttccgatccatgtgaggaggttgaggaaccaacctaatttcgaatcg
aagaactcttggtttctctacctaaaaccaaatagcatagtgacagtggtcgttatactatgaattccaag
ctttttgaccgaagatttcgaatcatcgagcatctttggccaagctattctaacacggttgactcagaagt
ctacgtttctatgcattgtgtatttgagtgttagttactatatttcgtgataaacaaaactgttgactcaa
aagtctacgtttatatgcattgtgtatttgtgtgttactgtatttagtgataaaccttaggtgtacatgtg
agggatttcatggataacacgtgcactacattcttgcctgttccactggtcaccatcagcaaatcgctcct
gtccctttcgtgtggctatcactggagctattcaattcttgaaaggctctgccgtgcaagcaaaccgtttt
ctttccaatgggataagtgtgtgactgtgctataatctcaggataaattcatcactaaatcgttgctatca
gttttggtttatccactcattaaatcaatgcaacaaatgtggtgatcaataattagtagtacttgtttgtt
ggtatgccgtgctgccaaactagttggataacaaagattcctattatattggggttaaccactgtatttc
ctaatcataatttttaggctccttattgtcattatcacttagcatcattgcataagagaaaaaaaagggg
ggtcaatactgcaggatggtattttaggaaggaaatgtgttatcgtgatattaacacagcctttcttccat
gttgcttgcactcctctcaaactggtgtagcttcctaaagactggctcagttacacaattttattcttaa
atgctggaatcctgggaaatccttaatgcgcctggaattgttgcactcaagtaaagctttagtttgctaca
cccgtgacactttcagagttggacatgtcaaagtttccttccctttttgataaaatgtccagtgtgatag

SEQ ID NO: 120 Promoter of Flavanone 3-hydroxylase, *Oryza sativa, ssp japonica*
22103bp – 27143bp AC098695 chr3

About the gene: complement(20272..22102)
/gene="OJ1126B12.4"
/note="Contains similarity to flavanone 3-hydroxylase"
CDS complement(join(20272..20532,21558..21882,21936..22102))
/gene="OJ1126B12.4"
/codon_start=1
/product="Putative flavanone 3-hydroxylase
/protein_id="AAN74829.1"
/db_xref="GI:25446682"

cacaccaacgagctccaatgagctcccattgaaatccccatccaagcactgatgagaagggaggtcctacg
aaaccgacactagtggattcttagcaggtgaaatgatcccagcactaggcatggatgcacgtgaccacttc
atcgtttctgatgttgggatcttcatgtgattgtgtacatgactgatgcgatgcgactttttcagtagggg
aaaaatgtggttctcattgcattgtcttactagtagctccaaccttctttctgtttcctcgatcgatgtct
gtgctaaaattgcctcttacagtatatgagtgcagagacataaaggcattgctagcatgacaggtcaacc
tcactagttcatgttgttacaatatataaaaatgatttgtaatactacttatcccatcaataatttatttt
aaatctcatcttacctctaagaggctctaactacctcctgcctcaagttgtttcttgttacacaaggggca
ccaaagtgtttcctcctcaactttaatctttgctatacaatctagaaatccttatattttaaaatggagag
aacaattgtctactgtctccaatatcaaacaacaagtgtaataatatagccaattattagtttcaaaagt
ggcacatcatctacagctaatctaatactctatccatacaatacttacacacaaatatatactacacacac
cgtcttatagcccgtgctactgttagctacacatatgtaacacacttttcttctctatctcctctcttctc
atctctgcttaacctacccataaatcttatttgccatgaaaatcactttcatataattatatttttaatgc
cagagtctcttcttctcaactttaatctccactaagaaacctagagatgctcataatttaaaactgagaaa
gtagttgtttactacctccgatctcaaatagcaagtataatagtatagccatctattattagcttcaaaaa
ttggcacatcatctacagctaatctaatagtctatctatataatagttacacataaatatttactacacac
gatgtcttataactcatgctatagctggctacaaatctataacaccgctattattctcatcttctatcatc
tctccacctaatcacaaatttgatgtggcaattttgaagcccgctacttcaattattgcactaactcaaa
taaatagcattatagaatgcgtgcagtcaaaccttgaatcttaaatgattaattcatgcaaaaatactaaa
atttaacatgagaaaatggtgttggtagatttggcatggaaatctcttttatataattatatttttaatcc
tttttaccgatagtagaaccaatctaaatcgtatatcttattctaatccaatagatcatatctatttctac
taccaaccaactactagtagttgtagcgcccgttccgtcgtggcgcctagcgggaaaactatctcttaaaa

FIG. 13B actctatttgcgaaatctgtttctttgcttgttgcctagtgtccgtgccatctcagatctcaaatccccga
tctatcgtcgagttcaatcccgaatccaaaccttcccaaatcgatccctccgcaaaagtttatttttcctc
cctcgggttcgatgggccgaatctctctcggcccatcttcccctccctccccggctatctctctctctcgc
tctctctctctccctccctcttctccgctctgcccgcgcgccgcgcgcgcgtgcgcatgagccgcgccgag
ccgagccctccctctccgctccctcgctgctgcttcccgcgcgccgttgttcgcatgcacgcgcccgtgcg
gtcgccgcccgtgccgcgcctgcgccgtctgcgccgcgagtcagcacgcgtgcccgagccgcgccgctcaa
atcgccgcgccgcccgttgcttcccgcgcgcgcgtgccgtggtggccgaccgcctggtcgccgctgccgtc
agcctctgccgcgcctgtccgcgcctgccgtccgtgtcgccgctccgctccaaaccgccccgccgtcatcg
ccgtcgtcatcaacccgaccccgccactccgcgcgctagcttccaagggacggaggcagagcccctcctcc
ctctgccgcgtcgcccccgctccctcctccttttcccaaagaggcaaggggcaagccccctttctctccct
cctttcccttttttcctcccgccggcgtcatcctccctccgccctgtcgccgatttggccgctagccgga
gcgccagctcgctggcttgaccgtccaaagtcggttcccctctcccaaaccgtcattgccatcctataaag
cccaggcgccctccctctcttctcctctcgttgtcccatcgcctccactccattgtcgccgcctcccgtgc
tctgttcgccgtcgccgtttgtcgtcgcgcgtgtcggaggagccggcacgagcgaggacgcggaaggggac
tccgggcgcgccctcttcttcctcttccccggcccgaggccggagagatcactcccgtgccgtcggcccat
cgtcactgcgccccgtcccgcacggtagcgcatctccctattctccctcctcgttccatccccttccctta
gactcgggtagtagcacgagtagcctccccgtagctagctggcgccgccccgactgctgccgtcgctcgcc
gtgtgctcgccgccgtcgccgcccgagctcggaagcgcctctcgtcgccggcctccctcgatgcgttcctc
ctaatccggcgcaagggacggattcccgtagccgcgtagatgctctcgccgccgggaatcggcccctcgtg
acctcgtcgccgtttccctcttccctccccgccggttgccgccgccgcaatccgccgccgacgcactccct
ccggcgaatccaagccgttggctcgtctcccctcgtctcgtgcaaccacccggtgtgctcgctttcgcctg
tatcgccgtggttcgctccgccgcccgccgctgtcgtccgccgtccgttccggccggcgtcgtcgtctacc
tcccgccggcccgcgtggctgccacttaggcgccatgtcggcgccacctcggccgcgaccggatcggctga
cccggccagccgctccctccgttcccccccgtgcgcatggtccgcggtgagccgtgaggctgcgcgtggg
cccgccgcaccgcatcttccgcgaaccgcgcgcgtgcaccgcgtccctcccccaaaccctagcgcgcgccg
cgtgcgcgttccgcacggtgaaccgtgtcaccgacaagcgggtcccacccgggaccacgcgggatggaccc
ggcccaccggctctctctcccctccccgcccgcgcgcgcgctttgggccgccttcttgggccggccggccc
atttagctcggccgagccgcccctttctctcgggccgcgccctagccgcccgagggaagtctacttcccc
tccctcttccttttctttttcaaaaggatttaaataaatcctttttcctttagaccaaaaatccaataat
cttagaaattcaatatcttcccaaccgtaaatccgtttgactccgttcaacttccaaaattcctcaaatct
cgagatctatctaatggcacgcttagaggtcattaatagggctttattttcgccgtttgttgagttgtccc
gttttgcgtgtagtttcggagcccgaagacccgcagtgcgaggatttcgaggatcaagctcaagatctcga
gcaaggcaagccacctttgaacatcttgagcctatatctgaacttaattatgttgcttgaaaaaaatatta
tgcattgataggatcgcacttaatttgcttgtcccgtctgcaaggcagattggcgaacctacctaatttgt
tgcatctgatccttcctttgttaattgttataccatgttcccttgtaaccatctagttgcgcctcgatatt
cgtgcactctatgcgagtatcgacggtcgccttcaaacttaaaatctgagtaacttcttgggtaaaacttg
ggttttacaaaagacttggaaaacccgacacctgggtcggtgcttgcgaactaaatgaatttccaaaacca
cggaccggggaacgtaccgggtgtacggtttcccgctcttgcacttaaggaccgtttccttggaatttcat
ccgaacataagacaagtacgaccacatgggtggaatgggacacccctggctgagtaactagtttatcaggg
gagccttgatgccgagagacatgtggattcgccggggtggtgtcggggaggacccctgggcttcctggcac
agtatggtctgggacctaacctgttgttggtctgggacccctctcgtcggcatatggtaaacctgtgtcgg
ctttggaaatgccttgtcatgaaagcttggagatctcccgacgtggctgatccccacgggttgggtgatcc
gggttagtaatgtcgtgtgggtaaagtgtacccctctgcagaggttaacaaactgttcgaacagccgtgc
ccatggtcatgggcggatgtgaggtgattcctagcgtagttttgtttgactactgccttgtgaaattgctg
ttgtgaaaaggggaatcgatgtttggaaaatctgcagctgatgggatcagctaggcccgggtggccgtttg
aaagttgttggcccgggtggccgtttgaaagttgatggccaggtgccaatcttgaacaattctaaagactg
atacattgcacatactccgaccggacgagacgcactgtctcatccgtgtcgtttgagaagcactcacttag
ttgttttcagaaaagagttcaaataaaatcaattgcaaaaacaacagcctttccttgaagcctgcattaaa
cacttatttcccatggcttgctgagtactcccgtactcacccttgctctatataaataatcccccccagtt
gctgaagaagatgaagcggatcccgctgacgaggagttcttccaggagcaaaccggctacgatgagtttt

SEQ ID NO: 121 *Oryza sativa ssp japonica* **v Nipponbare 3KB upstream from LOC Os01g27490, homolog of anthocyanin synthase (ANS) or anthocyaninless2 (A2) from *Zea mays***
tagtaacatgtatgtacaagactgaaagatgaaatataaatgtggcttgactctgaagttgcatgaatttc
agtttgcttcacccagagagaccacttaacgtttttttacgaaatttgagtgacttgatttagggtaatct
atttatcacaaatattatgccacatggattccacgtgcatacttactagctgtgcctggcaacctttattg
aaacgcttagcctgcacgtatttatacaacaatatctatttagcttaccaatttcgtgaaaacatattgtt

FIG. 13C ctttagcagtaaattgccatagttcattcgtggtccatgtgcatgcagtcatggtgttgccttggttctaa
gtttctaacagagggccatggaatgatcatgaccttttgaaggtacgattaaatttgtaagtgtaccctta
cttttatgcaatagccccaacacttcaaaaaatgctctatggaggtttacttgtgacagttctagagatga
atgttcttcggatgctattacgaaggattcttttgtagctcacactctgtttaatttatttttatagcagc
caccttttgtgatggtagcaggatgaagagcggattagtacaggtgagagatgaggatgacacagtggtgt
tggacaagtctatatctccgtatcttgcttgcggtggtcgattgcatcaaggggaaacttcattggagggt
gtcagctgtcatggatgcaaacgtggtgacccttctaatccaacggtttgagtggccacaatactggttaa
tattgattttggttcctaaccatctgacggctgacgagccggcaagtacgagcaatgtttttaggtgtgca
tctttgttacatgttgctataatatttctgtgtgtttaagcaccattgatcagcggcaagaaggtgtgtat
ctcgttgctccttgtctagatgtgcatatctaatctctggtagtttcaacagtctgtgttttgggcaatgg
ggagtccatcctttttttgggaggacaactggttggagggttcctccattcgctacatatctccggcggttt
gggcgtctgtcccaacacggcttcgctgtcgcagaacggtcgccaaggcccttcaagaccggagatggatt
agagactgcaccggagcgctgggtttgcaagctattcttcaatatcttcaactctggagtctcctgaggtc
gtcggtgcggctctctgaccaccccgactctttcatttggaagtgggaagcatcgggagtctactcttaac
gttcggcatacccgtgcactctttctaggtagggctcctttccactccgaacccatctagaagactccccc
ccctcgagatgccggttctttgcctggctggtcgcaatgaggcgctgttggacggtggaccgcctgtgttc
taggggtttgcctcacccggatggatgtgtgctctgcgaccaacatgaagagactattgatcacatcttgg
ttgcctgtccggagtctcatcagctttggtgggtcctcctttccagcactggtttgccatagtttctcccc
ttgaatgaagattccttttatctctgggtctacaattcctgccttaaagtggggagggctagcaggcgggg
atttgatacaatagcaacccttactgcgtggacaatctggaaggagaggaacaatagggtcttcaactctc
agcaaaggccctggtcagagatagcccgagctatgacggaagcgactctctggcggttggcacacgaggtg
ctgccggtgctaaccatttaggtcttgttctaggtcgtttccttctgatgtcgcgagaataggcttaagct
ttttattgttctcctgttttcgcatccccctcctaatttcttgtttggcttcgcttgtacatactcttta
tttctcttaatacaaatatgcgtgccttgcgtattcccaaacaaaaaaaaaactctggtagtaatatattt
ttttgtcatatcccttgtacattctataagtttgttgaattgtattttaggatggcaatctgtggatgata
aatcaaacccgtgatatgaagcttttagtttttccagacttttagtactactatttgctagatgattctg
agtagatacaattgctgatggttttgattaattttagacaatgtgatagttttgtactttttcttaaata
tatttcatatatgacatggatcaaatggacagaatttgggaaatttaatttgattaacatgaatttaataa
tttattaacacaaattttatagtgccgtagcgttagcacggacagattactagtagtgtaaaattttaaat
cttcttgtaaaatttagaagcacgaggactaaaatgagaagtgcccaaaagggtaggtttttttagaggt
gttgcctcagcgcctacctgttatttgaggccattggataggagtgggcctatattgttcatgccctcgtg
cgcgtacacaatcatagtttcacatagtagaaatggtgcttaagacttttaaactttcgttcttcactgtc
caaatatatgctaattaaggttggaaactagaaaacaatagaaaaaattcaactacaaaataagttctaca
atttaaatttctaacttgtaaaagtcaaattcttgttatgccttatataggctaacgagcatgcaatgagt
ttatacatacggatcgtatcatctgaattaagaaacaacaggggcattattgacagggaccaatcaaccaa
tgttacgaacgcgcacgtgattgatggatggagctaaccgcgcgtgcccgacaccgctggttgttgttagc
tacaaacgtaacacatgcatgcaccgatccatggatggagcaaagcggcggcagcgccggagtataaatct
acccgcgctctgcctgcctcgccatcaccggccgccgatcgagtacgtgcgcacgcagctcatctactagc
ctacttcgggagggcgac

SEQ ID NO: 122 *Oryza sativa ssp japonica* **v Nipponbare 3KB upstream from LOC Os06g42130, homolog of anthocyanin synthase (ANS) or anthocyaninless2 (A2) from *Zea mays*** tccataattagagaatgtttactgtagcatcacatgagctaatcatggattaattaggctcattagattcg
tctcgcgaattagtccaagattatggatgggttttattaatagtctatgtttaacatttataattagtgtc
caaacatccgatgtgataggaacttaaaaattttagtcctatctaaacagggtctaagatgcaaattcttt
agtcctatctaaacagggtctaagatgcaaattctatcctgatttttattagcacgtatattaaactgcta
aatgattttttttcaaactttctacatacgttgaaactaatctaaaatatcagtaaatttatttttaaa
atttacaataattaaaacttaattagttaagcgttaatgtttttattcgtatcctaacttcatcttttct
ataaaaaaaatacaaacaaacaccacctaagagacgcagtcgctgtgtgcggctcaaacgagcagtctttt
cgatgtggaggtttcagataggaataagttcacatggtgaccatcaagagtgattgaaatctaatcgatga
ccctaaaccataaaaccagatattttgaccccaaaactatggaaaccggtgcaatttgactccttcggcgg
ttttggagggcggtttcgcagacgtggcggtattgaccggcaatcctttacacgtggcgctgacgtggcat
ttagaattaaaaaatatgtgtggggcccatttgtcaatgacacagaaaatagattgtgggacccacgtgtc
ccttctctctccccttcctcagttccctctctctcctcgccattccctctctctctctcccgcggcaggcg
gagatggcggggcgacctgcgagcggtggcggcaaccgggctgagctccatcgtgacgaagacggaggaga
ccaaagcggcggcggcgggaggcacacgaggcggggtacggcgagctcggcccggcaatggaggacgagg
ggagccggcggcggtgcgagcggcgactgagggacgggggccgacgggccagagccggcggcggtggcggg

FIG. 13D agggcgggcgggtgagcacggcagcttgtggcaggaggacgtggggagccggcggcggcaggagggcgggcgggcga
gggcagcggcggctcgtggtagagggaggacgaggggaagctgcggccgaggtatctgagttcctctttggccgctt
cgccgccgaccacgccgccatcgccatcgccatttcaggagtcaaagtcgaagtcgccgccgcagcctgcttcttcc
gcccgccgccgttcccctcatcctcccactgcttctcccgcccgccgctgttcccctcgtcctcccactgcttctcc
cgcccgacgccgcccgcggccgccgccgctcggccgccgccgacgtctcaatgccggccgctgatgacgtctcgat
gccaggcgctgggtggtgtgggtggtggtggtgcgagaggaacggcaagcggccgccgcttcagctccagcccacgg
tcgccgccgcagctccagccgccgccgctcgctccccgcggacggctgtaggggagagggagcaagaaagagagaag
ggaggggaggaagaagaaagggagaagatggcgtgtggggcccacatgtcagtgggccccataattgtgtgtgtgaa
tgacaaatgggtcccacgtataacattttaattgaaatgccacctaagcgccacatcaacgccacgtgtaaagaaga
cccggtcaataccgccacgtcggcgccacgtcagcgaaactgccctccaaaaccgccgagggagtccaattgcaccg
gtttccatagtttggggtcaaaatatccggttttgtggtttagggtcatggattagatttcaatcacttttgaagg
tcaccaagtgaacttattcctttcagataaccttagcgagctctaaagcaaaattttcataaatataaatatatac
atataaattttcataaagggagcatctatccatttgtcgggtgatctaatacgtactactccctccgtttctccc
tccgtttcaaaatgtttgacaccgttgacttttaatacgtgtttgaccattcgttttattcaaatcatttaagtaa
ttatttattcttttcatatcatttgattcattgttaaatatattttcatgtacacatatagttttacatatttcaca
atttttttgaataagatgaacggtcaaatatgtgctaaaaaatcaacgatgtcgaacattttaaaacggaggaagt
acaagtctacaacgtacacatgcaccgatggatgggtgaagcaaagcagcggcagcgccgggtatatgcgtggtttg
caagggtctatatttgttgcaccctttggttatgcaattgctacactatttgtgtttaaacaattgctgttaact
ttagatactgtggtgatgcatgctgtgacatgctaatttgctaacggtgctgcttaagaacccgatagctttgtgtc
tctttacttttgacaaatgtggctggaagttcaatgttaaatatattattcggtatttccctattgccatttgcata
ttcaacaatatgtgaatttgtcatatacacaacagcaatcacaatgaatataaaagcctaatatctccacttctcta
acatttggcaagtataatctcaggcacaaattgaaccaaacagcacctgaccattgtatcccctcaggcttgtttc
agggcatcaaccaaacacactactctcagggagacatgcctaaccaggtaactttgctatctaagctcaggctactc
tcaggaatgtaaaatgctcaggcaggttgctcaggatagcaaccaaacaagctaaatctacccgcgctctgcctgcc
tcgccatcgccggccggccgccgatcgagtaattgcgcagcgcacgcagctcatcatccactagactaattacttcg
ggagggcgac

SEQ ID NO: 123 *Oryza sativa ssp japonica* **v Nipponbare 3KB upstream from LOC Os06g09230, homolog of flavonol 3-O-glucosyltransferase (UGFT or 3GT) or bronze1 (bz1) from *Zea mays*** gggcacgtgggggggagttgttgcatcggcgcggcgcgtgggtgggtagatatgattgggcgggttgggcc
tggaaattgtgacattgggcctgtttagatccatttggaataacaaatggtaaaagttttggtggcaaaag
ttttacaattgcaaaatactagttggtgtttagatgcatgttaaagttttgccattttagcactaaagtga
gagagagaaagagagagggagtgatcccaaagcacttttggcacaatttgctactatggattagcaaatg
ccaaatgccaaactgccaacttttgctactagtgtttggatctaaaatggcaaaaagtgctacaaaatagc
aaaacttttaccattttgaaagatctaaacagcgtcattattggtggacttggcgagtaggatgtacacac
gtacgaattttaggcaagacgtagctcgtgcagtcgtgctcgtcctcggctgcccttttctctagtcagt
tatccatcttccctcatcaacgggtgtgcttagttcacatcaaaattgaaagtttggtaaaaattgaaata
atgtgatagaaaagttggaaatttgtgtgtgtacgaaagttttgatgtgatggaaaagttgaaagtttgaa
gaaatagtttggaactaaactcggcccaacttaagctttcagatcgacttgactgatgcatataactcaat
ataatattagagccaaagggtacatgtacatagctcgtgcagttatactcgtcctcggctgcctatttttc
tcgtagtgattttgccttctgctcgctttttgcatataccgtactgctgtacatcagtcgattcatattt
tccctttccccaatctcagttgactgaatgaattccgttggttttaaatcgaacaaccaagtaattgtttt
taacctccagctgaatgagtgtgagagatgagcaggatggtatggaggactaactaggggggtgtaatttcc
tcgttaggggtagggacccggcgggtaccctacggtgacaagggcagagtagaaattttaccccacgtatt
tgccagggtaaggccgtaactattttcacgggtgggggcgggggaggaaagtgactcgtgaatgactcggc
aaccaccccgaagtgacaagaaacaacattcaccttgatctttagtccaggacccattaataacccatatg
ccttgtattcctccataaaacctatgttacaaaaacaatcaatattgttatagctcccattaaaggtagtg
gcgtatgtggagtcctctttatagctcctgagatactgacgcaattgattacctcccatacgtagctatgc
cggatgaccttgatatcctctttggcactccctctagttggatgcgacaactgcgagtactcatgtattgc
tcccgctttgacctcctcgccagtaaagcgacgcacaaacaacttccttcaatccagcgaggcggcaatta
aaactcttccaacatgacaaccaaccttaacctcctccttatggacatgccgacagctgaggttcaatatt
ctctcccttcaatccagtgaggtgacgatcagccctcctccgacatatctttcagctttgacctccttcat
ttttgtttctggtgtctcctctttcttctcattgatgaccctggatgggataggggacctaactccttcct
aattctaggagtagccaacgatgataggatggcttcctcagagagcccacgatgccggtagcacgcaaacc
ttagtaagcttcgcgggatttggttttgggctaatgagtgttaggaggggagtagagagagatgagagcag

FIG. 13E ctttagatggagggccatgtggtggaaatgggtgggcgcgaggtggcatcaacgccaacggaggttgctgg
aacaagagcggccatgtgattaggagatgatgggcaacatcggtggatctggcgtctcgctcaatcgaaga
ctgggaaggagaggttggtcggggataaagcttcggagtttgaacatagccacataggtgacgataacatc
atgaagaaagataagagggaaaactaaaaaggttgtgactggtggggctcgtcatcgtgaggatggaggt
ggtgctaagagtggcagagccgcgtacgtttcatgctcaacaacgcgagtggcagcattaaaattgcttat
gtatgaagtttaaaacaatttaaactgtccaaaaactgacttatagataatagaagaacaaaatgaccagt
tgataaaccctaataatttcatactattgggagttgggaccttatcttgcacgaccatccatagcagtacg
tgcaagcacatgccgcaagaaaatgttcctcacgcttagaaatttcttcaaacagataaggatatacgtgg
cgatagtttttttttctctcgaggggatgtctcttcctttcatgtcttgtatgttatccaaacaatataa
aaaaatgataatgtagattaatacgtgagttcaatttcgaccctacgagatataaagaaaaggactacttt
gactgatatttattagtttgatccctcttttatcaccatgtattgccctctttctatcttgtaagctaaaa
caagaaggccggattcatcgttcacccataaaattagccacgagcacaaatgaacacacatggctagacta
atcaccaccacatccaaatataggcaacacttaataatagaggataataaaagggagcaaaacaggttggg
tcttggctttctcccctctctctctccctcttgtcattgccttcctcccctttaggcaatgacagagtata
attaagctgaacaaacaacattgctaggagcttggaaaaacctaacaaaaccggcgtatccattttagcta
atctttctttaatctccccccattagagagcacttagaagatataggagtcggttggatagcgagagagag
agagagagtgagagatcc

SEQ ID NO: 124 ***Oryza sativa ssp japonica* v Nipponbare 3KB upstream from LOC_Os10g25590, homolog of glutathione S-transferase or bronze2 (bz2) from *Zea mays*** gatagaagcagacacagtttcaattatatttcttatccacgaaattggcatgaagtttaatttttagttgc
atgagaagcaagtagatatcacacaagaagttcttcgaataatggttggggtgggggatcaaaccttatgt
gttcaataagttggcgtgcacaagctagtagtaatggctgcggtcaaaacaatatgcacattcattagatc
tatccatggtctgaccttacattgaacagtataataaccttacctcatctctctttccaaaaagaacagat
acattgtaggttggatcagaaaaaacactttcatctttcctattaatgaggaagaaaacatgatcagaaat
actaaagtggcaggaaaaacagaacatagtaacaactacaatggtatatcatcaataaagtgctagctgtc
aactatcatctatcgtgtttaagaaataacagaagcattatcctgtataaactgtaacatcatgaggtcat
gagttatgacctgacatgcactccaaaatctatgttgacagtttcctagccttttgcaactagcggataa
acgcaccaacatatgtatgcggaattgtggatggatcctcactgttctttcagaaacataagctaaaagct
gagagctaaaggtttaaaatttggataggactaatagcatggaaagaattgtctatcctgaactggcaatg
cccagaataaaccatgctatatgtgagaataaacaacatacctggcagctagtatggttcccatgcatcct
atttgtgtcaccatcacctgtatattttattattaggtgagcatattttatatgtgaaaacttgtcatcca
atcaaataaatatcacttgcaaggtgtaactaaccataaagttatcctcatacttgctgataacaatatct
gtcttattgccctagaaaaccaagaaggaaaataagttagctgcacgcaaagaactgaaataactaacacc
aagcaatgcaaatgtggtttttgcaaggactagacaattacaatttgccaaagtgataacaattgactaaa
gtatgatagccaatgcagatcatgttcgcgtccaacgacagaacaaacttgttcttacgggcaatggctaa
cgatatgcgatgacatgttgaatcgagttctaatccaggaacagttttaacaaactgtttttctaaaaggt
gtttttatcgcagtcatatgcaatgcactaatatatgcttaacagttactggagcaaaggctctcacattg
atatccaaagagagggacttgtgcggcacaggaaactgagcattcggctgcacagaattcatccccatctc
catctgcgaaacaagcatactgcgagtaatcagagagaccacaaagaaggtcatcgacacaccaacacata
agagaacccaaataaacttctattcactaagcagaagttacagaacagccacgcagcttctgaatccctaa
atcacagcgttcgcttcgagaaatccccgcataattggctaaatggctggtgcgtaaaagatattgcccca
aacctttataaactggcaataaggaaaaatagaatggtgtcgaccgaacttcaagacaacacatggattac
ctccttccgacaaatcacagagattgaaaccatcaatgaactagttcaactaggtggactcatatctcaaa
ttcaattgcaattgggcactgaggatgacataatttggacaagaaatgaaactggaacctgcatatccaaa
agtgcctaccttgcgcaattcattggatcatgctctaaacaagaattcagtcatctttggggctctcaagc
acagccaaaacaataattttaggatggttgattctacaccaaaaaaccctaacggctgaaaacctgctaa
ttagacattggccttgccactggatttgctcgcattgcagcgaagattttgaagacaccgatcatctcttc
agagactgccccttcacgaggcaagtatggaacagagtttcgacaatgagagggtctgatccaaagccgcc
gtcacaaaacctcaaaatttgggtggatgatatcacggccaatggaagtaaaaaaaaacacaagcgagaac
agcttgatctcctcgtgatgacttggtggcacatctggctacaatgaaacacaagaattttttcagcagcaa
ccaagcacgacagcacaagtcgtaaacctaattatacaagacatagacctacgcgaattagctctcaaacc
gccttgattttctaccccatccttcttcccccgaagttgtaatctcttcaacctgtattcgtctaaaccac
cctattcttcttttatttacttcttctaatataatcggcagagctcctgccgccttattcttcaaaaaaag
aaatccccgcggaaatcccaaatcaacaaaggagttaggggggcaaagtactggggggggggggggggaag
aggagggttatggccgtcgggagctgtgaggttggcggcgcactcgaccaatccccctcctgcgcggcggc
ggccgaggaggggaagttgtcggcggttcacggcggcgaagccgtcgctagaaagaggggggctgagcaggt

FIG. 13F ggtcgaatcagggagttctccgagtaaatcaggaagaagaagaggtcataccggcgcaatcagacggcgagctctccgggccttcgccgccgccgccgtcgtc
gtctccggcggcgactcgagagagagagcgggggtggagcggaggagaggcggcggcgcaactcaaccaatgagcggaggacacgtatccccctcccgcgccc
gtccgatcagtagcaaccccccgcgccaagattcgtgcagaccacgcgcgtgcaggtagcaacggctcacgcacgcgccgcagctacccagccactcctcgatcgtc
tcctccccattataagcagcagcaagcaagcaaaccaaagcaaagcatcgatctccc

SEQ ID NO: 125 *Oryza sativa ssp japonica* v Nipponbare 3KB upstream from LOC_Os11g02440, Putative chalcone isomerase (CHI)

cgcggggaggtggtggcgaggagagcgctagttaagcacttggtttggggccaccgccgcggatccgcacggcgagagaggggcgg
agaagaggcagctgagggaggcgaacgcggccgccctggacctccgcgagcgctagtcagggaccggagacgaggaactgacccg
ccgtggggatgtacggtgggagggaggagacggtgcaggcgcggtcgacgaacgcggcgtgagctagcgagcacccgtgcgccggt
ggatgtgcaccccgctgcttgcttggtcggtgaggcctcctcgggagctaagcttgtatgcgtgtggctcgagggcgagggatgaggcact
gcgcagtggagggaggtgtcgtgccgctatgccttagattgtagccaaaataaaccttatcaaattttgtcaatttggcaatattgccaagttttg
acatgatttattacgtatttactccctgcatcccaaaatataagcatttttagcatagtgacaagtcagacattttcaactttgactattaatagaaaa
gataaaaaagatcattcatataaaattaatgttattagatttatcattaaacaaactatcaataatgtataactctttttatttaaaatattttacttttata
gatattattggtcaaaaataatatctcgttgaccgtgtcaaagtctaaaaatacctatatttggaacggagggagtactaaagtttgataaaaaa
aactaaattaatgtacatatttaacaacttaaaaaaagatatgatttaaaatgacatcaagctaaacatctgaagctaaatgcatcgttcggtgtg
aacctgtatatgttttggccacgatctagaacatggtacctacccccttctattagcaatttagctgctcttcttgtttttttttccttaagttcgtgggg
agcttggaactttcggagtggtaggtgtatctgaaagtctgagatgtgccacgcctcttttcttctgtcctgtcttcatctcctacctaacccctgc
ctgcatcaaccctcatatgttgtccttggcgaataaaaacatttccctactcacgctctttcgatcttcagctcctctctatttctctcgtcaacaatt
agcgctctctattcatcgcaaggagcaaaagcagtttcagttccaacctccttctggttccattgctaagaagtaagttaatctctctttcttgcttc
cttctgatggatccttgctagtagtagtattactccgagcatgtttaatttggttgctacctgagagaagcatgcctggacttatgtcctgtttgaat
ccagggactaaatcacatagaatgtttgatattaattagaagtattaaacgtagactaatgacaaaacctattctataatcttagactaattcgcg
agataaatctattgagcctaattaattcatgattagcctatgtgaagctaccgtaaaaatatgctaattatggattaattaggcttataaaatttgtat
cgcaaattaactctcatttatgtaatttgttttattattaatttatatttaatacttctagttagtgtcaaatatagtccttgtcacatcggatgtttagacg
ctaatttcgagtattaaatatagactaattagaaaactaattgcataaatgagagctaattcacgagataaatttttttaagcctaattaatctataatt
agcacatatttaatgctagcatcacatagactataatcatggattaattaggcctaaaaattcgtctcatgaattaggtcttatttatgcaattagttt
tgtaattagtctatgtttaatactctaaaatagcatctaaacatctaatgtgatagggactaaagttttaggctgtgtttagatccaggggtgaaaa
gttttaccgtgttacatcgaatatacggacatacatttgaagtattaaacgtagtctaataacaaaacaaattacagatttcgcctgtaaattgcga
gacgaatttattaaacctaactaattcatcattagaaaatatttactgtaacaccatattattaaatcatggagtaattaggcttaaaagatttgtgtc
gatcttgattggttgctacccaagactgttctccactggcctggcctgacgcatactccagccatagaggcgtgcaattagcgcggccgattt
ctgtcgcccgaggctccaggcgtaaacaaatgcgtgctttaccatcgaaatctcaactgtacgaagtcatcaccgcgtgccgccatcgcac
gaggctgcccctgatctgacgccactgcgtgaagcccacacctacctcaatcgccaccgccggcaagcgaagccactgccgtggtcgtc
gttgagcgaagtccccgcgttggtcgagtttgtacgaagcttcgcgtgatcccctttgccggatccagcttagagcgaagcttcaattcagct
gatgctgctgattttgctgatcgttattgcgactttggggatatttttggaaagttaggtatgtagcatatggattttgtgagatttttcccgagacg
ccaagccgttttgtcgagatttttgttcttcccgtctaatacttgagttagcagtaatcatctactcgatcaggcagcagcagcaaaccaaacaa
gcaactcgtcaggtggaacccatgagtttgttggagtgcaaattcttcaggcgtggtgctcaggtcaccaaccaaacaggccttctgtctttcg
tccgtcttgagggatatcaagaaaagacattctcatggttctaaaaaaaagggatatcaagaactcaaaaagactttctcatgaatgaatgtatc
taattccatctgaaactctggtggtagcttcatacccacttcggactttgcactagcttgtacatttagagaaattctgaaagtagtatgtgaaggt
tgttgaaatatgcttatatacaaaacatgaccatac

SEQ ID NO: 126 *Oryza sativa ssp japonica* v Nipponbare 3KB upstream from LOC_Os12g02370, Putative chalcone isomerase (CHI)

tgttaggacgagggatcagcgatctctgtgacgaactgctgcctccgacaaaggcgccggaaggcagacgg
ggacctgcgcgtaacgtatttagttaggacgtagtcatgttaccgagaataaatcatatatacttgaacta

FIG. 13G acctctgggcggagcagtaccgtgcgaagaaccagctgtaggtcgcacaactccggtactaggggcgcgtg
gacatggtggtactggaccaggtggaggtaccgcgtccatggcgctgcaacaagagaagacgcgcatgaca
gcgtgcatcttctcttgcatccggtcgaaggtaatcctctgctcagcatcactcaagtatagcccggcgtc
caacctcactattatcgaggtaatatcggcgttcacagctcgtgccgtgtcggcctattcaagacataaga
cagcatgtcagtaggaaaataattgaaggaactgagtagaaactattgccagaagtgagtagaagttcgac
ataccccccatgaagtagtctcggtcacggtgcgtggggtactcgtccctgacagtggcaagtcgcggctgt
ggtgcggctggagtgatgttgttgcggtgatgttgcagtgatacttcttgacatcttgtaagtggcactgg
tgctcggtcacaatgctaactttccaataatctttccatgtacccttatatgcatgaacacgccacggaca
atcttctttcacgcacctcacttcatacacataattggttgacttgaccaccctaaactctctcatcaatg
agaccgcccaatgcttcactgcctccttcatatcctccttatgagcatacgtagcaccctcaattacctcg
ttatccttgtattcctagggtacatgatgttcctctgagataacaagtcccgagaagtcctcatttgtcca
atcagtgggcattacatcaccttcctcgtcggatgatgcatcgccctccgcttgctcgttatccgaatctt
ccctcttcatttcatcaacgattgtactgattctctcccccctcatctgccacgcccatggcctgcaccacc
cctgtgtcatttccctcatcttcccccgatggttcaacaaaatcccccacatggcttggaccctcgacatc
ttcggtttccattgcaatatttctatcattttcatgcaccgacacaaaaataaccaagggccatgaccttt
caaaagccatctccagataccgtttccaagcaatagtgctatgcgcatcggcatgagttcccaaaaataac
cttccgttgcacgactcactacaaccgatactgacattgtgtggacttctgagtctattctatatccttgc
atcaaccaattataaattgactgaaatgatctctcagcaggcctatcgatgcccttcgatgtcattacaaa
atctgacagatcaacaccatcaggaccaaatctaaggttgccttcaccgtgaactatctgaaacatgacct
tacttgacattgtgcttgatgaaaaaatatctatgttaactaagttcatatcatactaaccagatctaacc
ccccattcatcaatacatactacgccctaagttaaagatactacaaataagttgtatgtcctatgtctcaa
attctaaaataggctgtgtgctacagatctactaaagtatatggtaaaaaaactaaaatgcaacaaaaaaa
atggaaacacatttcaaatgaatgtattacctgtgatggagtcagcaaaccagcagggcttcgccgctccc
cttctcttcctcctcacccctccctctttctctttttctggattttgagtgaatataatgaaaattctgag
agggggaaggggtttatactcggaggggtaaaaatcgccctccctaagggcggcaagggggccgcctgca
aaattccaggccgcctcgccgccctttttgcaggcggccccccgcacagtaataaatcgcccttcgggaggg
cggcaagggggccgcctgcaaaaaaccaggccgccctttttgcaggcggccccccgcaccgtagtaaaccgc
cctccgtaagggcggcgagggggcctcctgcaaaatggcagccccccctatagacggccgttaggcgtgcgc
taacggtggtcagccacgtcacgaaaatcgccctctgggaggaaaaaatcgccctcccagaaggcggcggg
cgactacttttgtaaaattttgaaacacaaaattacttttgtaaatattttaataaaaaaaattaaaaata
aaaaaaatttctccacccgggttggttcatcggtacatgaagaagcccatcggcccagcatcagtttaggc
ccaaatgatcaggcggcccatcaaatatgtgcacatgtgctcttcagtggtagcatagggtatagattatt
tgactgtacgattggaggggacaactcctctttttttatattactatatagaatatagattattttgtgaag
tcactcgcataaatacattaaatattataaagctaataaataactttgaaaaagaagctatttaaaccatg
cttaaaaagtttgagaaaacatactttcggaagcgtgctacctacattagctgtttaaaacgccaccgaag
tgatataagacgaggacgtcctaacaaattcagttttaatttcctcgtctttgcatatatggaaggaaccg
aagaacttcacctcaaaaaaaaaaaaagaaactctgctcttaacagattaaatcttgttaaactaggatta
gcttcggtttaagctgagactgcgtttggtgaacattgctacctacccatccattagcaatttaggtctca
ttttttcttgagttgcagcggtttgggactttgggagtggtaggtgtatctgacagtctcgaatgtgccac
atctcttttcttctctcctgtctccttctccaacctaacccctgcctgcctgcatcaaccatatatgttgt
ccttcaccaataaaacac

SEQ ID NO: 127 ***Oryza sativa ssp japonica* v Nipponbare 3KB upstream from LOC_Os11g32650, homolog of chalcone synthase (CHS) or c2 from *Zea mays*** agagccatgaacccacaaggatgagaatatatcttacttaaataagaaaagtaaataacaaagaaaatcac
aaatacatatataaaagaagcatccatcgtggtacaagatcgtaaagagtgtcaacatatccggcattcct
ccggagaaaatggcgacatctctggcacttctctgaaactcccctggagagaacttcaacatctccagcac
tcttccggaactcccccgaagagaactttgacatcaagggcactcctttcggagcttcccctcactctctt
cttatattctagttgtactagagagtagtctaaaaagtgagttgtactccacttgatttatgtgtcttgag
agtgagatgataatctcctttttatatccctcctatgatgcttactatgatggttataagatcggttcaccc
acaaccgtcatagggaatgaattaatctgggtcgtccacgtagaaggtggaggtgagagtccacaaaggcg
gtttgaccgaccttagggttcgggcgaccccttggtcctactttccgaccgctccttctgccgggaaatgg
tttataataaccactatctctaagttagatgttttatttcattcgcttttatatagggattgatggtcaga
tttaatacttaaggaccgtcaaaaacaattgtttcatcttctccggcactagcagcaccccccaaactacca
tagggacctatgtattacgttcccgggggtggggtcaggtgggaggggggtgggggagagggaaaaggggc
aattctctcgctttaaaggatggttctgggaggcggcagcccggcggtgggtgccggatcgaacgagcgg
cgagacaacggcagcgctaccgaagccgcagggtcagaagcgagtgctgggccagtgttggcgacggggac

FIG. 13H aaagaagaaggactggttagggggaggcgtctggtggtggcggattccgtggcggggagccaccgaagaag
gggaagacggcgacacgggagcagctcgccgccaccgtcttaaggagaggagagggtgggggttggggagg
ggggaacgggctcgcttgcggcgttgatgccttccggccaaccagcgaggctaggcagcggtgctctggga
tgggttggcggtgcggattgcagtctcgcacgagcaaacaacagcgacgtgagggatggagtaaggtgaaa
tggaatgaggtgagggttttagggtttggttgccctgtacgaattttaaaccaattagatgctctagaatt
tgaaagatttcttttccttggggttgggggggggggttattgacagtctcttaaaaaacctcgtgtgg
atgatctcccctagatacttttctcattgcaggactgagaaaaaaatactaaggcttcctctaggtttct
ctcaaagcagcaagggtgacgagggggtcctttttaacccaaccccgaaaatccactcctacgggggagt
ctaatgtcaccgtccgagttgaatcctagaattttctgatagcaccatttttactagctaaaatcctttt
tttttccttcccttcagttcatcaagattttgaagctctagccgcattacgcattatagtacgccatgtac
accaatgcctgagccaaaagcaattaagcagagatgatcatcgatctgatcgacctgaaacgatccccgaa
atatcatcatcgatcctaaccaaatcaagcaacaaaaggtacgttctcctcaaaaaaaacaaaaaagaaaa
aagtgagagagaaagaaataaagccgcagcagcagcaacagcaacagcgtacacacacacaagcaagcgta
cgcaccactgtacgcacgcgcgtatacgtgctgtccctagcaaatgcaccagcaaccagtctccttttccc
acaacgacaccacccagcattccagcaactagcagtccacgcctctccacgggcgcgcgcgcgcgcggcca
ccgtgagttggaccttccatccatcgatcgatcgatcgatccagcaacaaactggcatctcgcgcgcgcgc
gcgagcgagcgagcgacgtcgtcgtcatatcgcatgtggcgcagacggcacgcacacgtattactgttgtt
tcgacgacgatccaggaagaaaaggggaaagtgatttcatcccctcgtgtgcatatataccaactaaatag
tcatcaaaggatttgaaaattttctggcaagatagattaatataaaatatatagcactctacaaacatgc
aagttaaaaattcaacttgtacaagttgtaacaaaaatagcaaacatagatgcgaatgtacgttaactatt
ttcggtttgatttgttctttttttgttgtaacctgtagaagtcaaatttggtcttgtatgtttgtatagtgg
tgtatttcatgttaatatatattatcatttttttcaatttttttaactatttacttcctccgttttatgtt
ataatacattttaactttggtcaaaattaaactgctttaagtttgaccaaatttatagagaaaagtagtaa
tattttcaacctaggataaatttattatgaaaatatattgaattattgatttaatgaaactaatttagtat
tataaatatttttactatatttatctatatatttagtcaaacttaaaacagtttaattttgttcaaaatcaa
aacgacttataatctaaaactgaggaagtagatgacatataaacaaacgagagtacattcccacggaggaa
tgaaaatccatctccgaagaaaagctttagctttggtagagcgagcgagagctgcattggccacgcgagcc
aactaacccctccgagtccaggccggttggtacacgtgtcgccgccgccgtccgtttcccacccggagccc
acgtggccgccatccgcccgtccgcccgacctaaccaccccccctcccccccgcgcctatatatatcagca
cgcgccccaccacgcttt

SEQ ID NO: 128 *Oryza sativa ssp japonica* **v Nipponbare 3KB upstream from LOC Os11g32620, homolog of chalcone synthase (CHS) or c2 from *Zea mays*** cggtagtggcggggccgtcctccgcacggatctggtggcagcggcatccttcctgggcttgtccccgtgtg
cacaacggcgaaggtggcaggaggagcccgggagaggagggaaggggccgggtgacaacggcaacggtggg
gccatcccttgtgcggatccggcgacaaatccgcatctagctagggttttgatttttgggattttttttc
atatttctttttgtgtgcggacgacataagtactcgcaagcgaaaaaacagatttccgtgtgtgggtgtg
ctatccgcatgaaaaaaatagcgattttcgtagacactttcgtttatactggcgactcacccatacgaggt
tttgcccgtttggaaaaatgctttcttaaagtagtatagatctgctgtaatattcgttcaggtgagaagtg
aaaaaattgcaaccaaacgtgtagaaaacttatgacagattagtgtcaaaacacacgtgatcatgagagca
gtatgtatagatctgctcttatgacagattagtgtcaaaacacagtatagatctataccagaagaaaactt
tcaactttcacactgctaattagatctgctcaacgattattgtgcaggtgagaagtggaaaaactgcaacc
aaaatcgcaagcgcacgcagagtacttgtacgttagctaccgctgctggccaactgagcaaaggaggtctt
tttagttacatatgacttacatacatatatatatatatatatatatatatatatatatatatatatatata
tatatatatatatatatatatatatatatatatatatatatatatatatataatcatacaattatataaaatataatgtaatt
atagtatatgtgcaatatatataattacactacaattacatttgaaagatttttataaaaaaaatgctaga
tatttagatactccctaggtgtttcatccttgtactcatcaggccttctctagccagggtcaatctcggcc
catcgtcttgaagtcatatctgaagtccggcctccacaacaaggagctaaatgcgcaatgatccaactaat
caagtgaagtgtagtaattttgtttgggagtagcatacgtacttaaaaaatacttacaaaaatattactaa
ctaactcccaaccatttattttaagtatgtagttggaagctagaaaagctaaggcctcctttgattaatag
gaattcatggggaaaatgtaggatttcagcctttgatcacaggattatggcacaggaaagttagaggaaat
tttccttacaaactcatttcacaggaaaacataggaaaagaaaacatccagtaccctaagctctttgttcc
atctctttttttccatcatgtgtgcgtaggattgagataaatgacagacctatgcatcattgttgttctttt
ggaagaaaataagatcaaagtgacatgtattaatacacttcctgacattatctttccagtgaaattcctat
accttttcaaaggcctagtaacacaactttcctatgttttgcaatcctctatttttacaattactatacat
ttctacaagaatcctacgttttttttattcctccattttcgattcctgtgatttaaaatggccctaaatta
atcaatcctgctggtatgcaacatcacccttactaaaatgtttgtaacatttttttttaacttgtaggcaat

FIG. 13I atgaagctcaagcatgatcatcggattcgttttgtcttcatgcattagtcctaggttcagcaagttgaca
taaagtccacggtaacaacttaactaattacagttaaaaaaattggatgagcgtactacgacagtctgac
agggatacatgtacatctcaagttcttaaccttcaattcagtgtcctctttttttcgcggatgcgtaaaa
gtattacacaacaatatattaatagaattacacgacgtaactgccagaggtcacacaaggaaaagctagag
ggagaaaaaaatataaagggaataaggactccaaaattggcaaatgaaaaagtgctattatcctcccaac
aagactcctagatgatcagtattggcgcttgaccagttgaccacacatgaccttacagcttgaccagttga
ccacacatgaccttacagcttgattgaatcgaacaccgcaggaacagacgagagagaaaaaaacataaaa
acccttgcttgagatcctttccttccaaaattgcgaggacactagcaacacaaagaaatcgaagcccttgc
ggagaggcttcgggagaagggctctagaagtcggccaccaattttaaagtgagctgccatgggcaggagcg
agggctgaacaatcggccagtaacaacacgtggtgccagatctatcgagcgaacacacaatcgtttcgctg
tcttaagctcctggcacagaagggggcaaaccgagtggctgctttcacgcctcaacggaagatcgacggtc
cagtagcgctgctggagcgcaagcaaaagaaagagtttacatttggatggtcctttggccgaccacaatag
attagcacatgcataagagtagaggcccagaaagaaagcatggtaataggagtttgtcgatcgctcgtcca
acgccagacaagccgatcctcttaacttgggtgagctggacgtgacgcacaagatcctataccaccgagaa
ttgccagatgacagggacagttagagtaccgcggatgtcgcgaaccaataatccaaagcatgctgatttaa
ttacaaactcctgtcccaagcatgcaccaataatccaatatagaattaaagtcgcctctgctcgatcaact
aactggccagcttgcctttttatataaacggttaatcaacctggtcttagatatcgaccaataaacaaagg
aattactaatagcaagtcgccgctaccttgcccctgctgcctcgttaccacacgaaatcacgaaggagaa
ggctgaagaatagcaacc

SEQ ID NO: 129 *Oryza sativa ssp japonica* v Nipponbare 3KB upstream from LOC Os11g32610, homolog of chalcone synthase (CHS) or c2 from *Zea mays* cacactcaagtcaccatgtgacatcctacatactcttctaaaccgttatgtgacactctaataaattagag
aaaatcttaaaaattatgagaaaaaaaatcaccatccgttataacttataaactggtgaatctattattt
ctaaccattagatatatctcaaggatctgtttccaataaaagaaatctcccctctatatatacatactcct
cctccctctcctattttatactccctacattctaaaatatttgacaccgttgactttttaaaaatgtttg
accgttcgtcttattcaaaaaatttaagtaattattaattcttttcctatcatttgatttattgttaaata
tacttttatatatgtatacatatagttttacacatttcacaaaagtaagtttttgaataagacgaacggtc
taatatatttaaaaaagtcaacggcgtcaaatatttagggaatgagggagtacctagcaaccccatctaaa
aaaacttaagtgatcataattgtttctaagttatataataaaccacaacgatgcagataaatcaaaacatt
gaataggttttcaacgtgtgtgctgcttgctttaatttggttatccaaataggctaacctattcttgctag
ggattatcaatgcaattagcatgaggtctgctacaaataagggtgtgcacgtgttttcatcctgctaagct
ctactagacgatttatctttttactggctaaacaacaagcaccctaaataatcatcaaatttgcaaacaca
tctaaatttagatccatggtgtctttaaaaaacttaatgattcaaccgtggtaaacttctacggaaaagaa
taatttctagggcatgtcatcctaattaccatttaaaaataaaaaaaatataaactaaaaaaaatacaaac
actcctatacttccacgtggtacgcctataaacactaccaaaccgccacatggtattataataaattggta
aaccatctattttttcaactattatatttatctttttttccttaaaaaaatcacaatccacatccatcgcct
ctctcccaccggcacaactatcctctccccactagcccacccttcacaccaccctacgcacgtaagtatac
atacatacactttctccgtctccaataattctttctctcaccttcctattttataaataacaattttaatt
ataaaaaaaaattatgaagaaaacaaatctaaccatcaattttcaattaaattggcggactcataatttga
tcaattttttatttaaataagtggagttataattttaacaattggatttaaagacataaataattcaaacag
atgaacgcattaaatctacctcaataaaaataaaatctcattaccaaataacaacgaaacattgaaaaaca
tgacaacgcatcttatatattcttgaatcgttttacatagtaaagatcgattaaacatgctctatagtact
cttaagtcaccacagtcaccacgtatgatattttaaaactttgaaaaaattgaaattcaaagaaaaaataa
agtatatatatctatccacttaatttgatgacacattatttttaactattagaatacctttctctttataa
aaaaacttaagccaccacatgtcatgtcttaaatatccttagaatgagaaaacaacaaatcataggttctc
acttagattatttacaaagattaaaaaaaacaatgtaccctccacctccctctccaatcacatgcacataa
cactattgcattgcgaaccctttctcatatctgattcgagttctatgctattcatttctctccagtctcct
ccctattttcagctactaaactaaagagataaacaaatattaaaaagaccataattttaagctacacttat
aattttattttatatatcatctaatcgattttagatgatggtttctttttcatataaggtcgccacatgtt
accccataaatcctcctaggccttttttaaaccgatgaacctattatttccaaccattagatctatctcata
ttaaaagacaagcgtgtattcataatacatcatcttccaaaataatatattgcacaactatatatcttcat
ccaatattattcacgctaggttgcatggagtctcacacacactctacatggaacgttcacatatggattct
caaactaaacaataatattaggctatattaacccatgcatttagtggagccacatatcccacccaattcat
ccgtcaataaacaatgacaacctatactcaattaaaaaaatcttacttttgaatttacacttaatttgcta
tttgctatacatgttttctaacacaaaatatgagtacctacttttttagatgatgaagaatattataaataa
ttgcttgtagggattaattaaatatggtatgttataaagataactaatagctaggttagaacattataaaa

FIG. 13J gcaatgctaatgaaaataatttatggagaaatcatatattgtagatgttcaacatagtctacgacacatgc
ccgcgcattcgcgcgagctatcttcctagttaaactaattacgtaattgaactaagtaaaactggattagt
ctccttccacgtctaaatcctagctccgtcactaatatcgctcctcgtgtctgaacacgtatacattgctt
tttataaaaaaaattacacagtacaacgcatatattgcttaacatgactctaattccactcctttcacat
gttaacatgtgtaataccatgtgaccgtgtgatgatcgatcgatgatcaccattggcatgtgcatcagcaa
aatctcgcacgcacgcacgcacgcgcattggtgtaagctatatatagcccctgatcatctgtgtgcatctt
acagtgcagaggagcaagcaattgcacatcactcgacagtccacacagtgcatataatcgatctctctgcg
atcgaccgcggctgcgcc

SEQ ID NO: 130 *Oryza sativa ssp japonica* **v Nipponbare 3KB upstream from LOC_Os07g11440, homolog of chalcone synthase (CHS) or c2 from *Zea mays*** tcgagatctgctccctctaattcctctacgccctctcccatcaccgatgcgcctctcagctggcaggcttcgcaaggccatcgtcaatcatagc
caacgacatgatcaccgatgctgacaaggctcggcaggcgctgccgattgctacggcctcctgcgtactcaggagcggtggattcaccgc
ctgttggtgggctctaggcacccgctgacaacttcaacctccagtggacttgggagtggcagatctgctgccgatagggtttgttaaacgatg
acgacaattgtggtctcctaaaggctcataagcaaccggtccaccggaggttgcctcaccctgccttatcccctttcttccttcgcatccacca
caccactaccacctctagctagatccagatcaaggtacatggcaggagcgctgagatggaggctgatgatcaaggcagtgggagaaagg
ggccaatgctgagctcgataacggcaagctttgctgcagccttgacctatgttcacttcgcttttatttcgctatgagataaatgtgaatttgttat
ggaattgcgttatatatgtgttgagcattgttatggtgatgtggaagtttactctcgactttggatttgcggtgtgtctgatattgatttgcagtggtg
tggatccgtagaaatgggacgagcaggaaatggcactgcatctggatatttttgagctatattatttgttttcaccgaaaatcacctcccaagtt
gctcggcttaacctaaccacctgcaaaaattgatttttacatgtggttatggcaatttggtagaggcgcaggtggctcatccgcatgtacacata
tttttccgcctataagtccatcgaaattttgactaattattaatcttttagaaaaattattttgaaataaaccgtgtaaaaatcttcagcaaaaataaca
tgagctcaggggccgtatggcattgaggtccaatagctcagcatcgtccctgatcgatgccgctaaccccgtcaggcgttattcagcttaga
gggcgattggagaggattaaggggggaataattccagactataataggtgtgaaataaatcccctccaattcctctctcataaggattaaccga
ataaggcctcacggtgatgcgcgagaagatgcaatggattgaccaccataacgcttggcgctgacctcgtatactccaaaaagaagagtgg
gtacgtcatgtacatccacaagttgacaagttgtgtggtggttacattgttttgctatatatcttatgcacacatatcacctaagtttgaatctcacgt
acgatggttaggtggttaggttcttaatttgaatggttagttattactagcgcgcgcgcacaaacactgaaaaatataatttttttaaattgtgagtgt
atatttagtcataagaatttgattcataccaaagcaataaatcaacttaaattaaactttattttacaatccattattacatacctaagtaattatatata
agtttagatcctatatacctacaatcaaaatttaacaaaaagatattcaaatttagttcaaacttgtttgaactagctagtaaataagttaatgttcat
aactaaacatttttttaaaaaaatcagactcattagcattaggtacatactcaatttttaatcatgttggccgggccccatgaagccccagttaattt
taatatatatatatatatatatatatatatataaagttaaatttgagttgttttgttgctaggtataggtatgaatcgaatacttataactagatatatagaa
aattttgaaaaatttagacgaatttgtgtatttcatattatggtgcccgggtgcccatatatgtcctatgtgtgtgtatgtaaaccggagttgctcaa
agtatatatactataaaaagagtgtgctaaatatattcaattaaaaaagaaacacttatcatagaaatgataatttcataggatcaactccgacac
aataattttctcatcaatttaagattccatggttcaatataattatgctttagattttatatatgttctgtgaggataattagaagaaaatcgcgaagtg
agtatagctcaacttgttaggtttttttggtagaaccaacccacccggttttatgtcctagactttgatacgcgggtgtttgtgattacggctaacta
ttgttgtagtagtagccaacgtacctgtctacatcgaggcacttgtggtcaatttgtaaatcccaacatatgtcgtctcagtctttcaaaggtgctc
gtagaggtagggtagtgtgcgtgtgtgctcgtaggggtcattgtgcgcatattatgagcgtgtgcatttgtactgtttttcttaaaaaaatcataa
ctcgttaataagatagcaggttcataatatatagaatgaaataatatgtttttttccaaaaaaggtcatccacgcacaaaaatgcatatgttaggc
tagcaaaattttaagaaactttaaataagatgtccacgtttgtgtgcgcatgcttccttcctgtttagttagattacaaatatatttagttcaagaatta
caccaatatattcgtatatatattaaagtactggtttttgcagctgaaaagaatatatcttatgagatcgaattgaaacttttgttcaaacttcaatga
atcttaattaaacacgttttcagaaaaaaaaatagtatcgtcacacaaattcaacggagatatattattgttaggaaaattggaaaagggtacaa
cgttctggcagacaaacgtgcagctcacccctataaataacttagctgcgaccatttgttcgaatcagccgggctgagaggcagcagctagc
tagcgcacatgcattttcgttgtggcgaacaagctagctgctagtaccctcagttataccaagatatacactacattcctagctaggtacgatta
gccgccggtgagtggggag

SEQ ID NO: 131 *Oryza sativa ssp japonica* v Nipponbare 3KB upstream from LOC_Os01g44260,

FIG. 13K

**homolog of dihydroflavonol reductase (DFR) or anthocyaninless1 (a1) from *Zea mays*** tgacaataaaaaaggagtggtgggaaggtgacaatggtgtaacaaatttttataaactataaaaatgaaacccaaggaggaccaagtttgatttttaagaatcccaatgaca
gtaaaaataaatgtgattggtgggccataaaggagttaggtgacagcggttgacgatacttctaaaatctataaaagggaaacccaagataatcaggtttgaatcttagaat
cctaacgacattaaataggcggggtgataggtgggttgtaaagagtcacagtggttgacgagacttttaaaaacaataaaaatggaacaatgatgaccaggttcaaattta
aaaatactactaataataaaaacgatgggtggcgggcaattggcgtggcttttaaaaacgatgatcagattcgatttttaaatactgtaaacaataaagaggaggaacaac
gggcaggccatcaaggagtagggtgatggcggttgacataactactatagattataaaaataaaaccccaatgctaattagatttgatttattctattgaaaaaaaaaatgagt
gagaggcggaccgtaggagtagagtaatgacggttaaaaactataagaacgaaacagtgatcgataatgtttgatttttaaagtaccaagaacaattaatagaaatggtag
ccagccaggcaagcaaccggaggagcgacaaaggagaggggtggcgtctgatgcgacttttaaaactataatattataaagttgataataataatgttaatttaaaaaatat
catgtggaaatgagttaaccttttacaaattttcaagaaaataaagggtaaaaaattagatgattttatataagatacttagccgtgcaaatatgtgggccaccctactagtttttc
gctgaatctgaataattttgaacggtaaaaaaaatccggttcattctgtctcctctaccccccttcaaacgagaaccggccggtgtgcacgtgcacgtagctcacacctaccta
tcaaaacgctggtcattctgttctagcttgttagtagtacaagtgtgtctatgagagaatccattatatgccaaaaaaaaaacataagcacagacgaaattatagcgttatactt
catctatcttttatgtacacatttacatacaaaagttaatttattttgagacgaagggagtgattaataacaatatttattaacaaagtagaacaatatatttaggggaaaaattgtat
actaaaacaaatcctatattattattattattatttattaattgtgtaaaaatataattggatatgtaaaaatgggagtacacatgtgtgagcatctctaagtgacgaggaaaagga
atagcagaggacaagccaagggtcaagtagggtaatggcagctagagagactttgaaaaattataaaatagaacactaatgatgatcacgttcgatttttttaatttgcaatg
acaataaaaaaggagtggtggaaaggtgacaatggtgtaacagattttgtataaactataaaaataacccaaagaaggccaagtttaaattttaagaatcccaattgcaata
aaaatatgtgcgattggcgggccataaagttgttaggtgatagcggttgacgatacttccaaaatctataaaagggaaacctaagttaatcaggtttgaatcttaaaatcctaa
caacattaaagaggcgaggtgataggcgggctgtaaagagtcacagtggttgacgagacttttaaaaataataaaaacggaacaacgacgaccaggttcaaatttaaaa
atgctactaataataaaaacgatgggtggcgggtgagacgtaaaggagtagagtggcggcagttagcggggcttttaaaaacgatgatcagattggatttttaaatgcca
tcgacaataaagaggaggagcaacaggcaagccatcaaggagtagggtgatggtggttgacaggacttctatagattataaaaataaaaccccaataataatcagatttg
atttattctattgacaaaaaaaagatgagtgagagacggaccgtaaaggagcagagtaatgatggttaaaaactataagaacgaaacagtgatggtttgatttttaaggtac
caagaacaatcaatagaaatggtggccagccaggcaagcagctggaggagctacaaggagaggggtggcgcccaatgcgacttttaaaactataaaattataaagttg
gtaatgataatgttaattttaaaaaatatcatgtggaaatgagttgaccttttacaaattttcaagaaaataaagggtaaaaaattagatgattttatatcggtgctagatgtacaa
atgcgtgggccaacctactagtttttggctgaatctgaacaattttgaacggtccaaaaaaaccggttcattctgtctcctttgcctgtcgtcacgctgtcatcacgctgcggat
gcagcgtactaaacgcaccggcctttcaaacaagaaccggccggtgtgcaggtgcacgtagctcaaacctacctatcaaaacgctggtcattctgtctactccatccgac
cccaaaaaaaaaagacaaaccctgattttcgtgtctaacgtttgaccgtccgtcttatttaagaaaattatgaaaaaaaattaaaaaaacaagtcacacataaaatattaatcat
gttttatcatctaacaataatgaaaatacgaattataaaaaaatttcatataagacggacagtcaaagttggacacggaaacctagagtaacttgttaggcagtacaagtgtgt
gtagctatactccccctgtcctgtaccagcttatatatataggcgagccaacgagcgagagccatcaccaagtgcaaggtagctatcatatattctgcgaatccaacacaag
caccgcggcgtagtactactacttgcgcgcgcgtgttagattcgcgtgcgaatccaacacaagcagatcgatcacgcacggtacgccatgggcgaggcggtgaaggg
gccagtggtggtgacgggcgcgtcgggcttcgtcggctcatggctcgtcatgaagctcctccaggccggctacaccgtccgcgccacagtgcgcgacccctgtgagct
ctctcatcgtgcactctagctctctcctcgtagtttactgactccaattatatatgccgcttgcttgactctgacaagtgtacgtgttgttgttgttgttttcagctaacgttgggaag
acgaagccgttgctggagctggcggggtagaaggagaggctgacgctgtggaaggccgacctgggcgaggaaggcagcttcgacgcggcgatcaggggttgcac
gggcgtgttccacgtcgcgacgcccatggacttcgagtccgaggacccggagaacgaggtggtcaagcccaccgtggaagggatgctgagcatcatgcgggcctgc
agggacgccggcaccgtcaagcgcatcgtcttcacctcctccgccgggaccgtcaacatcgaggagcggcagcgcccctcctacgaccacgacgactggagcgaca
tcgacttctgccgccgcgtcaagatgaccggatgggtatgtatcgaaaatgttgtcgtgggttaggaacaacgatcctccacgtacataaaacgaaacgataagttaacat
gagcatgattaatattagtatggtataattgatatttgtttaaaaatctaaaaaatattaatatgatttttaaataactattttatagaatttttttatgaaaacacaaggaaacagaaa
ttgagaaatagtacgttcaaactcacccttaagcaactgaaactagcttagcacgtgaatttggccgtgtgagtcatatgatatga

FIG. 13L aggtcggggatgtttttttttttttgcggggatgtaattaactaattatgtaaaccatttctattgtctaaaagaagttagcaagtgataattgtggtggcag

SEQ ID NO: 132 *Oryza sativa ssp japonica* v Nipponbare 3KB upstream from LOC_Os06g46920, homolog of dihydroflavonol reductase (DFR) or anthocyaninless1 (a1) from *Zea mays* gaaatggtctgtctcactagagggcacatctttcagaaaaataatcctctgcttgaaaggctgaatattgggtatccatcgcttataccaccataggaaaaaaataatattcaa
gtttaaactgaaacataacaggccacatcccatggtagacaacacaatttctaacttctgaattcactcagttgatatactcaaacttgagatttcaagcattcattaattcatata
aaccctccttatactagccaactaggttcaactataccacaaaatccttgagaccttttctctaaaaaaaatataccacaaaattttgacacaacgttggttgttggctagttgag
gtcctgagcctgaactcctgaaggcaacaacagtacagtgaggcgatgtagacatcaccattgcaatgccacgctgttggtgagctctaaaatcctaaatctcagtgcaag
ctggcatttctacttttccagcgaatcataagagcagagcaaacataaaggaatgcgaaaaatgagaatcagggttgggagtcggcacaaaccccagccggcgcggcg
gcgaaggtggagagcgggtggccccagaagctgctggtgctcgccgcccccggcgcagagatggagagggacgccatcgcgccctgcaacgccgccaccccgg
ccatcttcgtctcctcccctcctcttcctccctcgctcgctcaaaccgcagagaagcagcagaggataacgaacgccttcgtgtgctcgcggacaggataatggcgagcg
cttttctacatgacaaatgggcctctaggccgaatggattggcccacttgtaagactcataaaggcctaatgaaaggcctatcgtaatccagcccaactacaacggacctta
cggcccaagtcagccgcgatcccgttcaggctcaaatatagcgggcctcacgtaagccgcaatcccgtctcgacccaacaagaacaggtcgcacctacacagataaaa
tctattgtacatttctcatctctgctcctgattgaattacctccctcaaccgcaaaatggaggaaaatcggtcttattgtttggttatgcttatatttatgagccaaaatttgaatttga
gaacttagttttgaatttgctttttgtttttttaaaatgcttatattttacaacatttgctttaagttattatggacatatataaacattttactcataaataaatttttatttgctaataaacg
attcgaataagcgaaaaccgtagcagatcaacccttagatggtttgtagggtggttcctgttgacgtggcaggctgactcgcagagaacatgagggaggcaaaatagact
tactatcacgcacgtcagcaatccggttaaggcccaaatgtcgtgggccgctcgtcgtccgcaatcccgtttgtggtcaagtaacgtgggccgaacgtcctgggttgatat
gggccgacacccgttttcggataaggcccagcccagcatacgctcgtcgtcttcctcgttgcgttgcgtggcttcgtctccacacgcatcatcaccacgccacgcgccgc
gagatgctgcttcggcgggggcgcccaggcgtggcgcctcccggattccggcggcttcgacgtcgccggcgacgcgcgcaagccaagcgacagttgcggaggca
agcaacccccccaagttccgtcccttttgcgcttttctgggacccatttcctctctcttttgggggggcgctttcgcggtgacgacgctgccgatgcgcgtacgcctgaggagtt
cttccccatcacgccgcgtgggggatcgggacgtcgccatttccgctgccgttttcttctctttgggggggttgcaatctcgcgtttcatttgatagggttgggcgtgggcggt
ggggaatggggatgggtaggtagatggcaccgatgtgaatcggacgacttcgaatcgaagccttccgatccatgtgaggaggttgaggaaccaacctaatttcgaatcg
aagaactcttggtttctctacctaaaaccaaatagcatagtgacagtggtcgttatactatgaattccaagctttttgaccgaagatttcgaatcatcgagcatctttggccaag
ctattctaacacggttgactcagaagtctacgtttctatgcattgtgtatttgagtgttagttactatatttcgtgataaacaaaactgttgactcaaaagtctacgtttatatgcatt
gtgtatttgtgtgttactgtatttagtgataaaccttaggtgtacatgtgagggatttcatggataacacgtgcactacattcttgcctgttccactggtcaccatcagcaaatcgc
tcctgtccctttcgtgtggctatcactggagctattcaattcttgaaaggctctgccgtgcaagcaaaccgttttctttccaatgggataagtgtgtgactgtgctataatctcag
gataaattcatcactaaatcgttgctatcagttttggtttatccactcattaaatcaatgcaacaaatgtggtgatcaataattagtagtacttgtttgttggtatgccgtgctgcca
aactagttggataacaaagattcctattatattggggttaaccactgtattttcctaatcataattttttaggctccttattgtcattatcacttagcatcattgcataagagaaaaaa
aagggggggtcaatactgcaggatggtattttaggaaggaaatgtgttatcgtgatattaacacagcctttcttccatgttgcttgcactcctctcaaactggtgtagcttcctaa
agactggctcagttacacaatttttattcttaaatgctggaatcctgggaaatccttaatgcgcctggaattgttgcactcaagtaaagctttagtttgctacacccgtgacacttt
cagagttggacatgtcaaagtttccttccctttttgataaaatgtccagtgtgatag

SEQ ID NO: 133 *Oryza sativa ssp japonica* v Nipponbare 3KB upstream from LOC_Os04g56700, homolog of flavanone 3-hydroxylase (F3H) from *Arabidopsis thaliana* gtgccctttaaggtctcatgatgtcccagtctgcaatgggcactgcaagaaggctacaaccaacggtgcaa
tttcacccaaatcagtaccagctccctctaatatggtttctgctgttagctcaatgctcttatcccttgga
gaggatcccttcaggaaagaacttgtaggtactcctcagcgttacgtgcaatggctgatgaagttcagagc
atgtaacctagatgtgaagctgaatggctttacactcaataatttgagtgtataccagagtccagctggag
atgctgctgaccatcgagcaatccattctgagctgcatttgccatttttgtgcgcagtgcgagcaccatctt
ctgccgttctatggagtagtgcatattggctaccttgacggcggagatggtgaagtgattgatcgatctca

FIG. 13M ttttgtgcgcagtgcgagcaccatcttctgccgttctatggagtagtgcatattggctaccttgacggcggagatgg
tgaagtgattgatcgatctcattttcaggccttggttcattttatggatgcaagcttcaggttcaagagagaatga
caaggcagatagctgaagcagtttattctgtttcgcattgtggggccatagttgttgtagaagctaaccacatttgc
atgatatcaaggggaatagagaaaatcaggagtagcactgcaacgattgcagttctgggtcagtttttgacggaccc
ttctgccaaggcacgctttctgcagaacgtagtagatacaactggtttggcagtatgaatcacttagatcatacaaa
ctagaatatcagctaagaatacatgattcagagaagtaccgcagccactttaatatggttgaaagttggtacccagt
tcggtgtgttaccggcaaacattgcccattggttcgagaccggggctggtgccacgtctctctggaaggaaaatgtc
catttgcttggtgagggaaaattttcgtcacatggaagattatattgaagctgtcactggaagcaccaaaagggttt
ggttttctctgtgttgtaccattttcatttgcacggcacttgaaatctatactgcactaattgcagatgtgccgag
aaagatatatacacagaagcaatgtttgtcacatcattttcactgtagcaaattttgatgagatcaatggctccag
ctcctgtgaaatgaatgtgattgttctcttgagtgttgacccgccaatgcactcgctgtcttcttctctcttttttt
cctgagggcatcatatgcatattttggctcgtggggtttgcaccaactggcattttgcccttttggtgcttgtaga
ttgcagatacgcggggctagcgatttactggtattttgacgggctgttgcgacaggttggtggagcacgcgacgtct
ccctccccgccgggagaacgcgcgccacggctacccgcccgctcaccaccaatcgttcaaagcggccgcgcgaacta
agcagcgggaccggatcttacatcactgttcactcatcgcgtgccatgcagacaaacgagacgtggtactatactac
ctcattcctaaccgatcccagtcgaacagttgttagttcatggtagcatgatgtgatcatcccagaagagtgtgttt
ttcctcgcgtagttgcggataatgcttctcctcgaacgtctgaagtaaggagaaaagtcggacaggcagcctctgac
acacgtacacctattcaagactatatctctatctccaaccatataacatacactttaacgatatttaaaacgaatt
tttttcttaaattacttagctgatctacaattcgatcacaccgttatattcgttataattaaatctttacaacaaga
tatcgcttgattatattccgatacaaaataatcatatgttttaatccattaacatttttttcttacgtgataggga
catgtttcaatatgtgtcttcagcgtgtttcacaaaattcactcacaaaactaactgttactactctctcctctctc
tctccacctcatgcatgcatgcatgcattttaactagtttcaaaacgatttttctcttaaactaattattcaaccta
cgatctgatcacaccgttgtattctttgtaattaaatctttaaaacaagatatcgcatgattatattttgatgaaag
aaaaacatatgtttcgatccattaacattggttgttttatatgtgatagtgatatgtttcaacgtgtatcttcatca
tgtttcataaacttttaaatgtttcagttgctgatattttgtttcaccatatataacttgatgtttcacttgtta
gttaactggaacatttgactgaccgatttttttttgcatgctgcatacacaggtggtgtgatgacgtgtaaacagtc
gggcgtccgatatttggtggaatatcggacgtccgatgcggagtcatctcccgtagttgcccgttgccaatttttt
ctacagtaactacaacttctctgatatggacaaaaatccaaactatttaggtgagtttctgtttatggaagaagctg
cagctgttaaaaactctcccaaacatatccaaagatatttcctacgctcatctctaggatatttgtaggtattgtag
ggctagtttagctcccatagtcccattgaagcgtacgtgcacacaaccaaaaatgtttgctggagcagtggagagca
cggaatgttagatagcacctacccttcaccgtcaaatcggaactacctaagcttatcgatcgggtgatcagttatgc
taaaggcctgcagctagctagagaacacaaacgcatcgatgagtagtagttggaacgtgccactgcccactgcacga
ctttagttcttcgaccctgtgtgagtagtagcgaacccagcctctctatgtagcgtgctccacccgtacagtacgcc
cctccctatatacggatgatcacgcagtacacgctctccctatcgtaaaacccgcgaaaaccacaaccgaaacgcaa
gggtcgatccatccacgcctatcgcgcgcgcgtgcatcgggtcgatcgatcgag

SEQ ID NO: 134 *Oryza sativa ssp japonica* **v Nipponbare 3KB upstream from LOC Os10g17260, homolog of flavonoid 3'-hydroxylase (F3'H) from *Arabidopsis thaliana*** ttggcgtactcgttggcttttcaaacataagcttgactgtcctgggaggcttacgcccaaacttgccgactagttc
ttcgtggcgaatccctttggtgaacgcggcgatgatgacgtcgtcggtgatgtcggagatcttgttacgttgttcag
aaaatcgccggatgtaatctcgaagggattctccggacttctgaatgacgttgtagagatcatattgtgtgccggga
cgctcgaaggtgccttggaagttggcgatgaagtggtcgcgtagttcggcccaagatccaattgtaccacggggcaa
tccatggagccaagatcgggcggaatccgctaaagccactggtaaatagttcgccatggccttgctgtctcctcctg
ctgcgcggatcgcgagaccgtagacggtaagccacgattcggggttagtggtgccgtcgtacttctctattccagtc
ggcttgaagccggctggccaatccactcgacgcaggtcgtcggtgaaggctgctactccgtcaaggtcgtcgtcgtg
gctgtccggcgagtgatggtagcctcgagctgctcggcgctgtatgattgtgtcgcgaagatcgatggggcggcgac
gaggtggtgagcgaggccgttccactcggcgctccctatgaaggtcgggaggtgagtgaacagaccgctcgtcgtga
cccctgctcctgcggttggatcctgcgccggtgatgctgaggcttggatgacggtagtcatgagatcggaagtgggg
aactcggctgccagtcggcgtgtggacgctttcggagttaactgggaccgaagccgcaatcatggtcttcgtctggt
tcaagatgttgacgacgtggtcggattgattgagctcgttttggttgaggagggtgtcgagaagggtgatcgcggca
accgcattctgttgaggggtgcggaaaaccggtgtcccttcgacatcttgctggccgatgagatcacgcgctcggcg
ccctgcttccaaagctcgctgacgtcgatcctcagcctccttcgcggtccgctcacggtcctgctgctcacgccgta
gccgttcttgttcttgtgcttgatgctcctcctctagtcggcgacgttcttcggtctcccgggcttggcgttgctcc
tccgtctcattattggccatgaaaacgccaaagtagagaggggtgtagttgt

FIG. 13N catctaggcttccgtcgaagtcgtcgaagtcgtcgaagtcgttgtagcgagaactaaattcgtcgtactccacaatg
tcagtaggacgtgagtcgacggtgggagagctgttgtagtcatccagctgatccgtcgaaaccgtgccgagtggttg
gaggatgacgccgacttccctgaagctaggcgaaatcggtgttgaagccgacttccgcctaggcctacgggatgaag
acgctgtcgtggtggagacggccgctaaatcgtcggggagcttcatcaggactggtgggtaagccccatcatcttga
tctggtgtcgttggagaagatgcgatctcggccgagtggtttgaagccgactcggtcgagatggtcttgaagtagct
ttcagccgcgttcgggaatccaaacgggaccgaaatccggttctctcccgactggtctgattccgagtcgaggagag
aaatcttgccgaagttgttggtgacgaagtcgaggctgccgaaccgaaacgtctgcccgggtgggaagacgaggtcg
tcgatgccggagatggaacccattgcactgatcggcgaaaagcttgacgcttcccctacctggcgcgccaactgtcg
aaactagatttcggcaataataaaaaggggtggctatcaagctaggaaagtgtatgggtttggagacaaaaagatt
tatacaggttcaggccttcttataaaagaagtaataccctactcctgtccggggatgaatccgccgagtgtgttatt
gattgtatgatttggagaaaatccaacaactgcccctagaggcgcccggacccccttatatataggaaggagtccg
ggttacaaaagataatctatatccctaacggaatacacagatacagattaaatacagtcgtgaccgactaagtctta
agttgtttccttgatatacaagtcaggaaacaaacccaggatacacataagatattctatctatattcggtatccta
tattcagtccaaatatcatcgccgtgtagatatgggatatccataatctccacatgatgtgatccgtaactttggtc
acattgccacgtaagataacatttgatatatgaagacagttaataatgcatattttgtatcgaatcatagggtagct
cctatatatttcagctctttggtcctttgacatctgatgctttagtttaggggaaaaaatcaagattaactataact
gactaatcaatatgtcaatgttgctaaaaaaacaaaatcaaaggaaataacttaatttttttaatgaaatggataag
tttttaataacatggatttacttaaatattaccgtagcgttagcgcggataaattactagtatacgtaaaaagaat
aacatcatgatttatttagaaagggtaaaaacggatggagtattgaatttgttgatatccgggacaatctcgtgtca
atgatgaaatttctttgataaaaaaggtgaaagttgcaccactacatgctgtgacatatttctttactcatttga
aacaagttgatttctatgatatgtgccaagtagtcgagagccaaataaaataaaattattagtgattgcaacaggtg
ggctggttttgcgtcatttgaccagtacacagccacacatgccatgaggagaaaaggaatcaagcaaacaacctttg
gtacctgttcggtggtaggtacgaagggtagtttgttagctgcacagcacgcggggtaccgtgtatatatcaacta
cccagtccgcgttttcctctct

SEQ ID NO: 135 *Oryza sativa ssp japonica* v Nipponbare 3KB upstream from LOC_Os03g03040, homolog of flavanone 3-hydroxylase (F3H) from *Arabidopsis thaliana* gccgtcgtcatcaacccgacccgccactccgcgcgctagcttccaagggacggaggcagagccctcctc
cctctgccgcgtcgccccgctccctcctcctttcccaaagaggcaaggggcaagcccccttctctccc
tcctttccctttttcctcccgccggcgtcatcctccctccgccctgtcgccgatttggccgctagccgg
agcgccagctcgctggcttgaccgtccaaagtcggttccccctctcccaaaccgtcattgccatcctataa
gcccaggcgccctccctctcttctcctctcgttgtcccatcgcctccactccattgtcgccgcctcccgcg
ctcgttcgccgtcgccgtttgtcgtcgcgcgtgtcggaggagccggcacgagcgaggacgcggaaggga
ctccgggcgcgccctcttcttcctcttccccggcccgaggccggagagatcactcccgtgccgtcggccca
tcgtcactgcgcccgtcccgcacggtagcgcatctccctattctccctcctcgttccatccccttccctt
agactcgggtagtagcacgagtagcctccccgtagctagctggcgccgccccgactgctgccgtcgctcgc
cgtgtgctcgccgccgtcgccgcccgagctcggaagcgcctctcgtcgccggcctccctcgatgcgttcct
cctaatccggcgcaagggacggattccgtagccgcgtagatgctctcgccgccgggaatcggcccctcgt
gacctcgtcgccgttcccctcttccctccccgccggttgccgccgccgcaatccgccgccgacgcactccc
tccggcgaatccaagccgttggctcgtctccctcgtctcgtgcaaccacccggtgtgctcgctttcgcct
gtatcgccgtggttcgctccgccgcccgccgctgtcgtccgccgtccgttccggccggcgtcgtcgtctac
ctcccgccggcccgcgtggctgccacttaggcgccatgtcggcgccacctcggccgcgaccggatcggctg
acccggccagccgctccctccgttcccccccgtgcgcatggtccgcggtgagccgtgaggctgcgcgtgg
gcccgccgcaccgcatcttccgcgaaccgcgcgcgtgcaccgcgtccctccccaaaccctagcgcgcgcc
gcgtgcgcgttccgcacggtgaaccgtgtcaccgacaagcgggtcccacccgggacccacgcgggatggacc
cggcccacccggctctctctcccctccccgcccgcgcgcgcgctttgggccgccttcttgggccggccggcc
catttagctcggccgagccgcccctttttctctcgggccgcgccctagccgcccgagggaagtctacttccc
ctccctcttcctttttctttttcaaaaaggatttaaataaatcctttttcctttagaccaaaaatccaataa
tcttagaaattcaatatcttcccaaccgtaaatccgtttgactccgttcaacttccaaaattcctcaaatc
tcgagatctatctaatggcacgcttagaggtcattaatagggctttattttcgccgtttgttgagttgtcc
cgttttgcgtgtagtttcggagcccgaagacccgcagtgcgaggatttcgaggatcaagctcaagatctag
agcaaggcaagccaccttgaacatcttgagcctatatccgaacttaattatgttgcttgaaaaaaatatt
atgcattgataggatcgcacttaatttgcttgtcccgtctgcaaggcagattggcgaacctacctaatttg
ttgcatctgatccttcctttgttaattgttatacccatgttcccttgtaacccatctagttgcgcctcgatat
tcgtgcactctatgcgagtatcgacggtcgccttcaaacttaaatctgagtaacttcttgggtaaaactt

FIG. 13O gggttttacaaaagacttggaaaacccgacacctgggtcggtgcttgcgaactaaatgaatttccaaaacc
acggaccggggaacgtaccgggtgtacggtttcccgctcttgcacttaaggaccgtttccttggaatttca
tccgaacataagacaagtacgaccacatgggtggaatgggacacccctggctgagtaactagtttatcagg
ggagccttgatgccgagagacatgtggattcgccggggtggtgtcggggaggacccctgggcttcctggca
cagtatggtctgggacctaacctgttgttggtctgggacccctctcgtcggcatatggtaaacctgtgtcg
gctttggaaatgccttgtcatgaaagcttggagatctcccgacgtggctgatccccacgggttgggtgatc
cgggttagtaatgtcgtgtgggtaaagtgtacccctctgcagaggttaacaaactgttcgaacagccgtg
cccatggtcatggcggatgtgaggtgattcctagcgtagttttgtttgactactgccttgtgaaattgct
gttgtgaaaaggggaatcgatgtttggaaaatctgcagctgatgggatcagctaggcccgggtggccgttt
gaaagttgttggcccgggtggccgtttgaaagttgatggccaggtgccaatcttgaacaattctaaagact
gatacattgcacatactccgaccggacgagacgcactgtctcatccgtgtcgtttgagaagcactcactta
gttgttttcagaaaagagttcaaataaaatcaattgcaaaaacaacagcctttccttgaagcctgcattaa
acacttatttcccatggcttgctgagtactcccgtactcacccttgctctatataaataatccccccagt
tgctgaagaagatgaagcggatcccgctgacgaggagttcttccaggagcaaaccggctacgatgagtttt

SEQ ID NO: 136 ***Oryza sativa ssp japonica* v Nipponbare 3KB upstream from LOC_Os08g37450, homolog of flavonol synthase (FLS) from *Arabidopsis thaliana*** cagtgaggaggagaatgaggagtgatgaaccaatttctggtttgtgcggtcaaaaggagagggaggagaag
aacagtaggggagggggaggaggaggagggagggccacaatgggtaaatcacttgggaattcatgaacca
aatacatgaacttttagaaataagaacaaccttactcagttaatgagttgcttggttggcctactcaatga
aaacattattaaaaccactccataagatatattgtcaccaacttcttattgatagcaatcaaagaaattga
tgaatagcttctattccgataatatcaacgacatgtatataaaataaagttgttactcccagtatattgcc
agcaaccatctttctctaagcgcacacacacctttttctgagcctataggattgaaaagaccaaaacgttgg
ggttgctatttggcgctcacgtgccaacaatagagctggtgtgcgcgccatctggcgcccccacgcacac
attttcatttcttttttttttttgcaatctttttccctattttggcgcccctcccctcgcgcgtattttcct
tttttcctgcgtttttttcccgattaaaaaatcgttaacacacgtgttttcgaatctcgatatgaaagtttt
ccaatctgaagaaagtttcaaatctagagttgaaagttttcaaattttgacttgaaagttttcaaacctga
gttgaaagtttcaaatttgagttaaaagtttttcaaatttgagataaaaagttgaaagttttcaaacttta
acttaaaagaattcaaatttcgagtgagagttttcaaagttagagttgaaagtttttaaaatttaatttca
aagtttaaattttgagttgaaattttcaaaatttcagtttagagtttcaagttgtaagttgatattcttaa
aatttaggtatggctttttttaagaaaaaaaatagaaagtttttttcacgtatagatttcttctaagtttca
acctttagggaaaaaaaaggaaaatcttaccttaatttctattattatgtaaaacatcatcagccctttag
tacagattaaaggcccattcctgtttgtgggccatgaaattagtacataatccccatccggaataagttca
ctttgagttccttaaaagtgaccagaatctaatccatgaccctaaaccgtaataccggatatctcgacccc
tcaactattaaaatcggtacaatttgactccctcggcagttttggatggtggtttcgctaacatggcgtct
acgtggcagtattgactaggtcttcgtcctatgtggcgttgacgtggcgcttaagtggcattagaattaaa
aatatatatgcgggcccatttgtcattcacaaaaagaaattgtgggcccactgacatgtggggcccacata
aatccctattcctcctccctctcttccttctttctctttctctccctttctcatcggttcttccccttcgg
ccggcggcgggcggtgagggccgaagctgcgctgggtgacgagagcgagcagctggcgggcggcgacgaat
ggctcgactgcgctggcgtgcacgggaggcggcagagagcagcgggccagctgcaagccgacagtgacgcc
ggcaagcaagcaggcaagtctgcaatttcattatcaccagcagatagatgctactgtagctttgatggggt
tactagctcagctcgggttcgagctcgtagaatgaattgacgagcacgtcgtcggcgagctccagcctgtc
gaactgcttcatcaccaagtcgaagtacgccgggtacgggccggggccgaccttaatgaaccacggcaagc
cctccagctccagcgccggcaagccgatcagcgcgatggcgccggcctccacggggatgtgtacacggccg
caccacgcgtggccgtacaccacgttgacggcgcacgactgcgtgaagaacgtgaacgccaccgccgctgc
ggcgcgccacggcgcgcgccaagaggaggaacgcgtcgtagaggaggacgcacacggggcgtccacctcca
ccccccggcggtggcagcggcctcgtcccggaggagctcgtccaacgtcaccgcccacgctgactcgaggc
gatggatgcggagccggcgaggagatgaaccccgatggagaggtcggggaggacgacgccagcagtggcga
ggtggaggtgccggcagtggcgaggtggaggcgccggcgacaggaactcatgacgccggcgtggccgcatg
ggggagagagagagaaggaagagagagagggaggatgaagaagggatgacgtacgggtcccagatatcagt
gggtcccgtatgtcagtggacccacaaaattttcttctgaataacaaatgggtcccatatgtatgtttta
atttttaatgccacccaaacgccatttcaacggcagacaaggtcaacattaccacatggacgccacgccag
caaaaccactcttcaaaactgccgagggagtcaagttgcaccggttttaacagtataggggtcaagatatc
tggtttatagttcagtggtatggattagattcggatcacttttaagggagtcaaagtgaacttattcctcc
ccatccacagatgtggtcaggcatgtattccggcccatccaagtatccacaacgaaatcgcggaaggaaaa
ccgaccgatctcgatatcacgcgccccacccccacgccgccaaaaatatctcaggaaaacaactgcaaatc
acaccacctgtacgctgtagtcctgtaccatgtggtcatgtctttgtcgtgcacggaggaagaaaaaaag

FIG. 13P gaaaaaaaaaccggcaaactttctcatttgccagtttttctcaccagcaacagcaaacgacggcagcttcc
tgcaccgaacgatccggcttacatatctccctccgaaagctcactttctcatttgccagtttgtttttctc
cctccacagtgcacagcc

SEQ ID NO: 137 *Oryza sativa ssp japonica* **v Nipponbare 3KB upstream from LOC Os10g25590, Homolog of ZmMRP3 (multi-drug resistance protein3) from *Zea mays*** atatatcatattcagttctatatattcgtttttttatgggacggagggagtatatggtatgacatgtggtgg
ttgatcaagagagttctacttatggagtagtggtggttgatcaagagagttctatttatgaagtaacgtta
ggggttgttcagaatgataccattttttaattataccattttttaaaaaagttgttaaaaaaatgtctacgt
ttagcttgttgccaattttggtaaatgcatgaaaaaaatcctattttagtaatatgtcaacttgctaaaat
ttaataaggtttattttgaaaacaatttgaacatgcccttagtaaatttatttactaaacactagtactaa
tcatgaactcggtcgatctatatacatatataatcacctaaagaactttacgtggaattgggaatcaagct
cgttggtgagtattagtttgattggcatactcaaatcgtcaaaattcaccatactttttttttactaacatg
tgactaataaaattaaaagccatatattagctagaagagagtaagtttacaacgagatacaaagctcatgt
aataatgaagaaatctataacacgtgatcaaacgataagtaacttgatcgaacatacttaactttatttat
ggtatggtcaatttgacacggatgttcgtatttataataaattattgtttagtaaaacagatatatttatc
agtaatatatatatacatatatatatattgactttgttaatatcacgataactcctagtaagaatgataga
gtgtatttgtcgatcaatttcaagacaccacgaatctcgcagagatgtgctaaactgctaataagaaaaac
cagtgcgcatttttcttttgtcttaaagaagagcagcgtttgaccagagtcacctattcacactaggtgact
agagcctgtttggtgcactaccacaatttaccttactgtaccacatctaaaatgagacatgtttgactaaa
ttagacgttcatttagttcgtgccatattaatgataaaatttcttcatcaggatgtgtgtcccatatatta
ttaacacattaaagcattgcaaacttgctttcttatagtaaaagtgcggctttgattttattagtcaggca
ggctagctaataagattatgggcctgttcgggggagctttagattctgagaaacagctgtttggtagccag
cttctgagaatctagaaaagctccgaaacccagcttctccagcttttggcttcttagttcattttttaaaa
tctgtaactacatattctcagaagttatgaattgtttggggcagtttctagcagaagcggcttttggaaa
agcccaaacagggcctatggcttgtttcggcaacgtgagtatgccaaccttggctcgcgcggacggagcaa
cgagtcgaacacgtgccgggcgcgccagtgaaacggatggcgcgcgagacgccaccagcggccacgccacg
gcaccggcacgtcggcgtcgtcgccacctgggacgaagtcgagagtcgagacatcgcacgttcgttcgcgc
gctgcccagcgcgcgccacccgcctcgccgcgccgcgccgcgacgcgacgcgacgcgcgccacctataata
aacaccacccgcgcgcgcgcgcgcccagcgcgtcgtctcgtcgtctccgctgttcgctcgcctcaacacac
gagtgcgacggcggcgaggaagaaggggggccacgattgggaaggtgtttggttggcgcaggaaggaggggga
aaaaaagaaaaagaaaagaaaagaaaagaagctgtttttggggagtcgtgctttggagagctgaaaaagaa
ggtgagtaaaaaggtttttttgatctttggttggttactgcttctcccgtgatctcctcctccttcttctcc
agtgcggctgctctgggctcgagggcatcgtgaatctacaacgtcaatcgcattgtcttgattaattccta
tgggagttcttggggatttgtcgaggggacgagatttttttaccccctaggcgatgcgattttggttgcgatt
tgttcttctcgtttggatcactggtccctgaatattttctttcctttcctcggtgaatgaatggtgttgac
tgttgaggtagctggttgatgaacactcatgcatacagtttttttttttttttttggtctctctcttcttc
tgctgacttattaagaagaaacattgcaatcttagactttattaccattttctctcttcttctgctgactt
atttaagtttcttgatttttttctttcggtgatatagtgatgtttgtgctgggtatagtgaaatttctgtgg
ttatcttgagcttctatagccacccgaaacactagtactaatcttgtgcagtacaagtccctatctagtcc
atgttcttcacttatttgctctgactagtttgctttgctgcaggtttaagctgtctgattcaacggacggt
gcaacagagattggacagatgggttccctcataagttagttgttttctcacaattctctcgtgcttgacag
ttgcatcattgattcatcattgagcccttttcacttttggactgtcacatttttttttttgagctttcctatt
aagggtgtgtttagatcccaaaaattttggccaaaaatatcacatcaaatgtgtcgtttggacacatgtat
agagcattaaaggtggacgaaaaaaaaactaattgcacaatttgcatgtaaattgcgagacgaatatttta
agcttaattgtgccatggtttgacaatgtgattctacagtaaatatttgctaatgacgaattaattaggct
taataaattcgtctcacagtttacatgcggaatctgtaatttgttttgtttaatacttcaaatgtgtgtcc
gtatgcttcaaaaataatttggccaaagaactaaacaccgcctaacattgatttttttggggggtaatgat
ttttcaggttcttgggcg

FIG. 13Q

Table 12-1. Example of Foreign Material and Low Milling Yield Effects on Rice Price and Net Profit

| Description | Sample 1 | Sample 2 |
|---|---|---|
| Sample weight, grams | 162 | 162 |
| Foreign material, grams | 0 | 12 |
| Head rice weight, grams | 94 | 88 |
| Brokens weight, grams | 18 | 18 |
| Milling yield percentage | 69/70 | 64/65 |
| Value per hundredweight[1] | $6.85 | $6.37 |
| Difference in price/cwt | $ 0.48 | |
| Value difference at 124 bu/A | $26.78 | |
| Value difference at 180 bu/A | $41.04 | |

[1]Prices based on long grain loan value of $10.71/cwt. for whole kernels and $5.36/cwt. for brokens.

Foreign Matter

Trash (leaves, stems, weed seed, etc.) often contains more moisture than the grain. Milling yield is lowered by the amount of foreign material in the rough rice sample. Foreign material contributes to heating on trucks and "fines" block air flow in bins. Consider cleaning rice that has high foreign material content. Another alternative is marketing rice with high foreign material content separate from cleaner rice to maximize income.

Rice Grades

Rice grades are U.S. No. 1 through 6 and sample grade, based on quality discount factors. These include weed seed, red rice, seed mixture, damaged kernels, chalky kernels, etc., shown in Table 12-2. Price discounts for milled rice in Table 12-3 are a general guide.

Table 12-3. Price Discount Estimates for USDA Grades of Milled Rice

| Grade | $/bushel |
|---|---|
| 1 | --- |
| 2 | .05 |
| 3 | .15 |
| 4 | .30 |
| 5 | .45 |
| 6 | .80 |
| Sample | 1.25 |

Table 12-2. Grades and Grade Requirements for the Classes of Rough Rice, USDA, 1996

| Grade | Maximum limits of: Seeds and heat-damaged kernels: Total (singly or combined) Number in 500 grams | Heat-damaged kernels and objectionable seeds Number in 500 grams | Heat-damaged kernels Number in 500 grams | Red rice and damaged kernels (singly or combined) Percent | Chalky kernels: In long grain rice Percent | In medium or short grain rice Percent | Other types[1] Percent | Color requirements |
|---|---|---|---|---|---|---|---|---|
| U.S. No. 1 | 4 | 3 | 1 | 0.5 | 1.0 | 2.0 | 1.0 | Shall be white or creamy. |
| U.S. No. 2 | 7 | 5 | 2 | 1.5 | 2.0 | 4.0 | 2.0 | May be slightly gray. |
| U.S. No. 3 | 10 | 8 | 5 | 2.5 | 4.0 | 6.0 | 3.0 | May be light gray. |
| U.S. No. 4 | 27 | 22 | 15 | 4.0 | 6.0 | 8.0 | 5.0 | May be gray or slightly rosy. |
| U.S. No. 5 | 37 | 32 | 25 | 6.0 | 10.0 | 10.0 | 10.0 | May be dark gray or rosy. |
| U.S. No. 6 | 75 | 75 | 75 | 15.0[2] | 15.0 | 15.0 | 10.0 | May be dark gray or rosy. |

U.S. Sample grade shall be rough rice which:

(a) Does not meet the requirements for any of the grades from U.S. No. 1 to U.S. No. 6, inclusive; or
(b) Contains more than 14.0 percent of moisture; or
(c) Is musty, or sour, or heating; or
(d) Has any commercially objectionable foreign odor; or
(e) Is otherwise of distinctly low quality.

[1]These limits do not apply to the class Mixed Rough Rice.
[2]Rice in grade U.S. No. 6 shall contain not more than 6.0 percent of damaged kernels.

FIG. 14

Table 6-3. Herbicide Ratings for Rice Weed Control

| HERBICIDES / WEEDS | Barnyardgrass | Crabgrass | Broadleaf Signalgrass (bracharia) | Fall Panicum | Flatsedges | Sprangletop (lighthead) (Christmastree grass) | Sprangletop (loosehead) (bearded sprangletop) | Red Rice | Nutsedge | Spikerush | Ammania (red stem) | Cocklebur | Dayflower | Ducksalad | Eclipta | False Pimpernel | Gooseweed | Northern Jointvetch (curly indigo) | Indian Jointvetch | Morningglory | Palmleaf Morningglory | Hemp Sesbania (coffeebean) | Smartweed | Water Hyssop | Groundcherry |
|---|---|---|---|---|---|---|---|---|---|---|---|---|---|---|---|---|---|---|---|---|---|---|---|---|---|
| Bolero - Water seeded | 8 | 7 | 7 | - | 7 | 8 | 8 | 8 | 3 | 5 | 3 | 0 | 6 | 6 | - | 5 | 6 | - | - | - | - | - | - | 5 | - |
| Ordram or RiceCue ppi - Water seeded | 7 | 7 | 6 | 6 | 8 | 5 | 5 | 8 | 3 | 5 | 0 | 0 | 3 | 0 | 2 | 2 | 2 | 0 | 0 | 0 | 0 | 2 | 5 | 2 | 0 |
| Facet pre/delayed pre | 9 | 9 | 9 | 9 | 5 | 0 | 0 | 0 | 0 | - | 3 | - | 5 | 3 | 8 | 3 | 3 | 7 | 7 | 7 | 7 | 6 | 0 | 6 | 0 |
| Command pre/delayed pre | 9 | 9 | 9 | - | 0 | 9 | 9 | - | 0 | - | - | - | - | 3 | - | - | - | 3 | 3 | 3 | 4 | 2 | - | - | - |
| Bolero delayed pre | 7 | 7 | 5 | 7 | 7 | 7 | 7 | 0 | 4 | 7 | 7 | 4 | 8 | 7 | 8 | 8 | 6 | 5 | 5 | 5 | 5 | 5 | 5 | 7 | 0 |
| Prowl delayed pre | 8 | 8 | 6 | 7 | 0 | 6 | 6 | 0 | 0 | 0 | 0 | 0 | 0 | 0 | 0 | 0 | 0 | 0 | 0 | 0 | 0 | 0 | 0 | 0 | 0 |
| Facet + Bolero delayed pre | 9 | 9 | 9 | 9 | 8 | 8 | 8 | 0 | 0 | 7 | 6 | - | 7 | 7 | 9 | 7 | 5 | 8 | 8 | 8 | 8 | 8 | 5 | 6 | 0 |
| Facet + Prowl delayed pre | 9 | 9 | 9 | 9 | 5 | 7 | 7 | 0 | 0 | - | 3 | 0 | 5 | 3 | 8 | 3 | 3 | 7 | 7 | 8 | 8 | 7 | 0 | 6 | 0 |
| Propanil early (weeds less than 2") | 9 | 9 | 9 | 9 | 9 | 5 | 4 | 0 | 4 | 9 | 6 | 5 | 5 | 7 | 8 | 7 | 5 | 9 | 9 | 4 | 4 | 9 | 6 | 8 | 0 |
| Propanil + Bolero early | 9 | 9 | 9*** | 9 | 9 | 9 | 9 | 0 | 5 | 9 | 8 | 5 | 8 | 8 | 9 | 9 | 6 | 9*** | 9*** | 5 | 5 | 9*** | 6 | 9 | 0 |
| Propanil + Prowl early | 9 | 9 | 9 | 9 | 9 | 9 | 9 | 0 | 5 | 7 | 7 | 5 | 5 | 7 | 9 | 7 | 6 | 9*** | 9*** | 5 | 5 | 9*** | 6 | 7 | 0 |
| Propanil fb propanil | 9 | 9 | 9 | 9 | 9 | 8 | 7 | 0 | 6 | 9 | 6 | 6 | 6 | 7 | 9 | 7 | 5 | 9 | 9 | 5 | 5 | 9 | 8 | 8 | 0 |
| Arrosolo or RiceSolo early | 9 | 9 | 9 | 9 | 9 | 7 | 7 | 0 | 5 | 9 | 6 | 5 | 7 | 7 | 9 | 7 | 5 | 9 | 9 | 4 | 4 | 9 | 6 | 9 | 0 |
| Facet early post | 9 | 9 | 9 | 6 | 5 | 0 | 0 | 0 | 0 | - | 3 | - | 3 | 3 | 9 | 3 | 3 | 8 | 8 | 8 | 8 | 8 | 0 | 3 | 0 |
| Facet + propanil early post | 9 | 9 | 9 | 9 | 9 | 5 | 4 | 0 | 5 | 9 | 6 | - | 5 | 6 | 9 | 7 | 5 | 9 | 9 | 8 | 8 | 9 | 6 | 8 | 0 |
| Propanil + Londax prior to flood | 9 | 9 | 9 | 9 | 9 | 5 | 4 | 0 | 8 | 9 | 9 | 8 | 8 | 7 | 9 | 8 | 9 | 9 | 9 | 9 | 9 | 9 | 8 | 8 | 0 |
| Permit prior to flood | 0 | 0 | 0 | 0 | 8 | 0 | 0 | 0 | 9 | - | - | 9 | 8 | 3 | - | - | - | 3 | 3 | 4 | 3 | 9 | - | - | - |
| Propanil + Permit | 9 | 9 | 9 | 9 | 9 | 5 | 4 | 0 | 9 | 9 | 6 | 9 | 8 | 7 | 8 | 7 | 5 | 9 | 9 | 4 | 4 | 10 | 6 | 8 | - |
| Whip 360 (half rate) | 4 | 4 | 4 | 4 | 0 | 7 | 9 | 0 | 0 | 0 | 0 | 0 | 0 | 0 | 0 | 0 | 0 | 0 | 0 | 0 | 0 | 0 | 0 | 0 | 0 |
| Ordram or RiceCue 15G early (3-5" barnyardgrass) | 9 | 9 | 8 | 8 | 5 | 5 | 5 | 0 | 4 | 7 | 0 | 0 | 7 | 0 | 8 | 0 | 2 | 0 | 0 | 0 | 0 | 2 | 4 | 2 | 0 |
| Londax early post flood | 0 | 0 | 0 | 0 | 8 | 0 | 0 | 0 | 6 | 8 | 9 | 5 | 8 | 9 | 8 | 9 | 9 | 6 | 6 | 5 | 5 | 6 | 6 | 9 | 0 |
| Basagran early | 0 | 0 | 0 | 0 | 8 | 0 | 0 | 0 | 6 | 8 | 8 | 9 | 9 | 6 | 8 | 7 | 7 | 3 | 3 | 3** | 8 | 3 | 7 | 8 | 0 |
| Blazer + propanil early | 8 | 8 | 8 | 8 | 8 | 5 | 4 | 0 | 5 | 8 | 6 | 5 | 5 | 7 | 8 | 7 | 5 | 9 | 9 | 8 | 8 | 9 | 7 | 8 | 8 |
| Basagran + propanil early | 9 | 9 | 9 | 9 | 9 | 5 | 4 | 0 | 6 | 9 | 9 | 9 | 8 | 7 | 9 | 8 | 7 | 9 | 9 | 5** | 8 | 9 | 8 | 9 | 4 |
| Grandstand + propanil early | 9 | 9 | 9 | 9 | 9 | 5 | 4 | 0 | 5 | 9 | 9 | 9 | 5 | 8 | 9 | 8 | 8 | 9 | 9 | 9 | 9 | 9 | 7 | 8 | 4 |
| Propanil midseason | 4 | 4 | 4 | 4 | 5 | 0 | 0 | 0 | 3 | 7 | 4 | 2 | 0 | 3 | 4 | 4 | 0 | 5 | 5 | 0 | 3 | 8 | 3 | 8 | 4 |
| 2,4-D midseason | 0 | 0 | 0 | 0 | 8 | 0 | 0 | 0 | 5 | 8 | 9 | 9 | 9 | 9 | 9 | 9 | 6 | 5 | 5 | 9 | 9 | 9 | 6 | 9 | 5 |
| MCPA midseason | 0 | 0 | 0 | 0 | 8 | 0 | 0 | 0 | 5 | 8 | 9 | 9 | 9 | 9 | 9 | 9 | 6 | 5 | 5 | 9 | 9 | 6 | 6 | 9 | 5 |
| Blazer midseason | 0 | 0 | 0 | 0 | 0 | 0 | 0 | 0 | 0 | 0 | 0 | 0 | 0 | 0 | 0 | 0 | 0 | 0 | 0 | 3 | 3 | 9 | 0 | 0 | 3 |
| Propanil + Blazer midseason | 5 | 5 | 5 | 5 | 6 | 0 | 0 | 0 | 4 | 7 | 5 | 6 | 2 | 4 | 5 | 5 | 2 | 6 | 6 | 8**** | 7 | 9 | 4 | 8 | 5 |
| Grandstand + propanil midseason | 2 | 2 | 2 | 2 | 5 | 0 | 0 | 0 | 3 | 8 | 9 | 9 | - | 6 | 6 | 8 | 7 | 9 | 8 | 9 | 9 | 9 | 5 | 8 | 3 |
| 2,4-D propanil midseason for levees | 6 | 6 | 6 | 6 | 8 | 6 | 6 | 0 | 6 | 8 | 9 | 9 | 9 | 8 | 9 | 9 | 9 | 8 | 8 | 9 | 8 | 9 | 7 | 9 | 5 |

*Water seed pin-point flood culture. 8 for palmleaf morningglory *Postemergence control only. ****Runners less than 1 ft. Rating Scale – 0 = No Control 10 = 100% Control.

FIG. 15

SEQ ID NO: 138
*O. rufipogon* predicted Basic helix loop helix region
485 and ends at position 534
VLKERRRREKLNEKFIILRSLVPFMTKMDKASILGDTIEYVKQLRNRIQE SEQ ID NO: 139
Corn - *Zea mays* Intensifier1 (IN1) protein sequence, NCBI accession #:AAB03841.1
predicted Basic helix loop helix region
VLKERRRREKLNEGFAMLRSLVPFVTKMDRASILGDTIEYVKQLRRRIQE SEQ ID NO: 140
Petunia - *Petunia hybrida* Anthocyanin 1 (AN1) protein sequence, NCBI accession #:
AAG25928.1 predicted Basic helix loop helix region
VLAERRRREKLNERFIILRSLVPFVTKMDKASILGDTIEYVKQLRKKVQD SEQ ID NO: 141
Arabidopsis – *Arabidopsis thaliana* TRANSPARENT TESTA 8 (TT8) protein, NCBI
accession #: Q9FT81, Basic helix-loop-helix protein 42,AtbHLH042 predicted Basic
helix loop helix region
VVAERRRREKLNEKFITLRSMVPFVTKMDKVSILGDTIAYVNHLRKRVHE

SEQ ID NO: 142
ACGCGAAAAGTCGG

SEQ ID NO: 143
Red rice seed indicator showing C at O. rufipogon genomic equivalent 1353
gtagtcactgCa SEQ ID NO: 144
White rice seed indicator showing A instead of C at O. rufipogon genomic equivalent
1353
gtagtcactgAa SEQ ID NO: 145
anthocyanin regulatory element consensus sequence
TTGACTGGNGGNTGCG

SEQ ID NO: 146
Oryza sativa (japonica cultivar-group) PAIR1 mRNA for coiled-coil protein, complete cds. ACCESSION AB158462 gcaggaagaaattcaaatttgcgaatattctctctctccccggcgaaggcgacggcgaaggagaaggctacggcgatcggcgg
cgatcggcggcatgaagcttaagatgaacaaggcctgcgacatcgcctccatctccgtcctccctccccggaggaccggagggag
cagcggcgcgtcggcttccggttccgtggcggtggcggtggcgtctcagccgcggtcgcagccgctctcgcagtcgcagcagtcc
ttctcgcagggcgcctccgcctcgctcttgcactcgcagtcgcagttctcgcaggtctccctcgacgacaacctcctcaccctcc
tcccttcccccacccgcgatcagagatttggcttgcatgatgactcatccaagaggatgtcctctttaccagccagttcagcttc
ttgcgcgcgagaagagtctcagctgcaactggcaaaattaccaagcaacccagtgcaccgctggaacccctccattgcagatact
agatcaggtcaggttactaatgaggatgttgagcgcaaatttcagcatctggcaagctcagtacataagatggggatggtggtag
actcagtccaaagtgacgtaatgcagttaaacagagccatgaaggaggcatcattagattctggtagcatacggcaaaagattgc
tgtccttgaaagctcacttcagcaaattcttaagggacaagacgatctcaaagcactctttggaagcagcacaaaacacaatcct
gatcagacaagtgttctgaattctctaggcagcaaattgaatgagatatcctcgacccttgcaaccttgcagacacaaatgcaag
caagacaactgcagggtgatcagacaactgttctgaattctaatgccagcaaatcgaatgagatatcctcgactcttgcaaccct
gcagacacaaatgcaagcagatataagacaactgcggtgtgacgtcttcagagtttttacaaaagagatggagggggttgtt
agagctatcaggtctgtcaatagtaggcctgctgcaatgcaaatgatggcagaccagagttaccaagtaccagtttcaaatgga
tggacccagattaaccagacaccagtagcagctggaaggtctccaatgaaccgagcaccagtagcagctggaaggtcccggatga
accaattacctgaaacaaaagtgctttctgcacatttggtttatcctgcaaaggtgacagatctgaagccaaaggtggagcaggg
aaaggtaaaagcagctccacaaaagccgtttgcttcgagctactacagggtggcacctaaacaggaagaggtagcgattagaaag
gtcaatatacaagtgccagcaaagaaggcaccagtcagcataatcatcgagtcggatgatgacagtgaaggacgtgcgtcctgcg
tgattttgaagacagaaacaggtagcaaggagtggaaagtgacaaagcaaggcaccgaagagggcctggagatcctgcggagggc
gaggaagaggaggaggagagagatgcagtccatcgtgctcgcatcctagctaattaatggtaacgccgcatgcatcgtcatcatc
atctcaagattgactgattgttttaacataaagccaaacaaaggaaagagataaagattacgacaagacgaaattaaaaggtaaa
tcaaccact SEQ ID NO: 147
Oryza sativa (japonica cultivar-group) OsASY1 mRNA for essential protein for meiotic synapsis, complete cds. ACCESSION AB109238 ctctcatctcgcgcgcggcgcgccgccgtagagacgaaatggtgatggctcagaagacgaaggaggcggagatcacggagcagga
ttcgctgcttctgacaaggaatttgctccgcattgctatatacaacatcagctacatcagaggtctattccctgagaagtacttc
aatgataagtcggttccggcactagagatgaagattaagaagctaatgcccatggatactgagtcgaggaggttgattgattgga
tggaaaaaggtgtctatgatgcactacagaagaaatatctcaagacccttctcttctgcatctgtgagaaggaggaaggcccaat
gattgaggagtatgcattctcatttagctaccccaacacgagcggtgatgaagttgcaatgaacttgagccgcacagggagcaag
aaaaacagtgctacatttaaatcaaatgcagcagaagtcactcctgatcagatgaggagctctgcttgtaagatgataagaacac
tggtttcacttatgaggaccttggaccaaatgccagaggagaggaccattctaatgaagctgctatactacgatgatgtcacacc
tgaagattacgagccacccttttttaagtgttgcgctgacaacgaggccataaatatatggaacaagaaccccttgaagatggaa
gttggaaatgtcaatagcaagcatctcgtgttagctttgaaggtcaagagtgtccttgacccttgtgatgataacaatgtcaaca
gtgaagatgataatatgagcttggataatgaatctgaccaagataatgatttttctgacactgaggttcgcccatctgaagcaga
gcgttacattgttgctccaaatgatgggacttgcaaaggtcaaaatggtacaatctcagaagatgatactcaagatcctgttcac
gaggaagagctaacagctcaagtaagagagtggatatgctcaagagacactgaaagtcttgaggtttcagatgtccttgttaatt
tccccgacatatcaatggaaatggttgaagatattatggagaggctacttaaagatggtttactatccagagcaaaaaaggatag
ttattctgttaataagattgctgatcctacaacaccacacataaagaaagaggtcatcatgcaaaatgtctcacctactgaagga
actaaaaatagcaatggtgatctgatgtatatgaaggcactgtaccatgcacttccaatggattatgtgtcagtaggcaaacttc
atggcaagctagatggggaggccagccagaacatggttcgtaagttgattgaaaaaatggtgcaagacggatatgtcaagaattc
agccaaccgaagactaggcaaagctgtcattcattctgaagtcaccaacagaaagctccttgagataaaaaagattctggaagtc
gatatagccgaacaaatggccattgataccaatgcagaacctggtgagcctgagcgcaaagaccacctgagtggccatgaaatga
gagatggatcgacgatgggttgcctccagtccgtcggatctgacctcacccgcacccgggagcttccggagccgcagcagaacgt
gtccatgcagagcgggcaggaagcttccacggtggataaggatccaagcaggactcctacaagcgtgcgcgagcaggcgtccgtt tgttccctggagagtggggttctcgggcagaaggtcagaaagtctttggctggtgctggcgggacgcagtgctcgcaggacaagc
gattcaggaaggccagcacggtgaaggagccgatcctccagtacgtcaagcgccagaagtcccaagttcaagttcaagttcagtg
agggttcgtgtcgcaagcgtcaggagcaactaacatcgtagttcaggtgcagaagaccacaagtagatatatccatcctattcct
agttccggtgctcaagtttgtgcagatagtcagagagcactcacgcacacgtagatatctgtccatgccgctgtcccaaatggca
aatggagatagacgctactatgtgctaacacacactcaaattaagcattcaaaacgcaaaaaaaaaaaaaaaaaa SEQ ID NO: 148
Oryza sativa (japonica cultivar-group) MSP1 mRNA for putative leucine-rich repeat protein kinase, complete cds. ACCESSION AB103395 tggatgtttcatgggcttcttgatcctatctccaggtttttaggctttacgatgagtggtttgcgtaacttctgcttttattctt
gctgatcagagagcagttcctggtttttgttatgatggtgttgtttcttttgggggctaagaccaagataatagtattagtatat
ccttgtggagttgttggagctatagtggcaactgccaaacacagcccaaccagcattgcttcgagtccttccactagatgttgat
tcaagtaggataggtttgcttgtttcatgttcttgtacatttgagctgacaatcgcatgaaagctgagtgttcctgttcttttct
aattgttcaggatgcatttctgagagggcgtaatggttcagactgcagaaggatgtgtattgcacagttttatctgtcagtcatc
tatatcctacttgaagttacaaggctacatcttataagataattgttacagtcccaaaaagaataacgtggaaatggtatccaat
agtttctggcttttcatcctgctagtgagcttcatccccatttctgcttgggcagaatcacgtgatataagtactctgttcactc
tgagggattcaatcaccgaaggaaaaggctttctccgtaactggtttgattcggaaactcccccatgcagctggtcaggcataac
ttgcataggacataatgttgtggcgattgatttgtcctctgttccactctatgctccgtttccattatgcattggggcattccag
tcacttgttcggctcaacttcagtggatgtgggttttccggagagcttccggaagctttgggaaatttgcagaatctccagtacc
tagacttgagcaataacgagcttactgggccaatacctatctcactatataacctgaagatgctgaaggaaatggtgcttgacta
caactccttgtcaggacaacttagtcctgctattgctcagctgcagcaccttactaagctatctatatccatgaattccatctcc
ggaagccttccaccagatctgggcagcctgaagaacctggagttgttggacattaagatgaacacattcaatggatctataccag
caacttttgggaacctgtcttgtctcttgcactttgatgctagccagaataacctaactggatcaatattccctggaataacctc
gttgacaaacctattgacacttgatctatcatcaaacagttttgagggaacaattcctagggagattggtcaactggaaaatctg
gaattactgattctaggaaagaatgatctcactggaaggattccacaagagattggtagtctgaagcagcttaagttacttcatc
tcgaggaatgtcagttcacaggcaaaataccttggtcaatcagtggactcagcagcttgacagaacttgacatatcagataacaa
ctttgacgctgagctcccatcatccatgggtgagcttggcaatctaacacagctgattgcaaagaatgctgggctcagtgggaac
atgccaaaagaacttgggaattgcaagaagcttactgttataaacctgtcattcaatgcccttattggacctattcctgaagaat
ttgcagatttagaggctattgtctcatttttttgtggaaggaaataaactatcgggtcgtgtcccagattggattcagaaatggaa
aaatgcaaggtccatcaggttgggacagaacaaattcagtggacctttgccagtgctgccattgcagcatctgctaagtttcgct
gcagaatccaaccttctctcaggttctataccttctcacatatgccaagccaactccttgcattcactcttattgcatcataaca
atctgactgggactattgatgaggcatttaaagggtgcacgaacctcactgaattgaacttgttagacaaccatattcatgggga
ggtaccaggatatttagcagaattaccccctggttactctggagttgtcacaaaacaaattcgcagggatgttacctgcggagctg
tgggagtcaaaaacccttctagagatatctctcagtaacaatgaaattaccggcccaatacctgagagtattggtaaactctctg
tattgcaaaggttgcatatagacaataacttactcgaagggcctatccctcagtctgttggtgatctaaggaatctgaccaatct
atccctgcgtggcaataggttatctgggatcattccactagcacttttcaactgcagaaaacttgccacgctggacttgagctat
aacaatctgactgggaacattccaagtgccatatctcacttgacattgcttgatagcttgattttgtcttccaaccagctgtctg
gttctatccctgctgagatttgcgtgggatttgagaatgaggctcaccctgactcagagtttcttcagcaccatggtcttcttga
tctgtcatacaaccaattgactggtcagatcccaacatctataaagaactgtgcaatggtgatggtgctcaacctccaaggcaat
ttgctgaatggcaccattcctgtggagcttggcgagctaacaaatcttacatccattaacttgtcatttaatgaatttgttggac
caatgcttccatggtctggacctttggttcaattgcaaggccttattctgtccaataaccacctagatggctccattcctgctaa
gataggccaaatccttcccaaaattgcagtgctagacttgtcaagcaatgcactcactggcactctaccacagtctttgctctgc
aacaattacctaaaccatctggatgtcagcaacaaccacctatctgggcatatccagttctcttgccccgatggcaaagaatact
caagtacactgctcttcttcaattcaagcagcaaccatttctcagggagcctagatgagtctatctcgaacttcacacaattgtc
tactcttgatatccacaacaatagcctcactggaaggttgccttcagcactttctgatctcagttctttgaattatcttgatctg
tcgagcaacaatctctatggtgccataccctgtggaatctgcaatatatttggcctctcatttgccaacttctcaggtaactata
ttgacatgtacagcttggcagattgtgctgcaggaggcatttgttctactaatggtactgatcataaagcattgcatccatatca
tcgggttcgaagggcaattaccatctgtgcctttacattcgtcatcatcattgttttagtgcttctggctgtttatctgagacgg
aagctggttagaagcaggcctttggcttttgaatctgccagtaaggccaaggctacagttgagcctacctcaactgatgaactgc

FIG. 17 CONT.

taggaaagaagtcaagggaacctctgagtatcaatcttgcaacatttgagcatgcacttctgagggtcaccgcggatgatattct
gaaagccacagaaaacttcagtaaggtgcacataataggtgatggtggatttggcactgtctacaaggcagcgctccctgaaggc
cggagagtcgcgatcaagaggctccatggtggccatcagttccaaggtgaccgtgagtttctagctgagatggagacaattggaa
aggtgaaacatccaaacctcgtccctctacttggctactgtgtttgtggcgatgaacgattcctgatctacgagtacatggagaa
tgggagcctcgagatgtggctgagaaaccgagcagatgcacttgaagctcttggatggccggaccgtctcaagatctgcctcggt
tcagcccgtgggctcgccttcctgcatcatggctttgtgccccatatcatccaccgggacatgaagtcgagcaacattctactgg
atgagaacttcgagccgagggtctctgacttcggccttgcaaggatcatcagtgcctgtgagacccatgtcagcactgacattgc
cggtacatttggatacattcctccggagtatggcctcacaatgaagtccaccacgaaaggcgacgtctacagcttcggcgtcgtc
atgctggagctcctcaccggacggccacctacaggccaggaggaggtgcaagggggtggaaacctcgtcggctgggtgcggtgga
tgatcgcccgcggtaagcagaacgagctgttcgatccatgcttgccggtttcaagcgtgtggcgggagcagatggcgcgcgtgct
cgccatcgcccgggactgcaccgccgacgagccgttcaagaggccgacaatgctggaggtggtgaaggggctcaagatgacccac
ggcatggaatgtggacctctggtggtgaccgtctccagggacatgtaatgctctctgcttgatcttcctgaaactaatgtagtaa
taatgtagtcagtagggagtaggctaatggtagttaggagtaactcgtagctatagagtaaccgagctatctggaggctgtaatg
agggaaactagagttactcatgttcaggctgtagttggaactagtattaagaccttttatcttgtactattgtcactggtggttc
ctgtggcaatgtgagtgcttaatgtgctgtcgtttgaataaaagtactgcttgcctgtttctaagtgttaaaaaaaaaaaaaaaa
aaaaaa SEQ ID NO: 149
SPOROCYTELESS Arabidopsis thaliana sporocyteless (SPL) mRNA, complete cds. ACCESSION AF159255 cacacttaaagctttcgtctttacctcttcccttctctctctctatctaaaaagagttccgagaagaagatcatcatcaatggcg
acttctctcttcttcatgtcaacagatcaaaactccgtcggaaacccaaacgatcttctgagaaacacccgtcttgtcgtcaata
gctccggcgagatccggacagagacactgaagagtcgtggtcggaaaccaggatcgaagacaggtcagcaaaaacagaagaaacc
aacgttgagaggaatgggtgtagcaaagctcgagcgtcagagaatcgaagaagaaaagaagcaactcgccgccgccacagtcgga
gacacgtcatcagtagcatcgatctctaacaacgctacccgtttacccgtaccggtagacccgggtgttgtgctacaaggcttcc
caagctcactcgggagcaacaggatctattgtggtggagtcgggtcgggtcaggttatgatcgacccggttatttctccatgggg
ttttgttgagacctcctccactactcatgagctctcttcaatctcaaatcctcaaatgtttaacgcttcttccaataatcgctgt
gacacttgcttcaagaagaaacgtttggatggtgatcagaataatgtagttcgatccaacggtggtggattttcgaaatacacaa
tgattcctcctccgatgaacggctacgatcagtatcttcttcaatcagatcatcatcagaggagccaaggtttcctttatgatca
tagaatcgctagagcagcttcagtttctgcttctagtactactattaatccttatttcaacgaggcaacaaatcatacgggacca
atggaggaatttgggagctacatggaaggaaaccctagaaatggatcaggaggtgtgaaggagtacgagtttttttccggggaaat
atggtgaaagagtttcagtggtggctacaacgtcgtcactcgtaggtgattgcagtcctaataccattgatttgtccttgaagct
ttaaatgttttatctttctatattgatttaaacaaaatcgtctctttaaagaaaaaacattttaagtagatgaaagtaagaaaca
gaagaaaaaaaagagagagcctttttttggtgtatgcatctgagagctgagtcgaaagaaagattcagcttttggattacccttttt
ggttgtttattatgagattctaacctaaacactcagacatatatgttctgttctcttccttaattgttgtcatgaaacttctcaa
aaaaaaaaaaaaaaaaaaaaaaaaaa SEQ ID NO: 150
NOZZLE Arabidopsis thaliana NOZZLE (NZZ) gene, complete cds. ACCESSION AF146794 atggcgacttctctcttcttcatgtcaacagatcaaaactccgtcggaaacccaaacgatcttctgagaaacacccgtcttgtcg
tcaatagctccggcgagatccggacagagacactgaagagtcgtggtcggaaaccaggatcgaagacaggtcagcaaaaacagaa
gaaaccaacgttgagaggaatgggtgtagcaaagctcgagcgtcagagaatcgaagaagaaaagaagcaactcgccgccgccaca
gtcggagacacgtcatcagtagcatcgatctctaacaacgctacccgtttacccgtaccggtagacccgggtgttgtgctacaag
gcttcccaagctcactcgggagcaacaggatctattgtggtggagtcgggtcgggtcaggttatgatcgacccggttatttctcc
atggggttttgttgagacctcctccactactcatgagctctcttcaatctcaaatcctcaaatgtttaacgcttcttccaataat
cgctgtgacacttgcttcaaggtttgtttgtttttaatcgttttcatcaacatgattgatatatatatagtttttgcacttgaa
aaagttttgatttttatttatgtaaaaaactgcagaagaaacgtttggatggtgatcagaataatgtagttcgatccaacggtgg

FIG. 17 CONT.

```
Tggattttcgaaatacacaatgattcctcctccgatgaacggctacgatcagtatcttcttcaatcagatcatcatcagaggagc
caaggtttcctttatgatcatagaatcgctagagcagcttcagtttctgcttctagtactactattaatccttatttcaacgagg
caacaaatcatacggtactaagtatagtccatttattaatactcatatataggtatatatgtatataactgttgatcttatttga
tttaactggtgggtttagggaccaatggaggaatttgggagctacatggaaggaaaccctagaaatggatcaggaggtgtgaagg
agtacgagttttttccggggaaatatggtgaaagagtttcagtggtggctacaacgtcgtcactcgtaggtgattgcagtcctaa
taccattgatttgtccttgaagctttaa
```

SEQ ID NO: 151
"Herbicide resistant AHAS sequence, variety Kinmaze" Sequence 4 from Patent WO0185970. ACCESSION AX300475 ctcgccgccgccgccgccgccaccacccaccatggctacgaccgccgcggccgcggccgccgccctgtccgccgccgcgacggcc
aagaccggccgtaagaaccaccagcgacaccacgtccttcccgctcgaggccgggtgggggcggcggcggtcaggtgctcggcgg
tgtccccggtcaccccgccgtccccggcgccgccggccacgccgctccggccgtgggggccggccgagccccgcaagggcgcgga
catcctcgtggaggcgctggagcggtgcggcgtcagcgacgtgttcgcctacccgggcggcgcgtccatggagatccaccaggcg
ctgacgcgctccccggtcatcaccaaccacctcttccgccacgagcagggcgaggcgttcgcggcgtccgggtacgcgcgcgcgt
ccggccgcgtcggggtctgcgtcgccacctccggccccggggcaaccaacctcgtgtccgcgctcgccgacgcgctgctcgactc
cgtcccgatggtcgccatcacgggccaggtcccccgccgcatgatcggcaccgacgccttccaggagacgcccatagtcgaggtc
acccgctccatcaccaagcacaattaccttgtccttgatgtggaggacatcccccgcgtcatacaggaagccttcttcctcgcgt
cctcgggccgtcctggcccggtgctggtcgacatccccaaggacatccagcagcagatggccgtgccggtctgggacacctcgat
gaatctaccagggtacatcgcacgcctgcccaagccacccgcgacagaattgcttgagcaggtcttgcgtctggttggcgagtca
cggcgcccgattctctatgtcggtggtggctgctctgcatctggtgacgaattgcgctggtttgttgagctgactggtatcccag
ttacaaccactctgatgggcctcggcaatttccccagtgacgacccgttgtccctgcgcatgcttgggatgcatggcacggtgta
cgcaaattatgccgtggataaggctgacctgttgcttgcgtttggtgtgcggtttgatgatcgtgtgacagggaaaattgaggct
tttgcaagcagggccaagattgtgcacattgacattgatccagcagagattggaaagaacaagcaaccacatgtgtcaatttgcg
cagatgttaagcttgctttacagggcttgaatgctctgctacaacagagcacaacaaagacaagttctgattttagtgcatggca
caatgagttggaccagcagaagagggagtttcctctggggtacaaaacttttggtgaagagatcccaccgcaatatgccattcag
gtgctggatgagctgacgaaaggtgaggcaatcatcgctactggtgttgggcagcaccagatgtgggcggcacaatattacacct
acaagcggccacggcagtggctgtcttcggctggtctgggcgcaatgggatttgggctgcctgctgcagctggtgcttctgtggc
taacccaggtgtcacagttgttgatattgatggggatggtagcttcctcatgaacattcaggagctggcattgatccgcattgag
aacctccctgtgaaggtgatggtgttgaacaaccaacatttgggtatggtggtgcaattggaggataggttttacaaggcgaata
gggcgcatacatacttgggcaacccggaatgtgagagcgagatatatccagattttgtgactattgctaaggggttcaatattcc
tgcagtccgtgtaacaaagaagagtgaagtccgtgccgccatcaagaagatgctcgagactccagggccatacttgttggatatc
atcgtcccgcaccaggagcatgtgctgcctatgatcccaattgggggcgcattcaaggacatgatcctggatggtgatggcagga
ctgtgtattaatctataatctgtatgttggcaaagcaccagcccggcctatgtttgacctgaatgacccataaagagtggtatgc
ctatgatgtttgtatgtgctctatcaataactaaggtgtcaactatgaaccatatgctcttctgttttacttgtttgatgtgctt
ggcatggtaatcctaattagcttcctgctgtctaggtttgtagtgtgttgttttctgtaggcatatgcatcacaagatatcatgt
aagtttcttgtcctacatatcaataataagagaataaagtacttctatgtaaaaaaaaaaaaaaaaaa SEQ ID NO: 152
Maize a2-promoter:
GCGATCGCAACCAGTCAAGACGAATGGCAGGCAGCTAAGTAGCTAACAACAACAGGCTTGTATTGTATG SEQ ID NO: 153
LOC Os01g44260, rice promoter for rice homolog of anthocyanin synthase (ANS) or anthocyaninless2 (A2) from *Zea mays*; Rc control element:
CCTGTCCTGTACCAGCTTATATATATAGGCGAGCCAACGAGCGAGAGCCATCACCAAGTGCAAGGTAGCTA
TCATATATT

SEQ ID NO: 154

Loc_Os03g03040, rice promoter for rice homolog of flavanone 3-hydroxylase (F3H) from *Arabidopsis thaliana*; Rc control element:
TTCAATCGTGGTTAATAGAACAACAAGGAGACAATAAGAGGCTGACGGTGCCTACCAAAGCTCAGGTTATA
CTTTT SEQ ID NO: 155
LOC_Os04g56700, rice promoter for rice homolog of flavanone 3-hydroxylase (F3H) from *Arabidopsis thaliana*; Rc control element:
TATCGATCGGGTGATCAGTTATGCTAAAGGCCTGCAGCTAGCTAGAGAACACAAACCGCATCGATGAGTAGT
AGTTGG SEQ ID NO: 156
LOC_Os06g46920, rice promoter for rice homolog of dihydroflavonol reductase (DFR) or anthocyaninless1 (a1) from *Zea mays*; Rc control element:
ACGGCACCGGCCCGCGACCCAGGTACGCCGTACGCGCGAGCTCGCTCGCTAGCATCGATGAAGCTCGTGGCG
TGGTGAA SEQ ID NO: 157
Loc_Os07g11440, rice promoter for rice homolog of chalcone synthase (CHS) or c2 from *Zea mays*; Rc control element:
TTCGTTGTGGCGAACAAGCTAGCTGCTAGTACCCTCAGTTATACCAAGATATACACTACATTCCTAGCTAG
GTACGATTAGCCGCCGGTGAGTGGGGAGATGGTGACATCAACAGTGAAGTTGGAGGA SEQ ID NO: 158
Loc_Os08g37450, rice promoter for rice homolog of flavonol synthase (FLS) from *Arabidopsis thaliana*; Rc control element:
GCCAGCAAAACCACTCTTCAAAACTGCCGAGGGAGTCAAGTTGCACCGGTTTTAACAGTATAGGGGTCAAG
ATATCTGGT SEQ ID NO: 159
Loc_Os10g25590, rice promoter for rice homolog of ZmMRP3 (multi-drug resistance protein3) from *Zea mays*; Rc control element:
GCTCACGCACGCGCCGCAGCTACCCAGCCACTCCTCGATCGTCTCCTCCCCATTATAAGCAGCAGCAAGCA
A-GCAAACCAAAGCAAAGCATCGATCTCCCATGG SEQ ID NO: 160
Loc_Os11g32620, rice promoter for rice homolog of chalcone synthase (CHS) or c2 from *Zea mays* ; Rc control element:
CTGCTGGAGCGCAAGCAAAAGAAAGAGTTTACATTTGGATGGTCCTTTGGCCGACCACAATAGATTAGCAC
ATGCATAA SEQ ID NO: 161
Loc_Os11g32650, rice promoter for rice homolog of chalcone synthase (CHS) or c2 from *Zea mays*; Rc control element:
TCGGCGATGTCCTTGGCGAGGCGGAGCGCGGTGCAGCCGGCGTTGCAGCCGTGCATGTAGAGGACGGCGCG
CTGCACGG SEQ ID NO: 162
Loc_Os11g32610, rice promoter for rice homolog of chalcone synthase (CHS) or c2 from *Zea mays*; Rc control element:
TGGTGTTTGAATGTCCTGAAGATGAACATGAAGATTTAAGTGTTTTACGTAAAATGAGGTTGTAATAACGT
GTGAT SEQ ID NO: 163
Loc_Os12g02370, rice promoter for rice Putative chalcone isomerase (CHI); Rc control element:

FIG. 18 CONT.

CTGCAAAATGGCAGCCCCCCTATAGACGGCCGTTAGGCGTGCGCTAACGGTGGTCAGCCACGTCACGAAAA
TCGCCCTCTGGGA

SEQ ID NO: 164
LOC_Os06g42130, rice promoter for rice homolog of anthocyanin synthase (ANS) or anthocyaninless2 (A2) from Zea mays; Rc control element:
GCCATCGCCGGCCGGCCGGCCGATCGAGTAATTGCGCAGCGCACGCAGCTCATCATCCACTAGACTAATTAC
TTCGGGA SEQ ID NO: 165
LOC_Os01g27490, rice promoter for rice homolog of anthocyanin synthase (ANS) or anthocyaninless2 (A2) from Zea mays; Rc control element:
TCGCCATCACCGGCCGGC-CGATCGAGTACGTGCGCACGCAGCTCATCTACTAGCCTACTTCGGGA SEQ ID NO: 166
Loc_Os10g17260, rice promoter for rice homolog of flavonoid 3'-hydroxylase (F3'H) from *Arabidopsis thaliana*; Rc control element:
ATGATATGTGCCAAGTAGTCGAGAGCCAAATAAAATAAAATTATTAGTGATTGCAACAGGTGGGCTGGTTT
TGCGTCA SEQ ID NO: 167
LOC_Os01g27490, rice promoter for rice homolog of anthocyanin synthase (ANS) or anthocyaninless2 (A2) from Zea mays; Rc control element:
TCACCGGCCGCCGATCGAGTACGTCGCCAGCGCACGCAGCTCATCTACTAGCCTACTTCGGGA SEQ ID NO: 168
LOC_Os06g42130, rice promoter for rice homolog of anthocyanin synthase (ANS) or anthocyaninless2 (A2) from Zea mays; Rc control element:
CGCCATCGCCGGCCGGCCGCCGATCGAGTAATTGCGCAGCGCACGCAGCTCATCATCCACTAGACTAATTA
CTTCGGGA SEQ ID NO: 169
LOC_Os01g44260, rice promoter for rice homolog of anthocyanin synthase (ANS) or anthocyaninless2 (A2) from Zea mays; Rc control element:
CCTGTCCTGTACCAGCTTATATATATAGGCGAGCCAACGAGCGAGAGCCATCACCAAGTGCAAGGTAGCTA
TCATATATT SEQ ID NO: 170
LOC_Os05g46920, rice promoter for rice homolog of dihydroflavonol reductase (DFR) or anthocyaninless1 (a1) from Zea mays; Rc control element:
ACGCCACCGCCCGCGACCCAGGTACGCCGTACGCGCGAGCTCGCTCCTAGCATCGATGAAGCTCGTGGCGT
GGTGAA SEQ ID NO: 171
LOC_Os04g56700, rice promoter for rice homolog of flavanone 3-hydroxylase (F3H) from Arabidopsis thaliana; Rc control element:
TATCGATCGGGTGATCAGTTATGCTAAAGGCCTGCAGCTAGCTAGAGAACACAAACGCATCGATGAGTAGT
AGTTGG SEQ ID NO: 172
LOC_Os01g27490, rice promoter for rice homolog of anthocyanin synthase (ANS) or anthocyaninless2 (A2) from Zea mays; Rc control element:
TCACCGGCCGCCGATCGAGTACGTCGCCAGCGCACGCAGCTCATCTACTAGCCTACTTCGGGA

SEQ ID NO: 173

FIG. 18 CONT.

LOC_Os06g42130, rice promoter for rice homolog of anthocyanin synthase (ANS) or anthocyaninless2 (A2) from *Zea mays*; Rc control element:
CGCCATCGCCGGCCGGCCGCCGATCGAGTAATTGCGCAGCGCACGCAGCTCATCATCCACTAGACTAATTACTTCGGGA SEQ ID NO: 174
LOC_Os06g46920, rice promoter for rice homolog of dihydroflavonol reductase (DFR) or anthocyaninless1 (a1) from *Zea mays*; Rc control element:
ACGCCACCGCCCGCGACCCAGGTACGCCGTACGCGCGAGCTCGCTCCTAGCATCGATGAAGCTCGTGGCGTGGTGAA SEQ ID NO: 175
LOC_Os04g56700, rice promoter for rice homolog of flavanone 3-hydroxylase (F3H) from *Arabidopsis thaliana*; Rc control element:
TATCGATCGGGTGATCAGTTATGCTAAAGGCCTGCAGCTAGCTAGAGAACACAAACGCATCGATGAGTAGTAGTTGG SEQ ID NO: 176
LOC_Os01g27490, rice promoter for rice homolog of anthocyanin synthase (ANS) or anthocyaninless2 (A2) from *Zea mays*; Rc control element:
TCACCGGCCGCCGATCGAGTACGTCGCCAGCGCACGCAGCTCATCTACTAGCCTACTTCGGGA SEQ ID NO: 177
LOC_Os06g42130, rice promoter for rice homolog of anthocyanin synthase (ANS) or anthocyaninless2 (A2) from *Zea mays*; Rc control element:
CGCCATCGCCGGCCGGCCGCCGATCGAGTAATTGCGCAGCGCACGCAGCTCATCATCCACTAGACTAATTACTTCGGGA SEQ ID NO: 178
LOC_Os04g56700, rice promoter for rice for rice homolog of flavanone 3-hydroxylase (F3H) from *Arabidopsis thaliana*; Rc control element:
TATCGATCGGGTGATCAGTTATGCTAAAGGCCTGCAGCTAGCTAGAGAACACAAACGCATCGATGAGTAGTAGTTGG

FIG. 18 CONT.

```
T-COFFEE, Version 1.41Fri Jun 28 14:24:48 MDT 2002
  Notredame, Higgins, Heringa, JMB302pp205-217,2000
  CPU TIME:53 sec.
  SCORE=13
  *
   BAD AVG G
  *
  Loc_Os01g44260   :  13   SEQ ID NO: 131
  Loc_Os03g03040   :  10   SEQ ID NO: 135
  Loc_Os04g56700   :  17   SEQ ID NO: 133
  Loc_Os06g46520   :  14   SEQ ID NO: 132
  Loc_Os07g11440   :   8   SEQ ID NO: 130
  Loc_Os08g37450   :  10   SEQ ID NO: 136
  Loc_Os10g25590   :  12   SEQ ID NO: 124
  Loc_Os11g32620   :  11   SEQ ID NO: 128
  Loc_Os11g32650   :  10   SEQ ID NO: 127
  Loc_Os11g32610   :  10   SEQ ID NO: 129
  Loc_Os12g02370   :  12   SEQ ID NO: 126
  Loc_Os06g42130   :  17   SEQ ID NO: 122
  Loc_Os01g27490   :  16   SEQ ID NO: 121
  Loc_Os10g17260   :  11   SEQ ID NO: 134
  CONSENSUS01      :  18   SEQ IN NO: 152

  Loc_Os01g44260   CCTGTCCTGTACCAGCTTATATATATAGGCGGAGCCAA---------
  Loc_Os03g03040   -----------------------------------------------
  Loc_Os04g56700   -----------------------------------------------
  Loc_Os06g46520   ------------AG---------------GCCA--------------
  Loc_Os07g11440   -----------------------------------------------
  Loc_Os08g37450   -----------------------------GCCAGCAAAACCA----
  Loc_Os10g25590   --GCTCACGCACGC---------------GCCG--------------
  Loc_Os11g32620   ---CTGCTGGCAGC---------------GCAAGCAAAAGAAAGAG
  Loc_Os11g32650   -------TCGGCGATGTCCTTGCCGAGGCGGACGGCGGTGCA---
  Loc_Os11g32610   -----------------------------------------------
  Loc_Os12g02370   --------------------------------CTGCAAAAT------
  Loc_Os06g42130   -------------G---------------GCCA--------------
  Loc_Os01g27490   ------------TC---------------GCCA--------------
  Loc_Os10g17260   --------ATGATATGTGGCAAGTAGTCGACAGCCAAATAAA---
  CONSENSUS01      -----------------------------------------------

  Cons
```

FIG. 19A

```
T-COFFEE, Version 2.11Wed Sep 29 19:21:53 MDT 2004
  Cedric Notredame
  CPU TIME:2 sec.
  SCORE=38
  *
   BAD AVG
  *
  Loc_Os01g27490    :   46   SEQ ID NO: 121
  Loc_Os06g42130    :   42   SEQ ID NO: 122
  Loc_Os01g44260    :   33   SEQ ID NO: 131
  Loc_Os06g46920    :   39   SEQ ID NO: 132
  Loc_Os04g56700    :   32   SEQ ID NO: 133

  Loc Os01g27490     1  -----TC---------ACGGGCCGCGGATCGA-GTACGTCGCGAGG   31
  Loc Os06g42130     1  CGCCATCGCC-G---GCGGGCCGCGGATCGA-GTAATTGCGCAGG   40
  Loc Os01g44260     1  --CCT-GTCC-TGT-ACCAGCTTATAT-ATATAGGCG-AGCCAAG   38
  Loc Os06g46920     1  -----ACGCC-----AGGGCCCGC-GACCCAGGTACGCCG--TAG   32
  Loc_Os04g56700     1  TATCG--ATCGGGTGATCAGTTAT-GCTAAAGGCCTGCAGCTAGG   42

  Cons               1                                *                   45

  Loc Os01g27490    32  GCACGCAGCTGA----T---CT---ACTAGCCTA----CTTCGGG   62
  Loc Os06g42130    41  GCACGCAGCGCA----T---GATCCACTAGACTAATTACTTCGGG   78
  Loc Os01g44260    39  GAGGCA---GAGC-CATCACCAAGTGCAAGGTAGCTATCATAGAT   79
  Loc Os06g46920    33  GCGCG-AGGGCGGTCCTAG-CATCGATGAAGCTCGTGGCGTGGTG   75
  Loc_Os04g56700    43  TAGAG---AACACA-AACG-CATCGATGAG-TAGTA--GTTGG--   77

  Cons              46                  *         *              *        90

  Loc_Os01g27490    63  A-      63   SEQ ID NO: 167
  Loc_Os06g42130    79  A-      79   SEQ ID NO: 168
  Loc_Os01g44260    80  T-      80   SEQ ID NO: 169
  Loc_Os06g46920    76  AA      77   SEQ ID NO: 170
  Loc_Os04g56700    78  --      77   SEQ ID NO: 171

  Cons              91          92   SEQ ID NO: 152
```

FIG. 20

```
T-COFFEE, Version 2.11Wed Sep 29 19:21:53 MDT 2004
  Cedric Notredame
  CPU TIME:1 sec.
  SCORE=42
  *
   BAD AVG G
  *
  Loc_Os01g27490  :  49   SEQ ID NO: 121
  Loc_Os06g42130  :  45   SEQ ID NO: 122
  Loc_Os06g46920  :  41   SEQ ID NO: 132
  Loc_Os04g56700  :  34   SEQ ID NO: 133

  Loc Os01g27490     1 ------TCA----CCGGCCGGCAGATCGA-GTACGTCGCGAGCGCA   34
  Loc Os06g42130     1 -CGCCATCGCCGGCCGGCCGGCGGATGGA-GGAATTGCGGAGCGCA  43
  Loc Os06g46920     1 ACGCCA-------GGCGCCGG-GACGCAGGTACGCCG--TACGCG   35
  Loc_Os04g56700     1 ----GATCGA---TCGGGT---GATC-AGTTATGCTA--AAGGCC   32

  Cons               1                                                  45

  Loc Os01g27490    35 CGCAGCTCATCT--------------------ACTAGCCTA----C   56
  Loc Os06g42130    44 CGCAGCTGATGA-----------------TCCACTAGACTAATTAC  72
  Loc Os06g46920    36 CG-AGCTGG-GTCCTA---------GCATCGATGAAGCTCGTGGC   69
  Loc_Os04g56700    33 TGCAGCTAG-GTAGAGAACACAAACGCATCGATGAG--TA----G   70

  Cons              46                                                  90

  Loc_Os01g27490    57 TTCGGGA-    63   SEQ ID NO: 172
  Loc_Os06g42130    73 TTCGGGA-    79   SEQ ID NO: 173
  Loc_Os06g46920    70 GTGGTGAA    77   SEQ ID NO: 174
  Loc_Os04g56700    71 TAGTTGG-    77   SEQ ID NO: 175

  Cons              91     *       98   SEQ ID NO: 152
```

FIG. 21

```
T-COFFEE, Version 2.66Fri May 27 13:41:08 2005
  Cedric Notredame
  CPU TIME:1 sec.
  SCORE=40
  *
   BAD AVG GOOD
  *
  Loc_Os01g27490    :  42   SEQ ID NO: 121
  Loc_Os06g42130    :  43   SEQ ID NO: 122
  Loc_Os04g56700    :  36   SEQ ID NO: 133

  Loc_Os01g27490    T--CA-------CCGGCCGCCGATG----GAGTACGTCGC---CA
  Loc_Os06g42130    GGCCAGGGCGGGCCGGCCGCCGATG----GAGTAA-TTGC--GCA
  Loc_Os04g56700    T---AGGGCAT---CGGG---TGATCAGTTATGCTAAAGGCCTGCA

  Cons                          ***      *                **    **

  Loc_Os01g27490    GC--GCACGGAGCTCATCT------ACTA-GCCTA----CTTCGG
  Loc_Os06g42130    GC--GCACGGAGCTCATCAT---CCACTA-GACTAATTACTTCGG
  Loc_Os04g56700    GCTAGCTAG-AGAACA-CAAACGCATCGATGAGTAGT-AGTT-GG

  Cons              **  **  * **  ** *        *  * *  **

  Loc_Os01g27490    GA    SEQ ID NO: 176
  Loc_Os06g42130    GA    SEQ ID NO: 177
  Loc_Os04g56700    --    SEQ ID NO: 178

  Cons                    SEQ ID NO: 152
```

FIG. 22

| RESULTS OF WEBSITE BASED SIGNAL SCAN SEARCH REQUEST for SEQ ID NO:185 | | Higo, *et al.* (1999) Nucleic Acids Research 27(1): 297-300; and Prestridge, (1991) CABIOS 7, 203-206. | |
|---|---|---|---|
| -10PEHVPSBD | site 53 (+) | TATTCT | S000392 |
| -10PEHVPSBD | site 1634 (+) | TATTCT | S000392 |
| -10PEHVPSBD | site 2512 (+) | TATTCT | S000392 |
| -300CORE | site 1332 (+) | TGTAAAG | S000001 |
| -300ELEMENT | site 320 (-) | TGHAAARK | S000122 |
| -300ELEMENT | site 1015 (+) | TGHAAARK | S000122 |
| -300ELEMENT | site 1899 (-) | TGHAAARK | S000122 |
| ABRELATERD1 | site 538 (-) | ACGTG | S000414 |
| ABRELATERD1 | site 584 (-) | ACGTG | S000414 |
| ABRELATERD1 | site 585 (+) | ACGTG | S000414 |
| ABRELATERD1 | site 590 (-) | ACGTG | S000414 |
| ABRELATERD1 | site 1048 (-) | ACGTG | S000414 |
| ABRELATERD1 | site 2137 (-) | ACGTG | S000414 |
| ABRELATERD1 | site 2830 (+) | ACGTG | S000414 |
| ABRELATERD1 | site 2982 (-) | ACGTG | S000414 |
| ACGTATERD1 | site 539 (-) | ACGT | S000415 |
| ACGTATERD1 | site 539 (+) | ACGT | S000415 |
| ACGTATERD1 | site 585 (-) | ACGT | S000415 |
| ACGTATERD1 | site 585 (+) | ACGT | S000415 |
| ACGTATERD1 | site 591 (-) | ACGT | S000415 |
| ACGTATERD1 | site 591 (+) | ACGT | S000415 |
| ACGTATERD1 | site 1049 (-) | ACGT | S000415 |
| ACGTATERD1 | site 1049 (+) | ACGT | S000415 |
| ACGTATERD1 | site 1447 (-) | ACGT | S000415 |
| ACGTATERD1 | site 1447 (+) | ACGT | S000415 |
| ACGTATERD1 | site 2138 (-) | ACGT | S000415 |
| ACGTATERD1 | site 2138 (+) | ACGT | S000415 |
| ACGTATERD1 | site 2230 (-) | ACGT | S000415 |
| ACGTATERD1 | site 2230 (+) | ACGT | S000415 |
| ACGTATERD1 | site 2830 (-) | ACGT | S000415 |
| ACGTATERD1 | site 2830 (+) | ACGT | S000415 |
| ACGTATERD1 | site 2857 (-) | ACGT | S000415 |
| ACGTATERD1 | site 2857 (+) | ACGT | S000415 |
| ACGTATERD1 | site 2983 (-) | ACGT | S000415 |
| ACGTATERD1 | site 2983 (+) | ACGT | S000415 |
| ACGTOSGLUB1 | site 538 (-) | GTACGTG | S000278 |
| ACGTOSGLUB1 | site 2828 (+) | GTACGTG | S000278 |
| ACGTTBOX | site 2229 (-) | AACGTT | S000132 |
| ACGTTBOX | site 2229 (+) | AACGTT | S000132 |
| ACGTTBOX | site 2856 (-) | AACGTT | S000132 |
| ACGTTBOX | site 2856 (+) | AACGTT | S000132 |
| AMYBOX1 | site 806 (+) | TAACARA | S000020 |
| AMYBOX1 | site 1112 (+) | TAACARA | S000020 |
| ANAERO1CONSENSUS | site 849 (+) | AAACAAA | S000477 |
| ANAERO2CONSENSUS | site 1779 (+) | AGCAGC | S000478 |
| ANAERO3CONSENSUS | site 505 (+) | TCATCAC | S000479 |
| ANAERO3CONSENSUS | site 2067 (+) | TCATCAC | S000479 |
| ARFAT | site 464 (+) | TGTCTC | S000270 |

FIG. 24

| | | | |
|---|---|---|---|
| ARFAT | site 2041 (+) | TGTCTC | S000270 |
| ARR1AT | site 12 (+) | NGATT | S000454 |
| ARR1AT | site 43 (+) | NGATT | S000454 |
| ARR1AT | site 48 (+) | NGATT | S000454 |
| ARR1AT | site 149 (+) | NGATT | S000454 |
| ARR1AT | site 361 (+) | NGATT | S000454 |
| ARR1AT | site 422 (-) | NGATT | S000454 |
| ARR1AT | site 450 (-) | NGATT | S000454 |
| ARR1AT | site 668 (-) | NGATT | S000454 |
| ARR1AT | site 786 (+) | NGATT | S000454 |
| ARR1AT | site 854 (-) | NGATT | S000454 |
| ARR1AT | site 1054 (+) | NGATT | S000454 |
| ARR1AT | site 1116 (+) | NGATT | S000454 |
| ARR1AT | site 1171 (-) | NGATT | S000454 |
| ARR1AT | site 1197 (+) | NGATT | S000454 |
| ARR1AT | site 1249 (-) | NGATT | S000454 |
| ARR1AT | site 1274 (-) | NGATT | S000454 |
| ARR1AT | site 1285 (-) | NGATT | S000454 |
| ARR1AT | site 1293 (-) | NGATT | S000454 |
| ARR1AT | site 1499 (+) | NGATT | S000454 |
| ARR1AT | site 1504 (+) | NGATT | S000454 |
| ARR1AT | site 1593 (+) | NGATT | S000454 |
| ARR1AT | site 1620 (-) | NGATT | S000454 |
| ARR1AT | site 1624 (+) | NGATT | S000454 |
| ARR1AT | site 1629 (+) | NGATT | S000454 |
| ARR1AT | site 1728 (+) | NGATT | S000454 |
| ARR1AT | site 1750 (-) | NGATT | S000454 |
| ARR1AT | site 1940 (+) | NGATT | S000454 |
| ARR1AT | site 1999 (-) | NGATT | S000454 |
| ARR1AT | site 2215 (+) | NGATT | S000454 |
| ARR1AT | site 2302 (-) | NGATT | S000454 |
| ARR1AT | site 2521 (-) | NGATT | S000454 |
| ARR1AT | site 2571 (+) | NGATT | S000454 |
| ARR1AT | site 2584 (-) | NGATT | S000454 |
| ASF1MOTIFCAMV | site 105 (+) | TGACG | S000024 |
| ASF1MOTIFCAMV | site 947 (+) | TGACG | S000024 |
| ASF1MOTIFCAMV | site 1234 (+) | TGACG | S000024 |
| ASF1MOTIFCAMV | site 1351 (+) | TGACG | S000024 |
| ASF1MOTIFCAMV | site 2057 (-) | TGACG | S000024 |
| ASF1MOTIFCAMV | site 2652 (+) | TGACG | S000024 |
| ASF1MOTIFCAMV | site 2686 (-) | TGACG | S000024 |
| ASF1MOTIFCAMV | site 2908 (+) | TGACG | S000024 |
| BIHD1OS | site 503 (+) | TGTCA | S000498 |
| BIHD1OS | site 1073 (-) | TGTCA | S000498 |
| BIHD1OS | site 1101 (-) | TGTCA | S000498 |
| BIHD1OS | site 1578 (-) | TGTCA | S000498 |
| BIHD1OS | site 1642 (-) | TGTCA | S000498 |
| BIHD1OS | site 2065 (+) | TGTCA | S000498 |
| BIHD1OS | site 2820 (-) | TGTCA | S000498 |
| BOXIINTPATPB | site 55 (-) | ATAGAA | S000296 |
| BOXIINTPATPB | site 176 (+) | ATAGAA | S000296 |
| BOXIINTPATPB | site 1029 (+) | ATAGAA | S000296 |
| BOXIINTPATPB | site 1587 (-) | ATAGAA | S000296 |

FIG. 24 CONT.

| | | | |
|---|---|---|---|
| BOXIINTPATPB | site 1636 (-) | ATAGAA | S000296 |
| BOXIINTPATPB | site 1755 (+) | ATAGAA | S000296 |
| BOXLCOREDCPAL | site 602 (+) | ACCWWCC | S000492 |
| BOXLCOREDCPAL | site 2149 (+) | ACCWWCC | S000492 |
| BS1EGCCR | site 1474 (+) | AGCGGG | S000352 |
| CAATBOX1 | site 32 (+) | CAAT | S000028 |
| CAATBOX1 | site 59 (-) | CAAT | S000028 |
| CAATBOX1 | site 170 (+) | CAAT | S000028 |
| CAATBOX1 | site 796 (+) | CAAT | S000028 |
| CAATBOX1 | site 819 (+) | CAAT | S000028 |
| CAATBOX1 | site 838 (-) | CAAT | S000028 |
| CAATBOX1 | site 885 (-) | CAAT | S000028 |
| CAATBOX1 | site 901 (-) | CAAT | S000028 |
| CAATBOX1 | site 1070 (+) | CAAT | S000028 |
| CAATBOX1 | site 1076 (+) | CAAT | S000028 |
| CAATBOX1 | site 1104 (+) | CAAT | S000028 |
| CAATBOX1 | site 1176 (+) | CAAT | S000028 |
| CAATBOX1 | site 1178 (-) | CAAT | S000028 |
| CAATBOX1 | site 1182 (+) | CAAT | S000028 |
| CAATBOX1 | site 1199 (-) | CAAT | S000028 |
| CAATBOX1 | site 1501 (-) | CAAT | S000028 |
| CAATBOX1 | site 1525 (+) | CAAT | S000028 |
| CAATBOX1 | site 1613 (+) | CAAT | S000028 |
| CAATBOX1 | site 1640 (-) | CAAT | S000028 |
| CAATBOX1 | site 1749 (+) | CAAT | S000028 |
| CAATBOX1 | site 1753 (+) | CAAT | S000028 |
| CAATBOX1 | site 1815 (+) | CAAT | S000028 |
| CAATBOX1 | site 2007 (+) | CAAT | S000028 |
| CAATBOX1 | site 2322 (+) | CAAT | S000028 |
| CAATBOX1 | site 2793 (+) | CAAT | S000028 |
| CACGTGMOTIF | site 584 (-) | CACGTG | S000042 |
| CACGTGMOTIF | site 584 (+) | CACGTG | S000042 |
| CACTFTPPCA1 | site 6 (+) | YACT | S000449 |
| CACTFTPPCA1 | site 75 (-) | YACT | S000449 |
| CACTFTPPCA1 | site 95 (-) | YACT | S000449 |
| CACTFTPPCA1 | site 100 (-) | YACT | S000449 |
| CACTFTPPCA1 | site 133 (-) | YACT | S000449 |
| CACTFTPPCA1 | site 159 (-) | YACT | S000449 |
| CACTFTPPCA1 | site 376 (+) | YACT | S000449 |
| CACTFTPPCA1 | site 406 (+) | YACT | S000449 |
| CACTFTPPCA1 | site 486 (+) | YACT | S000449 |
| CACTFTPPCA1 | site 542 (+) | YACT | S000449 |
| CACTFTPPCA1 | site 643 (-) | YACT | S000449 |
| CACTFTPPCA1 | site 646 (-) | YACT | S000449 |
| CACTFTPPCA1 | site 652 (-) | YACT | S000449 |
| CACTFTPPCA1 | site 721 (+) | YACT | S000449 |
| CACTFTPPCA1 | site 784 (-) | YACT | S000449 |
| CACTFTPPCA1 | site 812 (-) | YACT | S000449 |
| CACTFTPPCA1 | site 844 (+) | YACT | S000449 |
| CACTFTPPCA1 | site 921 (-) | YACT | S000449 |
| CACTFTPPCA1 | site 945 (-) | YACT | S000449 |
| CACTFTPPCA1 | site 987 (-) | YACT | S000449 |
| CACTFTPPCA1 | site 1035 (+) | YACT | S000449 |

FIG. 24 CONT.

| | | | |
|---|---|---|---|
| CACTFTPPCA1 | site 1088 (-) | YACT | S000449 |
| CACTFTPPCA1 | site 1240 (+) | YACT | S000449 |
| CACTFTPPCA1 | site 1345 (-) | YACT | S000449 |
| CACTFTPPCA1 | site 1414 (+) | YACT | S000449 |
| CACTFTPPCA1 | site 1456 (-) | YACT | S000449 |
| CACTFTPPCA1 | site 1461 (-) | YACT | S000449 |
| CACTFTPPCA1 | site 1561 (-) | YACT | S000449 |
| CACTFTPPCA1 | site 1658 (-) | YACT | S000449 |
| CACTFTPPCA1 | site 1685 (-) | YACT | S000449 |
| CACTFTPPCA1 | site 1718 (-) | YACT | S000449 |
| CACTFTPPCA1 | site 1983 (+) | YACT | S000449 |
| CACTFTPPCA1 | site 2089 (+) | YACT | S000449 |
| CACTFTPPCA1 | site 2180 (+) | YACT | S000449 |
| CACTFTPPCA1 | site 2394 (-) | YACT | S000449 |
| CACTFTPPCA1 | site 2409 (-) | YACT | S000449 |
| CACTFTPPCA1 | site 2415 (-) | YACT | S000449 |
| CACTFTPPCA1 | site 2429 (+) | YACT | S000449 |
| CACTFTPPCA1 | site 2492 (-) | YACT | S000449 |
| CACTFTPPCA1 | site 2545 (-) | YACT | S000449 |
| CACTFTPPCA1 | site 2547 (+) | YACT | S000449 |
| CACTFTPPCA1 | site 2550 (+) | YACT | S000449 |
| CACTFTPPCA1 | site 2553 (+) | YACT | S000449 |
| CACTFTPPCA1 | site 2644 (-) | YACT | S000449 |
| CACTFTPPCA1 | site 2728 (-) | YACT | S000449 |
| CACTFTPPCA1 | site 2760 (+) | YACT | S000449 |
| CACTFTPPCA1 | site 2784 (+) | YACT | S000449 |
| CACTFTPPCA1 | site 2825 (-) | YACT | S000449 |
| CANBNNAPA | site 2524 (+) | CNAACAC | S000148 |
| CANBNNAPA | site 2566 (-) | CNAACAC | S000148 |
| CANBNNAPA | site 2587 (+) | CNAACAC | S000148 |
| CAREOSREP1 | site 1891 (-) | CAACTC | S000421 |
| CARGCW8GAT | site 170 (-) | CWWWWWWWWG | S000431 |
| CARGCW8GAT | site 170 (+) | CWWWWWWWWG | S000431 |
| CARGCW8GAT | site 1645 (-) | CWWWWWWWWG | S000431 |
| CARGCW8GAT | site 1645 (+) | CWWWWWWWWG | S000431 |
| CARGCW8GAT | site 2246 (-) | CWWWWWWWWG | S000431 |
| CARGCW8GAT | site 2246 (+) | CWWWWWWWWG | S000431 |
| CBFHV | site 1520 (+) | RYCGAC | S000497 |
| CBFHV | site 2672 (-) | RYCGAC | S000497 |
| CBFHV | site 2922 (+) | RYCGAC | S000497 |
| CCAATBOX1 | site 31 (+) | CCAAT | S000030 |
| CCAATBOX1 | site 901 (-) | CCAAT | S000030 |
| CCAATBOX1 | site 1175 (+) | CCAAT | S000030 |
| CCAATBOX1 | site 1199 (-) | CCAAT | S000030 |
| CCAATBOX1 | site 1501 (-) | CCAAT | S000030 |
| CCAATBOX1 | site 1612 (+) | CCAAT | S000030 |
| CCAATBOX1 | site 1814 (+) | CCAAT | S000030 |
| CCAATBOX1 | site 2792 (+) | CCAAT | S000030 |
| CDA1ATCAB2 | site 612 (+) | CAAAACGC | S000440 |
| CDA1ATCAB2 | site 2159 (+) | CAAAACGC | S000440 |
| CELLCYCLESC | site 2218 (-) | CACGAAAA | S000031 |
| CGACGOSAMY3 | site 497 (+) | CGACG | S000205 |
| CGACGOSAMY3 | site 1386 (+) | CGACG | S000205 |

FIG. 24 CONT.

| | | | |
|---|---|---|---|
| CGACGOSAMY3 | site 2661 (-) | CGACG | S000205 |
| CGACGOSAMY3 | site 2671 (-) | CGACG | S000205 |
| CGACGOSAMY3 | site 2948 (+) | CGACG | S000205 |
| CGACGOSAMY3 | site 2984 (-) | CGACG | S000205 |
| CGACGOSAMY3 | site 2989 (+) | CGACG | S000205 |
| CGCGBOXAT | site 2536 (-) | VCGCGB | S000501 |
| CGCGBOXAT | site 2536 (+) | VCGCGB | S000501 |
| CGCGBOXAT | site 2558 (-) | VCGCGB | S000501 |
| CGCGBOXAT | site 2558 (+) | VCGCGB | S000501 |
| CGCGBOXAT | site 2560 (-) | VCGCGB | S000501 |
| CGCGBOXAT | site 2560 (+) | VCGCGB | S000501 |
| CGCGBOXAT | site 2562 (-) | VCGCGB | S000501 |
| CGCGBOXAT | site 2562 (+) | VCGCGB | S000501 |
| CGCGBOXAT | site 2658 (-) | VCGCGB | S000501 |
| CGCGBOXAT | site 2658 (+) | VCGCGB | S000501 |
| CGCGBOXAT | site 2719 (-) | VCGCGB | S000501 |
| CGCGBOXAT | site 2719 (+) | VCGCGB | S000501 |
| CGCGBOXAT | site 2950 (-) | VCGCGB | S000501 |
| CGCGBOXAT | site 2950 (+) | VCGCGB | S000501 |
| CIACADIANLELHC | site 1495 (-) | CAANNNNATC | S000252 |
| CIACADIANLELHC | site 2593 (+) | CAANNNNATC | S000252 |
| CPBCSPOR | site 1416 (-) | TATTAG | S000491 |
| CURECORECR | site 160 (-) | GTAC | S000493 |
| CURECORECR | site 160 (+) | GTAC | S000493 |
| CURECORECR | site 541 (-) | GTAC | S000493 |
| CURECORECR | site 541 (+) | GTAC | S000493 |
| CURECORECR | site 647 (-) | GTAC | S000493 |
| CURECORECR | site 647 (+) | GTAC | S000493 |
| CURECORECR | site 740 (-) | GTAC | S000493 |
| CURECORECR | site 740 (+) | GTAC | S000493 |
| CURECORECR | site 922 (-) | GTAC | S000493 |
| CURECORECR | site 922 (+) | GTAC | S000493 |
| CURECORECR | site 1739 (-) | GTAC | S000493 |
| CURECORECR | site 1739 (+) | GTAC | S000493 |
| CURECORECR | site 1962 (-) | GTAC | S000493 |
| CURECORECR | site 1962 (+) | GTAC | S000493 |
| CURECORECR | site 2088 (-) | GTAC | S000493 |
| CURECORECR | site 2088 (+) | GTAC | S000493 |
| CURECORECR | site 2410 (-) | GTAC | S000493 |
| CURECORECR | site 2410 (+) | GTAC | S000493 |
| CURECORECR | site 2444 (-) | GTAC | S000493 |
| CURECORECR | site 2444 (+) | GTAC | S000493 |
| CURECORECR | site 2546 (-) | GTAC | S000493 |
| CURECORECR | site 2546 (+) | GTAC | S000493 |
| CURECORECR | site 2614 (-) | GTAC | S000493 |
| CURECORECR | site 2614 (+) | GTAC | S000493 |
| CURECORECR | site 2828 (-) | GTAC | S000493 |
| CURECORECR | site 2828 (+) | GTAC | S000493 |
| DOFCOREZM | site 157 (+) | AAAG | S000265 |
| DOFCOREZM | site 218 (+) | AAAG | S000265 |
| DOFCOREZM | site 245 (-) | AAAG | S000265 |
| DOFCOREZM | site 266 (+) | AAAG | S000265 |
| DOFCOREZM | site 320 (-) | AAAG | S000265 |

FIG. 24 CONT.

| | | | |
|---|---|---|---|
| DOFCOREZM | site 343 (+) | AAAG | S000265 |
| DOFCOREZM | site 733 (-) | AAAG | S000265 |
| DOFCOREZM | site 757 (+) | AAAG | S000265 |
| DOFCOREZM | site 810 (+) | AAAG | S000265 |
| DOFCOREZM | site 956 (+) | AAAG | S000265 |
| DOFCOREZM | site 1012 (-) | AAAG | S000265 |
| DOFCOREZM | site 1083 (+) | AAAG | S000265 |
| DOFCOREZM | site 1096 (+) | AAAG | S000265 |
| DOFCOREZM | site 1145 (+) | AAAG | S000265 |
| DOFCOREZM | site 1212 (+) | AAAG | S000265 |
| DOFCOREZM | site 1257 (+) | AAAG | S000265 |
| DOFCOREZM | site 1308 (+) | AAAG | S000265 |
| DOFCOREZM | site 1335 (+) | AAAG | S000265 |
| DOFCOREZM | site 1359 (-) | AAAG | S000265 |
| DOFCOREZM | site 1451 (+) | AAAG | S000265 |
| DOFCOREZM | site 1481 (-) | AAAG | S000265 |
| DOFCOREZM | site 1529 (+) | AAAG | S000265 |
| DOFCOREZM | site 1651 (+) | AAAG | S000265 |
| DOFCOREZM | site 1675 (+) | AAAG | S000265 |
| DOFCOREZM | site 1823 (-) | AAAG | S000265 |
| DOFCOREZM | site 1844 (+) | AAAG | S000265 |
| DOFCOREZM | site 1899 (-) | AAAG | S000265 |
| DOFCOREZM | site 1922 (+) | AAAG | S000265 |
| DOFCOREZM | site 2047 (-) | AAAG | S000265 |
| DOFCOREZM | site 2105 (-) | AAAG | S000265 |
| DOFCOREZM | site 2203 (+) | AAAG | S000265 |
| DOFCOREZM | site 2372 (+) | AAAG | S000265 |
| DPBFCOREDCDC3 | site 535 (+) | ACACNNG | S000292 |
| DPBFCOREDCDC3 | site 576 (-) | ACACNNG | S000292 |
| DPBFCOREDCDC3 | site 650 (-) | ACACNNG | S000292 |
| DPBFCOREDCDC3 | site 924 (+) | ACACNNG | S000292 |
| DPBFCOREDCDC3 | site 927 (-) | ACACNNG | S000292 |
| DPBFCOREDCDC3 | site 2123 (-) | ACACNNG | S000292 |
| DPBFCOREDCDC3 | site 2413 (-) | ACACNNG | S000292 |
| DPBFCOREDCDC3 | site 2527 (+) | ACACNNG | S000292 |
| DPBFCOREDCDC3 | site 2563 (-) | ACACNNG | S000292 |
| DPBFCOREDCDC3 | site 2590 (+) | ACACNNG | S000292 |
| DPBFCOREDCDC3 | site 2823 (-) | ACACNNG | S000292 |
| DRECRTCOREAT | site 2672 (-) | RCCGAC | S000418 |
| DRECRTCOREAT | site 2922 (+) | RCCGAC | S000418 |
| E2FCONSENSUS | site 1199 (+) | WTTSSCSS | S000476 |
| EBOXBNNAPA | site 301 (-) | CANNTG | S000144 |
| EBOXBNNAPA | site 301 (+) | CANNTG | S000144 |
| EBOXBNNAPA | site 584 (-) | CANNTG | S000144 |
| EBOXBNNAPA | site 584 (+) | CANNTG | S000144 |
| EBOXBNNAPA | site 650 (-) | CANNTG | S000144 |
| EBOXBNNAPA | site 650 (+) | CANNTG | S000144 |
| EBOXBNNAPA | site 925 (-) | CANNTG | S000144 |
| EBOXBNNAPA | site 925 (+) | CANNTG | S000144 |
| EBOXBNNAPA | site 927 (-) | CANNTG | S000144 |
| EBOXBNNAPA | site 927 (+) | CANNTG | S000144 |
| EBOXBNNAPA | site 1176 (-) | CANNTG | S000144 |
| EBOXBNNAPA | site 1176 (+) | CANNTG | S000144 |

FIG. 24 CONT.

| | | | |
|---|---|---|---|
| EBOXBNNAPA | site 1781 (-) | CANNTG | S000144 |
| EBOXBNNAPA | site 1781 (+) | CANNTG | S000144 |
| EBOXBNNAPA | site 1880 (-) | CANNTG | S000144 |
| EBOXBNNAPA | site 1880 (+) | CANNTG | S000144 |
| EBOXBNNAPA | site 1965 (-) | CANNTG | S000144 |
| EBOXBNNAPA | site 1965 (+) | CANNTG | S000144 |
| EBOXBNNAPA | site 2131 (-) | CANNTG | S000144 |
| EBOXBNNAPA | site 2131 (+) | CANNTG | S000144 |
| EBOXBNNAPA | site 2413 (-) | CANNTG | S000144 |
| EBOXBNNAPA | site 2413 (+) | CANNTG | S000144 |
| EBOXBNNAPA | site 2490 (-) | CANNTG | S000144 |
| EBOXBNNAPA | site 2490 (+) | CANNTG | S000144 |
| EBOXBNNAPA | site 2823 (-) | CANNTG | S000144 |
| EBOXBNNAPA | site 2823 (+) | CANNTG | S000144 |
| EECCRCAH1 | site 2216 (+) | GANTTNC | S000494 |
| ELRECOREPCRP1 | site 982 (-) | TTGACC | S000142 |
| ELRECOREPCRP1 | site 1894 (+) | TTGACC | S000142 |
| ELRECOREPCRP1 | site 2234 (+) | TTGACC | S000142 |
| GARE1OSREP1 | site 1112 (+) | TAACAGA | S000419 |
| GAREAT | site 637 (-) | TAACAAR | S000439 |
| GAREAT | site 806 (+) | TAACAAR | S000439 |
| GAREAT | site 2399 (-) | TAACAAR | S000439 |
| GATABOX | site 140 (+) | GATA | S000039 |
| GATABOX | site 272 (+) | GATA | S000039 |
| GATABOX | site 298 (-) | GATA | S000039 |
| GATABOX | site 374 (+) | GATA | S000039 |
| GATABOX | site 609 (-) | GATA | S000039 |
| GATABOX | site 730 (-) | GATA | S000039 |
| GATABOX | site 905 (+) | GATA | S000039 |
| GATABOX | site 1225 (+) | GATA | S000039 |
| GATABOX | site 1238 (+) | GATA | S000039 |
| GATABOX | site 1321 (+) | GATA | S000039 |
| GATABOX | site 1856 (+) | GATA | S000039 |
| GATABOX | site 1877 (-) | GATA | S000039 |
| GATABOX | site 1948 (-) | GATA | S000039 |
| GATABOX | site 2156 (-) | GATA | S000039 |
| GATABOX | site 2312 (-) | GATA | S000039 |
| GATABOX | site 2505 (-) | GATA | S000039 |
| GCCCORE | site 1464 (-) | GCCGCC | S000430 |
| GT1CONSENSUS | site 62 (+) | GRWAAW | S000198 |
| GT1CONSENSUS | site 140 (+) | GRWAAW | S000198 |
| GT1CONSENSUS | site 272 (+) | GRWAAW | S000198 |
| GT1CONSENSUS | site 306 (+) | GRWAAW | S000198 |
| GT1CONSENSUS | site 329 (-) | GRWAAW | S000198 |
| GT1CONSENSUS | site 337 (+) | GRWAAW | S000198 |
| GT1CONSENSUS | site 347 (+) | GRWAAW | S000198 |
| GT1CONSENSUS | site 412 (-) | GRWAAW | S000198 |
| GT1CONSENSUS | site 441 (+) | GRWAAW | S000198 |
| GT1CONSENSUS | site 832 (+) | GRWAAW | S000198 |
| GT1CONSENSUS | site 833 (+) | GRWAAW | S000198 |
| GT1CONSENSUS | site 953 (+) | GRWAAW | S000198 |
| GT1CONSENSUS | site 992 (+) | GRWAAW | S000198 |
| GT1CONSENSUS | site 1016 (+) | GRWAAW | S000198 |

FIG. 24 CONT.

| | | | |
|---|---|---|---|
| GT1CONSENSUS | site 1850 (+) | GRWAAW | S000198 |
| GT1CONSENSUS | site 1856 (+) | GRWAAW | S000198 |
| GT1CONSENSUS | site 1885 (+) | GRWAAW | S000198 |
| GT1CONSENSUS | site 1908 (-) | GRWAAW | S000198 |
| GT1CONSENSUS | site 1916 (+) | GRWAAW | S000198 |
| GT1CONSENSUS | site 1926 (+) | GRWAAW | S000198 |
| GT1CONSENSUS | site 2217 (-) | GRWAAW | S000198 |
| GT1CONSENSUS | site 2255 (+) | GRWAAW | S000198 |
| GT1CONSENSUS | site 2264 (+) | GRWAAW | S000198 |
| GT1CONSENSUS | site 2310 (-) | GRWAAW | S000198 |
| GT1CONSENSUS | site 2329 (+) | GRWAAW | S000198 |
| GT1CORE | site 109 (+) | GGTTAA | S000125 |
| GT1CORE | site 315 (-) | GGTTAA | S000125 |
| GT1CORE | site 1694 (+) | GGTTAA | S000125 |
| GT1GMSCAM4 | site 62 (+) | GAAAAA | S000453 |
| GT1GMSCAM4 | site 412 (-) | GAAAAA | S000453 |
| GT1GMSCAM4 | site 833 (+) | GAAAAA | S000453 |
| GT1GMSCAM4 | site 1016 (+) | GAAAAA | S000453 |
| GT1GMSCAM4 | site 2264 (+) | GAAAAA | S000453 |
| GTGANTG10 | site 76 (+) | GTGA | S000378 |
| GTGANTG10 | site 134 (+) | GTGA | S000378 |
| GTGANTG10 | site 490 (-) | GTGA | S000378 |
| GTGANTG10 | site 508 (-) | GTGA | S000378 |
| GTGANTG10 | site 598 (-) | GTGA | S000378 |
| GTGANTG10 | site 785 (+) | GTGA | S000378 |
| GTGANTG10 | site 932 (+) | GTGA | S000378 |
| GTGANTG10 | site 946 (+) | GTGA | S000378 |
| GTGANTG10 | site 1047 (-) | GTGA | S000378 |
| GTGANTG10 | site 1100 (+) | GTGA | S000378 |
| GTGANTG10 | site 1223 (+) | GTGA | S000378 |
| GTGANTG10 | site 1319 (+) | GTGA | S000378 |
| GTGANTG10 | site 1341 (-) | GTGA | S000378 |
| GTGANTG10 | site 1442 (+) | GTGA | S000378 |
| GTGANTG10 | site 1567 (+) | GTGA | S000378 |
| GTGANTG10 | site 1659 (+) | GTGA | S000378 |
| GTGANTG10 | site 1719 (+) | GTGA | S000378 |
| GTGANTG10 | site 2059 (-) | GTGA | S000378 |
| GTGANTG10 | site 2070 (-) | GTGA | S000378 |
| GTGANTG10 | site 2286 (-) | GTGA | S000378 |
| GTGANTG10 | site 2486 (-) | GTGA | S000378 |
| GTGANTG10 | site 2605 (-) | GTGA | S000378 |
| GTGANTG10 | site 2633 (+) | GTGA | S000378 |
| GTGANTG10 | site 2651 (+) | GTGA | S000378 |
| GTGANTG10 | site 2742 (+) | GTGA | S000378 |
| IBOXCORE | site 140 (+) | GATAA | S000199 |
| IBOXCORE | site 272 (+) | GATAA | S000199 |
| IBOXCORE | site 1856 (+) | GATAA | S000199 |
| IBOXCORE | site 2311 (-) | GATAA | S000199 |
| INRNTPSADB | site 69 (-) | YTCANTYY | S000395 |
| INRNTPSADB | site 307 (-) | YTCANTYY | S000395 |
| INRNTPSADB | site 457 (+) | YTCANTYY | S000395 |
| INRNTPSADB | site 1886 (-) | YTCANTYY | S000395 |
| INRNTPSADB | site 2034 (+) | YTCANTYY | S000395 |

FIG. 24 CONT.

| | | | |
|---|---|---|---|
| INTRONLOWER | site 520 (+) | TGCAGG | S000086 |
| INTRONLOWER | site 2129 (+) | TGCAGG | S000086 |
| L1BOXATPDF1 | site 545 (+) | TAAATGYA | S000386 |
| LECPLEACS2 | site 2293 (+) | TAAAATAT | S000465 |
| LTRECOREATCOR15 | site 2188 (+) | CCGAC | S000153 |
| LTRECOREATCOR15 | site 2662 (-) | CCGAC | S000153 |
| LTRECOREATCOR15 | site 2672 (-) | CCGAC | S000153 |
| LTRECOREATCOR15 | site 2923 (+) | CCGAC | S000153 |
| MARTBOX | site 19 (-) | TTWTWTTWTT | S000067 |
| MARTBOX | site 63 (-) | TTWTWTTWTT | S000067 |
| MARTBOX | site 683 (-) | TTWTWTTWTT | S000067 |
| MARTBOX | site 892 (-) | TTWTWTTWTT | S000067 |
| MARTBOX | site 1367 (-) | TTWTWTTWTT | S000067 |
| MARTBOX | site 1418 (-) | TTWTWTTWTT | S000067 |
| MARTBOX | site 1600 (-) | TTWTWTTWTT | S000067 |
| MARTBOX | site 2196 (-) | TTWTWTTWTT | S000067 |
| MYB1AT | site 1693 (-) | WAACCA | S000408 |
| MYB1AT | site 1723 (-) | WAACCA | S000408 |
| MYB2AT | site 1469 (-) | TAACTG | S000177 |
| MYB2CONSENSUSAT | site 1469 (-) | YAACKG | S000409 |
| MYB2CONSENSUSAT | site 2874 (-) | YAACKG | S000409 |
| MYBCORE | site 108 (+) | CNGTTR | S000176 |
| MYBCORE | site 202 (-) | CNGTTR | S000176 |
| MYBCORE | site 1112 (-) | CNGTTR | S000176 |
| MYBCORE | site 1230 (+) | CNGTTR | S000176 |
| MYBCORE | site 1469 (+) | CNGTTR | S000176 |
| MYBCORE | site 1541 (-) | CNGTTR | S000176 |
| MYBCORE | site 2874 (+) | CNGTTR | S000176 |
| MYBGAHV | site 806 (+) | TAACAAA | S000181 |
| MYBPLANT | site 601 (+) | MACCWAMC | S000167 |
| MYBPLANT | site 1218 (-) | MACCWAMC | S000167 |
| MYBPLANT | site 2148 (+) | MACCWAMC | S000167 |
| MYBPZM | site 603 (+) | CCWACC | S000179 |
| MYBPZM | site 1977 (+) | CCWACC | S000179 |
| MYBPZM | site 2150 (+) | CCWACC | S000179 |
| MYBST1 | site 904 (+) | GGATA | S000180 |
| MYCATERD1 | site 301 (+) | CATGTG | S000413 |
| MYCATERD1 | site 925 (-) | CATGTG | S000413 |
| MYCATERD1 | site 927 (+) | CATGTG | S000413 |
| MYCATERD1 | site 1880 (+) | CATGTG | S000413 |
| MYCATRD22 | site 301 (-) | CACATG | S000174 |
| MYCATRD22 | site 925 (+) | CACATG | S000174 |
| MYCATRD22 | site 927 (-) | CACATG | S000174 |
| MYCATRD22 | site 1880 (-) | CACATG | S000174 |
| MYCCONSENSUSAT | site 301 (-) | CANNTG | S000407 |
| MYCCONSENSUSAT | site 301 (+) | CANNTG | S000407 |
| MYCCONSENSUSAT | site 584 (-) | CANNTG | S000407 |
| MYCCONSENSUSAT | site 584 (+) | CANNTG | S000407 |
| MYCCONSENSUSAT | site 650 (-) | CANNTG | S000407 |
| MYCCONSENSUSAT | site 650 (+) | CANNTG | S000407 |
| MYCCONSENSUSAT | site 925 (-) | CANNTG | S000407 |
| MYCCONSENSUSAT | site 925 (+) | CANNTG | S000407 |
| MYCCONSENSUSAT | site 927 (-) | CANNTG | S000407 |

FIG. 24 CONT.

| | | | |
|---|---|---|---|
| MYCCONSENSUSAT | site 927 (+) | CANNTG | S000407 |
| MYCCONSENSUSAT | site 1176 (-) | CANNTG | S000407 |
| MYCCONSENSUSAT | site 1176 (+) | CANNTG | S000407 |
| MYCCONSENSUSAT | site 1781 (-) | CANNTG | S000407 |
| MYCCONSENSUSAT | site 1781 (+) | CANNTG | S000407 |
| MYCCONSENSUSAT | site 1880 (-) | CANNTG | S000407 |
| MYCCONSENSUSAT | site 1880 (+) | CANNTG | S000407 |
| MYCCONSENSUSAT | site 1965 (-) | CANNTG | S000407 |
| MYCCONSENSUSAT | site 1965 (+) | CANNTG | S000407 |
| MYCCONSENSUSAT | site 2131 (-) | CANNTG | S000407 |
| MYCCONSENSUSAT | site 2131 (+) | CANNTG | S000407 |
| MYCCONSENSUSAT | site 2413 (-) | CANNTG | S000407 |
| MYCCONSENSUSAT | site 2413 (+) | CANNTG | S000407 |
| MYCCONSENSUSAT | site 2490 (-) | CANNTG | S000407 |
| MYCCONSENSUSAT | site 2490 (+) | CANNTG | S000407 |
| MYCCONSENSUSAT | site 2823 (-) | CANNTG | S000407 |
| MYCCONSENSUSAT | site 2823 (+) | CANNTG | S000407 |
| NAPINMOTIFBN | site 741 (+) | TACACAT | S000070 |
| NAPINMOTIFBN | site 923 (+) | TACACAT | S000070 |
| NODCON1GM | site 731 (-) | AAAGAT | S000461 |
| NODCON1GM | site 1651 (+) | AAAGAT | S000461 |
| NODCON2GM | site 1309 (-) | CTCTT | S000462 |
| NODCON2GM | site 1336 (-) | CTCTT | S000462 |
| NODCON2GM | site 1530 (-) | CTCTT | S000462 |
| NTBBF1ARROLB | site 156 (-) | ACTTTA | S000273 |
| NTBBF1ARROLB | site 265 (-) | ACTTTA | S000273 |
| NTBBF1ARROLB | site 1211 (-) | ACTTTA | S000273 |
| NTBBF1ARROLB | site 1843 (-) | ACTTTA | S000273 |
| OSE1ROOTNODULE | site 731 (-) | AAAGAT | S000467 |
| OSE1ROOTNODULE | site 1651 (+) | AAAGAT | S000467 |
| OSE2ROOTNODULE | site 1309 (-) | CTCTT | S000468 |
| OSE2ROOTNODULE | site 1336 (-) | CTCTT | S000468 |
| OSE2ROOTNODULE | site 1530 (-) | CTCTT | S000468 |
| PALBOXAPC | site 2238 (+) | CCGTCC | S000137 |
| PALBOXAPC | site 2715 (+) | CCGTCC | S000137 |
| POLASIG1 | site 22 (+) | AATAAA | S000080 |
| POLASIG1 | site 51 (-) | AATAAA | S000080 |
| POLASIG1 | site 340 (+) | AATAAA | S000080 |
| POLASIG1 | site 765 (-) | AATAAA | S000080 |
| POLASIG1 | site 801 (-) | AATAAA | S000080 |
| POLASIG1 | site 878 (-) | AATAAA | S000080 |
| POLASIG1 | site 1077 (+) | AATAAA | S000080 |
| POLASIG1 | site 1183 (+) | AATAAA | S000080 |
| POLASIG1 | site 1370 (+) | AATAAA | S000080 |
| POLASIG1 | site 1421 (+) | AATAAA | S000080 |
| POLASIG1 | site 1526 (+) | AATAAA | S000080 |
| POLASIG1 | site 1603 (+) | AATAAA | S000080 |
| POLASIG1 | site 1632 (-) | AATAAA | S000080 |
| POLASIG1 | site 1919 (+) | AATAAA | S000080 |
| POLASIG2 | site 1061 (-) | AATTAAA | S000081 |
| POLASIG2 | site 2271 (+) | AATTAAA | S000081 |
| POLASIG3 | site 275 (+) | AATAAT | S000088 |
| POLASIG3 | site 278 (+) | AATAAT | S000088 |

FIG. 24 CONT.

| | | | |
|---|---|---|---|
| POLASIG3 | site 428 (+) | AATAAT | S000088 |
| POLASIG3 | site 862 (-) | AATAAT | S000088 |
| POLASIG3 | site 865 (-) | AATAAT | S000088 |
| POLASIG3 | site 868 (-) | AATAAT | S000088 |
| POLASIG3 | site 871 (-) | AATAAT | S000088 |
| POLASIG3 | site 874 (-) | AATAAT | S000088 |
| POLASIG3 | site 1367 (+) | AATAAT | S000088 |
| POLASIG3 | site 1418 (+) | AATAAT | S000088 |
| POLASIG3 | site 1614 (+) | AATAAT | S000088 |
| POLASIG3 | site 1617 (+) | AATAAT | S000088 |
| POLASIG3 | site 2323 (+) | AATAAT | S000088 |
| POLLEN1LELAT52 | site 178 (+) | AGAAA | S000245 |
| POLLEN1LELAT52 | site 336 (+) | AGAAA | S000245 |
| POLLEN1LELAT52 | site 1757 (+) | AGAAA | S000245 |
| POLLEN1LELAT52 | site 1915 (+) | AGAAA | S000245 |
| POLLEN1LELAT52 | site 2254 (+) | AGAAA | S000245 |
| PREATPRODH | site 72 (-) | ACTCAT | S000450 |
| PREATPRODH | site 310 (-) | ACTCAT | S000450 |
| PREATPRODH | site 1655 (-) | ACTCAT | S000450 |
| PREATPRODH | site 1889 (-) | ACTCAT | S000450 |
| PYRIMIDINEBOXOSRAMY1A | site 319 (+) | CCTTTT | S000259 |
| PYRIMIDINEBOXOSRAMY1A | site 955 (-) | CCTTTT | S000259 |
| PYRIMIDINEBOXOSRAMY1A | site 1082 (-) | CCTTTT | S000259 |
| PYRIMIDINEBOXOSRAMY1A | site 1256 (-) | CCTTTT | S000259 |
| PYRIMIDINEBOXOSRAMY1A | site 1898 (+) | CCTTTT | S000259 |
| QELEMENTZMZM13 | site 1895 (-) | AGGTCA | S000254 |
| RAV1AAT | site 1301 (+) | CAACA | S000314 |
| RAV1AAT | site 1541 (+) | CAACA | S000314 |
| RAV1AAT | site 2525 (+) | CAACA | S000314 |
| RAV1AAT | site 2588 (+) | CAACA | S000314 |
| RAV1AAT | site 2833 (-) | CAACA | S000314 |
| RAV1AAT | site 2836 (-) | CAACA | S000314 |
| RAV1AAT | site 2839 (-) | CAACA | S000314 |
| RAV1AAT | site 2842 (-) | CAACA | S000314 |
| RAV1BAT | site 2131 (-) | CACCTG | S000315 |
| RBCSCONSENSUS | site 1502 (-) | AATCCAA | S000127 |
| RBCSCONSENSUS | site 2521 (+) | AATCCAA | S000127 |
| RBCSCONSENSUS | site 2584 (+) | AATCCAA | S000127 |
| ROOTMOTIFTAPOX1 | site 258 (-) | ATATT | S000098 |
| ROOTMOTIFTAPOX1 | site 259 (+) | ATATT | S000098 |
| ROOTMOTIFTAPOX1 | site 296 (-) | ATATT | S000098 |
| ROOTMOTIFTAPOX1 | site 390 (-) | ATATT | S000098 |
| ROOTMOTIFTAPOX1 | site 797 (-) | ATATT | S000098 |
| ROOTMOTIFTAPOX1 | site 798 (+) | ATATT | S000098 |
| ROOTMOTIFTAPOX1 | site 820 (-) | ATATT | S000098 |
| ROOTMOTIFTAPOX1 | site 823 (+) | ATATT | S000098 |
| ROOTMOTIFTAPOX1 | site 860 (+) | ATATT | S000098 |
| ROOTMOTIFTAPOX1 | site 895 (-) | ATATT | S000098 |
| ROOTMOTIFTAPOX1 | site 1189 (-) | ATATT | S000098 |
| ROOTMOTIFTAPOX1 | site 1875 (-) | ATATT | S000098 |
| ROOTMOTIFTAPOX1 | site 2296 (-) | ATATT | S000098 |
| ROOTMOTIFTAPOX1 | site 2297 (+) | ATATT | S000098 |
| ROOTMOTIFTAPOX1 | site 2511 (+) | ATATT | S000098 |

FIG. 24 CONT.

| | | | |
|---|---|---|---|
| S1FBOXSORPS1L21 | site 182 (+) | ATGGTA | S000223 |
| SEBFCONSSTPR10A | site 463 (+) | YTGTCWC | S000391 |
| SEBFCONSSTPR10A | site 1100 (-) | YTGTCWC | S000391 |
| SEBFCONSSTPR10A | site 2040 (+) | YTGTCWC | S000391 |
| SEF1MOTIF | site 798 (+) | ATATTTAWW | S000006 |
| SEF3MOTIFGM | site 1140 (+) | AACCCA | S000115 |
| SEF4MOTIFGM7S | site 18 (-) | RTTTTTR | S000103 |
| SEF4MOTIFGM7S | site 112 (-) | RTTTTTR | S000103 |
| SEF4MOTIFGM7S | site 151 (+) | RTTTTTR | S000103 |
| SEF4MOTIFGM7S | site 891 (-) | RTTTTTR | S000103 |
| SEF4MOTIFGM7S | site 911 (-) | RTTTTTR | S000103 |
| SEF4MOTIFGM7S | site 1133 (-) | RTTTTTR | S000103 |
| SEF4MOTIFGM7S | site 1185 (-) | RTTTTTR | S000103 |
| SEF4MOTIFGM7S | site 1363 (-) | RTTTTTR | S000103 |
| SEF4MOTIFGM7S | site 1372 (-) | RTTTTTR | S000103 |
| SEF4MOTIFGM7S | site 1405 (-) | RTTTTTR | S000103 |
| SEF4MOTIFGM7S | site 1423 (-) | RTTTTTR | S000103 |
| SEF4MOTIFGM7S | site 1485 (-) | RTTTTTR | S000103 |
| SEF4MOTIFGM7S | site 1599 (-) | RTTTTTR | S000103 |
| SEF4MOTIFGM7S | site 1697 (-) | RTTTTTR | S000103 |
| SEF4MOTIFGM7S | site 1730 (+) | RTTTTTR | S000103 |
| SEF4MOTIFGM7S | site 1988 (+) | RTTTTTR | S000103 |
| SITEIIATCYTC | site 396 (+) | TGGGCY | S000474 |
| SITEIIATCYTC | site 1973 (+) | TGGGCY | S000474 |
| SORLIP1AT | site 229 (-) | GCCAC | S000482 |
| SORLIP1AT | site 399 (+) | GCCAC | S000482 |
| SORLIP1AT | site 1435 (-) | GCCAC | S000482 |
| SORLIP1AT | site 1462 (-) | GCCAC | S000482 |
| SORLIP1AT | site 1764 (-) | GCCAC | S000482 |
| SORLIP1AT | site 1807 (-) | GCCAC | S000482 |
| SORLIP1AT | site 2723 (+) | GCCAC | S000482 |
| SORLIP2AT | site 397 (+) | GGGCC | S000483 |
| SORLIP2AT | site 555 (-) | GGGCC | S000483 |
| SORLIP2AT | site 1205 (+) | GGGCC | S000483 |
| SORLIP2AT | site 1974 (+) | GGGCC | S000483 |
| SORLIP2AT | site 2639 (+) | GGGCC | S000483 |
| SORLIP5AT | site 74 (+) | GAGTGAG | S000486 |
| SORLIP5AT | site 1657 (+) | GAGTGAG | S000486 |
| SURECOREATSULTR11 | site 465 (-) | GAGAC | S000499 |
| SURECOREATSULTR11 | site 773 (+) | GAGAC | S000499 |
| SURECOREATSULTR11 | site 1008 (+) | GAGAC | S000499 |
| SURECOREATSULTR11 | site 1355 (+) | GAGAC | S000499 |
| SURECOREATSULTR11 | site 1444 (+) | GAGAC | S000499 |
| SURECOREATSULTR11 | site 1663 (+) | GAGAC | S000499 |
| SURECOREATSULTR11 | site 2042 (-) | GAGAC | S000499 |
| SV40COREENHAN | site 1092 (+) | GTGGWWHG | S000123 |
| T/GBOXATPIN2 | site 1048 (-) | AACGTG | S000458 |
| TAAAGSTKST1 | site 156 (+) | TAAAG | S000387 |
| TAAAGSTKST1 | site 265 (+) | TAAAG | S000387 |
| TAAAGSTKST1 | site 342 (+) | TAAAG | S000387 |
| TAAAGSTKST1 | site 1211 (+) | TAAAG | S000387 |
| TAAAGSTKST1 | site 1307 (+) | TAAAG | S000387 |
| TAAAGSTKST1 | site 1334 (+) | TAAAG | S000387 |

FIG. 24 CONT.

| | | | |
|---|---|---|---|
| TAAAGSTKST1 | site 1450 (+) | TAAAG | S000387 |
| TAAAGSTKST1 | site 1528 (+) | TAAAG | S000387 |
| TAAAGSTKST1 | site 1674 (+) | TAAAG | S000387 |
| TAAAGSTKST1 | site 1843 (+) | TAAAG | S000387 |
| TAAAGSTKST1 | site 1921 (+) | TAAAG | S000387 |
| TATABOX3 | site 172 (-) | TATTAAT | S000110 |
| TATABOX3 | site 788 (-) | TATTAAT | S000110 |
| TATABOX3 | site 880 (+) | TATTAAT | S000110 |
| TATABOX3 | site 2298 (+) | TATTAAT | S000110 |
| TATABOX4 | site 366 (-) | TATATAA | S000111 |
| TATABOX4 | site 367 (+) | TATATAA | S000111 |
| TATABOX4 | site 2452 (-) | TATATAA | S000111 |
| TATABOX4 TATABOX4 | site 2796(-) | TATATAA | S000111 |
| TATABOX5 | site 21 (-) | TTATTT | S000203 |
| TATABOX5 | site 339 (-) | TTATTT | S000203 |
| TATABOX5 | site 766 (+) | TTATTT | S000203 |
| TATABOX5 | site 875 (+) | TTATTT | S000203 |
| TATABOX5 | site 1136 (-) | TTATTT | S000203 |
| TATABOX5 | site 1366 (-) | TTATTT | S000203 |
| TATABOX5 | site 1602 (-) | TTATTT | S000203 |
| TATABOX5 | site 1918 (-) | TTATTT | S000203 |
| TATABOX5 | site 2247 (+) | TTATTT | S000203 |
| TATABOXOSPAL | site 2248 (+) | TATTTAA | S000400 |
| TATAPVTRNALEU | site 365 (+) | TTTATATA | S000340 |
| TATCCAOSAMY | site 903 (-) | TATCCA | S000403 |
| TBOXATGAPB | site 809 (-) | ACTTTG | S000383 |
| TBOXATGAPB | site 1011 (+) | ACTTTG | S000383 |
| TBOXATGAPB | site 2371 (-) | ACTTTG | S000383 |
| WBBOXPCWRKY1 | site 2233 (+) | TTTGACY | S000310 |
| WBBOXPCWRKY1 | site 2368 (-) | TTTGACY | S000310 |
| WBOXATNPR1 | site 983 (-) | TTGAC | S000390 |
| WBOXATNPR1 | site 1233 (+) | TTGAC | S000390 |
| WBOXATNPR1 | site 1350 (+) | TTGAC | S000390 |
| WBOXATNPR1 | site 1577 (+) | TTGAC | S000390 |
| WBOXATNPR1 | site 1641 (+) | TTGAC | S000390 |
| WBOXATNPR1 | site 1894 (+) | TTGAC | S000390 |
| WBOXATNPR1 | site 2234 (+) | TTGAC | S000390 |
| WBOXATNPR1 | site 2369 (-) | TTGAC | S000390 |
| WBOXATNPR1 | site 2813 (+) | TTGAC | S000390 |
| WBOXHVISO1 | site 1339 (-) | TGACT | S000442 |
| WBOXHVISO1 | site 2284 (-) | TGACT | S000442 |
| WBOXHVISO1 | site 2368 (-) | TGACT | S000442 |
| WBOXHVISO1 | site 2787 (+) | TGACT | S000442 |
| WBOXHVISO1 | site 2814 (+) | TGACT | S000442 |
| WBOXNTERF3 | site 621 (-) | TGACY | S000457 |
| WBOXNTERF3 | site 982 (-) | TGACY | S000457 |
| WBOXNTERF3 | site 1339 (-) | TGACY | S000457 |
| WBOXNTERF3 | site 1895 (+) | TGACY | S000457 |
| WBOXNTERF3 | site 2168 (-) | TGACY | S000457 |
| WBOXNTERF3 | site 2235 (+) | TGACY | S000457 |
| WBOXNTERF3 | site 2284 (-) | TGACY | S000457 |
| WBOXNTERF3 | site 2368 (-) | TGACY | S000457 |
| WBOXNTERF3 | site 2787 (+) | TGACY | S000457 |

FIG. 24 CONT.

| | | | |
|---|---|---|---|
| WBOXNTERF3 | site 2814 (+) | TGACY | S000457 |
| WRKY71OS | site 105 (+) | TGAC | S000447 |
| WRKY71OS | site 504 (-) | TGAC | S000447 |
| WRKY71OS | site 622 (-) | TGAC | S000447 |
| WRKY71OS | site 947 (+) | TGAC | S000447 |
| WRKY71OS | site 983 (-) | TGAC | S000447 |
| WRKY71OS | site 1073 (+) | TGAC | S000447 |
| WRKY71OS | site 1101 (+) | TGAC | S000447 |
| WRKY71OS | site 1234 (+) | TGAC | S000447 |
| WRKY71OS | site 1340 (-) | TGAC | S000447 |
| WRKY71OS | site 1351 (+) | TGAC | S000447 |
| WRKY71OS | site 1578 (+) | TGAC | S000447 |
| WRKY71OS | site 1642 (+) | TGAC | S000447 |
| WRKY71OS | site 1895 (+) | TGAC | S000447 |
| WRKY71OS | site 2058 (-) | TGAC | S000447 |
| WRKY71OS | site 2066 (-) | TGAC | S000447 |
| WRKY71OS | site 2169 (-) | TGAC | S000447 |
| WRKY71OS | site 2235 (+) | TGAC | S000447 |
| WRKY71OS | site 2285 (-) | TGAC | S000447 |
| WRKY71OS | site 2369 (-) | TGAC | S000447 |
| WRKY71OS | site 2652 (+) | TGAC | S000447 |
| WRKY71OS | site 2687 (-) | TGAC | S000447 |
| WRKY71OS | site 2787 (+) | TGAC | S000447 |
| WRKY71OS | site 2814 (+) | TGAC | S000447 |
| WRKY71OS | site 2820 (+) | TGAC | S000447 |
| WRKY71OS | site 2908 (+) | TGAC | S000447 |

FIG. 24 CONT.

ATAACTACTATAGATTATAAAAATAAAACCCCAATGCTAATTAGATTTGATTTATTCTATTGAAAAAAAAAATGAGTGAGAGGCGGACCGTAGGAGTAGAGT
AATGACGGTTAAAAACTATAAGAACGAAACAGTGATCGATAATGTTTGATTTTTAAAGTACCAAGAACAATTAATAGAAATGGTAGCCAGCCAGGCAAGCAA
CCGGAGGAGCGACAAAGGAGAGGGGTGGCGTCTGATGCGACTTTTAAAACTATAATATTATAAAGTTGATAATAATAATGTTAATTTAAAAAATATCATGTG
GAAATGAGTTAACCTTTTACAAATTTTCAAGAAAATAAAGGGTAAAAAATTAGATGATTTTATATAAGATACTTAGCCGTGCAAATATGTGGGCCACCCTAC
TAGTTTTTCGCTGAATCTGAATAATTTTGAACGGTAAAAAAAATCCGGTTCATTCTGTCTCCTCTACCTGTCGTCTACACTTCACGAACGACGCTGTCATCA
CGCTGCGGATGCAGGTTACAGTTTACACACGTACTAAATGCACCGGCCCTTCAAACGAGAACCGGCCGGTGTGCACGTGCACGTAGCTCACACCTACCTATC
AAAACGCTGGTCATTCTGTTCTAGCTTGTTAGTAGTACAAGTGTGTCTATGAGAGAATCCATTATATGCCAAAAAAAAAACATAAGCACAGACGAAATTATA
GCGTTATACTTCATCTATCTTTTATGTACACATTTACATACAAAAGTTAATTTATTTTGAGACGAAGGGAGTGATTAATAACAATATTTATTAACAAAGTAG
AACAATATATTTAGGGGAAAAATTGTATACTAAAACAAATCCTATATTATTATTATTATTATTTATTAATTGTGTAAAAATATAATTGGATATGTAAAAATG
GGAGTACACATGTGTGAGCATCTCTAAGTGACGAGGAAAAGGAATAGCAGAGGACAAGCCAAGGGTCAAGTAGGGTAATGGCAGCTAGAGAGACTTTGAAAA
ATTATAAAATAGAACACTAATGATGATCACGTTCGATTTTTTTAATTTGCAATGACAATAAAAAAGGAGTGGTGGAAAGGTGACAATGGTGTAACAGATTTT
GTATAAACTATAAAAATAACCCAAAGAAGGCCAAGTTTAAATTTTAAGAATCCCAATTGCAATAAAAATATGTGCGATTGGCGGGCCATAAAGTTGTTAGGT
GATAGCGGTTGACGATACTTCCAAAATCTATAAAAGGGAAACCTAAGTTAATCAGGTTTGAATCTTAAAATCCTAACAACATTAAAGAGGCGAGGTGATAGG
CGGGCTGTAAAGAGTCACAGTGGTTGACGAGACTTTTAAAAATAATAAAAACGGAACAACGACGACCAGGTTCAAATTTAAAAATGCTACTAATAATAAAAA
CGATGGGTGGCGGGTGAGACGTAAAGGAGTAGAGTGGCGGCAGTTAGCGGGGCTTTTAAAAACGATGATCAGATTGGATTTTTTAAATGCCATCGACAATAA
AGAGGAGGAGCAACAGGCAAGCCATCAAGGAGTAGGGTGATGGTGGTTGACAGGACTTCTATAGATTATAAAAATAAAACCCCAATAATAATCAGATTTGAT
TTATTCTATTGACAAAAAAAAGATGAGTGAGAGACGGACCGTAAAGGAGCAGAGTAATGATGGTTAAAAACTATAAGAACGAAACAGTGATGGTTTGATTTT
TAAGGTACCAAGAACAATCAATAGAAATGGTGGCCAGCCAGGCAAGCAGCTGGAGGAGCTACAAGGAGAGGGGTGGCGCCCAATGCGACTTTTAAAACTATA
AAATTATAAAGTTGGTAATGATAATGTTAATTTTAAAAAATATCATGTGGAAATGAGTTGACCTTTTACAAATTTTCAAGAAAATAAAGGGTAAAAAATTAG
ATGATTTTATATCGGTGCTAGATGTACAAATGCGTGGGCCAACCTACTAGTTTTTGGCTGAATCTGAACAATTTTGAACGGTCCAAAAAAACCGGTTCATTC
TGTCTCCTTTGCCTGTCGTCACGCTGTCATCACGCTGCGGATGCAGCGTACTAAACGCACCGGCCTTTCAAACAAGAACCGGCCGGTGTGCAGGTGCACGTA
GCTCAAACCTACCTATCAAAACGCTGGTCATTCTGTCTACTCCATCCGACCCCAAAAAAAAAAGACAAACCCTGATTTTCGTGTCTAACGTTTGACCGTCCG
TCTTATTTAAGAAAATTATGAAAAAAAATTAAAAAAACAAGTCACACATAAAATATTAATCATGTTTTATCATCTAACAATAATGAAAATACGAATTATAAA
AAAATTTCATATAAGACGGACAGTCAAAGTTGGACACGGAAACCTAGAGTAACTTGTTAGGCAGTACAAGTGTGTGTAGCTATACTCCCCCTGTCCTGTACC
AGCTTATATATATATAGGCGAGCCAACGAGCGAGAGCCATCACCAAGTGCAAGGTAGCTATCATATATTCTGCGAATCCAACACAAGCACCGCGGCGTAGTACT
ACTACTTGCGCGGCGTGTTAGATTCGCGTGCGAATCCAACACAAGCAGATCGATCACGCACGGTACGCCATGGGCGAGGCGGTGAAGGGGCCAGTGGTGGT
GACGGGCGCGTCGGGCTTCGTCGGCTCATGGCTCGTCATGAAGCTCCTCCAGGCCGGCTACACCGTCCGCGCCACAGTGCGCGACCCCTGTGAGCTCTCTCA
TCGTGCACTCTAGCTCTCTCCTCGTAGTTTACTGACTCCAATTATATATGCCGCTTGCTTGACTCTGACAAGTGTACGTGTTGTTGTTGTTGTTTTCAGCTA
ACGTTGGGAAGACGAAGCCGTTGCTGGAGCTGGCGGGGTAGAAGGAGAGGCTGACGCTGTGGAAGGCCGACCTGGGCGAGGAAGGCAGCTTCGACGCGGCGA
TCAGGGGTTGCACGGGCGTGTTCCACGTCGCGACGCCCATGGACTTCGAGTCCGAGGACCCGGAGAACGAGGTGGTCAAGCCCAC SEQ ID NO: 185

FIG. 25A

*CACCTACC, etc.* = Myb motif

TA… = annotated 5' UTR

ATG = start codon

*CAAGTG,* etc = *E-box motif*

*A = SNP (A/C)*

ACT = consensus with regulatory element

ACTACTTGCGGCGCGCG SEQ ID NO:186    mACTnGCGnnGCG SEQ ID NO:187
TTGACTGGnGGnTGCG SEQ ID NO:143 (*for eg., see,* Maize Anthocyanin Gene a2 anthocyanin regulatory element consensus sequence, (Lesnik and Chandler, 1998, Plant Physiol 117, 437-445; herein incorporated by reference)

AGATTCGCCGTGCCGA SEQ ID NO:188    nGAnTnGCnnGnGn SEQ ID NO:189
CGACTTGCnGGTGC SEQ ID NO:190 (*for eg., see,* myb-like and bHLH-like consensus DNA binding sequences for Consensus Sequence for Anthocyanin Promoters in Tuerck and Fromm, 1994, Plant Cell 6, 1655-1665; herein incorporated by reference)

FIG. 25A CONT.

ATAACTACTATAGATTATAAAAATAAAACCCCAATGCTAATTAGATTTGATTTATTCTATTGAAAAAAAAAAATGAGTGAGAGGCGGACCGTAGGAGTAGAGTAATGACGGTT
AAAAACTATAAGAACGAAACAGTGATCGATAATGTTTGATTTTTAAAGTACCAAGAACAATTAATAGAAATGGTAGCCAGCCAGGCAAGCAACCGGAGGAGCGACAAAGGAG
AGGGGTGGCGTCTGATGCGACTTTTAAAACTATAATATTATAAAGTTGATAATAATAATGTTAATTTAAAAAATATCATGTGGAAATGAGTTAACCTTTTACAAATTTTCAA
GAAAATAAAGGGTAAAAAATTAGATGATTTTATATAAGATACTTAGCCGTGCAAATATGTGGGCCACCCTACTAGTTTTTCGCTGAATCTGAATAATTTTGAACGGTAAAAA
AAATCCGGTTCATTCTGTCTCCTCTACCTGTCGTCTACACTTCACGAACGACGCTGTCATCACGCTGCGGATGCAGGTTACAGTTTACACACGTACTAAATGCACCGGCCCT
TCAAACGAGAACCGGCCGGTGTGCACGTGCACGTAGCTCACACCTACCTATCAAAACGCTGGTCATTCTGTTCTAGCTTGTTAGTAGTACAAGTGTGTCTATGAGAGAATCC
ATTATATGCCAAAAAAAAAACATAAGCACAGACGAAATTATAGCGTTATACTTCATCTATCTTTTATGTACACATTTACATACAAAAGTTAATTTATTTTGAGACGAAGGGA
GTGATTAATAACAATATTTATTAACAAAGTAGAACAATATATTTAGGGGAAAAATTGTATACTAAAACAAATCCTATATTATTATTATTATTATTTATTAATTGTGTAAAAA
TATAATTGGATATGTAAAAATGGGAGTACACATGTGTGAGCATCTCTAAGTGACGAGGAAAAGGAATAGCAGAGGACAAGCCAAGGGTCAAGTAGGGTAATGGCAGCTAGAG
AGACTTTGAAAAATTATAAAATAGAACACTAATGATGATCACGTTCGATTTTTTTAATTTGCAATGACAATAAAAAAGGAGTGGTGGAAAGGTGACAATGGTGTAACAGATT
TTGTATAAACTATAAAAATAACCCAAAGAAGGCCAAGTTTAAATTTTAAGAATCCCAATTGCAATAAAAATATGTGCGATTGGCGGGCCATAAAGTTGTTAGGTGATAGCGG
TTGACGATACTTCCAAAATCTATAAAAGGGAAACCTAAGTTAATCAGGTTTGAATCTTAAAATCCTAACAACATTAAAGAGGCGAGGTGATAGGCGGGCTGTAAAGAGTCAC
AGTGGTTGACGAGACTTTTAAAAATAATAAAAACGGAACAACGACGACCAGGTTCAAATTTAAAAATGCTACTAATAATAAAAACGATGGGTGGCGGGTGAGACGTAAAGGA
GTAGAGTGGCGGCAGTTAGCGGGGCTTTTAAAAACGATGATCAGATTGGATTTTTTAAATGCCATCGACAATAAAGAGGAGGAGCAACAGGCAAGCCATCAAGGAGTAGGGT
GATGGTGGTTGACAGGACTTCTATAGATTATAAAAATAAAACCCCAATAATAATCAGATTTGATTTATTCTATTGACAAAAAAAAGATGAGTGAGAGACGGACCGTAAAGGA
GCAGAGTAATGATGGTTAAAAACTATAAGAACGAAACAGTGATGGTTTGATTTTTAAGGTACCAAGAACAATCAATAGAAATGGTGGCCAGCCAGGCAAGCAGCTGGAGGAG
CTACAAGGAGAGGGGTGGCGCCCAATGCGACTTTTAAAACTATAAAATTATAAAGTTGGTAATGATAATGTTAATTTTAAAAAATATCATGTGGAAATGAGTTGACCTTTTA
CAAATTTTCAAGAAAATAAAGGGTAAAAAATTAGATGATTTTATATCGGTGCTAGATGTACAAATGCGTGGGCCAACCTACTAGTTTTTGGCTGAATCTGAACAATTTTGAA
CGGTCCAAAAAAACCGGTTCATTCTGTCTCCTTTGCCTGTCGTCACGCTGTCATCACGCTGCGGATGCAGCGTACTAAACGCACCGGCCTTTCAAACAAGAACCGGCCGGTG
TGCAGGTGCACGTAGCTCAAACCTACCTATCAAAACGCTGGTCATTCTGTCTACTCCATCCGACCCCAAAAAAAAAAGACAAACCCTGATTTTCGTGTCTAACGTTTGACCG
TCCGTCTTATTTAAGAAAATTATGAAAAAAAATTAAAAAAACAAGTCACACATAAAATATTAATCATGTTTTATCATCTAACAATAATGAAAATACGAATTATAAAAAAATT
TCATATAAGACGGACAGTCAAAGTTGGACACGGAAACCTAGAGTAACTTGTTAGGCAGTACAAGTGTGTGTAGCTATACTCCCCCTGTCCTGTACCAGCTTATATATATAGG
CGAGCCAACGAGCGAGAGCCATCACCAAGTGCAAGGTAGCTATCATATATTCTGCGAATCCAACACAAGCACCGCGGCGTAGTACTACTACTTGCGCGCGCGTGTTAGATTC
GCGTGCGAATCCAACACAAGCAGATCGATCACGCACGGTACGCCATGGGCGAGGCGGTGAAGGGGCCAGTGGTGGTGACGGGCGCGTCGGGCTTCGTCGGCTCATGGCTCGT
CATGAAGCTCCTCCAGGCCGGCTACACCGTCCGCGCCACAGTGCGCGACCCCTGTGAGCTCTCTCATCGTGCACTCTAGCTCTCTCCTCGTAGTTTACTGACTCCAATTATA
TATGCCGCTTGCTTGACTCTGACAAGTGTACGTGTTGTTGTTGTTGTTTTCAGCTAACGTTGGGAAGACGAAGCCGTTGCTGGAGCTGGCGGGGTAGAAGGAGAGGCTGACG
CTGTGGAAGGCCGACCTGGGCGAGGAAGGCAGCTTCGACGCGGCGATCAGGGGTTGCACGGGCGTGTTCCACGTCGCGACGCCC

SEQ ID NO:191

FIG. 25B

RICE COMPRISING AN RC RESPONSIVE PROMOTER DRIVING EXPRESSION OF A HETEROLOGOUS NUCLEIC ACID MOLECULE

SEQUENCE LISTING

The instant application contains a Sequence Listing which has been submitted in ASCII format via EFS-Web and is hereby incorporated by reference in its entirety. Said ASCII copy, created on Aug. 25, 2011, is named 50341016.txt and is 504,473 bytes in size.

FIELD OF THE INVENTION

The present invention relates to the production of red pericarp and seed coat in rice, and in particular, compositions comprising a basic helix-turn-helix red anthocyanin transcription factor, Rc, and methods using Rc for identifying rice germplasm comprising Rc including but not limited to grain quality grading and seed certification analysis. In a preferred embodiment, the present invention further relates to promoter sequences Rc binding elements including but not limited to regulatory elements of genes associated with anthocyanidin/proanthocyanidin pathways and the use of these elements for controlling weedy red rice plants and controlling the spread of transgenes into weedy red rice plants.

BACKGROUND OF THE INVENTION

The majority of rice (*Oryza sativa*, L.) crops that are grown and consumed throughout the world are white-grained varieties, however rice grain may also be brown, red and/or purple. Rice plants producing red grain are ubiquitous among wild rice plants and in some regions of the world rice cultivars producing red grains are preferred over white grains for their taste, texture and ceremonial or medicinal value. Consumer interest in red or purple rice grains represents a growing specialty market in the United States. However, the ubiquitous presence of red rice plants as a weed in farmers' white rice plant fields is the most economically important pest and grain quality problem faced by United States rice growers today, leading to losses of as much as $50 million per year (Gealy et al. (2002) Weed Science 50:333-339). In fact, in the United States the United States Secretary of Agriculture classifies red rice as a "Noxious Weed" such that importation and red rice plant cultivation is highly regulated.

Although naturally occurring relatives of *Oryza sativa* (Asian cultivated rice) are not native to the United States, weedy rice plants producing red grain are a constant problem in the rice growing areas of the United States. These weedy red rice plants were ubiquitous contaminants of the original white rice plants imported into the United States where efforts to remove them completely from the white rice growing areas have been ineffective, in part due to red rice plants out-crossing with cultivated, white-grained varieties and due to growth of red rice plants in uncultivated areas near cultivated white rice fields. These weedy rice plants exhibit increased dormancy and shattering allowing red rice plants to persist in white plant rice fields despite vigorous attempts to remove them. Efforts to manage the problem genetically have been fraught with difficulties, in part because both red and white-grained varieties appear to be the same color until the husk is removed. Thus millers must dehusk and sample each load of rice in order to determine the degree of red rice contamination. Further, breeding efforts are difficult because rice plants in general may display an unstable color phenotype, making it difficult to genetically track the character in breeding populations. While the red color can be removed by polishing in order to provide white grains, red rice must be polished longer than white rice to remove all traces of color, with the increased polishing resulting in more broken grains and a decrease in market value of red rice. Thus causing a decrease in market value of white-grained rice crops with substantial red rice contamination.

Recent efforts to control red rice include transgenic herbicide resistance systems such as the Clearfield-Newpath™ system wherein transgenic white rice plants "Clearfield™" expressing resistance to Newpath™ herbicide allow the removal of red rice plants susceptible to Newpath™ herbicide. However there is recent evidence that the white rice plants are cross-pollinating with red rice plants thus transferring the herbicide resistance to the weedy red rice plants.

Thus, there is a need to identify molecular components and methods for the production of red pigmentation in rice. These novel components will offer new methods for identifying and controlling "red rice" plants for seed and grain certification analysis and further for breeding strategies aimed at minimizing the extent of the red rice problem in the United States and internationally.

SUMMARY OF THE INVENTION

The present invention relates to the production of red pericarp and seed coat in rice, and in particular, compositions comprising a basic helix-turn-helix red anthocyanin transcription factor, Rc, and methods using Rc for identifying rice germplasm comprising Rc including but not limited to grain quality grading and seed certification analysis. In a preferred embodiment, the present invention further relates to Rc responsive promoter sequences and Rc binding elements including but not limited to regulatory elements of genes associated with anthocyanidin/proanthocyanidin pathways and the use of these elements for controlling weedy red rice plants and controlling the spread of transgenes into weedy red rice plants.

The inventors discovered novel rice alleles encoding a putative bHLH transcriptional protein, Rc, associated with enhancing red pigmentation in pericarp and seed coat of rice plants. Further, the present inventors discovered single nucleotide polymorphisms that when present indicate that red pigmentation will not be produced even when nucleotide sequences encoding the novel bHLH transcriptional protein are present. Further, the present inventors contemplate the identification, composition and methods for using Rc responsive promoter elements comprising the promoter regions of genes that enhance red rice pigmentation. In particular, the present inventors contemplate the use of Rc responsive promoter elements for providing red rice plant containment vectors.

The present invention provides nucleic acid and amino acid sequences for Rc alleles encoding bHLH type transcription factors for enhancing red pigmentation in rice plants. The present invention also provides novel PCR primers for identifying rice germplasm indicating the potential for red and non-red pigmentation in rice pericarp and seed coat. The invention further provides Rc responsive promoter elements for controlling red pigmentation production, specifically for enhancing red pigmentation in pericarp and seed coat of red rice plants.

The inventors further provide gene silencing vectors comprising Rc responsive promoter elements for containment of red rice plants and/or production of red rice seed. The present invention is not limited to any particular sequence encoding Rc alleles.

In some embodiments, the invention provides an isolated nucleic acid molecule selected from the group consisting of SEQ ID NO:03 and sequences at least 96% identical to SEQ ID NO:03 and a nucleic acid sequence that encodes a polypeptide at least 56% identical to SEQ ID NO:01, wherein said nucleic acid encodes a basic helix-loop-helix protein that regulates to an Rc responsive promoter for enhancing red pigmentation in a plant part. Accordingly, the present invention provides an isolated nucleic acid molecule comprising nucleotide sequences encoding a polypeptide at least 56%, 60%, 70%, 80%, 90%, 95% (or more) identical to SEQ ID NO: 01. Accordingly, the present invention provides an isolated nucleic acid molecule comprising nucleotide sequences encoding a polypeptide at least 96%, 98% (or more) identical to SEQ ID NO:03. In some embodiments, the present invention provides a plant part from a variety of plant types. The present invention is not limited to any particular type of plant providing the plant part. Indeed a variety of plants are contemplated. In some embodiments, said plant providing a part is a grass family plant or Gramineae family plant. In some embodiments, said plant is selected from the group consisting of a rice plant, a wheat plant and a maize plant. In some embodiments, said plant part is a rice plant part. It is not meant to limit the type of plant part. Indeed, a variety of plant parts are contemplated, including, but not limited to a pericarp and a seed coat. In some embodiments, the present invention provides nucleic acids and proteins for enhancing red pigmentation. It is not meant to limit the type of red pigmentation. Indeed a variety of types of red pigmentation are contemplated, including, but not limited to producing molecules of proanthocyanidin and/or altering production of a leucoanthocyanidin molecule or a anthocyanidin molecule. In further embodiments, enhancing red pigmentation is enhancing genes that encode an enzyme. It is not meant to limit the type of enzyme. Indeed a variety of types of enzymes are contemplated, including but not limited to a reductase, hydroxylase, synthase, transferase, isomerase, dihydroflavonol reductase, dihydroflavonol-4-reductase, flavanone 3-hydroxylase, flavonoid 3'-hydroxylase, anthocyanin synthase, anthocyanin reductase, leucoanthocyanidin reductase, flavonol 3-O-glucosyltransferase, flavonol synthase, glutathione S-transferase, chalcone isomerase, multi-drug resistance protein3 and a homolog thereof. Further embodiments include but are not limited to genes for enhancing red pigmentation such as anthocyaninless1, anthocyaninless2, tt2, bronze1, bronze2, c2, and a homolog thereof. In some embodiments, enhancing red pigmentation is increasing the production of molecules associated with red pigment production. It is not meant to limit the type of molecules. Indeed a variety of molecules are contemplated, including but not limited to a flavonol, cyanin, anthocyanin, proanthocyanin, catechin, leucoanthocyanidin, cyanidin, anthocyanidin and proanthocyanidin molecule.

In some embodiments, the basic helix-loop-helix protein (Rc) that regulates an Rc responsive promoter alters expression of anthocyanidin and proanthocyanidin pathway associated genes. In further embodiments, the basic helix-loop-helix protein (Rc) responsive promoter is selected from the group consisting of SEQ ID NOs: 119-137, 191, and 193. Accordingly in other embodiments, the (Rc) responsive promoter is at least 96% (or more) identical to any of SEQ ID NOs: 119-137, 191, and 193. In further embodiments, the (Rc) responsive promoter comprises an anthocyanidin regulatory element. In yet further embodiments, the anthocyanidin regulatory element comprises SEQ ID NOs: 119-137, 153-178 and 186-190. Accordingly in other embodiments, the anthocyanidin regulatory element is at least 96% (or more) identical to any of SEQ ID NOs: 119-137, 153-178 and 186-190.

In some embodiments, the invention provides a vector construct comprising the nucleic acid molecule selected from the group consisting of SEQ ID NO:03 and sequences at least 96% identical to SEQ ID NO:03 and a nucleic acid sequence that encodes a polypeptide at least 56% identical to SEQ ID NO:01, wherein said nucleic acid encodes a basic helix-loop-helix protein that regulates to an Rc responsive promoter for enhancing red pigmentation in a plant part. Accordingly, the present invention provides vector construct comprising nucleotide sequences encoding a polypeptide at least 56%, 60%, 70%, 80%, 90%, 95% (or more) identical to SEQ ID NO: 01. Accordingly, the present invention provides vector construct comprising nucleotide sequences encoding a polypeptide at least 96%, 98% (or more) identical to SEQ ID NO:03. In some embodiments, the invention provides a vector construct comprising the nucleic acid wherein said nucleic acid is operably linked to an exogenous promoter. It is not meant to limit the type of promoter, indeed a variety of vectors are contemplated, including but not limited to a eukaryotic promoter. In some embodiments, a eukaryotic promoter is active in a plant. In some embodiments, the invention provides a vector for expression in a plant. It is not meant to limit the type of vector, indeed a variety of vectors are contemplated, including but not limited to a eukaryotic vector. In some embodiments, a eukaryotic vector is a plant vector. In further embodiments, a plant vector is a pANDA vector or a T-DNA vector.

In other embodiments, the present invention provides a transgenic plant comprising an exogenous nucleic acid molecule encoding a polypeptide fragment at least 56% identical to SEQ ID NO: 01, wherein said nucleic acid encodes a basic helix-loop-helix protein that regulates to an Rc responsive promoter of genes for enhancing red pigmentation in a plant part. Accordingly, the present invention provides an exogenous nucleic acid molecule comprising nucleotide sequences encoding a polypeptide at least 56%, 60%, 70%, 80%, 90%, 95% (or more) identical to SEQ ID NO: 01. Accordingly, the present invention provides an exogenous nucleic acid molecule comprising nucleotide sequences encoding a polypeptide at least 96%, 98% (or more) identical to SEQ ID NO:03. In some embodiments, the present invention provides a plant part from a variety of plant types. The present invention is not limited to any particular type of plant providing the plant part. Indeed a variety of plants are contemplated. In some embodiments, said plant providing a part is a grass family plant or Gramineae family plant. In some embodiments, said plant is selected from the group consisting of a rice plant, a wheat plant and a maize plant. In some embodiments, said plant part is a rice plant part. It is not meant to limit the type of plant part. Indeed, a variety of plant parts are contemplated, including, but not limited to a pericarp and a seed coat. In some embodiments, enhances red pigment production is enhancing proanthocyanidin production. In some embodiments, the exogenous nucleic acid molecule is operably linked to a eukaryotic promoter. In some embodiments, the eukaryotic promoter is active in a plant. In yet further embodiments, the present invention provides a variety of plants. It is not meant to limit the type of plants. Indeed a variety of plants are contemplated including but not limited to Gramineae plants, such as a rice plant, a wheat plant and a maize plant. In some embodiments, the present invention provides a seed of the transgenic plant. In some embodiments, the present invention provides a cultivar of the transgenic plant.

In other embodiments, the present invention provides an expression vector, comprising a first nucleic acid sequence encoding a nucleic acid product that interferes with the expression of a second nucleic acid sequence encoding a polypeptide at least 56% identical to SEQ ID NO:01, wherein said nucleic acid encodes a basic helix-loop-helix protein that regulates to an Rc responsive promoter for enhancing red pigmentation in a plant part. In other embodiments, the present invention provides an isolated nucleic acid molecule comprising nucleotide sequences encoding a polypeptide at least 56%, 60%, 70%, 80%, 90%, 95% (or more) identical to SEQ ID NO: 01. In other embodiments, the present invention provides an expression vector wherein the nucleic acid product that interferes is an antisense sequence. In other embodiments, the present invention provides an expression vector wherein the nucleic acid product that interferes is a dsRNA that mediates RNA interference. In other embodiments, the present invention provides a method for altering the phenotype of a plant, comprising: a) providing; i) an expression vector comprising a nucleic acid sequence encoding a polypeptide fragment at least 56% identical to SEQ ID NO:01; and ii) plant tissue; and b) introducing the vector into the plant tissue so that the phenotype of a plant derived from said plant tissue is altered. In other embodiments, the invention provides the method wherein said plant tissue comprises a pollen or primordial meristem. In other embodiments, the invention provides a method wherein said altered phenotype of a plant is altering phenotype of pericarp. In other embodiments, the invention provides a method wherein said altering phenotype of pericarp is selected from the group consisting of enhancing red pigmentation of pericarp and decreasing red pigmentation of pericarp.

In other embodiments, the present invention provides a composition for determining levels of red pigmentation in grain samples comprising a fragment of a nucleic acid molecule selected from the group consisting of SEQ ID NO:03 and sequences at least 96% identical to SEQ ID NO:03 and a nucleic acid sequence that encodes a polypeptide at least 56% identical to SEQ ID NO:01, wherein said nucleic acid encodes a basic helix-loop-helix protein that regulates to an Rc responsive promoter for enhancing red pigmentation in a plant part. In other embodiments, the present invention provides an isolated nucleic acid molecule comprising nucleotide sequences encoding a polypeptide at least 56%, 60%, 70%, 80%, 90%, 95% (or more) identical to SEQ ID NO: 01. In other embodiments, the present invention provides an isolated nucleic acid molecule comprising nucleotide sequences encoding a polypeptide at least 96%, 98% (or more) identical to SEQ ID NO:03.

In other embodiments, the present invention provides a method for certifying grain, comprising, a) providing, i) a polymerase chain reaction primer, wherein said primer is selected from the group consisting of SEQ ID NOs:52, 53, 54, 55, 56, and 57, ii) a grain sample, wherein said grain sample comprises genomic DNA; and b) using said primers for identifying red pigmentation in the grain sample. Accordingly in other embodiments, the (Rc) responsive promoter is at least 96% (or more) identical to any of SEQ ID NOs:52, 53, 54, 55, 56, and 57. In other embodiments, a grain sample is selected from the group consisting of a rice grain sample and a wheat grain sample. In other embodiments the certifying is detecting the absence of a nucleotide sequence encoding a protein comprising SEQ ID NO:138. In other embodiments, the certifying is detecting the presence of an A instead of a C in nucleotide sequence at least 95% identical to SEQ ID NO:144. In other embodiments, the certifying is detecting a lack of a red pigmentation in a grain sample. It is not meant to limit the type of grain sample, indeed a variety of grain samples are contemplated, including but not limited to a seed grain sample, a field grain sample, a harvested grain sample, and a bagged grain sample. It is not meant to limit the type of certifying, indeed a variety of types of certifying are contemplated including but not limited to a breeder certification, a grower certification, a miller certification, and an import certification.

In some embodiments, the invention provides a method for certifying grain, comprising, a) providing, i) a fragment of a nucleic acid molecule selected from the group consisting of SEQ ID NO:03 and sequences at least 96% identical to SEQ ID NO:03 and a nucleic acid sequence that encodes a polypeptide at least 56% identical to SEQ ID NO:01, wherein said nucleic acid encodes a basic helix-loop-helix protein; and ii) a grain sample, wherein said grain sample comprises genomic DNA; and b) using said fragment for quantifying the amount of red pigmentation in the grain sample. Accordingly, the present invention provides a fragment of a nucleic acid molecule selected from the group consisting of nucleotide sequences encoding a polypeptide at least 56%, 60%, 70%, 80%, 90%, 95% (or more) identical to SEQ ID NO: 01. Accordingly, the present invention provides a fragment of a nucleic acid molecule selected from the group consisting of nucleotide sequences encoding a polypeptide at least 96%, 98% (or more) identical to SEQ ID NO:03.

In other embodiments, the present invention provides a vector construct comprising an Rc responsive promoter, wherein said Rc responsive promoter is selected from the group consisting of SEQ ID NOs: 119-137, 153-178 and 191. In other embodiments, the Rc responsive promoter is operably linked to a containment gene. In other embodiments, the containment gene is expressed in a red rice plant. It is not meant to limit the type of containment gene. Indeed a variety of containment genes for gene silencing are contemplated including but not limited to an endogenous gene or homolog thereof wherein said endogenous gene is a developmental gene, a fertility gene, and a seed forming gene, SEQ ID NOs: 146-150. In other embodiments, the vector construct comprises a pANDA vector. In other embodiments, the containment gene is an exogenous gene. In further embodiments the exogenous containment gene is an herbicide resistance gene for providing resistance to herbicides in non-red rice plants while inducing containment of red rice plants. It is not meant to limit the type of herbicide resistance, indeed a variety of herbicide resistance is contemplated including a glufosinate, an imazethapyr and a glyphosate based herbicide. In further embodiments the herbicide resistance gene for providing resistance in non-red rice plants and susceptibility in red rice plants provides resistance to a Newpath™, Beyond™ or Belero™. In yet further embodiments, the herbicide resistance gene is SEQ ID NO:151.

BRIEF DESCRIPTION OF THE DRAWINGS

FIG. 2 shows exemplary sequenced genes from genomic DNA of an *O. sativa* Nipponbare (white) SEQ ID NO:09, *O. sativa* Jefferson (white) variety SEQ ID NO.06 and an *O. rufipogon* (red) parent SEQ ID NO:04 identifying numerous polymorphisms including an *O. rufipogon* sequence in SEQ ID NO:04 that demonstrated genomic nucleotides in *O. rufipogon* positions 5141-5154 that were not present in *O. sativa* Nipponbare (white) SEQ ID NO:09 and *O. sativa* Jefferson (white) variety SEQ ID NO:06, see, boxed regions. Please note that base numbering is relative for this comparison.

FIG. 4 shows an exemplary published version of a preliminary fine mapped QTL of a pericarp color loci associated with red grain pigmentation, Rc (brown pericarp and seed coat) PAG poster (January 2005).

FIGS. 5A-5BBB show exemplary amino acid and nucleic acid sequences for Rc alleles associated with red rice pericarp color comprising an *O. rufipogon* sequence (SEQ ID NOs:01, 03, and 05) and Rc alleles that associate with white rice color that do not comprise an *O. rufipogon* sequence, i.e. *O. saliva* Jefferson (SEQ ID NOs:02, 04, and 06) and *O. sativa* Nipponbare (SEQ ID NOs:07, 08, and 09).

FIG. 6 shows exemplary polymerase chain reaction (PCR) primers SEQ ID NOs:10-77 for sequencing (SEQ ID NOs:10-43), detecting polymorphisms using INDEL and SSR mapping (SEQ ID NOs: 44-57), detecting the presence of an *O. rufipogon* sequence (SEQ ID NOs: 52-53 and 52-55), and fine mapping (SEQ ID NOs: 58-75), and mRNA sequencing (SEQ ID NOs: 76-77). Base pair (bp) position for each was established using TIGR assembly for chromosome 7 psuedomolecule (version 3) by BLAST comparing each primer to genes through a Gramene database. Other bp numbers were obtained through BLAST searching the same sequences in NCBI, therefore the Gramene BLAST search results were chosen as baseline numbers.

FIGS. 7A-7I show exemplary sequence variations (within coding regions, not over the entire gene) of sequenced varieties of rice and full sequences of Rc alleles (SEQ ID NOs:97-115). Sequences were aligned with bp positions of the varying nucleotides noted in the header column. A 1408-1421 bp difference is amplified by the RID4 (AFex5d/RID12; SEQ ID NOs: 52-53) primer set, a 1833-1844 bp fragment by the RM631 (Afex7d/RM651; SEQ ID NOs: 54-55) primer set, and a 1982-1987 bp fragment by the RM632 (Afend/RM652; SEQ ID NOs: 56-57) primer set. RID5 and RM21197 amplify differences within intronic sequence. Two Up primers are in the upstream (promoter region) of the Rc gene. Two functional single nucleotide polymorphisms (SNPs) detected that distinguished white vs. red grained rice were a 1408-1421 bp insertion that were predicted to result in translation into a protein product comprising a *O. rufipogon* or *rufipogon* domain fragment (SEQ ID NO:138) and a SNP nucleic acid change that would result in an amino acid change at 1353 bp relative to a *rufipogon* genomic sequence. This second SNP introduces a premature stop codon before the *rufipogon* bHLH domain thus identifying a red rice grain indicator SEQ ID NO:143 and white rice grain indicator SEQ ID NO:144.

FIG. 8 shows exemplary Rc homologues in other types of plants (SEQ ID NOs: 116, 117 and 118).

FIGS. 9A-9J show an exemplary screening of 380+ varieties of rice wherein a *rufipogon* domain deletion was detected that associates with a white rice seed phenotype using PCR primers, for example, RID12 (Afex5d) primers (SEQ ID NOs:52 and 53).

FIGS. 12A-12B show an exemplary gene-silencing vector contemplated for use in the present inventions, i.e. pANDA vector.

FIGS. 13A-13Q show exemplary promoter sequences contemplated for use in red rice containment vectors for regulation with an Rc bHLH transcriptional regulatory protein (promoter SEQ ID NOs: 119-137).

FIG. 14 shows exemplary economic loss due to red rice contamination of seed lots (See, Page 114: Rice Grades/red rice percentages in USDA Rice Production Handbook).

FIG. 15 shows exemplary herbicides for treating weedy rice plant infestations of commercial rice fields in the United States (See, Page 39: Table 6-3, Herbicide Ratings for Rice Weed Control, in USDA Rice Production Handbook) and exemplary herbicide treatment for containment red rice in a commercial nonred rice field (See, Page 30: pesticide Ordram 8E (4 pounds per acre)/Bolero in USDA Rice Production Handbook) and an exemplary chart demonstrating a general lack of herbicide control of Red Rice (See, page 46: Red Rice description and image, in USDA Rice Production Handbook).

FIG. 16 shows exemplary sequence fragments for identifying red vs. white pericarp genotypes SEQ ID NOs:142-144.

FIG. 17 shows exemplary developmental genes SEQ ID NOs:146-150 contemplated for targeted knock-out by a red rice containment vector in order to prevent the development of viable seeds, i.e. control (inhibit) the spread of transgenes to red rice.

FIG. 18 shows an exemplary gene for inducing herbicide tolerance (SEQ ID No:151) and contemplated Rc control elements (SEQ ID NOs:153-178) based upon bioinformatic comparisons as presented in the following Figures.

FIGS. 19A-19C show an exemplary clustal analysis where rice promoter regions (SEQ ID NOs:121-123, 124, 126-137) were compared to a maize promoter comprising an anthocyanin control region (SEQ ID NO:152) using Tcoffee for alignments for identifying potential Rc control regions (SEQ ID NOs:153-166).

FIG. 20 shows an exemplary promoter alignment of 5 closely related sequences compared using Tcoffee alignments for identifying Rc control regions (SEQ ID NOs: 167-171).

FIG. 21 shows an exemplary promoter alignment using the 4 most closely related sequences identified in FIG. 20 using Tcoffee alignments for identifying Rc control regions (SEQ ID NOs:172-175).

FIG. 22 shows an exemplary promoter alignment using the 3 most closely related sequences identified in FIG. 20 using Tcoffee alignments for identifying Rc control regions (SEQ ID NOs:176-178).

FIG. 24 shows exemplary cis-elements identified in a 3Kb region upstream of *O. sativa* DFR (SEQ ID NO:185) as determined using a "PLACE" website (PLACE: Plant Cis-acting Regulatory DNA Elements Database). FIG. 24, page 106 discloses "CAANNNNATC" as SEQ ID NO: 195 and page 110 discloses "TTWTWTTWTT" as SEQ ID NO: 196.

FIGS. 25A-25B show exemplary_annotation of e-box, PLACE cis-elements and Myb protein binding motifs in a 3 kb upstream region (SEQ ID NO:185) of *O. sativa* DFR gene (SEQ ID NO:131), including sequences and motifs (SEQ ID NOs:145 and 186-190) comprising anthocyanin regulatory elements.

DEFINITIONS

Figure 1A:
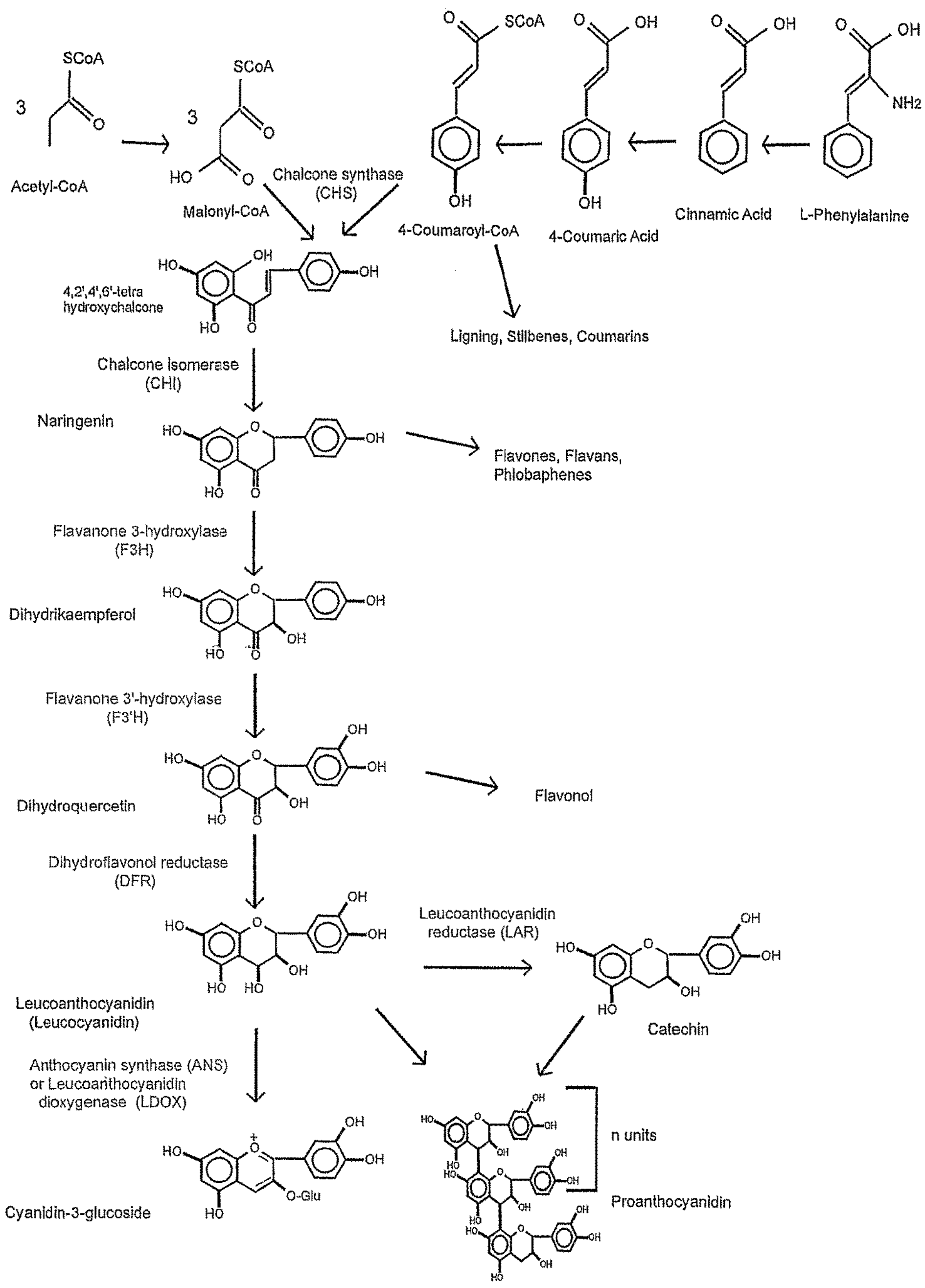
FIGS. 1A-1D show an exemplary biosynthesis pathway for proanthocyanidin and anthocyanidin pigment production in relation to precursor acetyl-CoA and L-phenylalanine molecules; exemplary phenotypic features, description and image of an exemplary red rice plant (See, Page 46: Red Rice description and image, USDA Rice Production Handbook); an exemplary diagram of a seed demonstrating the location of a pericarp layer; and an exemplary diagram for plant proanthocyanidin production, such as in rice, and phlobaphene production such as in maize kernels.
Figure 1B:
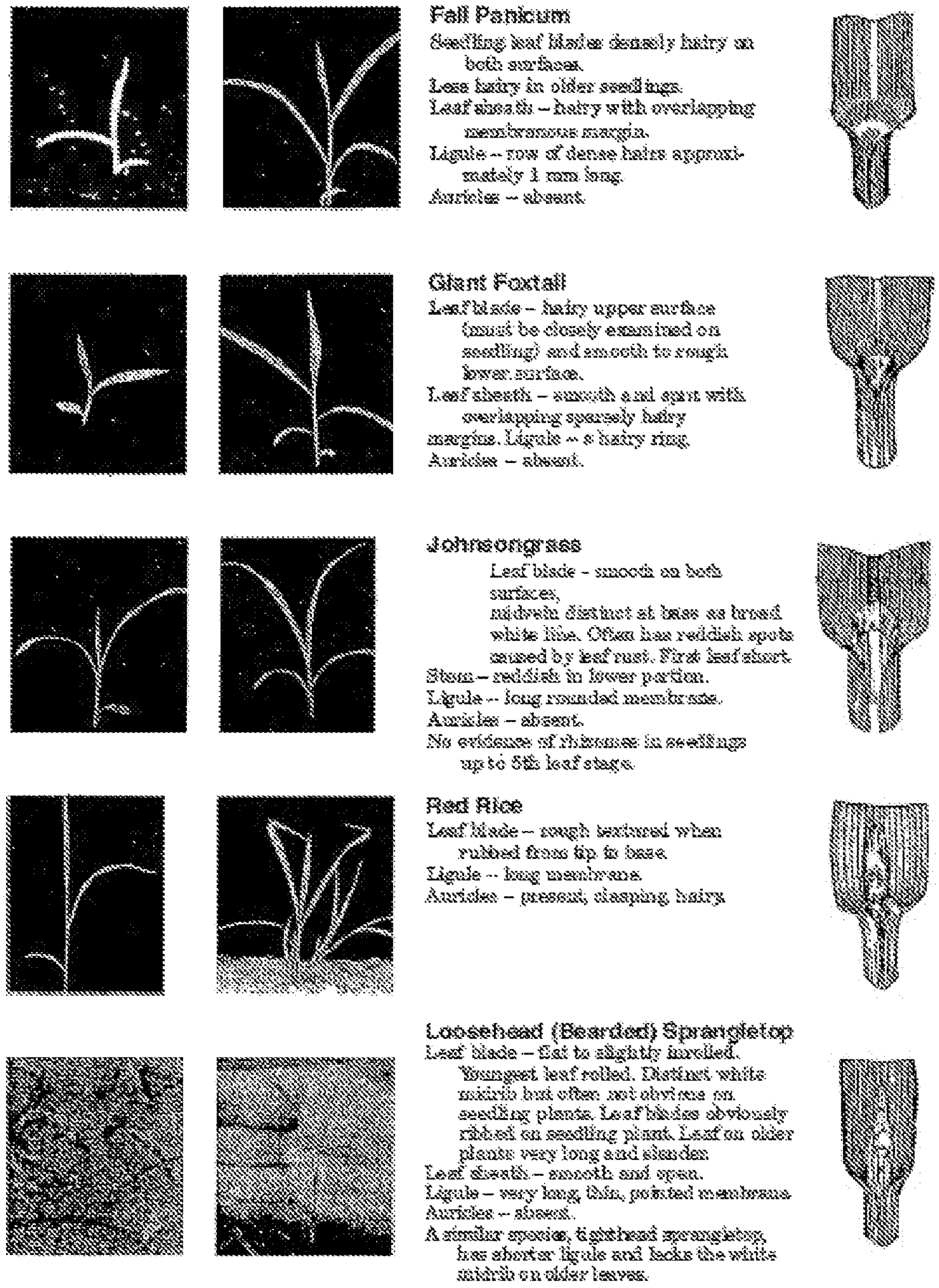

To facilitate an understanding of the present invention, a number of terms and phrases as used herein are defined below:

The use of the article "a" or "an" is intended to include one or more.

As used herein, terms defined in the singular are intended to include those terms defined in the plural and vice versa.

As used herein, the term "plant" is used in it broadest sense. It includes, but is not limited to, any species of woody, ornamental or decorative, crop or cereal, fruit or vegetable plant, and photosynthetic green algae (for example, *Chlamydomonas reinhardtii*). A plant also refers to a plurality of plant cells, which are largely differentiated into a structure that is present at any stage of a plant's development. Such structures include, but are not limited to, seed, meristem, primordial meristem, fruit, callus, shoot, stem, leaf, flower petal, et cetera.

The term "crop" or "crop plant" is used in its broadest sense. The term includes, but is not limited to, any species of plant or algae edible by humans or used as a feed for animals or used, or consumed by humans, or any plant or algae used in industry or commerce, in particular, a crop plant is a grass plant, such as a rice plant, a maize plant and a wheat plant.

As used herein, the terms "grass," "grass plant" and "grasses" refer to plants of the family Gramineae. Grass plants may have a variety of phenotypes, ranging from small to large, twisted to straight, creeping to erect, and annuals to perennials, for example, rice, wheat, and corn are grass plants.

As used herein, the terms "gramineous," "Graminaceae," and "Poaceae" refers to plants belonging to the grass family.

As used herein, the terms "maize," "*Zea mays*" and "corn" refer to a crop plant used as animal and human food.

As used herein, the term "rice" in reference to a "rice plant" is a *Oryza* spp., i.e. cultivated varieties, noncultivated rice plants and ancestral rice plants, and to "weedy rice" plants, e.g. any undesirable rice plant growing in a cultivated area, such as a "weedy red rice plant" growing in or near a white rice plant paddy/field or in any area where a red rice producing plant is not a crop.

As used herein, the term "brown rice" in reference to a food product is a grain wherein the husk is removed leaving bran intact on the kernels; or a rice seed wherein the husk is removed leaving a brownish colored bran layer intact.

As used herein, the term "red rice" in reference to a grain is a rice grain or seed with brownish to reddish pigmentation in its pericarp and seed coat, such as "brown pericarp." Red rice in reference to a rice plant is a plant that produces a brownish to reddish pigmentation in the pericarp layer or seed coat of a rice seed. In reference to a Rc sample labeled "red" wherein a sample is predicted and/or shown to express a functional Rc molecule, i.e. the Rc gene or protein comprises a "*rufipogon* element" or "*O. rufipogon* 14 bp element," as described herein. In contrast to a Rc sample labeled "white" wherein the Rc molecule is predicted to be nonfunctional, i.e. lacks a *rufipogon* element.

As used herein, the term "red" in reference to a "red rice plant" refers to a rice plant that not only produces rice grains with brownish to reddish pigmentation, red rice plants, i.e. *O. rufipogon*, that also exhibits numerous undesirable commercial traits, such as long dormancy of its seeds; unpredictable germination in that red rice seeds may readily germinate or stay latent for years before germinating; and uneven development or growth period producing seeds that shatter quickly upon reaching maturity.

As used herein, the terms "wild rice" and "wild red rice" in reference to a red rice plant is any variety of rice plant, such as *Oryza rufipogon* that produces seed and grain with red pigmentation and that is considered a wild ancestor of the Asian cultivated rice, *Oryza sativa*.

As used herein, the term "white rice" in reference to a grain product is a dehulled rice seed that has a white color. White rice may also refer to any color of rice that has had its bran and hull layers removed by milling and may further be referred to as "table," "polished," or "milled rice."

As used herein, the terms "domestic rice plant," "domestic rice," "common rice" and "common rice plant" refer to a rice plant (e.g. variety) cultivated for a particular variety of grain, for example, Asian rice refers to *Oryza sativa* varieties while African rice refers to *Oryza glaberrima*. Two subspecies of *O. sativa* are recognized, as indica and *japonica* of which selectively bred subspecies may comprise varieties producing colored rice such as red rice, white rice, and black rice.

As used herein, the term "weedy" in reference to a rice plant refers to any rice plant that produces colored seed growing in or near a noncolored rice plant in a paddy or field. Currently in the United States, red rice plants are classified as a "noxious weed." In some States, a noxious weed refers to *Oryza rufipogon* spp. In some states a noxious weed refers to *O. sativa* varieties producing red seeds.

As used herein, the term "native American wild rice" refers to a marsh grass such as a tall North American aquatic plant (e.g. *Zizania aquatica*) that was traditionally harvested as food by native Americans. This species belongs to the family Gramineae that is a genus different from common rice plants (e.g. *Oryza* spp.). Native American wild rice, such as Canada rice, Indian rice, and water oats, is an annual plant that is an important source of food and shelter for fish and waterfowl and is often sown for this purpose. Wild rice may be planted as an ornamental grass in home garden ponds and bogs and may be grown commercially, e.g. in the state of California, United States of America.

As used herein, the term "domestication syndrome" refers to a trait that may distinguish a crop plant (for example, a domestic white rice plant) from its wild ancestor plant (for example, a wild red rice plant) (See, "Plants Genes and Crop Biotechnology," by Crispeels and Sadava (2003)). In reference to crop domestication and a wild or weedy variety of that crop, farmers select against a large number of traits that were valuable for wild species, but undesirable in agronomic practice. These differences between wild or weedy species and crops are farther accentuated by selective breeding, and even more so by genetic engineering, thus introducing traits that were not expressed in the original gene pool of the species, genus, family, or kingdom of the crop.

The term "plant tissue" includes differentiated and undifferentiated tissues of plants, including those present in roots, shoots, leaves, pollen, seeds and tumors, as well as cells in culture (e.g., a single cell, protoplast, embryo, callus, etc.). Plant tissue may be in planta, in organ culture, in tissue culture, or in cell culture.

The term "plant part" as used herein refers to a plant structure, a plant organ, or a plant tissue. Plant parts may comprise one or more of a tiller, plug, rhizome, sprig, stolen, meristem, primordial meristem crown, pericarp and seed coat.

As used herein, the term "cereal plant" refers to a crop plant of the grass family (i.e. Graminaceae) cultivated for the food value of their grains, e.g., rice, wheat, sorghum, maize, oat, barley, rye, millet and the like.

As used herein, the term "cereal" refers to "grains" and "seeds" of a flowering plant of the grass family (i.e. Graminaceae) cultivated for the food value of their grains, e.g., rice, wheat, sorghum, maize, oat, barley, rye, millet and the like.

As used herein, the term "flowering plant" refers to a seed plant wherein a male gametophyte is at least 1 cell contained within a pollen grain and wherein a female gametophyte is about eight cells contained within an ovule.

As used herein, the terms "pollen," "pollen grain," and "male plant germ cell" refer to a male gamete of a plant.

As used herein, the terms "egg," "egg cell," "ova," "ovum," and "female plant germ cell" refer to a female gamete of a plant.

As used herein, the term "ovule" refers to the ovum of a seed plant.

As used herein, the term "female organ" of a plant refers to a "gynoecium," "carpel," "ovule," "embryo sac" and "ovary" which contain an egg and is a site of fertilization.

As used herein, the term "fertilization," "fertilization," and "syngamy" refer to a process of a sperm fusing with an ovum, i.e. a union of pollen (male gamete) and egg (female gamete) that may lead to the development of an embryo (i.e. zygote).

As used herein, the term "pollination" refers to a step that leads to fertilization and reproduction of a seed plant. Pollination occurs when a pollen grain contacts a female organ part, such as a stigma that is a sticky tip of the pistil, in a flower of an angiosperm or a micropyle in a gymnosperm, enabling fertilization to take place. Natural pollination occurs when pollen from the anther is transferred (by wind, rain, insects, or gardeners) to the stigma.

As used herein, the term "cross-pollination" refers to pollen that is delivered to a flower of a different plant.

As used herein, the term "self-pollenization" refers to pollen that contacts a stigma that derives from the same plant. Following fertilization the ovary begins to swell and becomes to form a seed (sometimes referred to as a fruit or a fruiting body).

The term "seed" as used herein includes all tissues that result from the development of a fertilized plant egg; thus, it includes a matured ovule containing an embryo and stored nutrients, as well as an integument or integuments that differentiated into a protective seed coat or testa. The nutrients in seed tissues may be stored in the endosperm or in the body of the embryo, notably in the cotyledons, or both.

As used herein, the term "seed" may also refer to a mature and fertilized, i.e. ripened, ovule of a seed plant comprising a plant embryo (i.e. miniature plant) and further comprising an endosperm (i.e. supply of food for the plant embryo) and may be enclosed by a seed coat.

As used herein, the terms "seed coat," "testa" and "husk" refers to an integument of the ovule that has harden to become a seed's protective coat.

As used herein, the term "pericarp" refers to a wall of the ripened ovary.

Figure 1C:
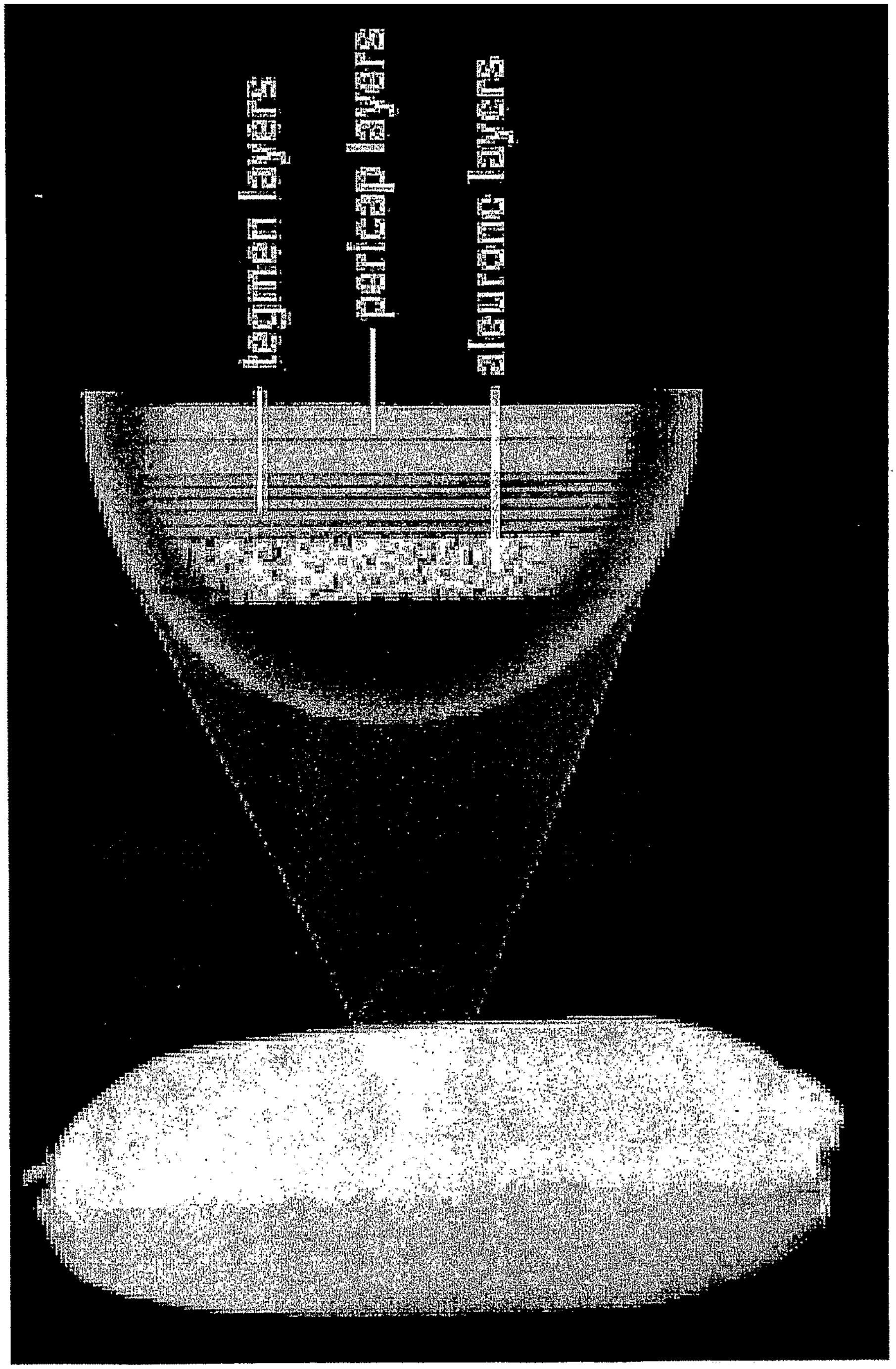

As used herein, the term "pericarp layer" refers to a wall of the ripened ovary and the outermost layer of cells covering the caryopsis (seed), see, FIG. 1C diagram.

For the purposes of the present invention, the terms "grain" and "seed" refer to a composition comprising endosperm, germ, and pericarp. For the purposes of the present invention a rice seed comprises an embryo, i.e. a tiny plant-to-be, tucked into one end of the seed that further contains germplasm and cells that will become a rice plant; at least one cotyledon that provides for the growth of the plant; endosperm that may be a milky white or solid white substance that fills the seed, further comprising a starch or other nutrient; a seed coat of several layers; and a hull on the outside of the seed coat.

As used herein, the terms "hull" and "husk" refer to a palea and lemma, or glumes of the spikelet.

As used herein, the term "kernel" refers to interior contents of a seed that are surrounded by the hull.

As used herein, the terms "rough rice," "paddy," and "padi" refer to harvested rice that retains its hull (husk).

As used herein, the term "outer bran layer" refers to a fibrous layer that may have color that can vary from light yellow to red to dark purplish black.

As used herein, the term "shattering" refers to separation of grains from the panicle.

As used herein, the term "panicle shattering" refers to when the rice grains fall from the panicle before harvesting.

As used herein, the term "threshing" in reference to rice grain refers to operations of detaching or separating the rice grains from the panicle by hand or mechanical means.

As used herein, the term "rice processing" refers to any one of milling, polishing, parboiling, and grading of rough rice.

As used herein, the term "panicle threshability" refers to a descriptive term for how easily the grain is removed from the panicle during threshing. These qualities vary with different varieties.

As used herein, the term "milling" refers to a process of separating the hull or husk and bran from paddy or rough rice resulting in milled rice and bran-and-chaff components.

As used herein, the term "degree of milling" refers to a percent efficiency of bran removal from brown rice during milling, e.g. in Thailand, milled rice may be classified into "ordinary," "reasonably well," "well", and "extra well milled."

As used herein, the term "milled rice" refers to rice from which the hull and bran have been removed.

As used herein, the term "polished" refers to grains (especially rice) having the husk or outer layers removed; "polished rice".

As used herein, the term "parboiling" refers to rough rice that has been subjected to a steam or hot water treatment prior to milling.

As used herein, the term "grade" in reference to a grade of rice refers to separated milled grain when separated according to size and quality, i.e. whole grain, broken grain, short grain, and long grain.

As used herein, the term "red pigmentation" refers to the presence of a range of brownish to reddish colored "proanthocyanidin," also called "condensed tannins." For the purposes of the present invention, "enhancing red pigmentation" refers to increasing gene expression and/or protein expression that contributes to increasing proanthocyanidin production including increasing a compound, for example an anthocyanidin, proanthocyanidin, etc., when compared to a control.

As used herein, the term "decreasing" in reference to "decreasing red pigmentation" refers to the opposite of increasing, such that decreasing results in a reduction of red pigmentation when compared to a control. In particular, the increasing and decreasing of red pigmentation refers to a rice grain or rice seed, i.e. pericarp of a rice grain. The increasing or decreasing in red pigmentation may or may not result in an increase or decrease of red coloration discernable by eye.

As used herein, the term "altering" in reference to "altering pigmentation" or altered pigmentation refers to increasing or decreasing pigmentation, for example, altering red pigmentation may refer to enhancing red pigmentation or decreasing red pigmentation.

As used herein, the term "wild type" in reference to a rice plant and a gene of that rice plant refers to a rice plant that produces a red seed pericarp (seed coat) such that the genome of a red rice plant carries functional alleles at Rc loci and functional alleles at Rd loci. In other words, wild type refers to an ancestral gene whose sequence and thus gene product enables and/or enhances red pigment production in a rice plant part.

As used herein, the term "functional" as in "functional allele" for the purposes of the present invention refers to alleles that allow red pigment production, such an Rc allele that enables and/or enhances red pigment production and an Rd allele that enhances red pigment production in a rice plant part.

As used herein, the term "variant" in reference to genes that are associated with pigment production refers to alleles of one or more of an Rc and an Rd wherein red pigmentation of a plant part is altered. In one embodiment, altered red pigmentation is increasing or decreasing pigmentation. In one embodiment, altered red pigmentation is reducing red pigmentation. In one embodiment, reducing red pigmentation is a lightening of red pigmentation. In one embodiment, reducing red pigmentation is a loss of red pigmentation. In one embodiment, a loss of red pigmentation produces a white rice seed, such as in a white seeded cultivated variety of rice plant. In one embodiment, reducing red pigmentation is a reduced function of an Rc and/or an Rd allele. In one embodiment, reducing red pigmentation is a loss-of-function of an Rc and/or an Rd allele.

As used herein, the term "mutant" refers to a plant line (e.g. variety, cultivar, and the like) that shows qualitative variation due to an alteration in a single gene. For the purposes of the present invention a "mutant" in relation to a rice gene refers to a gene comprising a polymorphism that reduces red pigmentation.

As used herein, the term "indel polymorphism" and "INDEL" refers to insertion/deletion polymorphism.

As used herein, the term "positional cloning" refers to the identification of a gene based on its physical location in the genome. For example, an individual plant has a phenotype, but the gene underlying this phenotype is unknown. By using linkage mapping in order to locate the position of the gene responsible for a phenotype, the phenotype can be assigned a position in the genome. Once a gene for a phenotype has been localized, overlapping sets of clones (for example, BACs) that cover the region are identified. Genes within the region are identified and compared to DNA from individuals that display the phenotype until the underlying mutation is identified.

As used herein, the term "centromere" refers to a chromosomal region wherein sister chromatids are attached in during mitosis; for example, a centromere regulates to several proteins with high affinity to form a kinetochore which is the anchor for the mitotic spindle. A centromere is an A-T region of about 130 bp and is generally flanked by repetitive DNA sequences.

As used herein, the term "crossing-over" and "recombination" refers to an exchange of genetic material between non-sister chromatids of homologous chromosomes (i.e., between maternal and paternal chromosomes) during meiosis. This results in a new and unique combination of genes on the daughter chromosome that will be passed on to the offspring (if that particular gamete is involved in fertilization).

As used herein, the term "Lod score" refers to a log base 10 value of the likelihood ratio of the odds favoring linkage obtained from the statistical analysis of linkage, as examples, a Lod score (Z) of +3 means 1000:1 odds of linkage and is considered evidence for linkage and Lod score of −2 is odds of 100:1 against linkage however this scoring system does not apply to sex-linked diseases.

As used herein, the term "recombination," "somatic recombination," "sister chromatid exchange," and "crossing-over" refers to an exchange sometimes referred to as reshuffling of genetic material between a homologous pair of chromosomes during meiosis. Recombination fraction is the proportion of gametes in which recombination is expected to occur between two loci. This genetic distance is usually a function of physical distance between them. The unit of recombination is the Morgan (M), defined as the genetic distance in which exactly one crossover is expected to occur (1 Morgan=100 cM) meaning a crossover value of 100%; one cM distance indicates two markers are inherited separately (recombination separates them) 1% of the time.

As used herein, the term "repetitive DNA" refers to non-coding DNA, which consists of nucleotide, sequences repeatedly occurring in chromosomal DNA. They do not normally have any function but those capping the chromosomes prevent the loss of genetic information after each replication (as this would cause a 3' overhang). In human genome, at least 20% of the DNA consists of repetitive sequences.

As used herein, the term "Single Nucleotide Polymorphism" and "SNP" refers to A single nucleotide change in the DNA code. It is the most common type of stable genetic variation and usually bi-allelic. SNPs may be silent—no change in phenotype-(sSNP), may cause a change in phenotype (cSNP) or may be in a regulatory region (rSNP) with potential to change phenotype. Anonymous SNPs are the most common ones. These are in non-coding regions and used as genetic markers. On average, each 1 kb of human genome contains 2-10 SNPs, i.e., one in every 100-500 nucleotides is polymorphic most frequently a C to T substitution.

As used herein, the term "transcription" refers to a first step in protein synthesis, transfer of genetic information from the DNA template to RNA molecule mediated by RNA polymerase. A transcription unit is a segment of DNA between the sites of initiation and termination of transcription. It may contain more than one gene.

As used herein, the term "transcription factors" refers to proteins that are directly involved in regulation of transcription initiation through binding to regulatory elements, such as regulatory elements within promoter regions, or binding to other proteins for collective binding to thus allowing RNA polymerase to transcribe DNA. There are ubiquitous transcription factors as well as cell and tissue-specific transcription factors including families of genes that encode such examples of helix-loop-helix proteins, basic helix-turn-helix proteins, such as Rc of the present invention, Leucine zipper proteins and zinc finger proteins.

As used herein, the terms "DNA binding motif" or "consensus sequence" refer to common sites on different proteins that facilitate their binding to DNA, specifically regulatory elements of genes, wherein any such protein is called DNA-binding protein. For example, DNA binding motifs include but are not limited to helix-loop-helix proteins, helix-turn-helix proteins, Leucine zipper proteins and zinc finger proteins. Further, DNA binding motifs may be an anthocyanin regulatory element or an anthocyanin regulatory consensus sequence.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. Cell Biol. 13(2):244-248 (2001)) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

The terms dsRNAi and RNAi are used interchangeably herein unless otherwise noted. In a more preferred embodiment, the methods and compositions are useful for regulation of gene expression in rice. Thus, in one embodiment of the invention, dsRNAi molecules are provided which are useful in regulating gene expression in plants; the dsRNAi molecules are also useful for the regulation of levels of specific mRNA in plants, particularly rice. In one embodiment, gene silencing is provided using a gene silencing vector, for example, using a pANDA vector.

An example of the use of RNAi to inhibit genetic function in plants included using *Agrobacterium tumefaciens*-mediated transformation of *Arabidopsis thaliana* (Chuang and Meyerowitz [2000], Proc. Natl. Acad. Sci. USA 97:4985-4990; herein incorporated by reference). Chuang et al. describe the construction of vectors delivering variable levels of RNAi targeted to each of four genes involved in floral development. Severity of abnormal flower development varied between transgenic lines. For one of the genes, AGAMOUS (AG), a strong correlation existed between declining accumulation of mRNA and increasingly severe phenotypes, suggesting that AG-specific endogenous mRNA is the target of RNAi. Examples of RNAi inhibition that include rice plants are disclosed in U.S. Patent Appln. 20050026290A1, herein incorporated by reference.

As disclosed herein, 100% sequence identity between the RNA and the target gene is not required to practice the present invention. Thus the invention has the advantage of being able to tolerate sequence variations that might be expected due to genetic mutation, strain polymorphism, or evolutionary divergence.

RNA may be synthesized either in vivo or in vitro. Endogenous RNA polymerase of the cell may mediate transcription in vivo, or cloned RNA polymerase can be used for transcription in vivo or in vitro.

For transcription from a transgene in vivo or an expression construct, a regulatory region (e.g., promoter, enhancer, silencer, splice donor and acceptor, polyadenylation) may be used to transcribe the RNA strand (or strands); the promoters may be known inducible promoters that respond to infection, stress, temperature, wounding, or chemicals. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874; 5,698,425; 5,712,135; 5,789,214; and 5,804,693; and the references cited therein, all of which are incorporated by reference). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

Preferably and most conveniently, dsRNAi can be targeted to an entire polynucleotide sequence set forth herein. Preferred RNAi molecules of the instant invention are highly homologous or identical to the polynucleotides of the sequence listing. The homology may be greater than 70%, preferably greater than 80%, more preferably greater than 90% and is most preferably greater than 95%.

Fragments of genes can also be utilized for targeted suppression of gene expression. These fragments are typically in the approximate size range of about 20 nucleotides. Thus, targeted fragments are preferably at least about 15 nucleotides. In certain embodiments, the gene fragment targeted by the RNAi molecule is about 20-25 nucleotides in length. In a more preferred embodiment, the gene fragments are at least about 25 nucleotides in length. In an even more preferred embodiment, the gene fragments are at least 50 nucleotides in length.

Thus, RNAi molecules of the subject invention are not limited to those that are targeted to the full-length polynucleotide or gene. Gene product can be inhibited with a RNAi molecule that is targeted to a portion or fragment of the exemplified polynucleotides; high homology (90-95%) or greater identity is also preferred, but not necessarily essential, for such applications.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The terms "hpRNA" and "hairpin RNA" refer to self-complementary RNA that forms hairpin loops and functions to silence genes (e.g. Wesley et al., The Plant Journal 27(6): 581-590 (2001), herein incorporated by reference). The term "ihpRNA" refers to intron-spliced hpRNA that functions to silence genes.

The term "target RNA molecule" refers to an RNA molecule to which at least one strand of the short double-stranded region of a siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

As used herein, the term "knockout" refers to a host cell or organism, such as a plant cell or a plant tissue or a whole plant, lacking a functional gene, such as an Rc gene. In some embodiments, the entire gene is deleted. In other embodiments, the gene is inactivated via other means (e.g., deletion of essential portions or inversions of some or all of the gene). In other embodiments, the gene is inactivated using antisense inhibition. For example, an RNAi knockout includes conditional knockouts (e.g., selective inhibition of gene activity, such as a fertility gene). Knockout plant cells may be made using any suitable method including, but not limited to, those described herein.

The terms "posttranscriptional gene silencing" and "PTGS" refer to silencing of gene expression in plants after transcription, and appear to involve the specific degradation of mRNAs synthesized from gene repeats.

The term "cosuppression" refers to silencing of endogenous genes by heterologous genes that share sequence identity with endogenous genes. The term "overexpression" generally refers to the production of a gene product in transgenic organisms that exceeds levels of production in normal or non-transformed organisms. The term "cosuppression" refers to the expression of a foreign gene that has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "Ranking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

The terms “allele” and “alleles” refer to each version of a gene for a same locus that has more than one sequence. For example, there are multiple alleles for eye color at the same locus.

The terms “dominant,” “dominant allele,” and “dominant phenotype” refer to an allele that has an effect to suppress the expression of the other allele in a heterozygous (having one dominant allele and one recessive allele) condition. The terms “recessive,” “recessive gene,” and “recessive phenotype” refer to an allele that has a phenotype when two alleles for a certain locus are the same as in “homozygous” or as in “homozygote” and then partially or fully loses that phenotype when paired with a more dominant allele as when two alleles for a certain locus are different as in “heterozygous” or in “heterozygote.”

The term “heterologous” when used in reference to a gene or nucleic acid refers to a gene that has been manipulated in some way. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The terms “nucleic acid sequence,” “nucleotide sequence of interest” or “nucleic acid sequence of interest” refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term “structural” when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, and the like.

The term “oligonucleotide” refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term “polynucleotide” refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term “an oligonucleotide (or polypeptide) having a nucleotide sequence encoding a gene” or “a nucleic acid sequence encoding” a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc., or a combination of both endogenous and exogenous control elements.

The terms “complementary” and “complementarity” refer to polynucleotides (i.e., a sequence of nucleotides) related by the base-pairing rules. For example, for the sequence “A-G-T,” is complementary to the sequence “T-C-A.” Complementarity may be “partial,” in which only some of the nucleic acids' bases are matched according to the base pairing rules. Or, there may be “complete” or “total” complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms “EST” and “expressed sequence tag” refer to a unique stretch of DNA within a coding region of a gene; approximately 200 to 600 base pairs in length.

The term “recombinant” when made in reference to a nucleic acid molecule refers to a nucleic acid molecule that is comprised of segments of nucleic acid joined together by means of molecular biological techniques. The term “recombinant” when made in reference to a protein or a polypeptide refers to a protein molecule that is expressed using a recombinant nucleic acid molecule.

The terms “protein,” “polypeptide,” “peptide,” “encoded product,” and “amino acid sequence” are used interchangeably to refer to compounds comprising amino acids joined via peptide bonds and a “protein” encoded by a gene is not limited to the amino acid sequence encoded by the gene, but includes post-translational modifications of the protein. Where the term “amino acid sequence” is recited herein to refer to an amino acid sequence of a protein molecule, the term “amino acid sequence” and like terms, such as “polypeptide” or “protein” are not meant to limit the amino acid sequence to the complete, native amino acid sequence associated with the recited protein molecule. Furthermore, an “amino acid sequence” can be deduced from the nucleic acid sequence encoding the protein. The deduced amino acid sequence from a coding nucleic acid sequence includes sequences which are derived from the deduced amino acid sequence and modified by post-translational processing, where modifications include but are not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence. The term "X" may represent any amino acid.

The term "isolated" when used in relation to a nucleic acid or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "portion" when used in reference to a protein (as in "a portion of a given protein") refers to fragments of that protein. The fragments may range in size from four amino acid residues to the entire amino sequence minus one amino acid.

The term "sample" is used in its broadest sense. In one sense it can refer to a plant cell or tissue or a rice grains. In another sense, it is meant to include a specimen or culture obtained from any source, such as fields, as well as biological and environmental samples. Biological samples may be obtained from plants or portions of plants or cells and encompass fluids, solids, tissues, and gases. Environmental samples include environmental material such as soil, water, and industrial samples. These examples are not to be construed as limiting the sample types applicable to the present invention.

The terms "homolog," "homologue," "homologous," and "homology" when used in reference to amino acid sequence or nucleic acid sequence or a protein or a polypeptide refers to a degree of sequence identity to a given sequence, or to a degree of similarity between conserved regions, or to a degree of similarity between three-dimensional structures or to a degree of similarity between the active site, or to a degree of similarity between the mechanism of action, or to a degree of similarity between functions. In some embodiments, a homolog has a greater than 20% sequence identity to a given sequence. In some embodiments, a homolog has a greater than 40% sequence identity to a given sequence. In some embodiments, a homolog has a greater than 60% sequence identity to a given sequence. In some embodiments, a homolog has a greater than 70% sequence identity to a given sequence. In some embodiments, a homolog has a greater than 90% sequence identity to a given sequence. In some embodiments, a homolog has a greater than 95% sequence identity to a given sequence. In some embodiments, homology is determined by comparing internal conserved sequences to a given sequence. In some embodiments, homology is determined by comparing designated conserved functional regions. In some embodiments, homology is determined by comparing designated conserved "motif" regions. In some embodiments, means of determining homology are described in the Experimental section (Examples 4 and 8).

The term "homology" when used in relation to nucleic acids or proteins refers to a degree of identity. There may be partial homology or complete homology. The following terms are used to describe the sequence relationships between two or more polynucleotides and between two or more polypeptides: "identity," "percentage identity," "identical," "reference sequence," "sequence identity," "percentage of sequence identity," and "substantial identity." "Sequence identity" refers to a measure of relatedness between two or more nucleic acids or proteins, and is described as a given as a percentage "of homology" with reference to the total comparison length. A "reference sequence" is a defined sequence used as a basis for a sequence comparison; a reference sequence may be a subset of a larger sequence, for example, the sequence that forms an active site of a protein or a segment of a full-length cDNA sequence or may comprise a complete gene sequence. Since two polynucleotides or polypeptides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of in internal region of a polypeptide. In one embodiment, a comparison window is at least 77 amino acids long. In another embodiment, a comparison window is at least 84 amino acids long. In another embodiment, conserved regions of proteins are comparison windows. In a further embodiment, an amino acid sequence for a conserved transmembrane domain is 24 amino acids. Calculations of identity may be performed by algorithms contained within computer programs such as the ClustalX algorithm (Thompson, et al. Nucleic Acids Res. 24, 4876-4882 (1997)), herein incorporated by reference); MEGA2 (version 2.1) (Kumar, et al. Bioinformatics 17, 1244-1245 (2001)); "GAP" (Genetics Computer Group, Madison, Wis.), "ALIGN" (DNAStar, Madison, Wis.), BLAST (National Center for Biotechnology Information; NCBI) and MultAlin (Multiple sequence alignment) program (Corpet, Nucl. Acids Res., 16 (22), 10881-10890 (1988), all of which are herein incorporated by reference).

For comparisons of nucleic acids, 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2:482 (1981)) by the homology alignment algorithm of Needleman and Wunsch (Needleman and Wunsch, J. Mol. Biol. 48:443 (1970), herein incorporated by reference), by the search for similarity method of Pearson and Lipman (Pearson and Lipman, Proc. Natl. Acad. Sci. (U.S.A.) 85:2444 (1988), herein incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., herein incorporated by reference), or by inspection, and the best alignment (i.e., resulting in the highest percentage of homology over the comparison window) generated by the various methods is selected. The term "sequence identity" means that two polynucleotide or two polypeptide sequences are identical (i.e., on a nucleotide-by-nucleotide basis or amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) or amino acid, in which often conserved amino acids are taken into account, occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g. in FIG. 10).

The term "ortholog" refers to a gene in different species that evolved from a common ancestral gene by speciation. In some embodiments, orthologs retain the same function. The term "paralog" refers to genes related by duplication within a genome. In some embodiments, paralogs evolve new functions. In further embodiments, a new function of a paralog is related to the original function.

The term "partially homologous nucleic acid sequence" refers to a sequence that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely complementary to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of identity (e.g., less than about 30% identity); in the absence of non-specific binding the probe will not hybridize to the second non-identical target.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. Melting temperature $T_m$ is the midpoint of the temperature range over which nucleic acids are denatured (e.g. DNA:DNA, DNA:RNA and RNA:RNA, etc.). Methods for calculating the $T_m$ of nucleic acids are well known in the art (Sambrook, et al., *Molecular Cloning: A Laboratory Manual,* $2^{nd}$ ed., Cold Spring Harbor Laboratory Press, New York (1989) pp. 9.50-51, 11.48-49 and 11.2-11.3, herein incorporated by reference).

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml:05 g Ficoll (Type 400, Pharmacia):05 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "amplification" as used herein, refers to nucleic acid replication involving template specificity as contrasted with non-specific template replication (i.e., replication that is template-dependent but not dependent on a specific template). For the purposes of the present invention, the term "template specificity" is distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (Kacian et al., Proc. Natl. Acad. Sci. USA, 69:3038-3042 (1972), herein incorporated by reference). Other nucleic acids will not be replicated by this amplification enzyme. Similarly, in the case of T7 RNA polymerase, this amplification enzyme has a stringent specificity for its own promoters (Chamberlin et al., Nature, 228:227 (1970), herein incorporated by reference). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989), herein incorporated by reference). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press (1989), herein incorporated by reference).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The terms "primer" or "polymerase chain reaction primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, and the like.

Transcriptional control signals in eukaryotes comprise "promoter" and "enhancer" in reference to an element. Promoters and enhancers consist of short arrays of DNA sequences that interact specifically with cellular proteins involved in transcription (Maniatis, et al., Science 236:1237 (1987), herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al., supra (1987), herein incorporated by reference).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. For the purposes of the present inventions, the terms "Rc responsive promoter" or "Rc control elements" refer to nucleotide sequences that enhance gene expression in the presence of a functional Rc protein, such as an Rc protein isolated from red rice grains when compared to gene expression in the presence of a nonfunctional Rc protein, such as an Rc protein isolated from white rice grains, for example, see, FIG. 23.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer. In one embodiment, a promoter is less than 4 kb in length. In one embodiment, a promoter is less than 3 kb in length. In yet another embodiment, a promoter may comprise a regulatory control element of the present invention. Promoters may be tissue specific or cell specific or plant specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be "constitutive" or "inducible." The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098, herein incorporated by reference), and ubi3 promoters (see e.g., Garbarino and Belknap, Plant Mol. Biol. 24:119-127 (1994), herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid sequence in the presence of a stimulus (e.g., heat shock, chemicals, light, etc.) that is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, and the like.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2$^{nd}$ ed., Cold Spring Harbor Laboratory Press, New York (1989) pp. 16.7-16.8, herein incorporated by reference). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s). Transfer can be into a cell, cell to cell, etc. The term "vehicle" is sometimes used interchangeably with "vector."

The term "vector construct" refers to an engineered vector comprising nucleic acid sequences of the present invention.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens* (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain GV3101, LBA4301, C58, A208, etc.) are referred to as "nopaline-type" *Agrobacteria; Agrobacterium* strains which cause production of octopine (e.g., strain LBA4404, Ach5, B6, etc.) are referred to as "octopine-type" *Agrobacteria*; and *Agrobacterium* strains which cause production of agropine (e.g., strain EHA105, EHAL101, A281, etc.) are referred to as "agropine-type" *Agrobaceria.*

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "stable transfection" and "stably transfected" refer to the introduction and integration of foreign DNA into the genome of the transfected cell. The term "stable transfectant" refers to a cell that has stably integrated foreign DNA into the genomic DNA.

The terms "transient transfection" and "transiently transfected" refer to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb in Virol., 52:456 (1973), herein incorporated by reference, has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles, such as vectors of the present invention, into the target biological sample. Methods for biolistic bombardment are known in the art (e.g., U.S. Pat. No. 5,584,807, herein incorporated by reference), and are commercially available (e.g., the helium gas-driven microprojectile accelerator (PDS-1000/He, Bio-Rad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location, as does the naturally occurring gene. A transgene may also refer to an "exogenous gene" such that exogenous genes include but are not limited to reporter genes, marker genes, selection genes, and functional genes. The term “endogenous gene” refers to a gene naturally encoded and expressed.

The terms “transformants” and “transformed cells” include the primary transformed cell and cultures derived from that cell without regard to the number of transfers. Resulting progeny may not be precisely identical in DNA content, due to deliberate or inadvertent mutations. Mutant progeny that have the same functionality as screened for in the originally transformed cell are included in the definition of transformants.

The term “selectable marker” refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be “positive” or “negative.” Examples of positive selectable markers include the neomycin phosphotrasferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term “reporter gene” refers to a gene encoding a protein that may be assayed. Examples of reporter genes include, but are not limited to, luciferase (See, e.g., deWet et al., Mol. Cell. Biol. 7:725 (1987) and U.S. Pat. Nos. 6,074,859; 5,976,796; 5,674,713; and 5618682; all of which are herein incorporated by reference), green fluorescent protein (e.g., GenBank Accession Number U43284; GFP variants commercially available from CLONTECH Laboratories, Palo Alto, Calif., herein incorporated by reference), chloramphenicol acetyltransferase, β-galactosidase (lacZ gene), alkaline phosphatase, and horse radish peroxidase. An example of using lacZ as a reporter gene for *Arabidopsis* DREB1A is provided in U.S. Pat. No. 6,495,742, herein incorporated by reference. The term “antisense” refers to a deoxyribonucleotide sequence whose sequence of deoxyribonucleotide residues is in reverse 5' to 3' orientation in relation to the sequence of deoxyribonucleotide residues in a sense strand of a DNA duplex. A “sense strand” of a DNA duplex refers to a strand in a DNA duplex that is transcribed by a cell in its natural state into a “sense mRNA.” Thus an “antisense” sequence is a sequence having the same sequence as the non-coding strand in a DNA duplex. The term “antisense RNA” refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. “Ribozyme” refers to a catalytic RNA and includes sequence-specific endoribonucleases. “Antisense inhibition” refers to the production of antisense RNA transcripts capable of preventing the expression of the target protein.

The terms “overexpression” and “overexpressing” and grammatical equivalents, are specifically used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms “Southern blot analysis” and “Southern blot” and “Southern” refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook, et al., *Molecular Cloning: A Laboratory Manual,* $2^{nd}$ ed., Cold Spring Harbor Laboratory Press, New York (1989) pp. 9.31-9.58, herein incorporated by reference).

The term “Northern blot analysis,” “Northern blot,” and “Northern” refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al. supra, pp 7.39-7.52 (1989), herein incorporated by reference).

The term “polymerase chain reaction” (“PCR”) refers to the method of K. B. Mullis U.S. Pat. Nos. 4,683,195, 4,683,202, and 4,965,188, all of which are herein incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one “cycle”; there can be numerous “cycles”) to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the “polymerase chain reaction” (hereinafter “PCR”). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction, such as an amplification reaction.

As used herein, the term "certified seeds" refers to seeds used for commercial crop production produced from "foundation" and "registered seeds" under the regulation of a legally constituted agency.

As used herein, the term "certified fields" refers to fields used for commercial rice crop production wherein no red rice plants are found.

GENERAL DESCRIPTION OF THE INVENTION

History of Rice Cultivation

Two rice varieties were domesticated: Asian rice *Oryza sativa* and African rice *Oryza glaberrima*. It is believed that common wild rice (*Oryza ruflpogon* Griff.) was the wild ancestor of the Asian cultivated rice *Oryza sativa. O. sativa* is believed to have originated around the foothills of the Himalayas, with two subspecies, indica and *japonica* being domesticated separately. It is believed that rice cultivation began simultaneously in many countries over 6500 years ago. Basmati rice is considered the oldest common domesticated progenitor for most rice types.

*O. sativa* was adapted to farming in the Middle East and Mediterranean Europe around 800 B.C. The Moros brought it to Spain when they conquered the country, near 700 A.D. After the middle of the 15th century, rice spread throughout Italy and then France, later propagating to all the continents during the great age of European exploration. In 1694 rice arrived in South Carolina, probably originating from Madagascar. The Spanish took it to South America at the beginning of the 18th century.

African rice *Oryza glaberrima* has been cultivated in Africa for 3500 years. Between 1500 and 800 B.C., the African species (*Oryza glaberrima*) propagated from its original center, the Delta of Niger River, and extended to Senegal. However, it never developed far from its original region. African rice cultivation even declined in favor of the Asian species, possibly brought to the African continent by the Arabians coming from the East Coast from the 7th to the 11th centuries.

World Production and Trade

World production of rice has risen steadily from about 200 million tons of paddy rice in 1960 to 600 million tons in 2000. Milled rice is about 68% of paddy rice by weight. In the year 2000, the top three producers were China (31% of world production), India (21%), and Indonesia (9%). World trade figures are very different where an estimated 5-6% of rice produced is predicted to internationally trade. The largest three exporting countries are Thailand (26% of world exports), Vietnam (15%), and the United States (11%), while the largest three importers are Indonesia (14%), Bangladesh (4%), and Brazil (3%).

Varieties Suitable for the Present Invention

Rice varieties are often classified by their grain shapes. For example, That or Siamese Jasmine rice is long-grain and relatively less sticky, as long-grain rice contains less starch than short-grain varieties. Chinese restaurants usually serve long-grain as plain unseasoned steamed rice. Japanese mochi rice and Chinese sticky rice are short-grain. Chinese people use sticky rice which is properly known as "glutinous rice" (despite the fact that no form of rice actually contains gluten) to make zongzi. The Japanese table rice is a short grain non-sticky rice while Japanese sake rice is another variety. Indian rice varieties include long-grained Basmati (grown in the North), medium-grained Patna and short-grained Masoori.

Aromatic rice plants have definite aromas and flavors; the most noted varieties are the aforementioned basmati, and a hybrid of basmati and American long-grain rice sold under the trade name, Texmati, both of which have a mild popcorn-like aroma and flavor. In Indonesia there are also red and black varieties.

High-yield varieties of rice suitable for cultivation in Africa and other dry ecosystems called the new rice for Africa (NERICA) cultivars have been developed. Their cultivation will hopefully improve food security in West Africa. Golden rice plants are genetically modified to produce beta-carotene, the precursor to vitamin A. The creation of these plants has generated a great deal of controversy over whether the amount of beta-carotene would be significant and whether genetically modified foods are desirable. Draft genomes for the two commonest rice cultivars, indica and *japonica*, were published in April 2002, however the Rc regions of the present invention is different from these published varieties.

Rice contains three major classes of flavonoids or pigments: the anthocyanins (red to deep purple pigments), the flavonols (colorless to pale yellow pigments), and the proanthocyanidins (colorless to tannish pigments). Proanthocyanidin is also known as condensed tannins. Anthocyanins and flavonols are synthesized in vegetative parts, whereas flavonols and proanthocyanidins accumulate in pericarp (Reddy et al. 1996). Colorful grains are ttractive to consumers, but also act as a strong antioxidant, predicted to be a health-promoting chemical (Myara et al., 1993, J Pharmacol Toxicol Methods. 30(2):69-73) Within flavonoid pathways, the anthocyanin biosynthetic pathway is the most extensively studied. In the initial steps, dihydroflavoniol is converted into anthocyanin by multiplex processes. In the later steps, dihydroflavonol is reduced to leucocyanidin by dihydroflavonol reductase (DFR). Anthocyanin is synthesized using leucocyanidin as substrate by anthocyanin synthase (ANS). Leucoanthocyanidin become the substrate for proanthocyanidin synthesis called condensed tannin.

Rice Pigmentation

Wild and weedy rice plants as well as many highly valued cultivated varieties produce grain with red pericarps and thus red seeds. The red pigment is proanthocyanin and its production is conditioned by two dominant loci, Rd located on chromosome 1 and Rc on chromosome 7. Red pericarp is associated with multiple traits in rice, including flavor and aroma of the grain, seed dormancy and decreased micronutrient bioavailability. It also represents an enormous economic problem for rice growers in the United States.

The majority of rice plants and rice grains (*Oryza sativa*, L.) that are grown and consumed throughout the world are white-grained varieties, but rice grain may also be brown, red, purple and other colors. Rice plants producing red grain are ubiquitous among wild rice plants and in some regions of the world rice cultivars producing red grain are preferred for their taste, texture and ceremonial or medicinal value. Consumer interest in red and purple rice plants represents a growing specialty market in the United States but at the same time, the ubiquitous presence of red rice plants as a weed in farmers' white rice plant fields is the most economically important weed and grain quality problem faced by United States rice growers today, leading to losses of as much as $50 million per year (Gealy et al., 2002, Weed Science 50: 333-339). Thus there is a need for discovering the genetics and molecular biology of red grain production and the association of this character with other wild/weedy traits for providing essential information for better management of both the negative and positive features associated with red rice plants and red rice production.

Red pigment in rice grains results from "proanthocyanidin" accumulation and red pigmentation is also referred to as "condensed tannins" (Oki et al., 2002, J Agricultural & Food Chem 50: 7524-7529). Proanthocyanidin is a polymer that breaks down into molecules of the anthocyanin pigment cyanidin when treated with acid (Oki et al., 2002, J Agricultural & Food Chem 50: 7524-7529). Proanthocyanidins have been shown to have important deterrent effects on pathogens and predators, such that it is likely that spontaneous mutations that inhibit pigment production would be selected against in the wild (Shirley, 1998). On the other hand, the production of white grain appears to be associated with the domestication syndrome and remains under strong selection pressure in the majority of modern rice breeding programs.

Although naturally occurring relatives of *Oryza sativa* (Asian cultivated rice) are not native to the United States, weedy rice plants producing red grain are a constant problem in the rice growing areas of the United States, see FIG. 14, in addition to their ability for interbreeding with cultivated, white-grained varieties. Weedy rice plants exhibit increased dormancy and shattering along with red colored grains, allowing them to persist in rice fields despite vigorous attempts to remove them. Efforts to manage the problem genetically have been fraught with difficulties, in part because both red and white-grained varieties may display genetically unstable color phenotypes, making it difficult to track the trait. While the red color can be removed by polishing, red rice must be polished longer than white rice to remove red coloration, whereby the increased polishing results in increased number of broken grains and a corresponding decrease in market value.

Despite problems associated with red rice plants as a weed, the red pigment of their rice grains is of interest for nutritional reasons. Red pigment molecules are a powerful antioxidant that has been demonstrated to reduce atherosclerotic plaque formation, a risk factor associated with cardiovascular disease (Ling et al., 2001, J Nutr 131: 1421-1426). However, on the negative side proanthocyanidin pigments may reduce the bioavailability of iron, protein and carbohydrates (Eggum et al., 1981, Qual Plant Plant Foods Hum Nutr 31: 175-179; Carmona et al., 1996, J Nutritional Biochem 7: 445-450; Glahn et al., 2002, J Agric Food Chem 50: 3586-3591), with important implications for people with generally low nutritional status.

Using classical genetic analysis, two loci, Rc (brown pericarp and seed coat) and Rd (red pericarp and seed coat), were identified which, when present together, produce red seed color (Kato and Ishikawa, 1921). Both loci have been mapped using standard two-point analysis on the morphological map of rice; Rc on chromosome 7 and Rd on chromosome 1. Rc in the absence of Rd produces brown seeds while Rd alone has no phenotype. There are three known alleles of Rc; Rc which exhibits brown spots on a reddish brown background, Rc-s which produces a light red color and Rc+, which is a null allele.

Proanthocyanidin biosynthesis is a branch of the anthocyanin pigment biosynthetic pathway, a well-studied system in multiple species due to its visible phenotype and lack of detrimental effects to the plant. In addition to the proanthocyanidin pigment that is visible in red seeds, rice can also produce purple anthocyanins, which are typically observed in vegetative tissues as well as in the seeds. It is of fundamental interest to determine how both pathways are regulated to control pigment production in various organs and tissues of the rice plant.

Figure 1D:
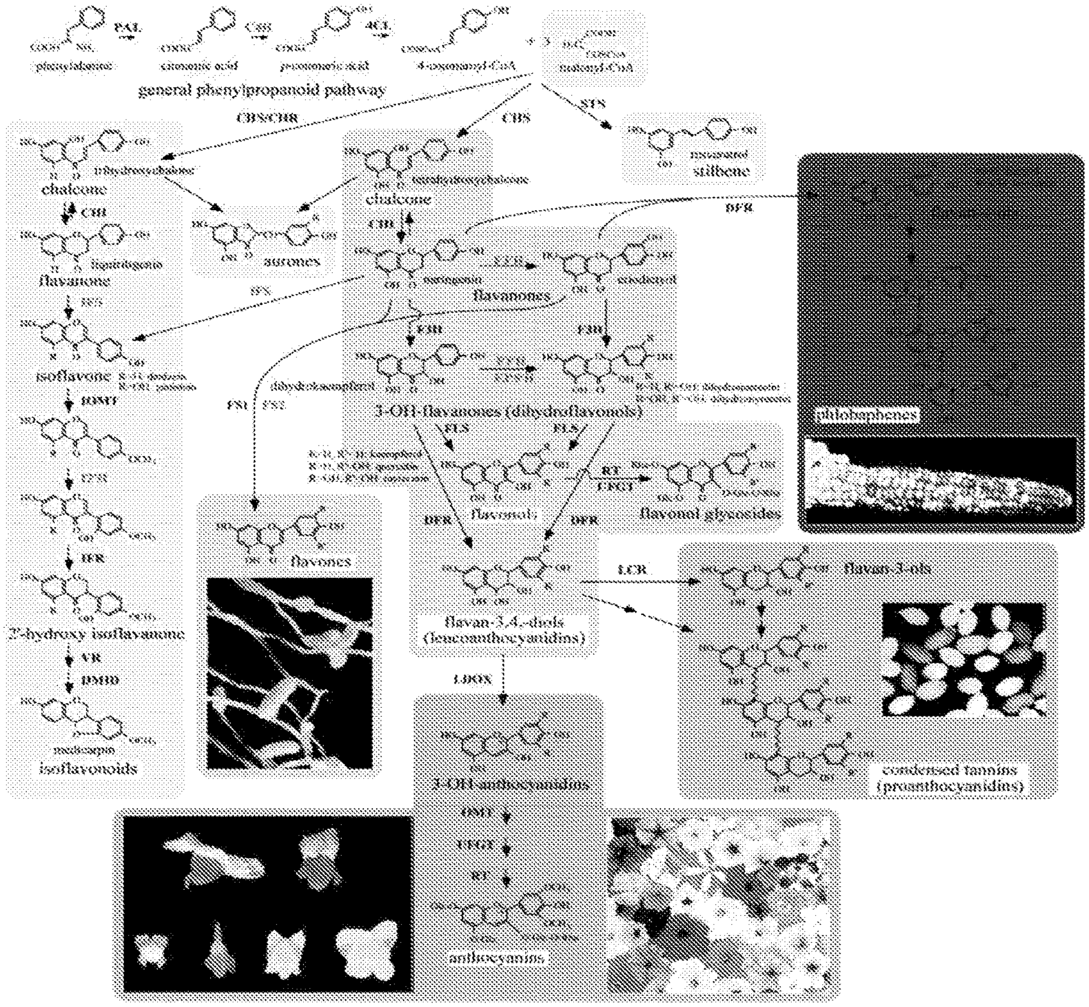

Organisms produce proanthocyanidin for inducing red pigmentation through several pathways, examples shown in FIGS. 1A and 1D. In one pathway, anthocyanidin is a precursor for proanthocyanidin production. For example, *Arabidopsis* plants produce anthocyanidin molecules that are then converted to proanthocyanidin molecules for enhancing red pigmentation. One enzyme involved in this conversion is anthocyanin reductase whose mutant form is called BANYULS (BAN). In *Arabidopsis*, anthocyanin reductase encoded by the BANYULS genes are DFR-like enzymes with similarities to other enzymes of the phenylpropanoid (PA) biosynthesis pathway. Mutations in the BANYULS (BAN) gene lead to precocious accumulation of anthocyanins in immature seed coat in *Arabidopsis*. Gain-of-function experiments showed that an 86-bp promoter fragment functioned as an enhancer specific for proanthocyanidin-accumulating cells.

Mutations in regulatory genes of PA biosynthesis abolished BAN promoter activity (transparent testa2 [tt2], tt8, and transparent testa glabra1 [ttg1]), modified its spatial pattern (tt1 and tt16), or had no influence (ttg2), thus revealing complex regulatory interactions at several developmental levels (Debeaujon, et al. (2003) Proanthocyanidin-accumulating cells in *Arabidopsis* testa: Regulation of differentiation and role in seed development, The Plant Cell, Vol. 15, 2514-2531; Devic et al., The BANYULS gene encodes a DFR-like protein and is a marker of early seed coat development, Plant J. 1999 August; 19(4):387-98). Within the rice genome, there are several genes encoding putative DFR-like proteins, such as those on chromosome 1 and 6, thus providing several gene candidates for rice homologs to anthocyanin reductase/BANYULS. In one embodiment, Rc is a transcriptional regulator for one or more rice plant alleles encoding genes homologous to *Ara-*

*bidopsis* BANYULS. In one embodiment, Rc is a transcriptional regulator for genes whose promoter sequences are SEQ ID NOs:119-137.

In one pathway, one or more of a catechin and a leucoanthocyanidin are precursors for producing proanthocyanidin molecules for enhancing red pigmentation. In one embodiment, leucoanthocyanidin reductase (LAR) catalyzes the conversion of leucoanthocyanidin molecules into proanthocyanidin molecules for enhancing red pigmentation. In one embodiment, enhancing red pigmentation is increasing expression of rice LAR-like sequences homologous to known plant LARs. In one embodiment, one or more of a catechin and a leucoanthocyanidin spontaneously converts into leucoanthocyanidin molecules for enhancing red pigmentation.

Anthocyanin and proanthocyanidin regulation has been studied in several model systems, such as in *Arabidopsis*, maize and petunia, suggesting that many of the same genes and proteins appear to play the same roles in these different species. An upstream component involved with pigmentation is a R2R3Myb homolog that contains an acidic activation domain in the C terminus. Myb domains exhibit DNA binding ability and function in protein-protein interactions. These domains contain three α-helices, the third helix of the Myb domain provides the DNA binding specificity, and with the second helix, forms a helix-turn-helix (HLH) structure (Ogata et al., 1994, Cell 79: 639-648). In maize these proteins are encoded by the P1 (pericarp color)/C1 (colorless) genes; in petunia these are anthocyanin2 (an 2) and an 4 genes (Spelt et al., 2000, Plant Cell 12: 1619-1632); and in *Arabidopsis* there is a tt2 gene, (Nesi et al., 2001, Plant Cell 13: 2099-2114). These proteins are necessary but not sufficient for pigmentation in these plants. In maize, deletion of the activation domain produces suppressor alleles of C1, presumably due to their ability to bind interacting factors, but not to activate transcription (Singer et al., 1998, Genet. Res., Camb 71: 127-132).

Proanthocyanidin and anthocyanin pigments are built from acetyl-CoA and L-phenylalanine. The biosynthesis of many other secondary metabolites branch off this pathway (FIG. 1A). The step catalyzed by anthocyanin synthase is the first dedicated step in the anthocyanin pathway. At this step, the product becomes colored (Holton and Cornish, 1995). The pigment can then be further modified by methylation or glucoylation. Glutathione is conjugated to the pigments and this conjugation leads to the transport of the cytoplasmically synthesized pigments to the cell vacuole (Marrs et al., 1995). In addition to the anthocyanin biosynthetic enzymes, proanthocyanidin production requires the enzyme leucoanthocyanin reductase (FIG. 1A). Functional copies of chalcone synthase, chalcone isomerase, and leucoanthocyanin reductase have previously been cloned from rice (Reddy et al., 1996; Druka et al., 2003; Lei et al., 2002).

The majority of publications demonstrating regulation of anthocyanin biosynthetic pathways is from work on maize plants. While pigments found in red rice are not exactly the same as those found in maize, there is enough similarity to identify biosynthetic enzymes in common. Additionally, an understanding of the anthocyanin regulatory system will help elucidate how rice differentially regulates both proanthocyanidin and anthocyanin expression. Various maize tissues can be colored red, purple or blue, depending on the accumulation of different anthocyanin pigments, for example, red kernel in maize is a result of the accumulation of phlobaphene pigments, a polymer of anthocyanin precursors (FIG. 1A).

Two regulatory proteins are needed for expression of anthocyanin in maize, one member from each of the R (red)/B (booster) and P1 (pericarp color)/C1 (colorless) families. The R/B genes are Myc homologs containing a basic helix-loop-helix (bHLH) domain. Proteins containing a bHLH domain function in protein-protein interactions and the basic region allow DNA binding. R/B proteins exhibit no activation domains (Goff et al., 1992, Genes and Dev. 6: 864-875). Functional analysis of B shows that deletion of the HLH domain results in a partial loss of function while deletion in the N terminus resulted in a complete loss of function (Liu et al., 1998). The N terminus is the site of binding to C1/P1. Evolutionary comparisons demonstrate that the rate of non-synonymous substitutions between R genes from maize and snapdragon is much lower in the bHLH region and in a 150 bp region at the N terminus that is assumed to be the site of interaction with C1/P1 (Rausher et al., 1999, Mol. Biol. Evol. 16:266-274; Goff et al., 1992, Genes and Dev. 6: 864-875). This would indicate that the bHLH region is under selection pressure and likely has a functional role.

Many instances of unstable color phenotypes have been noted in maize and provided the earliest evidence for the existence of transposable elements in any organism (McClintock, 1962, *Carnegie Institution of Washington Year Book* 61 [Issued 10 Dec. 1962, submitted June 1962]: 448-461). More recently, examination of the loci in plants that give rise to seeds segregating for color have documented insertion and excision events associated with transposable elements that appear to be responsible for the changes in color (Liu et al., 1998 Genetics 150(4):1639-48; Walker et al., 1997, Plant Molecular Biology, 47: 341-351).

The maize P1/C1 genes are R2R3Myb homologs that contain an acidic activation domain in the C terminus. Myb domains exhibit DNA binding ability and function in protein-protein interactions. These domains contain three α-helices, the third helix of the Myb domain provides the DNA binding specificity, and with the second helix, forms a helix-turn-helix structure (Ogata et al., 1994, Cell, 79(4): 639-48). The location of the interaction between C1 and R was examined using chimeric proteins made between C1, which is dependent on the binding of R/B protein for activation, and P, a Myb protein that controls the expression of phlobaphene pigments and is not dependent on binding of R/B for activation (Grotewold et al., 2000, Cell 76:543-553). The binding and dependence for activation of C1 to R was localized to different parts of the R3 domain. Extensive mutagenesis work has identified two residues in the acidic activation domain that are critical for activation (Sainz et al., (1997) Mol Cell Biol 17:115-122). Deletion of the activation domain produces suppressor alleles of C1, presumably due to their ability to bind B, but not to activate transcription (Singer et al., 1988).

Basic HLH (bHLH) proteins were first identified in animals where they play developmental roles. In plants they function as homo or heterodimers with the basic regions of the dimers holding the DNA in a scissor like grip and the HLH regions mediating protein-protein interactions between dimer partners. In plants these proteins are involved in plant specific functions, such as anthocyanin pigmentation and phytochrome signaling Heim et al., 2003, Mol Biol Evol 20:735-747.

Myb proteins have been shown to interact with a basic HLH (bHLH) protein in each of the three model plant systems; *Arabidopsis*, maize and petunia.

In *Arabidopsis* plants the tt8 gene encodes the bHLH protein Baudry et al., 2004, Plant J 39: 366-380. While in maize several genes belonging to the R (red)/B (booster) families encode these bHLH proteins. Maize bHLH genes have different tissue specificity and exhibit no activation domains or DNA binding activity alone (Goff et al., 1992, Genes and Development 6:864-875). Recent experiments in maize suggest that R functions in part to free C1 from interaction with a repressor protein as well as recognizing R-specific anthocyanin promoter elements (Hernandez et al., 2004, J Biol. Chem. 279(46):48205-13. Epub 2004 Aug. 29). Functional analysis of B shows that deletion of the HLH domain results in partial loss of function while deletion in the N terminus results in complete loss of function (Liu et al., 1998, Genetics 150:1639-1648). The N terminus is the site of binding to C1/P1. Evolutionary comparisons demonstrate that the rate of non-synonymous substitutions between R genes from maize and snapdragon is much lower in the bHLH region and in a 150 bp region at the N terminus that is assumed to be the site of interaction with C1/P1 (Goff et al., 1992 Genes and Development 6: 864-875; Rausher et al., 1999, Mol Biol Evol 16: 266-274). This would indicate that the bHLH region is under selection and likely has a functional role. Maize also contains a bHLH protein, intensifier that acts as a negative regulator of pigmentation, an1.

Another model system for anthocyanin accumulation is petunia, where the pigments produce different colored petals. Mutagenesis work in petunia has identified four regulatory loci, anthocyanin 1(an1), an 2, an 4 and an11. An2 encodes a Myb homolog with homology to the maize C1/P1 (Spelt et al. (2000) Plant Cell 12:1619-1632). An11 encodes a WD40 protein, which has been shown to physically interact with proteins containing a bHLH domain (Sompompailin et al., 2002. Plant Mol. Biol. 2002 October; 50(3): 485-95). An1 encodes a bHLH protein and the identity of an4 has yet to be determined (Spelt et al. (2000) Plant Cell 12:1619-1632). Different an1 mutants have demonstrated that truncated proteins lacking the C terminus, including the bHLH domain, are able to promote anthocyanin synthesis (Spelt et al., 2002, Plant Cell. 14(9):2121-35). Insertions that cause a frame shift within the bHLH domain produce null alleles and in frame insertions into the bHLH domain have been shown to cause a quantitative decrease in the expression of AN1 anthocyanin target genes and in the intensity of the color expressed (Spelt et al., 2002, Plant Cell. 14(9): 2121-35). These results are similar to those obtained with maize R genes. The An1 locus is pleiotrophic, influencing anthocyanin accumulation and vacuolar pH and seed coat development, activities that are moderated through different regions of the protein (Spelt et al., 2002, Plant Cell. 14(9): 2121-35). Variegated petunia petals showing different intensities and levels of expression of pigments throughout a common genetic background are common. The variegated plants, like the unstable anthocyanin phenotypes in maize, are the result of transposable element activity in regulatory genes (Uematsu and Katayama, 1998, Acta phytotaxonomica et geobotanica 49(2):171-192).

Recently, *Arabidopsis* has emerged as excellent model for studying the proanthocyanidin branch of the pathway. Proanthocyanidin accumulates in *Arabidopsis* seeds, specifically in the testa layer. Oxidation of the proanthocyanidin pigments results in a brown color. Mutagenesis screens have identified a series of mutants lacking seed pigmentation, called transparent testa (tt) mutants (Abrahams et al., 2002, Plant Physiol. 130:561-576). These mutants have been shown to correspond to both biosynthetic and regulatory genes in the proanthocyanidin pathway. Biosynthetic genes unique to *Arabidopsis* include the tt15 gene that encodes a multiple drug transporter, presumed to transport pigments into the cell vacuole. Despite the fact that *Arabidopsis* produces proanthocyanidin rather than anthocyanin pigments, the regulatory genes governing this pathway have notable similarities to the maize anthocyanin regulatory system. The tt2 gene has been cloned and shown to be a R2R3Myb factor with homology to the maize P1/C1 gene family (Nesi et al., 2001; herein incorporated by reference). tt2, together with tt8, a bHLH protein with homology to the R/B maize family (Nesi et al., 2000, Plant Cell. 12(10): 1863-78; herein incorporated by reference), activates the transcription of dihydroflavonol 4-reductase and banyuls, two genes that act late in the proanthocyanidin biosynthetic pathway. Other regulatory factors whose absence results in a complete lack of pigmentation include transparent testa glabra1 (ttg1), a WD-40 repeat-containing protein with homology to an11 (Walker et al., 1999), tt1, a zinc finger protein (Sagasser et al., 2002, Genes Dev. 1; 16(1):138-49; herein incorporated by reference) and anthocyaninless2 (anl2) a homeodomain protein (Kubo et al., 1999, Plant Cell 11: 1217-1226; herein incorporated by reference). The relationships among all of these regulators remains to be clarified. Several of the *Arabidopsis* mutants also display pleiotrophic phenotypes. The ttg1 mutant is known to have trichome abnormalities and root phenotypes (Walker et al., 1997, Genetics 146: 681-693; Payne et al., 2000, Genetics 156: 1349-1362; all of which are herein incorporated by reference).

Petunia has two bHLH proteins involved in anthocyanin regulation, an1 and jaf13. Different an1 mutants have demonstrated that truncated proteins lacking the C terminus, including the bHLH domain, are able to promote anthocyanin synthesis (Spelt et al., 2002, Plant Cell. 14(9):2121-35; herein incorporated by reference). Insertions that cause a frame shift within the bHLH domain produce null alleles and in-frame insertions into the bHLH domain have been shown to cause a quantitative decrease in the expression of AN1 anthocyanin target genes and in the intensity of the color expressed (Spelt et al., 2002, Plant Cell. 14(9):2121-35; herein incorporated by reference). The results are similar to those obtained with maize R genes. The An1 locus is pleiotrophic, influencing anthocyanin accumulation in addition to vacuolar pH and seed coat development, activities that are moderated through different regions of the protein (Spelt et al., 2002, Plant Cell. 14(9):2121-35; herein incorporated by reference).

In the vegetative tissue of maize one member from each of the Myb and bHLH families is sufficient for pigmentation. However in petunia, *Arabidopsis* and maize seeds, genes encoding a WD40 protein are also required for expression of anthocyanin biosynthetic genes. The WD40 repeat proteins have been implicated in protein-protein interactions. These proteins are encoded by the transparent testa glabra1 (ttg1) gene (*Arabidopsis*), an11 (petunia) and pale aleurone color1 (pac1) in maize. They have been shown to physically interact with the bHLH protein in petunia and *Arabidopsis* (Walker et al., 1997, Genetics 146:681-693; Sompompailin et al., 2002, Plant Molecular Biology 50: 485-495; all of which are herein incorporated by reference). Like the an1 locus, the ttg1 mutant is pleiotrophic, demonstrating trichome abnormalities and root phenotypes (Walker et al., 1997, Genetics 146:681-693; Payne et al., 2000, Genetics 156:134 91362; all of which are herein incorporated by reference). In petunia and *Arabidopsis*, other regulatory factors whose absence results in a complete lack of pigmentation include tt1, a zinc finger protein (Sagasser et al. (2002)

Genes Dev. 16, 138-149) and anthocyaninless2 (an12) a homeodomain protein (Kubo et al., 1999, Plant Cell. (7): 1217-26).

DETAILED DESCRIPTION OF THE INVENTION

Certification and Analysis for Detecting Red Rice Seed/Grain

Weedy red rice plants such as *Oryza longistaminiata* A. Chevalier & Roehrich, *Oryza punctata* Kotschy ex Steudel, and *Oryza rufipogon* Griffith are listed under 7 CFR Ch. III (1-1-05 Edition) §360.200(b) as "Noxious Weeds" by the United States Secretary of Agriculture as authorized under section 412 of the Plant Protection Act (7 U.S.C. 7712) within the definition of "noxious weed" as defined in section 403 of the Act (7 U.S.C. 7702(10)). Importation of seed is regulated under 7 C.F.R., Ch. III §361.5, wherein "Sampling of seeds" describes testing procedures for detecting the presence of noxious weed seed while §361.6 states a "no tolerance" for the red rice species listed above in §360.200 (b). In addition to Federally mandated noxious weedy red rice plants, individual states list additional red rice varieties, for example, under "Noxious Weeds Of Arkansas . . . . When found in rice, the following weeds shall, in addition, be classed as noxious, and their presence must be indicated in accordance with the requirements for other noxious weeds: (a) Red Rice (*Oryza sativa* var.), . . . " Therefore, numerous areas of the rice industry including such areas as importation, breeding rice plants and growing rice plants, etc., are highly regulated in order to exclude noxious weedy red rice plants. Current methods for detecting red rice and red rice plants rely upon visual identification of seed lots, growing fields and dehulled rice seeds. However these methods are limited to small sample sizes, ranges in expertise of the viewer, are labor intensive, and will not detect genetic capability for reversion to a red phenotype. Also, since the pericarp is material tissue, a when a plant grown from a white seed is pollinated by a red rice, its seeds will be white, but will carry the red gene and will produce red seeds in the seceding generations. PCR testing for the Rc allele will detect these seeds while visual scanning will not. While not intending to limit the compositions and methods of the present invention, numerous types of testing for the presence of red pigment enhancing germplasm are contemplated herein. In one embodiment, testing for red pigment enhancing germplasm is testing using standard molecular biology procedures, such as, PCR, sequencing, Southern Blotting, Northern Blotting, etc. In one embodiment, PCR testing is testing for the presence of a *rufipogon* DNA fragment. It is not meant to limit the PCR primers used for testing. In one embodiment, PCR primers are one or more of SEQ ID NOs:10-77.

In one embodiment, PCR testing is testing for the presence of a C to A conversion, for example when SEQ ID NO:143 found in red rice is replaced by SEQ ID NO:141 found in non-red rice.

In one embodiment, testing for red pigment enhancing germplasm is testing for a functional Rc protein. In one embodiment, testing for a functional Rc protein is testing for an intact bHLH motif. In one embodiment, testing for a functional Rc protein is testing for Rc binding to a target. In one embodiment, said target is a DNA molecule. In one embodiment, said binding is to a protein. In one embodiment, testing for red pigment enhancing germplasm is by Western Blotting.

Further, even low levels of contaminating red rice in nonred rice grain harvests causes significant economic loss to the grower, see, FIG. 14. Moreover, many commercial varieties of white rice have genetically unstable white rice phenotypes that may allow red coloration of otherwise white rice grain. Thus growers, breeders, seedsmen, millers, retailers, etc., have in place a wide variety of testing measures and agencies for identifying red rice plants and red rice grain.

International and Domestic testing agencies specifically include standards for red rice testing, for example, Internationally, an International Seed Testing Association (ISTA), comprising at least 163 Member Laboratories and at least 49 Personal Members originating from 70 countries (June 2004) while in North America The Association of Official Seed Analysts (AOSA) is an organization of member seed testing laboratories. Members of AOSA include official state, federal, and university seed laboratories across the United States and Canada and further, individual states within the U.S. have their own regulations such as Arkansas State Plant Board that lists red rice growing in rice fields as a "noxious weed" while the California Rice Commission lists red rive varieties as a "specialty rice variety" grown in California. The principles that are laid out for sampling and the methods and procedures are those set out in the International Seed Testing Association (ISTA) Rules for Seed Testing, Association of American Seed Control Officials (AASCO) Handbook for Seed Inspectors and the Association of Official Seed Analysts (AOSA) Rules for Testing Seed. The principles apply equally to domestic and export sampling. An exception to ISTA International Rules for Seed Testing is that maximum lot sizes do not apply when sampling for domestic purposes . . . . Seed is sampled for the purposes of issuance of seed analysis certificates (domestic or international), quality control, or other official purposes. It is important that the sample be taken in accordance with approved methods and techniques to ensure that it is representative of the entire seed lot.

As a specific example, the Mid-West Seed Services (MWSS), an ISTA accredited laboratory, lists Rice Seed Testing Services as stated: "Mechanical Purity and Red Rice Examinations are conducted in accordance with the Association of Official Seed Analysts (AOSA) "Rules for Testing Seeds;" ISTA tests are also available. Red rice examinations are conducted following hull removal. All-states noxious weed examinations are also available." Further, MWSS offers qualitative PCR, which detects the presence or absence of genes in addition to qualitative PCR for determining approximate amounts of target gene sequences. Specific examples of testing procedures offered by MWSS include: "Rice Seed Testing Services . . . . Mechanical Purity and Red Rice Examinations are conducted in accordance with the Association of Official Seed Analysts (AOSA) "Rules for Testing Seeds;"; ISTA tests are also available. Red rice examinations are conducted following hull removal. All-states noxious weed examinations are also available . . . . Herbicide Trait Tests Mid-West Seed Services developed a herbicide bioassay test for Clearfield® rice . . . ."

The Arkansas State Plant Board offers several tests for red rice including "Noxious Weed Exam (NWE) Consists of the determination of the number and kind of noxious weeds found in the sample per pound. Red Rice Exam (RRE) consists of the determination of the number of Red Rice found in the sample per pound . . . . There are two kinds of service samples: Certified Samples that are produced from crops that are in the Certification Program. This seed was field inspected by the Plant Board and has met field standards. The samples must be taken by Plant Board staff and must pass the strict standards of laboratory testing before being allowed to bear the official Arkansas Certified label.

Non-Certified Samples of seed which were not grown under an application for Seed Certification or do not meet the requirements under the Certification program. Samples may be submitted by the seedsmen/farmer.

Further, The Arkansas State Plant Board offers Rice Seed Certification procedures as briefly outlined below: "Outline Of Steps To Follow In Certifying Seed:

1. Call or write for the regulations (Circular 15) [See, FIGS. 19-20] and an application blank for the crop to be certified. These are furnished by the Plant Board. Study these regulations carefully (Application for Soybeans, Rice or Small Grains), (Application for Cotton). A list of seed applied on for certification is maintained in the Arkansas Certified Seed Directory.
2. Secure an approved source of seed. Check the regulation on this point.
3. Send the completed application to Plant Board Office, Little Rock. Unless certified seed was supplied personally, a copy of the invoice showing purchase of the seed should be included, in addition to a set of tags from one of the bags and about a one pound representative sample of the seed. Check the regulations for each crop as to time applications should be made.
4. Completely clean all planting equipment of other seeds and plant the seed for certification in a field which is relatively free of noxious weeds, and one which conforms to the regulations as to isolation from other crops and to crops grown on this field in previous years. Check the regulations on these points for the seed.
5. Prior to the field inspection by the Plant Board, be sure to rogue the field of noxious weeds, other crops and off-type plants. This is a very important point and if the job is done well it may mean the difference of the seed being certified or disqualified.
6. Be sure to notify the Plant Board office about two weeks ahead of the expected harvest date so that the necessary field inspection can be made. (Always make sure the field has been inspected before harvesting the field.)
7. Completely clean all harvesting equipment and storage of all other seeds so that no mixture will occur at this point. The method of harvesting and the storage should be approved by the Plant Board (check the cotton regulations for special requirements as to ginning and storage of seed).
8. After harvest is completed, report to the Plant Board the number of bushels of seed saved for certification.
9. Keep a close check on the seed in storage to see that the moisture content is low enough to prevent heating. Before cleaning, send in a representative sample for a preliminary test. This would not be an official test, but would give information as to the quality of the seed for conditioning decisions.
10. Use the best equipment available for cleaning and treating seed. For seed cleaned using someone else's facilities, the Plant Board may inspect the cleaning equipment just prior to the cleaning of the seed.
11. New containers, approved reusable containers, or dedicated bulk bins must be used for seed that is for certification.
12. After the seed has been cleaned, notify the Plant Board and an official representative sample for an analysis and moisture test will be taken by the Plant Board Inspector. (Note: only certified blue-tag grade may be sampled in the bulk and be eligible for tags or certificates.)
13. Tags and/or bulk certificates are issued when ordered by the applicant.
14. By carefully following the outline above you should not experience too much difficulty in getting the seed certified. If at any time you have questions or are in doubt about the next step to take, please feel free to contact the Plant Board Certification office.

Controlling Growth and Containment of Red Rice Plants

The presence of red rice plants as a weed in farmers' nonred rice plant fields is the most economically important weed and grain quality problem faced by United States rice growers today, leading to losses of as much as $50 million per year (Gealy et al., 2002, Weed Science 50:333-339).

The total potential market for rice varieties that may be used in controlling or suppressing red rice is about 5.3 million acres in the United States, and the potential market outside the United States is much larger. World rice production occupies about 400 million acres. Red rice and other weeds are major pests in rice production in the United States, Brazil, Australia, Spain, Italy, North Korea, South Korea, Philippines, Vietnam, China, Taiwan, Brazil, Argentina, Colombia, India, Pakistan, Bangladesh, Japan, Ecuador, Mexico, Cuba, Malaysia, Thailand, Indonesia, Sri Lanka, Venezuela, Myanmar, Nigeria, Uruguay, Peru, Panama, Dominican Republic, Guatemala, Nicaragua, and other rice-producing areas.

Current Methods Used and Remaining Problems for Controlling and Containment of Red Rice Plants in Commercial Rice Fields Water-Seeding Water-seeding rice is a cultural system that can be used to control red rice plants southern Louisiana Missouri, Arkansas and areas in Texas and California. In general, water-seeding suppresses red rice and other grasses because the soil's oxygen is replaced with water once the field is flooded. A rule of thumb is that grass or rice will emerge (germinate) either through soil or water but not both. For red rice control, flood fields immediately after land preparation. This limits the amount of red rice seed that might germinate prior to flooding. The water-seeded system alone may provide up to 50 percent red rice suppression when done properly. If herbicides such as Ordram™ and Bolero™ are integrated into the system, red rice suppression may approach 90 percent. Fields should be small mall fields with acreage of approximately 40 acres are desirable for optimum precise water management. Poor water management results in loss of both preplant nitrogen and red rice suppression. The methods of water management used in water-seeding rice are pinpoint and continuous flood. The pinpoint flood is recommended especially if Ordram™ or Bolero™ is used preplant. In pinpoint flooding, the water is drained to allow seedlings to anchor (peg down) their roots in the soil.

Some rice varieties are sensitive to both Bolero and Ordram™ in the water-seeded system; therefore, these varieties are not recommended for water-seeding . . . ." (Chapter 4-Water-Seeded, page 30: Rice Production Handbook).

Crop Rotations

Rice producers in the southern United States typically rotate rice crops with soybeans to help control red rice infestations. While this rotation is not usually desirable economically, it is frequently necessary because no herbicide is currently available to control red rice infestations selectively in commercial rice crops.

Herbicides

Genetic similarity of red rice and commercial rice has made herbicidal control of red rice difficult. The herbicides Ordram™. (molinate: S-ethyl hexahydro-1-H-azepine-1-carbothioate) and Bolero.™. (thiobencarb: S-[(4-chlorophenyl)methyl]diethylcarbamothioate) offer partial suppression of red rice, but no herbicide that actually controls red rice is currently used in commercial rice fields because of the simultaneous sensitivity of existing commercial cultivars of rice to such herbicides.

Herbicide Resistance

Several rice varieties have been developed with selected herbicide resistance that are contemplated for use in the present invention. For example, a transgenic rice plant comprising maize XI12 mutant ahas2 gene providing resistant to the imidazolinone herbicides is described; U.S. Pat. No. 6,653,529 and U.S. Patent Application No. 20030167538, herein incorporated by reference; CL121, CL141, CFX51; BASF Inc.; Tolerance to the imidazolinone herbicide, imazethapyr, induced by chemical mutagenesis of the acetolactate synthase (ALS) enzyme using ethyl methanesulfonate (EMS). *Oryza sativa* (Rice) Liberty-Link™ Direct DNA transfer system. Phosphinothricin (PPT) herbicide tolerance, specifically glufosinate ammonium; Aventis CropScience Rice lines LLRICE06 and LLRICE62 genetically engineered to express tolerance to glufosinate ammonium, the active ingredient in phosphinothricin herbicides (Basta®, Rely®, Finale®, and Liberty®). Glufosinate tolerance in these rice lines is the result of introducing a gene encoding the enzyme phosphinothricin-N-acetyltransferase (PAT) isolated from the common aerobic soil actinomycete, *Streptornyces hygroscopicus*, the same organism from which glufosinate was originally isolated. The PAT enzyme catalyzes the acetylation of phosphinothricin, detoxifying it into an inactive compound. The PAT enzyme is not known to have any toxic properties. The PAT encoding gene (bar) was introduced into the rice genome by direct gene delivery transformation, and the resulting rice lines displayed field tolerance to phosphinothricin-containing herbicides; PWC16 BASF Inc. provides tolerance to the imidazolinone herbicide, imazethapyr, induced by chemical mutagenesis of the acetolactate synthase (ALS) enzyme using ethyl methanesulfonate (EMS); Herbicide tolerant rice plants such as Glufosinate tolerant rice transformed with a bar gene U.S. Pat. Nos. 6,333,449 and 6,468,747; Newpath™ Herbicide, EPA Reg No. 00241-00412-1-00000 Newpath™ Herbicide, EPA Reg No. 00241-00412-1-00000 Newpath™ Herbicide, EPA Reg No. 00241-00412-1-00000 herbicides and the CLEARFIELD™ Production System for rice, herein incorporated by reference. Newpath™ provides growers in Arkansas, Louisiana, Texas, Mississippi and Missouri with superior control of a broad spectrum of grass weeds, including red rice in rice, and broadleaf weeds that can impact rice yields by providing a AHAS/ALS inhibitor for controlling weeds, such as Barnyardgrass Crabgrass, Large Johnsongrass (Seedling) Morningglory, Cypressvine Morningglory, Palmleaf Morningglory, Pitted *Nutsedge*, spp. *Panicum*, spp. Red Rice Signalgrass, Broadleaf Flatsedge, Rice *Smartweed*, spp. Sprangletop Shattercane in U.S. Pat. Nos. 6,274,796, 5,952,553, 5,773,704, 5,773,703, 5,736,629, 5,545,822, and U.S. Patent Application Nos. 20030217381, 20020019313, all of which are herein incorporated by reference. Glyphosate resistance such as provided by Roundup Ready® rice, Monsanto, Corporation.

Natural crossing between red rice and rice was documented by Beachell and his co-workers in 1938 and other researchers in the following decades. Studies at the Rice Research and Extension Center, Stuttgart, Ark., showed pollen movement from cultivated rice to red rice and vice versa when they flowered at the same time (Gealy et al., 2003, 3rd Temperate Rice-Conference Proceedings. Paper #140, 7 pp). Outcrossing rate of up to 0.011 to 0.046% has been reported between glufosinate-resistant rice and red rice (Chen et al., 2002, International Rice Congress; Sep. 16-20, 2002; Beijing, China P.273). A study conducted by Song et al., 2004, Biodiversity and Conservation, 13(3):579-590), also showed that gene flow from cultivated rice to wild rice (*O. rufipogon*) occurred at 2.94%. This experiment was conducted to determine the extent of natural outcrossing between Clearfield® rice and red rice, and to evaluate the effect of cultivar and distance from pollen source on outcrossing rate. The results of this experiment revealed that Clearfield® rice pollen could move within at least 33 ft, which indicates that transgenes from genetically modified rice varieties will escape to red rice populations around the periphery of a rice field. Although the outcrossing frequency found in this study (0.008%) is very low, it still amounts to numerous hybrids in farmer's field. If the resistant population gets established, herbicide-resistant technology becomes ineffective. Cultivar and separation distance must be considered in planning management strategies to mitigate outcrossing. It was concluded that controlling red rice escapes is necessary (Burgos et al., Hybridization Between Clearfield® Rice and Red Rice Under Field Conditions AAES Research Series 517:103-109).

Thus these attempts at controlling red rice contamination of nonred rice crops demonstrate the need for a more effective means of controlling red rice plant growth in and around commercial rice fields.

Figure 11A:
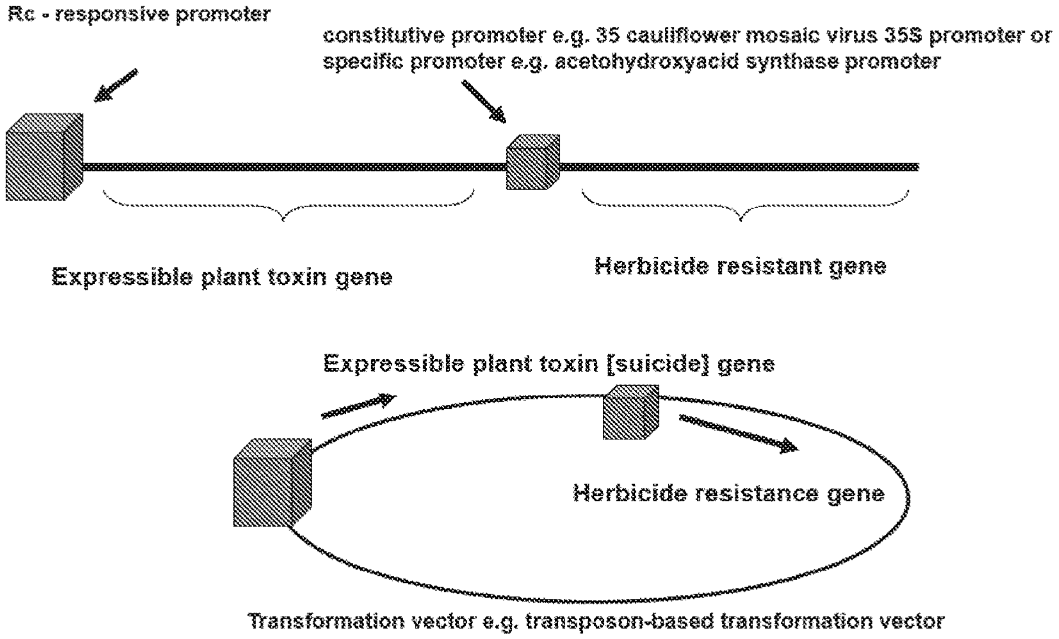
FIGS. 11A-11C show exemplary designs for contemplated red rice transgene containment vectors wherein a functional Rc would trigger expression of a molecule either toxic or inhibiting fertility or reproduction in a rice plant that would produce red rice grains but not in a white grained variety of rice, for example, a duel vector containing an herbicide resistance gene and a plant toxin gene that would prevent seed development from pollination of red rice plants with pollen comprising the a transgenic herbicide resistance gene, a duel vector containing a herbicide resistance gene and an RNAi vector providing a gene silencing system for inducing infertility, inhibiting seed formation, and inhibiting development in the presence of a functional Rc gene; and a duel vector insert for providing herbicide resistance to white rice producing rice plants while preventing spread of herbicide resistance to red rice plants.
Figure 11B:
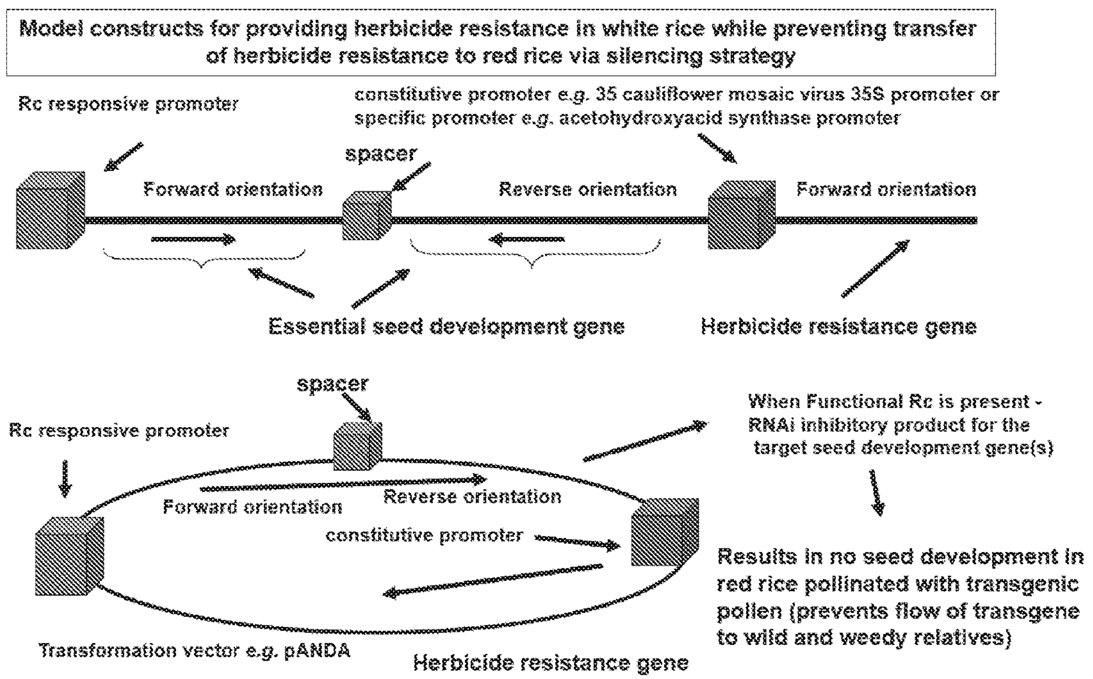
Figure 11C:
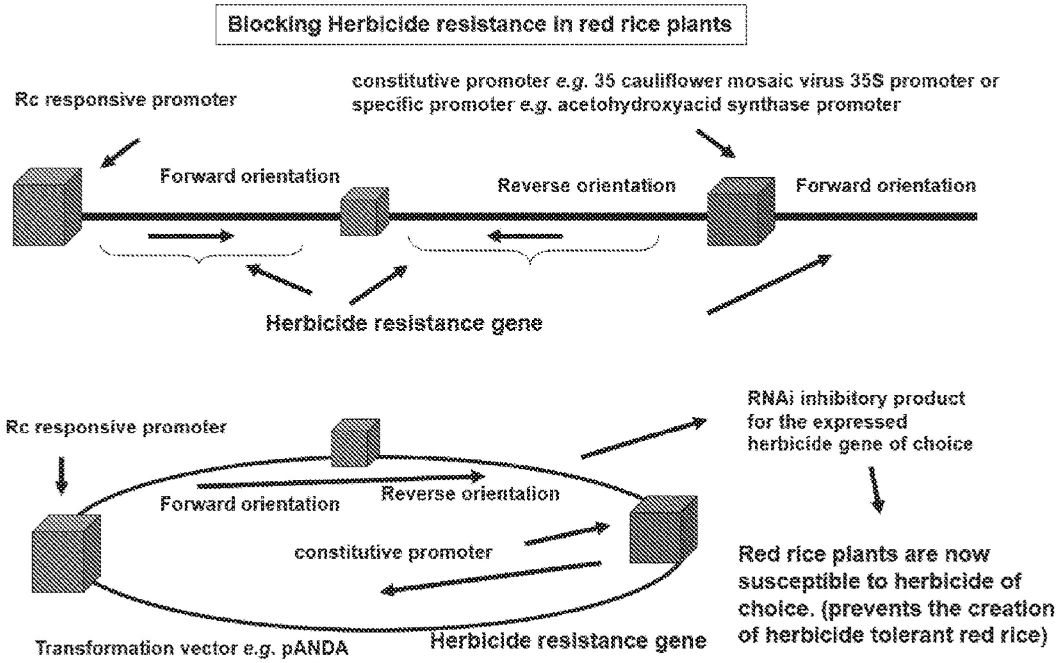

Thus the inventors have designed red rice containment vectors for several purposes. First, for containing the spread of red rice plants while sparing non-red grained varieties, and second for providing duel herbicide resistance to nonred varieties while at the same time providing red rice containment by silencing the exogenous herbicide resistant gene, see, FIGS. 11A-C.

Gene Silencing Constructs for Containment of Red Rice Plants

The present invention contemplates gene-silencing constructs for eliminating red rice seeds from non-red rice crops. That is to say red rice seeds may be eliminated from a non-red rice grain crop by reducing the expression of seed development genes upon which a red rice plant depends upon in order to produce seeds. In one embodiment, reducing the expression of one or more seed development genes is reducing the expression of a gene for inducing red rice fertility. For the purposes of the present invention, a gene for inducing red rice fertility is one or more of a gene for inducing sperm development, pollen development, egg development, ovule development, embryonic development, development of any portion of a seed, and the like. In one embodiment, reducing the expression of one or more seed development genes is reducing the expression of a gene for inducing seed development. In one embodiment, reducing the expression of more or more seed development genes is delaying seed development. That is to say that by delaying seed development non-red rice seeds are ready for harvest from rice plants while red rice seeds are immature and thus remain attached to the plant for elimination from a non-red rice grain crop.

It is not meant to limit the type of gene silencing construct. Indeed a variety of genes silencing constructs are envisioned. In one embodiment, a gene-silencing construct is an RNAi construct. In one embodiment, a gene-silencing construct is an siRNA construct. Examples of methods for providing compositions of silencing genes are shown in U.S. Patent Appln. Nos. 20040053876, and 20020108142, herein incorporated by reference.

As used herein, the term "containment gene" refers to a gene that may inhibit the formation of seeds and or inhibit growth of a plant, including killing a red rice plant, that for the purposes of the present invention are for inhibiting red rice seed formation and/or growth of a weedy red rice plant but not inhibiting white rice seed formation and not inhibiting the growth of a rice plant producing white rice grains. In one embodiment, a containment gene is an endogenous gene. In one embodiment, a containment gene is homologous to an endogenous gene. In one embodiment, a containment gene inhibits the growth of a red rice plant. In one embodiment, a containment gene encodes a toxin for killing a red rice plant. In one embodiment, a containment gene induces herbicide susceptibility in red rice plants. In one embodiment, a containment gene inhibits the formation of red rice seed. In one embodiment, a containment gene inhibits the formation of fertilized red rice seed. In one embodiment, a containment gene is a developmental gene. In one embodiment, a containment gene is a fertility gene. In one embodiment, a containment gene is a grain-forming gene. A containment gene may be a gene that will eliminate seed fertility.

A containment gene may be incorporated into a vector so as to allow for selective inducible containment of a cell containing a transgene. For the purposes of the present invention, a containment gene may be a construct comprising a gene that inhibits (i.e. disrupts) gamete formation, for example, a gene under the control of an Rc responsive promoter could be an RNAi complex targeting developmental genes that are necessary for seed development, such as "HOMOLOGOUS PAIRING ABERRATION IN RICE MEIOSIS1" (PAIR1 as in SEQ ID NO:146) wherein the pair1 mutation, tagged by the endogenous retrotransposon Tos17, exhibited meiosis-specific defects and resulted in complete sterility in male and female gametes (Nonomura et al., The Novel Gene HOMOLOGOUS PAIRING ABERRATION IN RICE MEIOSIS1 of Rice Encodes a Putative Coiled-Coil Protein Required for Homologous Chromosome Pairing in Meiosis, Plant Cell 16: 1008-1020 (2004a) SEQ ID NO:147), "HOMOLOGOUS PAIRING ABERRATION IN RICE MEIOSIS2" (PAIR2) as in SEQ ID NO:148, wherein the PAIR2 gene is essential for homologous chromosome pairing in meiosis, as in the case of the genes ASY1 gene of *Arabidopsis thaliana* and the HOP1 gene of *Saccharomyces cerevisiae* (Nonomura et al. (2004b), Mol. Genet., Genomics 271: 121-129), MSP1 (MULTIPLE SPOROCYTE), which controls early sporogenic development, encoded a Leu-rich repeat receptor-like protein kinase (Nonomura et al., Plant Cell. 2003 15(8):1728-39), The SPOROCYTELESS gene SEQ ID NO:149, (Yang et al., Genes Dev. 13, 2108-2117 (1999), NOZZLE, SEQ ID NO:150, (Schiefthaler, et al., Proc. Natl. Acad. Sci. USA 96, 11664-11669 (1999)) and the like. A containment gene may be a gene that functions as a herbicide resistance gene in plants not comprising an Rc protein, such as herbicide genes currently in use for providing herbicide resistance to white rice plants. For example, a vector comprising an herbicide gene would also comprise a construct for providing herbicide protection to white rice plants that in red rice plants would interfere with the translation of the herbicide gene thus inducing herbicide susceptibility in red rice plants that cross-pollinate with white rice plants protected by the "containment" vector, (See, FIG. 11). An example of RNAi based gene silencing in rice is provided by Miki and Shimamoto Plant Cell Physiol, 2004; 45:490-495; herein incorporated by reference.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, [1982] Gene 19: 259]; Bevan et al., [1983] Nature 304:184), the bar gene which confers resistance to the herbicide phosphinothricin (White et al., [1990] Nucl Acids Res. 18:1062; Spencer et al., [1990] Theor. Appl. Genet. 79: 625), the hph gene which confers resistance to the antibiotic hygromycin (Blochlinger and Diggelmann, [1984] Mol. Cell. Biol. 4:2929), and the dhfr gene, which confers resistance to methotrexate (Bourouis et al, [1983] EMBO J., 2:1099).

In some preferred embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967, herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are contemplated for utilization into vector contructs derived from plant (+) RNA viruses (e.g., brome mosaic virus, tobacco mosaic virus, alfalfa mosaic virus, cucumber mosaic virus, tomato mosaic virus, and combinations and hybrids thereof). Methods for the construction and use of such viruses are described in U.S. Pat. Nos. 5,846, 795; 5,500,360; 5,173,410; 5,965,794; 5,977,438; and 5,866,785, all of which are incorporated herein by reference.

In some embodiments of the present invention, the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278, herein incorporated by reference).

Transformation Techniques

Once a nucleic acid sequence encoding a containment gene is operatively linked to an appropriate promoter and inserted into a suitable vector for the particular transformation technique utilized (e.g., one of the vectors described herein), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; PCT application WO 95/16783, herein incorporated by reference). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al, PNAS, 87:8526 [1990]; Staub and Maliga, Plant Cell, 4:39 [1992]). The presence of cloning sites between these markers allowed creation of a plastid targeting vector introduction of foreign DNA molecules (Staub and Maliga, EMBO J., 12:601 [1993]). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, PNAS, 90:913 [1993]). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway, Mol. Gen. Genet, 202:179 [1985]). In still other embodiments, the vector is transferred into the plant cell by using polyethylene glycol (Krens et al., Nature, 296:72 [1982]; Crossway et al., BioTechniques, 4:320 [1986]); fusion of protoplasts with other entities, either minicells, cells, lysosomes or other fusible lipid-surfaced bodies (Fraley et al., Proc. Natl. Acad. Sci., USA, 79:1859 [1982]); protoplast transformation (EP 0 292 435); direct gene transfer (Paszkowski et al., EMBO J., 3:2717 [1984]; Hayashimoto et al., Plant Physiol. 93:857 [1990]).

In still further embodiments, the vector may also be introduced into the plant cells by electroporation. (Fromm, et al., Pro. Natl. Acad. Sci. USA 82:5824, 1985; Riggs et al., Proc. Natl. Acad. Sci. USA 83:5602 [1986]). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.). (See e.g., U.S. Pat. No. 4,945,050; and McCabe et al., Biotechnology 6:923 [1988]). See also, Weissinger et al., Annual Rev. Genet. 22:421 [1988]; Sanford et al., Particulate Science and Technology, 5:27 [1987] (onion); Svab et al., Proc. Natl. Acad. Sci. USA, 87:8526 [1990] (tobacco chloroplast); Christou et al., Plant Physiol., 87:671 [1988] (soybean); McCabe et al., Bio/Technology 6:923 [1988] (soybean); Klein et al., Proc. Natl. Acad. Sci. USA, 85:4305 [1988] (maize); Klein et al., Bio/Technology, 6:559 [1988] (maize); Klein et al., Plant Physiol., 91:4404 [1988] (maize); Fromm et al., Bio/Technology, 8:833 [1990]; and Gordon-Kamm et al., Plant Cell, 2:603 (maize); Koziel et al., Biotechnology, 11:194 [1993] (maize); Hill et al., Euphytica, 85:119 [1995] and Koziel et al., Annals of the New York Academy of Sciences 792:164 [1993]; Shimamoto et al., Nature 338: 274 [1989] (rice); Christou et al., Biotechnology, 9:957 [1991] (rice); Datta et al., Bio/Technology 8:736 [1990] (rice); European Patent Application EP 0 332 581 (orchardgrass and other Pooideae); Vasil et al., Biotechnology, 11: 1553 [1993] (wheat); Weeks et al., Plant Physiol., 102: 1077 [1993] (wheat); Wan et al., Plant Physiol. 104: 37 [1994] (barley); Jahne et al., Theor. Appl. Genet. 89:525 [1994] (barley); Knudsen and Muller, Planta, 185:330 [1991] (barley); Umbeck et al., Bio/Technology 5: 263 [1987] (cotton); Casas et al., Proc. Natl. Acad. Sci. USA 90:11212 (sorghum); Somers et al., Bio/Technology 10:1589 [1992] (oat); Torbert et al., Plant Cell Reports, 14:635 [1995] (oat); Weeks et al., Plant Physiol., 102:1077 [1993] (wheat); Chang et al., WO 94/13822 (wheat) and Nehra et al., The Plant Journal, 5:285 [1994] (wheat); all of which are herein incorporated by reference.

In addition to direct transformation, in some embodiments, the vectors comprising a nucleic acid sequence encoding a containment gene are transferred using *Agrobacterium*-mediated transformation (Hinchee et al., Biotechnology, 6:915 [1988]; Ishida et al., Nature Biotechnology 14:745 [1996]). *Agrobacterium* is a representative genus of the gram-negative family Rhizobiaceae. Its species are responsible for plant tumors such as crown gall and hairy root disease. In the dedifferentiated tissue characteristic of the tumors, amino acid known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237: 1176 [1987]). Species which are susceptible infection by *Agrobacterium* may be transformed in vitro.

Regeneration

After selecting for transformed plant material which can express a containment gene, whole plants are regenerated. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. 1, 1984, and Vol. III, 1986. It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

Generation of Transgenic Lines

Transgenic lines are established from transgenic plants by tissue culture propagation. The presence of nucleic acid sequences encoding an exogenous or endogenous gene or mutants or variants thereof may be transferred to related varieties by traditional plant breeding techniques.

These transgenic lines are then utilized for evaluation of seed formation, color and viability of Red Rice plants v. non-red rice plants and other agronomic traits.

Evaluation of Seed Formations Color and Viability of Red Rice Plants

The confirmed transgenic plants and lines are tested for the effects of the transgene on a variety of parameters but particularly on seed development. The parameters to be evaluated will depend upon the type of containment gene in a containment vector but will primarily focus on seed development compared to that in control untransformed plants and lines. Parameters evaluated include determining time to flowering from germination and corresponding seed development, and for those vectors comprising herbicide resistance gene the effects of herbicide treatment on plant viability. These tests are conducted both in the greenhouse and in the field.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade/Celsius).

Example 1

Basic Protocols

General Rice Plant Growing Conditions

Light: Rice plants are grown in greenhouses with a 12 hr day and high intensity lighting (500-1000 micro mol photosynthetically active radiation (PAR) m-2 s-1). For DNA extraction, some rice plants are grown with 300-400 PAR just to sustain minimum growth. For robust plants, greater than 500 PAR is used. For reference, full noon summer sunlight is around 1800-2000 PAR depending on haziness, but excess light usually comes with high temperatures in the field, and this leads to photo-respiration during the heat of the day. Greenhouse light is produced with a mix of 1000 watt metal halide and sodium bulbs as supplemental light in addition to natural sunlight. On sunny days temperature is monitored to dissipate heat from the 1000 watt bulbs. Most rice varieties flower earlier when given short day treatments (such as, 10-11 hours of daylight and 13-14 hrs night).

Temperature: Day temperatures of 28-32 C are standard, with night temperatures about 3 degrees lower. Temperature may be critical to optimize growth for specific cultivars or wild species, and this needs to be determined for each variety or species, depending on its zone of adaptation.

Watering: Soil was well watered before planting took place. When seeds were first planted, sprinkle the pot surfaces with ‘light rain’ as needed until germination. The soil surface was watered to keep the soil moist at all times. Soil was not allowed to dry. After germination, soil was kept well watered at all times. This was done by under watering or by adding water to soil surface 1-3 times per day. Under watering required sitting pots in tanks containing about 3-4” of room temperature water that was “wicked” up to maintain soil moisture without constant addition of water from above. Water at room temperature was used when adding to the tanks—no cold water was used at any time because rice roots were sensitive to water temperature. Sturdy plastic trays capable of holding 4-8 pots each were generally used in growth chambers, whereas tanks covering an entire bench area were used in greenhouses. Potting Soil and Fertilizer Regime: (ingredients obtained from, Griffin Greenhouse Supply unless otherwise noted).

PROCEDURE 1: Standard Cornell Procedure for growing rice plants: This procedure was less labor and time intensive than Procedure 2, and allowed the production of thousands of healthy plants for genetic and phenotypic evaluation, but there was some cyclic variation in physiological condition due to the timing of fertilizer application. For this procedure, plants were underwatered at all times. Fertilizer solution was applied onto soil surface.

Soil: Rice Cornell Mix: 1½ bales (=5.7 cu ft) peat; 2 bags (=12 cu ft) medium to course vermiculite; 5 lbs lime; and 1 lb 3 oz Peter’s Unimix Plus III.

Fertilizer: make two types of Fertilizer stock solutions and dilute 1:100 with water just before use: stock A) Peters Water-Soluble Fertilizer N.P.K-15.16.17, 15 lbs with 5 gallons water and B) Peters Water-Soluble Fertilizer N.P.K-15.16.17, 15 lbs plus 5 lbs Sprint 330 (IRON) with 5 gallons water. Peters Water-Soluble Fertilizer: by SCOTTS, Sprint 330 (Iron. Fe) 10%-10% Chelated Iron: by BECKER UNDERWOOD, Inc.

Fertilize with 1:100 dilution of Solution B (with iron) at 3-5 days after germination and again with Solution B one week later. From 2 weeks of age until booting (flowering), alternate with 1:100 dilution of Solution A and B every 7-10 days. Once plants flowered, Solution B was stopped. Thereafter, Solution A Was applied, every 2 weeks (10-14 days) until harvest.

PROCEDURE 2: Boyce Thomson Institute Procedure: This procedure was more labor and time intensive, but produced vigorous, physiologically stable plants under green house and growth chamber conditions. Plants were watered from above (onto soil surface) 3× per day. A dilute fertilizer solution was applied with the last watering on a daily or every-other-day basis.

Soil: ⅔ Rice Cornell Mix+⅓ Desert Mix.

Rice Cornell Mix: 1½ bales (=5.7 cu ft) peat; 2 bags (=12 cu ft) medium to course vermiculite; 5 lbs lime; and 1 lb 3 oz Peter's Unimix Plus III.

Desert Mix: 2 bu soil; 5.5 bu turface; 2 bags of silica sand; 885.44 g Dolomitic Lime; 1517.90 g Gypsum; 379.48 g Superphosphate; and 284.61 g Micro-max.

Fertilizer: make two dilutions of fertilizer. Each 1 gallon of stock (A & B below) will make 101 gallons of useable watering solution when used with a 1:100 injector system. Stock A) 50 ppm (1 gallon stock); 3.38 oz Peters Peat Lite Special Fertilizer; +58.8 oz Sprint 330 Fe Chelate and Stock B) 100 ppm (1 gallon stock); 6.8 oz Peters Peat Lite Special Fertilizer; and 58.8 oz Sprint 330 Fe Chelate. Include fertilization with 1:100 injector system in the last watering of the day. Start fertilizing seedlings when second leaf appears. Follow the following fertilization regime: Day 1 (emergence of 2nd leaf): Add 50 ppm; Day 2: Add 75 ppm; Day 3: Add 100 ppm; Day 4 and every other day thereafter until 2 months of age: Add 100 ppm. When plants are over 2 months old then fertilize at 100 ppm everyday.

Special Growing Conditions for RED RICE: Red Rice plants were grown as described above. However because red rice plants were designated "Noxious Weeds" by the U.S. Federal Government, Red Rice plants were grown under Federally mandated guidelines. Specifically, red rice plants were grown in Guterman Bioclimatic Laboratories and associated greenhouses and growth chambers designed for research related to controlled plant environments.

General Molecular Biology Techniques.

Cereal DNA Extraction Microprep Protocol: Two sets of microfuge tubes (1.5 mL) were labeled with sample names groups of 24 for 48 or 96 samples); a small cooler was provided with two tube racks positioned approx. 6 cm from the bottom of the cooler, and filled with liquid nitrogen up to the top of the tube racks, immediately before harvesting tissue; water bath was 65° C.; fresh, young tissue was collected (young plants worked best, new leaves on old plants were also used). A piece of leaf tissue was cut (approx. 4 cm long, and 1 cm wide), folded several times, inserted into a labeled microfuge tube (room temp.), and placed in the cold tube rack in the liquid nitrogen cooler—for extraction the same day the tubes were kept open (the tops broke easily when frozen), but for long term storage, the tops were closed. Ttissue was crushed in each tube using a wooden stick (i.e. the end of a paint brush). For fresh tissue, adequate amounts of DNA (for PCR, etc.) were obtained with crushing plant parts. After crushing, tubes were removed to a room temperature rack, 700 microL extraction buffer was added and mixed well by vortexing (and/or scraping against an empty tube rack); tubes were placed in 65° C. water bath in tube holder for at least 20 minutes (but this was extended up to 60 minutes for extracting multiple sets); tubes were removed (mixed again), and brought to room temperature under with the fume hood; tubes were filled with 24:1 mixture of chloroform and isoamyl alcohol (approx. 600-700 microL chloroform mix was added); tubes were closed tightly, placed in tube rack and covered with paper towels or cardboard and taped closed. Rack was placed in the circular turning machine, taped securely and mixed for 5 minutes of mixing in the machine; tubes were centrifuged for 10 minutes at maximum speed in microcentrifuge; upper aqueous layer was removed to a fresh tube (already labeled) approx. 550-600 microL of the supernatant. C500 microL ice-cold isopropanol was added and mixed by inverting; tubes were placed in −20° C. freezer overnight; After freezing, tubes were centrifuged for 12 minutes at maximum speed (13,000); to harvest the small DNA pellet. The remaining liquid was removed with a P-200; pellet washed with 800 microL ice-cold 70% ethanol, liquid was removed with a P-200 pipet; the pellet was dried but not overdried which makes it more difficult to resuspend); the pellet was resuspended in 50 microL. TE buffer for long-term storage. For PCR reactions, a 1:40 dilution (with $H_2O$, not TE) was made with optimal PCR dilutions rangeed from 1:5 up to 1:200 with this microprep protocol.

Protocols and Multi-Plex kit for Semi-Automated SSR Analysis of Rice: The use of fluorescently labeled primers for SSR detection provided a method for allele sizing with improved accuracy and efficiency over traditional silver staining techniques. Efficiency in use of time and resources was maximized by multiplexing multiple samples into a single lane for analysis. The following protocols were designed to used for implementation of semi-automated SSR analysis using fluorescently labeled markers. They included the procedures necessary for sample preparation and PCR, as well as suggestions for multi-plex panel design and analysis of results.

SSR and TNDBL Markers and Panels: Pπmers for SSR and INDEL identification are provided in FIG. 6. For more information on rice SSRs refer to: Design and Application of Microsatellite Marker Panels for Semiautomated Genotyping of Rice, by Coburn et al. (2002) Crop Sci 42:2092

General Computational and Experimental Analysis of Microsatellites in Rice (*Oryza sativa* L.): Frequency, Length Variation, Transposon Associations, and Genetic Marker Potential, by Temnykh et al. (2001) Genome Research 11 (8): 1441-1452//ricelab.plbr.cornell.edu/publications/2001/temnykh/, and //www.gramene.org/microsat/for additional citations.

General PCR: Polymerase chain reaction (PCR) conditions were described in Panaud et al. (1996) Mol Gen Genet. 252:597, in brief, standard reactions were heated at 94° C. for 5 min, followed by 35 cycles of 94° C. for 45 s, 55° C. for 45 s, and 72° C. for 1 min; lastly, 10 min at 72° C. PCR products were separated on 4% denaturing polyacrylamide gels, followed by silver staining as described in Panaud et al. supra Development of microsatellite Markers and characterization of simple sequence length polymorphism (SSLP) in rice (*Oryza sativa* L.). Mol. Gen. Genet. 252:597-607 (1996).

AGAROSE GELS: NEB (neutral electrophoresis buffer) or TAE was used to make A 0.9% agarose gels. For samples that required crisp separation of bands with only slight size differences, 2% agarose was used. The NEB stock kept in the lab is a 10× stock and the TAE is a 50× stock and must always be diluted to the desired concentration. Use the same concentration of buffer in making the gel and filling the tank. When gels ran overnight (slowly), 1×NEB or TAE was used. When day gels were ran (a few hours), 0.5×NEB or TAE was used.

Sequence Analysis: Following PCR amplification, amplified products were sequenced directly using the Applied Biosystems Automated 3730 DNA Analyzer, Big Dye Terminator chemistry and AmpliTaq-forward strand DNA Polymerase using standard techniques.

Heat Shock Transformation of *E. coli*: In brief, tube of competent cells was removed from a −70° C. freezer and thawed on ice; ampicillin plates (50 ug/ml) were warmed in a 37° C. incubator, X-gal and IPTG stock solutions, see, below, were thawed with 60 ul stock spread on each plant; 20 ul of competent cells was aliquoted into a 1.5 ml centrifuge tube; approximately 1 ng of plasmid DNA containing a rice nucleotide insert was added in a volume of 1 ul; the tube was tapped gently to mix; the tube was kept on ice for 30 minutes; cells were heat shocked in a 42° C. water bath for 90 seconds and then chilled immediately to 0° C. (ice) for 2 minutes; 80 ul of sterile SOC medium was added and tubes were incubated at 37° C. with moderate agitation (225 rpm) for 45 minutes. 60 ul stock was plated onto LB plates; cells were spread gently; and plates were incubated upside down at 37° C. overnight. X-gal/IPTG stock solutions were prepared containing 0.5 ml X-gal (stock 3% in N,N Dimethyl formamide) and 100 ul IPTG (100 mM).

Example 2

Rough Mapping of OTL Associated with Red Colored Rice Grains

Grain color is an important quality trait with nutritional and financial implications to rice growers and consumers. Rice grain with red coloration is of particular importance because red grain color is associated with conflicting qualities; in general, nutritional components and insect resistance vs. persuasive growth as an economic contaminant in nonred rice crops.

Rough Mapping of OTL Associated with Red Seed Pigmentation

The inventors' identified a single, significant QTL associated with red grain (rg 7.1) on chromosome 7 (FIG. 4). This QTL was identified in two independent $BC_2$ populations derived from crosses between an accession of *O. rufipogon* (IRGC105491) from Malaysia and, in one case, a U.S. tropical *japonica* cultivar, Jefferson and in the other case, a widely planted tropical indica cultivar, IR64.

The LOD score associated with the rg7.1 QTL peaks in both populations was 99 and 33, respectively and the QTL was detected in multiple environments in both studies. (Thomson, M personal communication; Septiningsih et al., 2003, Theor. Appl. Genet. 107:1419-1432). The peak of both QTLs LOD scores, in the experiments of the present inventors and that identified by Thomson, see, above, that corresponded to the previously mapped position of the mutant locus, brown pericarp, Rc (Kinoshita, 1998, RGN 15:13-74). $BC_2F$, plants had red seeds, thus the rg7.1 locus was dominant for red color, donated by the *O. rufipogon* parent.

Using the Jefferson/*O. rufipogon* population, the inventors discovered that rg7.1 encompassed an 5.1 cM region which represented about 7.2 Mb straddling the border of the centromere on chromosome 7 (FIG. 4). The genetic to physical distance in this region averages 1,440 Kb/cM, much above the genome average of 200 Kb/cM, as expected for a pericentromeric region. Their investigation of the genotype-phenotype relationship in the 285 $BC_2F_2$ families demonstrated that eighteen known rice families with red grain contained the *O. rufipogon* allele at either RM125 or the adjacent marker, RG30, suggesting that the gene underlying rg7.1 lay between these two markers.

Example 3

Fine Mapping rg7.1

Figure 10:
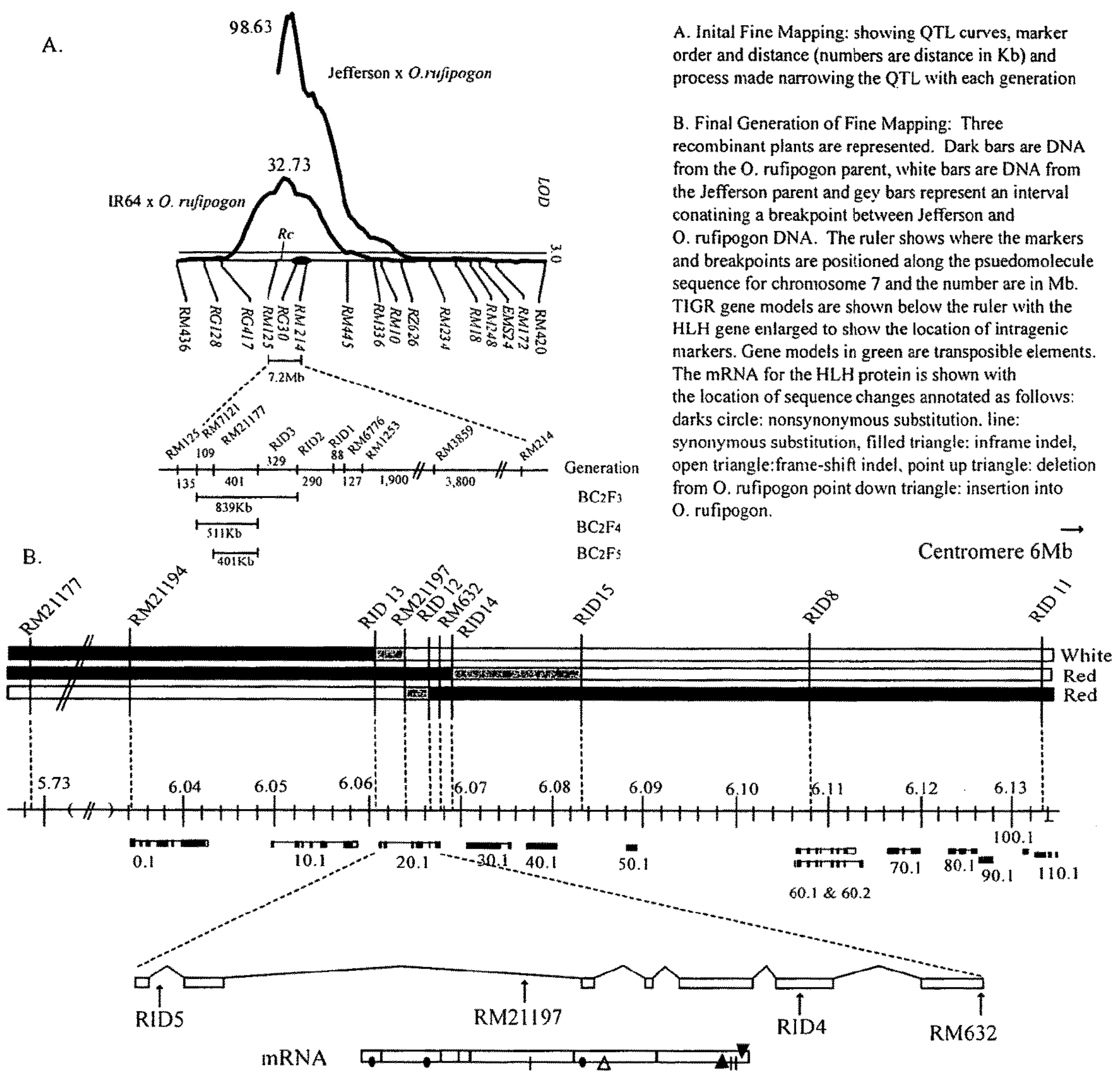
FIG. 10 shows an exemplary fine mapping of an Rc gene that used novel PCR primers of the present invention (see, FIG. 6): A) Initial Fine Mapping: showing QTL curves, marker order and distance (numbers are distance in Kb) and process that narrowed the QTL position with each successive generation; and B) Final Generation of Fine Mapping: Three recombinant plants are represented. Dark bars represent DNA from the *O. rufipogon* parent, white bars represent DNA from the Jefferson parent and grey bars represent an interval containing a breakpoint between Jefferson and *O. rufipogon* DNA. A ruler shows where the markers and breakpoints were positioned along the pseudomolecule sequence for chromosome 7 and the number are in Mb. TIGR gene models are shown below the ruler with the bHLH gene enlarged to show the location of intragenic markers. Gene models in green (lighter colored bars) represent transposable elements. mRNA for a bHLH protein is shown with the location of sequence changes annotated as follows: dark circle: nonsynonymous substitution, line: synonymous substitution, filled triangle: inframe indel, open triangle: frame-shift indel, point up triangle: deletion from *O. rufipogon* point down triangle: insertion into *O. rufipogon.*

In order to fine map rg7.1, 1410 $BC_2F_3$ plants were genotyped using markers flanking the rg7.1 QTL. The seventy-two recombinant plants were genotyped using six markers within the QTL region to locate the recombination breakpoints more precisely and seed color of each recombinant line was recorded. By determining which segments of DNA from the red donor parent, *O. rufipogon*, were present in all red-seeded progeny and discounting the *O. rufipogon* segments that appeared in white seeded progeny as possible gene positions, the region was narrowed with each generation to rg7.1 (FIG. 4). New SSR and INDEL markers were developed during the development of the present inventions helping order to farther define breakpoints across the region (FIG. 6). In the final $BC_2F_6$ generation, 4,000 plants were genotyped and three classes of informative recombinants were identified which narrowed the rg7.1 QTL to a 18.5 Kb region (FIG. 10). Physical to genetic distance varied greatly over this region with some areas of very high recombination and others where recombination did not occur (FIG. 10).

The Rc/rg7.1 locus is positioned in the pericentromeric region of rice chromosome 7, 6 Mb from the centromere. This area is rich in gypsy retrotransposons and other repeated elements that are associated with repression of recombination in this pericentromeric region. These gypsy retrotransposons are presumably contributing to repression of recombination was observed in the region. Within the Rc gene target, the recombination rate was higher than the reported genome average for rice. This suggests that positional cloning is still a viable option for genes located in these centromeric regions.

Thus, intragenic recombination in a cv Jefferson by *O. rufipogon* cross, narrowed the region down to a 3 Kb region bracketing exons 3 through 7 within the LOC_Os07 g11020.1 gene. The Rc mutant mapped directly beneath the peak of this QTL (FIG. 4). The peak of rg7.1 corresponded to the previously mapped position of the mutant, brown pericarp, Rc. In the initial $BC_2F_2$ generation, rg7.1 encompassed an 8 cM region on chromosome 7 which represented about 6 Mb of centromeric and pericentromeric sequence. As expected in centromeric areas, the recombination rate was repressed compared to other regions of the genome. To fine map the gene, 1,410 $BC_2F_3$ individuals were screened for recombination within rg7.1 and 55 recombinant $BC2F_3$ plants were identified. Genomic sequence data was used to generate new SSR markers, however numerous repetitive sequences in this centromeric region impeded the development of further necessary number of SSR markers. Therefore, Indel markers anchored in predicted ORFs were designed to amplify through intron sequences to maximize the likelihood of detecting polymorphism. The new Indel markers, see, FIG. 6, were used to screen the progeny of heterozygous $BC_2F_3$ and $BC_2F_4$ individuals to identify additional recombinants. Information from these screens allowed us to further narrow the region containing the gene(s) to 562 Kb. The region contained 55 predicted genes, which were investigated as candidate genes

Example 4

Additional Sequencing of Rc Alleles

The inventors fully sequenced an Rc gene in both the Jefferson (white) and the *O. rufipogon* (red) parents and aligned them to show several polymorphisms (FIG. 2). These two alleles were run though the FgenesH program, described above, to see if the polymorphism were predicted to alter the intron/exon boundaries. Several differences were observed. As *O. rufipogon* contains the functional allele, the gene model predicted for its sequence will be the reference SEQ ID NO: 139. The Jefferson sequence again contained a 14 bp deletion in exon 6, which would lead to frame shift before the HLH domain in exon 7. However in the Jefferson/Nipponbare annotation this deletion was intronic and did not appear to frame shift the amino acid sequence, allowing the bHLH domain to be annotated.

Additional genetic markers were added to map the region between RM7121 and the AF loci and these were used to screen 2,000 $BC_2F_6$ plants. Several informative recombinants were identified in which the break points fell within the bHLH candidate. These plants definitively narrow the rg7.1 locus to a 3 Kb region, falling entirely within the bHLH candidate gene. This 3 Kb region contains three coding sequence polymorphisms that distinguish the parents; a synonymous SNP SEQ ID NO: 140, a non-synonymous SNP SEQ ID NO: 141, and the 14 bp frame shifting deletion resulting in a loss of the bHLH portion of the Rc polypeptide, SEQ ID NO: 134. To confirm which of these changes would be functional, the allele in an Rc genetic stock was sequenced. This line produced colored seeds and thus, predicted a functional copy of the gene. It also falls within the same subpopulation group as the Jefferson parent (spp. *japonica*). A polymorphism was found in the Rc stock line that distinguished the Jefferson from a *rufipogon* and further a Rc sequence from a Jefferson white grained rice plant again showed a 14 bp deletion compared to a homologous sequence from a *rufipogon* red rice grained plant.

These experiments further supported the inventors determination that the sequence encoding the putative bHLH protein located within QTL rg7.1 and the putative encoded bHLH protein encoded the Rc protein.

Example 5

Positional and Functional Candidate Genes

The one nontransposable element gene was located within the 18.5 Kb region was LOC_Os07g11020.1, a single copy gene encoding a protein 668aa in length, and containing a predicted HLH domain. This domain was common among transcription factors regulating pigment synthesis. The promoter region and the first two exons of the HLH gene had been eliminated via recombination as the source of the functional nucleotide polymorphism; however exons 3-7 fell within the 18.5 Kb region. Other genes within the 18.5 Kb region were two putative transposon proteins, both of the CACTA type, En/Spm sub-class. Theses 2 genes with corresponding proteins are LOC_Os07g11040.1 that contains a transposase domain and LOC_Os07g11030.1 that has a proteinase domain. Neither of these types of domains were found in either the regulatory or biosynthetic proteins responsible for anthocyanin and/or proanthocyainidin pigmentation. When compared using BALST searches, the sequence of both of these proteins have over a hundred BLAST hits in the rice genome with greater that 98% identity over the entire length of the sequence. Therefore the function of these genes was not likely to be lost if they were mutated since many other copies should remain functional. Transponsable elements (TEs) can be responsible for phenotypic changes when inserted within functional genes, however unlike the HLH region containing gene, neither of the two TEs within rg7.1 showed evidence of having disrupted any other genes. Therefore, the inventors contemplated that the putative bHLH encoding gene in LOC_Os07g11020.1 was responsible for rg7.1 (Rc) associated phenotypes.

Example 6

Re Mutant

Sequence Comparisons of a Candidate Rc Gene

During the development of the present inventions, a locus encoding a predicted bHLH protein, as shown in EXAMPLE 4, from Nipponbare and rice variety 93-11 was sequenced in order to find differences that would explain the difference in pericarp color. There are many changes found across the genomic sequence (for example, see, FIG. 2). As both Nipponbare and 93-11 produced white-grained rice, both sequenced genomes were expected to contain a non-functional allele at the rg7.1 locus.

Further, a sequence for a bHLH allele from O. ruβpogon (red) was also analysed using FgenesH prediction software by Softberry, Inc then compared to the gene model annotated from Nipponbare sequence: Several shifts in the gene model were found (FIG. 2). A short piece of *O. ruflpogon* mRNA was used as a sequencing template from a region where the gene models differed between white and red grained varieties and confirmed that an intron/exon junction for exons five and six are transcribed as predicted from the *O. ruflpogon* allele and not as publicly annotated (url). Using the *O. ruflpogon* based gene model, nine of the sequence polymorphisms fall within the coding sequence and six of those affect protein sequence (FIG. 2).

In order to identity which of the sequence polymorphisms between the parents was responsible for the altered function of the gene, the HLH locus from a Rc mutant stock that falls within the same subspecies as the white parent, Jefferson, was sequenced. These lines were more closely related then the Jefferson and *O. rufipogon* lines, and showed fewer sequence changes than expected from sequence comparisons. The Rc stock carries a functional allele, so a comparison between Rc and Jefferson sequence was done to locate candidates for the functional nucleotide polymorphism. The coding sequence of the Rc stock was found to be identical to the Jefferson sequence except for a 14 bp section which was present in the functional Rc, and *O. rufipogon* but deleted from exon 6 in Jefferson. This deletion would frame shift the sequence before the HLH domain in exon seven. As this deletion was the only difference between the Rc (pigmented/red seeds) and Jefferson (white seeds), then the 14 bp deletion was determined to be responsible for the lack of pigment in the pericarps of white Jefferson seeds.

The inventors contemplated that if the HLH encoding gene is responsible for rg7.1 and thus the Rc gene, then the inventors predicted that the third allele of Rc, Rc-s, which conditions light red seed pigmentation would also have specific changes in the sequence of this locus that could affect the function of the protein. Therefore, the HLH gene in the variety Suramkuhi, which carries Rc-s allele was sequenced. This sequence was found to be similar to the *O. rufipogon* allele, with the exception of a C to A change in exon 6 that causes a premature stop codon before the HLH domain. Since rg7.1 mapped on top of the Rc locus and the different alleles of Rc show sequence differences in the candidate HLH gene that clearly account for the observed phenotype differences, the inventors concluded that the HLH protein is both responsible for rg7.1 and is the mutant Rc.

Example 7

Expression Profiles of Re in White and Red Rice

To examine the timing and localization of the Rc transcript, RT-PCR was used to amplify mRNA from leaf, young panicles (before fertilization), pericarp of young seeds (at the milk stage or dough stage of grain filling) and pericarp from mature seeds (seeds with hard endosperms) using PCR primers SEQ ID NOs:32-33. The mRNA was collected from both Jefferson (white seed) and *O. rufipogon* (red seed) plants. Rc expression is seen in both red and white seed plants, but the RNA transcript from Jefferson contains the frame-shifting 14 bp deletion (FIG. 3A).

Since the promoter region of the HLH gene had eliminated as the source of polymorphism based on a recombination screen conducted during the development of the present inventions, the inventors expected that the expression levels of Rc from red and white seeds would be the same. Indeed, RT-PCR results showed equivalent expression levels of Rc between red and white seeds (FIG. 3A)

The inventors further contemplated that expression levels would be different when RID4 PCR primers, that amplified the nucleic acid sequences of the *rufipogon* sequence were used. Indeed, FIG. 3B shows a high level of Rc expression for *O. rufipogon* (red) but not in *O. saliva* Jefferson (white) plant samples.

Rc expression in general was limited to the panicle and observed before fertilization and not observed in mature seeds (FIG. 3A). Thus supporting the inventor's identification of Rc as enhancing red pigmentation in rice pericarp.

Figure 3:
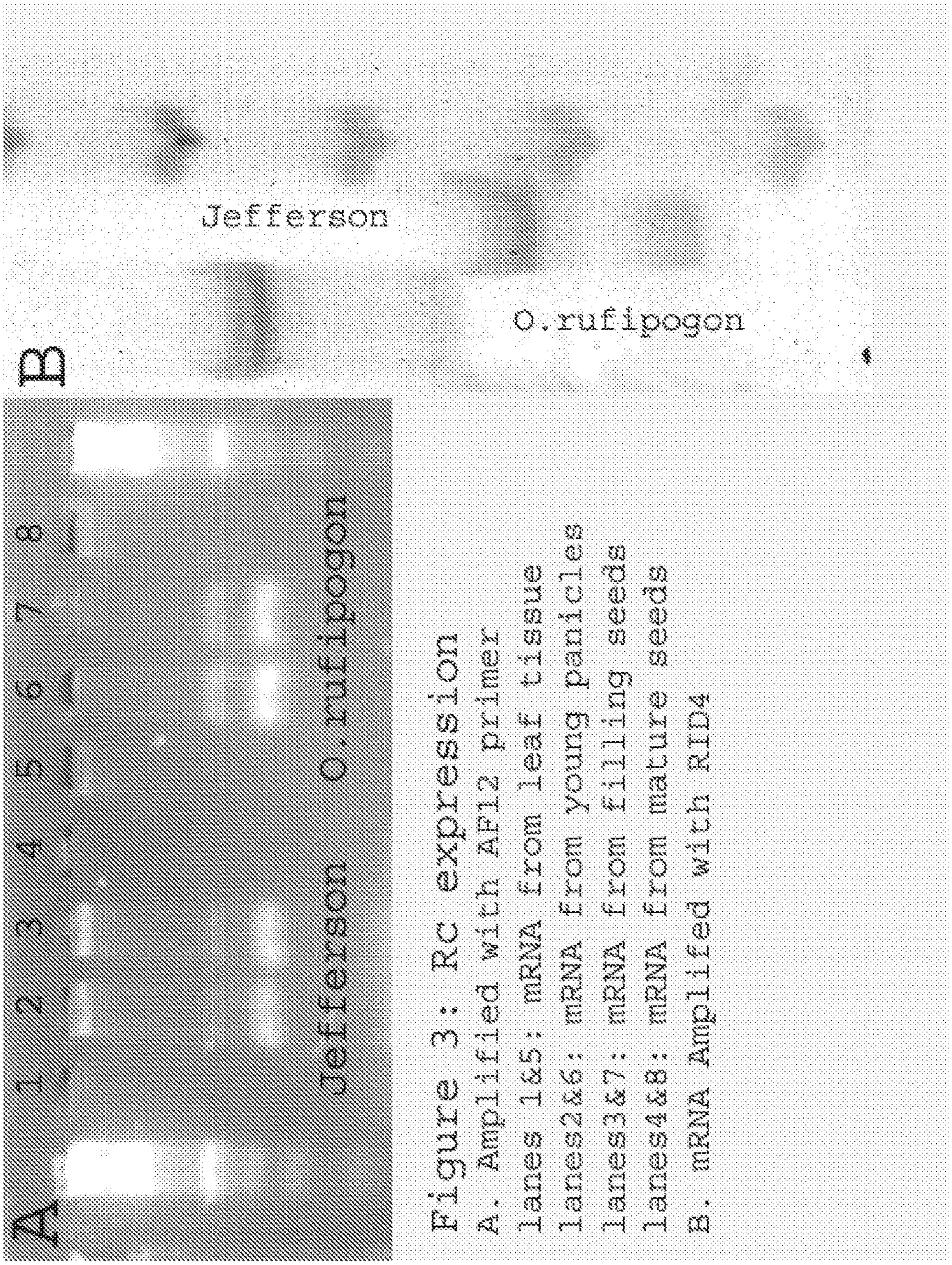
FIG. 3 shows exemplary Rc protein expression by RT-PCR amplification of Rc from mRNA from red seeded plants, A) such as *O. rufipogon* lanes 5-8 (for example, SEQ ID NO:01), but not from white seeded plants, such as *O. saliva* Jefferson lanes 1-4 (for example, SEQ ID NO:02) and B) Rc expression shown in *O. rufipogon* (red) but not in *O. sativa* Jefferson (white) when PCR primers spanning the *rufipogon* region were used for amplifying the Rc transcripts.

In summary, unexpected results demonstrated that *O. sativa* Rc RNA transcript from Jefferson contained a frame-shifting 14 bp "*rufipogon*" deletion (FIG. 2) with equivalent levels of expression compared to *O. rufipogon* plants. Further, Rc expression of mRNA transcripts comprising the *rufipogon* fragment was significantly higher in *O. rufipogon* red rice samples than in *O. sativa* Jefferson (white) plant samples. Finally, Rc expression in seed, panicle and leaf samples was limited to young panicle tissue, prior to fertilization, developing seeds but not detectable in the mature seed (FIG. 3).

Example 8

Phylogenetic Comparison

The sequence of Rc was compared to other HLH transcription factors (TFs) involved in plant pigmentation (FIG. 4). The closest sequence match to Rc was IN1 (SEQ ID NO:116) from maize. It is not unexpected that Rc would be most closely related to a protein from the grasses, however, IN1 functions as a negative regulator of maize pigmentation such that when IN1 was knocked out an intense color was produced. This was a very different mode of action from Rc, which is a positive regulatory of pigment production. Rc was more closely related to the dicot TFs AN1 and TT8 (SEQ ID NO:117-118) then it was to the positive regulators of maize anthocyanin pigmentation or the HLH protein that regulates purple anthocyanin production in rice leaves. This suggests an ancient duplication of pigment-regulating transcription factors and the duplicated genes were then able to evolve separate functions. In rice, duplicated genes may have specialized into either the proanthocyanidin or anthocyanin pathways while in maize the duplicated genes became positive and negative regulators.

Example 9

Fine Mapping of Rc

QTL mapping described in Example 2, provided evidence for a single significant QTL associated with red grain (QTL rg 7.1) located on rice chromosome 7 (FIG. 4). To fine map the gene, 1,410 $BC_2F_3$ individuals derived from selected $BC_2F_3$ families identified as recombinant in the target region of Rc with RM125 and RM214. Fifty-five $BC_2F_3$ plants were identified that contained recombination breakpoints in the target region of rg 7.1 therefore the pericarp color was determined for each plant. SSR markers were obtained from a Gramene Internet Databease (Jaiswal et al., 2006, Nucleic Acids Research, I; 34(Database issue):D717-23; 2006, Ware et al., 2002, Nucleic Acids Research 30(1): 103-105; Jaiswal et al., Rice Genetics Newsletter, 22(1): 9-16; Comparative and Functional Genomics, 3(2) 2002; Ware et al., Plant Physiol, 2002, 130:1606-1613; all of which are herein incorporated by reference) that identified regions between RM125 and RM214 were synthesized and used to examine these regions for polymorphism(s). Four such markers were used to narrow the rg 7.1 target Rc region to approximately 1.3 Mb. Eight of the $BC_2F_3$ families had recombination break points in this 1.3 Mb region. New markers were developed by anchoring primers in predicted ORFs to target single copy DNA in this heterochromatic centromere region and positioned to amplify through intron sequences to maximize the likelihood of detecting polymorphisms, (for example, SEQ ID NOs: 44-57. Three of sixteen primers designed using this strategy produced PCR products with a size polymorphism that was readily detectable on polyacrylamide gels, allowing us to distinguish alleles from Jefferson and *O. rufipogon* (SEQ ID NOs: 52-57).

These rice indel (RID) markers were used to screen the $BC_2F_3$ and $BC_2F_4$ recombinants. Information from this screen allowed us to further narrow the region containing the gene(s) to 513 Kb. Nineteen $BC_2F_4$ individuals, recombinant between RID3 and RM7121, were identified, for example, SEQ ID NOs:66-67.

Fine mapping narrowed the region containing this QTL to a 562 Kb region which appears to bracket Rc and contains a candidate gene with homology to an anthocyanin regulatory protein.

This region contains 55 putative genes, 43 of which are annotated as hypothetical (The Institute for Genomic Research (TIGR). As the anthocyanin pathway is well characterized, the gene annotations from the Nipponbare sequence for these positional candidates were examined for homology with known anthocyanin biosynthetic genes or regulatory genes for an anthocyanin pathway. One putative gene contained a HLH domain, a motif common among anthocyanin regulatory genes.

Therefore, the rufipogon deletion in the white rice plant sequence was contemplated as the responsible factor resulting in the lack of pigment in the pericarp of white Jefferson seeds. Since rg7.1 mapped on top of the Rc locus and the Rc genetic stock contain a functional allele at the locus cloned from rg7.1 the inventors determined that rg7.1 is Rc.

Example 10

Figure 19B:
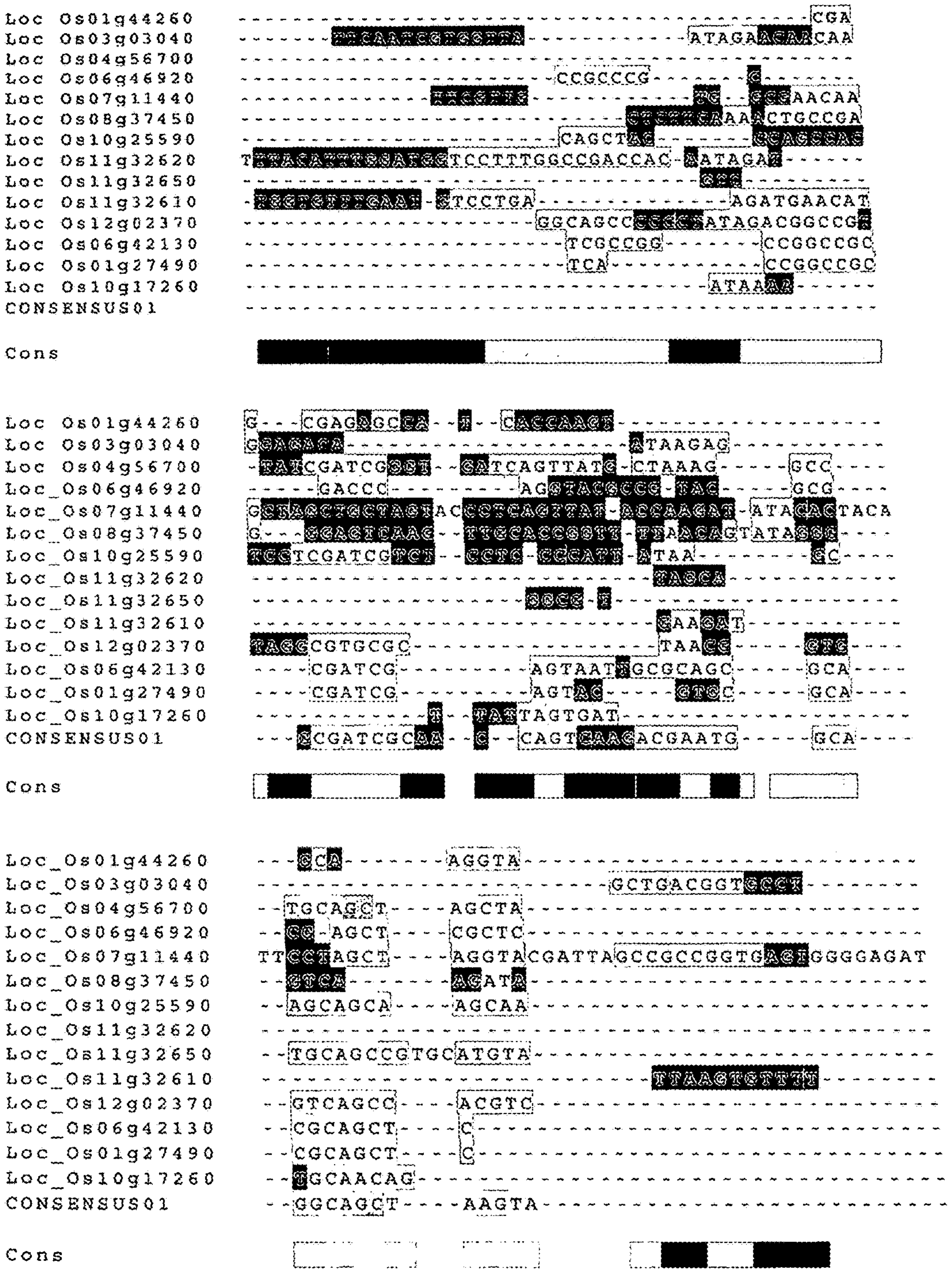
Figure 19C:
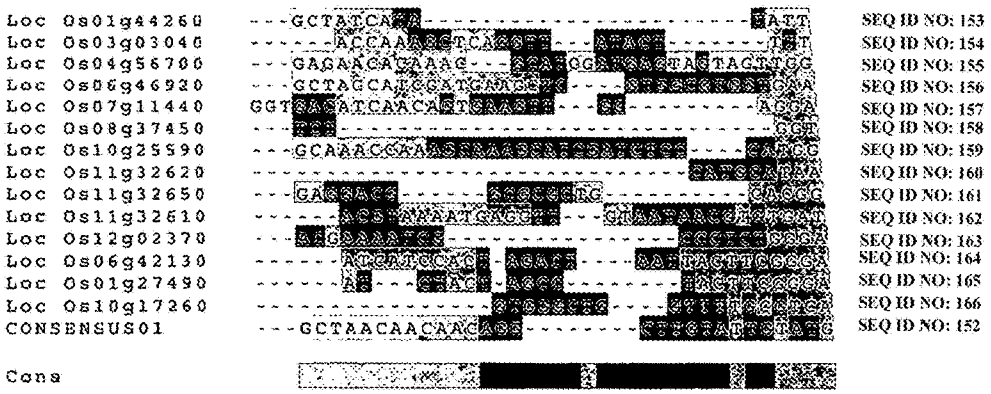

Identification of potential Rc responsive promoter or Rc control was regions based upon identifying candidate Rc controlled genes and then comparing these promoter regions to a maize promoter comprising an anthocyanin region regulated by a maize homolog of rice Rc. Clustal comparisons were made of SEQ ID NO: 165 to individual SEQ ID NOs:119-137 (FIG. 19). Selected homologous regions were used for Tcoffee for alignments in order to identify shorter potential Rc control regions (SEQ ID Nos: 152-164) (FIGS. 20-22).

Specifically, a consensus 01 sequence was determined in a maize a2 promoter seq (SEQ ID NO: 165) −112 to −41. The consensus sequence3 was used to search the Gramene database where approximately 1300 bp promoter sequences for LOC_Os06g42130 (SEQ ID NO:122), LOC_Os01g27490 (SEQ ID NO:121) and LOC_Os01g44260 (SEQ ID NO:131), were identified. LOC_Os06g42130 (SEQ ID NO:122) is a rice homolog of anthocyanin synthase (ANS) genes from *Zea mays*. LOC_DsO1g27490 (SEQ ID NO: 121) and LOC_Os06g42130 (SEQ ID NO: 122), are a rice homologes of anthocyaninless2 (A2), while LOC_Os01g44260 (SEQ ID NO:131) is a rice homolog of anthocyanin synthasel (A1) from *Zea mays*. These 1300 by sequences comprise 1000 bp and +300 bp of the two loci. The sequences for these two loci were compared using one of the programs (WinClone) while inversing complement regions of the sequence because the above two genes were on minus strand and the exported sequence from Gramene were from plus strand. These three sequences were compared using ClustalW with first comparisons using the default values, then modifing the parameters for a better alignment, specifically setting the GAP OPEN to 5.

The inventors set ATG at position 1000 bp in LOC_Os01g27490 and LOC_Os06g42130 as a translation start site. Based on the alignment the previously identified consensus sequence from maize matches promoter regions of rice anothocyanin genes for comparing to a maize ACE consensus sequence (Maize a2-promoter):

```
                                    (SEQ ID NO: 152)
GCGATCGCAACCAGTCAAGACGAATGGCAGGCAGCTAAGTAGCTAACAAC

AACAGGCTTGTATTGTATG.
```

Example 11

Identification of bHLH Transcription Factor Elements as Exemplary Rc-Responsive Promoter Elements In order to predict the minimal promoter region for efficient trans-activation by the Rc protein, the inventors identified candidate Rc regulated rice genes, whose homologes are associated with the anthocyanin pathway in maize, (for example, see FIG. 23), and then searched the upstream regions for known cis-regulatory elements (for example, see FIG. 24). As used herein, cis-elements refer to short nucleotide sequences that are recognized with high specificity by their cognate transcription factors. Numerous cis-regulatory element nucleotide sequences in plant gene promoters of genes expressed in the anthocyanin production pathway have been published, see, FIG. 24.

The Relative Importance of Identifying bHLH and myb Binding Elements for Potential Rc Regulated Promoters of the Present Inventions.

Published information on bHLH proteins (of which Rc is predicted to function as a bHLH protein) in other systems, demonstrated bHLH protein binding to sequences known as "E-boxes," (for example, CANNTG is an e-box element). Similar cis-elements are required for efficient regulation of the target gene. In contrast, bHLH proteins in the anthocyanin pathway may not interact directly with DNA binding elements. For example, removal of the C-terminus of the B protein in maize results in the loss of the entire bHLH domain. Yet, the ability of this modified B protein to activate genes of the anthocyanin pathway is minimally disrupted.

Essential molecular partners of bHLH molecules, known as myb transcription factors, interact with bHLH protein sequences and this interaction is required for proper transactivation of anthocyanin biosynthetic genes. In maize, *Arabidopsis*, petunia, and snapdragon, some myb proteins and their associated bHLH binding partners have been identified and cloned. Myb transcription factors are known to recognize specific cis-elements in the promoters of the genes they regulate. The recognition sequences for the P and C1 myb proteins from maize have been published (for review, see, Sainz et al., (1997) In Vivo. Mol Cell Biol 17:115-122; Grotewold et al., (1994) Cell 76:543-553; all of which are herein incorporated by reference), including the elements specific to the A1 gene, which corresponds to the DFR gene in rice (Tuerck and Fromm (1994) Plant Cell 6:1655-1663; Lesnik and Chandler (1998) Plant Physiol 117:437-445; all of which are herein incorporated by reference).

Myb transcription factors are predicted to regulate highly conserved genes of the anthocyanin pathway across plant species. Thus regulatory control of the proanthocyanidin pathway in rice was contemplated by the inventors to also require active Myb transcription factors. However, during the course of developing the present inventions, a Myb transcription factor was not implicated as a candidate gene for altering red pigmentation in rice grains. In contrast to Myb, sequence analysis of a bHLH nucleotides and a bHLH protein putatively encoded by a Rc genes was shown by in these examples to be directly associated with differences between red pigmentation and white rice grains. Thus functional red rice plant Myb proteins were contemplated to directly interact with Rc protein forming a active complex that can regulate the expression of the biosynthetic genes, where the Rc protein is functional in red rice plants and not functional in white grained producing rice plants. When Rc is not functional the active complex cannot be formed and the functional Myb proteins cannot activate the biosynthetic genes alone In addition, the Rc bHLH and Myb complex are contemplated to interact with the promoter sequences of genes associated with proanthocyanidin production pathways for activating transcription of red pericarp producing genes. Therefore, the inventors proceeded with the following experiments in order to identify bHLH and myb binding regions in promoters of genes expressing proteins for producing red pigmentation in rice grains.

Dihydroflavonol reductase (DFR; SEQ ID NO:192, a fragment of SEQ ID NO:131) was expressed in red rice seeds but not in white rice seeds. Thus, the inventors contemplate that expression of rice DFR requires a functional Rc transcription factor and that DFR is an Rc regulated promoter.

Figure 23:
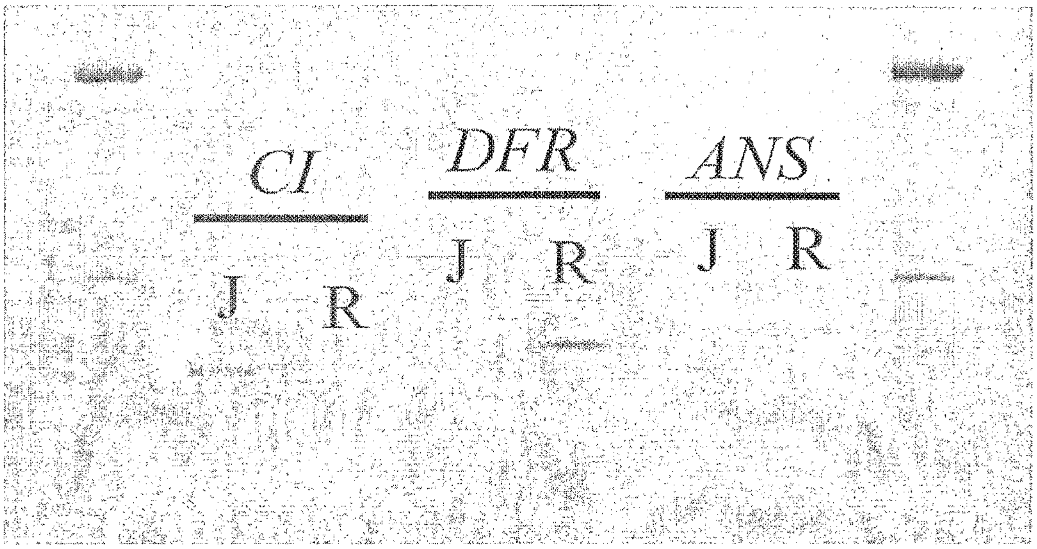
FIG. 23 shows an exemplary RT-PCR experimental result that demonstrated the expression of DFR in *O. rufipogon* (R) red rice grains while not expressed in *O. sativa* white (J, Jefferson) rice grains.

Expression of three genes, chalcone isomerase (C1), dihydroflavonol reductase (DFR) and anthocyanin synthase (ANS), previously reported to be in the proanthocyanidin biosynthetic pathway, in the developing seeds of red and white grained rice plants was demonstrated using RT-PCR experiments (FIG. 23).

RT-PCR Amplification methods. Standard RT-PCR methods were used for producing amplified DNA gene fragments from mRNA samples obtained from pericarps isolated from milk and dough stages of grain filling. Primers designed by the inventors for amplified chalcone isomerase (CI), dihydroflavonol reductase (DFR) and anthocyanin synthase (ANS) fragments are shown below. In brief, the annealing temperate was 55 degrees for all three sets of primers. Amplified DNA, as labeled in FIG. 23, and 100 bp ladders as a size reference placed at the sides of the gel, were separated on 1% agarose gels, stained with ethidium bromide and photographed. The ladder 600 bp band was three times darker than the other ladder bands.

```
CI RNA PRIMERS:
                                  SEQ ID NO: 179
forward:
TAGGGCATTTGGAGAGTTGG,
reverse:
                                  SEQ ID NO: 180
GCAGATTCTCCACCGAGGTA;

ANS RNA PRIMERS:
forward:
                                  SEQ ID NO: 181
GAAGAGGGAGTGGGAGGACT,;
reverse:
                                  SEQ ID NO: 182
CAGAAGACGACCCAGGAGAC;

DFR RNA PRIMERS:
forward:
                                   SEQ ID NO:183
GCCCACTACTCGATCCTGAA,;
reverse:
                                   SEQ ID NO 184
TCATTTGACCAACGCTTCTG,:
that amplified a sequence of the DFR

amplified fragment corresponding to:
                                  SEQ ID NO: 192
aacgggatgccgccgagccacgtcaccgcgctggcgctgctcacggggaa
cgaggcccactactcgatcctgaagcaggtgcagttcgtccacctcgacg
acctctgcgacgccgagatcttcctcttcgagagccccgaggcgcgcggc
cgctacgtctgctcctcccacgacgccaccatccacggcctcgcgacgat
gctcgcggacatgttcccggagtacgacgtgccgcggagctttcccggga
tcgacgccgaccacctccagccggtgcacttctcgtcgtggaagctcctc
gcccacgggttcaggttcaggtacacgctggaggacatgttcgaggccgc
cgtccggacgtgcagggagaaggggcttctcccgccgctgccgccaccgc
cgacgacggccgtggccggaggagacggctcggcgggtgtggccggcgag
aaggaaccgatactggggagggggaccgggacggcggttggtgctgaaac
agaagcgttggtcaaatga,.
```

Following the identification of the DFR gene as a contemplated Rc regulated gene, the rice DFR promoter was analyzed using a PLACE cis-element database to search for known regulatory motifs. Several types of regulatory cis-elements were identified (FIG. 24).

Numerous E-box motifs (putative binding sites for bHLH proteins) and myb-binding sites were found in the DFR promoter as shown in FIG. 25. Additional regulatory elements for maize consensus myb-binding sequences for anthocyanin production and anthocyanin regulatory elements as candidate sites for bHLH, such as Rc, protein binding for enhancing anthocyanin production were also identified ((Tuerk and Fromm (1994), supra, and Lesnick and Chandler (1998), supra), are shown in FIG. 25. Further, the inventors identified an additional candidate Rc responsive promoter from a region 1.3 kB upstream of DFR in the red rice plant varieties Mudgo and Kasalath:

```
                                  SEQ ID NO: 193
gtaatgatggttaaaaactataagaacgaaacagtgatggtttgattttt
aaggtaccaagaacaatcaatagaaatggtggccagccaggcaagcagct
ggaggagctacaaggagaggggtggcgcccaatgcgacttttaaaactat
aaaattataaagttggtaatgataatgttaattttaaaaaatatcatgtg
gaaatgagttgaccttttacaaattttcaagaaaataaagggtaaaaaat
tagatgattttatatcggtgctagatgtacaaatgcgtgggccaacctac
tagtttttggctgaatctgaacaattttgaacggtccaaaaaaaccggtt
cattctgctcctttgcctgtcgtcacgctgtcatcacgctgcggatgcag
cgtactaaacgcaccggcctttcaaacaagaaccggccggtgtgcaggtg
cacgtagctcaaacctacctatcaaaacgctggtcattctgtctactcca
tccgaccccaaaaaaaaaagacaaaccctgattttcgtgtctaacgtttg
accgtccgtcttatttaagaaaattatgaaaaaaaattaaaaaaacaagt
cacacataaaatattaatcatgttttatcatctaacaataatgaaaatac
gaattatataaaaaaatttcatataagacggacagtcaaagttggacacg
gaaacctagagtaacttgttaggcagtacaagtgtgtgtagctatactcc
ccctgtcctgtaccagcttatatatataggcgagccaacgagcgagagcc
atcaccaagtgcaaggtagctatcatatattctgcgaatccaacacaagc
accgcggcgtagtactactacttgcgcgcgcgtgttagattcgcgtgcga
atccaacacaagcagatcgatcacgcacggtacgccatgggcgaggcggt
gaaggggccagtggtggtgacgggcgcgtcgggcttcgtcggctcatggc
tcgtcatgaagctcctccaggccggctacaccgtccgcgccacagtgcgc
gacccctgtgagctctctcatcgtgcactctagctctctcctcgtagttt
actgactccaattatatatgccgcttgcttgactctgacaagtgtacgtg
ttgttgttgttgttttcagctaacgttgggaagacgaagccgttgctgga
gctggcggggtcgaaggagaggctgacgctgtggaaggccgacctgggcg
aggaaggcagcttcgacgcggcgatcaggggttgcacgggcgtgttccac
gtcgcgacgccc,.
```

The inventors noted that the consensus myb-binding sequences fall within the annotated 5' UTR of the DFR gene. Thus the inventors further contemplate a new annotation of this gene where transcription starts closer to the proximal to the ATG start codon.

Therefore, the inventors further contemplate compositions and methods comprising regulatory regions of a rice DFR promoter isolated from red grained rice producing varieties of rice plants for use in red rice plant containment vectors as described below. The inventors contemplate amplifying and using regions of a DFR promoter containing a Myb or bHLH binding motif as targets in gel retardation binding assays. In these assays, nuclear extracts, containing transcription factors, would be mixed with a promoter target, such as isolated portions of promoter sequences and incubated under conditions for allowing protein-DNA interactions. The mixture would be separated on an agarose gel and observed for bound complexes. When binding occurs, then movement of the DNA and protein complex through the gel is retarded compared to the movement of unbound DNA and unbound protein. A motif would be considered a binding target of Rc if bound complexes are shown following incubation of isolated promoter regions with nuclear extract from the panicles of red-seeded plants (containing a functional Rc) compared to no bound complexes when nuclear extracts from the panicles of white seeded plants (lacking a functional Rc).

When a Rc responsive promoter (Rc promoter) motif (Rc regulatory element) is identified, the inventors further contemplate the ligation of a nucleotide sequence comprising a Rc promoter motif in operable combination with a reporter gene for providing a test red rice containment construct. In one embodiment, the inventors contemplate transforming a test red rice containment construct into red rice plant tissue and white rice plant tissue. In a further embodiment, the inventors will identify a promoter motif and surrounding promoter sequence sufficient to drive expression of a reporter gene. Further, the inventors will identify promoter sequences where expression is specific to red rice tissues, in particular panicle tissue pigmentation affected by functional Rc. When Rc responsive sequences are identified for driving expression of a reporter gene in red rice plant tissue but not white rice plant tissue, the inventors contemplate using Rc responsive promoter sequences in a red rice containment construct.

In one embodiment of the present invention, a red rice containment construct expresses a toxin under the control of the Rc-responsive promoter. In one embodiment of the present invention, a red rice containment construct is an RNAi construct expressing a nucleotide sequence for altering growth and reproduction in a red rice plant under the control of the Rc-responsive promoter. In another embodiment, the red rice containment construct is transfected into red grain producing rice plants and white grained producing rice plants. Examples of such white grained rice plants for use as host plants are commercial varieties of rice plants including but not limited to Roundup Ready® rice plants, Liberty Link® Rice plants, and elite rice varieties grown in particular areas of the United States and Internationally.

In yet another embodiment, transformed red rice plants are tested for growth and reproductive traits. In a preferred embodiment, transformed red rice plants are sterile while transformed white rice plants are fertile. In yet a further preferred embodiment, hand pollination of transgenic pollen from rice plants producing white grains onto a rice plant that would naturally produce red rice would cause the red rice plant to fail to produce viable rice seeds.

Therefore, the inventors further contemplate compositions and methods comprising regulatory regions of the rice DFR promoter for use in red rice plant containment vectors. The following sections describe a means of identifying Rc responsive promoters and additional constructs for containment vectors.

Contemplated Embodiments of the Present Inventions

Identify Nucleic Acid Sequences Comprising Rc Responsive Promoter Elements

The inventors contemplate creating and cloning gene segments for insertion into test vectors, then testing using promoter testing procedures as demonstrated in Lesnick and Chandler, (1998) Plant Physiol. 117:437-445; herein incorporated by reference. However these techniques would be modified for identifying Rc responsive sequences.

In brief, PCR amplification of candidate nucleic acid promoter sequences would be followed by cloning sequences into a blunt end vector such as pGEM-T Vector from Promega, see, for example, cloning techniques described herein and in Lesnick and Chandler, supra. The candidate promoter would then be place into front of a GUS or GFP gene and transiently transformed into the target tissue (in this case young, developing red seeds). The target tissue contains all the correct transcription factors needed for expression of the reported gene. If the Rc responsive elements are present, then transcription factors in red rice seeds will bind to the construct and express either GUS or GFP, both of which are visible and can be screened for easily.

Results would be evaluated similar to those reported in Lesnick and Chandler, (1998) Plant Physiol. 117:437-445; and Marc and Chandler, (1998) Plant Physiol. 117: 437-445. Briefly, two transcription factors, C1 (a Myb-domain protein) and B (a basic-helix-loop-helix protein), mediate transcriptional activation of the anthocyanin-biosynthetic genes of maize (*Zea mays*). To begin to assessing the mechanism of activation, the sequences required for C1- and B-mediated induction were determined for the a2 promoter, which encodes an anthocyanin-biosynthetic enzyme. Analysis of a series of 7- to 13-base-pair substitutions revealed two regions crucial for activation. One region, centered at −99, contained a C1-binding site that abolished C1 binding. The other crucial region was adjacent, centered at −91. C1 binding was not detected at this site, and mutation of this site did not prevent C1 binding at −99. An oligonucleotide dimer containing these two crucial elements was sufficient for C1 and B activation of a heterologous promoter. These data suggest that activation of the anthocyanin genes involve C1 and another factor binding at closely adjacent sites. Mutating a previously postulated anthocyanin consensus sequence within a2 did not significantly reduce activation by C1 and B. However, sequence comparisons of the crucial a2 regions with sequences important for C1- and B-mediated activation in two other anthocyanin promoters led to a revised consensus element shared by these promoters as in Marc and Chandler, (1998) Plant Physiol. 117: 437-445.

Constructing Specific Rc Promoter Testing Vectors:

Test vectors would use vectors and methods such as pGEM®-T and pGEM®-T Easy Vector System: The pGEM®-T and pGEM®-T Easy Vector Systems are convenient systems for the cloning of PCR products. The vectors are prepared by cutting Promega's pGEM®-52f(+) and pGEM®-T Easy Vectors with EcoR V and adding a 3' terminal thymidine to both ends. These single 3'-T overhangs at the insertion site greatly improve the efficiency of ligation of a PCR product into the plasmids by preventing recircularization of the vector and providing a compatible overhang for PCR products generated by certain thermostable polymerases. These polymerases often add a single deoxyadenosine, in a template-independent fashion, to the 3'-ends of the amplified fragments.

High copy number pGEM®-T and pGEM®-T Easy Vector Systems contain T7 and SP6 RNA polymerase promoters flanking a multiple cloning region within the alpha-peptide coding region of the enzyme beta-galactosidase. Insertional inactivation of the alpha-peptide allows recombinant clones to be directly identified by color screening on indicator plates. The multiple cloning region of the two vectors includes restriction sites conveniently arranged for use with Promega's Erase-a-Base® System (Invitrogen Catalog #E5750) for generating nested sets of deletions.

Protocol for Ligations: Using the pGEM®-T and pGEM®-T Easy Vectors and the 2× Rapid Ligation Buffer. 1. Briefly centrifuge the pGEM®-T or pGEM®-T Easy Vector and Control Insert DNA tubes to collect contents at the bottom of the tubes. 2. Set up ligation reactions as described below. Note: Use 0.5 ml tubes known to have low DNA-binding capacity (e.g., VWR Catalog#20170-310). 3. Vortex the 2× Rapid Ligation Buffer vigorously before each use. 4. Mix the reactions by pipetting. Incubate the reactions 1 hour at room temperature. Alternatively, if a maximum number of transformants is desired, incubate the reactions overnight at 4° C.

| | Standard Reaction | Positive Control | Background Control |
|---|---|---|---|
| 2X Rapid Ligation Buffer, T4 DNA Ligase | 5 pl | 5 pl | 5 pl |
| pGEM ®-T or pGEM ®-T Easy Vector (50 ng) | 1 μl | 1 μl | 1 μl |
| PCR product | X μl | — | — |
| Control Insert DNA | — | 2 μl | — |
| T4 DNA Ligase (3 Weiss units/μl) | 1 μl | 1 μl | 1 μl |
| deionized water to a final volume of | 10 μl | 10 μl | 10 μl |

Protocol for Transformations Using the pGEM®-T and pGEM®-T Easv Vector Ligation Reactions Use high-efficiency competent cells (≥1×10$^8$cfu/ttg DNA) for transformations. The ligation of fragments with a single-base overhang can be inefficient, so it is essential to use cells with a transformation efficiency of 1×10$^8$cfu/μg DNA (or higher) in order to obtain a reasonable number of colonies (see Section VI.E).

JM109 High Efficiency Competent Cells (Catalog# L2001) are recommended; these cells are provided with the pGEM®-T and pGEM®-T Easy Vector Systems II. Other host strains mar be used, but they should be compatible with blue/white color screening and standard ampicillin selection. JM109 cells should be maintained on M9 minimal medium plates supplemented with thiamine hydrochloride prior to the preparation of competent cells. This selects for and should maintain the presence of the F' episome, containing both the proAB genes, which complement proline auxotrophy in a host with a (proAB) deletion, and lac1qZAM15, required in blue/white color screening. When using competent cells other than JM109 High Efficiency Competent Cells purchased from Promega, use the appropriate transformation protocol. Selection for transformants should be on LB/ampicillin/IPTG/X-Gal plates (see Section XI. A). For best results, do not use plates that are more than 1 month old. 1. Prepare 2 LB/ampicillin/IPTG/X-Gal plates for each ligation reaction, plus two plates for determining transformation efficiency (see Section VI.E). Equilibrate the plates to room temperature prior to plating (Step 10). 2. Centrifuge the tubes containing the ligation reactions to collect contents at the bottom of the tube. Add 2 μl of each ligation reaction to a sterile 1.5 ml microcentrifuge tube on ice (see Note 1). Set up another tube on ice with 0.1 ng uncut plasmid for determination of the transformation efficiency of the competent cells (see Section VI.E). 3. Remove tube(s) of frozen JM109 High Efficiency Competent Cells from −70° C. storage and place in an ice bath until just thawed (about 5 minutes). Mix the cells by gently flicking the tube. 4. Carefully transfer 50 μl of cells into each tube prepared in Step 2 (100 μl cells for determination of transformation efficiency). 5. Gently flick the tubes to mix and place them on ice for 20 minutes. 6. Heat-shock the cells for 45-50 seconds in a water bath at exactly 42° C. (Do Not Shake). 7. Immediately return the tubes to ice for 2 minutes. 8. Add 950 μl room temperature SOC medium to the tubes containing cells transformed with ligation reactions and 900 μl to the tube containing cells transformed with uncut plasmid (LB broth may be substituted, but colony number may be lower). 9. Incubate for 1.5 hours at 37° C. with shaking (~150 rpm). 10. Plate 100 μl of each transformation culture onto duplicate LB/ampicillin/IPTG/X-Gal plates. For the transformation control, a 1:10 dilution with SOC medium is recommended for plating. If a higher number of colonies is desired, the cells may be pelleted by centrifugation at 1,000×g for 10 minutes, resuspended in 200 μl of SOC medium, and 100 μl plated on each of 2 plates.

Plates would be incubated overnight (16-24 hours) at 37° C., typically, approximately 100 colonies per plate are routinely observed using 100 μl of plated competent cells, at 1×10$^8$ cfu/ttg DNA. Longer incubations or storage of plates at 4° C. (after 37° C. overnight incubation) are used to facilitate blue color development. White colonies are chosen for inserted sequences.

Blunt-Ended PCR Products for use in Rc promoter test vector constructs: Thermostable DNA polymerases with proofreading activity, such as Pfu DNA Polymerase(e) (Catalog# M7741), Pwo DNA polymerase and Tli DNA Polymerase$^{(e)}$ (Invitrogen Catalog# M7101) generate blunt-ended fragments during PCR amplification. Nevertheless, PCR fragments generated using these polymerases can be modified using the A-tailing procedure (FIG. 4) and ligated into the pGEM®-T and pGEM®-T Easy Vectors (6). Using this method, one insert will be ligated into the vector as opposed to multiple insertions that can occur, with blunt-ended cloning. In addition, with T-vector cloning there is no need to dephosphorylate the vector, and there is a low background of relegated vector.

Using this procedure with optimized insert: vector ratios, 55-95% recombinants were obtained when Pfu and Tli DNA Polymerases were used to generate the insert DNA (Table 2). It is critical that the PCR fragments are purified using the Wizard® SV Gel and PCR Clean-Up System (Invitrogen Catalog# A9281) or by direct isolation from a gel by other means. In the absence of purification, the proofreading activity of the Pfu, Pwo and Tli DNA Polymerases will degrade the PCR fragments or remove the 3'-terminal deoxyadenosine added during tailing or the 3'-terminal deoxythymidine from the vector during the A-tailing reaction or ligation.

To optimize cloning efficiency, the amount of DNA in the A-tailing reaction and the ligation volumes must be adjusted depending on the molar yield of the purified PCR product. When molar concentrations are high due to small fragment size and/or good amplification, small volumes of the PCR fragment are needed for the A-tailing and ligation reactions. However, when molar concentration is low due to large fragment size and/or poor amplification, large volumes of the PCR fragment are needed for the A-tailing and ligation reactions. One-7111 of purified PCR fragment in the A-tailing reaction using Taq DNA Polymerase should optimize the insert:vector ratio. Recombinants are identified by blue/white screening, and 70-100% of the recombinants may be shown to have the correct size insert by PCR amplification of DNA. Few recombinants were observed in the control reactions in which the PCR fragment was not tailed. These control results confirm that the majority of the pGEM®-T Easy Vector used contains 3'-terminal deoxythymidine and that, during the A-tailing, Taq DNA Polymerase added a 3'-terminal deoxyadenosine to a significant proportion of the PCR fragment.

One-7 μl of purified PCR fragment generated by a proof-reading polymerase (e.g., Pfa DNA Polymerase) is added to the following reaction solutions.

Add 1 μl Taq DNA Polymerase 10× Reaction Buffer with $MgCl_2$.

Add dATP to a final concentration of 0.2 mM.

Add 5 units of Taq DNA Polymerase.

Add deionized water to a final reaction volume of 10 μl.

Incubate at 70° C. for 15-30 minutes.

Use 1-2 μl in a ligation reaction with Promega's pGEM®-T and pGEM®-T Easy Vector.

D. Screening Transformants for Inserts: Successful cloning of an insert in the pGEM®-T and pGEM®T Easy Vectors interrupts the coding sequence of β-galactosidase; recombinant clones can usually be identified by color screening on indicator plates. However, the characteristics of PCR products cloned into the pGEM®-T and pGEM®-T Easy Vectors can significantly affect the ratio of blue:white colonies obtained following transformation of competent cells. Clones that contain PCR products, in most cases, produce white colonies, but blue colonies can result from PCR fragments that are cloned in-frame with the lacZ gene. Such fragments are usually a multiple of 3 base pairs long (including the 3'-A overhangs), and do not contain in-frame stop codons. There have been reports of DNA fragments of up to 2 kb that have been cloned in-frame and have produced blue colonies. Even if a PCR product is not a multiple of 3 bases long, the amplification process can introduce mutations (e.g., deletions or point mutations) that may result in blue colonies when competent cells are transformed with the fragment inserted into the pGEM®-T or pGEM®-T Easy Vectors. Control Insert DNA supplied with the pGEM®-T and pGEM®-T Easy Systems is a 542 bp fragment from pGEM®-luc Vector DNA (Invitrogen Catalog# E1541). This sequence has been mutated to contain multiple stop codons in all six reading frames, which ensures a low background of blue colonies for the control reaction. Results obtained with the Control Insert DNA may not be representative of those achieved with a PCR product.

Isolation of Recombinant Plasmid DNA: A standard plasmid miniprep procedure, which takes 30-60 minutes to perform, is described in Promega's *Protocols and Applications Guide* (8). The miniprep process can be both laborious and time-consuming, particularly when large numbers of minipreps are required. A convenient and reliable method is the Wizard® Plus SVMinipreps DNA Purification System (Invitrogen Catalog #A1330).

Generation of Single-Stranded DNA from the pGEM®-T and pGEM®-T Easy Vectors: For induction of ssDNA production, bacterial cells containing either the PGEM®-T or PGEM®-T Easy Vector are infected with an appropriate helper phage (e.g., R408 Helper Phate, Invitrogen Catalog# P2291). The plasmid then enters the f1 replication mode, and the resulting ssDNA is exported as an encapsulated virus-like particle. The ssDNA is purified from the supernatant by simple precipitation and extraction procedures, which are described in detail in the Protocols and Applications Guide (Invitrogen Catalog# P1610). For further information, please contact a local Promega Branch Office or Distributor.

General Guidelines to Use AcTEV™ Protease: Follow the guidelines below when using AcTEV™ Protease. For optimal yield of cleaved recombinant protein, partially purify or purify recombinant fusion protein before performing cleavage. Use the following digestion conditions as a starting point, and optimize the cleavage reaction as necessary by varying the amount of AcTEV™ Protease, incubation temperature, or reaction time.

For a cleavage reaction using 20 μg of fusion protein, use 10 units of AcTEV™ Protease in a reaction volume of 150 μl. Incubate the reaction mixture at 30° C. for 1 hour or at 4° C. for 4 hours to overnight. For detailed instructions to set up the cleavage reaction, refer to the manual included with the product. After cleavage, remove AcTEV™ Protease from the reaction mixture using affinity chromatography on a nickel-chelating resin (e.g. ProBond™ Resin; Invitrogen Catalog No. K801-01).

Vector Construction First generate 5' and 3'entry clones using Invitrogen's MultiSite Gateway® then use the 5' and 3' entry clones, the entry clone containing a gene interest, and the other reagents supplied in the MultiSite Gateway® Three-Fragment Vector Construction Kit (including Invitrogen LR Clonase™ Plus enzyme mix and Invitrogen pDEST™ R4-R3 destination vector) in a MultiSite Gateway® LR recombination reaction to generate an expression clone.

For instructions to generate 5' and 3' entry clones and to perform the MultiSite Gateway® LR recombination reaction, refer to the MultiSite Gateway® Three-Fragment Vector Construction Kit manual. Analyzing Transformants: Analyzing Positive Clones: 1. Pick 5-10 colonies and culture them overnight in LB or SOB medium.

Note: When transforming using One Shot® Machl™-T1® competent *E. coli*, inoculate overnight-grown colonies and culture them for 4 hours in pre-warmed LB medium containing 50 μg/ml kanamycin before isolating plasmid DNA. For optimal results, inoculate as much of a single colony as possible. 2. Isolate plasmid DNA using a method of choice. 3. Analyze the plasmids by restriction analysis or PCR (see below) to confirm the presence and correct orientation of the insert.

Analyzing Transformants by PCR: Use the protocol below (or any other suitable protocol) to analyze positive transformants using PCR. For PCR primers, use a combination of the M13 Forward (−20) primer or the M13 Reverse primer and a primer that hybridizes within an insert.

Materials: PCR Super Mix High Fidelity (Invitrogen, Catalog No. 10790-020): Appropriate forward and reverse PCR primers (20 μM each).

Procedure: 1. For each sample, aliquot 48 μl of PCR SuperMix High Fidelity into a 0.5 ml microcentrifuge tube. Add 1 μl each of the forward and reverse PCR primer. 2. Pick 5-10 colonies and resuspend individually in 50 μl of the PCR SuperMix containing PCR primers (remember to make a patch plate to preserve the colonies for further analysis). 3. Incubate reaction for 10 minutes at 94° C. to lyse cells and inactivate nucleases. 4. Amplify for 20 to 30 cycles. 5. For the final extension, incubate at 72° C. for 10 minutes. Store at +4° C. 6. Visualize by agarose gel electrophoresis.

Sequencing: Following identification of candidate clone(s), a construct is sequenced to confirm that a gene is cloned in the correct orientation. Use the M 13 Forward (−20) and MI13 Reverse included for sequencing an insert (see the diagrams of the priming sites in each pENTR™ TOPO® vector).

Model Construction of Red Rice Containment Vector

Designing PCR Primers: Design primers such that a gene of interest, i.e. containment gene, will be optimally expressed and fused in frame with a TEC recognition site (for us in pENTR™/TEV/D-TOPO® or for use with a Gateway® destination vector, following recombination use N- or C-terminal tags, if desired. Include the 4 base pair sequences (CACC) necessary for directional cloning of the 5' end of the forward primer.

Amplifying a gene of interest i.e. containment gene: 1. Use a thermostable, proofreading DNA polymerase and the PCR primers above to produce a blunt-end PCR product. 2. Use agarose gel electrophoresis to check the integrity and determine the yield of a PCR product.

Perform a TOPO® Cloning Reaction: 1. Set up a TOPO® Cloning reaction such as those provided in the following chart. For optimal results, use a 0.5:1 to 2:1 molar ratio of PCR product:TOPO® vector.

| Reagent | Chemical Transformation | Electroporation |
|---|---|---|
| Fresh PCR product | 0.5 to 4 μl | 0.5 to 4 μl |
| Salt solution | 1 μl | — |
| Dilute salt solution (1:4) | — | 1 μl |
| Sterile water | to final volume of 5 μl | to final volume of 5 μl |
| TOPO ® vector | 1 μl | 1 μl |
| Total volume | 6 μl | 6 μl |

2. Mix gently and incubate for 5 minutes at room temperature. 3. Place on ice and proceed to transform one or more of One Shot® chemically competent *E. coli*, One Shot® competent *E. coli*, an *E. coli* of choice, see, below.

Transform One Shot® Chemically Competent *E. coli:* 1. Add 2 μl of the TOPO® Cloning reaction into a vial of One Shot® chemically competent *E. coli* cells and mix gently. 2. Incubate on ice for 5 to 30 minutes. 3. Heat-shock the cells for 30 seconds at 42° C. without shaking. Immediately transfer the tube to ice. 4. Add 250 μl of room temperature S.O.C. Medium. 5. Incubate at 37° C. for 1 hour with shaking. 6. Spread 50-200 μl of bacterial culture on a prewarmed selective plate and incubate overnight at 37° C.

Transforming One Shot® Competent *E. coli*: Introduction: Following a TOPO® Cloning reaction, transform a pENTR™ TOPO® construct into one or more of a competent *E. coli*, such as a One Shot® TOP10 or Mach1-TI® Chemically Competent *E. coli*, electroporate an electrocompetent *E. coli*. Protocols to transform chemically competent or electrocompetent *E. coli* are provided herein.

Materials for transformation: In addition to general microbiological supplies (i.e. incubators, plates, spreaders, etc.), the following reagents and equipment can be used including TOPO® Cloning reaction (see previous methods), One Shot® TOP10 or Machl™-T1® chemically competent *E. coli.*, such as those provided in kit referenced herein, S.O.C. Medium (such as that supplied with the kit, Box 2), pUC19 positive control (to verify transformation efficiency, for use if desired, Box 2); a 42° C. water bath (or electroporator with cuvettes, optional), 15 ml sterile, snap-cap plastic culture tubes (for electroporation) LB plates containing 50 μg/ml kanamycin (at least two for each transformation) or LB plates containing 100 μg/ml ampicillin, such as when transforming a pUC19 control, and a 37° C. shaking and non-shaking incubator. Most transformants will contain recombinant plasmids with the PCR product of interest cloned in the correct orientation and sequencing primers are included in the kit to sequence across an insert in the multiple cloning site to confirm orientation and reading frame.

Preparing for Transformation: For each transformation, use one vial of One Shot° competent cells and two selective plates. Equilibrate a water bath to 42° C. (for chemical transformation) or set up an electroporator for electrocompetent *E. coli*. Warm a vial of S.O.C. Medium from Box 2 to room temperature. Warm selective plates at 37° C. for 30 minutes. Thaw on ice one vial of One Shot® cells from Box 2 for each transformation.

General Recommendations and Guidelines: pENTR™-gus is provided for use as a positive control in the LR reaction, and is an entry clone containing the *Arabidopsis thaliana*-glucuronidase (gus) gene. One fig of supercoiled pENTR™-gus plasmid is supplied in TE Buffer, pH 8.0 at a concentration of 50 ng/tt1. Note: See Invitrogen.com for a map and sequence of pENTR™-gus. Plasmid DNA was purified with the S.N.A.P.™ MiniPrep Kit (Invitrogen Catalog no. K1900-01). Mini-prep (alkaline lysis) DNA preparations are adequate for Gateway® cloning reactions; however, in general, such DNA cannot be quantitated by UV absorbance due to contaminating RNA and nucleotides. Concentrations are estimated by gel electrophoresis in comparison with standard DNA, i.e., DNA Mass Ladder (Invitrogen Catalog Nos. 10068-013 or 10496-016).

LR reactions: recommended are supercoiled attL-containing entry vectors and supercoiled attR-containing destination vectors. For large (>10 kb) entry clones or destination vectors, linearizing the entry clone or destination vector may increase the efficiency by up to 2-fold. To increase the number of colonies containing the desired expression clone, increase the incubation time from the recommended 1 hour to 2 hours or overnight. Longer incubations are recommended for plasmids ≥10 kb to increase the yield of colonies. 100-300 ng entry clone per 20 μl reaction is suggested. Highest colony yields are typically obtained using 300 ng entry clone and 300 ng destination vector. Using <100 ng entry clone should generate fewer colonies.

Model LR Reaction Procedures:

Use the following procedure to perform an LR recombination reaction. For a positive control, use 100 ng (2)μl of pENTR™-gus. 1. Add the following components to a 1.5 ml microcentrifuge tube at room temperature and mix:

| | |
|---|---|
| Entry clone (100-300 ng) | 1-10 μl |
| Destination vector (150 ng/μl) | 2 μl |
| 5X LIZ Clonase ™ Reaction Buffer | 4 μl |
| TE buffer, pH 8.0 | to 16 μl |

2. Remove LR Clonase™ enzyme mix from −80° C. and thaw on ice for about 2 minutes. Vortex the LR Clonase™ enzyme mix briefly twice (2 seconds each time). 3. To each sample (Step 1, above), add 4 μl of LR Clonase™ enzyme mix to the reaction and mix well by vortexing briefly twice. Microcentrifuge briefly. 4. Return LR Clonase™ enzyme mix to −80° C. storage immediately after use. 5. Incubate reactions at 25° C. for 60 minutes. 6. Add 2 μl of the Protemase K solution to each sample to terminate the reaction. Vortex briefly. Incubate samples at 37° C. for 10 minutes.

Model Transformation Procedures:

1. Transform 1 μl of each LR reaction into 50 μl of Library Efficiency® DH5α™ Competent Cells (Catalog No. 18263-012). Incubate on ice for 30 minutes. Heatshock cells by incubating at 42° C. for 30 seconds. Add 450 μl of S.O.C. Medium and incubate at 37° C. for 1 hour with shaking. Plate 20 μl and 100 μl of each transformation onto selective plates. Note: Any competent cells with a transformation efficiency of $>1.0\times10^8$ transformants/μg may be used. 2. Transform 1 μl of pUC19 DNA (10 ng/ml) into 50 μl of Library Efficiency® DH5α-Competent Cells as described above. Plate 20 μl and 100 μl on LB plates containing 100 μg/ml ampicillin.

Model Results An efficient LR recombination reaction will produce >5000 colonies if the entire transformation is plated.

Transformation Procedure: A stock pUC19 solution (0.01 μg/ml) is provided as a control to determine the transformation efficiency. To obtain maximum transformation efficiency, the experimental DNA must be free of phenol, ethanol, protein and detergents. 1. Thaw competent cells on ice. Place required number of 17×100 mm polypropylene tubes (Falcon® 2059; see Note 1) on wet ice. 2. Gently mix cells, then aliquot 100 μl competent cells into chilled polypropylene tubes. 3. Refreeze any unused cells in the dry ice/ethanol bath for 5 minutes before returning them to the −70° C. freezer. Do not use liquid nitrogen. 4. To determine transformation efficiency, add 5 μl (50 μg) control DNA to one tube containing 100 μl competent cells. Move the pipette through the cells while dispensing. Gently tap tube to mix. 5. For DNA from ligation reactions, dilute the reactions 5-fold in 10 mM Tris-HCl (pH 7.5) and 1 mM EDTA. Add 1 μl of the dilution to the cells (1-10 ng DNA), moving the pipette through the cells while dispensing. Gently tap tubes to mix. 6. Incubate cells on ice for 30 minutes. 7. Heat-shock cells 45 seconds in a 42° C. water bath; do not shake. 8. Place on ice for 2 minutes. 9. Add 0.9 ml of mom temperature S.O.C. Medium (Invitrogen Catalog No. 15544-034). 10. Shake at 225 rpm (37° C.) for 1 hour. 11. Dilute the reaction containing the control plasmid DNA 1:10 with S.O.C. Medium. Spread 100 μl of this dilution on LB or YT plates with 100 μg/ml ampicillin. 12. Dilute experimental reactions as necessary and spread 100-200 μl of this dilution as described in Step 11. 13. Incubate overnight at 37° C.

One Shot® Chemical Transformation Protocol

The following protocol for transforming One Shot® TOP10 or Mach1™-T1®b chemically competent *E. coli.* 1. Add 2 μl of the TOPO® Cloning reaction from Performing the TOPO® Cloning Reaction, Step 2, page 12 into a vial of One Shot® Chemically Competent *E. coli* and mix gently. 2. Incubate on ice for 5 to 30 minutes. Note: Longer incubations on ice seem to have a minimal effect on transformation efficiency. The length of the incubation is at the user's discretion. 3. Heat-shock the cells for 30 seconds at 42° C. without shaking. 4. Immediately transfer the tubes to ice. 5. Add 250 μl of room temperature S.O.C. Medium. 6. Cap the tube tightly and shake the tube horizontally (200 rpm) at 37° C. for 1 hour. 7. Spread 50-200 μl from each transformation on a prewarmed selective plate and incubate overnight at 37° C. Two different volumes are plated to ensure that at least one plate will havenad well-spaced colonies. 8. An efficient TOPO® Cloning reaction may produce several hundred colonies. Pick 5-10 colonies for analysis (see Analyzing Transformants, below).

Constructing a PANDA Gene Silencing Vector

Figure 12B:
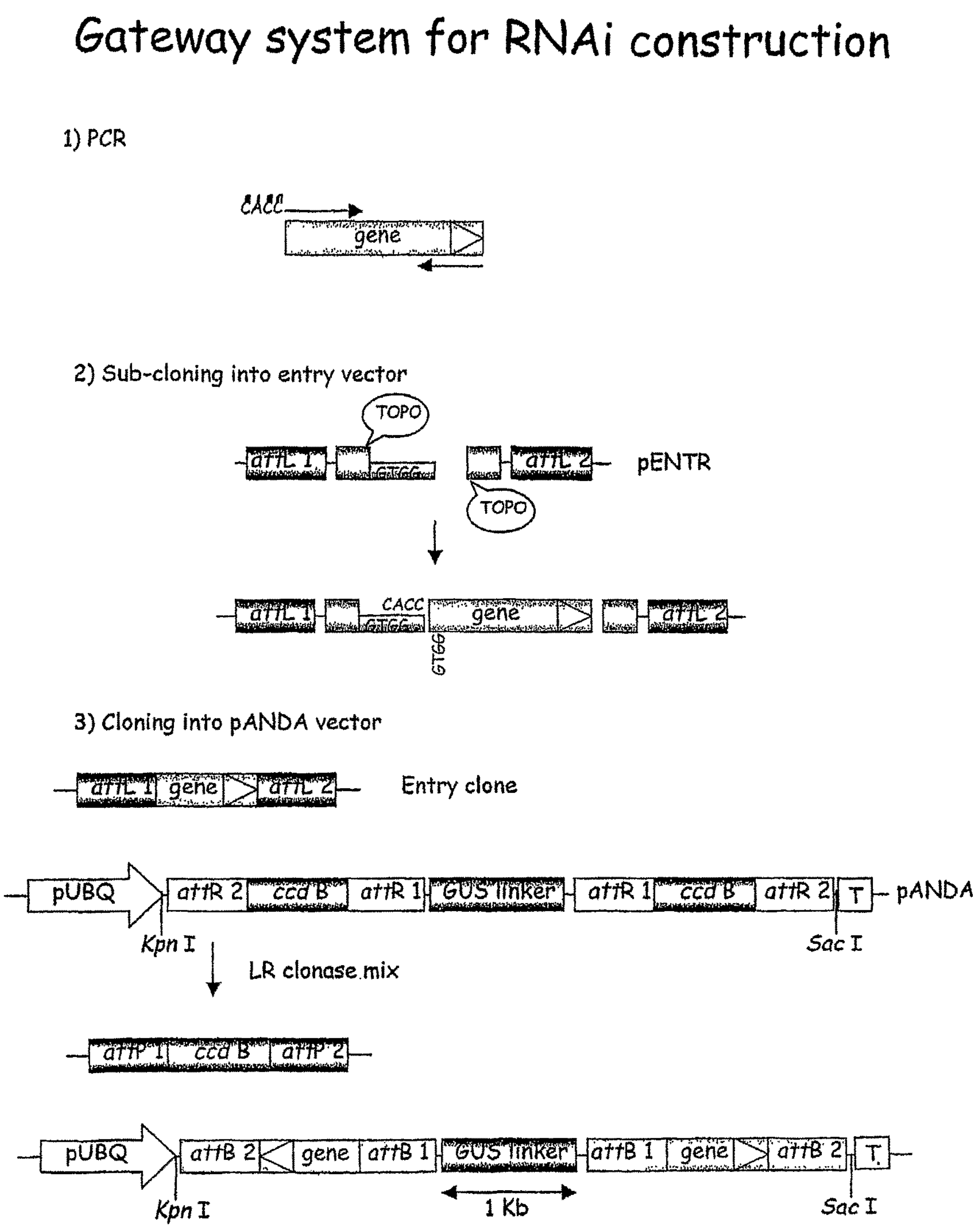

1) PCR for providing gene sequences for inserting containment genes (i.e. SEQ ID NOs: into pANDA in a forward and reverse transcriptional orientation: Amplify a gene sequence using appropriate PCR primers, forward and reverse, with a "CACC" added to the 5' end of the forward primer, using a proofreading enzyme for DNA replication (e.g. Pfx, Invitrogen). This "CACC" sequence addition is for guiding the intended direction of copying for providing the PCR product. 2) Subcloning into an entry vector: The PCR product from step 1) is mixed with a directional TOPO® pENTR vector (pENTR/D-TOPO® Cloning Kit, with One Shot® TOP 10 Chemically Competent *E. coli* (Cat. No. K2400-20, Invitrogen)) according to manufacturer's instructions, herein incorporated by reference. pENTR is then transformation into *E. coli* for transformant selection using 50 μg/ml Kanamycin; for more specific details, see, instruction manual of the pENTER/D-TOPO cloning kit, herein incorporated by reference. 3) Cloning into the pANDA vector (FIGS. 12A and 12B from //bsw3.naistjp/sinamoto/pANDA/real/pANDA_top.htm). Once transformants are selected, individual clones are isolated and grown in order to provide aliquots. One aliquot will be used to confirm integredy of the containment gene sequence through PCR amplification and sequencing of the containment gene (Maniatis, herein incorporated by reference). Another aliquot will then be used to combine with a pANDA vector using the LR Clonase enzyme mix (2 μl LR Reaction Buffer (5×), 100-300 ng DNA). Entry clone with containment gene inserted, 300 ng pANDA vector, bring to 8 μl with TE; then add 2 μl of LR Clonase enzyme mix, and mix by vortexing briefly; incubate at 25° C. for over night; add 1 μl of Proteinase K solution; incubate at 37° C. for 10 minutes; transform *E. coli* (DH5a) and select transformants with 50 μg/ml Kanamycin and Hygromycin; for details, see, instruction manual for Gateway LR Clonase Enzyme Mix (Cat. No. 11791-019, Invitrogen, herein incorporated by reference). Library Efficiency DB3.1 Competent Cells (Cat. No. 11782-018, Invitrogen). The final binary vector should have the attB sequences that are approximately 50 bp.

All publications and patents mentioned in the above specification are herein Incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A rice plant cell comprising a promoter responsive to a basic helix-turn-helix red anthocyanin transcription factor (Rc responsive promoter), operably linked to a heterologous nucleic acid molecule, wherein said Rc responsive promoter comprises a nucleic acid molecule having at least 96% identity to SEQ ID NO:131.

2. A rice plant cell comprising an Rc responsive promoter operably linked to a heterologous nucleic acid molecule, wherein said Rc responsive promoter comprises a nucleic acid molecule having at least 96% identity to SEQ ID NO:185.

3. The rice plant cell of claim 1 or 2, wherein said plant cell is a pollen cell or primordial meristem cell.

4. The rice plant cell of claim 1 or 2, wherein said heterologous nucleic acid molecule is a nucleic acid encoding a selectable marker.

5. A rice plant comprising the plant cell of claim 1, wherein said rice plant comprises a plant cell comprising an Rc responsive promoter operably linked to a heterologous nucleic acid molecule, and wherein said Rc responsive promoter comprises a nucleic acid molecule having at least 96% identity to SEQ ID NO:131.

6. A rice plant comprising the plant cell of claim 2, wherein said rice plant comprises a plant cell comprising an Rc responsive promoter operably linked to a heterologous nucleic acid molecule, and wherein said Rc responsive promoter comprises a nucleic acid molecule having at least 96% identity to SEQ ID NO:185.

7. A seed of rice plant of claim 5, wherein said seed comprises a plant cell comprising an Rc responsive promoter operably linked to a heterologous nucleic acid molecule, and wherein said Rc responsive promoter comprises a nucleic acid molecule having at least 96% identity to SEQ ID NO:131.

8. A seed of rice plant of claim 6, wherein said seed comprises a plant cell comprising an Rc responsive promoter operably linked to a heterologous nucleic acid molecule, and wherein said Rc responsive promoter comprises a nucleic acid molecule having at least 96% identity to SEQ ID NO:185.

* * * * *

SEQUENCE LISTING

```
<160> NUMBER OF SEQ ID NOS: 196

<210> SEQ ID NO 1
<211> LENGTH: 668
<212> TYPE: PRT
<213> ORGANISM: Oryza rufipogon

<400> SEQUENCE: 1

Met Ala Gly Gly Glu Ala Gln Ala Ala Leu Gln Ala Val Ala Gln Ser
```

-continued

```
1               5                   10                  15

Leu Arg Trp Thr Tyr Ser Leu Leu Trp Gln Leu Cys Pro His Gln Gly
            20                  25                  30

Ser Ser Leu Val Trp Gly Glu Gly His Tyr Asn Gly Ala Val Lys Thr
        35                  40                  45

Arg Lys Ser Thr Val Met Gln Pro Pro Pro Ala Glu Glu Glu Asp Asp
    50                  55                  60

Ala Asp His Ala Ala Arg His Arg Ser Arg Gln Leu Arg Glu Leu Tyr
65                  70                  75                  80

Asp Trp Leu Gln Gln Ala Gly Glu Asn Ser Ser Gly Gly Val Gln Thr
                85                  90                  95

Ser Ser Thr Thr Ala Ser Arg Arg Pro Gly Ala Ala Leu Ser Pro Glu
            100                 105                 110

Asp Leu Thr Glu Thr Glu Trp Phe Phe Leu Met Ser Ala Ser Tyr Ser
        115                 120                 125

Phe Pro Pro Gly Ile Gly Leu Pro Gly Arg Ala Phe Ala Arg Arg Gly
    130                 135                 140

His Val Trp Leu Thr Gly Ala Asn Glu Val Asp Ser Lys Val Phe Leu
145                 150                 155                 160

Arg Ala Ile Leu Ala Lys Thr Val Val Cys Ile Pro Val Val Asp Gly
                165                 170                 175

Val Leu Glu Ile Gly Thr Thr Glu Lys Val Glu Glu Asp Met Gly Leu
            180                 185                 190

Ile Gln Tyr Ala Arg Gly Ile Phe Met Asp Gln His Gly Ile His Met
        195                 200                 205

Lys Pro Thr Leu Ser Gln His Ser Thr Ser Asn Pro Val Thr His Cys
    210                 215                 220

Thr His Gln His Pro Ile Gln Val Gln Met Gln Leu Gly Ile Thr Ser
225                 230                 235                 240

Gln Thr Lys Phe Asp Tyr Ser Asp Glu Leu Asn Ala Asp Glu Glu Asn
                245                 250                 255

Asp Asp Thr Glu Glu Glu Gly Met Ser Gly Ser Asp Thr Asn Asn Thr
            260                 265                 270

Asp Thr Glu Arg Asn Ser Gly Gln Leu Gln Leu Gln Met Gln Asp Gln
        275                 280                 285

Leu Asn Met Val Ser Asn Asp His Gln Thr Met Pro Asn Asn Ala Val
    290                 295                 300

Ser Ser Glu Leu Met Gln Cys Glu Met Ser Glu Val Val Arg Asp Gly
305                 310                 315                 320

Cys Ser Asn Asn Ile Leu Glu Asp Glu Ile Gln Met Leu Met Asp Cys
                325                 330                 335

Gln Asn Ser Asn Cys Gln Leu Asn Leu Gln Gly Pro Asp Glu Pro Cys
            340                 345                 350

His Ser Trp His Phe Leu Cys Glu Glu Leu Gln Asn Asp Tyr Gln Pro
        355                 360                 365

Ala Thr Glu Asp Gln Val Ala Ser Pro Glu Asn Thr His Tyr Pro Lys
    370                 375                 380

Thr Leu Met Thr Ile Leu His Tyr Asn Thr Leu Arg Gln Gln Glu Met
385                 390                 395                 400

Asn Ile Lys Asn Tyr Leu Pro Val Ser Glu Lys Ser Ser Phe Ser Arg
                405                 410                 415

Trp Thr Thr Pro Glu Gly Ser Asp Asp Asn Lys Thr Met Ile Ser Pro
            420                 425                 430
```

Gly Thr Thr Gln Arg Met Leu Lys Ser Ile Leu Met Ile Val Pro Ser
        435                 440                 445

Ser His Cys Ser Tyr Arg Gly Ala Glu Thr Pro Glu Ser Arg Gly Gly
    450                 455                 460

Lys Gly Ala Ser Gly Thr Arg Lys Val Gly Ala Ile Gln Gly Asp Phe
465                 470                 475                 480

Ser Ala Asn His Val Leu Lys Glu Arg Arg Arg Arg Glu Lys Leu Asn
                485                 490                 495

Glu Lys Phe Ile Ile Leu Arg Ser Leu Val Pro Phe Met Thr Lys Met
            500                 505                 510

Asp Lys Ala Ser Ile Leu Gly Asp Thr Ile Glu Tyr Val Lys Gln Leu
        515                 520                 525

Arg Asn Arg Ile Gln Glu Leu Glu Ser Ser Ser Ser Ser Ser Arg Ala
    530                 535                 540

Ala Ala Arg Ala Pro Ser Ala Ala Ala Ala Gly Arg Arg Arg Lys Arg
545                 550                 555                 560

Ser Ala Ala Ala Ala Thr Ala Thr Ala Ala Glu Gly Met Ser Ser Ser
                565                 570                 575

Asn Gly Arg Asn Gly Gly Glu Ala Ala Glu Val Val Gln Val Ser Ile
            580                 585                 590

Ile Glu Ser Asp Ala Leu Leu Glu Leu Arg Cys Gly Cys Gly Gly Gly
        595                 600                 605

Gly Gly Gly Gly Gly Gly Gly Val Val Leu Leu Arg Val Met Gln Ala
    610                 615                 620

Met Gln Glu Leu Gln Leu Glu Val Thr Ala Val Gln Ala Ser Cys Ala
625                 630                 635                 640

Gly Gly Glu Leu Leu Ala Glu Leu Arg Ala Lys Val Val Val Met Ile
                645                 650                 655

Leu Ile Cys Met Lys Met Gln Met Gln Met Gln Asn
            660                 665

<210> SEQ ID NO 2
<211> LENGTH: 660
<212> TYPE: PRT
<213> ORGANISM: Oryza rufipogon

<400> SEQUENCE: 2

Met Ala Gly Gly Glu Ala His Ala Ala Leu Gln Ala Val Ala Gln Ser
1               5                   10                  15

Leu Arg Trp Thr Tyr Ser Leu Leu Trp Gln Leu Cys Pro His Gln Gly
            20                  25                  30

Ser Ser Leu Val Trp Gly Glu Gly His Tyr Asn Gly Ala Val Lys Thr
        35                  40                  45

Arg Lys Ser Thr Val Met Gln Pro Pro Pro Ala Glu Glu Glu Asp Asp
    50                  55                  60

Ala Asp His Ala Ala Arg His Arg Ser Arg Gln Leu Arg Glu Leu Tyr
65                  70                  75                  80

Asp Trp Leu Gln Gln Ala Gly Glu Asn Ser Ser Gly Gly Val Gln Thr
                85                  90                  95

Ser Ser Thr Thr Ala Ser Arg Arg Pro Gly Ala Ala Leu Ser Pro Glu
            100                 105                 110

Asp Leu Thr Glu Thr Glu Trp Phe Phe Leu Met Ser Ala Ser Tyr Ser
        115                 120                 125

Phe Pro Pro Gly Ile Gly Leu Pro Gly Arg Ala Phe Ala Arg Arg Gly

```
    130                 135                 140

His Val Trp Leu Thr Gly Ala Asn Glu Val Asp Ser Lys Val Phe Leu
145                 150                 155                 160

Arg Ala Ile Leu Ala Lys Thr Val Val Cys Ile Pro Val Val Asp Gly
                165                 170                 175

Val Leu Glu Ile Gly Thr Thr Glu Lys Val Glu Glu Asp Met Gly Leu
            180                 185                 190

Ile Gln Tyr Ala Arg Gly Ile Phe Met Asp Gln His Gly Ile His Met
        195                 200                 205

Lys Pro Thr Leu Ser Gln His Ser Thr Ser Asn Pro Val Thr His Cys
    210                 215                 220

Thr His Gln His Pro Ile Gln Val Gln Met Gln Leu Gly Ile Thr Ser
225                 230                 235                 240

Gln Thr Lys Phe Asp Tyr Ser Asp Glu Leu Asn Ala Asp Glu Glu Asn
                245                 250                 255

Asp Asp Thr Glu Glu Glu Gly Met Ser Gly Ser Asp Thr Asn Asn Thr
            260                 265                 270

Asp Thr Glu Arg Asn Ser Gly Gln Leu Gln Leu Gln Met Gln Asp Gln
        275                 280                 285

Leu Asn Met Val Ser Asn Asp His Gln Thr Ile Pro Asn Asn Ala Val
    290                 295                 300

Ser Ser Glu Leu Met Gln Cys Glu Met Ser Glu Val Val Arg Asp Gly
305                 310                 315                 320

Cys Ser Asn Asn Ile Leu Glu Asp Glu Ile Gln Met Leu Met Asp Cys
                325                 330                 335

Gln Asn Ser Asn Cys Gln Leu Asn Leu Gln Gly Pro Asp Glu Pro Cys
            340                 345                 350

His Ser Trp His Phe Leu Cys Glu Glu Leu Gln Asn Asp Tyr Gln Pro
        355                 360                 365

Ala Thr Glu Asp Gln Val Ala Ser Pro Glu Asn Thr His Tyr Pro Lys
    370                 375                 380

Thr Leu Met Thr Ile Leu His Tyr Asn Thr Leu Arg Gln Gln Glu Met
385                 390                 395                 400

Asn Ile Lys Asn Tyr Leu Pro Val Ser Glu Lys Ser Ser Phe Ser Arg
                405                 410                 415

Trp Thr Thr Pro Glu Gly Ser Asp Asp Asn Lys Thr Met Ile Ser Pro
            420                 425                 430

Gly Thr Thr Gln Arg Met Leu Lys Ser Ile Leu Met Ile Val Pro Ser
        435                 440                 445

Ser His Cys Ser Tyr Arg Gly Ala Glu Thr Pro Glu Ser Arg Gly Gly
    450                 455                 460

Lys Gly Ala Ser Gly Cys His Pro Arg Phe Gln Cys Gln Pro Cys Ala
465                 470                 475                 480

Glu Arg Glu Glu Lys Lys Arg Glu Ala Gln Glu Val His Asn Ser Ala
                485                 490                 495

Ile Phe Gly Thr Phe His Asp Lys Asp Gly Gln Gly Val Asp Thr Arg
            500                 505                 510

Arg His Asp Arg Val Arg Glu Ala Ala Lys Glu Pro His Thr Arg Ala
        515                 520                 525

Arg Val Val Val Val Val Val Thr Ser Ser Arg Pro Gly Ala Ile Gly
    530                 535                 540

Gly Gly Arg Arg Glu Ala Glu Glu Glu Ile Arg Arg Arg Arg His Cys
545                 550                 555                 560
```

-continued

His Gly Gly Gly Arg Asp Glu Gln Gln Gln Trp Pro Gln Trp Arg Arg
565 570 575

Gly Gly Gly Gly Gly Ala Gly Val His His Arg Glu Arg Arg Ala Ala
580 585 590

Gly Ala Pro Val Arg Leu Arg Arg Arg Arg Arg Arg Cys Gly Ala Ala
595 600 605

Pro Gly Asp Ala Gly Asp Ala Gly Ala Pro Ala Gly Gly His Arg Arg
610 615 620

Pro Gly Leu Val Arg Arg Trp Arg Ala Ala Arg Arg Ala Ala Arg Gln
625 630 635 640

Gly Arg Arg Tyr Asp Pro Asp Leu His Glu Asn Ala Asn Ala Asn Ala
645 650 655

Asn Ala Glu Leu
660

<210> SEQ ID NO 3
<211> LENGTH: 2007
<212> TYPE: DNA
<213> ORGANISM: Oryza rufipogon

<400> SEQUENCE: 3
atggccggcg gcgaggcgca agcggcgctg caggcggtgg cgcagagcct ccggtggacc 60
tacagcctcc tctggcagct ctgcccccac caaggtagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggcgctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatgcca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca acaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500

```
attctgcgat ctttggtacc tttcatgaca aagatggaca aggcgtcgat actaggcgac   1560

acgatcgagt acgtgaagca gctaaggaac cgcatacaag agctcgagtc gtcgtcgtcg   1620

tcgtcacgag cagccgcccg ggcgccatcg gcggcggccg ccgggaggcg gaggaagaga   1680

tccgccgccg ccgccactgc cacggcggcg gaagggatga gcagcagcaa tggccgcaat   1740

ggcggcgagg cggcggaggt ggtgcaggtg tccatcatcg agagcgacgc gctgctggag   1800

ctccggtgcg gttgcggcgg cggcggcggc ggcggcggcg gcggtgtggt gctgctccgg   1860

gtgatgcagg cgatgcagga gctccagctg gaggtcaccg ccgtccaggc ctcgtgcgcc   1920

ggcggcgagc tgctcgccga gctgcgcgcc aaggtcgtcg tcatgatcct gatctgcatg   1980

aaaatgcaaa tgcaaatgca gaattaa                                       2007
```

<210> SEQ ID NO 4
<211> LENGTH: 6408
<212> TYPE: DNA
<213> ORGANISM: Oryza rufipogon

<400> SEQUENCE: 4

```
atggccggcg gcgaggcgca agcggcgctg caggcggtgg cgcagagcct ccggtggacc     60

tacagcctcc tctggcagct ctgcccccac caagggtacc taccctacct acctacgaca    120

cgatgcacag tgttcatcca tggcggatcg tcgtcgttgt cgatgatcat cgaaggaagc    180

tagaggatat ggctcaatac tttgataata tatatactga tctctccgta caacaaaaat    240

ataaaaattc tagctagtat cgaatgagac atatgctatg ctagtactat tattaggata    300

tatcacgagt ttttatattt tgagacggat gtaataattc tgaatttagt tgtgatcgca    360

tggcatgcag tagctcgctg gtgtgggggg aggggcacta caacggcgcc gtcaagacgc    420

ggaagtcgac ggtgatgcag ccgccgccgg cggaggagga ggacgacgcc gaccacgcgg    480

cgcgccaccg gagccggcag ctgagggagc tctacgactg gctgcagcag gccggggaga    540

actccagcgg cggcgtgcag acgtcgtcga cgacggcgag ccggcggccg ggggcggcgc    600

tgtcgccgga ggacctgacg gagacggagt ggttcttcct catgtcggca tcctactcct    660

tccctcccgg catcgggtat ataataaaaa atatagatat aaatatttaa gcatgcatgc    720

ataaattaaa ccacacttct tgttacgtgt tcttggcaaa atgatgaaca attaccacta    780

attaattgga gccagaaacc ctaaagattt acccacctgg ttaattaatc ggtgtgttga    840

tccacgcatg catgcatgca gaaaatcaag atcaggatag ctccttttct tttgcaggtt    900

aattagctag atcttcacgt aaaattagct agctagattt taaaatataa tttattcaat    960

ttgatttatg atttttattt tttatttcaa atagatacaa ctgtatacaa aattttattt   1020

tggtacatac ctccgatcca actacatcag aggtaaaaaa aaaaattaaa ccgttggaat   1080

tgattagaac aagatcgtgc ggtcaaatta tatcataact aacttttttg attctctaaa   1140

gcatagagat gtatatatac atcgtactat taggctctat atttcctgat taacactaga   1200

tgcatatata attttgatag tcaaaatata cttttgatag gctctaaaga aaaacttaat   1260

aacatgtact ccctccatat acttttgata gtcatatttc atcttgacac acagatcaag   1320

tataagtaat tttacttatc atccatttaa acacgctact agttattcct cgtaaacaag   1380

cgattcatta atatttacat ttctcgatgc ttgtgtagcc aatattgtgt ggaagaatag   1440

aatgtcatta agaggatagg ttgttggatt gaaatatgcc tatcaaaaat aaatttttag   1500

atttgaaaat atgtctatca aaagtagatg gagggagtat taattaatgt gaatttccaa   1560
```

-continued

```
tcctactgtt gtgatattag gctttgtacc ttcttgtcca ggaggtatat atatggctct   1620
tttaaggatg ggagaaaata tcatctttaa tacaactata tatggctttt gtttgataaa   1680
tacaactttt attttgtatg aacacaaata tattgataaa tatccaccat tataatccta   1740
acccattagg atcatatggt gtatattttt ttaactattt gtttttttata aattaatatt   1800
aagagatcac aatacaaata tagtattatg aaagtactct taacaacata tccaatgata   1860
aaattattat tattacaaaa tatagtggtc aaattgtata gaattcaata gcctgatttt   1920
atgacgtcaa gtaaattaaa taaagaatga aggtagtgct agagtgatca aacaatatct   1980
ctcctaaaat atgtcctata agttttactc cataaatcca agggtcaaaa gttgttgggt   2040
tattttttta gataataaca tactacccct tttcaaaatg tatgattcta ttgacttttt   2100
gcacaacatt taaccatttg tcatattaaa aattagtata aacatctaaa aatataagtt   2160
acgattatat tttatttgat gataaaacaa ctcacaacaa aataaataat atttatataa   2220
tctttttgga ataagacgaa tgatcaaaca ttattcaaaa agtcaatggt atagtacgtt   2280
ttgaaattga tagactatga gagcaaaatt ttgagataac atggaaaatt atcctcttag   2340
acattgcact gtgtaataat taataataat gaatgaaagg ctaagacttt tcttccacct   2400
tataaaggtg gttgaatata tagcaatcac atcattacat gattttgtaa ccaaccgtct   2460
ctatagctcc gatacagtgc tagtttcaca tcgtaataat taaagagtat aataataaat   2520
cgaggtgtac ttctcatcga tgaagtgatg tgccgcttag ctaaattaaa ctcgtatgcg   2580
aaaaatcagt atatgtccgg ttaatttcta agagagagat tgagagagaa taattgcgcc   2640
cctccaaatc cccctcttgg acgttaggga gctatataga cggtattgct aagtgcgatg   2700
tgtacataac gtacctgtcg taggaacatt tctcatccaa attaagtagt aatgcatggc   2760
atgaaatcca tttttgtatt ttgcatggca aagaatgaca acaaggaata cactagctag   2820
ccctgccctt tttcaattta atttaacatc aaacttagtt attgtatttc ttttgtcaga   2880
atagcatgca ttgcatactc tttaaaaata attaattagt gtattttact agtcttacaa   2940
aggtatcaag agagacaact aattatagtt gggagacacc aaacttgttt ttaataatga   3000
caattaaaac cctacctcta catccaacat agacgtacat agtccgaagg cgccaaatat   3060
ttgtacattt agctaccaga tttcagtacg agttctcaca ttataatttt gattttttta   3120
ttttttttat aaacaatctg gtaccctttt atgtctggaa ggaaaaaaaa atctaaattg   3180
caacatttta gtcggtgaga atggtactct gtcctagcta ctttctacac atgagagaga   3240
gagagagaga gagagagaga gagcctttaa ttgcccttgc ccatgcatct ttctttgcac   3300
acatgtatgc ttttcacatt gtcatgagga gagaacttgt taagttgcac acatgtgtgc   3360
tttgcatgtc ttcaggttac ctggaagggc atttgcaagg agaggccatg tatggctcac   3420
tggagcaaat gaagttgaca gcaaagtatt cctaagagca attcttgcca aggttcagcc   3480
atcaccttct cttacctatt tttcactctg aatgccaaca gtgctttgca cattgtagtc   3540
tgtttgcaga ctgcaaatga tgaccataat cagatcagaa aataaaataa tattatatac   3600
tttttgagcc agctagcaag aatatgtaac aataattctc cttttttttc ttgttcttct   3660
ccctgatgtg gtgcataaca aataaccaaa ctgatgaatg gcagagtgct ggtatccagg   3720
tatttgcctc taaaagtagc tacacgttta ctatgaaatt ttgtggcttt ttttcatctt   3780
tggatgcagt ggccattatc taaaaactat gaatttccag actgcagttt ttatctaatt   3840
ttgtgacttt gtacatcaga cagttgtgtg cattcctgtt gtcgatggcg tcctggaaat   3900
tggaactacg gaaaaggtga tttcgtatat tatcagctga caatctaatt atatgggcca   3960
```

-continued

```
tataattaag tataaatcaa aatacctcat aatacattat aaagtatcta atgtgattat   4020
gtgaatattg gctatttcaa tgtaatttga tatatgaaac tgataatcct ctgaaactcc   4080
gtaaggatca aactaatcaa aatgtatata ttttcaaggt ggaggaagat atgggcctga   4140
ttcagtatgc aaggggcatc ttcatggatc aacatggcat ccacatgaag cctaccctct   4200
cacagcactc aacatccaac ccagtcaccc actgtactca tcagcatcca atccaggttc   4260
agatgcaact aggtatcacc agccaaacaa agtttgatta ttcagatgag ctcaatgcag   4320
atgaggagaa tgatgacaca gaagaagagg gcatgtcagg ttcagacact aacaacactg   4380
acactgaaag gaattcaggc cagctgcaac ttcaaatgca agaccaactg aacatggtga   4440
gcaatgacca ccagacaatg ccaaataatg cagtttccag tgagctaatg cagtgtgaga   4500
tgtcagaagt ggtaagagat ggctgctcaa ataatatttt agaggatgaa atccaaatgc   4560
tgatggattg ccaaaacagt aattgtcagt taaatttgca agggccagat gagccttgtc   4620
actcttggca ttttctctgc gaggagttac aaaatgatta ccagccaggt attacatttg   4680
agaagataat ccttcaaaag caccccttgtt ccaaaaatat atatttgtac tcttcacaca   4740
agcactgcca tttttttct tttttgcata catcctcaat tcttgcattt cttttccata   4800
tatttgatac aactgtctcc atttcccttc tgtcacagct actgaagatc aagtggcatc   4860
acctgaaaat acccattacc caaaaacact catgacaatc ctacattaca acacgctgcg   4920
acaacaagag atgaacatca agaactactt gccagtttca gagaaatcat cattctccag   4980
atggactact cctgaaggaa gtgatgacaa caagaccatg atcagtccag gcaccacaca   5040
gagaatgctc aagagcatcc tgatgattgt tcccagtagt cactgcagtt acaggggagc   5100
agaaacacct gaatcaaggg gcgggaaagg cgcaagtgga acgcgaaaag tcggtgccat   5160
ccaaggtgat ttcagtgcca accatgtgct gaaagagagg agaagaagag agaagctcaa   5220
tgagaagttc ataattctgc gatctttggt acctttcatg acaaaggtaa ttaagtactc   5280
cctctatttc tataaagccg tatttgacta gttatcttat ttagaaagta tgtgcaaata   5340
tgtaaaatat aagtcatact taaaagaact tttaatgtta ttaaataata agtcacacca   5400
aaaataaaac atatatattt ttaataagat aaatgattaa atgtatatat aaaaattaat   5460
agcgtcacat attttaaaat agaggggtat ttaagtaccc acaggatcat caaaattcag   5520
ttatcttttc ttaagcctct aacgaacatt ggaagatcct cactaatggg cagcatgaat   5580
ctagggttca ctatttcgga atgcaaaata tgttttgccg ggcatccgat ttttaaaaaa   5640
ttcagaatga agaaaattga atcttttta tggatttgaa taaatcttga taaattcgaa   5700
aaaatttccg aacttttggc cagaagtgaa tcctacccgt atccaccggt aataaaccta   5760
aatttttggg agtaatgaat taatgttata tataatccat gaattatata gttccaaact   5820
actccgtaac aaattttcag gagtagtgaa attaatatta ttacaatctc agaaaaaaat   5880
ggcagaaaca attaatctgt tttcaattat taattaattt gtttttgtgt ccagatggac   5940
aaggcgtcga tactaggcga cacgatcgag tacgtgaagc agctaaggaa ccgcatacaa   6000
gagctcgagt cgtcgtcgtc gtcgtcacga gcagccgccc gggcgccatc ggcggcggcc   6060
gccgggaggc ggaggaagag atccgccgcc gccgccactg ccacggcggc ggaagggatg   6120
agcagcagca atggccgcaa tggcggcgag gcggcggagg tggtgcaggt gtccatcatc   6180
gagagcgacg cgctgctgga gctccggtgc ggttgcggcg gcggcggcgg cggcggcggc   6240
ggcggtgtgg tgctgctccg ggtgatgcag gcgatgcagg agctccagct ggaggtcacc   6300
```

-continued

```
gccgtccagg cctcgtgcgc cggcggcgag ctgctcgccg agctgcgcgc caaggtcgtc   6360

gtcatgatcc tgatctgcat gaaaatgcaa atgcaaatgc agaattaa                6408


<210> SEQ ID NO 5
<211> LENGTH: 1987
<212> TYPE: DNA
<213> ORGANISM: Oryza rufipogon

<400> SEQUENCE: 5

atggccggcg gcgaggcgca tgcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggctctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag ggcatcttc     600

atggatcaac atggcatcca catgaagcct accctctcac agcactcaac atccaaccca    660

gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatacca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgtcagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca gcaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggcg ggaaaggcgc aagtggatgc catccaaggt gatttcagtg ccaaccatgt   1440

gctgaaagag aggagaagaa gagagaagct caatgagaag ttcataattc tgcgatcttt   1500

ggtacctttc atgacaaaga tggacaaggc gtcgatacta ggcgacacga tcgagtacgt   1560

gaagcagcta aggaaccgca tacaagagct cgagtcgtcg tcgtcgtcgt cacgagcagc   1620

cgcccgggcg ccatcggcgg cggccgccgg gaggcggagg aagagatccg ccgccgccgc   1680

cactgccacg gcggcggaag ggatgagcag cagcaatggc cgcaatggcg gcgaggcggc   1740

ggaggtggtg caggtgtcca tcatcgagag cgacgcgctg ctggagctcc ggtgcggttg   1800

cggcggcggc ggcggcggtg tggtgctgct ccgggtgatg caggcgatgc aggagctcca   1860

gctggaggtc accgccgtcc aggcctcgtg cgccggtggc gagctgctcg ccgagctgcg   1920

cgccaaggtc gtcgttatga tcctgatctg catgaaaatg caaatgcaaa tgcaaatgca   1980

gaattaa                                                             1987
```

<210> SEQ ID NO 6
<211> LENGTH: 6429
<212> TYPE: DNA
<213> ORGANISM: Oryza rufipogon

<400> SEQUENCE: 6
atggccggcg gcgaggcgca tgcggcgctg caggcggtgg cgcagagcct ccggtggacc 60
tacagcctcc tctggcagct ctgcccccac caagggtacc taccctacct acctacgaca 120
cgatgcacag tgttcatcca tggccggcca tggcggatcg tcgtcgttgt cgatgatcat 180
cgaaggaagc tagaggatat ggctcaatac tttgataata tatatactga tctctccgta 240
caacaaaaat ataaaaattc tagctagtat cgaatgagac atatgctatg ctagtactac 300
gaatctaaaa agatgtacat attttgattc gtattattag gatatatcac gagtttttat 360
attttgagac ggatgtaata attctgaatt tagttgtgat cgcatggcat gcaggagctc 420
gctggtgtgg ggggaggggc actacaacgg cgccgtcaag acgcggaagt cgacggtgat 480
gcagccgccg ccggcggagg aggaggacga cgccgaccac gcggcgcgcc accggagccg 540
gcagctgagg gagctctacg actggctgca gcaggccggg gagaactcca gcggcggcgt 600
gcagacgtcg tcgacgacgg cgagccggcg gccgggggcg gctctgtcgc cggaggacct 660
gacggagacg gagtggttct tcctcatgtc ggcatcctac tccttccctc ccggcatcgg 720
gtatataata aaaaatatag atataaatat ttaagcatgc atgcataaat taaaccacac 780
ttcttgttac gtgttcttgg caaaatgatg aacaattacc actaattaat tggagccaga 840
aaccctaaag atttacccac ctggttaatt aatcggtgtg ttgatccacg catgcatgca 900
tgcagaaaat caagatcagg atagctcctt ttcttttgca ggttaattag ctagatcttc 960
acgtataatt agctagctag attttaaaat ataatttatt caatttgatt tatgattttt 1020
attttttatt tcaaatagat acaactgtat acaaaatttt attttggtac atacctccga 1080
tccaactaca tcagaggtaa aaaaaaaatt aaaccgttgg aattgattag aacaagatcg 1140
tgcggtcaaa ttatatcata actaactttt ctgattctct aaagcataga gatgtatata 1200
tacatcgtat tattaggctc tatatttcct gattaacact agatgcatat ataattttga 1260
tagtcaaaat atacttttga taggctctaa agaaaaactt aataacatgt actccctcca 1320
tatacttttg atagtcatat ttcatcttga cacacagatc aagtataagt aattctactt 1380
atcatccatt taaacacgct actagttatt cctcataaac aagcgattca ttaatattta 1440
catttctcga tgcttgtgta gccaatattg tgtggaagaa tggaatgtca ttaagaggat 1500
aggttgttgg attgaaatat gcctatcaaa aataaatttt tagatttgaa aatatgccta 1560
tcaaaagtag atggagggag tattaattaa tgtgaatttc caatcctact gttgtgatat 1620
taggctttgt accttcttgt ccaggaggta tatatatggc tcttttaagg atgggagaaa 1680
atatcatctt taatacaact atatatggct tttgtttgat aaatacaact tttattttgt 1740
atgaatacaa atatattgat aaatatccac cattataatc ctaacccatt aggatcatat 1800
ggtgtatatt tttttaacta tttgtttttt ataaattaat attaagagat cacaataaaa 1860
atatagtatt atgaaagtac tcttaacaac atatccaatg ataaaattat tattattaca 1920
aaatatagtg gtcaaattgt atagaattca atagcctgat tttatgacgt caagtaaatt 1980
aaataaagaa tgaaggtagt gctagagtga tcaaacaata tctctcctaa aatatgtcct 2040
ataagtttta ctccataaat ccaagggtca aaagttgttg ggttattttt ttagataata 2100

-continued

```
acatactacc ccttttcaaa atgtatgatt ctattgactt tttgcacaac atttaaccat   2160
ttgtcatatt aaaaattagt ataaacatct aaaaatataa gttacaatta tattttattt   2220
gatgataaaa caactcacaa caaaataaat aatatttata taatcttttt ggaataaaac   2280
gaatgatcaa acattattca aaaagtcaat ggtatagtac gttttgaaat tgatagacta   2340
tgagagcaaa attttgagat aacatggaaa attatcctct tagacattgc actgtgtaat   2400
aattaataat aatgaatgaa aggctaagac ttttcttcca ccttatataa gtggttgaat   2460
atatagcaat cacatcatta catgattttg taaccaaccg tctctatagc tccgatacag   2520
tgctagtttc acatcgtaat aattaaagag tataataata aatcgaggtg tacttctcat   2580
cgatgaagtg atgtgccgct tagctaaatt aaactcgtat gcgaaaaatc agtatatgtc   2640
cggttaattt ctaagagaga gattgagaga gaataattgc gcccctccaa atccccctct   2700
tggacgttag ggagctatat agacggtatt gctaagtgcg atgtgtacat aacgtacctg   2760
tcgtaggaac atttctcatc caaattaagt agtaatgcat ggcatgaaat ccatttttgt   2820
attttgcatg gcaaagaatg acaacaagga atacactagc tagccctgcc ctttttcaat   2880
ttaatttaac atcaaactta gttattgtat ttcttttgtc agaatagcat gcattgcata   2940
ctctttaaaa ataattaatt agtgtatttt actagtctta caaaagtatc aagagagaca   3000
actaattata gttgggagac accaaacttg tttttaataa tgacaattaa aaccctacct   3060
ctacatccaa catagacgta catagtccga aggcgccaaa tatttgtaca tttagctacc   3120
agatttcagt acgagttctc acattataat tttgattttt ttattttttt tataaacaat   3180
ctggtaccct tttatgtctg gaaggaaaaa aaaaatctaa attgcaacat tttagtcggt   3240
gagaatggta ctctgtccta gctactttct acacatgaga gagagagaga gagagagaga   3300
gagagccttt aattgccctt gcccatgcat ctttctttgc acacatgtat gcttttcaca   3360
ttgtcatgag gagagaactt gttaagttgc acacatgtgt gctttgcatg tcttcaggtt   3420
acctggaagg gcatttgcaa ggagaggcca tgtatggctc actggagcaa atgaagttga   3480
cagcaaagta ttcctaagag caattcttgc caaggttcag ccatcacctt ctcttaccta   3540
tttttcactc tgaatgccaa cagtgctttg cacattgtag tctgtttgca gactgcaaat   3600
gatgaccata atcagatcag aaaataaaat aatattatat actttttgag ccagctagca   3660
agaatatgta acaataattc tccttttttt ttcttgttct tttccctgat gtggtgcata   3720
acaaataacc aaactgatga atggcagagt gctggtatcc aggtatttgc ctctaaaagt   3780
agctacacgt ttactatgaa attttgtggc ttttgttcat ctttggatgc agtggccatt   3840
atctaaaaac tatgaatttc cagactgcag tttttatcta attttgtgac tttgtacatc   3900
agacagttgt gtgcattcct gttgtcgatg gcgtcctgga aattggaact acggaaaagg   3960
tgatttcgta tattatcagc tgacaatcta attatatggg ccatataatt aagtataaat   4020
caaaatacct cataatatat tataaagtat ctaatgtgat tatgtgaata ttggctattt   4080
caatgtaatt tgatatatga aactgataat cctctgaaac tccgtaagga tcaaactaat   4140
caaaatgtat atattttcaa ggtggaggaa gatatgggcc tgattcagta tgcaaggggc   4200
atcttcatgg atcaacatgg catccacatg aagcctaccc tctcacagca ctcaacatcc   4260
aacccagtca cccactgtac tcatcagcat ccaatccagg ttcagatgca actaggtatc   4320
accagccaaa caaagtttga ttattcagat gagctcaatg cagatgagga gaatgatgac   4380
acagaagaag agggcatgtc aggttcagac actaacaaca ctgacactga aaggaattca   4440
ggccagctgc aacttcaaat gcaagaccaa ctgaacatgg tgagcaatga ccaccagaca   4500
```

-continued

```
ataccaaata atgcagtttc cagtgagcta atgcagtgtg agatgtcaga agtggtaaga   4560
gatggctgct caaataatat tttagaggat gaaatccaaa tgctgatgga ttgccaaaac   4620
agtaattgtc agttaaattt gcaagggcca gatgagcctt gtcactcttg gcattttctc   4680
tgcgaggagt tacaaaatga ttaccagcca ggtattacat ttgagaagat aatccttcaa   4740
aagcaccctt gttccaaaaa tatatatttg tactcttcac acaagcactg ccattttttt   4800
tctttttttgc atacatcctc aattcttgca tttcttttcc atatatttga tacaactgtc   4860
tccatttccc ttctgtcaca gctactgaag atcaagtggc atcacctgaa aatacccatt   4920
acccaaaaac actcatgaca atcctacatt acaacacgct gcgacagcaa gagatgaaca   4980
tcaagaacta cttgccagtt tcagagaaat catcattctc cagatggact actcctgaag   5040
gaagtgatga caacaagacc atgatcagtc caggcaccac acagagaatg ctcaagagca   5100
tcctgatgat tgttcccagt agtcactgca gttacagggg agcagaaaca cctgaatcaa   5160
ggggcgggaa aggcgcaagt ggatgccatc caaggtgatt tcagtgccaa ccatgtgctg   5220
aaagagagga gaagaagaga gaagctcaat gagaagttca taattctgcg atctttggta   5280
cctttcatga caaaggtaat taagtactcc ctctatttct ataaagccgt atttgactag   5340
ttatcttatt tagaaagtat gtgcaaatat gtaaaatata agtcatactt aaagaacttt   5400
taatgttatt aaataataag tcacaccaaa aataaaacat atatattttt aataagataa   5460
atgattaaat gtatatataa aaattaatag cgtcacatat tttaaaatag aggggtattt   5520
aagtacccac aggatcatca aaattcagtt atcttttctt aagcctctaa cgaacattgg   5580
aagatcctca ctaatggcag catgaatcta gggttcacta tttcggaatg caaaatatgt   5640
tttaccgggc atccgatttt taaaaaattc agaatgaaga aaattgaatc ttttttatgg   5700
atttgaataa atcttgataa attcgaaaaa atttccgaac ttttggccag aagtgaatcc   5760
tacccgtatc caccggtaat aaacctaaat ttttgggagt aatgaattaa tgttatatat   5820
aatccatgaa ttatatagtt ccaaactact ccgtaacaaa ttttcaggag tagtgaaatt   5880
aatattatta caatctcaga aaaaaatggc agaaacaatt aatctgtttt caattattaa   5940
ttaatttgtt tttgtgtcca gatggacaag gcgtcgatac taggcgacac gatcgagtac   6000
gtgaagcagc taaggaaccg catacaagag ctcgagtcgt cgtcgtcgtc gtcacgagca   6060
gccgcccggg cgccatcggc ggcggccgcc gggaggcgga ggaagagatc cgccgccgcc   6120
gccactgcca cggcggcgga agggatgagc agcagcaatg gccgcaatgg cggcgaggcg   6180
gcggaggtgg tgcaggtgtc catcatcgag agcgacgcgc tgctggagct ccggtgcggt   6240
tgcggcggcg gcggcggcgg tgtggtgctg ctccgggtga tgcaggcgat gcaggagctc   6300
cagctggagg tcaccgccgt ccaggcctcg tgcgccggtg gcgagctgct cgccgagctg   6360
cgcgccaagg tcgtcgttat gatcctgatc tgcatgaaaa tgcaaatgca aatgcaaatg   6420
cagaattaa                                                           6429
```

```
<210> SEQ ID NO 7
<211> LENGTH: 630
<212> TYPE: PRT
<213> ORGANISM: Oryza sativa

<400> SEQUENCE: 7

Met Ala Gly Gly Glu Ala His Ala Ala Leu Gln Ala Val Ala Gln Ser
1               5                   10                  15

Leu Arg Trp Thr Tyr Ser Leu Leu Trp Gln Leu Cys Pro His Gln Gly
```

```
            20                  25                  30

Ser Ser Leu Val Trp Gly Glu Gly His Tyr Asn Gly Ala Val Lys Thr
        35                  40                  45

Arg Lys Ser Thr Val Met Gln Pro Pro Pro Ala Glu Glu Glu Asp Asp
    50                  55                  60

Ala Asp His Ala Ala Arg His Arg Ser Arg Gln Leu Arg Glu Leu Tyr
65                  70                  75                  80

Asp Trp Leu Gln Gln Ala Gly Glu Asn Ser Ser Gly Gly Val Gln Thr
                85                  90                  95

Ser Ser Thr Thr Ala Ser Arg Arg Pro Gly Ala Ala Leu Ser Pro Glu
            100                 105                 110

Asp Leu Thr Glu Thr Glu Trp Phe Phe Leu Met Ser Ala Ser Tyr Ser
        115                 120                 125

Phe Pro Pro Gly Ile Gly Leu Pro Gly Arg Ala Phe Ala Arg Arg Gly
    130                 135                 140

His Val Trp Leu Thr Gly Ala Asn Glu Val Asp Ser Lys Val Phe Leu
145                 150                 155                 160

Arg Ala Ile Leu Ala Lys Thr Val Val Cys Ile Pro Val Val Asp Gly
                165                 170                 175

Val Leu Glu Ile Gly Thr Thr Glu Lys Val Glu Glu Asp Met Gly Leu
            180                 185                 190

Ile Gln Tyr Ala Arg Gly Ile Phe Met Asp Gln His Gly Ile His Met
        195                 200                 205

Lys Pro Thr Leu Ser Gln His Ser Thr Ser Asn Pro Val Thr His Cys
    210                 215                 220

Thr His Gln His Pro Ile Gln Val Gln Met Gln Leu Gly Ile Thr Ser
225                 230                 235                 240

Gln Thr Lys Phe Asp Tyr Ser Asp Glu Leu Asn Ala Asp Glu Glu Asn
                245                 250                 255

Asp Asp Thr Glu Glu Glu Gly Met Ser Gly Ser Asp Thr Asn Asn Thr
            260                 265                 270

Asp Thr Glu Arg Asn Ser Gly Gln Leu Gln Leu Gln Met Gln Asp Gln
        275                 280                 285

Leu Asn Met Val Ser Asn Asp His Gln Thr Ile Pro Asn Asn Ala Val
    290                 295                 300

Ser Ser Glu Leu Met Gln Cys Glu Met Ser Glu Val Val Arg Asp Gly
305                 310                 315                 320

Cys Ser Asn Asn Ile Leu Glu Asp Glu Ile Gln Met Leu Met Asp Cys
                325                 330                 335

Gln Asn Ser Asn Cys Gln Leu Asn Leu Gln Gly Pro Asp Glu Pro Cys
            340                 345                 350

His Ser Trp His Phe Leu Cys Glu Glu Leu Gln Asn Asp Tyr Gln Pro
        355                 360                 365

Ala Thr Glu Asp Gln Val Ala Ser Pro Glu Asn Thr His Tyr Pro Lys
    370                 375                 380

Thr Leu Met Thr Ile Leu His Tyr Asn Thr Leu Arg Gln Gln Glu Met
385                 390                 395                 400

Asn Ile Lys Asn Tyr Leu Pro Val Ser Glu Lys Ser Ser Phe Ser Arg
                405                 410                 415

Trp Thr Thr Pro Glu Gly Arg Glu Gln Lys His Leu Asn Gln Gly Ala
            420                 425                 430

Gly Lys Ala Gln Val Asp Ala Ile Gln Gly Asp Phe Ser Ala Asn His
        435                 440                 445
```

```
Val Leu Lys Glu Arg Arg Arg Arg Glu Lys Leu Asn Glu Lys Phe Ile
    450                 455                 460

Ile Leu Arg Ser Leu Val Pro Phe Met Thr Lys Met Asp Lys Ala Ser
465                 470                 475                 480

Ile Leu Gly Asp Thr Ile Glu Tyr Val Lys Gln Leu Arg Asn Arg Ile
                485                 490                 495

Gln Glu Leu Glu Ser Ser Ser Ser Ser Ser Arg Ala Ala Ala Arg Ala
            500                 505                 510

Pro Ser Ala Ala Ala Ala Gly Arg Arg Arg Lys Arg Ser Ala Ala Ala
        515                 520                 525

Ala Thr Ala Thr Ala Ala Glu Gly Met Ser Ser Ser Asn Gly Arg Asn
    530                 535                 540

Gly Gly Glu Ala Ala Glu Val Val Gln Val Ser Ile Ile Glu Ser Asp
545                 550                 555                 560

Ala Leu Leu Glu Leu Arg Cys Gly Cys Gly Gly Gly Gly Gly Gly Val
                565                 570                 575

Val Leu Leu Arg Val Met Gln Ala Met Gln Glu Leu Gln Leu Glu Val
            580                 585                 590

Thr Ala Val Gln Ala Ser Cys Ala Gly Gly Glu Leu Leu Ala Glu Leu
        595                 600                 605

Arg Ala Lys Val Val Val Met Ile Leu Ile Cys Met Lys Met Gln Met
    610                 615                 620

Gln Met Gln Met Gln Asn
625                 630
```

<210> SEQ ID NO 8
<211> LENGTH: 1893
<212> TYPE: DNA
<213> ORGANISM: Oryza sativa

<400> SEQUENCE: 8

```
atggccggcg gcgaggcgca tgcggcgctg caggcggtgg cgcagagcct ccggtggacc      60

tacagcctcc tctggcagct ctgcccccac caagggagct cgctggtgtg gggggagggg     120

cactacaacg gcgccgtcaa gacgcggaag tcgacggtga tgcagccgcc gccggcggag     180

gaggaggacg acgccgacca cgcggcgcgc caccggagcc ggcagctgag ggagctctac     240

gactggctgc agcaggccgg ggagaactcc agcggcggcg tgcagacgtc gtcgacgacg     300

gcgagccggc ggccgggggc ggctctgtcg ccggaggacc tgacggagac ggagtggttc     360

ttcctcatgt cggcatccta ctccttccct cccggcatcg ggttacctgg aagggcattt     420

gcaaggagag gccatgtatg gctcactgga gcaaatgaag ttgacagcaa agtattccta     480

agagcaattc ttgccaagac agttgtgtgc attcctgttg tcgatggcgt cctggaaatt     540

ggaactacgg aaaaggtgga ggaagatatg ggcctgattc agtatgcaag gggcatcttc     600

atggatcaac atggcatcca catgaagcct accctctcac agcactcaac atccaaccca     660

gtcacccact gtactcatca gcatccaatc caggttcaga tgcaactagg tatcaccagc     720

caaacaaagt ttgattattc agatgagctc aatgcagatg aggagaatga tgacacagaa     780

gaagagggca tgtcaggttc agacactaac aacactgaca ctgaaaggaa ttcaggccag     840

ctgcaacttc aaatgcaaga ccaactgaac atggtgagca atgaccacca gacaatacca     900

aataatgcag tttccagtga gctaatgcag tgtgagatgt cagaagtggt aagagatggc     960

tgctcaaata atattttaga ggatgaaatc caaatgctga tggattgcca aaacagtaat    1020
```

-continued

```
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca gcaagagatg   1200
aacatcaaga actacttgcc agtttcagag aaatcatcat tctccagatg gactactcct   1260
gaaggaaggg agcagaaaca cctgaatcaa ggggcgggaa aggcgcaagt ggatgccatc   1320
caaggtgatt tcagtgccaa ccatgtgctg aaagagagga gaagaagaga gaagctcaat   1380
gagaagttca taattctgcg atctttggta cctttcatga caaagatgga caaggcgtcg   1440
atactaggcg acacgatcga gtacgtgaag cagctaagga accgcataca agagctcgag   1500
tcgtcgtcgt cgtcgtcacg agcagccgcc cgggcgccat cggcggcggc cgccgggagg   1560
cggaggaaga gatccgccgc cgccgccact gccacggcgg cggaagggat gagcagcagc   1620
aatggccgca atggcggcga ggcggcggag gtggtgcagg tgtccatcat cgagagcgac   1680
gcgctgctgg agctccggtg cggttgcggc ggcggcggcg gcggtgtggt gctgctccgg   1740
gtgatgcagg cgatgcagga gctccagctg gaggtcaccg ccgtccaggc ctcgtgcgcc   1800
ggtggcgagc tgctcgccga gctgcgcgcc aaggtcgtcg ttatgatcct gatctgcatg   1860
aaaatgcaaa tgcaaatgca aatgcagaat taa                                1893
```

<210> SEQ ID NO 9
<211> LENGTH: 157205
<212> TYPE: DNA
<213> ORGANISM: Oryza sativa

<400> SEQUENCE: 9

```
cactcagatc tacacaggag ttcttgcaat ttctcaacat caacctcatt agggcataaa     60
aagatgtcat gacagtatcc aagcttctct agaacgttcc ttgaaattcc ttcaacatct    120
ctagtacgga gcgacctttt caatttcctg ttttctctca gaatttcact attcattgac    180
ctgacctcat ccagctgctg tctagcacat tccaactcgt ggacaaggta ttctttctcg    240
tctagaacct ctttcaagcg aatcctataa aaatacaggt cgatatcctc atctgatttg    300
gttggctgaa aacataggtc tcaattagtt agaaaaaacc acatggaccc ttcaatttgt    360
tagggaaaga aaactacaac aggagcttct actgtgatag gttttttaat gactgatatg    420
actatatttc aaaattgagc atcaaagcca ctacatccaa accaatcaga gtctgggcac    480
attgaagatc caacattttc aagatgtgct ttaatttgcc gaccatgcca aagcagttag    540
aagttttaac agaattgaat atagaaagtt aacacagacc ataaccgaac aaacaataga    600
acttacaaca ctgaataata cctgtttttc acgtggccta tcagaagaac aactttcttg    660
gaatgttggt cttgaatcag agtcagctgc ataggaaaaa gtatttctca agaaatgata    720
aaagatgaag tatttacaac ttaacaacac aaacacatat ataaaaaatc ctaggacaaa    780
cttaaatgca acaaaaagta ttacttatta acacccatat ttggcatctt aagtgaaaat    840
agcaagatat ggtcaaattt gtagaggacc cggcttgctg cgcgaggccg gtctgaccgc    900
cgccataggg ccgatcagac caacggtgtg gggccagttt gactggcggt atgtagccga    960
taagaccggc agggtccagt tctgagtcta gtttcatcgg ttctcgggat ttttttgctt   1020
gggttgaggt tttcgagtc ctaattggtt tctacaccta gtgggacgtg gagagggtcc    1080
tgtggagggc ctgaccaacc cctttataag ggtcatggct ggttcaattg agatacacaa   1140
tgtacaacaa cgcaatttgc taattgaatc gttctttcaa taaagcatct actttttgcc   1200
tagcttttag cctagtttgt ctatcttcgt tggtttgtgc ttgttggaga aacgggaacc   1260
```

```
agggtcccct tttccccagg atcatgagac acaggggccc acaaaaatca ctttctacca    1320

catacatata tgtatctata attcgttgcc aggtcagaaa ccacggaagt ggaggacaac    1380

agttggcgag gaatggggac ctgggccctt atccaaatag ggcccggggc accgacactt    1440

ttgaaagttt tcatttattc gtcttcgccg caagagtgca agtactcttt gtaggttagt    1500

cctgaaaacg ttccgctcca cccatgatat gggttttttct ccctattcgt ctaaatcggc    1560

tccgctaatt ggttttgatc tctaaacccg tcttgaccag ggggtttctc aaggttgagg    1620

tggttggcga ctccatgcac cacaaagcct tttctagttc atattgggta ctaagttcac    1680

ttaattggac tggaataggt cgatgggtac cagattgacc cccagtccgc tctcatccct    1740

actaaatatt tatatgtaca cttggttaag atcattttaa tgtaaactga aatagcttat    1800

ttgctctgat aaaaaagaga aaacatatca aaatttatca tagtggttta cctcggacta    1860

ataggggcag gggatcattt ctcaagcttt cttctacttt ttcatggcac acagtacgga    1920

tttcctcttc acatctgtca tcataagcag caaaaaatga tgaggttgat tccctaataa    1980

aatattaaac aaaaagtata ccggtgttat aatcagaccc aacaaaaaat ttctgatgga    2040

taggagttta gcagactgta ataaaatgaa caaaaagtaa cttcaaagag acaattatct    2100

atactctata gggtgtagct tctggcagaa actaagcctt cagttatagc atctacagat    2160

taagaaaaat tcaacacaat aatcacaaca tacatctttc caaagctgtt ctgggaacac    2220

tcatttgttt tgtagccagg atagatgagc agagatcctg attgctggtc ctggagaaac    2280

aaaagtgtct tagcagaaaa acaaaataaa ccatcaaaag aattagtcat tttgtttcct    2340

gcaactaaaa tccaaaaatc acatatcaat catctggttc tagtcttcta tcatgaatgt    2400

gagattgaca cgttgcttaa attctaaaat taaattgaat ttattgaatg gaaatccata    2460

ttaacaagag tgctccattg ttacaagcat ttactttata atcagttcat taagagtgct    2520

ccattgttac aagcatttac tttataatca gttcattaaa catatctttg taagagcaac    2580

taaatgaggt aatataaaac acattaagag ctaataagta ataactaaaa aagaacagta    2640

cgcaaattca atgtgtcaaa agagaaaggt gagatgcaat aaagttcagt tttggggatt    2700

ttttctggtg tgttgttcac agccacacac acactatttc acttagctac atatgcaagc    2760

aggtccccaa tacaagagca tattacatca acactccccc tcaagatggg caaaagatat    2820

caatcatgcc catcttgtta cacattgact cactctcact aggacctaat cccttggtta    2880

aacaatcagc tagctgctca gaagatttaa tgtattgtag tctaagagcc ccactatcga    2940

tcttctcttt gatgaagaac ctatcaattt cgatatgttt ggtgcggtca tgttgaactg    3000

gattgtttgc aatgttgata gcagatttgt tgtcacaatg aagcaccaca gtattatttc    3060

tgaacaaccg tagctccaac aatagattct tcacccacaa catctcactt aaactcaatg    3120

ccatggctct atactcagct tccgcggtag atcgagccac taccgcctgc ttcttgcttc    3180

gccaacagac aacattgcca cccacaaata cacaatatcc tgatgtagat cttctatcat    3240

ccacactgct tgcccaatca gcatcacaat atccttccac atccaagtgt tggttctttc    3300

taaaccacaa ccccttacca ggagttcctt tcaagtacct caagatccta tgaaccacct    3360

ctagatgagt tgttctagga tcatgcatat acctactaac cacactcacc gcataagaga    3420

tatctggtct agtgtggcat agatatatca aacgtccaac caacctctga taagtttccc    3480

tatcaactgg atcacctgac tgtgcactca attggtgatt cctatcaatg ggagtagcac    3540

ttgtacgaca tccaagcatt ccggtttctt ttaacaaatt aaggacatac tttctttgag    3600
```

-continued

```
agagaactat ccccttttgat gatcgagcaa cctcaatccc aagaaagtat cgaagaggtc 3660
caagatcctt cacctcaaag gcctctccta atcgctgctt taagcatttg atctcttcta 3720
catcatctcc agtgatcact atatcatcaa cataaacagc caagatagtg atgtgtgccc 3780
ccctatgtct atagaaaact gtgtgatctc cattacattg tgaatatccc atattgcaca 3840
atgcacgcct aaacctgtca aaccatgcac gtggggattg tttcaaaccg tacaaggact 3900
tcttgagcct acataccttc ccaacagtct ggctatttcc aaatccaggg ggaatctcca 3960
tatatacctc ctcttgtaaa tcaccatgta gaaaagcatt cttgacatct aactgatgaa 4020
gaggccatcc aaagttaact gcacatgata tcaaaatcct caccgtactc atcttagcca 4080
caggtgcaaa tgtttcatca tagtcaattc catatgtttg actataacct tttgcaacta 4140
atcttgcttt atatctatcc actttccctt caggggtttg cttcactgta aatacccatt 4200
tacatcccac tgctcttttc cccattggta gtttcacaag ttcccatgtc ttattctttt 4260
caagggcacg caactcctcc ttcattgcat ccttccatct tggatcttgt tttgcacatc 4320
tctagtcctt tggaataggc actatttgca atgatgcaat gaatgcttta tatgcaggtg 4380
aaatatgaga gtatgagata tagtttgcaa tgtcatgtct agaactaagg tgttcaaaac 4440
caaggcgtat aggaggtctt ccagcattag atctagtttc tctacgttgt gcaagaggta 4500
actctacttg ttcaaaggta ggagaaatgt taccacttgt ctcaaggagg gaggaacttg 4560
ttggagagag gctagaggag gaatctggga ctgcgtactc aaactgttgc agctgttgtg 4620
actccttgtc ttgctcttgc ataggctcac cacttctctc cccctgattc tgaatttggc 4680
tcctctggtg cacttgctcc ttccctgtca ccttatcaac ttggttcttg ttccttcttt 4740
gatatactct catttcagtt tgttgtactt ccacacgctc cagaggacat gggattgtcc 4800
cgacaactac cccctcatcc ttgtcacaac taatgtctac taccttctca ccaatgtcca 4860
caaccttctc aatagtatca ccaacaaaac tcggaattga cccaataacc acatcctcat 4920
caccttgctt atgtgcatca acctcaacta tctccccctc tcgactgtcg atctcgatga 4980
cagttgagaa ctcctctaga aattgatcaa ggtctcctcg actcctgtaa taaggttcaa 5040
actctcgaaa tgttacatcc atactaacaa ataacctctt cccaataggg tcccaacact 5100
tataaccttt ctggttagat gcatagccaa caaagacaca ttttactgca tgaggatcca 5160
acttgccaac aaaaggtcga tgatctctca caaaacaaac acaaccaaat acctttgggg 5220
gaactttaaa ttctcgcttc ccaagtaaaa gttcagctgg tgatttcata ccaagtatcc 5280
tggatggcat gcggttgata aggtatgcgg ctgtcatcac tgcctcactc cacagatact 5340
taggtacgtt catttgaaac attaatgacc gagccacctc tagcaaatgc cgattcttcc 5400
tctcagctac accattttga gggggggctc caggacaagt ggtttgatga ataattccat 5460
gatctgagac atatgacaca aactcactat taatatactc cgtcccattg tcagttcgaa 5520
taatccgaac ccttgcatca aactgattgg taaccaattt gtggaagtct tgaaagcaac 5580
gaaggacctc attcttatgt ctaagcatgt aaatccaagt catacgagta taacaatcaa 5640
taaaggtaac aaaccatttg aatccactca cagaagtaac tgggcatggt ccccaaacat 5700
cagaatgtat taatataaaa ggttcacaac tacgaagacc aattccagca tatgtagacc 5760
gtgtatgttt gccaaactca caagcatcac aaacaagtct actcttgtcc actttggtaa 5820
agaggtcagg atacagctta ctcaaactct cgaaagatgg atgtcctaat tgacaatgaa 5880
gcaaaataat ctccttctca gtatctccca ctactacagc caatcccatc tcctcttgat 5940
tgatgtacca cagcccatta cgcctgactc cagtcccaat cctcctccca ggcagtagcc 6000
```

-continued

```
aaaaaacaag caaaaacaag agacgtacca cctccttcct agttcctgca gcaaacaatc   6060
ctcctatgtc accaagtctg cagccaagcc accatcctcc ttttccctta gctgagctcc   6120
tcacatttcc tgcgtgagca gcaggttaca acacacgcgc tgcgcccgcg cggccgcgcg   6180
cagcgcgcgc tcaccagccc ctcaacgtgg ctgtgtgtag aggctggtca ggccggatga   6240
gagcaggggc gacgtgcgac gacggcagcg gcgacggcgg cggcgatgga cggcggcggc   6300
ggcgacagca agctagggtt agggctctga taccataaag ttcagttttg ggatttttt    6360
ctggtgtgtt gttcacagcc acacacacac tatttcactt agctacatat gcaagaaggt   6420
ccccaataca agagcatatt acatcaacat gcaaaacatc catcaagtca aataatctga   6480
aattacttct gcaattataa tgctgacaac atgctaacgc atccaacagt taaaagtgtg   6540
caggaactaa taccactcaa tttagtaatt cattacagcc acgcttgatg gaaacagaga   6600
gaaattaagc aatggtttat tggaaattag ccgtgcctag agaagaggat ggacgcctca   6660
ctgccgcaag gccattaact gatcaggatc aaactatgac tgccaaaaac atctccaact   6720
aaccatctca attcttacaa gttacaacta tgaaccagat gatgagaagt tgagaaccca   6780
cgcaattcca aaacgatcat agagcatcga cgcgcgggtt aggaacacac ttgcattgcc   6840
ataacacgat caaaaacaac aagcgatcga atgatacggg ggagtcgagt acgcaccacc   6900
acctcctgat cgggcttctc cttgtcaaac ttggagcacg aggacttgtt gatgatgtcg   6960
ctggccatct tgtcgtgcgg agaggagagt ttatcaccat ctgcgccgtg ctcggccgcc   7020
gccgaggacg acgccgaggt cgcggaggcg cagtccatgg ccgtgggcac ccccacctgc   7080
ggtgccccag acagcgtcgt gccgtgggtg gtcatcatct cgacgccccc ggaggactcg   7140
gcgggacggg gcgacgacgc cggggtggag gaggaagccg ccgcggcgtc catggcgccc   7200
ttgggctctt ccgcttcagt agttaagtcc cgcttgccct gcaatcgaga gagacatcag   7260
gaacacacac ccgtgagtcg tgagcgtagt tggtgccgga gaaggagaaa cgagggacgg   7320
cgtacgaggt cgtggcgggg aggcattggg cggcggcgcc gccgcggcgg aggagcagcc   7380
cgacacggcg gattctggaa ggttcggcgt ggggaggaag acggcttcgc ggggaaatga   7440
ccagccgctc cgcttttttt tttttccttt cccgtttttt caggagagag agagatgggt   7500
ttgggtttcg tcgggtcggg tgggtttggg ttttggagcc tctgaagttg gacatgggtt   7560
tcgttgcatt ccacgtcgtg cgggttgggg atttggattg ggcccacagg gcgtacgtgg   7620
ccccgcgtcg tgcgggttag attcttcgct tgagctaata agttcaatcg ggactgtatg   7680
tttatttgtc gggtgatttc caaaaaagga aaatcatcta gattttttt acctttagat    7740
ttacatccaa cagactacaa aagaatataa caaatacata tttatttata tattattttt   7800
atcaaaatta cagtatactt acatgtcaca tcaactgaat ttacaaatgt aattttagtt   7860
atataggcct ataactttat atttcacgac gacgatgatg agagaggcgg tatcgctcgc   7920
cgaacagctt tggccgtact gccggcggcc agctcgatca gaggccaccc tggcaccgtg   7980
cttctccaac atcgcgcgcg ggcgtacgta ccagccggcc ggcgagcttc atgcaacgtt   8040
cgatgccgtt cacattgcaa gctgcatgga tgctaaaacg tatcaaatgc cagaaaaaaa   8100
atcacacgag agatggatag caaaaccgag ttcgatggga gtagactcaa cttcggctgt   8160
gtctcgtgtt tttttagtaa gtttacctga cgtctctcaa ttatccacag agcagcccaa   8220
caaatcagga aagacattca agaaaataac ttcgtttttc agcctccttg atgatctcat   8280
tttcttcctc ttctcctccc ctattgttgt cccctctcta tcgttatttc tatttcctaa   8340
```

```
gaatgtcgct tcatatctcc ggtaacagtt cacttgtaag ctctatgtaa cctactaatt   8400
tcaccccctc taatgtattc ggcaataatc ttgccgcttt cacctaaaaa aactatacgc   8460
tgagtatatc tgagatcccc taactgcaat atcaaaaatg tgcaccacgg actatgtaaa   8520
acagttcaaa aaaggtccca gattatagat ggccaaacgg gccacccggc ccgacacaac   8580
ccagatacaa ccggtacggc acgacctaca tgtcgggtcg tgtcgtgtca gcccgcgagc   8640
tgcacacaca gcccaggcac gatccaataa gacttgggcc atgccaggcc ggtccgaagg   8700
catgacaacc catcatgttt ctctataaaa taagtctatt tttcctccct cgactctttg   8760
ggttgtgtct tatatggcta aaaaataagt ctattttgta ttcctcttct ctttgggcct   8820
tgtcatatat ggttaattaa gtctatttta gatccctcta ctattttctt ccaccgtgcc   8880
gggccgggcc agcccaccgt gccaaggcat cagccttggc acgacccaac tgtcgagccg   8940
tgcaagcaca ggcccgacaa atagtcgggc catgcaatgc ttgggctggg cgatcgggcc   9000
ttaggcctta tggccatcta tagtatagat acctggtttc gctgacgtgg catcctagtc   9060
agaaaaaaat aaaaaaaatg taaggcccac atgtaagtga gaaggaaaat gtgggcccca   9120
cgtgtcagca tcatcttctt cctttcgctg acgtgacatc ctagtcagaa aaaatttaaa   9180
aaaaagtaag tggggcccac atggaagtga caaaaattat aggcaaaatt tgctacagga   9240
cactgaaata ttgcggtctt tgctgtgaga cacccgaaga tcgtgtattt gctggtggac   9300
attgtaaaga agtggtaatt agctgctgga cactcctccc attattttat tatttccggt   9360
caaaatggag agagaaagag ttgtgtaagt actaaaatgc ccctggacac gtactgttct   9420
tcctctctct ctcctttttct tttcccaatt cttcctcgcg acggcggccg gcccgagccg   9480
ggatggctcg gccacggcgg ggcggcggcg gcggcgcatc accggggttc accgccgacg   9540
gcgatgacgc acggcggtgg cccggcgcac aaatgaggtc ggcaaagctt ggttgtcgac   9600
gatggctcgc gaaatgtttc ggcggcggcg cttcaccttg gatgaacggc gatggctcaa   9660
tttcttcaaa ggattgtcat gcatgcatgt ctttcgtgtt agagaggtcc atgcgaggct   9720
accatggcaa ggaatcggat tggactcac  cggagaggga gaaatcaaag atggagctca   9780
gcgaccggag ttggagaaag atgatgccga tctctaagat cgctgcgcga ctggataggg   9840
tacttggggg taaatagaga ggaggtcgag gtgaagctga tggcgtggtg gctcggccta   9900
caacgatcca ctgcacccgg aacggtgacg acgtcgaggc ggcgacgcgc agagcgcgct   9960
ccaaggccgg cgatgacacg atggcgttcc cgtcgatccg ctgcacgaga gaggatggaa  10020
tcaaaatgaa aaatcttcgg catgttaagg taagtatgga acggtggtga ggcagacatg  10080
gagatagctc tacagtgaca gcgggcgttt tcttcttcat ggccggcgag ggatttgagg  10140
acggcgaaga gattgagggc ttcctctctc agtttggtcg acactagagc tggggttcac  10200
cgccgacggc gacgacgcac gacggctcag ccatggtgga gctcggcggc ggcgcaatga  10260
gaaagagacg aacagagaga gaggaagaag aagaacagag agagagagat tgacaagtgg  10320
gcccatgggc aaacttgtct ttaaccaaag tttctctctc cattttgatc ggaaataata  10380
aaataataga aggagtgtcc agcagctaat taccacttct tgcagtgtcc accagcaaat  10440
acacgatctt ggggtgtctc acagcaaagg ccgtaatctt tcggtgtcct gtagcaaatt  10500
ttgccaaaat tatagggtcc acatcttttt tcccttctct tttctttttt cttttattct  10560
cttctcttct ccttcagccg aacggcggtg gcaggtggcg acgggcgacg tacgagagcg  10620
gcggcggcga cagatgcctc tttccccctc ccgccgacgc ggccgacatc ctcacccccct  10680
ctcctgtcgg cctcatctcc cctcactcgg tcggcctcca ctccccctct cccgtcggtc  10740
```

```
gcttggcgaa ggtggctcgt gggcctcttc cgaggctcgg cgggtaggcg gctgtagacc   10800

cccgatttta gaaatcggaa atcttctgtg tttatccgta ccaatccctg gatcagtagt   10860

tggtacacac atatatagtt ggatcacaac atatcacgaa tgaatttagg ctaaaagagt   10920

taaatactta cattagggcc aggtaggcca acaactatca gagaacaaca gcggaagaca   10980

aaataatata agggcccggt taacatgcca caggcagtcg actagggaac gagacctaga   11040

acaagaccgc actccgatca tcttgttgga tacgcaagcg taccgacaag ggcttctctt   11100

caacactctc ctaaaagata tatgaatagc aagggtgagt accaaccgta ctcagcaagc   11160

caccacaaca acaatgcata tgatagaggg tatttcaagg aatggcttca ggttcttttg   11220

cataaagcta attttacaat tcttttcaca agcctaaaac ctagcataga ctgatcaaat   11280

tttagtacca gtgttcactt taaacaacga cggttctgtc caccatccat tgtgatccca   11340

aggatagctt cccgccattg aatcgtcatg gttttctgag gatgtccacc ttccctccta   11400

tcgggaagtg gctccatcag cataaaattc atcatgcaat aacccatccc ccacaagtta   11460

agaatttaga gtctagccaa gtgtaataca tgtcccggtg ctcaataacc gcgagcacgg   11520

ctattcgaat agatttggtt tactcacact gcagtggatg tacactttac ccgcactccg   11580

cgactgccca acacatgagc ctcgtcccaa cacatgaaac gcgtcacggc aaagcttttc   11640

gataacctcg cattggcagt acccgctcca tgaacttttc atcctcatgc actctaggcg   11700

tacacggttt ctagcagtga gaggagttct ggcgcacccg ggaagggaag actcacacat   11760

gcattaagtt ataattatgt tttagattct cacatggcag tcctaccgat ggcgacacca   11820

ctgtagacac ccgcctcgcg gtcctaccaa tggctgcccc accgtagagc ccctgcctca   11880

cacatcaaga aaccactatg catggatact gcctccgctc agctatctac tccgctaggt   11940

ctatacccat acgagaagtg cggttgtacg ggggtcgttt cctgcttaac ttcatggctc   12000

ggtccttaat tgaccaggga cggcactagc cttttccgga caccacccaa gtcctccagc   12060

cgccctagtc gaaaacagtt gttttacttt attttccttt cacaaatcat gtcatcaata   12120

tcatggcaat gtggcgctca tgtctccaca tgccgtatct caattacctt cccaaaggta   12180

attgcccaag catatagcat ttgataaata tgagtatgca tgaatctaaa atagcatttc   12240

taagcaagtg tcatagttga ctagggactc gtacgtatct atggttacaa agatttaaag   12300

gtgaacaata atcaaggcat ggtataatca caagtaggat gttcataatt gcatgcaatt   12360

ttatttgtaa acaaaacaat ttcgcaattg ggatcaacat gttcaaggaa tagtgatgac   12420

ttgccttgct caggataatc cttattactg atataatctt gatcaacctt cacctcctgg   12480

aagttgcaga cgttgcctca cgtctaaccg atacacaagg tctataatac gcgagaaaaa   12540

ccaatattca acaacaatc aaatacgcgc aacaaaatgt actattcatg tctgctaatg   12600

gattccaatc acgctagggg ctaaggtttc ttaatctttc tattgtcaac gtggcctatt   12660

taggagttaa ccaacatagc atttatggga tacatatata tttggctaat cggtggttta   12720

gtctatcaaa tggcttatgg aaggattatg gctaagcatg catctatcta aataggacgg   12780

tcatatacta gaggttctat tgttagatgg atttaggatc aatcaaataa ttatagtgaa   12840

tcatttgtat tatttatttt attgatggaa gctttacttt aattatgaac atattttact   12900

tgtcacaata aattataaaa ggttaataat tatccatgct ctatatgtta agttcgggaa   12960

gtttataata ttatagttac agattatctc ttaatgaaca atccggagtt acaatcgaac   13020

tatgaacata tgaggtcaag atttataatt aggacttatc tactattcat gtttgttata   13080
```

-continued

```
tactccccag tttgatatat gaaaaagata aattaattgt gtaactataa tgggatgtac  13140
aatatatgtg tgcaacaagg tataaggttt tggtcgccta ctatacatga gcttatttag  13200
aaagtgtact acccaatgct ccaagtgatt cctgaatata ttgtagttta attatacatt  13260
agctagtttc tatgagtgat attgtatatg tgatgcgaca agtttaagca ctggttctat  13320
tgggttacta ataagtggta atcaatttag gcatatataa gctattctat atggtattgc  13380
atcgattatt ttacttagtg attcctccac atctagctct attattattc tcctaaacag  13440
gttaaagatt catctatgtg tgttcatatt ttagttgcat aatcataagg ctacacttga  13500
tttaaataac ctataagcca tggatttaat tatatggcca tcgaaatttt cctatacatc  13560
cattcatttg atacatcaca taaaattagt ttgtgtggtt gttacagtgg caagacatgt  13620
tagagacaaa tattattata tctactctac tgtacaatac taattttatt tattaacata  13680
tttttttaa gttgactatt atgcatcatc ttgatattaa ttatttaatg tttataaata  13740
tattttatca aatagtgaat tatatatcat tggaaagctt atgaatttag atgaatttgg  13800
gttcaagttt cactcaaatc ggagctaaat atcgaacgaa atcctagaaa tattatatga  13860
tttaatttag tctatgacta aatgattaaa tataatacac ggctaaaatc cctagtaatt  13920
aaatctgaat ttctaccgtg aatcgattac ttatagggtt tacccaaaaa taatctataa  13980
taatctataa gaattcatct atttgtttag ttattaatta cgtctaaatt actaccgcga  14040
attgatttct tatagaaatt accaagaata atccataatt tatattaaat tttgcaattc  14100
tatgactata attaatctat aattaaattc taattatttt aaattttcta aacttcccta  14160
atctccctct aatttcctat ttacttcctt ttccttttc tccctttct ctcttttcct  14220
tttcttttct ttctctcctc tctttccctc tctttctttt tctctccttt ttttctctcc  14280
tccttttctt ttctttttcc ttctctctct ccctcccggc ttctttctct cttcctcggc  14340
ttctcccttt ctctctctct ctctcggctt cttctccctg gtgacgacga ccgagcaagg  14400
ggaggaggcg gcggcttacc gacgacggcg gcggcgacgg cggcacgacg accgagcaag  14460
gggaggaggc ggcggcttac cgacgacggc ggcggcgacg gcggcacaac gacggcgcac  14520
ggcgcggcgg cacgaaggcg gcggtgcggc ggcgcgaggg cggcgccacg acggcgcacg  14580
gcgcggcggc ggcggtgcag gcggcgcggt ggctcaaagc ggcggtgcgg cggcgtggag  14640
gcgggaggcg cagtggagtg agtagaggag aggaggtgag aatgggggaa aatgggtgtg  14700
gggtggggaa gaggaggggg ccggggtttt tataggggcg agcggcctca tgacgcgacg  14760
ggcggcgcgg cgcggggctc ggcgcggctc ggtatgacgg cgacggcgac gcggcgcggc  14820
agcggcgcgg ggtgcgaggc ggcgacgcga cgggcgagcg gcgcacgggg cgcgaggcgt  14880
gggcgcgctg cgcgaggcgg cgcgcgacgt tggcgcggcg cggcaacggt gacgcgaggt  14940
gcgcggcgcg gtgacgagac gacgcggcag cggcggtgcg cggcgcgagg cgtggggcgt  15000
gggcgcggcg acgcgacggc ggcgtgacag gcgcgcggcg ggccaggggc gcggggacga  15060
cgggaccggt tcgcggcgac gggacggccg acggcgacgg cgcggcagcg gcgacgcaac  15120
gcgggcggcg tggcgcgggg agcgaggcag ccaggcgcgc gcggctgagg gggaaaatag  15180
agccagggac cacgtcgagc acctagagtg caatgaacag tgacttttcc tatttatccc  15240
gattttagtg tattttccat ataaatttga ttccacaatt cctagtttta catatatgca  15300
ttttactcaa tatttgtgtt atcttaacta atgaattcac cctagattaa tattatccat  15360
atttatttat ttatcgcaca aatgaattct ttttagatta atttgagtta ttggccctaa  15420
ggtgaactta tatatttttg aagactttgg ggtactatta aatttaatat aacgacttgt  15480
```

-continued

```
catgattaat acattagcag attggtcaag tttagttgta tagcaatata ttttacacgg  15540
ataggtttaa tctatttatt ctataaatag taaattaaga ctcggtacaa cattaatcta  15600
attttaaaca ctcacatatt cttgtttata tataaggatt aatttattta tatgaccatt  15660
attttatatg agtgattttc atgtcatgag taactcggcg acatgttgca agtatcaatc  15720
tatatattcc ggtgaattac ttatttataa acacgatcac tataatggtg atcatcattt  15780
catgtgttct tatatttcat gtgagattcg attcaaatga attagattta atcttactat  15840
ttctttagct aattgtgaca tcaagctatc aatcatggtt cgaatattta atacctgatt  15900
tgtaatttgt aatagaaatt aatatttgac ttaactatct tgtgcataat tatttgtagg  15960
attaacaata ttatattctc gtaaatttac ctattactta aatttttaga tccttacttt  16020
actttctttg tgatcattta cggtttggca agcaattgca atcataacaa ccagcatgat  16080
gaaaaagttt tgaaaagttc gaaattttag tgatttttat tgttgggaat tttcaggatg  16140
ttacagcggc gcaggagggg tggagccgcg tcgtgaccct cttgcgagcg tctccactac  16200
tgtgtcgccg tactctacga gtttgttcta ggcgcggcgg tgtccctcat gacgccgagc  16260
gtgcgatgcc gacaggtggt tctcggggcg tggcgcaccc ttgtcggctt cttccttgcc  16320
gagcacgacc gcgagctcga agcggtcgtg cgtgatctcg cacgccgtct cccgcgtgtg  16380
cgccttagat ctccgccacg ctcatctgtc gccgccctcg ctccgctccg tcgggcgctt  16440
cgcccctact ccgctccgct gccacctcct caccgcctag ccgccgacgc tgcctcctca  16500
ctggccctag tcggcattgt ttcctcgccg gcccaagcta tcgaccatca ttagctcgtc  16560
gttgccgtga gccttagccg acgcccccac gccacctcat cgccgcccgg gctgtaacgg  16620
ccgctgccac cgtcacctcg gcgagggagg agagaccaag agtagggtag agagagtggg  16680
agagagcagg agaagagata aggtggagaa taaggatgac aggtgggtcc tacatttttt  16740
ttcccacata agcgtctagt cagcatgagt ggaccgggtc aaattgccac gtcagcaaaa  16800
ccaggtgtct attctgctat aggacctaga ctggacggtt ttgtatagtt taggggtaaa  16860
gatatctggt attgagaata agggatgtca aggtataaaa ttgagggacg acagtgaatg  16920
tatagttaat taagtactag cttcatttca tattattcgt ttgacttttt ttctttagtt  16980
aaacttcttt aggtttgact aaattttata agaaaaaaat agtaacatct acatcaccaa  17040
attagtttca ttaaatctaa catttgatat attttgataa tatgcttatt ttgtattgaa  17100
aatgttagta tatttttcta taaacttggt taaatttaaa gaagtttggt tgagaaaaaa  17160
gtcaaacgac ttataatatg aaacaaaggg agtattaggc ttaaaaaaac ttgaaaattt  17220
gattaatatg attttcacga caacttttct atagaaattt tttataaaaa aataccgttt  17280
agtagttttc gaagcgtacg cgcggtaaac gagggagtaa ggttgggaac ctcaaattga  17340
gagcacagca tcatcatttt tggatgggct tggtgcgcat ggttggatga actacgaatg  17400
agtttacttg gaaatttttt catctcgacg tcgagtttga atcgtgttga caaaccgtaa  17460
taccatatac aatagattct taacttgtaa tactggagta cttgagatcc tatagcagta  17520
ttgtgcttgg tttcaactaa tgtggcgagt tgaatgtggt caacctggcc gagttttgcg  17580
tgggatccac atgggcccca cttgttaggg cccattctct ctctacctat ctctattttt  17640
tttctctttc gctcttcatt tgtaggctgg cgccgcccaa catcatgtgg tcgagctaga  17700
ggagttgctt tggcaggtgg ccacagcggc agtggcactc cccctctctc tttcgccctt  17760
tgctcgatga tggttgcgta gggcagcggt ggtgcttccc cttccccgac taggtcgggc  17820
```

-continued

```
ttgcaacgac gacaaccttc tccccgtcga gctcctcacc catcactgta gttggtgagc  17880
tatagggtaa gatagactta aacctagggc cttatcactt tacagttaaa attaaccgta  17940
caaagttttg gttttctcaa aatttgggga ggtaacaatc caaacattgc caaaaattgc  18000
tccactatca aagtttggca attttagaat cttcctctca caaaaaattt aaaaaaaaac  18060
aaactaaaca tagcctacac ttgttaactt taccaaatat tgataaattt ggtactgtca  18120
aaatttggca atgttgatat ttaggcatca aaaagtgaac aacccgttcc gatgccacaa  18180
gcccacaacc cacctcaccc tgccgaccat gtcaaaccaa gcagaagctt ccagagcaag  18240
gtgcccgcgg cccacgtagc ccacgccgcc gaacagcaca cagccgcaac tcgcacgaac  18300
ccccgggcat gcctgacctt gtgcggcggc gaccatggct gccccctcgc cggagcggag  18360
ccctcgtcgc cggggaccga ctccccggtg ctctgcgtgc gaatcgtatc cctcgactac  18420
cacatggcgc cgcccctccc cggccggatt cgacttctcc tacagccact tccacggtgc  18480
gtttccctcc ccgcccctt tctccacccg cctctctcga gcccccgttt cgcccccctt  18540
gtgctatgcc tctgcaccgc gcccacgtca cgtcaagcgg ttgatgagtt tgatgtgtgg  18600
tggatttagg tgaaggaggt gatcaggctc cactccttac ttgcctccac atccatctgg  18660
tgcgtagcag cttctctgat gagtgctttt ttttttctct ctgttgatat tacggatgag  18720
ctagttttgg tcgtcatgtt tggttgcagc ttcaagcttt caaccgagtg cgtcgcgtcc  18780
tttcaagtgt tttgagtgtg agttacgctg tgagggtata atacatttgt gtttgctgtt  18840
aggtagccat gcgcagcaac taatcctcct catgtattac acggtatcta tgcccaacaa  18900
ttgatgccca tggagggaat gtggcaatgt gctctttgtt gatactgtac gcgcaccaaa  18960
ttcgaagttt ggagatccaa cttcactttc gaagttcact aaatttgaag ccctcttatc  19020
ctgcatgggc ttaacattat tttctataca cttggtgttt gcttgtaata tatgcaatat  19080
ttacttctgt gtgcacttga tttttgtttt ttttttgttt tggttgagtt tggacatgca  19140
tatgatgatt agctctatta tattttgaat tcatgttttt gaatgaatac agatatactt  19200
caattttttt tatatcgctt ctctatggaa agttgctcac actattccat tcatcattag  19260
ttgtgccaac tagtttgtaa acgtttgctg tttttttgtat ctccttcaat ttctgtctgt  19320
gccttgcaca gaggaccttc ttcataacat tgaaaaaggt aattcattat ttgtagttat  19380
gcaaccctga tgtatcatgt atatgctatt actgttactt ttgcaatttg ttacatggat  19440
tgttctattt tgaattgtac tgctgatttt ctatctacat tacctgaaaa ctttttgctg  19500
atgattttca tatctacatc acctgaaact tgaaattgat tgttatttat tcatattcta  19560
actgagcctt actgctatct cacaaacttt ttagacacta attcctcttg tatatggcag  19620
ttgcacaccg ctgttgcaat tttattgact taattaatta attcgtgatt tgaaaggtca  19680
cttcttcatc tgtcgaaagc ttgccttgta tgcatctgca acacatttag ataacttaaa  19740
cagtaggctg aacccttttgt atgtgcatgt ggctcggtaa gcatctctta gattttgtac  19800
tggtgaaaag ggcacctgtg tctagaaata agtggccgtt actttttcttt aaccaaatag  19860
cctaaatgtg ttattctctg caaatggtag aactgaatac tgatgctccc tgattaactg  19920
ttgcttgtaa tgtcaagaac atcgcttgat gacaaggaga aattgatatg tctctttcct  19980
gccctttctc taggtaattc atatataatt ggggtctatc aagtgacctt gagaaagctt  20040
tgcaggtatt tgtgatgtcc agttatgtat ccataacttt attgttttct aaaaagtatt  20100
ttggctgcta tggatgtttg aaccagttct agattacctg ttctttcctt cacacctagt  20160
gtttccatga acatattcca tatgattaat tataaatcaa aaccaaacaa agtatttact  20220
```

```
gaaatcttca caaaagatat actgagttgt ggaacacagt aactgcatcc tcgctgtttc  20280
ctttgctgtg caatttctgc ctatcagtgt tcatcctgaa agattatatt aggttctcct  20340
ttaattaatt aattttgatt tatttctgta tttttttcct tcagaactaa ttcttgattt  20400
cttagcatta actcctattt tatatttatt gtctagcttc tccttgtcaa tattgaaact  20460
gttgtactca ctatatgttt ctgtttcagt gtcctaatag tttatcagta aatatactga  20520
ccatttatta ctggctcaat gcttggtgtg agtatctaag ttctgatgtc ttatgattgt  20580
tgcttccacc tagagtttgc aaccatgata tattattcca attctggact tcaaggtagt  20640
ctatgtaaaa tggtaaaaat gcaaaacttc cttcatttgt tctgtgttgg agttatcatg  20700
agaaaaatct actgatttgt tttgtagcta attggctata cataattgcc tatgcatata  20760
ttcttgacaa gcattaaata agtcagtggg aattttattg gtgttccgtg atatccttaa  20820
tatttgttga tattgaatcc aactattgaa taccatgttg cttgtttaaa ccacaatttc  20880
atgagaaatc atctactgca caagtgcaca ttctgctgca gcccagctat tggtctgttg  20940
acccccttctg cttaatttat gaccttggta ttttccaaat ttccagtagc taaacatgtc  21000
tgacaggagg aatatagctg ttatacttct agattttttt ttctttcact attttttggc  21060
aatggtactt tgttttatta tcccctctat ttcttcttaa ttgttactag tattgtttat  21120
atttcactgt ctcggagtta caatttggac cttctctgct atagtttaac atcaaggtat  21180
atcaataaaa ctataatatt acagcagtat gttcagcaag gaatctattg atataatatc  21240
tatatagcca atctatctag ttgttgacat attaatggtc aaactttgca gaattttatg  21300
gctagttctg acactggaag gagtatttat tgaaagagag agttgtaata gatatttcaa  21360
tattattatt tgcttttgtt cattgcgtat gtttcctttc agctttacat taataatgac  21420
tacacttgtc tgctgtagga aactagtatt tttacgtgaa agatttgatt tcaaacgcct  21480
tctgttgcat gccatttcac ttgaaaaatg tgcattgtgt ctcagtgttg catgtgtatg  21540
ttgctttatt ttcatgatgt gaagctgtgg attcattctc ctagcaacat gaaacttggc  21600
ctctagacag ttatgccatc taggatcgag tctgttctct gtacagacta tcatatgtta  21660
tagtaatttg aaattgttca gtttatcttg tgatcttcct tgtaaataca ctttactctt  21720
ctcgaatggg agtattttaa actatttcct gtggttcctg attttgagat gcttggtttc  21780
aggatggtgc tgttcttaat agagtattcc aaccttatga gtctcacatt ccctatcttc  21840
ttcacttttt ggtaagagca acacttagtt tcttttcata gttgttgtga actgcaagaa  21900
cagtatttca ttttgtctct tatgcagtct taacataata aataccacag tctagctttt  21960
atgatatata gtatattgat atttgagcgg ctggagtgcc aggatattaa tgattgaatt  22020
gaacctgtga atggagaaga acaaccaaat gatcaaatat cttaccgcag ttctgtaagg  22080
ctcgatgaga gtagttcgct gagcaataat attcctcagc ttgatgggtc atctgatgaa  22140
aaccaggaag ttccacaaga agatggtaag tataaaatca acaggaaaag tgcaggattg  22200
cctagttact catctcctca aagtagttga acttctctgg tgctctttgc cacctcccat  22260
taaaaagagg tcagatgtaa atgttgatgg tcatgttaaa acctctccag acggtgcgat  22320
gccaactgag aaggaaccaa gtgtttcttt catgagtaga actggaaaga actcccatgc  22380
taccacagat aagactggca gggaatcttt tagtcgatca ggtgaacatg acccattgtg  22440
tgattctgtg agggtctgag agacttgatg atgaggagga ggatatcttt tcagtctgaa  22500
caatcagaag ttggcaagtc tggagatgca atatacatca tttgtaaaga gaatgaaatt  22560
```

```
gtgaattccg agggactaga atggcctgat tcatccagtg gcctttcgaa ttcataaatg  22620
tgtttttctg gcagtgaata ttagcagatg acctttgcac agaagcctcc aatgaagaat  22680
gaagtattat gttgtttgga gggctcttca gcaggtagtg agctgcctca gtttaagtta  22740
aagtggtatt tatttatcat ggtcaatgta agttccacaa gtgatcttta ttttatcatg  22800
gtgaatgcaa ttcatttgat gtatactgta gttgttgctc atgtaaattt tgtagtagtt  22860
ttgatgttgt tgttaacgat ctaatatata aataattgta ttagtgccta cgtatgatta  22920
tgtaacagat gttcattgtt ttctttcagt ttttctagca ttaggctttt aggtcctttg  22980
ccatttacat agcttagcat gtatgcaaaa atagtactcc ctccgtttca caatgtaaga  23040
ctttctagca ttgcccacat atatatagat gttaatgaat ctaaacacat tcatttagat  23100
gctaatgaat ctagacatat gtatgtggtt agattcatta acatctatat atatatatat  23160
atgggcaatg ctaaaaagtc ttacattgtg aaacggagaa agcattattt atttgtttgt  23220
tatcatttgc catttacaca gcttatcatt atttattatt gttttccctc tagaacagtt  23280
tggactatca accaaatgaa atagtatacc actataactt actataagta cagtgctatt  23340
ctgttaaaac ttaatctttc ttgaattttc cggtatcatc attcacttca tatcatttaa  23400
aacacattat attttctctg ttaatccaca ttcgctcttc tgctattttt caacttctaa  23460
actgggattt atcgatatcc ctctgttttt caatcagaat gctgaagcga ataagcagaa  23520
tgaatcattt caacacatgg aaagtagcga gttttcattg gatacatggg gtgttccaac  23580
tcatttccaa aatgattggt cagccctata tttgctaaca catgcatttt tgccaccccg  23640
tgggccagtg gctaacctaa caatcttgtt ccattagtgt ctccggtata gattatttcc  23700
tgcacagtca atttaatgac catgtatcga tgttgtcaca cactgttatc ttaggccatt  23760
tcaactgtag tgagagagtg tctgttgatc aggaacgagc aaacaattct actctttcac  23820
catactagca aattacccat gccatgctat gccatgggat aaaaaatgaa actgctttgc  23880
tgtgttatta ctacgcagca tttgggtgtt tttccccctt ttttttgttt tttcctaatt  23940
ggcggttttc tggagaaact gtttggtttt ttctagaggg ggtggagcac agaattggtt  24000
gggtggagag gaggaggacg atgactccct tttagtgtag tagagatatg ggaggtccta  24060
ctttgatgga cgattctctt gcatccaaat tggctttgga gcatagccct acaacctttc  24120
ctaatggtac agttatgatg gaaccagatc tttccaacca agtaatgaaa aatctactcc  24180
ctccgtttca aattataagt cgttttgact ttggtcaaag tcaatctact ttaagtttga  24240
ccaagtttta gaaaaaaggt agtaacattt tcaatccaag ataaatatat tatgaaaatg  24300
tattcaatta tcgattaaat gaaactaatt ttgtgctgta aatattacta tatttgtcta  24360
caaacttaat caaacttgaa ttagtttgac tttgatcaaa gtcaaaacga ctaataatct  24420
gaaacggaag gagtagctga ttggcatgag ttttcccaga tcttaggaag agatgagaag  24480
gataaactaa cacctctcag tcaaattgga ttccgtggtc ctactagcac tggtagtgga  24540
ttacaattga ctataagtag catagtggtt gtaccacatt ctttttttctt ttgttcctga  24600
cgtacatatg tttctttttg ttaattcttc atacaatgta ggtgctaatt tactgttcgt  24660
ggaaaaatct atgtctgcaa ccagcagttc ttttttgtta ttattaatca tgtcagtttg  24720
acttgctcta tccagtgaaa agaaaatgca aagttgaatt accagtttat cacatgacat  24780
ttatttcatt aatacatgta ttaacagaaa gcagaggaga gctgcatcct gatccacgat  24840
ttcgtgtcat caacgctgta tcgctggctg ttgaggatga tgctgacaac actactgaaa  24900
tcatgtgctt tatacgtgga aacaatgaca gttcacacag gaggaggttg tgtgaaatca  24960
```

-continued ctcaaatctt ggaattgttt gttgttttac ttttccgttt cttcttgttt tggcactaac 25020
cagtcatctt ttccttttta atcaaaattc cattctgttt aattttgttt ttctcaagca 25080
acatatatct taatgagtct acagaatctc aaggaattga actgtcctaa tcagaagagt 25140
tgtgtgcttg tgttaaatgt gaaatttagt acattagtat gtgagtcata atcctagttc 25200
aacaagagaa gtctgcatgg acatcgagtg actatggtgg tgactgctac agtgcagtag 25260
caactgatgt catttgacga gagtactttg gatcattact tttatttatg ggtctgttaa 25320
ggatttgata tggtaccatc aaaaacacat ttgttgcttc catgtgatgg gcctttcata 25380
tgtgctgaac atatcctatg cttctggact tgaagaacac catataactt cgggttcttt 25440
tatttagaat ttgttggatc ataaaccaca gttttactgt tttagagtta cactctcatg 25500
tagccataat tgtttgtttt cagctaagga acttgtttga ttcttttttta agggctgtaa 25560
gagttcaacc tgttgtattg agatgtcttt attgtccttt ttcttgtaac tgcagaaacc 25620
tggatagagt tgccggttgc gacataaacg tatttccttg agagacagaa actttttaaac 25680
catcttatta atgaaatatg ttcaatcgat ccagatatta tagttggatg ggagattcag 25740
ttgggatctt taggattttt tgctgaagga gctggtatag gcttactgaa aagaatttca 25800
aggacaccac caaatcagat gaaacatcca cctatgaacc cagtggagga atcttgtcag 25860
gagtttcctg gagcatcttc agctgatgat gttattgatg atgctagtga gagcaattgg 25920
agtcatactc atgctagtgg tatacatgtt gatggaagaa tcattctgaa cttatggcgt 25980
ctcatgcgtg cagaaattaa gcttaataat tactcccttg aggctgtagc tgatgaagtc 26040
ttgaggaagg taccattagt accaaccaag atattgaatc gatggtttgc aacaggtcct 26100
ggacgaggaa gataccggtg catagaatat gttaacaatt gatcttctct caaccttgaa 26160
atattaaata tacttgacct ggtaaatgga atcccccaca tttatcgtgc tggtacatca 26220
tcaagatatt gctatttgag atttcctttg tatttctagt tgaaaacttt tatcaatttt 26280
gcatcttctc cttaacaatc tcctagccac gatttatcac acagaaatgc agttggtttt 26340
gttgacattt cttgcacaag ctacttctaa atgttgttct tctatagcca tttttttccg 26400
acaaatatta cctgaccatg caggtaaaga ggacatctgt acttgcctgt gtatttagta 26460
ttgatttctt ctctgttctt tcacgaagtt ctctgtatcg tgttgaatct atctatgctc 26520
ttgagattgg cccatacaca aaactacctt gcaatttccc caggaaatta acaggtgaaa 26580
tcactcccta acatattaag atctcttcag atatatagtt tctcgttcac atttaccaca 26640
aattctggaa catgtcctag agatgatgtt atggattcta ctggcaggta acaggcttgt 26700
attgtataca tgatttcttt gtgccaaaga tggccttttg cccatttggt cagcagggat 26760
ccaaaagaag ttactacctc cgttttatat tataagtcat tttgactttt ttactaatca 26820
aacctttttaa gtttgattaa gtttatagaa aaatatagca acgtctttaa cacaaaacaa 26880
gcatgttatt aaaatgtaat caatattata ttcaataaaa ctaaattggt gttatcgatg 26940
ttgctaaatt tttatataaa tttgttcaaa cctaaagaag ctttactaag aaaaaaaagt 27000
caaagtgcaa ggaaaaaaaa tatttaggac acttttcaag attttgatgg gagtgctatt 27060
ttaagcacca tgaaaactta actttacctg tgcatagaaa caaaaaaaaa aagggactcc 27120
ccctgcgtcg ctctcgcgcg ggcggctcgg ggggcgaaaa accctagccg cccgcgcctc 27180
ctctcaatcc cctacctcgc cactgctgga gcttgtcggc gcgaagccgg tagctagcag 27240
ggaaggtggc agcgaggact tctcttcgtg gcgcgaagtg gacgggacga agacgacgaa 27300

-continued

```
gctccccgcc ggcgcggtcc gaggaggcca cgacagcaag gtggggtgag gcggcggatc  27360
cggccttccc tcgcctagat ctgtgcggcg gcagcgggag gaggcttggg gcagcgtggc  27420
ggcgggctgc tgcggctcgg ccggcctggc tcggcagctg cgcggcggac ggccacggca  27480
ggccacgcgg aggcggcgga cagcgcagcc tgcccagggc ggctcactcg cttgccctgg  27540
ccgcccagcg gcagcccaag acgcagcgac cgccccttgg gcgcggtggg tctcctcggc  27600
gtccaggcct cggtggcggc tcggcgtggt gaccggacag tcgggatgcc gccgcgatgg  27660
ccaggtgaga tgcggcggcc gaagaacagg ggcaccggcg ggtggcgccg atccggagcg  27720
gctgcgccac tagcggccag atggcagtgc aaagggagct ggcagtggtg ggtcgtcttc  27780
ctcattgccg gtcggcaccc tcgcccttcc cggagctcct cctcttcttt gcagggagtt  27840
tctaggttgg attgaggtgg ccgctcgtca acgggggaag ctcatgctgc cgaagcaatg  27900
tcacctagtc ccgggttctc ctaaagccaa aactgacgag gcggccggtg ggtggtggaa  27960
tagaggggtc ctgggccaac tctcaggggt ggtggttagc tgaagtcggc cgacggaggg  28020
gcgttggtgc ggtgtggtgg atgctatgta ctgccatttg tctgtgtggt agttctgagt  28080
tggtggatgg cgatctgcag tcaaggttat agggtaccag gcgaaagcct agttcggtgg  28140
ttcaccgggc cagcagcggc tacgtcttcg ggcgtcgtaa cctccttggg cgttgtcaag  28200
ggttaccatc ttcctttctc gacgagcttc tttaggtgaa aactgttaga ataggtgtcg  28260
aatatacttc ctatttggtt acagttggac ttagagttgt aataggtgtt aggggatgga  28320
gttagagtca gactctgtaa cccatcatct ctcttaaata gagagggagg caccacaatg  28380
taaccatggc gactgcaatg tagcgtagac acgcagggag atgatgacgg cgtggccatg  28440
aactcgtagc ggctaggagc tatattggtt ggggaggagc gcccataatc agagccccgg  28500
ggatgtaggc tttgggtgaa cctcgttaac aaatatcgtg tgttcttgtg tcatcatctg  28560
gcatgtcttg ggtgatcaat gactgaagcg atcgggaagg ttagtcgtcg ttccgctata  28620
tcgactaact tttataacaa aaaccacatc tttttagatg ggtgatggcg gcatcctgta  28680
tgtcgtgacc accgtggtgg catcgttttc ggagcgtcat ctatgtggta caaaaaccac  28740
atctttttag atgggtgatg gcggcatcct gtatgtcgtg acaccgtggt ggcatcgttt  28800
tcggagcgtc atctatgtgg tgttaccata agcctagcgg tgttcggcca tacttagcgg  28860
gggtcgttta gtgctaggtt tcaccctcag cagtttgtgc ttgggtgtta gtgcgtggtg  28920
tgtggcaatg caccttggta cattttaatg ttttttctta taacttttac tccttaatat  28980
actcggttag cctccttcgg tccttccggc gaaaaaaaaa actttcatgc cgggcatcat  29040
tttatccatc tgtctatctt ctggtttgtt actcacataa agttagaaaa ttggatctgt  29100
tctttgctac aatttaatta aatatgaatg cctaaaaata tagattccag tattttaagt  29160
gttctgtgca acttcgcagg ttgcttctca gccagtcatg gaatgcttgc cactatggaa  29220
ccagagtcag gtttctgctc tgacccattg aatcctttta tccctccatg ataataagca  29280
tatacttggg taaagttttt tccgtcatag tcaagggtac ttggtgtcag ctcatattca  29340
gccagatcca cacggaagat tgctgactcc aaaatggttc ctttacgtgc aacctgaggt  29400
aatgcttttc ttgggtgagc taaattgttt tcaaacatta cagttactag ataaaaccac  29460
gcgcattgct acaggaattt aaacaataaa aaaataacat gtaagatagg tagataacat  29520
tatattaagt aaattgatat ggtttatgat aatttaaatt taaatagtac gtagaatgat  29580
gattcaaatg taaaaagtaa gatgatatga ttttatggaa gaaaaaaagt agggagataa  29640
tttgaactgt agattaatct tctaagggct aaaaacaatt gatgtgatat gacttaatta  29700
```

-continued

```
aagggaaaaa gaagaaagat aatttagacc atagattaat catttaagca ctacctaagt  29760
gaggatgaac tatataaata tataggatat cataaaatat aacaaagata tacattgaaa  29820
cattatgtga attatgttgg ataataattt aacatgtttg tatatgaaaa gctcctaatt  29880
tataaaacta taaagatata gcatgtttgc atgatgttta aatgtgatga ttattagtgg  29940
atgatgatgt ggcatcttgt taattagtat atgaagatgt gacatcttgt tagtggatga  30000
tgatgtgtca tctttgcatg tttaggttaa ggagtttgtt agaggaaaaa aaggagaaag  30060
ataatttgga ccatagatta atcatttaag cactaagtga ggatgaacta tataagtatg  30120
taggatatca taaaacataa agatatacat tgaaacatta tataaattat gcggaatgat  30180
aatttaacat gcttgtattt taaaagctct taaattataa aaactataaa attataggta  30240
atataacatg tttgcatgat gtttaaatgt gataattagt ggatgatgat gtggcatctt  30300
tgcatgttaa atttaaggag ttagtggggg ataactttat agtaagatac taggttagga  30360
ttacatggtt ttttatttac tttgttatag ggcatgccta gcatcatatc tgtagactgt  30420
agctcatatt cagcggtggg tgaagtgacc gaaaatcttg ggaaaaagta cattgaaggt  30480
ccctcaactt gtcatcgagt tacaaaatcg tcccccaacc acatttattt gatcatttga  30540
tttgatgtcg attcttctcc actttatggt tattctctgc aaaagattag taatcctaat  30600
actagtgaaa agttattatt ctaacttaaa tatgcattgc aagtataact agttttcctc  30660
tattttggta atattaacgg tcgaaactga ttgcgaacga tcgtcaataa ggtcgaacac  30720
ccgagcggtg gagtggccgt tgccggaggt gcgagcggag tcggcaactt gacccaatgg  30780
ctcgtcttgt ggccgccgag cgcttggtag aagctaaagg acttgccgta tacggagcac  30840
ttgaactccg cacctaccgg tgctggcccc gtcgtcgaga gaggaggcgg cgcctggaca  30900
cggtggtggc ccccgcgggc gagcatgagg aggcagagcg cgaggttctc ctccgatcgc  30960
tggcggcgcg acctcttccg cttcacccac ccctgcggca ggtgcccgcc ctcctccccg  31020
cttgtggcgc tgctgcttgt cacgaccgct gcctcctcca tctcgtgctg ctgctcctcc  31080
tccttaagca ccgcggcgtg gagcgcttcc gtctcgccat tcgcgacagg ccgccgccgt  31140
cgcctcctcc tctcctgcct cgcctcgatg gcctccgccc cagctgccgc ccgacttgcc  31200
gagaagagtg agagagagag gaggaagaga gagggtgctg acgtggccac gcggacctac  31260
gtgggtccca cgctgactca gccatcacat aggacgaaac cgggttcgaa accatcaaag  31320
aacataaagt gaatggtttt tgtaagttga gggatggctc tatatctggt tttgtggttg  31380
gatgatgatt ttgtaactca gatgacaagt tgaggtgcct tcggtgtacc ttttccaaaa  31440
tcttgtgcta gtaaatgggc caaaagggta ttcgtaacag gacggcccgg cccatatgca  31500
ggaagaggaa tcgtcttgat gtctcctcag tcctcaacct aaggatacat ttccccgtct  31560
cctcgagacc ttcgactgcg gccccaagcg ccgccgatcc ccatcccatc ccatccatcc  31620
cgccttcgcc gcgccggagg ccgctggtgt tcgtccacct attcccgccg tatcgcatcc  31680
atttctggtg agcgtccaat cctctttctc atctctattt ctctctcaca cgcacatttg  31740
ctcgcgttaa cccttgtttc tctcttctag tagagcattg cctgtggggg acaaaagttt  31800
cttttttgtt taaggtattc ggaatcaaat cagtctccgg ttcgtaaacg gattagcggt  31860
gcgtattccg attcgattcc gattcttaga cggagttttt ttagtttagg ctttatatat  31920
ccagcaaatt ggatgtaggc tttccccagc tcatgttaaa ccttgaggtt gtcgctgtgc  31980
agatacaaaa agagtgaagg gagggagggg cagatccaga tcgagaggaa gcaaatgtca  32040
```

-continued

```
tcagaaataa taatgtcgtc caagaggcta tgcagagagt cagatgacga agacgaacgc  32100
cattgcagca gcagcacgaa cacgaagaag agggcgtgca gagagtcaga ggaggaagac  32160
gaacgccatt gcagcagcaa cagcagtacg aagaagaaga gcctgaagct gggtttggtt  32220
cccttcagct ctcacaacca caaccacaag cagcggcacc tgtacctggt gctggacgac  32280
tgggaggcag gatacagcat ccacaaggtt gtcgacgacg acttcggcgc ccgccctgcc  32340
gccgccgccg ccaagcacaa cccgctcatc cgcatccagg cgcagcacgc ctactcaagg  32400
ttcttcgctg cccacggcac caagatcatt gccatgcatc ccgccagctt cagccctggc  32460
atccctgtgt tcgacacccg gaccctcgag atggcggtgt accctccccc taagagcaga  32520
tccatcatct gtccacccgt gtatgcctcc gtcggcgaca ggctcgtcac attcgtccac  32580
caatatctcg aggtgctggg gccccatcca ccacgctccg ccgccgtcga cgacgacgat  32640
gagccagagc cgccaccgtg gtcctggacc accgtggagc cactcccgca attccactcc  32700
ggcctcgtca ccggctacgc cttgcacccg gatgggcgca ccatcttcat ttccatcgag  32760
gattgcgtta cgtttggcac gcgtaaatcc accttcagct tcgacgcggg gcgcctcgag  32820
tggacccgcg tcggcgactg gatgctgccg ttcgagggcc aagctcacta cgaccgtgag  32880
ctggacgcct gggtcgggat ctgccgctac ggtgaaggaa ccgggcatct ctgttgctgc  32940
gacgtccctc cttcgcccgc cgccgatgct gcttgtacca ccaccttgcc tgcctggaag  33000
ttttgcaagg aggtgatgtt caagaagggc ttcaccgggt actggggggc tacgctcgtg  33060
tacatgggcg acagcaggtt ctgcctggtg gattgccggg tgcctgatga ctgtgacgtc  33120
cgcaccaccc tccgtgtgct caccatcacc tcctttggtc tcaagtatga taaggccggt  33180
gaactggtca ccactcggta ccgtgcttac gcatcgatct cataccagat tgctggcaaa  33240
tttaagagac tcgaggatcc tatagcattc tggatgtaat ttatttatga tcatgcaaaa  33300
ctagttagta gtatcaggtg ttattgtcct actcagtttt attatatata tatgtgagca  33360
tgcaattttg gcataacctg ttttatatat ggtcgccttg tcaatttggt ccatctttgt  33420
cagcactgtg ttttgctgta aactgctttt ccctcttgta gcacaatgct taaaaaactg  33480
ggggaaatga atccctataa ctttacaaag tgagttatgt ctgatgccta atcagtacat  33540
tttgcccaag cttggctttg attgtgtgat gttgctccct ttggtacaca atttatttgc  33600
tgaataagct gggtttttgt acagcatgtt tttgtaccag tgcgtagttt tgtgtttatc  33660
tcataagttt ctgctccgag tacattattg aaattttaga cttgaatcaa aattcgtatt  33720
aatgattttt tttttcttca ctacaaatta tgacgaaatg tcacatcctc aaaattaacc  33780
ctaaaatttt tttgactgca ttatgaagga attttagttg aattttgaaa agcttaggaa  33840
catatataat gacttaacta caattttatt tctttgagtt ttattcttta actaattcta  33900
attttggtac aaatcaatcc aaagctatat cctacactta ttatttgctc agacaccaaa  33960
gtgaactcat tttcttcttc aatataattc ttcctctagg ttatatccat ttaaatttaa  34020
atctatttca aatttcaaac cagagaaaat ttccttgaga ttcctacaat agtagatatc  34080
tctattcttg aacacttgtc attttaacgc ccactattct ctctatttag gccccatttg  34140
gtatggctcc aaactccaac tctcaactct aaacttcaac ttcagtgaga gctagctcct  34200
atagaaactg aagtgggtat gaaagtgttt ggctagattg gttagctcca cgccaccacg  34260
tacctagttg gcatctcatc gaacacctgg ttggcattgc cctaccatcg ccgccgccac  34320
tgccacacgc gcatcgtcct tggttgtcgc cgttgccgac tctgcgcctg cgcccgcgca  34380
ccgccgaccc cgtgcctccc gcacaccacc aaccccgcgc ctcccgcgca ccacctgccg  34440
```

-continued ccgccgccgc ccgtacccct tgtgcgccgc gccgcgcaac ccacccgccg caaccgacgc 34500
ccgtcaccac cgcccgtcgc cgctgccacc agcgattgct gctgtaaagg aggaagatgg 34560
gaaggagaga gaacgggagg agaggggggtg tgaaagggac agtttagtgg catatcgtgt 34620
aaatatatga aaaatttaaa gggtagtggg ccttttgggg tggagtggag ctgtggagca 34680
gcaaaaacct agctctaccc tcatagtaca aacttgtaga gcaactctgc taattccgct 34740
ccaaaaaata gcgaatctac accgtttggc gcagctccag ctctaggtaa gttagagttg 34800
ggagctagag ctgtgccaaa cggggcctta aatccttcaa ttgctggaaa aatttgaagg 34860
ttactgttca tagcacagaa gatgtttgac gaaatgcacc caccaatcca ttttggccca 34920
tcttctagaa accttgtctt tgattctcta taagcccaac ccaaccgaag tatgccccta 34980
gcagccccaa catgacaccg ctgaacaagt gggtgtgcca gcgcggtcgg cttcaccgga 35040
tgtgtttggt ttgtggtcaa aattgaatag aatatgatca tttatatttg tggaaaaatg 35100
gtggcctgtg ttttttttgg ttggatgcat atgatcatct aattatttgt ttggttgcat 35160
gaatgaaaag aaataaaatg aaaagataat atattgagta atgataaaat atgttattta 35220
tcattaatat agctataatc tatactaatt aaaaacaata tagattactt atatctaatc 35280
aacactaatt ttgataagtt gattgtacta attaacaata aaatacatta atgatggata 35340
atcaattact aatgattgag attagcaaat gtggatatac tcatctagga tctttgtgaa 35400
atattccttt ccagaccact ctaacctttg tctaccaacc aaacagacta aaactgaatc 35460
atcatctcct attcgacata tccttccaag caaacacacc gcaagtcaca catgccgtca 35520
tgtggcctcc atgccatgaa atagggaaaa tctctcacat agtctcttat tggggcaacc 35580
acgttaacga gaatccaccc taccatcgca catgtgtcac cctccatgct accgaagcct 35640
agtgctaggg ttcacaatta agtggaatct ggttcggatt tcgcatattc tggatatttg 35700
gatttcagtt ttccggattc aaacttaatt ttaaaatttt tacaaaattt atctagattt 35760
catcgagttt tgttagtttt taatggattt cacgaaatcc aatgagacaa ggaagtataa 35820
agagctaata cacatatatg tccaaattca tagtagtaac atgtctaata tagtgatata 35880
gtattagatt gctatatttt ggtcagaagg actactcctt ccgggttaat aatatttatc 35940
gttttggaca agggcacggt ctccaaaaaa caactttgac cattattttt cattataata 36000
tgtataaaaa tattaataaa tatatgattt tattaaagta ctttttaaga ctaatttata 36060
catgtagtca ccatatttaa aagacaaata ttttaaaaat aattcataat caaagattct 36120
aaagtttgat ctcacccttg tttaaaacaa agtattatga gcccggaggg agtattactt 36180
ttagggtata ttttagggaa attctgtttt gaaacgaatg agtagcggcg catgcttaat 36240
attcacattc tcactattac atcattcggc cccaaaaaag ttattttctc cattccataa 36300
gataagacac agtttcatga tataatgcat gcatgaattc atgccattaa ctaacactta 36360
tttttctcta aattattttt ttaggccttc attctcaatc tctttaattc tattgggtgc 36420
atgtatatga ggtgataata actatttctt ggtatttagg ttgagggtaa ttgagcctta 36480
tattttgaaa cggagaaagt aatatagtat gagacgtgac atattttagt attacgaatt 36540
ttaatgtcaa atttagatta cagtagtcct aaaatatatt atatcttata ctaaattaac 36600
tgttaattgc gaggaagaaa gtatttcata gcctcatagg tgtatttaga ccatccattt 36660
gcaccttcca cttgccggta aactgacacg gtaataatga gagttagggt ttacattatc 36720
ggttgaccac taaatttcga gcttcatcga tatcacggtt ttcgataaat ttcgatcgtt 36780
tttttgataa atttcgacca aatctactgt ttaaccttcg aaattctaat cgaaacttaa 36840
ttccgagcca tgtcgaaaca tcgaaatttc gtggaattcc accggttttt atcggagctg 36900
tgaactgtat tagggtgtgt ttggatggtg gtcaaggatg gatagaatat ggccatccat 36960
attttcaggg atatggccat ccaatttttt gtttggttcg acggatagga tgagccaagt 37020
ttatgtttgg ttggaaggaa aagaggtgga tatggtgagc caattttttg tttggtagga 37080
tggatgggtg ttgtgatcac cttttggatg aaatggtgag aatacctcct tctccttata 37140
gatggcctaa ctatcttttt tttgtctgat tttacaatat aatgtaagca aataagttgt 37200
attaatgtta tagagcagat tttcatcgga caattcaaag acaagcacct gtactacata 37260
tccgatgttg caatgcactc ctctctgtga atgacatttt gtgccatttc tagttatttt 37320
tggaagtttc gttatcagca cctgtttcat ctcatagctt aatcatttta ctggttttca 37380
agttgaatga aaaatcctgc ggaaagttct gatggaactc ttttcaggtt gttgaggtac 37440
tacacaggca gcacagctat acttgtgttt caacaaactg aactgacgaa tctgaatcta 37500
aatccacaaa ccaatgagtt ttgctgttgt gtctctgtgc attgcttggt tgaccatcaa 37560
gaagaacatc aaataccatt tgccgctcct gaactgccgg acaccgccta ccgccgccgc 37620
cactgcaagc cgccgctgaa cgccgcccac cgcctccacc tgtgtgtctg ccgctcccct 37680
gcgcctcctc ccacgaccct gcgcctcctc ccacgcagcc cttcgtgccg gtgcttgaga 37740
ccgttggtgc ctccggctgc gccaccaggg gagacgaagg ggaaatgaag ggagaaaagc 37800
tagggttcag acttgagagc tccagagact cagaccggtg agaaagaaag aaaagaagag 37860
gagaggaaga gaaaacgagg gggaaggagg agcgaatgcc actttttttct ttcacgtgcg 37920
ctcgcccgtc cctggatcgc cccgtccgcc ccattcggct ggatgcatct gtccggtatt 37980
tactgcgaat attccttagg gggtggctat atcccatact agcccagcaa ccaaacacct 38040
aaaaaaatct ggcggccatc tcctatccaa gcaaaaccca ccatccaaac acatcctcaa 38100
tgactagagt tcaacgtgag cttctaaaga aaagagagaa gttcaacgtg agctgctcct 38160
gttcacgggt cccacgcccc cacgtcatca cgcgggcagg ataaaaaaaa ccgacagcga 38220
aagtgcgcga tgacgtcacg acagcgacgc accacgcatg ctcatccccc tacagtcccc 38280
tcggcccact catcccggcc caaataaaaa gcccatccgc cgcctcgctg tacagtaccg 38340
cggggcccac gccccgcact acgcacggat cccgccgcgc gtccgactca gcgcccacgc 38400
cacgtccgca cccaccgcat ctccacccac acccactgac ctatgggccc caccacccca 38460
ccccacccac cgggcaacac ctgtacccgc accgaacagc gtactagtgt actactacta 38520
cttggaccca tcagaccgac acgtgggccc cacagcaacc gcgccgtcca cgtgtcaccc 38580
tacatgcgcg acggaccaat ggaagggcgc cacgtgggag tgtgaaccgt taggcgtaca 38640
cggcggtgtg tacacgaggg ggaggagggg ggtcaccgat tcaccaaacc ctagggcctc 38700
cttttttttt ttttttttcg ctgcttcgct ttttttgctg ctgctgctgc tgctgcttcg 38760
tcgcaccgcc ccggtagcct caccgccggc gaacgcgcag cgcgcgacca ccgttgcttg 38820
gagctagctc gcggggatct gcagatctcg cccatggcgt cctcgtcgga cgagcagccg 38880
aagccgccgg agccgcccgc ggcggcggcg gtggcgggga cggccgtggc caccgccgcc 38940
gcggcggtgc cgacgcacgc cgagtgggcg gcttcgctgc aggcgtacta cgccgccgcg 39000
gggcacccct acgcgtggcc cgcgcaggta ggattccgcg gaattccggg ttggggtggg 39060
gggggggga aggtttggtg gttggttttc gggttctgac tagggtttgg ttttgcttct 39120
ctcggatgca gcatctgatg gcggcggcgg ctgcgggggc gccgtacggc gcgccggtgc 39180

-continued cgttcccgat gtaccacccg ggcgccgccg cggcgtacta cgcgcacgcg tccatggccg 39240
cggtgagacc ctctcgcctc tgctcgtttt gattgccaat tgggcttgga tttgggtctg 39300
aaatcgttgc tcctgcgtag ggtgttcctt acccgacagc tgaagccatg gcggcggcgg 39360
cggcggcggc ggcgggggcg gtgccggaag ggaaggggaa ggggaagggc gccgccgcgt 39420
cgcctgagaa gggaagctcc gcggcgccct ctggggatga tgcatcccgg aggtacagtt 39480
tcgtgtccct gcacttcatc gagtgtattt ttggtctcct ttttttctct tttatgtttg 39540
aatttaagtt ttgagttttg ttgcgtgcgc agtggtgaca gtggcagcga ggagtcgtct 39600
gatactagag atgatgacac tgaccacaag gtaccaaagc aacctggttt gacgcgaagg 39660
gccgtttaaa atttggcttt gctttactgt aataactatg ctgatggcct tgtgtggttg 39720
aaatttgatt tcttcaggat tcgtctgcac ctaagaaaag gaaatctggt aatacatcgg 39780
cagaaggtgg gttgttggaa tgcttaacta tgtgtttttt tggactgagt tgtttttatt 39840
tttgagggga atgtgtggat gattagagac tggtgtttgc caggtgagcc gtctcaagct 39900
acgcttgtgc cctatgctgc tgtcgagtca ccgtatccgt tgaaggggag gtctgcgtcg 39960
aagcttccag tttctgcacc agggcgggcg gcacttccta atgccacacc taatttgaac 40020
atagggatag atctttggag tactccccca gccttagctg tgcccgcagg gcaggggggaa 40080 gcaagtcctg ggttggcact tgctcgacgt gatggtgttg ctcacctggt atgtatggcg 40140
tcatgagaga gattttttac agtgtgtctt agcctatgtg gaatgtctca tgaatgactg 40200
atgacatgag cttttgtctt cttacacata attatcatat ttatggctat atcgttattc 40260
gtctaaatcc accttttggt atattcttac cttttcagga tgagcgtgaa ttgaagaggg 40320
agaggcgcaa acaatctaac agagagtctg ccaggagatc aaggttgcgc aagcaggtat 40380
ttctggaaca ttacattctt atttcctgcg aaatgtcaca ttgagaaata aaccatgcct 40440
ggttttaatt tggtgattct gctcgcatta ttgtagtact agtgaacctg gtaagatctg 40500
ctttgatgac cctacaaaac aagacaagtg gacaacacaa atcatatggc agttatgagc 40560
caatttaggc agaaattgat gtgcacatgt tactttccta ttggtatcac atcggttact 40620
aaacgatatt tcaaatgaag catctttggt tagttgatgt taacatagtt aaaacaaaac 40680
taacttagta atgcggtacc tagctggagt tgtttgtttg aagcgatgct actaaagtcc 40740
atcggtttta tcaaagaccc taccatgttt gtttttattg gttttgcaaa ttacacatca 40800
ccatacgtag agcaacatac tgaagtatga taaactgata ctagaaacaa taactgctgt 40860
ttcatttttc tcatttatac gtgagtcagt agtattgatt tcagtaacat ttagaatttg 40920
ccacatgact cctcacatga tacggacata tggcttatta ggttttgtat cgtttcatta 40980
tgctcagtat tttctagaac cagtttcgac gtactgcctt ctgaattcag taagctgcat 41040
gacgcaaaag aaaaaaaaac atttggttca acattcactt aaaagaatgc ataaaaagtc 41100
gcaaggaaga tcagaaagac atgggatata ttcattgttt aagatcactg tcaaagaaga 41160
gatctaatac atctaatttc agtaggttgg atacctctat gggtctggca gtagatggca 41220
gacctggaaa gaaacactta ttctgcttgg tgctgccata tttctggcag gaggaataga 41280
gtgcatgcta gatgccggga gaggcatttg gtatgatgtc agcacttcac cagatgttgg 41340
cttgtctgca cacgggcaat atgcacaaca agccatgctc caagaaactg acaaacagca 41400
tgctcccagg ccttaacgga tcttgtactt aaaagtctta ggtcccaaat aaaaatgcaa 41460
catctataac atatgattgg tactttcctt ttccaatatg gtccgttagg acttaggagc 41520

-continued

```
tgatgtgaaa taactgacac aaacccttt accaaactga gcatgcaaac accaagtaat  41580
agtattggaa ccggagaata atggacctct agtacagaaa actgtttgct atagaaccaa  41640
attttccttg cctacaatga atttgttgcc agtgctgatg tccaattgaa atggccacgc  41700
tgaaacatat cctttatttc gtaaacatgg ccagctggtg gttgatgctt tgcctctggc  41760
catcttataa aaatcgaagg taccaaatgc ctatctgtag ttgtgagatg gcatttgtta  41820
gttttcttgt caaaaatcaa atatcatcag aacaaaaatt tttcttctgg caaccacacc  41880
agctagttga catttatttt ttagccaacc atgtgagcat atatctcaag ttccattagg  41940
cggcatgaaa agtttatttc gtggtttcct tactttccat ttttttctg atggggtgtg  42000
gatctaacca acggatggct acctgaaatg tatagaagat gcaagaaaaa atgtagatgc  42060
taaaattaca atgtctatga cttgagttta caacatctgg ttttgtaaac aaattgacct  42120
gtccatcttg tcagctactt ggctcttgag ctccctagct tttttattcg gtattttcaa  42180
caggagattt taatgttaga acatttgttt cacgtctgac acatttcaat ctaccactgt  42240
ttatcagcaa gagtgtgagg aactagctcg gaaggttgct gaactgacaa ctgagaacag  42300
tgcccttcgg tcagagcttg atcagcttaa gaaggcctgt gaggatatgg aagcagagaa  42360
tacacgactg atggtgagca catggcactc cacccatact ttgccattag ttgagacagg  42420
aaatgctact tctttccaca ttacccaatt cttatggata attttaaact ttatgaaggg  42480
tgataaggct caatacaagg gaccaactgt gacaaccact ctgggtatga gcatcgactc  42540
atcgaagacg caacaccatg acgacgaggg ccagcttcac aagaacacta ataataacag  42600
caacgggaac tatgtaggtg gcagccacaa accagaggct aactctaggt gagagagaat  42660
catgaggaag tgacgacaaa gatgagatga ggtgttcttc ttatctaacc acaacaccca  42720
tcatcaaacc agtgtgtgtt ctttttttagc aaaaagctgt tgttttagtt cttctcacaa  42780
ctcaccgggg ccctgtagag ctgcccccaa atcgcagcca tatgtattat ttatggctcg  42840
ttgccgagaa gaaatgagtt tgtgttttgt gtttgtgtgg tgtgtgtttt gtaaaccgat  42900
tgatgtagct attgtaacaa acctagcgct tagaattttt atgtttgcta acatttgatg  42960
agggaatgta accggccaat tcggtggcct gatcggtttt atgatgaaat gcgtaacaaa  43020
tagcatttat attttctatg tctggttgct ggcatgatta tggaggatct tatgctcagg  43080
aggtggtcgg attgaatgtc ttgtatcgct ccttaatttt cttgcccaat gtcactctgt  43140
atacatggta tggtaagaac agtgagatac tactattttt caaactgaga cagtgagata  43200
atatcagtgg ctggatgatt ttttgccata tactccatct tgtcgtaaat atttgaccaa  43260
tagtttttca aacttttgaa ctttgactac caattaggga gtaacttcat aaaatcgtaa  43320
atacacccac ctcgttttca cttctgaagt acttagttta aaacatacta tcggtagatt  43380
ggccttgata tatcatatac tacaaacttc atgcatttta tgttcctact tattcacccc  43440
tctcttatat tatactcctg accatgcaac cgccttttgg tgctagctcg ggaagatggg  43500
ggtgcggtgg aggatgagcg gtggcggcgc aataggtatg agagggaagg agggtgatgg  43560
cattaaagct ggcatgaggt gcgaatggcc gggccggcgc ccgtgtgaga agagcaaagg  43620
ggaatgggga caaggggatg ttcggaggtg gaaggatatt ttgtgaaagc acccgaaaat  43680
tattagggtt aattagattc atgccattat aaattcttag ttttgaaata tgccattact  43740
atttatcaat tcgtagtaat gctattacaa cttttcaagt attggaaata taccatgaag  43800
cacccttca aggcatatat caaaattttg agaccaaatt gcccccatct tcttcctttc  43860
tcctctcagc tctcttttgt tcatcttctc tctttcttcc aactcctaga tctgggtctt  43920
```

-continued

```
cccatctcct ctctcccatt tttcagtgaa tctcagccac gatgaacctc gaatcccaat  43980
gaggtggaga tggtcggacc agtaccacag ctcgactcga gctcgaccac agcagcaaga  44040
ggtctcttga ggtgacaact aagggaagcg gaggccgcag cgacggcaac ggccggggag  44100
gcacttgaag gactgcacgc gcgaagatgg cctccacgga gagggaacgg ggtcgcggtt  44160
gtcacgcggg gccaggcgct gcagtagccg gggtacgcgc gtggggttga gatgaagtgc  44220
aggaggacgg agtggctgct gctcgaatca tccacggcca ccgcgccata caggttgttg  44280
tcatcccagc cgtcgtggga aattgggagt ctcaagaaag accatgttgt gtagctcaac  44340
aatgctggga agcgtgggca tgacgacgga tttagaaggg gaggaaagag gaagaagatg  44400
aacagaagaa agctgaggga agaaaggaag aagatgaggg caatttagtc tcaaaatttt  44460
gataaatgca ttgaaagggt gtatagcggc atatttccga tatctggtat agttatgaat  44520
tgatgaataa cagtggcata tttcaaaact agaaaattta taatggcatg gatccaatta  44580
acccaaatta taatgtctag agcgatacct ttagaagcat atttttttc tatcttcatg  44640
ttgtatcttg tgtagacgag gttatctttt tttaagaaaa aaacacatag ggatatcaaa  44700
cgatgcgagg gcctatgcga gatacataca tatacgagtt tcttttcaaa gcagccggcc  44760
acgtgacaat ttctccgagg agccaaaaac aattgcgaaa aatgaaaaaa agaacatagt  44820
ggcaaggggt tttactaaag gaggatatac tctacactct ctgctaatga actatggtac  44880
tccattctta ttttagttca tgatatttat gataatattt tggccgaact tttaaaattt  44940
ggacaatcaa ttatctatta aaacaagttt ataaaatcta atagtttacg gtagcaagat  45000
gatattttta agatgaatct acacatgcca tttatattgt tttaaaatta agcatatgag  45060
aaaaaactga tggttcattt tgacgaaatc ttttctaatc atcgtatatt aaaacaagga  45120
gggaccagta ttttttaatc catttcttag cacttatcct aggtgctaat gatcacaatt  45180
tcgcttcata tgatagcgtc gactacaata aaaacaaaac agattgctca ccatcagatg  45240
ctaaacttgg catggatgat tggatgctaa gcattttagc tttagcatct gacccgtcct  45300
agttctttct ctccctctaa cattcttggc aactcattat ctaaaaaaac attcttggca  45360
actaaataag taaatatgca caattgcaca tcctcttaga gtgagaacta aaattgtggc  45420
cttgtggatt tcacccacta gtatttaaat tctggtgttg caactacaag catgcatggt  45480
caagactttt atatatagag tacgtgcgtg atgtacttta tatagttgaa atgttgatgg  45540
aggttatatt tgttatgatt tttttccttt aattaaaatt tgagtttgat aaaatcattc  45600
agatttttttg atggaaccaa atatatccac atcggtgttt ggaattcatg aaactcggac  45660
cgggttccaa cagaaatgta accttgagca caggtataaa atctggctca aatgcaatta  45720
gcgtaagcta agcatttgag aaattattga tgccgaaagt tttaaaagta ttaaccaaat  45780
ttgtaaacat caaataatat ttatgatgag ggaagggggg agggggtagg gttgtcaacg  45840
agaatgaatg caaggcaacc ccttcctctt cacggcatcc aatcctggta acgcattctg  45900
tctttaggtc aaccaaaatg gcctcgttag atgaaaatgg gggctaccgc taggaaacga  45960
attcttatcc tcgatgggat ttaccctcat gtacattttt ctaccaaatt taataaaaaa  46020
aagttgttcc aaaaactgaa agaaattaac aatgtgtaga gtacagtgac acctatcact  46080
tcaccaaaaa tctaagttta aatttggcct acacattgag aaaaagaaaa caaaatcagg  46140
tattgatagc atcaccacta ttaatacctt aaatttgtct tttttatatc ttaatgtgtg  46200
agttgagttt agacctacga ttttgtggac tggaatatgt ttgttgtata aatgctgtca  46260
```

-continued

```
aactttttga gaagttttca taactatttg gatgattttt aaaaaacaaa gggacattct  46320
ttcaagggat caaaaacagt ttccctactg tcggctctcc ctctcaatgc tagatccgaa  46380
agaaatggtg gaggataaaa aaaaccacta cttcctccat ccacaaaagt taaacatatt  46440
tcacatttga gtttttccaa ataagttgtt cctatttgta gtttttatgc atccaagact  46500
taaatgaaga gataaattaa atgtttgatt agaatctaag gagtcatcta aatactcatt  46560
ggttgcatgc ttgtattcac tcattgattt tgtaacatgc aagatgattt aatatcttct  46620
tggtcatcta gactaatata aaaagtacaa gttcatcaaa cacctgtctt tcctaaccct  46680
tagatctatt catccaatgg cttatatcaa aagttggatc accccagcaa ttagcgatcc  46740
gtgtcctccc gctccacttc gcgtaaaatt agcgtcggtt aacaaaaagg gaaaaagaac  46800
aaagcttttc tccaccccga ctgctcccaa cgagacctcc actacgtctc tcgccgccgt  46860
cgacggcctc caccgtaccg ctgccatttt ctccctcttc accgctcgcc ctaccctttg  46920
tcctgcctcc tcgcgtgctt gcgctgccga catcagaggc cggagagcgt ggggtcgccg  46980
ttggccactt ccccgctctt ccccttcgtc gctgcatcac cgtccaccca tcaccgtgca  47040
ggcggagatc aacctcgccg ccctccctag acctctctcc ggcgaggtgc atggactcat  47100
tgatagggtt ctctattgga tcacctaggt ttagatctag ttgggtggtt ctattttcga  47160
tggatggttg aacaacaata gagattaagg gaaaagggtt tagggatgtg actggttgac  47220
gcgttggatg aggaggaagt cccggccatc gccgttgacg ttgctctgct tgtcgaggat  47280
ggcggcgacg atgtgcttga cggcgacggt ggttgtagta gtgggagtcg tggtcgacga  47340
taaggcgtgg ggcggcggtg gcgcgttccc gtcactggct gcgccccctc tcgatcggat  47400
tagggtttgt ggggtggagt ggtggtggcg atgaaccttg tttcttgtgc cgtcccgtcc  47460
tccacccctc tttatatggc acagtgtgac gggggcccac cagccattgg gctgggcgcc  47520
cccgatcaag gcgcgggtca aggccccctt gagccgttgg gctcaagggg agggagatct  47580
atctaacatt ctccccccttg atctcactat ttcttttagc tttttctatt ccatcacaga  47640
tttacatata cagcatgttt catcatcaca gttaattacc gctggattcg acagccacta  47700
tacacatctc tattcagaaa tagatacttt aacttttggg ccctatagtc caggattcat  47760
aaggcttccc ttaaacccat gcatgctaca tgttccttga acatgttggg aggtaggcct  47820
ttcatgagcg gatccgcgag catcctttct gttcttatgt gctcgagact gattgtttga  47880
tcccagactt tgtctttcac aacatagtac tttatgtcaa tgtgtttggc agcaccactt  47940
ggctgattgt tgtgagagaa cattactgtg ggtttgctat cgcagtataa ctttagtggt  48000
ttctcaatac tgtcaaccac ctttaaaact gggtatgaac ttctttagcc agttcacctg  48060
ccctggatcc tcatagcatg ctataaactc ggcgtacata gtagaccctg tagtgatggt  48120
ctgttttgag cttttccatg aaatagctcc tactgccagg gtaaacacgt atcccgatgt  48180
tgactttata ttatcttttg caaagtcaga atctgaatac cccactgtct ggagcgattc  48240
tgattttctg taagacagca tgaggccttt tgttccttgc aaataacgca agactttctt  48300
ttccaatatc cagtgctctg ggcctggatt actctgaaat ctgccaagta accaggtaac  48360
aaatgccaag tcaggtcgta tgcacacttg agcgtactgt aggcttccta cagctgatgc  48420
atttggcttt gttttcattt cattgagctc atactgattt ctgggacatt gcgatgcccc  48480
atacttttcg cctttcacta taggagcagg tgtagcactg catctgtaca tgttgaattt  48540
cttcaacacc ttttctatat atgcatttga gaaaatccca atgcatactt tgttctatct  48600
cggtgaatct ctatgcccaa aacatatgaa gcctcaccga ggtctttcat gtcaaagttt  48660
```

-continued

```
gaggataaga atttctttgt ttcctgcagt agactgacat cactactagc cagtagaatg  48720
tcatctacat acagaattag gaaaatgaat ctcccattct taactttgaa tcaatacagt  48780
tgtcctcgac attctcttga aaacccaaaa tttctttatt gtcccatcaa acttcaagta  48840
ccattgtctc gaagcgtgtt ctcatccata aatgcatcta ttttgacgac atcccatatt  48900
tttgtttcct ttcatgacaa aacctttcgg ttgtgccatg tgtacttttt tcctccaaat  48960
ctccatttag gaatgtcgtt tttacatcta tctgatgtaa ttccaaatca taatgtgcca  49020
ctagtgccat tataattctg aaggaatctt tacaagagac tggagaaaat gtctcattgt  49080
aatcaatccc ttctctttgc gtgaagcctt ttgccacaag taacgcttta aacttttcta  49140
tattccctct ggagtcatat ttggttttgt agacccattt acagcctact gttttgactc  49200
ctttaggaat ttcttctaaa tcccagacac catttaattt cattgatttc atttcatctt  49260
tcatggcttc caaccattca gatgagcgag cgcttctcat ggcctcttca tatgaggtgg  49320
gatcatcccc catatgtgac tcttctatat tataaacatg atagtcatca cggatagccg  49380
atcttctgac tctttcagac cttataggag cctcctcatt tggcacatta tctatatgag  49440
actgttgcag ttcctcctct ggtgtggcaa taatttctgt tgaatcctgt agaacaggtt  49500
cctcattttc attcattgtt gccacaggag aaataacaac aggtgttggt accgcaacgt  49560
catgcattgc tggcacaaca tcagcaggta gagagaagaa aggttcctaa gtagacggag  49620
tgggtacaga cacccgcctc tcctcaagat caatttctcg aactaccgag ctccccctaa  49680
tcatttcgtc ttccaagaag acggcgtgtt tcgtttctac aaactttgca caactatttg  49740
ggtagtagaa acgataaccc tttgatattt cagaatagcc aataaaatgg cagcttactg  49800
ttttgggatc caatttccca agatttgggt taaatacttt attctttgca agactctccc  49860
acacacggag gatccatagc tcatacggtg ttttgggcac cgatgcattc tatgcattgt  49920
atgcattgtt ctaaaattga gaactccaat ggaggaagaa ttacattctt aaacagtctc  49980
tcaattctcc ccctcgaaat atggcctaaa cgacagtgcc ataatttcga tgagacatca  50040
ggagttcgct ttcttttctt ttgtcaacga ggacacaaca ttcacattct cagaaagaga  50100
taacaaataa agctgatttt gcaatagagc aagaccaaca catgcattat tataccatag  50160
ttcacatttg ccatttccaa aatggcaatc atatctatca aaatccaatt tggatacact  50220
tattaagttt ctttgcaaag aagagacata aaaacatctc gaagtaaaag tattaagcca  50280
ttcgcgagct ctaggcaaag atctccaaca gcttcaactt ttgcttcaac tccattggca  50340
actctaatgg atctttcact tctttgcgta gtcctcattg aacagaatcc ctttaaacaa  50400
ttaaacacat gaatagttgc tccagaatca atccaccatg tggatctaga ataactaatg  50460
ataatgagat tcacttacaa atgcaataat gttctcacct ttctttgcta tgatcactgt  50520
taggaagtca ggacgatctt tcttggaatg tcttgtcttc ttgcagtgga tatactgatc  50580
ctgtctcaat tgtgaactgt tgttcctgag gcagatgctg aggctgtttt gcttttgagg  50640
aggatgacct gtggctcttt tccatgttat ctttaacaag gttaatggag tcaccattgg  50700
tctctttgat tctttcctcc tcttgcacac aattagagat gagctctgat accattgata  50760
gggttctcta ttggatcacc taggtttagg tctagttggg tggttctatt tgcgatggat  50820
ggttgaacaa caatagagat taagggaaaa gggtttaggg atgtgaccgg ttgacgcgtt  50880
ggatgaggag gaagtcccgg ccatcgtcgt tgacattgct ctgcttgtcg aggacggcgg  50940
tgacgatgtg cttgactgtg acggtggtcg tagcagtggg agtcgtggtt gacgatgagg  51000
```

cgtggcgcat tcccgtcact ggctgcgccc cctctcgatc ggattagggt ttgtggggtg 51060
gagtggttgc ggcgatgaac ctcgtttctt gtgccgtccc gtcctccacc cctctttata 51120
tggcacagta tgacgggggc ccactagcca ttgggctggg agcgggtcaa ggccccccttg 51180 agccgttgag ctcaagggga gggagatcta tctaacactc atcgctcatc ccggctctcc 51240
ctgagctgtg gaatcgtcgt cagtccgcca cgcccgacga cttcccggtc accgccacga 51300
gggacctcca tatctagcat ttggaaacag cggttcgttc aatttctact attcggttta 51360
ctccttttct tggttctatt tgattgtgac ttgaacaatc aaccaatgaa gtaaattctt 51420
ttctgtacat acgtgtgaag aatctactat gattgtattg tgccctgcgg ggtgttgatg 51480
aattgccgtt gagggaggga tggtctaaga taatcagttc acacccttta gtttggttgt 51540
tcacttgctt tcaggtgaca taaagctact gacattgtgg cctatttgca tgtcccattt 51600
ttcaggtatt tagaattcac catagatgta aagtatttaa ggggacatca cgaatgtagg 51660
cggtatgctc ttcttccatg gagagatctt caattatcga gctgaagatg cagatggata 51720
tgttcaagat caagggcagc tacttcaata aatcatgcat cttctctctt agcaacttaa 51780
acactaccat atcttagcta aggtaagtac ctgaatcagc taagatttcg aaaaatcata 51840
tatatggcag ttccttcata tttatcatcc cttttttttg tttttgtgga atattgttct 51900
ttgattaccc tgctttcgaa ggaaatgatg tttgctaata ttataatttc atttttaaaa 51960
atggctattg aagaaattaa aaaaaaatgt gtacttatac tactcaattt cttctctggt 52020
ctttaacctt gccaatttgg catgtgtaat ttttttttac aaaatcagtc ttgcatagct 52080
acatctgtgt ctaacgtaag actgactagg aaattattca tgtcttcagg catgttatca 52140
acagtgaata tatattgatg aaacaagttg atctgcagat caaggtgaag gagagggtac 52200
tcttttaatt gaggcaaaaa cattgtttgg ttgttcagtt aggtcccaga tgaatttgag 52260
acgatatcgt ctcttttcag ttcattcttt agtttacatt ctttgagaat tgcactgtga 52320
ataattttgg ttttctatat atgctgcatt acagtttcat gcggtgggat ctgagatgat 52380
atgaatatgc acaacatctt ttgacttgct gactggtaca acttaaattg caattggaat 52440
gaatgaatag tccaaacact attgcctttc tgacaagagt cctcttttgc tcctagattt 52500
tttttcttcc ttggattgga ttgctgccag aatttttttt accttggatg gactcatcac 52560
aaccccaagc tggattctgc atgctgtcct tcataagttg gacaaagtgc tacaatgcgt 52620
gctgtaaact gtgaaaaaat ctcatatttt ctttatgttc tccctatacc tagctgcttg 52680
cttccgtatt ttgtcatgtt tacaaactac tgtctttgta catgatgaaa cacaaattct 52740
tagccatttc catgtattta ttcttaacca cttttgatat tactcatgtt tacaaactgc 52800
tgctatctta acttattatt agaccatgtt ccgtcagcac tattaccacc aaaactccat 52860
agttttagac tggtagcttc aaaatttgcc ttcaaaaact cgattgtttc ttgccgcgac 52920
attgtaaagt tagcacaatc tgtgaaattg ttcatgtcaa ctgacatcct gtttagacga 52980
tagtaatttt gaaatgcgtt tgactataca atctgcatta tatttttgca tcatattggt 53040
gttttcaaat cctatgaatt ctagagctct gtatctagaa cccaggcaat gtgaattcta 53100
gacctctatt cgaaaagttg gcaaaatttg aaatccaact tctcctgtag tttagtacat 53160
actctacaca ttagcaaagt gtgatctaca gctacccatg gaattcacct gcagtcagca 53220
cacatatgcc tataacagtt aacatgagat taattgccat gcttcaaatt attttccttc 53280
aattgaaaat aattgaaatg ttatatgtgt ttatgttctc cttctaatgc tcggcctgca 53340
ccatggttct ctcctttcat tcttttgtac aacagcgtgg ctattgtttg tttgttaaaa 53400
agctcaccat atatttgttg agatgctcta tgaatatttg ctccaaacag ccgttgcttc 53460
accaccaggc acctacaatg gacatcacta ttagggcctc cacaccaata tcatcaacaa 53520
gctcggctaa attgtcttgc tgctgatgtc aacaaagagg tgttgtattt ctacctgttg 53580
tagcttttat cttacattaa catgacatgt tcccatactt ttatgtatgt ttgaacaacc 53640
tttgtaatat tactaatttg agcgcgcatc tattaaatag tgcagaatgc agtccctttt 53700
cctctttctt ttttttccca ttgaagaaat ctgttctctg aaatatgaag tttcaggaaa 53760
cctccaaggt gaaattgtcc aatctccaca tccaacaatt atgcatgaag ttcaaaccac 53820
tgtttttcta gcatcaggat gagaaaaatg attactccca ttcaccaaaa gacgcacaag 53880
cattcattca gtgagtaacc acttttaata gtgaactacc taatgggcac atcaccgacc 53940
ggttagccta acatacttta ttatttgaga cggttttatt acataattcg tagcacaaat 54000
gaacaccatc aactggtcat ggtcttgatg tgtggctggc atcaagtaaa ttggttatca 54060
gttatatcgt gtttggcatt ttggaaaaag ttgataattg atgttattag ttacattctt 54120
cacattcaca ttagttcctc gacattttac atctgtaaga tcctttttgg tgtccttggt 54180
ttttgtctag aaattaaatt gacattgttc ttctgtccat tatgtattct ggacgctttt 54240
aggtggtaga tagctagata ctaaacagaa acacaagaaa ggtatttttta ccaaggaatg 54300
tagaacatgc attaagtata tatgttgcat atgcacttag ccctttttcat ggtggctccc 54360
atcacgtatc ttgctgataa taggtattaa gaacgcattt tttgcaatac cgtagtcaat 54420
atggtagttt tttctccatt ttattttgat ctaaaactca aaactcagtc gtatgaatcc 54480
aaactctcct atgatacttt tccgacttac atttcagtct aacttgtaat gattactgta 54540
attcaaaact aagagatcaa ggcatcgagc tgtcttttgt tcgtgtagat gaaggatgtt 54600
tgatgatttg tattattttc caaggctcat cgtttgtatt tgtattagac tgatgaagac 54660
atgactagct aaatgtgttc tcatcctgaa ccagaaagtt taatgtgttg tgatgatgat 54720
tttgacaagc aagtaaaggc acatataact tgatagattt cttgataact tttgttgctc 54780
cctgtacctg tggtgatcag cctccatgag gaactccaag tatttagctt ttaatgaaca 54840
caaaatgcat ttttttgaaa gtcttttaac tttctttgat acaactgatt gtcactctac 54900
ttagttctac tggttatttg tgagtaacaa ttgatagtgc aatacatgag taaatcaagt 54960
gtacacgtaa atcattcgca acatatattc gcttccatat cataggcatt gtctgatatg 55020
tgcttgagac ataaattatc attagtaaac aagagttgtg cctgtgcttt agcataggca 55080
tattacggtg gttatgtttt gctttggata cttgaaattt atgaaataac ataactcaaa 55140
tgaattttga ttgattatgt tcttcaattt aatccttcaa tatatgtcaa cgtgccttgc 55200
acgtgcacac tcactagtgg cgataaaagt aataggttta acttttgtgg atggagagag 55260
tactactgtc tagactagta ggtaggggtg aaaagagaaa gggtatttcc cgcctgctca 55320
cccgacacta ggctcaaggg aaagaaagac atgtgagaga aaaattgagt ttttcttagg 55380
gtacagacat gggtgcaggg tacagacatg ctactttttt tagggattgc tacttactgt 55440
aaacagtggg caacatgtag tgtagtagtt tccgaaatcc tattacaatg ttactaaaaa 55500
taaataaaat tattttttta agaaatgcgt tataatcttt tcctataggg aatactgacc 55560
ctaacttgat atgtacatgc ttatctattt agatttaatt tttttagtat tacgaagttc 55620
aagggttaaa ctaccaaatt aataatgaga ataagtggta ggcaaattca cttaccccat 55680
cattaccttc ttgcttaaaa aagtatagat tcgtgtcctg ctgctcgact gttgtcccca 55740

-continued

```
ttgtcttcac actggcagat cggtctgagc attgacattg ttgttgaatt gtactccatg  55800
tttcaacagt taaacgacca tgtttcatgt acgagaagga aaatgttttt gtaacttgac  55860
catgttgcac atttaagatt ttggttctat gaatttttgg tgtctcactg aaattcaata  55920
tttatatgtg gaagcaaaat gcttcgagtc aaatggattt gaaagtttcg cttttttttt  55980
tttacttatt tcctgacatt gcactccact tcttaatatt gcttcgcggt gcattttttt  56040
tatgtatttt ctttgaaatg ttttgatgac tttttttccca gaacatataa cctgacggtt  56100
ttggctgatg gtcacctgaa acatcttgtt ttaaccgccc gatgctattc ttgtcaagat  56160
ttaaatgctt gtgtgtgaag tcattcacac gtaactccac catcagtcca tcacacacac  56220
taaaagcacc cgcaatagta aaataaggtg ctctctataa aacatataca tctcaataat  56280
agactcgatt aatagtaaac caccttaata gtatgtctac attggtatct atagctctct  56340
cctgcattgc ctcgtttttc tctatagcct atctctaagt tagtacatag ctttgctctc  56400
tctctcttta tttaatacat tctaagtagg aaaatatgct gacatggatc tcttgtagag  56460
agcctataga taactattgt gggtgcccta atgtatatgg ggttagaaac tgatcatttt  56520
cctcgtaaaa cggagtaatt cgttaatgta tgattaatta agtattaatt tttttaaaa  56580
aagattattt ggcttttaaa aaagcaactt tcatatataa tttttaaaa aaacatatcg  56640
tttagcagtt tgaaaagcgt acgcgcaaaa aatgaaaggg gttggttggg aaaggaagga  56700
aacaaactca ggccttgttt agttccaaac tttttcttca aacttccaac tttttcatca  56760
catcaaaact tttctacaca cataaacttc caacttttcc atcacatcgt tccaatttca  56820
accaaacttc caattttgac gtgaactaaa cacaccctca gtcaaagtaa tatgtaaagt  56880
aatatataga tgtaagtcaa aaataaaaca agaaacacaa tagaatacaa acgcattatg  56940
tagcttaaca tgcaaaggag tagtttttat agctcattaa agacatatta aagcatgatg  57000
ttaaagatta ccgtgccctt tattaacata tataattaat ataatagaga gaacacgagg  57060
aggggcgagg aattattatt ggttcaatcg cttaaaaatg agtagaagaa aaataaaata  57120
ttattaaaga tgtctagcaa atcagatcac aatctcattt tcccatcatg ctcgagcata  57180
ggatgagatt gaagcagcat taggcagatc gatcgagccc atgagtcaat gccacgtctt  57240
gtcttagctt atcctcgtct cactggcttc ttttagtttc tgtccatcag aagcagcagc  57300
aagcggaggc aacaaatttg agggctggag ttaatttggg attgctcctg ttcgaagata  57360
cacctacaag gtttcattct ggcattattt atttctccct ctcttttta atacgttgtt  57420
gacgatttta gatatgaatg aggtgggaca tgcaggatcc agaggtaagc cccctcctat  57480
tcgaagccgg gtggctaagc cattcccatc tcaagtggtg gcccgattcg gtaatttcgg  57540
taagactttt taaaatatat ttgactatta gttttatttg aaaattttat ataattatca  57600
tttattttat tatgatttga tttatcgtca aatgttctag aagcatgact taaacttttt  57660
tttatattca taaaagaatt ttaaacaaga cgaatagtca aacatttgtc aaaaaatcaa  57720
cggtgtcgta tattataaaa cggaggtgga ggtaatacca tgctggagta agatggtgtt  57780
tggatttagg gactaaattt tagttcctgt tacatcggat gtttgtacac taattagaag  57840
tattaaaagt agactaataa taaaattaat tgcataaatg agaactaatt cgtgagacaa  57900
aattctttaa atctaattaa tacataatta gcacatgttt actgtagcat catataggct  57960
aatcatggat taattaggct caatagattc gtctcacgaa ttaatctaag gttatgaaat  58020
gggttttatt attagtctac gtttaatact tctaattagt ttcaaacatc cgatttaaat  58080
ttagtccctg gatctaaaca tggtctaaat atgtacgtac catgatggta tcattttttt  58140
```

-continued

```
cttttggct agaatgggca ttgattgatg atgaccatgc cggcagtagg agggcaagaa  58200
ggtgcccagt gcgactcgct agagttggac gatgcggagt cagaacttag aacttatacc  58260
atatagcata ccataacatc ttttttttat aatggaataa caattcggcc tttgctcaac  58320
gagctacacc aattattaca aaatccacac aaaaacaaat tcagcacaca ctgattgata  58380
taaagaaaac acaaactaaa agacaccaac acaagataaa agaatcctaa attgctgaat  58440
tctattcgat aatctccatc cgaagttgac aagaagttga caaaaaggta catgattgtc  58500
gactcaagtt tacgacatgc atcatttgtt agctcgatat catcattttt aacttaatat  58560
cataacatca tacaacagta aggtgatttt tgtaaatttc agtggacttg cattgtaaaa  58620
aaaagtgatt cacaaggtgt ttgagaaaag ctgtggggtt agctgatccc acggtattgt  58680
acatggctct atcattgacg gtgacgactg catatgttaa ggggaagggg caaaaagcta  58740
gcccaatgta taacataagg caaaaatccc tggtctaagg tgaaaagttg gatatggtcc  58800
tagaccaaaa taaaacttta tggtaattat aaggtgaaat tcagtcgtta aacataattt  58860
ttaagctaaa attatattcg acctatattc catttggaac agaggcagta catgcaatcc  58920
tcaaagtcaa acaacgacat cgacatggat agcaaccaat acggcaacat tatctacatt  58980
gaaaaggacc ctaaaaaaga atctactttt tgaaaaaaat gatccatata ataggttaat  59040
gcttagagat caccatcatg ttccaacatc aaattaaagc ccagctcttt tctgatttag  59100
atataatttt tacgtcggtt ttcgtcgtca cgtttttcta agggataccc aatacatttc  59160
gtgtaataac tttctattaa aaaactattt taaaatatca aataaattta ccttttaaaa  59220
ttataacaat tactccctcc gtttcatatt ataagacttt ctagcattgt ttatattcat  59280
ttattaacat ctatatctat atgaatatga gcaaaatctt ataatatgaa acggaggaat  59340
taaaacttat caatcatgcg ttttcttgtt ttcgtggatc atcatcaacc tcaatagaaa  59400
cgtaaacgta agcgcaccac acggccgaga atgctcgtga gcagcgcctg cgcctggcat  59460
ggacgtgccg ctggtgccag tgccaacgac ggcggccgac gacgacgcgg cggcggggtc  59520
gccgtcgccg tcgccggaga tggagatgga agaagacggc ggcggcggca aggtggtgta  59580
cgtggcggtc agcggcaaca ggaacaaggc gctgccgacg ctgcggtggg cgctgcgtcg  59640
ccacgccccg gcgccggagg ggaggaagaa gaccgcgctg ctggtgctcg tgtatgtgca  59700
ccggccagcc accatgatcc caatcttcag tgaggcttcc cattgtttaa tttctcttgt  59760
tttttttttc tttcaaggaa atggtgatga ttcagtgcat ataagtttcc tgtgtcgtaa  59820
tgagggtttt gaattttgaa acatgggttt ttgccggtgg ggaccgaaag aaccgaaatt  59880
ttgttttttt aaaagaattt taacatattt taactgaatt taaataaatt ttaatcaaat  59940
ttacaaatat ttgataaaaa caagtaattt tggggagatt tttgcttgcc agtgggggcc  60000
gaaattacca aaattttcga accgaaattt caacccatgg tcgtaaaaca ccttgtagaa  60060
aagaaaaaaa acctttcgta aatagcgtac catgaactca ggactttagg gtgctagtca  60120
ggtcacttaa accactagcc tatatagctt ttcgcaaggc gtctttgttg tgatgttggt  60180
gggtggtggc cgaatttgtg gggagaaaaa aaaagagata cttgagatta agatcctccc  60240
aattttgtat tccagcagga gcaaaggtgc cttcaattgt tctcaaggat gaaatagtca  60300
cttcttaccg gcagcaagag aggaggatta ctgaaaaatt tctccaacaa tacctggaca  60360
tctgcacatc tgaaaaggtg gaaaatcaag ctcattatac atatcactga ataaaattcc  60420
ttcttctgtt ggttgttggt gtctctgcaa tctgcatttc cctctagctt ttgtgtacag  60480
```

-continued

```
aatgtctcta gagaaccacc tcaccacctc attttgtcga tattttgcta cagagaatgt  60540
ctctagcaaa ccacctcatt ttgccgatat ttcattacag gttcaagctg aggcattcat  60600
gattgcgaat gacaacattg cgcatggcct catagggcga attcaagagc ataagatcag  60660
cacactcatc atgggagctg gcatatatgg gtatccagcc ctcccaaagt tatttatttt  60720
tatcacttca atttccattt ctaacaaaat tctccgaact gatcggtgct cttgtaacaa  60780
tgtgatgcat tattgcacct tttcttcttg gcaggaaaac aagcacccaa aggacaaagc  60840
tagcaatcac catggagaag gaagctgatc catcttgtaa gattttgttt gtccacaagg  60900
gaaatctatt ctccatcagg tagttgttct ttgaggagca ctcagtattc atggcttctt  60960
ttctttctaa gacaatacaa gaaaaattct ggcatctaca cctgtagata gacataacag  61020
ttacattaca taaatgcgac aatctgccaa atctttatct attatatact ataaaagtcc  61080
attaaacatc ctacaaacgc tcttaagccg ccacgtggta ctcctacaaa tactcctata  61140
acgcctcgtg gcactctaat atattaaaga aattgctata aattgtaaga ataaagtaaa  61200
acatctagcc ttcagttttc atttaattcg gcgggcctgt tattttgatc catcagatca  61260
aatcacatgc taatctccat ggccccaccc ctagcctgta tgtaatccag tttgtgcttc  61320
cgcatcacgt atgcatactc ccgtccgctc cttcacgccc tccaatttcc tttcaattcc  61380
caatttatgt tagttagaaa acataattta taataaaaat taaaaacatc taaatcatag  61440
agataatttt tcatctgctt atgtatcact aatttacatg gtaaaaactc atatttaatt  61500
atattttaac ttgcaaaaaa gaaatttgtt agcgttgggt tgtaacaatt ataagaaaat  61560
atgaaaataa taattgtata gtagtagatt ttagagatta ccatcgtaca tcacctcata  61620
ataattaaat tagatctata attgtaaaaa taaaaatgaa cctagttatg agtgatattc  61680
taaaaaacta ttccctccat tatgaaatta ttacaagtca aaataacatt attgtattta  61740
tcatgaaaac tactttcata tggatgcata cttttcatat ttacactaat acatttttaa  61800
tatgtttcct actctctcca tcccaaaata taagggattt tggatggatg tgacacatcc  61860
tagtactatg aatctgaaca tgatatgtca catccaccta aaataccta tagtttggga  61920
tggagggagt aggaaaaata ccttactttt aatttacgct taattttttt agtcattgtt  61980
ttaaataaac aatttcctat agggatgaat taaatatttt ataatataaa ggtaacaaat  62040
agcttagaaa aattatctaa gcaattctag taaataaaat ttatggagaa atagtatact  62100
tttaaagcgt ggtagatatc ctccggttga tggtccacat ttataagttc tttaaacata  62160
gcctacgacc ctatgctcgc gtatttgggc gggctacctt gttgataaaa tgaatgtata  62220
actagctaca gcaactcaat aattccaacc atgttcatgg ttttttgcct tgtacttttt  62280
aaaatggaaa atgctgtcaa caaccagaga tgcaatgttt tgcaggccca ggactacaag  62340
catccccatc tctgtgaata gtgatgttcc tactatggca ggttctcaca taccttggtt  62400
cagcttcatt cctccttggc accatgatga ccgcagcagc gtcacatctt cttccttcct  62460
caccgactcg caaaccatga ccgacaatgg gcttgatcca gaaaatctag accaccaatt  62520
cttcgaaaat gcgatgccca tgttcgatta tgacagcttc agccttatca gacatgaatc  62580
cctccatggc ctaaatgaga tagctagcca gatcatactg tctggccatt cacagtactt  62640
gcgccagttg aatttcgatg taagctgcaa tgaggaagta agaaaccgcc agttcattca  62700
cggtatcgac tcgatcctcg gagtcgattc gatgaacctt gaggaggtgt actggaaggc  62760
ctacatggag gacaagacaa tcaagtggat ttatctactg gagtacatcc ataagattgt  62820
atcagtctca ctgaagcaaa tccaggagca gcatgatggt gcctctagtg gcctgacact  62880
```

tgaaggcctc tcagatgctg caaccaagcc tatcaatcga ttgctcacat ttgcgtcgac 62940
ggtcagtaag gtgaatggtt cgccggagaa gctcttccat acgttgcaga tgcacaaggc 63000
attgtcagaa gcttctccga tgatccaaca agccctcttg ggagaacaga aagagttctt 63060
cgtcagagag cttcacagaa ttcttgacac gctggaggac tctgcaaggg aaatacttgg 63120
taagctgaaa gtccagattc aatcacatga ttcaccgatc ataccaggag gcagtgtaca 63180
cttggttaca acatacctca tgagatatat cacattgttg gcacataaca ccagctcact 63240
gaacaccatt ctaggtcatg atcatagtga ccatctgttg gcagctgacg gaatcaactt 63300
gctgttgcca agccacctaa tttctggctt gatattcgat cttggctcga tgcttcagaa 63360
gcagtctaag ctgtacaaac ctgaaggatt gcagtacctg ttccttatga acaatgagca 63420
ttttattctt cagcactttg agcgggaaga cataaaactt atgataggaa ctgagtggat 63480
tcaaaagtac tgtcataaca tcaaccgata caaagtgaaa tatatagaag caacatgggc 63540
tactgtggta tcttgtttgg acaagaagat cagcatttca ctaaattttc tgcaaccttc 63600
acccttgaaa gaatttattt cctctttcga aacagagtat agactccaga tgcactggaa 63660
ggtccctgat ccaaagctcc gtattgagct gagacaaact gtctgtgact atgttctgcc 63720
agcctattgt gaattcatgg agaagcatcc aaatttagag aaatcagggg acaatcttga 63780
agatatcagg aacaaattaa atgaactgtt tgaaggatga gttgatactt ttatgattac 63840
aaaaacaaat tcttacttgt tctcttgttc cttcaattca tgcaaggaaa attgtaacac 63900
atactaattc aatgattgtt aaattaactt ttcattatgc aacattactt gccagtaatt 63960
gcgtattttg atgcgtaagt tgagttgaca gtaatgttgg ataaaatcat aaaatacttt 64020
tttatttcac attatgtcaa agtgtaatgt ttggagtacg cacacatctc tgcaccaact 64080
agggattagc taatcgccaa ctcaacttac caaaaggttt aagccaaaaa tggcatggca 64140
cagaaaaaac atgagtgaag aggtaactgc ttcagaagca aaagtagcga agcaaagaaa 64200
tgtcaaatgt tgttttctag atgattctga tgcagaggct tcttaaatca cttgcatttt 64260
ggggggaaaa aacagggaaa gaacatagta aaatatttcg ccatcctgaa cacgaataca 64320
agagtacaca agaggaaagt gcattaccag aaatttcaca ctggttctga ttgtacaaat 64380
aatcaaaaac tgttgtagtg agcattaaca ggggtttgat tctggttcta tatataatct 64440
aacttttgca gcaagcagtc tacccttcga ataactccat cagcttattc tcaatttcct 64500
gggggatata cttatggagc ttcataccct tcttctgcaa gtgtgcctga taacattgga 64560
cgacatggga tgaaacagct ttcctcacat tgttccgaag tttcggatcc tcaattctcc 64620
agttctgttg ctctgcacaa gtgctctcca gcatctcgta aaacctagtc gtcaggggta 64680
gatgaaagca agggaacagt gcttgcgtcg gtgtatgagc atccaagcaa gacatgacgg 64740
gtagccatga gagctcaagg tatcttgtga tctggtgctt gacctggttc tcgtacctga 64800
gaatccaatc ctgctgcagt gcagacttca cctctagctt gcgaagccgg ttcaatatga 64860
aatgggcatt gttcagcaag gaaatgcatt ccagccccat catcgattca tgcctcgcca 64920
tcctctcgag caaggcgtcg aggcgtccga tgaagtgctg cacaaaggaa tccacctgcg 64980
tccattcctc accgttctcg ctctccccat cagcttgata agcaataata ttgttgatca 65040
cgctgtcatg ttcccacaaa aacttgacgt agttcatcac gtacagagtg atcttgtgaa 65100
cgccacctct ctgcgctaca tggtacaggc cactttgagt ttgagatagt gaacataccc 65160
gtcgcaagat cttccttaca cacttcctga gctctttggt gatgccgttt agctggtcga 65220

```
tcgggaaagt cccgagcgtc gcgtacagac gcagtatgac aggcaacaga tcaggcgagg  65280
ttggcagcat ggtaatcacg acagctagct tcagcaggcg acgcatttca gatgctcctc  65340
gagcttggcc gtgctcgcgg ttgatttctt gaatgcttcg atcaatcaat gccaccaatt  65400
ctttcccaaa cagttggagc atctgcaagt ctgccctctg aatccaggtg ccgatatctg  65460
ttggatcgtg tgcatcttca gggatgtcct ccagaagttg tatttagtgg gagacattac  65520
cgggttcatc agagaagctg tggctatcgt acgaagagga ttctgtggtt gcaaagcgaa  65580
tagacaaatc tgttgaagat gtgaaacttg gcatccttgt tccagataga aaaatatcaa  65640
agattcagaa aggaggaata ctatcaacgt atgaagtggc aagaaacaat tctgatgaac  65700
tattatatga tgagaggagt tgttgggaaa acgagtgagg actcatgaaa ggaagtttcc  65760
tgcagctaat caaggtcatc tctgttctgt tttttttttc tttttcacta ttaaagaaat  65820
gatggaattt tctgcagcga gtcaaggtgg atgctttttc cttgcactgg agtacacatc  65880
tcttccccct agccttcaag attagaaaaa tggctaccca cggaagtttt tttttttag  65940
aacaactacc cacacaagtt gacatgggct aaaagattca acaaccatag cataaatttg  66000
tgtaggaaca ctcactcaaa atttgaagaa aaatgcgcat cgcttcccac tgatccagtc  66060
aaaatgaatc cccttttctt ccagagaagg gatttttttt ttttctatat agataagggt  66120
acattaccaa acgggctaag acccaagttg ttgtcgcttt tgcaatattg ctcatccaga  66180
tgagatgatc cacaaccata tggagcagat ccccttcgcc tccagttgcg caagacctag  66240
ccgcaactac ctccagatcg gctcggccaa gaaattcttg gatccacata cctgcgcaac  66300
agtggattgg aactcgaaat tagtcccaac tgaaatgggg aattcctttc tctctctcat  66360
caaaagaaaa agagagcaaa agaatctggg aaatcgagag agcaaaccct catccccatg  66420
attccgtctg gatttggcaa ccgcagtttg gagcaagttc aatagtatag ctttggttat  66480
tagagtggtt acagtaccag gctataaact agctataaac atattttaaa aagataaata  66540
aagagagaag agcagtgact ctaagatgta atctgtgtat aacaggcggg actaggtatt  66600
aatagtatag taagcaacta ttgtatgaat tggctataga taatttggag ctagtagtgg  66660
gttgcaccat taagggcctg tttggcacag ctccagctcc agctccaccc cttctggagc  66720
tggagctcag ccaaatagtt tcagctccac cagaactggg agtagagttg ggtggagctc  66780
tctcacaaaa tatactacag ttgtggagct gggtttaggc agctccacaa ctccactcca  66840
gactcaactc ctggagttat atttaggagt tagagctgta ccaaacaggc cctaagtttg  66900
ctcttacctt acaggaagtc tgacattaaa tgaaagagtg cgaatgaatg attatgattt  66960
aaagttgttt ttggtggtga gtgggaaatc attttcctat ccaattagcc aaacaccacc  67020
tatttctctc gtataaattt aatttaaatg ttttagagca agtgtattag ttaattttta  67080
catgagtgtc aacaatcctt actttttttt atttcttttt tcacgtaagt ttacagttgg  67140
tgagtctatt attatccttg cttaatgcca cgtgagtgtt gtccatgatc tcgaacacag  67200
gagcggcgac gctgggcttc tagcaagcga aggtgagcat ggtgccgagc aggaggtaag  67260
tggcgaggat aaagggtaaa tagcatattt agcacttatt tgaaccgcta ttatgaaatt  67320
gctataaaaa tataattgta tatttgaatt ggatactaaa cagttggaaa ccataataca  67380
tgccacttac aacttagact aacaccatta gagcaaggtt aatacttaat agtgtatagc  67440
caactggtgg ctctaattat tttgatgtta ttttacagtt gattctagag ctaactacta  67500
ctctcttcgg gctgataata ttagttgttt tggataaggt ttggataagg gtaaagtcaa  67560
actttaaaat ctttgactac aaataatttc taaaatattt atcttaaaaa tataaaaatc  67620
```

-continued

```
acatgtgtag attagtctta aaaagtactt caataaaatc atatatttgt tgaaatttct  67680
atatatttta taatagaaaa tagttgtcaa agttacattt ttgaagaccg tgcccttgtc  67740
caaaacaaca agtattatca acccgaaggg agtagtccaa taagttggct attgtggtgg  67800
ctacacttca tttattaaat aattaattat atatgcacac atcactatgt aggatgagac  67860
aaactttttc ttcaaccttc caatttttcc atcacatcaa aactttccga cacatacaaa  67920
ctttcaactt tttcatcaca tcgttccaat ttcaatcaaa ttttcaactt tggcgtgaac  67980
taaacacacc agaagtgaac tcaggctatg ttcttccgcc acctctccca actacatctt  68040
ttgtttttca cgcacacgct ttccaaacta ctaaatggtg cgtattttgt aaaagagttc  68100
tatagaaagt tgctttaaaa ttatattaat atatttttca agtttatttt agctaatact  68160
taagctgtgt ttagatccaa aggtataaag ttttggcgtg tcacatcaga tatacggaca  68220
cacgtcttaa gtattaaacg tagactaaaa acaaaataaa ttacagaatc cacatgtaaa  68280
cagcgagacg aatttattaa gcctaattaa tttgtcatta gtaaatgctt aatgtagcac  68340
catattgtca gatcatggag caattaggtt taaaagattc gtctcgcaat tttacacgcc  68400
aatgtaatta gttatttttt ccatttatat ttaatactcc atacatgcat caaatattcg  68460
atgtgacaag atgaaaaatt ttgccaggag atctaaacag ggccttaata aattactaac  68520
ctccgctcta ttttgtgtgt tgggagcgag ggttcctgtc tgttactagc aaacgaaagg  68580
aggacctccg tagatggcag aattcacaac gcgaaatatc atgcggaacc aaaacatcga  68640
tcgaatatta caactcgtac agtattccgc gaggaagagt ttataatata cacaaagcaa  68700
attgttttga ctcaagtact caacacttca atccagtttc atcaaattca aacgcagcga  68760
cctagaaatt tacctactga tccccttcct tatactacct cttttaaaaa tatatgacgc  68820
ccttaatttt tcattcattt tatttgaaaa aattaatata aatataatat tttttacttc  68880
ttttaccatc aaataaaata taatcttaat ttatactttt acatatttat attaaatttt  68940
taataaaatg aatagtcaaa atgtttaaaa aggagtatat aataacttga taagtgtggc  69000
ccgcctatcg gtccatcttc cttttctatt ttcttcctcc tccactttaa tggtggtgtt  69060
tttctcctga agataaggat gaagatgaag atgaagatga atgtttttta cacaaaacga  69120
gatgttatta atgtatgatt gattgagttt taattattat aaacttaaaa aatagattaa  69180
tatgatattt tagagtaact tatatatata aagtttccac acgaaacaca tcgtttaaca  69240
gtttgaaaag ctttgccacg aaaattttta tcttcataca actcttgttg gagaagagaa  69300
atgaatggga ccattttctc tctgtctccc cttctcctgc acggctgcat gactagttgg  69360
tggcgccatg aatcggggcc ggtagcggac gatccagctc acaacggccg gcgacagtgc  69420
aaatcgggcg ttggcggtgg gcgacctcac gaggactagc gcggcatgaa tcaatccttt  69480
ggcaatgagc tcgagacagc cggaggcggc gtaaaacaag gctccgggag gcgcgaatgg  69540
agccggtggt ggacgagcga gtgacaacgc catgggcgcg aatcggggct cgcgcggcgt  69600
agcggacgaa ctcgcgacgg ctgccagcgc gacgcaattc ggggtccggc gtctgcgtga  69660
atcaagccgg tggaggagga acttagcgat aggtttgcgt tggatcgaca agcttgcggc  69720
gaccgccggc ggaggaggaa ctagcgacag gcctacagtg gatgagctct gaggccggca  69780
gcagcgcgaa ttggtgcggc agcgaatgag ctcgggggt cggtgatgcc aaacgagctc  69840
gcgacagacg agcttggggg ttgccggcgg tggcagatga gctcacaacg gtgaggacag  69900
ttcaccagcc tgcgtgaatt cctatgatcg acggattggg aggagtcgtt ggtcttccca  69960
```

-continued

```
acatgtggag atcgagaatg acggagttgg gatttccaat tttttgatat tgattggagg  70020
tttgttggat ccattttttt tttctataaa actccaaaaa gttttaggat tgggagtagt  70080
attgggcatt tcttgtgcat gctctaagcc catacaaccc aataaatagt actccctcca  70140
tttactcttg atagtcatat ttccaaatct gaaaatttta tttttgatag gcatatttca  70200
attcaacaac ctatcctctt aatgactttc ttggatttaa tgcgtgactc tctattcttc  70260
cacacatgat tggctatatg ggcactgaga aatgtaaata ttaatgaatc gcttgtttac  70320
gaggaatgag tagtaccata tttaaatgga tgataagtag aattacttat tcttggtctg  70380
tgtgctaaga tgaaaatatg actatcaaaa atagatggag ggagtatcat ataaaaataa  70440
tgcctcggcc ttttaaccac tgctatcaat ttttgatagg ggacaaaacc caacaagtta  70500
caagtggtat gaagttgcac gctctaacaa gtagtatcat cctccatctt tgatccactc  70560
gactctgaat ctcccgcttc accatatgta acagcttgcc ctccaaaatc acacagtcca  70620
gtctatatat cttatgaatg gacccacttg cacataccac cccacttaca ctttcgtaat  70680
tacttcgtgt aaaagggtta acctaaagta ttataattag agggacaagc cgttataaat  70740
taattccact cttgctcaac actagcaagg tgttactaat caagtactca tatcactggt  70800
ggagaaatgc tctttactcc cggtttaaaa cctttgtagt cccggttttc caaccgggac  70860
tacgaatccg agactagaga tcgctatctt tagtcccggt tcaaataacc gggactaaag  70920
attgatcttt agtcccggtt ggtaacacca accgggagta atggggaagc gacagttcct  70980
caagatcttt ttttattatt ttattgttgc taatagctag tgttaatcca tgtattttct  71040
ctcgaatcga atgggatgca catcccaaat attaagttac ttatacacac agatcctaca  71100
cacagatcaa atacatcaca aatcctaaaa aactacacac aaattaaata catcacagat  71160
tatacaagat tatacatctc agatccatgc gatgcaatga atcacaaaat ctaaaaagtt  71220
atacatccag tgaaacacaa attataaaaa aaaagaaagg aaagcaaacg agccggcgcc  71280
ttgccgcctg cccgcgcgcg gccgcgccgc cgcccgcctc cacgcgcgcg ccgcctgcct  71340
ccccgcccgc ggtcgagctg tggccgcccg ccgcagtgcg ccgctgcctc cccccgtgcg  71400
gccgcgccgc cgtcgcccgc cgccggccgg ctgatggaag agggagtaga ggggaggagg  71460
aggaagggcc ggctgatggg agggaggaga ggggaggagg agaggaagag gaggagggga  71520
ggaggaaggg attggatctg agaagagaaa gagaggggat gttctaatct tatctaaata  71580
tctatctggg acttaaccga tcagatgtgg gagagaaata tttactcctg gttgataact  71640
ccaaccggga ctaaagatcc cggttggtag tatcaatcgg gactaaagat cctcggcccg  71700
ctgacataca tctgacaggg gatgaaccgg gactaaatat catctttagt cccaggacta  71760
aagatcaaaa attttttaac cgggactaaa aatcagtttt agtcccggtt tttaatggaa  71820
ccgggactat tgtggaattt gatcgaccga ccaaatatgg tttctccacc agtgtatact  71880
acactgtaat taggactaat caactacaca tataccacac tctgattagg actaatcaag  71940
tacacatata ccacattcaa attaggctgg gatgtcatac aacccaccct tctaacccta  72000
gagaattcta cgtccccgtc aatctaacca cacaagcata taagcaaatt tccagaaaca  72060
cgcgtcctct tagtgcacgt ctatatgtgc agtggcactt atgggtcatg tagaccacat  72120
cttaattaat agggtcagga cgtgacatgc ataccagtcc cgctcctccc tcaaaggacc  72180
caacgtccac attggtccaa cttacacaaa ataaccaaat aggtatatag accaactttc  72240
atgaaatagc tgtgagggtc gactctgata tcaccctctg gtaccatttg taatagccag  72300
ccctccaaaa ctacgtgtcc caactatctg ataggagggt ccagttacac atactgttat  72360
```

aagttgatta tactctactt ataatttcat tctcacatca tgtaaaagga tcaatccgaa 72420
agtgatatga ttgaaaggac aaactcttat aagttgatta tactcttatt caactatagt 72480
aaggtgataa taaataatca agtgtacaca acactcatta cacaaatcgc atactaattg 72540
gacaaggata tcacaccatc cttaagtggc gtagccagga attttttctt aggtagtcct 72600
agtttacaag ttcacatcac atactaaaat tttataatac tataaatacg atatatatat 72660
ataggacact catatggggc atcatggtgc ccgggcacca tggtttcaaa tacacaaaat 72720
cacttaaatt tttcaaaatt ttcaaattgt gagtatatac ctagttataa gaattcgatt 72780
catacctata cctatcaaca aaacaactca aatttaactt tatttcacaa tccatgatta 72840
catacctaac taattatatg tatggatgct atatacctag aatcaaaatc taacaaaaac 72900
aagttcaaat tcagttcaaa cttgctttca actagttagt aaagtagtta atattaatac 72960
ctaaataatt gaaaaagttt catgctcatt tgaattgggt atatactcaa tttcaacaat 73020
ggtgcccggg caccatggag caccaaacaa atttactata tatatatata tatatatata 73080
taagtacaaa attagtgaaa atgcaataga aatgtaataa taatatcata tagcataaag 73140
aacatgcttc tcagttccaa taaattttaa tagaaagctc acctgttttt aggcctccaa 73200
ctctatcctc ttccctcata tatcatcaat aaaagtatca atttagaact caaatcttct 73260
caagtccgag ctttaaatgt cattgggata aaagttggca actaatcaca aatcgatttt 73320
tgaagccatt atctacaaag gcaaagaact agtcagctag aggaaagaga gtagaagcaa 73380
gcaagcagtt gttcattacc tgcagactgc gggaggccat tccatatttt cgttcaatcg 73440
gagtcgaagc gaaggctgga ggctgtgagg atgccgacct acggtagcag gcgaccgccg 73500
agcgccgaag cgggaggccg gctggtcact tggccgggag caccagagcg gagacggtgg 73560
gtcggtgccg ccgcggcggc acgaggaatc agcgtccccc gtccagcagt acggcgccac 73620
gaagagtggc gcagcgcagc gcggtgcgga gggcggaccc acggcggcat ggcgcacggg 73680
cctcgccttg gcggcgactc agcggcggca cgtggcttgg gcgtcgggcg aatccgaagg 73740
gagacaggga gtagtagctg ctcgtcctct caactcaacc ctagttgttt ggttccctta 73800
gagcaagttc aatagtatag cccactggta gcttcaattc atgtatagcc aatctaatag 73860
ccaattcata caatagtagt ttactatact attaatatat ggtcccactt gtcatacaca 73920
cattgcgtct tggagtctgt gctgcagctg gctataaatc tgtagcctgc tactcttctc 73980
ttatcgtcta tctcattaaa atatgtttat agctggctaa tagcttacta ttgtacctgc 74040
tcttagcctt gggttgttga tatttgtttg ggccattgga tttcgttatt tgggtctgat 74100
tttttaatgg ggtagggggt ctctgcctct ctgggttaaa atcgggggta gtcccgcgcc 74160
caccaggact accccctggct acgcccctgc catccttctc catttgcagt catcacgtcc 74220
cacccatgac ttaaccactc cctttctcca tgccctagcc tcccacttgc attccccacc 74280
atccttgcct ccctcttaag ggtgcaatcg tttcagtgat ggcggtggac agtttagccg 74340
cacacaaaac acgagaaatg tgattagcat atgattaatt aagtattaat atatatattt 74400
ttttatgaat aaatttgttg gattttttta acaacttttt atagaaagtt tccatacaaa 74460
atatactgtt tagcagtttg aaaaatgtgc taacgaaaag cgaggagaat ctaaccctat 74520
aagctgaaaa gagcgcaccc taagtcctct gaagtagaac ttcacttccg tagcacacag 74580
ctcgaaactt gagtagtcac taggatcatt agagcttgtg tggcctctca caaatcaaaa 74640
ggtcagcgtc tgtcaggttt tatcctaatt ctcatataat ccagatttgt tgtactagga 74700

-continued

```
tacgatatcc agttctagat ttttttatg cgaaggaatg agatatatat atagtagcaa  74760
acccatgctt ttaatatgca tcatatccaa cgttgagaaa tggcgaatcc acccaaagta  74820
gtgaaaatga agcgcatgca tattctatca tggtagcagc tgaaacgaga aaagaatatg  74880
tattcattat gcgttgtcaa aagccacagg taatttccta ctgatacctt gatcgatcga  74940
tcgatgaata ttctgcgagc gacgccgccg ccgtctagct catgatctgc acgcggccgg  75000
ccggctccgg aatcaacgga tgcatcctat acaaatctcc gccatgtgcc cggccatcca  75060
cacacaaatt aagtcagacg ccagcaacta ccgatagcta gctgagctcc cgctcccgct  75120
cccagccaga tcaagttgac cagcgacggc ggcggcggtg gcggcggcgg ctgatgagat  75180
ggccggagaa ggaggagcag aggaggagaa ggtgtacgtg gcggtcggag gcgagccgga  75240
gaggtgcttg ccgacgctga ggtgggcgct gagctacacg ccggccggga gcacgctcgt  75300
cctcctctac gtccaccgcc ccgacgccat gatccccatc ttcagtgagc gatccaccga  75360
tttatatata tccatctgac atttccgtc gtcccgctct ttcatgatcc aaatcttttc  75420
cgtcatcccg tgattcacgc tacgaaacta gcatattagg atgtgtttta ttcaactaaa  75480
actctttata ttttaggaca gagaaaatat cttttagttt gctttagcca catcttaatt  75540
tacatcctga atttgccacg gctcccgaca ttttctttag ccccatctta acttacatct  75600
gaattcgcca cggttcccaa catacgggtc ctttcctttt ttttcgagat actcccttta  75660
tccacaaaag ttacacctat ttcacatttg aggttttcca aataagttgt tcctatttgt  75720
agtttttatg cattcaaaac ttaaatgaag agataaatta aatattttta ttagaaccca  75780
ataagtcatc taaatactta ttggttgcat gcttgcattc actccttaat tttgtaatat  75840
tcaatataat ttaatttctc cttggtctta gtattaaaag taatatatgt aacttttatg  75900
gatgaaggga gtaatagatc tcgcttcatt aatttcatca cataatgaaa gtgtatattt  75960
taaaagttag tgaacattag cgttaagtct agcgcatata tgaattaatc ctactagtct  76020
agtgggctga gagtgaagac cacagtacct atatctagat atgtgtagcc atggcaagct  76080
ctccctcgta cgtgaaagtt tcttcgttta aggtcataat atgttttgag ttaaagttaa  76140
actgctttaa gtttaactaa gtttatagat aaatataata atatttatat taccaaatta  76200
tttttattaa attaataatt aaatatattt ttataatgaa tttattttgg atcggaaata  76260
ttactatttt ttttctataa acttgatcaa acttaaagca gtttgatttt aactatttta  76320
tagtctaaaa cagagggagt agtaattaag actaattatt tttttctcca atgcactcag  76380
agtttaatga gagtactttt cgaaagtaaa atagatcaaa acaaggactt tacaaccaac  76440
tccatatcat atgtacacag tttaatgagg ttggctacat ctcccatact cgcgacaata  76500
gctctatatc gattcgtcaa atgacgatat atatatatat atatatatag agagagagag  76560
agagagagag agagagagag agagagacac acttgccgtt gggggcagag gtaagcttag  76620
atcagttagg gtttgaactc taagcctagc tacctccaaa atcatgattt aattttagta  76680
ttatctcaaa ataaggcagc aacaaatgta actataaatat gaatacactg taattgctat  76740
ataattacgg tgtaattaag atgtaatttt agttttagtt caaaacctgc tgattgctca  76800
cttggttaaa gcgtgatgtt atcgaccagt tagtcagtcc ccccagcccc accccctgat  76860
ttctctagct acacaactag cacatggacc gaaaattgaa atatatatat atataaacgt  76920
cgacaaattt atagcctttc tgttatttat ttttgttaaa tcaccatgta cgtttcttac  76980
aaatctaaca tctcattagt taagacctat cttagcccta gtctttattt ctctagacaa  77040
ctagcacaaa tcttaacaca aaatcaatag accagaaatg aaaacatacc aagagaaaaa  77100
```

ttgttgatag atttatagcc tttccgttat tatttgttaa atcaccatgc atataagttt 77160
catagaaatc taacatctca ttagttgaga cctatcttag ccttagtctt tagcaatttg 77220
tggcttcgct agcgccgcca tgcatgtttt catttactaa ctcatgacga tcacagttat 77280
atattcaagc taaatattat agttagagga aaattgaccg tttctatagt tgaaaatata 77340
tgtctcgcat caaaatttga ctattgcagt tgaaaatacg tcgtcgcatc atgtatagaa 77400
gcacccttat ataaattcgt ctcttttact atgcatacgg tatcatcttc tttcggtgct 77460
atatgtatat atgcagctgg agcaagggta cctgtgtgtg ttcttaagga tgaagtcatc 77520
aacgttcaca ggcagaagga gaggagcatt gtccaggaga ggctaagaat attcactgcc 77580
gaatgcgagt ctaaacaggt acttatgtaa gggtgtgttt ggttcagggt catacatgga 77640
tgaattttaa gcctgaccaa acacaccata agtgcattat caagcacagc gtaaaaattt 77700
tttaagcctg accaaacaca ccataagtgc attatcaagc acagcgtttt tatggtacaa 77760
cttattttta gcctaacact tattaatggc aaaaaaaata atttataagt aaaattttat 77820
atttatatat gttcttaatg atttaatctg aaaaataaac tatgataaaa aaataaaata 77880
ccaagttttg agtgcgatat gtgcgcacgc gcctctagag atggattcca acggacgatt 77940
ataggctgta tatttttcga cgtgtgatgt attcatacca aacatttgac attataaacc 78000
aagtcatgct tttcatttcc aggttcatac tgaggttatc atagctgaga acgacagcat 78060
aggacttggc attgtgaagt taattgaaga acataagatc ggcacactca tcatgggagc 78120
tggatattat gggtacgtat catcttaatt atgtaatata ctactgtgtc tcaaaaacag 78180
tttttgcaaa cggatcaaaa cgatttttcc agacgaagct ccacctcacc tgtacatgaa 78240
gacctgcaaa attagatgac ttttacatac ggacattagc cccgcctatg agaattattt 78300
ttgcaggcgg acttctacat attcgcaggc gctacattca cccacctgcg aaaaccacct 78360
caccgaataa aataaaaacc cctgccacca ccctgacccc tcaccgccct tcccgccggt 78420
ccctcctcct ccggccagat ctagaaggag gaagggaagg gagcgccgcc tccgccgctg 78480
ccggccagct ccctcctctg gccagatctg ggagggaggg agggagggga ggaagcgctg 78540
cttacaccct gccgccagca ctcctcctcc gtccaccgcc gatgttggcc ggctcccctc 78600
ctccagccgg atctgggagg gaggaaggga ggggagcgct gccggctctc ctcctagtcg 78660
ccacgcacct ccacgtcact agtggctgcc gcctctgccc ttcgccggag gagtgaggga 78720
gtgaaggggg aggggagggg atctgggggg gaggaatgag ggagtcaagg ggaaaggagg 78780
ggaaggtgag ggatagagat aaggggtggg tggcgtgggt ggtggatatt actaagtcga 78840
ttggtgtggc aagcgaagac ctaaggtgcc gcttgcgaaa atcgattttc gcaggcgtca 78900
tgcaaaaata atccttattt tttttatttt tacaggcaga cctcttaagg ctatgcatgt 78960
gaaaattaat tttcgcagac gggactagat ttatgatatt ttgagctttt tttttttgta 79020
aacggtgatt ttataatccg cctgaaaaaa taaaattgta acgttgggaa aaaccatttt 79080
ttctagtaga gagatcatca attttcttat gatatatcat aatatactac agaattaaca 79140
cgggaaattc agtggtgtac cactaatgag acaagaaatt tatgcgtagt tagtttaatt 79200
tagtcaaaaa gttatgaatg ttgattttct ttccctaaaa actgcatgcc ttatatttta 79260
ttttagggct gttttgtgtc tgtaattctt gttcactata cattattcaa tataagcacg 79320
tgatcgatat gcatgttttc ccccaaatca accatagtga gataataatt tagaaaaatt 79380
aataaccaat taaatatcat ctaatttagc atgtatacgt gtcttaggag acgaaaaaaa 79440
aacaagattt cgtctgtcta ttggctaggc acaatgtggt acgaaataaa ctataagtgc 79500
aatgcgtgca ggcactacta cgagaaagat tttcgcgtgc ggtcaaaacc ggttttcgcg 79560
agcaggtggg tggccctcac gcacctaggg gtctgcaaaa attgcggatg gcgcacccgc 79620
acgcagaaat tggtgcttat gttgcccgca cggaaaaaca acaattcgaa gaaaagaaat 79680
aaaagttcaa aaaaaatgaa aaccctaaaa tcggcggcag cgctgccgct cccggctatc 79740
gccacctcct cctcctcctc gttggccgag gacatcgctc ctgccctcgt cgtcgtcgtc 79800
ggccgaggac gctgctcccg ccctcatcgg cgacctccac gctgcccgcc gccggatctg 79860
cgctcctctc tggccgcacc gccgccgacg cccctcccct ccgccagatc tagggaggga 79920
aggaagggga ggggagggga tcaggatccc tcgcgggggg agggcggctg tccgctagat 79980
cagtgcaggg acggccgccg ccacctaatc cgtgcgggag ttggtcaccg cacaccggat 80040
cccgtgcctc caccgccgca gcgtggagga ggccgttgtg cgcgtggaag aggccgctgc 80100
gtgccgccgg cgcctacgcc cgccgctgcc atcgggagga gaggagagga gagaggagtg 80160
agaagaggag aggcaccgcg cgaagagaga ggagtgagga gaaaaagaga tagagagaag 80220
tgaggagaaa aagagataga gaggagagga gaggagagaa agaggggaaa atttaaagtg 80280
ggtaagaggg aaaagagtaa gggtattttt gcatgcggcc ctcttaatag gttcgcacgc 80340
aaaaataagc ctattttctc atatacgacc agttatggtc cgtctgcaat ataaatgggt 80400
ccatgtatag gaaaatcgtt ttttagtagt gaggcattca tgttttttttg gagtttacaa 80460
acaaattaaa tggatccact tgaaccaact atttttagat gactcgcgaa gttcatattg 80520
atatagaaga aaaaaattac aagattataa ccttgagagg ttgtaaccag gaaaaacaaa 80580
agaaaacatg cacgccgcca gcgagagctg gcagctcctc gcaccacacc ctggagaaga 80640
cactagaacc aagtcgaccg ctgtgaagcg tgatcaattg ccactaggcc aaccaggagg 80700
ttacaaatgc tccgccaaac actgactcaa catatagaag gacgtcaaaa agctctcggt 80760
tatcctcaca tagaaggatt gaggagagtg agagggcgag agagaaggag atccactcgt 80820
ccctcgctcc aacctgatga agacaatcaa gaactgccag cgaccaaact gagagaacac 80880
agcgaaggta aggaacaaga cctcctagac aatgtctcca ggaaggccat ggtgtcttag 80940
acgtcaccat tacccgtccc attggactca gttttcacct ggagggtctg ctaagggtga 81000
aatggtggcc gctcgacaaa gccccaaagg gggaacgtgg tgcttgaaaa tgtcgccgtt 81060
gccagcttgg gaagttccga aataggtttt tacctgtaaa cctccacacc acacctgcta 81120
ccgccacccc cgagcaccgc cacttgcaca acctccgcca actcaaactc aaccgcacca 81180
gcaccccacc gccagccagc cctgccacgg tctcccgcac gtccatgcca cctcctgcag 81240
ctccctagct cccttgctga tggcgcagct gaccaccgca tgctacctcc tgctgtcaac 81300
gcgaaacggt cactgcagcc aaacacgtcc gcctctcgcg gtcacaggct gcgacggcct 81360
ccctgccatc gcccgggctg catctcgcat tcgcaggcca cgacggcgtc cctgttgttg 81420
cccacgctgg cctctgccgc catcagatgc gccagtctgg ccgccgaccg cgtcgtgcag 81480
ccgttgcttg tgccatcctc cttctccatc atcagccacg tcttgcagcc ccatccgccg 81540
gccacgacaa tgctctcctc gtgccagcct gagccttcaa agccgccctc tcccgatcta 81600
gtccgggggg gggggggaa ggggggcaga tccacctcca gggaggggtg gatccgccgc 81660
accaactact ccgaccacca gtccccgcac tcgacacgtg ccgctccgcc tctcgcgccg 81720
aggaggactt tccttggggt tgttttcccc gctttgaacc ttccctgcta gctagccgct 81780
cagtttctag tggcggtgag gtggcgagga agggtgaggg tgatggcgag gattttgcaa 81840
cccctcccca ccacctcccc cgggcatctg tgcaagaacg acgcaggaag aatatatgaa 81900
ttaccattag ccaatttcta catatcctca aacaatactt gggcaatttc aacatttgtc 81960
tacaatatta agtaccacat atttgtctgg catgtgcgga cttaaactca tatgtcatag 82020
atatatatat acatgtatat atacttatat aggctttcaa attctgaaat ggcaccatca 82080
gtgtaaagtt acctaatgag gcagcacagt attcctgata attaagcttg gatgtttcat 82140
gagcaggccg aaatcaagca caggtgagtt caaggtgagg acaaagcttg cgactattgt 82200
ggaggaacaa gctcatccat catgtaagat cttgtttgtg cacggtggaa aggagctgtc 82260
cacaaggtac gtataaattt gttaatttcc tataaatttt tcaatccgac aaaaatcata 82320
ttttctaaca ttaaaatcag taccagatca acacgtcaga aatatatccc tctattttat 82380
ataataaatc actttgacat tttatatagt caaacttctt aagttctacc aaatttatag 82440
aaaaatctaa taatattttc aacacaaaac aagcatattg tcaaatagat taattcaatg 82500
ttatatttaa ttcaactagt tttaatgtcg taaatgttac tatatttttc tataaatttg 82560
atcaaatgta aagaagtcta agtagtaaaa aaaacaaaga aacttataat attataatat 82620
aaaatggatg aataatgaat aatatacagg tctttctagg attttcgctg atatttatta 82680
tagttggtaa cgcgctttac gatgatacat ttaaattaga tgattgtctc catccataag 82740
accttgtcgg ttaatcctta tgcgagaggg atatagtata tatagaattt attccacacg 82800
tattgtagta tagaattatt ccccctcaat cgcctccaat acttttcaat cccctttaaa 82860
ctaaacaagc cctgaatggg aaatactttt aatcatcatc aggaggaccg ggtgactgat 82920
aaatagcaaa attatatgta tataactgta aatttgcaga ccaagactaa tcaacatcag 82980
ggcggcgagg aacgagaacg gcgagattcc tcgtgcagca tggcgtctgg atgatgagga 83040
agtggaagaa gagtgcagat gcagcgcatt atcttcttcc tcctcgagca ccgccagcta 83100
tggtgctctc aagctcgaga agctagacaa tcccgtcata gagaagttgg agtcgtcgtc 83160
gccgtcctcc gctgaccatg gcagcttgtt aaccctcatg gcccctgcct cgctcgtcgc 83220
cctaaacgag atggtgaacg agatgatcct cgccggcatg tcgccggagc tgcggcgggc 83280
tccgttcggc gccggctgcg acgacgacgg ccaggtgagg aggtcgttgc acgccatcat 83340
cggcatcgac gccgcgctgg ggctggaatg gaggaacctc gaggaggtgc actggagggg 83400
atacatggag tacaagacca ccaggtggct ccacacgctg gagtacgtcc gctgcgtcgc 83460
cgccgtcatg caccgcggtg gccaggcccg cgcccgggcg ctctcggcgg cggcggagaa 83520
gcccgtcgag acgctgctcg agttcgccac ggccgtcagc agggtgagcg gctcgccgga 83580
gaagctcttc cacatgctgc acatgcacaa ggctctcgcg cacgcggcgc cgctcctcct 83640
cgccgccttc atcggggacg ccaaggagcg gttcgccggc gagctcgagc gaaccctagc 83700
gtcgctgggc gtcgccgtgc gcgggatact cagcaagacg aaggccctga tccactcgta 83760
cggtggctcg cctggacaga acgtcgtcgt cgtcgtcgtc gtccccgacg gcggcggcat 83820
acacgtggtc accagctacc tcgcgaggta cgtcgagctg ctggctcagc acgccgcctc 83880
gcttaacgtc attctggccg gcgacgtcga cgtcgacgac gacgacggta gccagagcca 83940
gatgatgtca ccgctcggcc gcctcgtcgc cggcgtgatc ggcagcctcg gcgtgatgct 84000
ccggagaacg gcggagctgt acgaaacaga aggaggtgaa ggtctccggc acctcttcct 84060
gctgaacaac gagcacgcca tcctccaagc catcgagacg acgacgctgc tacccctagc 84120
agccgagtgg acgcaggcgt accgccatgg gatcgagcag cacaagcagg ggtacataca 84180

-continued aacatgggcc gccgtggcta cttcctgtct accacgagat gatcctcctc ctcctccgac 84240
gtcggcgaag aaagccggct tcctacgccg ccgccgtcgc tcgccgccgt tgagagaatt 84300
cgcggcgtct ctggaggaga ccagcgttga gcagatgcag tggaaggcgg ccagtccgca 84360
tctccgcgac gagctgcgaa gagccgtcaa ggagtgcgtc gcgcaggcct actccgagtt 84420
catggacaag catcctacct ccaatgctgg cgaggagttc gctaccgtcg atgatttgat 84480
tctacgctgc cagatagatc aaatccttga agggtgatga tgatcgtacg tcgtcagtat 84540
attatatatt aattgcagca gatatgatgt aatttaggac tccttccgtt tcatatacat 84600
tcgtttgacc cttttttttt tatcaaacgt tgttaagttt gtccaaattt ataaaaaatg 84660
tttaagaaca cgtaaaatat caaattagtt ttactaaatc taacactaaa tatattttga 84720
taatatgttt gttttaggtt gaaaatatta ttatattttt ttataaactt ggtcaaattt 84780
aaaaacttag gaaaaaaatc aaacgacata taatatgaaa cagaaacaga gtactagcaa 84840
gccttttctg atcatcgtgt gtattggtta gtgtgttttt tgttcgagtt agaactgtta 84900
aaacaaaggg ttgcccattt gtcgattttg ttttcctcca tcgatcattt ttttaacact 84960
atgtcaacaa tcaatcaaca acttatactt ttttccttct tatatatttt tgttaagggt 85020
atggataata catacctcat atccttggcg ttatgaagta tacaaatacg atatatcctc 85080
aaatatatgg gaaggttacc ttcatattaa ggaattaggc caatgcataa ggaagcagac 85140
tccccgaata tctcatatgc ataaggttct ctctaagttc tacctgtaag ccaaggcagt 85200
ttgaggtata aatacaagac cccccccgg acaccccaa ggaggtacgg gatcatcaaa 85260
atcatagcat agccaccacc catagcagaa gcaatccaga ggactcgaag ctaactcgtc 85320
ggtttgatct cgccgagtcg ttctcgacag gggtctagtc ggtaactcgc tagttctgtt 85380
gttctctact ataatctcta tggttctcat cataatccca tataaactcg attacatcta 85440
ttacctttac aagggacttg aaagagtata atccttatct tctatgtgtt tgatgtcgct 85500
tcgtgtagat tcttgtttcc aacttaccct aataccctct ggatacggtc tatgggtatc 85560
acccatcgac agtgacgtgc cgggtaggga tacttgatgc tcaaggtttc gttgagatgg 85620
cttcaagctc aaggccttcc aacaaaaatg cctacaatcg ttttggcttg ggagatccta 85680
cccagccgac gtttgcatgg actcgagttg gatccatcat ctttcccata ttcaccgcaa 85740
ttccaacctc gccttcccta atgctagctg gggttgagat tgccaccgca aggatgatgg 85800
aaaacaaccc tcagccagct gctcctcgca ttgagtcaaa aaagagggcg tcaatgactt 85860
caactcccta gagaactcct aaagtggcca aacccaagac atctcttagg gccccttga 85920 ttcaaaaaaa attcatagga attttagggc ccctttgatt cgcaggatag gaaaaacaca 85980
ggaatagaaa aaacacagga ataggaagta gtatgattct tcaatcccgc aggaatcaaa 86040
aacataggaa aaaatgaaag gtgccctttg atagtgctat aggaaaaata caagatttct 86100
cttccggttt gaatttgaac agatagccgt tggcgttcaa agcaagtact agccgttgca 86160
tgtccttata tatattgctg tagctgcaac tggacatcaa caaaactagc tcacctcacc 86220
ttcgattgta tcggccaagc atgacaagag ctcaaacgtg gcaattcatt tggtaagtca 86280
taaatgattt tttttctttt tggtatgtat gtaaggatta gcaacttatt tgcttgcttc 86340
tgctctccta tatatattgg tagaccaaac catcagattt attatttgtt gttgatttcc 86400
cctgtgattg tcatggatcc aagttatcga cgacggtcac agaatgaaga tgagttcatg 86460
ctttttgttc tccctaccat cgaaggagat tcgtcacaac catcatctag taggaaaccg 86520
atgcacacat caaaactttc aggggcttgt cgtgttaatg aaatcttaac aggtcatcag 86580
agcctaagca aaaggaattt tcgcatggaa gttaatgttt ttcgagcttt agtcgataag 86640
ttgcgtgaga aacaactact tgctgatgca agagatgtct cagtagaaga acaagttgct 86700
atattcttgt atgcactagc aaaaaatgca agtaatgaga ccttgcaaga tcagtttcaa 86760
cacagcgggc aaacaataag caagtatttt ggggttgtgc ttgatgcagt tacacaactt 86820
acatgtgtat atatacggcc acctttccta cacccccatc atatcttgag aagaccaaaa 86880
tttcacccct tttttgaggt atgaacagat tcatgttttg attttttttt actttgagtt 86940
aaaccaatca ttgtacataa aaagacttaa tcaaggttat atttgtattt gtatagaatt 87000
gtgttggctc tattgacggg acacatgtac caatgatact tccactagac cagcaagaac 87060
cataccggaa tagaaagcaa acaatttctc agaatgttat ggtagcttgc gacttcgatc 87120
tgaaatttgt acatgtacat gccggctggg agggatcagc ttcagacgca agagttcttc 87180
aagatgcact aaaccatggt tttgaagtac ctcctggtaa atttttttctt gtagatgctg 87240 gttatgcaaa tacaacacag tttctagcac cgtatcgtgg gacaagatat catttaaagg 87300
aacagggcag agctaatcaa aagccacaaa attataagga gttattcaat cttcggcatg 87360
cacaactcag aaaccatata gagagagcaa ttggtgtatt aaaaatgaga tttcctatac 87420
taaagaccgg ctcacaccac ccaactcgta aacaagttga tatttcggtt gcctgttgtg 87480
ttctacacaa cttcatacgc ctgcataatg gagatatggt gtggccaagt aattgtcgtt 87540
tggagattga tccagatcat attgttgatg tgccaaatgg agacgagaac tataatggtg 87600
atgtacaaga atttaacaac tctagagaag ctgggaatag aaaacgagat gacatggcac 87660
aacggatgtg gaaccattac gtagcacgaa ggaaataata tattgcattt gaccaccatg 87720
gcattcaagg tcaattacta gtcttgtact ccaagtttgt cacattctac ttaatgaagt 87780
aactacttgc atgcactccc tctaagcaaa agtacatcct actactatct gcttcacaaa 87840 agtacccccct ttgtttcaca aaagtactat ccttctattt gcatgccatc tatttcacaa 87900
aagtactatc ctactacttg catgccatat gttacacaaa agtactcact ctaatgctgc 87960
gatttccttt ctaatccaag ccaggcgtaa tgcatcactt gaaaaggaca agaaaacttc 88020
cctattatcc ttacctttga agatatcagc tgccaccaat atatctccta tttgtagacc 88080
atgtaaacct tcaagcactg tgatacactt gttgatgctg taaggatcct ccaatttctt 88140
ctcctcaatt gcagcaaatc gatctatttc ttcttttta agttttaggt atctctcatg 88200
aaatccatca tcaggactaa cagatttgat cttttgtttc ttcccaggtc gagattcagg 88260
aacctctgaa ggtgtttgtg ccgagctagg tgggactttt gtgagatgga caggggtagg 88320
tgaatgctat gaaaagtcca aattggctgt ctcaacctct tcaccaaaag gaaattgcaa 88380
acctgattca cctggagcat ttgaattagg ggatggtgac tgatatgtat caaccgcatt 88440
tgcttcttgt gttgaatgag ctggtgcatt ctttgtcttc cttgcataat ggtccatacc 88500
atggcgagtt ctcccttcag cataacgacc tgcacaatta tattctcctc acgatcagca 88560
taacttgcct aaaacatttc aacaaaacaa acaaaccact gataaaaaaa atataaagct 88620
caccatcata aagtggagct aaatcatcaa aatatgggaa cgacttatct cgccaatgaa 88680
ttgcatcttt gttcttgcga tcagcaaaag tgtcccaaac actttgtggt gcactcacca 88740
tcattctgtc actatcccac ccaaaaccac tttgatccaa caaatcttta acactgcgat 88800
aatctttctt caaatcctgc tccttttgct tgacttggtt ggtcgtaaat gatgtaccga 88860
attttgtatt caggcggcaa acaatatttg tccatgcttc cttactccaa gcattttgtg 88920

-continued

```
ttcgaaaacc tggcacgtca tgatctgtta ggagctcaat aaggaacatc ttcatctggt  88980
gactccatct ggctctcttt gtcgtcccta aatttgacaa acatttaaca atttcaattt  89040
cagcagtaat atgaaacaaa aaaggtttga tgcaaacaac aagtgaaact gaatttgcaa  89100
atattaccta tttcttgacg ctctgcagtc ccatgctcac tgtcaacatc aacataaacc  89160
tgtgatagag gttgctgggc tcgtcgatcg gacaaattgc gttgatttgt catggtcatc  89220
tgagaagagc ctttcgatgg cattgctttc ctaactccca aaaaaaaaga aagaaaaaag  89280
aaatacacaa tccttatcag agagggattt acacctacag tgccaatgaa acaaactagt  89340
tccaagtagt cagcttaaaa attcactaat ccatagatcc aaagtacaga agcactaata  89400
agtcaataat aagtcaagta tgaaagctca aaagtgcaga caaataccaa atcgatggcc  89460
ctggctgctg ccctcgatgg cggacctgcc gcacgcctcc gcctagcgga gcccaacctg  89520
cgcgccagat ggatgctgtg cttggttgct gcgtgctgct agttgttggg ccggcgtccc  89580
cagcggaagc cacatacgcg actgagccgg cgagccttgc ctccgccttg cacccccagc  89640
ggccggctca agctgctgtc tatctctatc acagttggct ttcttggctg ctaatatgtg  89700
gtcctcggtg ttctcgttcc catctttctc tctctctctc ttttctggaa gaagcgcgaa  89760
gggccacggt ttaccgccaa acacacaaaa gtggcgccaa cgacgacgtg cgcacgcgtg  89820
ggcgcgccct tctttcgcgc caggaaagtt tccaaagagg tcagacctct ttcttatttt  89880
cctgtgaaaa tgaactaaag gaatgcaatc ctaaggaatg tttcctttca tttcctatga  89940
atcaaagaca tacataggaa aaaatccata ggattgtaaa tcctacaaaa gtcctatgcc  90000
aatcctttga atcaaaggag cccttagagg atttcattcc tatagaaatt tttcctatat  90060
agccctttga atcaaaggaa tggatcctat gaaattccta tggaatgact cttcccatgc  90120
aagttttaga ggaaatttaa tatgaggtag aacctcatgg aaagaatcct ttgagtcttt  90180
atctctcctc aaattcctgt atttttcctg tggcccaatc aaacagtcat tcctatgttt  90240
ttcctgtgtt ttgcaatcct ctgttttaca cttgcattcc tgtcagaatc ctatgttttt  90300
cctattcctc cgttttttca ttcctatgat tcaaatgggc ccttaagggt caggtgccaa  90360
taaggaaatc tccgccaaac caccacacct ggtgttcgaa tcacaagaca tcccatcact  90420
ctttggtcga atgtcgggtg atacttcaca tgaagattga actcgatgct tgcaaagatc  90480
aagctatcca gcgcacatct ccacacaagg catggtgccc aaccacaaat cgaaaagtca  90540
ccccccttact ggctgcaaga tcttcttgga gattgccgga tctaagatcc gcgccccctg  90600
ctgtctgatg caccaccacc gagatcaacc tcgagacata tgtgtggatg atagcaagat  90660
gggaactcca gatcgcctgg tcggattcat cgacatcgat cctcgtgaac cctctgtcct  90720
tcacagcttg gatgatcagg aatcttcagg atccaattcc ccgcacgaag tgaatgtgat  90780
cgaaggcatc gtcgaggaag tacacgaaga gggcgagatt cgtccacgag aagaaccccg  90840
agctcctatt ccaccacatc cacgctaaaa agaaatttaa gaagcatgga tcccacacgt  90900
ttgccataat tttattttgt cttcctcttt ttttgaggga catttctttt atttttgaaa  90960
acattttttt attgttcacc aaattttcat ttaaacaaaa ctcataagga ctgaggtaaa  91020
tttgcatgaa caaggtaaat gagaatttag caatatacgc accgtgcacc ttgagaggtg  91080
atatgtttct cctttcaatg ttagcaattg atttttttcc cggccctaac ctacctccag  91140
tgtgacttga acttaaggac tcacccgtca atttgaaaaa attcctgcat gggttagtcc  91200
ataaaggata tacatccgaa gtccatgaaa gtacctgctc tacagttcat taatctaact  91260
tgataccatg tcaaatttga ttaaagcagg ctatttaacc taagcatcat gcttaattta  91320
```

aaaagcctat gaatgcctac agcacaccca aaccagagca tacgaaaata gacaaaggaa 91380
acataaccat atatgatcaa gtcaaactca actggagata agtatgagta aaagaatggt 91440
gaaccccttt ttctatcagc aagataggac taacaccaac tttaaaccaa gatggccttg 91500
gttgatgtaa cttgtcatga caagcacgtt gaccaccccc ctccccacac acacacacac 91560
acacttggac tttcgtgtcg caagacatca aaaaccaatt gtgtgatgtt ggagtctcct 91620
ataaggtgtg ttccaacacc aaggatcacc taattgttta gttgatgtag ctattgtgtt 91680
cttaggcatc atatgaccct cgttgttaat ctcaacctga aatggttaac gatcaagaat 91740
acctgaagat gcatactatt ctaaaaaaat ggttcatgct tttattggaa tggaacttac 91800
catgataatc cgggttatct cccggtaatg ctttgtttat ggtctcaagg tcgaccatgg 91860
ggacatcgtt atgcaagatt agtgccacaa acaaatacaa gatttgcaat atttatgatg 91920
aatataagca tccacaacca cacttctaaa catgctagaa attagggccg taaggtggat 91980
gtggtcctcg cacaaggaag cgacattaac cagacatgac tcaggggatt ctttaagtga 92040
gcatgaatcc tttggaactt tgagagaaaa actttcatgc tcatttgtgg aattctcatc 92100
cttcagagtt gatgtctcaa gcttgtccat agcctgcaag ttctctttct caagagatgc 92160
atcgtgcaag aatggggttg tttcttgatg actaaaaatt ttctgagggc cagagaaaca 92220
aggtttttgc ttgattggag gttgtgatgg tggttcggcg gagggcaatt taagggtctc 92280
gccagaatct tcattttgaa tgaaataatg agcgtcctgt tctagaagag attcagggga 92340
ctcgtgagac agagccacca tcacttcctt tattggtgca tcgtagaatt tcaaggagct 92400
ttgatggttg ctagatgaat tatcctcaaa ttggaaaggg gacttcggag gctgaatttc 92460
ttctcccttt gatgttcctg gttcgggtga gggctctaga gttgaatcta cgggttcatg 92520
gagattgcca taatgtcgtt aaactcctaa gcaagattta tgggtggcga ataatcacaa 92580
agctggcaat tatgtattat aattctttct tgtaaatatt ccttctttaa ttttaaacga 92640
aaaacccatt cttcctatcg atgcattggt cacacttcta catataaaaa aaatgtcatt 92700
gaaactcatt gcacttatag ctcaatttta tgcatgatca agtagtctaa gactttttac 92760
tggcacttga agaaataagg ataggtgcaa atattactta accatggtta gtacagataa 92820
acttatttct ccctccctcc gctgcctatc caagcatacg cccccgccac caatgttgat 92880
gatttaatta caatgctgca accgtgcagt gcctactgat gcaaataaag taggatcaga 92940
atgaagcatc ctaatatgtg ccgatgttga ccaaaactgc atgttgcgtg agttcattct 93000
tttgttcaac aattagggct attcctatat caacatatgc tactgaactt tctactgcag 93060
gcgcagggaa aaataatttc agtcgagatg tcttcagtaa cgtcgatata aataacttct 93120
agaaaaataa actgaataat aggagccagg gaggctccta ttatcgcttt gtggtagggt 93180
actttgttca attaggataa gaaaccaagt tgcttgtttt gtttgtctag aatccaacgg 93240
gcattatcgc ttcaaatgcg tagagagagt aaaattggag ttaagatttc tcaaaactaa 93300
catacaaaca gatccaataa cctatcaaga aacaaatttt gactaactaa tactctgtga 93360
tgcaaaacgg ttaaactaaa tattttttag tttcatttgc cgtttgatca atctgaaaaa 93420
ttatcctttc taatagtatt tctatctaat tacagtaccg atttagtgca cataacttag 93480
caagataaaa gtgtatatat tattgcagcc cttagaaaag cgcattatgt aatctgctga 93540
aatcctttcc atgaacaaat aatttttaat tcagtcataa atgaagatag tgatccactc 93600
tccatgaaca gattattagt gtaattaagc attggtggct tgagctgtat atgcatctgt 93660

-continued

```
gagtcagatt tgctcctagg atcattcctg taaattaaga ctagctaact acaatggatt  93720
tacatgagtc tttaattgtc tggtccctct gaagttgtgg ctggaatttt tcttttggtg  93780
tatttggttg tgattcatga aatatttaga tataattcat catctgttgt gcaagcatta  93840
gagaatcatt tacttgagta gaaagtaaac agatctacat tctacaaact attttaattt  93900
gctaatactt gcagtgatct acgctcattt gtctcaaact tgattttgtc aattgtgatt  93960
atagctaatc tctcttataa cgaattcagg gcacgttcac ggccggacaa ccccgccacg  94020
tggcatcgcg caattgatgg aattggctct cacccgcatc cgttggataa gaaaacaacg  94080
gtatagacga aggaacaatg gacctaactg taattttaga tttcccaggg ggttaaacag  94140
aaaaattggc atcactcttc cttgcaagtc gcgattcgtc tccagcgccg gccaccgcca  94200
ctccgcatca gtgccggacc tcgccgattc atccagtgcc gccaaaccct atcccacagc  94260
gccgccctca ctttaccgcc tcctccgtcc gtctgcctcc ttccttgccg atgcgctcga  94320
cccggcaggc cagcggttgc ggttgagctt ggcagcttcc gtggggctcg gtggtatcgt  94380
atggatctgg tggtggaggt gttgcagttt atttgaagcc accgcctgtg gcatgacggc  94440
actaaacatg cttataacat acaacagatc tggatattag gagtatctgt tggaatttga  94500
aagtctacaa gaagaagaaa ttcgcattga tggatcaaaa cattccaata acgataataa  94560
gaaggaatcc ttctgaggta caagtatatc gatcttagtc gttgtagtct agctgtactt  94620
atgtagctgc ttagctagct ctagttcaat ctgccgttct gacaggtagc taattgccag  94680
attatggagt atgatatcct tatttaggta aacatattgt ggtatgatat ggagaattat  94740
gccgcttatg ctttgctgat tagtgattag agccaagttt tagctgtcga cttgtataat  94800
ttcgaacccc ctttgctcct tggctcttaa atctttgcat ttcaaaccaa ccgaagcttg  94860
tagtcttagc aatctactaa tgtctatttt acagatctaa gtattttaat ataagtatga  94920
atgagtctaa aactatgatg tgctatgtaa tattgcagaa ctcttgggct agaacttatt  94980
attacctatc tatataacta atttatttat ttatttaaaa ttgacaagtc aaagatatta  95040
ttcgataata ggttccttgg taataagtag tgattccctt gatatatcta ggtacctata  95100
catactacaa caagattatg attatgtcag agtgtgtaga ctaaatccca aagagacgct  95160
tctatttacc ttaatcctat tttagaacga agttatatga tgttcatata aagtcaaaat  95220
ttgattgcag agtaatgtaa caaaatctta gcttttgttc taaataattt tgttggaagt  95280
tacagcggca aggcatgata ctaaaatcga tctgtcagct tgacataatt acataagatt  95340
tcgtgtgcta tatgcatgta tggagtccag gagttgtcta taaatgatgt gctaatatgc  95400
cttgattttg cataaccccc cagtttctat ctttgtttct atgaatattt actatcataa  95460
aaatggtagg tgtcttaact atgtgagctc ttgctttcag tgctttatag taaacacata  95520
atgttcattt aaatgtttgg gtatcaataa cctttattta acttccagct gttattatta  95580
cagcaaaatg atgaagaaaa cactgaacat ttttggttca agcaaagggt ataacagctc  95640
cattaatgtg catggagaaa agaaacagtt cacttcatat atctgttcaa gagtactttt  95700
ggtgtatata tataatagct ccattatata tgtatggaca aaaaaaacca ctggtccagt  95760
aactagaccc ataagtatgt ctgtgtaatt cagatggagc tctatcaaaa gctctgaagg  95820
tatgaactac tgtcctattt ccaaatatga gcagcaatat tcgctaaatt gataaatttt  95880
cacattaacc tttctatttg tcaattggtc cataccatca tggagcacca tggtttcaag  95940
ataccgaaaa gttgaaatag gattgcctgg atcaaaatct gaatattcat aaattgataa  96000
ttccaagttc agtgaagttc tctgattctt cacttatgtg tgaagtgaac aacagattag  96060
```

tagtattatt cagccatatt tgggtaaatg acatgtttca gtttataagt gttgaatgtg 96120
atagttgatc taatgcactt gcagtaattc agatattgag agttttatat tccaatctcg 96180
atcgatatgc aaatcacatc cgctcgatag atccatggca aagccgcgcg ggtactttct 96240
agtcatggaa cctaaattga tacaattttt gggcttatga aataaaggct aatcaagtta 96300
attaataatg gaatttataa cgtgcataca tataatacaa atcaatatag tagtatttga 96360
aaggctaaca tgctatcaac agtcaagaaa ggaagattga gaaggaagca gagaatgagg 96420
aacagagagt gaccttgact attctgccct ggatgccgat ctggtggaat aggtgtgtgg 96480
aggcagctcc tgcggatacc ctcctcctcg ccgtcgctat gcatctgtca tcccttttcc 96540
cctctacttc aaggctacgg gggactagag gtggatgtga tgcgccgacg ccagtggggt 96600
atacggcggc ggcaggatcg ggatgaagcc gcggtgatga gagcaagttt aatagtatag 96660
ccaactacta gcttaaaatc atctatagtc aatttaatag tcaattcata caatagttac 96720
gtactacact attaatatcc ggtcacactt attatacaca cattacgttt tagagtccgc 96780
gctagagcta gctacaaatc tatagcccgc tgctcttctc tttcctcttt tatctcatta 96840
aaatatgttt atagctggct tatagcatac tattgtatct gccctgaggg gggagatagc 96900
gccagcgatg gagatggaga ggactagagg gggaggcaat ggcagtgtgg aagatgaggc 96960
ggcgcggcgg ctgggcctcg agagcggagg cggcgtgaag atgagaagag tcatgttctt 97020
tttttttctt ttacctcagg gacgtggaaa gacctcattg tgaaaggaat ttctcgaaga 97080
accaagaaga tattttgctg atcatatgat ctgccggcct gaaactgcag gaatagaaat 97140
cggacagtcc atgtttagtt gataacgtgg cttattattg ttttgagaaa ggtcactact 97200
ttagatttag atagattgta tgagttatgc acaaattgtc tgaatatgcc atagaaagtt 97260
tatataggca gcaacagtct aaactagaag actcatatct tctcatactg tttgtgtgcc 97320
ttccctcata caataaggga tttataaaca tatcaatgtt cccataatcc catctatcta 97380
ttatatacta aaagtccatt aatctcccta caaacgctcc taaatcgcca catggcaatt 97440
ttcaatctaa ccgttaagtt tcacttaaat tggtgggcct attattttac accattagat 97500
tagatctact tgaaaagtca ttgctacacc cataacgtat aagctttata catgagaaag 97560
ttttacgaga aaaattaaag tatattctga tcggatataa acccatacgt actgctcgct 97620
taaaaaaaaa aacaaacaaa catacgtgca gctataaaac caaaaaaaag tactacatta 97680
tacattgaag ccgtatatac cggaaaatca tgtccatacg agtgaaaccg ctcaaatcta 97740
cgtacgtacg cacaattaaa aaaaacaaaa actttaggta cttttattta aaaaaaacga 97800
acgtacatac gcgtagacaa aaccaagaaa aaaaaatgta cgtatgcgta gacaaaaaaa 97860
acagatagtt ttttaaaata gtattttcta tagtagaaaa acaaaactta ttacttcaca 97920
aatatggtaa aaaaacgtac aataaaaaat atatgatttg aaaatatatg ttttcagcta 97980
cgcgggcatt ctttaaaaag ttgatctaac aatatataca gtgactgact ttatttatac 98040
atgcaagtga agtggtactg gaagaaataa tatatagtca cttttctttt ataatttttc 98100
atatacgttt gaatgacatg cataggatag taaatggaac atggaagaat atacatgtat 98160
aggatagtaa atagaacatg gaagaatata cattttatga gtgaagtaga taacttaagt 98220
atgaattcta attgtgattt ttatcataaa taacacaatg gtccaaatag ataaaaaaaa 98280
tgaaggtatg atttaaaagt taaaaattat aatgagttaa aatatattgt tacaaataaa 98340
tatataattc agaaggttgt ggttatttaa aaattattgt tgcaaatatt ttcataaaga 98400

-continued

```
gaaaaaggga gaaaatgtaa tcaagaggat aaacttccta caaacgcttc taatccggac  98460
atagtaccct ataaatgctc atagaccacc atgtggtact ctaataaatc atagaaattg  98520
tataaaataa gaaaaaatct cgaccaatcg gttttcattt aatttggtgg acccattatt  98580
ttcaactatt agatctatct taaaactaca aaataaattt atttgtaaaa aggcccatgt  98640
cgtattggca cgaccggcaa aaatacatgc acgtaggtat gtaggtattc cttcttaaga  98700
aaagtacgta cctacgtaga gtatgtacac agctattcct atgaacagtg cgtatacaca  98760
ccgcgtccca catccttatt ttttttcttc tcatcatttg gattagatgg aaaaccaaac  98820
taataattta aactaatatc aactatgctt tgagttgtaa aaatatatgc tatttcgagt  98880
tgtattcaaa ttaggcgcat gtcatcgaaa cacccataaa aaatataaat aaattgaaag  98940
tatagattat gtgatagtta aattagactt acattttcca aaataaaaac aacttcaagt  99000
gtgtgtagaa tttcaaaaat tactcactct ctcttgtaaa aaatactgat atggaaaatg  99060
atgttataaa tttatcagaa atatttttt atgtattatg tgtttactct attcatatat  99120
tattagaaaa ttaaagatca aatatattca tttgacacca cgtcaatatc tttttttctcc  99180
tacttagcct tcgttcgatc tagctcattg acttagcgta tccagggcac acgaaaagtc  99240
acaagtcatt agcacaagat taatcgagta ttaaatatta aaagcttgaa aatggattta  99300
tttgtatttt tagaaaactt ctataataaa aaatattttg taaaatatgc accgtttaac  99360
aattcggtaa atatggtcat gataaataat gaagtagcca ctccgataag cactttagaa  99420
cttaaccata aatttattaa ttatgcacta aaactaaata tgtagtgtat aatatacttt  99480
gtgaatctag aatagtataa tataacaatc gtatgtcccc gataaattct atgtaataag  99540
ttctatatac aaaccagtgt caacaatcgt caagttatat tgtttataat acatccatgc  99600
acaatgcact taataattag ttgacatcca ataagcacgt gcgtcatcaa gcactgaaga  99660
tatatgatga tacttagtgg taacccatta ataaaaaaaa taatagataa gtagaggatg  99720
acacaaaatc acaacaaaca atagttgact acaagtagac taagagttta agcaatagcg  99780
ttcctatact tctacaaaca cctgtgagat gtcatgtgat gctctaataa ataggaggaa  99840
atttaagaaa aaaatataag gagaaaacaa aacatctacc catcgattta cacttaaacc  99900
gatgaatcca ttattttcaa ccattaaatt agatttattc agataagccc ttgcttctat  99960
aaactagcta atccctctct atgcacgtac atatacaaga gatgacaaaa ataaaaaaaa 100020
aagaagtgcg tgtatatatg cacgtacata tacgagatgt caaaaataaa aaagaagtat 100080
gtgtatatgg tccaccacgt ctagtagttt tcaatttctt tctttgtagc cctaaagttc 100140
ttctcaaatt atacatatat gtagcgacca ctctttacga ggttgtcgaa gaagccacgc 100200
tgccatggcg ccgcttcatg tcaccctcgc caattttctt gaaaatattt ttttgaccaa 100260
cgatataaaa cgcaatcata ggcggttgtt taaacgtgtg cacacccacc ctatgaatac 100320
acatacgcac accctacctc ctatgagaga gaaatatttg tcaaaaaaaa catgaaaaag 100380
aacgaacata cgagagacta ccattcggga aaaaaaaact tacgtacata cgtacaataa 100440
aaaatgtcat atggaatcat attttatccc ttttaattat gtcgttctca tataaattgt 100500
gttaacaatt agtacaaata attttgacaa tatagagtat ttctttgtac attacccatg 100560
aacatgcgca agtgaattag atgtataata aaagaaaaaa aacatcaaaa ctcatattat 100620
gtttgcaaag gatgatgata ggtaagttta catataacca aaacaaagtg attttttgtt 100680
tgaatatgat agacactatc atttacctta tcaaattcac ggtataaata tttccttctt 100740
ttatggaaag gttacgaggt aatctactgt tcttatagtt aatatgatga tatatgactt 100800
```

ttttcagatt tttttatata aacataaaat aaattgcccg cgtatctgca cgggctacct 100860
tcctagttaa acaaaaaaga ggctgctttt tttaatagta aaactataag ttcataaccc 100920
ctggcctctg cgccaaccag agattagcta atcggttatt acaactaaaa agctaaaacc 100980
aactagtgtt cttccctcaa gattccgaac ctcacatctc ttgttttccg catacacact 101040
tcccaaacta ctaaacagtg tgtttttttg tcagaaaagt ttctatacaa aacttgccgt 101100
gaaaatcata ttaatccatt tttcattttt tttaagataa tacttaattg atcatgtgtt 101160
aatttgtcgc tccatttcac gtatgaattg gagttcccaa ccctttcaaa agaacacagc 101220
cgacttcgtt agaaactgct ttcgggatta gattccctgt agaacgcgaa acgagacgtt 101280
gcattagcac atgattaata acaagggagt agccaaccca agaagcactt tagaaatcag 101340
ccaaaggaat aatgtagtcc tcagggcatc taaaaaacta tgaataaaga gctaattgat 101400
tcagaagcca aaaataacaa aacaaagaaa tgtcaaatgt tgcttttcag atgattgtga 101460
tgcaagatct gcttacattg ttactgaaaa tgatttcctg gtagctgcat acatttctga 101520
agaaataggg taagaacaca ataaaatatt tagccaaact gaaaaccact acggcagatt 101580
gcataattca tgcaaaatag ggataagtgc atcatatgta tgacatagaa aaaaaatgcc 101640
atttgccgta tggaacttgt acctacagga ttaaatacca ggacgaccac agatcgagtt 101700
tgcttcattc agatagtcat atgagtgatg aagcatgcat acttgttttt ttatttaaat 101760
cattaaaata attggtatgg gataggcata aaaggacagt tatattctgt caagcagcga 101820
tcacgcttat ttatccaggc agtaacgcca cttgatcgat aaatataacc aataagcaaa 101880
aaagcaagtt ctgatgaacc tcaatatata attcatcatt tgggtcaagc taacactact 101940
ccaaatgatc cataagtttc tgtgacatca catgtttcaa aaatattagc agcaacccaa 102000
aaatcctcaa ataatcaacc aatcatttcc ttggcctaaa tggctaaacc tgtgaaaatg 102060
aaatcataca cccctcaatg catatagcat tacttaacat tatttggact aacaaatccc 102120
taagtaaaaa cgttccaaga ttacagcttg aagttctacc atctgaatct tccatccgca 102180
gcacccagaa acccctcaaa gtactactgc tgttatgaac tcagtatttt tagccaaaat 102240
attaattatt gattatatat tctagaagct gaagcaaaaa cctattctta tatacaccgg 102300
tccatatttt tcttttattt aattcgaaac ccaaggacaa cagctcagcc ccagagtgaa 102360
ccaacccact agtttgacct gatgcagagt tgaatttcct gttgtatata aaatatagca 102420
gcgaaaaaaa aataataaaa aaaaaactag caacatgctg atgcagatat cctagttcca 102480
gacttggtgt atatatattt catactcgca tttgcaaata agtacacaga tagatcatgc 102540
aatgatggcg caaaagatga tagaagatga ttgcgagaag gtttatgtgg caattagccc 102600
catccaaagc ttgtgcccgc caatgctgct gtggacgttg cgcaacaccc caccggggaa 102660
gacggtgata gtgctcctcc gcatctaccg accagccaga accaacctga ttcctagtat 102720
gcatcctccc tctctgtgaa ttgtgtgatt gttgtagtgt gttctttgac agtacagttg 102780
ctgctcagca caaacaagac tacctgctgg tttttatacg caagaggcga gaactggtga 102840
gaaaatgcta agagattacc tgcatgtctg cgagtctcag aaggtgaagt ttaattgctt 102900
ccagtgtatg tattcaattg tgagaaatgt atccagacaa tttcacagac atgttacatc 102960
tcttcttctc cagttccatg ctgaggtgtt aacagctgag aaggagaatg ttgaacttgg 103020
tctagtagag ctagtttcag agctcaagat cacaacactc atcatgggag gtggcctcta 103080
taggtatact catgaggttg ccgacttact cagaatcaca tatgtttcta atgccaaact 103140
gccctggttt ctgtagaatt gtatcaaatt ttcattgtga caactcttga ttcaaaatca 103200
tcagactcca ctttttaatg accaggaagg aggcatgaaa aatatgatgc tcacagatcg 103260
cacgatcacc gtgttggaaa aggctgatcc atcatgcaag atctttgttc tcaatagagg 103320
aaacctattc ttcatcaggt acctgtttcc cagaagcagc actagatcaa tcttttttac 103380
gcgtaatctt atttgagttg ctctccaaat gtgtcgatgg caatgaaaga tacataacgc 103440
agggaaaggc gtatcaccat ctccacatcc acgaaaaatg ggtttgctcc tgtggaagtt 103500
tctgatttcc ccactagcag ctaccatttt ttaggatggc atccgaatga ttatgccagt 103560
cgcagcagca tatctttgtc actcctctca gaaactcaga gcatgacaga cgacggatgc 103620
gactcagaac aacttgatct aatgctggag tacttgcatc cgggcttcga taatgacagc 103680
ttcagaattg tcagcaaaga atccctcata taccttgaca agatagcaaa ccaatcaaca 103740
caatctggcc atgcacagga cttgcaccag gctccatttg atgatcgttg tcactgccac 103800
ttcattcctg atatggaccg gattcttggc attcaatcaa ggaacgatga cgaggcacga 103860
tggaggaact gcatcaaaca taagatgact gagtggcttc atgaactgcg gtatgtctgc 103920
acaatagtgt tatctgcaca caagcaactc atgcagtggc atcttgctgt ccatgatagc 103980
ctggcacttg acaaactatc aaaagcagta aaagaaccca tcactcaatt actcaccttt 104040
gcatctacag ttagtaagat gcatggttca ccagagaagt tctttcacat gctgcacatg 104100
caccaggctc tgacagaagc gtatccagtt ctacaggaag tgttctcagg agagctcaag 104160
gaatccttta ctggtgagct tcacaaaatt cttcacaccc taaaagatgg tacaaaagaa 104220
acacttgatc agttaagagt ccaaattcag tcatatagtt cagaagacat gccagaggga 104280
ggcggcatac atttggtcac aacttacctc atcagatata tcatgtcact aacacaaaac 104340
acaggttcac tggatgcaat tcttgctcac agttacgaag accatgcatt agcagaagag 104400
aggatgatga acacatcagg tcacctgata tctatgctga tatctgatct tacatccatg 104460
ctctacaggc tgtctaagtt gtacatgtct aaatctgaag gtttacaatg gttattcctt 104520
ctgaacaatg agcatttcat acttcggaaa attgaagaag cagatataag gtcgatgcta 104580
ccagctgatt ggattcaaaa ttaccagcac agagtcgagc agaacaaagt gaattatata 104640
gaagcaacat gggctctgac cctgtcttat ctgaagaaag gaccaaaagt cccttcaatt 104700
tccttcatcc ttcaaccatg aaagagttca cttcatcatt tgaaacaact tgcaatgcac 104760
aggcacattg gaaggtccct gatccaaagc tccgtgttga gctgagacaa actgtttgtg 104820
actatgttct acctgcttat tatgcattca tggagaatca tccaaattta gagaagtcat 104880
ctggacgtag tctggaagac attagaaaca aattgagttg tttgaaggat gaattaatac 104940
tattgcctgt ccaggcaaaa aataattcac tctgtttgtt cccttctttt tccttttctt 105000
ttttacagag gacttagcat agaccataac agtgcaactt ggaatttcat ttgcagtcta 105060
acacttgtaa gcttcactaa caatgaatgt aatgacagga atggttgcat acaatatttt 105120
tgtaatctca tatgggacta tctagaccta atttcactac tattttttttg aggggaaatt 105180
tcacaatttc aaattatcta agcaacgaaa aaactgctaa atcatgtagg cctacctgtt 105240
gatttttcct ctccatctgc agcccagtgt gctaagacta gcagcccaca aaagctgatg 105300
cacaaatctt aaggtgtatt gaacagtcaa gaatttgact gatactagct ctcatcaaat 105360
gtcaacatat ctatagaaaa actgatattc ttgagaattc ttacaaagct atttaatgac 105420
aagtatgatg tttagagtgt tgttttattt tctcacggta cacatgcttg tgactcaacc 105480
tacaactgat aacttcactt tatagcaatg aaaaagagag aaaatgaaat gttatcaaaa 105540

-continued gcaagtatga agatatcttt ttaaaaattg ggtttcaatg tcagatctat acctgcaatt 105600
cagtaaagac ttcatatgaa gtcatggacc atgaatgtac aagtcagtca ccatcacatg 105660
actaatttgt atggaactta aaatcagaat cagttagttg tccaagggaa aggcacttta 105720
tattatctag tgcttacagc atgtgaggtt atactaatca gacaatatac tttgtggcca 105780
catcaaccga caaaatagag cttcatacgg attaggaaga aactgatatg gagggttaac 105840
tggagagttt gaacaagtaa gaaattgaaa attcagtagg tgtcttctgc aaatgtaaat 105900
gtaggtacag agtaaattcc agactaatta taacaaaaaa acatagttgg atttggcatc 105960
ataggttgat ttagaaatga atttgcatcc agtaatttag cagaaacact tcaatataaa 106020
ctccatatta actgacagaa ttgtcccagg agcttaactg ctaaatttgc ctaatagaga 106080
aattttgaat gtgtctgttc ggttgtttct agaacttctt tagcaacgaa ttattactgc 106140
aactgtttag gcactagctg cttgtaaatt aaagcttaga aaggtttgcg ctcccatatc 106200
tcaacaaatt agtagttcta ggacaagaaa aaaatgctac tccctagaaa ttaccacaca 106260
gtagatggtt gtaataccac gcaataggag caacattcaa ccaagaaact agtatgacaa 106320
atcctctgag gtgtagtgtg cacgcttctg attcttaaca ctccttccca ggtatgcttg 106380
ataacattga gtgactcggg atgatatggt ttttctcacc acttgccgaa gtttggggtc 106440
ttcaattttc cagtactttt gcactgcaca attgttgttc aacattgtgt aaaattcagt 106500
taaaggaggc agatgaaagc aaggaaaaag tatgttcttc cttgcaacca ggcgtgacag 106560
gattggttcc catgagtgct caaggtatct cgctatctga tactcgacct ggttgtggtg 106620
cctcgtaatc cagctttgtt gcagcgctga cttcatgtct aatttctcga gtatctccaa 106680
tatgaaatga gcattgttta gtaagaaaat gcattgaaac tctgttgact gatactttga 106740
tatcgtctca agcaaggagt ctaggtatcc gatcaaggac tgcacaaaat aatccagtcg 106800
cgtccatttc ccatcgtgta agggattctc gctctccccg tcatcttgag cgagaataac 106860
gttaagcaag ctatcatgtt cccacatata tttgatatag ttcatcatat atgaagtaat 106920
attgtggatg ccgcctcccc gcggcacact gtaaatgcca tttagagcta gtgaacactg 106980
cccctgaaaa atctccctta cacacctctt gagctcactg gcaatgccgt ttacctggtt 107040
gacagggaag atttcaaggg tcacgtatag acgcaaaata gcagggagca gatcagatga 107100
cggtgacaac atagtcatta cgcctgcaag cttcagcagg cgatgcatat cagattcttg 107160
ttcttgccca tgcttgctgt tgatttcttg aatgctctga tcaatcattg ccaccaattc 107220
ttccttgaac agttcgagca tccgcgagtc tgccctctga atccagatac ggatatttga 107280
gagatcgagt ccatcttcag ggatgtcccc cagaagttgc ttatagatgc gaataccggc 107340
ttcataagag cactgctgat actgggaaat agcagcttcc tcagaggagc tttggatatc 107400
atacgaagag gccaattctg ttgtgcttgt gaggacaaaa gacatatttg ttgatgaaga 107460
tgtggaagct ggcatcttgt accaggtatc taccaaggac aactctatag aacaatatca 107520
agattcagaa aggaggaata ctatgaagtg gcaagaaaca gttctgatga actattatat 107580
gatgagagga gggaagacac ggagttagtt gggaaaacga gtgaagactc aggaagagta 107640
gtcaataagt caaaccaatg cacctccaat taaagagaat gcatttttct gcagctagtc 107700
aaggtcttca tatgattttt cctcgttgca cccttctgtg cagaaagatc aacatgcgga 107760
aaataaaaca attttttcct acaattccta atctaatgga ctagaaaatg gccacctcat 107820
tcttttactg aacaataaac agattattat tctttgcctt agattatacg atcgattatt 107880

-continued tccaaactac gatttcttca aaaactttct acatcagcat tgctgaaata acttaacctg 107940
agctatttat tagctttatt acatataata tttaatttat ccctcactaa tccaccatcc 108000
atcatctttg ctccacattt cattcatgaa cacccagaag ttcaaatgtg ccgaaatagg 108060
caaaacatga aacatggcag aagtttctgt agcatttcta tagcacccag aatatatgaa 108120
aaaataaaac gcaccttatt tctcactgtt ccatgcatct gtgtttcatt ccagaaaaga 108180
gttcttcata ttattcaaca atggcagccg gacatatcca gaaggatata tatattacct 108240
accaccccca tcgcctccgg ttgcgcaaag acctatctgc gactgcagaa tccagatccg 108300
ccgatttctt ggatccatcc ctgcggaaca gtagggcaag aggaggattg gaagtttgga 108360
actcgaaaat tgtttcaaac tggaataggg aattaattcc cctctcaaca aaaggggaaa 108420
aaggaaatgg ggaatacaga tagaaaaccc tacgagattt cgtcttgatt tcacagccgc 108480
gggtactctt gcttcctgcc ttcctggcga ttgagctcgc tcgagaggat ggagttggga 108540
gacagaaaga ggagaaattt tgataattac aatatttttt ttattcccat cacttaggtc 108600
tgttcagatt ggtgtaaaaa tgaactatac ttaaaatttt agtaatatta ctaatttgtc 108660
aaaattttag cattgacaat tttttgatgt gattagctta aaattctata cacattgcca 108720
atatttaata acaaactaaa cctagccaca taattatcaa ttttatcaaa taatggtatg 108780
gttgaaaatg tcattaatct gaataggccc ttagaccctg tttacatggg actaaaactt 108840
tttagtccct atcacatcgg atgtttggac actaattata aatattacac atagactatt 108900
aataaaaccc attctataac cctggactaa ttcgcgagac aaattcttta agcctaatta 108960
atccatgatt agcctatgtg atgctacagt aaacatgcgt taattatgga ttaattaggc 109020
ttaaaaaaat tatcacgcga attagatctc atttatgtaa ttagttttat aagtagtcta 109080
tgtttaatac tctaaattca tccgatataa cagggactaa agtttagtcc ctacaccctc 109140
ttagtctgag ttccttagtt tactttccac acgcacgttt ttcaaactac taaaagatac 109200
tatatctttt gcaaacaaat ttctaaacaa aagttgtttt aaaattcata ttaattcatt 109260
tttttaaaaa aataactaat accaattaat catgtgccaa taatttgctt cattttacgt 109320
gcgcggagta ttagtttcca acccccgaag ccaaacgtaa gtagtaagcc ttacttgctc 109380
cgtctcaaaa ggagtatatt tctagagttt aaaatatatt tctcacttca gagcagtggt 109440
tgccctattg gttatcttcc atccaaattt cttttcatcc ggtcttaatc atcctcctac 109500
ttggattaaa ataaacggaa atatagagct tgtttagttt agtgttctac aaagttttag 109560
cgctatcagt attttggtag gcgtagcata taattgatta gttttgtatt gaaatcaatt 109620
ggaaccaaat ttcatgatat agagaagaaa gttacagaac tgaccaaaat taagtatggg 109680
cattaccatc tacttctatt tgatttcaaa ccaaaccatc atacttacta ttcaaactac 109740
caaaaaaatt gatagagcat atttttgtca tcaattcaaa atgacccaca atctctttct 109800
catatcttaa tttgtgctaa actatttaga atgataagta taggatgggg ttattagtat 109860
tagaggtagg attatctgag tctactgcag tgacccatga ttttcaaata cgataaattc 109920
acaaatacga ataatttccg tggaaaaaaa acgtgcactt gggaattaat tttgtaacac 109980
actacttcta cgattagagg aaatgtgggc cgctagcagt tagaggacac tacttagaga 110040
aggattgtca tctttgttgc agggatcaga taaaatatca cttcttgctg taagtacttt 110100
taaaaatatt atatttctgt atatttcctt gtctgatttc ttttcatttt taatgtctca 110160
agcccatttt aatttaattt ccactttttt ccctacatga tacactaaat aagcaaacta 110220
ccaatatatg agcatgttct cataaaaaaa caatatatga gaacattatg ttatattttt 110280

-continued

```
ttagggacat aataatagac cgtttccact taactacatg gcatatattt acaagactaa 110340
cgcacttgat gataaattta caagtaaaaa taaattttgt cacaaggaat gtacatttag 110400
ggaaacaatt aattaagaga aagtactctg taacacacta cttccacgat tgagacatgg 110460
gacaaagagg ttatagacaa gtggaataag ttcaccggag gtccctcaac ttaatagcga 110520
gatttttga ggtccctcaa ccagtaaacc agaaatgttc gcccctaaac tcattcaaac 110580
cgtttactgg aggtcccttg gtagtatttt tgcccggttt tactgacgtg gcatcctagt 110640
cagaaaaaaa attaaaaaaa aatcgtgggg cctatatgta agtgagaaaa aatatgggtt 110700
caaccattct agtcagcaat cttctctctt ttcctttttc tcttcttctc tttcggcgtg 110760
tgcgcaccgc ggcgacctta ggctgggcgg cggcatgcgc ctcgacccac gcaagagcat 110820
cagcggcggc agagggcggc ggcgcgtggc cagagcagat agaggggtgg catcaacggc 110880
tgcagtcggc gggcgagctc ggccacagag agcgagcggt ggcggcgcgc ggctagagca 110940
gccaaagggg tgcgtcggcg gccgcagagg gcgagcggcg gcgtgcggcc ggagcaggca 111000
gaggggcgga ggacacgggg tgcgcggtgg cgcagatagg gagcggcaac ggcacgcggc 111060
tggaggcagg cggagcagcg gcaggcgagc gcggctgcgg agcatcggcg tcggcgggcg 111120
agcgacggag ggcggagcag gcaggcggcg acgggcgagc gcggagggag acaaggtcat 111180
tgccgccgct cggagagagg cgaggtcgtc gccttgggtg cctctcgtcc acccccgaca 111240
acaacgatta cgagcccccc gcgccgccgc ccccgcccgg gaacaacgat gacgcctccg 111300
accgcctgcc gccacctcct tcttctcccg gtctcgcccg ccgtccgctc tgcccgcagc 111360
ctgccgccgc tctgctgcct cctccttcct ctcccagtct cgcccgccgt ccgctccgcc 111420
cgtagcccgc cgccgtcgtg ctgccaccgc ctccttcctc tccaggtctc acccaccgtc 111480
cgttccgctc cgctccgccc gccgccgctc cgctgcctcc gctcgtccgc cgtccgctcc 111540
gccgccgcgc tcgtccgccg tccgcttcgc ctgcagcccg ccgtcgctct gctgccgtgc 111600
tcgcccgcca cccgcatcca cgctcgccat cgcggttgtg cccgcctccg gcctgaagaa 111660
gagaagagag aggagagaaa agagaaggga aggagaagaa aagagaagaa aaaagatgtg 111720
tcacttacat gtgggcccca tgaatttttt ttaatttttt ttgctgacta ggatgtcgcg 111780
tcagcaaaac caggcaaaaa tactaccaag ggacctccgg cgaacagttt gaatgagttt 111840
aggggtgaac atttctggtt ttgtgatgag ggacctcaaa aaatcccgtt gttaagttga 111900
gggacctgcg gtgaacttat tcctagacaa gtcccaagac tgttacttct cttgttgggc 111960
tttctcatgc aaattcctca tcgaaattct catgtatttg cgcgcaaagt ttgcatgaac 112020
atgggcatga catgccgaca tttctttata ttaaattgtt gaatgaccgt ataagttcta 112080
tatatatgcc cgtatgtagc catctttaat tcttttccct atataccgtt ttacagcttt 112140
atactaaagg ttgaattact gacaagtaac aatatagaag ggtgagttct atagagaagt 112200
tgagatgggt tactttatca tttttactac gtttttaaa ctactaatct gtgttaacta 112260
aaaaatattt atatgaaagt ttcttaatta aaaaatcaaa caaattcact ttttaaattt 112320
acaatagcta gtacagtact taattaatca tgaacagggt gttcgtttca aattatgata 112380
caaattttat ctcagtttc gttacaacgt attttttca aactgctaaa tagttttttt 112440
tcaaaagttt ttatatagaa gttgccttaa aatatcagat aaatttattt ttttaataaa 112500
ttaattaaaa ctcaattagc ctcgtgctaa taactttttt tgtttgatat gctcgtactt 112560
aatcctcatc catcgcagct tcgaacatgg ttagtaataa ctcttctcgt tttacatgcc 112620
```

aaaaatctct cttttaaaat cagccttcat gcgtagcatg tggctcgaag gggagcagta 112680
tgtataataa gctcaagctc cagcacgatt attatgccca gatttgcttg tcatcagata 112740
ttcggatcca atccaatcga atcacacaac cgccagccgg gatacgatat cgttccacag 112800
caaagttaat tagtacgtca tgctatgatt gtatactcga cgatcagtcc aaatcccaat 112860
atgggaaatt attttgttct attgagagaa tgttcccatg tttgtttaca aattatctaa 112920
aggttatgaa aatattcgaa atatttgaaa acactcacgc aacatgtatg tgccactcca 112980
aaaaatttta gatccaaact caactcacat atcgagatat caaaagataa attcaagccc 113040
tgtttagttc ctccaaaata gcaaaagtac tttttgctaa aatagatcta aacactacta 113100
gcaaaagtta gcaatttggc atttgtcatt tgggagtcta gagtagcaaa ttttatcaaa 113160
aaatgtgttg ggagccgtgc tctctctgcc tttactagta aaatggcaaa actttaccat 113220
gcatctatcc actaactagc aaaatttcaa taccaaatct tttaccacca aaacttttgc 113280
aaaaaaattt tgctaagcac gccctcaacg tatacagcaa atttatcctt tttttatta 113340
tttcattgtt taggtggaat ttaaacttca tttttttggt agatggattg atgtcactat 113400
actgtacatt gtaattgtta ttcataaact ttcacaacta tttacgttgg atttagaaga 113460
aaaaaagtta tatgagagaa tatcgaattc tcaatggatt ataatctatt ccatcgaaat 113520
atttctcttt agttggagag aggaggttgg tgagacaagt tggggttttg gtttggttac 113580
cttaaatgag taaagtggtg ctggtagcct ggtactacta gtaaaccgac gataagaaca 113640
catgccaaca aatgacagtt agctagcagc agcagcacag cacacaaacg acacgacaac 113700
ccaacaacac tcgcgcagat gagagtgaga ctagtctgac caaccaccct cctctccagc 113760
tctcctccac gagtggttgg ttcgttgagg gtgacgcgcg ccagacgcca tcatcatcct 113820
ccctatcgga gaggatgttt ggacactaat attaaatata gactaataat aaaacttatt 113880
ccataactct gactaattca cgaaacgaaa taattaatcc atgattagcc tatgtgatac 113940
tattgtaaac atgtgctaat tatggattaa ttaagattaa aaaatttatc tcgcgaatta 114000
gctctcattt atgcaattag ttttaatact ctaaattagt gtccaaacat ccgatatgac 114060
agggactaat gtttagtctc cggatccaaa cgtctcaact ctcaggacaa agcttgtccc 114120
gtactaggaa tcagtggcac agaaggtgtc gaattataaa aggaaaaaat acgaattacc 114180
ccctaaacta ttgggtgagt acgaattacc cctctagaca tgaaaaccgg acgttttttt 114240
accctcaact atcgatactg aatgtccccc ccaccccacc cccccgcgaa cagttttgca 114300
agcgattttg gtctacgtgg ctgtccagtc agcaattcat ttttttaaa tcagcgagcc 114360
ccacctgtca gtctcccacc ctctcgtttt ccctcacctc tccatctctc tccaaaatcc 114420
actctcttct ccctccctca cctcgaggac ggcgggcaga gctcggggcg acgaagggga 114480
ccgcggagct tgggacggtg gcaggaagag gtcgggacga tggcgggtgg agtgggctgt 114540
ggaggggacg gcggcgggta gagctcgggg cggcggagct tgggacggca gcgtgaggag 114600
gggtggcgga ggggacggca gaggacagag ctcgagacga cggcgaacgg agctgggggc 114660
cgaggggggcg acagaactcg gggcggcgga tggcggagct tggggcgaca gagggggcgc 114720
ttgcagccac cggcgctggg gacgacggcg ggcggagctt gatgcaaagg gggcgacgga 114780
gctcggggtg gcgtaggggt gcccgcagcc accggcgcgc ggctcgtcga ggtagcggag 114840
gggacgcccg cagccagtgg tgctcgggga gttggagggg gcggcggagg aagctcccgc 114900
agccaccgct gcgcggctcg ttgaggcgac ggaaggggcg tccactgctg tcggtgttcg 114960
agctgcagcc accagcattt gagagagaga gggtgggtga gagcgaaaga gatagagtgg 115020
agaaatatct gacaagtggg ccccatcatt tttataataa aaaaattgca gctgccatac 115080
cataccacaa gagagggtcc gccactagac atggcgcatc ctaatacatc aaatcagggg 115140
cttgtccaga ttcgttgtaa tgtgtctcat tttgtactag gtttgttttt ttatggtttg 115200
gagggagtaa ataccataca taactatttg ctagagtctg taaatagctt ggaaaaaact 115260
aattaattgt ccttcagctg tttatttttt tcttccatgt agcaagcatt ttagctatca 115320
aactgaaaat taatacaaat atttaatatt aaaactatag gttctagcta agaatctgga 115380
cataactaaa aattcatttt tttatagatt tggcaggcag taggggctac tcaggccagc 115440
tgctcagctc aggctcacct tctcccccgc taggatcgcc acggctacga atagtattgt 115500
tacaccataa taagcacgtt accaaatgta cgatcacatt cggtgtaacc acgagttgga 115560
agattatcat caccatgtag ctaatctagc cctattacgt accaaggttg tcgttggaaa 115620
tttggtcata aatcgacata ttttaattca gaaaattaag atactaagca ttacaggtac 115680
atagttgaat gatctagtga atgtatatta aacatgagca tgcttttgaa aatataagca 115740
taaacatcaa gtatattcac atatgattgg catgatgata aacatgaata tactaacagg 115800
aactatggta tctaacagca agtttaaaac gaggatgaat atatccggag aatgctccag 115860
tactagttga gacattgttg gtgttgttgc ctccgttggt attgccgttc ttaccttctc 115920
cagtactggt gcgggtgttg gtgtcggtgt tgacggtcga catggcgttg cagaggaagg 115980
agagcctgac aaagaggatg cagcgtagtc aaagcagaac aggagcagtc cgccgagacg 116040
ctccccaaaa acttgttcgt tttacctacc cgtgtagatt ctcaagcaga cagcgtttcg 116100
gaggcacctt ctcatcccgt gtacctgtgt gcataggtga ataggaccag ggaagcggtg 116160
gctagcgcag gaatagaggc acaaagagtt tccgaggaag agtaagcgag agaaaggaag 116220
acacagagca gctgaggtgt gtcagctgtc tgtcccggtg gcggcctttt atagtgcgtg 116280
agaaggagag aagaatcaat acgttactgc agtaacaacg gaatcaatct gatttaagtc 116340
aggattgatt cattcgttat aggagtaatc gcacccatat tgaaatcgta tcaattgcga 116400
tttaagtcgg gtaatcgtgc acgtattgaa atggtatcaa ttgcgattta agtcgggatt 116460
gattcatccg ttataggagt aatcaagccc atattgaaat cgtatcaatt gtgctgaatg 116520
aattggattc aattcttgtc cgttgcaaaa tttacaagag agagaagcag tcgccgcctt 116580
cctcgccacg gcccagccca gctcgtgcaa gcgcgtgcgg caatcccacc accatctcaa 116640
ccggttaaca ggggctctct gatagcttcc tgtttaagtt gagatcttcc ccacttaaat 116700
ttctaaggtg atattaatcc ctatagtagg gtctagccta tttattccat cagttgtcat 116760
catttttaaa agtagatagt tatgtccaaa tttgtatctg tttttttttt tacggagaga 116820
gagtactata ctactcctac ttcccttcta aataggtatg tccacattca tatttggaag 116880
tgaagttgag tgcattgtaa ctgaaaggat cgagccaaca aaccacaacc gatataaagt 116940
acagttagca gcagcaccac cacaaaccaa acgacagcac aacagactcg atggtaagac 117000
tattctatgt ccaactcact ttccctctcc ctcatcgagt catcgtcgcg tcggtttaat 117060
tttgcttcct tgagagtgac gcatggccga cgccatctac ttcgtcaggt ctctgtctct 117120
ctctctgcct gcttgccact gcctttcggt ggttcgtggt aggtgacaga catggccgcg 117180
ccgcagcaag cagcacgagc acgagcaagc accaacgcgc gccacactcc ggctattcga 117240
aatttgatat catagggttt gaaattgtgc gagtaaaact ttatagtgaa cttaacgttt 117300
attctacaga attgctaacc tttattcggg agaaatttga gatgaattat atttatgtca 117360
gatcctcctg ttggaatcgt gtcatgattc gtgctgcact tctttttcgc cggctcggtg 117420
cgatggtgag aactccgatg agataaaggc ggcccgacca gctagagtgc tgagttgagg 117480
taagagtgga aaggggtcag ggaaagggga agagggttgc aagcttagag agtgatggtt 117540
gtggaacacg gcggaacggg cgagcggtga ggtggatgct accgaaacca cagggtcgac 117600
agcatgcgtg gatcaatgtt gacatcaggg gcaaagcaaa gtgagtagtt aagaagtggg 117660
agaaacggtg gcatctccgg cggtgggaat ccaccaaaaa cagggaagaa ggggtagggg 117720
caccgtcacc agcttaagga ggagaggcga aaaggggtga gggggaagtg cgatggaatg 117780
tatggcaagc cctgtcggta tggttgcttc ttttctgacg ccgatgaggc caggtggcag 117840
tgcagtaggg gcgatgatag ctgggatcgg gcatagggag tgtactcgat tggtcaagat 117900
tgggtggcac agtcgtggta acatgaggcg gagaaagaga gttagggttt aacagatgca 117960
tggatcttaa aacaaattta acgatccaaa aaatatcaaa tgtgggatga aattttctgt 118020
cacatagtag tattaaatca gcaatacctt ttatttaaga catgtttaat ttattgacac 118080
tttcaacttc gctaaatttc ggtaggacaa caaactacac acatttcaac cattactacc 118140
ttacaaaatt ttggcagtta ttagaagctt tctctcgtaa cactctaacc gaatttagca 118200
atgtcatcga agcaaacgaa atcaacaccg ccaaaatttt gtagtgtcaa aatatgtaca 118260
aatctcgcat tatcaaaata tgctatggtt gatttgggaa acaaaataaa ccagccctta 118320
atcctgccac tgttgaagca aactttaggg agttttcaac gcaaataagc gcagttctca 118380
aaagaaaaaa gaaatgcaaa taagcccgta ctcccagtcc cacggtccca ccgcggctgt 118440
cgccgtgggg cccgctatcc gactcttttc tttcgctttc tcgctgccgg ccggggagac 118500
ctcgtccaca cacgccaacg gccggcagag gggtgggggg tgtggggccc accatgtcag 118560
tgggcgctgg gccgcgtggt tgtgtgctcc gtttgtcgtg ctccgcggtg caacgtcgtt 118620
tgaggtgggc cccgcaccgc cgggatccgc tgcgcctgga gggaacagac ccactttgtt 118680
gctcaggtgc acgcgtgcag ccgcacaccg ccggacagaa ggaactactc cgtcaaaaaa 118740
aaaaaaaact tatatatgtc caaattcaaa ctcagtatta gattttttttg acagagggag 118800 tactctgcta agttcatttc caagctttct caactcaccc ctcttttttta gcgcgcatat 118860 ttttaaaact attaaacaat actctctctg tcctaaatta taaagacata ttttttacat 118920
ggtcttcaat aacatatctt gactagtatt ttattacatt ctatgatccc aataaatatg 118980
aaattagcat cacatgaaag tacttcaaaa tatgaattta atgacataac atgtataata 119040
tttactatag atatagttag gctgtgtttt tacctttaag ttcccaaccc ctctcactca 119100
ttttccgcgc gcactttttt aaactgttaa atgatgcggt tttttaaaaa gtttctatat 119160
ataagttgct ttaaaaaatc aaattaatat atttttttaa aaaaattagc taatacttaa 119220
ttaatcatgc aataatgcat gcttcgtttt gcgtgccggg gaggagtggt tcccaaccct 119280
cctcccgaac atcaaggttc ccaacttctc ctcctcgttt tccgcgcgca cgcttttcaa 119340
actgttaaac aatgattttt ttgcaaaaaa gtttctatac gaaagttgtt taaaaaatca 119400
tattgatcca tttttgaaaa aaaaaattaa ctaacactta attaatcaca cattaatgga 119460
ctactccatt ttccgtgcga gagggtaggg ttcccaacca ctgggaacga gcacagcctt 119520
agtatggtta ttagtcaaaa gttaccgagt ttgattttcc ttaaaaatgg ggcactatat 119580
aatttgggac ggaaggatta tgtttttcgt aaaaatttaa tatagaaaag ttgctttaaa 119640
aatcatatta atctatttta aaaaatagat taatactcaa ttaatcatac actaataaat 119700
tgctccgttt tacgtgcgtg agggattagt ttctatcccc aagtgccctt aagcaccgta 119760

```
cttttaagtt tttaaataaa gctcttgtac taccttcgtc ctatgatata gcaacctaat 119820
atcggacgag acatatccta atactacaaa tctagccatg tttgcttgtc cagattaata 119880
atattaggat gtctcgtcta gtatgtacta ggttgctata ttttgaaacg gagatagtag 119940
tatactccct ccttcctaaa ttgatcatca tataatggaa ttcaaaattt cttaaattga 120000
tcattatata accgcatgaa cactgatttt atcataatac aattaataca gcatgggaga 120060
atgtgtgcat ggtgtcttga ttaatgtgat ttaaattatc cttggtcttg gtgcataaac 120120
atatatgatg atcatttttg gaaagaaggg agtattattt tagtatcaga tgagacacat 120180
tctaatttta cgaatctgaa cagagtctat tcatgttcat aatactatga tgtggcaaat 120240
tcggtgctat attgttatat tctggataaa ggtagtataa gtcatataac aatatcaaaa 120300
atatatttta tgctacgagt ataggcacga gaagaccgct tcacgcggag agctatcgca 120360
aagccgatag cggtaaaaaa tttcccctct tccctctagc ctctcttcct actcaaatat 120420
ggcggttcac cacaggtaaa gggaggggga gaagtcagtc taccttctct gctaggtagt 120480
agtaggtata atcgggcttt tcctattttc tagtccaacc catttctttt gtgcagtgca 120540
agaaggtcgt cggtgttcgg cctcccttat cccaagaact ctagaacttg ttgggctcct 120600
ctcaaacaag gtcttctata tgggaatcat tgggtctctc caagacgtca aaaactgaag 120660
gagcaataga tcttctcggg ttggtggttt caccctcaat cacaacatca accaggtagc 120720
gctgacccac ttctccttct ccggcgatct tctaattctg tctttggttc tcttattttt 120780
ctctagcgac ggtctcaaag cggcagcaaa gttttcccat gatgccaagg cagctgtaac 120840
ctccatcttc aagaggcccc atccgggtct actacttggc aatttgcagc ttgccataat 120900
ttttgcgaat ttgcagtctt tgccgtcatc gatcaaggta cagatgcaga ggaagaagca 120960
agattatgga tgtcatggtt atggatacca cgtacctaat agtagttgac taagctcggc 121020
agggcccatt atgtaccaag tcttatacgg aatcatacct cgtatataga aggagttccg 121080
gataaggaag gatgaataga gttctatatg gaaatgacaa ggactacccg gattgtatcc 121140
atattggtct ctctagttct acttggacaa ggggacatct atgggtataa gtgcggattc 121200
gatgaggaag actaccctgt catcgactac gtgttggtta tccatgccgc caagtcgacg 121260
acagctagat aggttatcca aatcattgta cttgtgtgat tcagatgaat aaagagcaac 121320
actggcttcg gccaacagga gtagggctat tacctggcag ataaggggtc cgaacctgta 121380
taaaaatcct tgtcttcatc tcttttacct caatctcgca tatactttgg tgccaacgat 121440
ccccatacta tacaaaatac cgtagtcgtg atatcaaaca tcgacaatgg acatgattgc 121500
tttttcctta tcttttgaag tccttgtgtg cttaattcgt gctcaagttg taatttgccc 121560
ttttctttag ggcctcatgt gtaaatctat ctatcctctc aagtctcgac tagcctttta 121620
ataaatacgc cttagctgat gttttctaaa aaatacgagt atagaatgaa ggaaatgaga 121680
tatatgtata gccatttgca gtgtcatagt aatatctcaa ttggaatctt ctatattact 121740
agtagattct gcttatatac attcatattc ataacattag caaccgctaa ataattcatc 121800
ctaaacatgc ggaatatatc aatagtaaac aacctactct agtatcactt actgtgaccg 121860
catctgacaa aggttctctt cagaggacta gaggagttta tatcaactgc agcttgatct 121920
aaattcatag ttaaatttta ataatatata gttgtagaat atagaaaata aataagaaat 121980
taaatagaag tacaggaaaa ctacatttta catgttttca tgaggtactg ctagtagcta 122040
ctcaacggtt gcttaggctt gattcgttta tctgggttgg gaacctttca tcgaacacgc 122100
```

taaatggagt ggtagattta cacatgatta attaagtatt agctaaaagt atacacatgg 122160
aaaatgatag ggtataagtt ggaaaagctt gctgtgttct ttgttcagag ttcccaaccc 122220
ctctacctcg tgttccgtgc gcacgctttt caaacttcta aacggtgtat tttttaaaaa 122280
aagtttctat ataaaagtta cttaaaaaat aaattaatct atttttgaaa aaaagctaat 122340
acttaattaa tcacgcgcta atggactgct ctgttttctg tgcgtactgt tccggttggg 122400
aatcagagat accgaacaca tcctaaaaga acacgacttt gatattcctt aggggaatgc 122460
taggaatcgg tcgctcaggg gagggagaaa aatcgggcgc tccctcctcc cacgacgcgc 122520
actgccctgg gccccaccac gtctctaccc ccacctgcca cttatctcta tcacatactc 122580
cattgcaaca aatcacctat atattttgga aacactctat taagggaata catttcattt 122640
ttttccacga agaatgtttt accttttata cccacaatat tccactgtgt atagatctaa 122700
tgtcgcagtg aactgaaaca ttctttcact atttgctgaa acattatttt tatataaggt 122760
gaaacaacgc ccgacttaaa ctattgaaac attttcgatc tcttagtgaa aaaattccga 122820
tatacttggt agaatatcgt gcaacatttt aaaataattc aataataagc taaatttttt 122880
ttcatcggaa tatatctatg tgtgtgatct tgttttgaag atttaattgc aacgaattta 122940
atggtgaaat catgatttgg ataaataatt taagagaaaa attagtttaa agtagttttg 123000
cacgcatgcg tcatactgat gtcagcgtcc gatttttctc caaacccatc ggtcgcccga 123060
cgcgtaggct cctcttattc cttgaattag aataggtatg gctacacgcc tacacgcaca 123120
caagatagat gaggtgggtg aggcggagca gaggatccgg cgggctggga ccacctcgtg 123180
ttggtgcctg gtggtgatgc agtgggcgaa gtggttacac caacgcgcac caccaccacc 123240
atctctctct ctctctctct ctcttcctcc ttcccaccaa acaaacatcc cacgcttcgt 123300
ccctcccact ccactcccca cccccgcgac gcctgcggcg acgacgacgg cgacggcgag 123360
gaaggctggc cacggcacgc ggcggcgagt agtccagcat ggcggcgccc tcggcggcgg 123420
cggcgtgggt ggactgggcc gcggagtaca ccaaggcggc ccaggcggag tcgcgcccgc 123480
ccgcggagtg ggccgcgcgg gtggcctccg tcgtcgccgc cgccggggac gcgccgtggt 123540
cgcccgggct cgccgagatg ctcgcccgcg cgctgctgta tggcggtggc ggcgcggcgt 123600
ggaagtacgc cgaggcagcg ctcgccgcgg gcctcgcgtc gccggcgctg ctcctcgcga 123660
tcctctccac caggtacgga cggcgcggcg cccccgctcc catccattgc cctcccccca 123720
cgcgcgcgca gtggcgtttg tgcgcgcgcg cggggagaga cgaatttgcg tgcgtggtat 123780
ctgacatggg ctcctgctca cgtggggtgt actgtctgat ggaatccgcg caatcgcgat 123840
cggatcaggc tactagtttc gatctatgag atttccctcg caaccagatt accacaaatg 123900
caagttgttc tacagcgtgg cctgtacatg atcataaaca atctgatgtt ttgggccctg 123960
taaatttgag aaggaaaagg gatggtggcg tgcttactgt gcgtaatacc cataaatttg 124020
agaagtatat gaatggcagt gtatgtagag tactcgagtg tgcagtgtaa tgcagatcaa 124080
tttaatacat gtatagcagc agaatactct gtttcatttt tttcactttt tttcttctct 124140
ctagagtcta gatcatgcta gttggaataa caagtgcagt ttgaaatgtg cttttcagca 124200
gtaatcgtat aaccaactgg cgaaatccgt gcacattttc aatatctgct atgctgctgt 124260
ggaatgttct ataaaataga atataagact gattgcaaat attccgttga tggtttctct 124320
ccattcaggg tcattcctca ccggttcaca aggccaactg catatagact ttatctggag 124380
ctcttgcgga gacatggatt caattttgct tttcagatga aagcggcgaa tttcaaaaag 124440
tgaggtttcc ttctatgagg tgttcccagt agtttcataa tgcacgcatt ctatgttcag 124500

-continued aggtttcgaa atatacatca caggaacatg tacatcattc tgaacgattc agtactgttc 124560
aaaagaatta tataagacgg gaattttaat acgatatgct gacaattaga gttttgggtg 124620
tctaccacaa tacatctaga ccaccttatt gcatctgcat actggacata tcaagatctg 124680
ttccaaagag caacaatttg caaaggaaga atttcacctg gttgaaaggg ccagttctgc 124740
agtgatacat aatattttcg gttgaattgg ttaaggtgtc actttatatg ttttcaactc 124800
gcatatagtt ctttcatgtt agtttttaaa gagtttgttt cttgtgacat gtctgttctg 124860
ttagcatcct atgtttatgc cttgtgtagg tatctgtcat tctgtctgca acttatcatt 124920
cctttagttg tcttctaaat gcaaagtttc atgacacctt ctcatatttc cgcaggatca 124980
tgcaattaat agatgataac cttggtctct caaagatatt tggcttttca acatgcgaac 125040
caggggtttt tgttgttgaa tttacccttt gcatgttatg gcagttggtt gatgctgcat 125100
tagatgacga aggcctgtta gagttgatac cggataagaa agctcattgg ccaactagat 125160
cagatgatgt gagtgcattt gatggaactt tctctgaaca aagaatagac aaaattgaca 125220
agttacagaa gatgaataat gtgataacta tagagctcat tgggcatctt cttcatgaca 125280
aagtaattac tcatatcctc tcattggcac gcgaaaacat gtatggcttt tcaacttcat 125340
gtactgcttt actgagttat tccagctctt tcttcctatc actaaaaaca gtgaatttat 125400
ccctttgtta ttatatcaat tgatagcaac ttaattttat tttagtgagt taatgtatgg 125460
cttaaatatc tctgtgttcc atatgcacca tataattgaa aacattctct ctattggctt 125520
aaggttctca agtcaagctt ctgtgtcttc tgagtataca gggtattgcc aatatttttc 125580
tggaatatat cagattcatt gtatttatgg aatggctgta cacttttata aaacaactgt 125640
cgaccgcaat gctaaaatgt gaactaatag tactctagaa ggactactgg ttgtatgaac 125700
aagcaagctt gattggttgc aactgtaatg ttcaaatgat tttctctact actttataac 125760
caagaaggat cactgataga atcatagaaa ctctggccat gggggacaag ctctgatata 125820
ctcatgccaa tattgtctga tattgctgtt tgtgttcata actgtactag aatcgtacac 125880
aaatgaacta ttgggataac agtacattgg tagaaggcat tcgtttaaac ttccaaagtg 125940
gggatcaagg gcatccttaa gacaccacaa ctgaattcac ttactgtttt tatttttat 126000 tttttgaaa aagtatgcta ctttaatttg ttattattac caccagtact aacgagtctt 126060
gatgattcag gcaatctcag tgggcagcat tcactaatcg gttacaattg cttattacaa 126120
agtcatctac cttacaaact tcaacagtag ccttggaagc atttcaacag ttgaatcttg 126180
atgtctgcaa tatattcaga gaaaataaac attggttgcg tagaaaattc caccccatag 126240
tgacttctaa ccctctatct tctccaaatg gacggtgcct tggagctagc tattctgcac 126300
aatggattcc tattgatatg tatcttgagg attgtctcga tggctcaatt gctgcaacga 126360
attccattga gactttaagt ggtaattttt tcccatcaac agaatcatat cttttggttt 126420
gcattgaagc atctttttcc ttgtatcatt gctttctgct attgtttctg taactaaatg 126480
ggagcttgtg ctcttcgcag gattgatcaa ggccctccaa gcagttaata gagccacctg 126540
gcatgatgct ttcttggccc tttggatagc atcacttcgc cttgtacaaa gggtgagtct 126600
tcacgcttca ttgcatttat tcaaacttaa aactgtcttt aagatcctca tcttggatct 126660
tataaaacaa gcaggaaaga gaaccaatag aaggtcctgt gcctcatcta gacacacggg 126720
tatgcatgct tttgtctatc acaacacttg cgattgttga cataatcgag gaatcagatt 126780
cagagatgaa cagtaactgg aaagaaaaga gaacgagtga tgatctgcgc aaggaattga 126840

-continued

```
tgctaagttt acagacactt ggtgattatg aaagtttgct tgtccctcct ccatgtatca 126900
tctcggtagc taatcaggct gcttccaaag ctgcaatgtt tgtttcaaga accaacatta 126960
gcagtggata catggaaaat gtcaatgaca ggacaacaaa ttattgtaag tgtctgctct 127020
ttatcttaga aatacataca taattagtga tctcattgac cttttttttt ttttgcttca 127080
gagtagtata cataaacttg aatatcaatc ttcctttaat tttgagcagc tggaaacatg 127140
tggcatttga ttgtggagtc atgtatctca aggaacttgt tggaaacatc agtttactat 127200
tggcctggtt atattaatgg tcatgtcaat tccataactc atgcactccc aagccaactt 127260
gctgcatggt catctttcat gaagcgtgcg ccattaactc agtcattggt taatgtgttg 127320
gttgcaactc ctgcaccaag gtgtgtatct ttttccctag gaaacaagtg atgttagttt 127380
accatattaa tttggaatgg gcatttctca tgagaagtca tcagttactt aaaagagaaa 127440
actacattat gttccttatc atgatcatca tttgtatgcc tgtccaagtg tccatgtgct 127500
ttggggaaaa aagtcaaatt aagctgccag tcagatacaa tgtcaatggc tgcgttgttt 127560
agatgtgcta tgccatagct tatgtttgct gtaaatttat tctctgagat gtggttagtt 127620
tctatggctg tgtatatctg aatcatagca tatgcattat ttaatgctca tacaatgttc 127680
ctgttaataa atcactgaat gaagctcata aacatggaag cttagcagag gttcagaagt 127740
tgtatgaagt tgcagtcgat gggtcagatg aggacaaggt ttctgctgcc actattctat 127800
gtggtgccac tttgctgcgg ggctggaatt ttcaggttag tgttgtgtag cttgcatatt 127860
atgaaatgtt tctgttggtc ctagtcatat gatttattcg aagggaaaat tcttcttttt 127920
tttttgcaga agaaagaacg tatattcttg taccgctcca aaatgactac tctcttttgc 127980
catgtggcat tttccttttt attctttctt gccactagca actcttgggt cattgaaaaa 128040
ataatcagga aatccaagaa ctcaacttag gaaactgtag taaattaaaa aaaatacaga 128100
tagagaactg gaaaacacca aaaatgaaat taaatatttg aaagttttgg gaaaataatt 128160
ttatgatgtt aaatttatct ataatacaaa ctttaagttt taagttcaaa attcatcctt 128220
gaacttgttt taatttctgt gatttcaaaa taccattatt ggtttctgaa aattctactg 128280
ttggtggcgt gggaaatttg gaagcagagg aatgacttgt gttttcaatg gctctattcc 128340
gagtgtgtca atggtgcttc aatcagtagc acatgaaggc acacttcggt ttttagccag 128400
agcttcaaag ctccgagagg tggtggcgag gtcaatagcc cttgcggctt aagtggtctt 128460
gttggtgttt tttttttctt tttgtaactg taatagtgtt tagtgtgggg agtttccgga 128520
ttaccatccc ggtgtatctt cttcttatta ttattaatga aatgatgcac agatctcctg 128580
cgcattcgaa aaaaaggaag aaatttctac tgttttcttc agtcaatggg agctgaccta 128640
atagtagtga caaatagaga agtgctatat tttattggta gaagagaaaa tggaaattcc 128700
ttggtagtaa aaagaaaagt tcctcttgtt gatttctatg taaaagcagc atgcatcttc 128760
attttttaat atcataatga ggtaaattaa catctgcttg tcttgaagtt attaatatta 128820
agaccttttg ctctcttatc ttgcaggagc atacagttcg gttagttgtc aaactactct 128880
caagttctga tccaatcgat ttttctggag gagagagcca gttagtaaag catggcccaa 128940
tgctcaatgt tattgtcact ggaatatcac ctgttgacta tgttccaatc ttctcattcc 129000
atggcctagt atggttcata tgctagccta tctttacttc tatttgatgg tttatattta 129060
ccatcttatt ctgaattata tggttttgct ttttaaaaaa tgaacagatt ccagagctgg 129120
ctgctgcact catggcaata tgtgaagttt ttgggtccct gtccccaagt gtttcctggt 129180
ctccgagaac aggagaggaa atatctgctc acacagtctt ttcaaatgca ttcattctac 129240
```

tattgaggct ctggaagttt aaccatccac cacttgaata ttgtgtaatg ggagatggtg 129300
ctccagttgg ttctcagctt actcctgagt atcttctgtt attgcgaaat tcccaagttg 129360
tatctatcag aagttcagca aaaaacagaa atacccagaa acagttgcca gttacttcaa 129420
acccatcgtc tgagcatcct attttcatgg attcatttcc aaagttgaag ttatggtacc 129480
gacaacacca agcttgtctg gcctcaactc tctcgggatt tgctcatggc acaccagtac 129540
ataagaatgt agacagcctt ctcaatttga tgttcagaaa ggccaacaaa gaaagcactt 129600
ctattggttc tttgtctggg agtagcagca taagtaattc ttcgggtcct ggtgttgatg 129660
attcacatct ttggcctcag ttacctgctt gggagatact ggaagctgtt ccatttgtgg 129720
tggatgctgc tctaactgcc tgttcccatg gaagactgtt tccacgagaa ctggctacag 129780
gtttgttttt gccgattctt tttttttttt tttgacgtaa aatttttgcc gattcttgtt 129840
tgaaaattaa gatgattgaa gagtgaacct tattatttaa ccattactat gttctatgtg 129900
atcatcagtg tttgatacta ccttttccat tccaggtctc aaagatctga ctgattttct 129960
ccctgcatct cttgcgacaa tagtaagtta cttttcagcc gaagtaacac gaggtgtttg 130020
gaaaccggca ttcatgaatg gaacagattg gcctagccct gctgccaatc tatctatggt 130080
tgaagagcat ataaaaaaaa ttgtagctgc cactggcgtt gatgttccga ggcttgtcac 130140
aggtgcttat ttgtgctacc atttagtcca ttgtacaagc gattagcgca tttatgcttt 130200
actatcatta gtcctgccag caattttgct cttattatct tttcacctgc cgtgaataaa 130260
atgcattttt tttccaacac taatctagtt ctgtatccca caggaggaag tactttgggt 130320
acacttccat tgccattggc tgcttttgtg agcctaacca ttacatacaa acttgacaag 130380
gcatcagagc gtttccttaa ccttgccggg ccagctttag agaaccttgc tgcaagctgc 130440
ccatggccaa gcatgccaat cgtcgcggca ctgtggactc agaaggtgaa gcggtggagt 130500
gatttcctag tgttctcggc ttcacgcacg gtgttccacc ataacaacga cgcagttttc 130560
cagctcctcc gaagctgctt caccgccacc cttggaatgt cgtctaccac atcagtatgc 130620
agctgcggtg gcattgccag ccttcttggt cacggcttcg gctctcattg ctccggtggc 130680
ctctccccag tcgcgccggg aatcctctat ctccggatat tccggtgcat caaggactgc 130740
tccatactcg cggaagatat actgcgcctc ctcatgctct cggtgaaaga catagccgaa 130800
acaacggtgt cgaggcaccg atccgacaag gtcaggaaga ccaagtacgt gatgagacat 130860
ggccaggtat ccctctcttc cgccatgacg caggtgaagg tggcggcgtc gctcggcgcg 130920
acgctggtgt ggctctccgg cggcacggcg ctcgtccagt ccctgttcca ggagatgctg 130980
ccgtcgtggt tcctgtccgt gcaggacctg gggcgaggcg gcgcggcgag cgggggcacg 131040
gtgtacaagc tgggcggcca cgcgctggcc tacctcgccg tctacgccgg catgttcgcc 131100
tggaggatcg acccgacgcc ggtgtcgcgg cggcgggagc gggtgatgtg gtcgcacttc 131160
gagttcctgg cgagcgcgct ggacggcaag atctccctcg gctgcgacct ctcgctgtgg 131220
cgcgcctacg tctccgggtt cctgggcctg gtggtggagt gcacgccgtg ctgggcgcac 131280
gaggtggacc tgagggtgct caggaggctc agcgccggcc tccggcagtg gaaggaggac 131340
gagctcgccg tcgcgctcct ccgccgtgcc ggcccggagg ccatggccgc cgccgccgag 131400
ctcatcatcg gcggcgactg gtgacactac gccggcgatc tgtacataac tattgccatg 131460
tgcatgcgtg tgtagttgat ttcgatattg tggtagtaat tgatgacttt gctgatcgat 131520
cgctaggctc gttgctctct ttcgctaatg ctagtgtcca cttattagta tatcttggaa 131580
ggaaggaaac tgctcaatat atgtgtgtta aaaatggtgt tcttgaagaa gccacccgtc 131640
tctataggtt atcgctgtat ctaacatgtg tgtcgtgtgt tgctatagtg caattaattg 131700
atgtggatgg cgtggtagat gtaattaggc aaattttgca ataggacact tgttacgtgt 131760
ggttttagcc ctaggacact gcccaaactc acttttgggg aaaaacactc cataaacatg 131820
gtaatttgcc agtggatacc gcgccgatta aataatattt tctggttgag gaggaaagag 131880
aaatcgtgtg aaatgtcaaa aatgctcttg ggcccacatg tcagctctat ctcctatctc 131940
tctcctcatc tctctctttt ctctctcaga gtgcgctcgc acggggtggt gtcggtcgcg 132000
gcggagatgg cgaggacggt ggccggcgga gtggagtggg gcggcggcgg tggtggtcat 132060
gttgcttggc cacgttgtcg tggggggtgc gacacgatcg attatgggga tttcttcgca 132120
tgtggcagta gtgctcggcg agctcctctc ctcgcgcgcc gctgccgacg actccttccc 132180
ccacgcgcag ccggccggca ttccccttcc agcgcgttgc agccagccag gtcctcccct 132240
gtcttgctcg cgcggccgcc gacgagcttc tcctccgcag ccagccatcc tctcgcctgt 132300
ttgtccctcc cctgcatctt gctcgcgcgg ccgccaatga gcttcttctc cgcagccggc 132360
ccacctcccg cccgtcgttc cttcccttgc ctcgtgctca ctcggcttca cgtcgtcctc 132420
cccgaaactc accggctcta catcgcgtcc ccctcacccc gccgtggcgg cggcgcccct 132480
ttctgctgcg ggcacgggca cgacgagggg tggctccggc ggccgtgcac tcgtccaccg 132540
ccgccgccgc cctgctccac tccgccggcc gccgtcctcg ccatctgcga gagaaaagag 132600
agagagaaaa gagagagatg tggagagaga taggagatat agctgacatg tgggcccaaa 132660
ggcatttttg acatttcacg cgatttctct ctcctcccca actgaaaagt attattttaa 132720
tcggcgtggt gtccactagc aaattaccac gtttatggag tgtttttctc taaaagtgag 132780
tttgggcagt gtcctagggc taaaaccaca cataacaagt gtgctatagt aaaatttgcc 132840
atgtaattaa ggggctaggt ttggtattct atctttgtcc gtttatctct ttgtcctctc 132900
gctttgctaa atcgttgcgt tggccgagat ttcgttctgt cgaataggat gtcatgttag 132960
gatttctaat aatacgataa gaaactaata aagtgagaga tggaatggat ttgctatatc 133020
tatacagttt tcaatacagg ttgtcttttg catgtatttc ctgtaaaaca acaaatataa 133080
aataatatga tattgtatga gctatttcaa tcatcaaata aatacaacgt ttcttatatc 133140
cctcataaac ataaaaatga tactatcttc tattggaaat tggcaaaatg ccttatactt 133200
tgtatttctt attttcactt catgagaagg ggaagatggt aaactagtca tcaatctgaa 133260
aatgtcgatt gaattgcact tcagagggag atctaattaa acgttggagt cacgtggctc 133320
ctcttaatta atcccgtatg cgtatgttgc ttccctctcc ctactttatg tctcgttact 133380
ttatccgcat catcattccc ccaaagattc tggcgttacc tcactacttg gcggattaac 133440
cgatgaaaat catcgattag taaatcggtc acggccatca ggaataatat tgttgctaca 133500
tcggcactat cagatgtgga gaagaaacta tccgatgtgg agaaaaacta tcccattaaa 133560
taagttcgga ggggatttta ggcatgtgaa ataaaataag ccattaaact tgaaaattga 133620
atttatttat tttggggaaa aacttttgtg tagaaaactt ttatacaaaa tgtattgtag 133680
aaaacatgat catatattcc aatagttgtt taagaaacaa tataattagc tggtgaaaat 133740
ctagttagtt tatagtttat aaatgttaga aatatatgaa attcattatt ttcatggtga 133800
agaataaagt agagactaaa tttataaata ttgaatgtcc tatacatact cactacacac 133860
atgcacgtca catcctaatc aacatcactt cataaaatta tcattttcaa gttattttgg 133920
tcctcgttta catgaactag acaaattcat atactgaaat gagtatttta caagtttact 133980
aaattgcacc cacctaacaa gtttgtgtac cactaatgta atttactcat tctataaata 134040
atagttgcat aatcttttga aatctggatt gtttggagtt agagattctg tgactagccg 134100
cggttgttag aagctgcaca aagaaaatcc aagacaatga tactggggag gaatacatgc 134160
acggtaagca ctgatcaacg tggagaagag ttgtcatgaa catggatgaa aaggtgatgt 134220
agggttgtgt aggatgatga gatcgaggag tgcggtaacg tgaaaatctt aatcagtgaa 134280
attgcatgct tgcgacaatg agcatatggc atgaagttat tcatcagttg agttattatg 134340
gtagtagtgt aggagtatct actagtgaat ttagtaggcg gtgcacatct ccagcctgat 134400
ttggaattgg taaccaggtt gacgaaggga agagaaagag agggtggtag gtaggacgaa 134460
atgagatacc actctgatat atagttcctt atgcttcagt gtgaacttag accctttaca 134520
ctactgtgtt gctatagtat ttttgtttgc cttgtatagt gttctaatag acaaacaatt 134580
atattgtgtt aaacaacaat tgttcatgtg gctgctagat gatataatac cggttcatat 134640
atagtaacta ccatatatat atatatatat atatatatat atatatatat atatatgaaa 134700
atggttctat aaacccaggt gtatgtactc cctctcccat ctaccgtcca tctcaaccag 134760
cctcgatgaa gctccttaac ggatcaacga gcggacccgt tttgattacc caggtgtatg 134820
tacacccctt tcttatttct tattggatat ccatatacta aataattgga ttaataagaa 134880
aatttttaaa gagaataccg ttccctttat ttttcaaatt cctgcatgtg catgcactcc 134940
ggccggccgg tacaaggtca ggatcaaaaa tttgtagcat gcaattgggt ggcatccagt 135000
atatactaaa tccctcgcta gatttgagca gtatatactt tcttgtagga tcctcatggt 135060
actggtgatt tactagaaca tgcatgctaa taattaacga tagatgtata tactggttca 135120
tcagtgcttc attcgtctgg tttgttggtt tgctccatcc ggaatcacat tcatcgccag 135180
cgtgtacagc taccgttgga tcaaattaat atacaatcat tcagatgata attttttaaa 135240
ggtagtatat actgttcttg aagtaaggag tagtatgcat gtactgtttt ttaaatttag 135300
tagcagtata tactgttttt taagttagta gcagtacata ctgttttttt agtagcagta 135360
catacctgtt tttaagttag ttgcagtaca tactttagta tatactgttt ttagtagtag 135420
ttagtagaag tatatacttt ttgttagcta gtagcagtat gtactgtttt tagttagtag 135480
cagtatatac ttttcgttag ttcgtagcag tatatactgt catcctataa gttcagtata 135540
tatgtgaaaa atgcagtaaa tactgtcatc ctataaaatt cagtatatat gtgaaaaatg 135600
gagtatatat tgtcatctta caaagttcag tatatatgtg gaaaatgcag tctatactgt 135660
catcttacaa agttcaaagt tcagtatata tgtgaaaaat gcagtttata ctgtcatctt 135720
acaaagttca gtatgaaccc cttcatagaa attcagtgta tagcatcatc taaatagttc 135780
agtgcgtacc actccgtagg caaaaaaaaa aaaaaaacagt ataaacctct ctatagagaa 135840
atgcagtatc tacaaagttc aaaacatact actgacaatc aaaaaatcag cttatacttc 135900
tctatgtaga attgcagtat atacttctgc ttaacaaagg acagcttaca aagttcagta 135960
cgtacccctc cataaaaaag ttcagtatat accaatccaa aaaaatgcag tatgtactac 136020
catcttaaaa agattaagta catacccctc caaagaaaaa ttcagtatat acaaatgcat 136080
agaaatgcag tatatgcaaa acccctctct atacagaact gagatcgtgc atgaaccata 136140
ctatgcagaa cccctgtcta taggcatcaa gatttccatt tctggtgaca taccttggac 136200
tgtggtgaca cactgatttt cttgtgaccc tgcaaacaag aaaatttaag gcatcgagca 136260
tcgatctcgt cgtagaaaaa aaaccaatac taacctactg ctttggatga cctccactac 136320
tgagacccgt cgattttgcc acggctgctc tgctcctgca ttcaggcgac tccaaatcga 136380
tgacctctac tcctggaaca ccaacgagtg gcaggttctc caggtcgatt atctctgtct 136440
ccgattggtg aaggaggagc catcactgga gcaaggaacg agcagattca aagatcagaa 136500
aagatcgctt ctatgatcct ccaccagcca cccagccgcc gctgaatcgt cgcggagtca 136560
atccgaggag gtgtcgtcgc tgcctccacc tcgcgtcaaa ccgcaaatgt agcgagagct 136620
gttcgattgg ctgagtacta actgttgtga tttagataat taagcgctaa ttaaggatcc 136680
agattatttt acaaaaggaa aatcaaaaca ggtccgctcg ttgatccatt aaggagcttc 136740
atcgaggctg gttgagatgg acggtagatg ggagagggag tacatacatc tgggtatata 136800
gaaccatttt cctctatata tatatatata tatatatata tacacacaca tacatactat 136860
tgaactgtgt atatggatat tgggttcact aattaggcta ttgacacaac cgatgtaggc 136920
aataagagat tgttgacgtg tcactttaat ctaccgatta ccctaaagat atagttgacg 136980
catccaacta gagataacag acatgtcact attggagaca ttcactattg gtatatgatt 137040
gggtacattg ggtatgcgtc caacttgaga actagatata ttgagcatgt cactatcaac 137100
atatggttca cttgccatac gtttgagtag agacagtggg catgtcgcta ctgctttaga 137160
taggtacact aagcagcatg gagagaaagc cattatcttc gactagagat agcaggtata 137220
tcactactcc tttagattca tccgaatttt atccgccagc caacgtagtg atgcggtcga 137280
cgtgtcaaac ttgacaagac atgtatgtca ctgctgctac tttaggatgg aagcataagc 137340
caacctagtg atataattga cgtgtccaac caagatagtt gtcatgccac tactacttta 137400
gaatggtttc actggctagc ttatttatgt aaccgaggca tgaggcatct gaacaaaaaa 137460
tagcagacat gtcactattg ctttaggatg gtaattctaa gcagcatagt catgcacccc 137520
gaaggcgatg cgtccaaaca aaaatagtat gtatgtcact atagccatat gttgagtccc 137580
ttgcccgttt actaatgtaa ccgacgagta atgttagtac aactatagaa ttgggttgat 137640
agctggctag agatagtggg cacgtcactg tagccgtagc ttagatccat caattgtggc 137700
tagtctcttg gcagacctgt catagctaat atggccaact agagactata gatgttacca 137760
atatggccaa ttggagtttt ctcataatca tttattcgta acacaacatg acctatgagt 137820
aatgcaccat gaataaataa attttacaaa cctttggtta ttattaaact agaaaacttt 137880
cggtgctttt taagctaaac cattaaatta aaaaaacaaa acaaaggaag ttatatcata 137940
ttaggggcat ttctcataga caattgtcat ggcagctatt tgcttaacca taatgcatac 138000
ggtgaagatg cacacaatgt tctattttct catgtatcaa cttgtcgtcg cgaataaaat 138060
tatttaacga atgctatgta atatattcat tattttttc cttattttgt atggcaatcg 138120
ttttttcctt aatacttgaa ttctagatat aacctttcaa tagaacgtaa aaaaatccat 138180
gtttcctcat gcatgcaaca acaaataatt aaagttaact aaaatacagc actatataat 138240
attatatagt aacaatctta tatctttctc gactaatata tagcttcttt ttttttccaa 138300
ctatgattct attattatcg tatatcagca cacacattca acgttaaaac catgaacaac 138360
attgatgtga aagctagaga aaaaaaaaga aaaaaaaagg gagaaaggaa aaaaaactct 138420
ttttctttct ttcaagagct acaccgcaag ctcgtctcgc aattgacacc gaattcacgt 138480
tgcccccgaa aataggggtt gagagagagg aaaaaaaagt aaaaatccca cggacgctaa 138540
aaaacgcacg cgcggcgcac gcgagaaaga gagagaaaaa aaaaatggcg atggcgacgc 138600
agccgtcgtc ctaggcaagc ttcccccctc caccaccacc ccctccatgg ccgcgccgcc 138660
cctccccctc gtcctcgccg ccgccgccat agcctccctc gtcattctcg tcctcgtcgt 138720

-continued cttcgcctgc cggcgatggc ggcgcgcggt ggtagcggcg gcgccgcagc cgccgccgcg 138780
ggcggcggcg gatgtcgtcg ccgcatctcc ggtccgcagc caggttaaag atccgagctc 138840
ccctcctccc tcgctttgat ccgcacccgc gtcgacggaa tcgaacgttt cgtcggatta 138900
atctgttatt attgttgtta ctattattat tgctacgaac atttggggct ggccgccgtg 138960
gagcgagctt gttcttgcga attttcgctg tttgttcgtc gtttctttcg gatatggcct 139020
atcgttcgct gttccctcgt ctggttgctg aggaatccgt ggaaatgggg ggcgatttgg 139080
taaacccttg atggagacga acatgtgtat atgctgattt tggttgtttc actaatggtt 139140
gcaaatctgg ggtcggatta tgcgcattag ggagacgtag ccatgcttaa agatacagta 139200
cattaatgca ttactacttg ctacagatca attaaattag tatgggtata aaaacaagca 139260
ttgggttcgt ggacattaag gctgctttat tgttgctatg attatagtat accaagcgca 139320
ttgatgtatt cattaggaaa atgcggaaat aaatgtacgg cgttacacga tattctgtgg 139380
accatgtttt ttctaaaatg gaaattcaga aattgtcgga gtaatctgag gaagcgtatg 139440
gttagagtca catttgaagc ttggttctga acggtggata tcgggtttgc gctaactttg 139500
tttatgtgtg cttccatgtt ggacagcggg aaatatcatg caatttaatg gctattcata 139560
attctttgct tcataaattt tgtaaatcaa atctttacac tttacagtag caaaatactg 139620
tggaatgaac acaagttgtt gcttccttca attgaaaatt aggaagaatt ttctgttctt 139680
tttttatttt tggaaaattt tagaaagaac acatggagac aaggaaaaga ataaaacggc 139740
atgcaaaaag tgggggaaaa agagggagga tgagttggcc gtcttccccg caccgctacc 139800
ccgtcacgag ataggcactc cgtcaccctc cccccgtgtc catctgctgc ttatatcttg 139860
catccatctt ctcccatcaa cagattccat ccataagcac tgctgctgct ctcttctata 139920
tgcagcacat ctttcctacg tactaactga aatctgatca gttacttctt ggtggtattt 139980
gatcccctca cgatccgttc ttcatctctg tgtggaatgc tcatggaagc attccacaaa 140040
tcaaagaaga tggagcaaaa accggtgagc tggatacagc accccctgat atgttgtcct 140100
tttctttttc tctccaaatc gtgatttttc caaaggaaaa aaagtttttt tccttgtccc 140160
tcaactcttg gtttggtttg gtttgtattt ctcgtctcca aaactgataa aactcgtccg 140220
tcaactctca aaactgttta gatctcacct ctcactcgtt tataagtggt ttttgaccta 140280
cttggtgtag atatgggatc tgaggttgct ctagctcact tgtcagagag gttttggcgt 140340
ccatgtaaga tctacggtgg cagcggcggg gcctgcttgt catagaatcc tcatgacagc 140400
gggccctaca tagacatatg atcccgacac cacgtgggtg aaaaccacta ttagacaggt 140460
tgagggacga ttgctatgtg gttttaagag ttgagggatg atatttatcc agttttgatg 140520
ctgagggacg gaaattaaat tgagtgaaga attgagggac aagaaataga cgtttttctt 140580
tcaaaatgat gagccagtta ggtgtctagt ggcacaaata caacatctaa aatatgagat 140640
accagaacca aaatttggaa ggctaactcg ttgttcctct tgtagtttgt ctttgttgta 140700
tattagagtc aaggtgtgat gaaatttgta agtactgtag ttccatttat tctctgattc 140760
aaccctggcg tgtttttttt ttgtcattag tgatacgaag ttactgcaag tatgttagag 140820
atatttcaga agatttacag tgtgtcccat gctcaataat atattgagtt tcacagttgt 140880
atcttgcatt tttggacagt aagttagatg atttattcaa tttcatgaac cttccagatt 140940
cactcactta agcatttcgt tttgatggga acttgctcaa gttattgtct aagctgacaa 141000
aactccatgg agtatgtttc ttgcatgcaa gatgtttgag aggatgaagt ttcacatttt 141060

-continued gttttatctt ctaaaacctt ttcttataaa atctgactgc actcttaatt atttcttgaa 141120
aaattcccac cacatgatct acatcaatct cttccttcca ttgattgcag cgtggaaatc 141180
catgtatttt ttgtttgatg atttgcgctc tgcatttgca gaatgaggat ttaaataagc 141240
ctctccttga aattctggat gatcactcta gccagagtaa cacttttcct ggaaatgttg 141300
ttggagaatc ttcaaaagtt caaacaagca ggagtgatac ttcaccaaga agtcatggaa 141360
taagtgattc tggcaggact tatcctgctg attcctgcac tccgcaaggt atgtataatg 141420
atgcccaaac ctttagtagc ctcctgacat aaaaatcaac tttcttcaat ttctctcgtc 141480
tttgttgcgt tgatcatctc agttgaatat tgagtgttta ccaatgtcaa ctcttgagta 141540
acagaaattg ctatgaattt tgtaggagaa actcatgtga tcgatgttac agatgataca 141600
tctgaagagt tccatttggg aagcacactg aagtgtacaa aacagacaag ttggtcaagg 141660
cctgataaaa aacacaaaag atggggttct ggagaggata ataagaatgg aagcatttct 141720
ctaaaagata atacatatcg tacgatatcc ctcaaacctg attagaatgt ttcagtagct 141780
atgccttgca aaggtttgaa tttgtatacg catctaaccc aatcttttgc tagaaatgca 141840
ggaagcaacc tagacgtaga ggtcattgct ggcccatctc acggaataag ttgttcccga 141900
cagtcaacta gtcctacaat cccgataact cttggaaggg tccccccaag tgatttggtg 141960
ttgaaggact ctgaggtgtc agggaaacat gctcgaataa attggaatgc aaaggtaagt 142020
tgttcaggaa ctatttattc atttcttgtg ccttcgattt agtgctattt atctagttgt 142080
ttccccagcc ttgtaactaa actggaatag tgatgtttgt aatgaaactt aacattacca 142140
ttttgtttga tttgtttggt caaatatgtg cttttgttca atagtaagat gcaccttttg 142200
ttcaattaga gcccaggact cagctgactg atcaaaatgt tgagaattga gatgctaggg 142260
tggtatgatg gacacatact cctgacctaa tgccacaaga tcctgaactc acgcttttag 142320
agaaaactat tttttagttt ttgttcatac aggaactcaa taaacatttt catccatttc 142380
taaagagaaa ctgtttctgc cagaaaggtt tgcatgctac attttctttc agcatctctt 142440
tactgttagc tagttattaa cgagcagaag cttatttcct tggctgtaac tatgaaaaat 142500
tatctttgag cacaggatat gtgtgcacaa gaaggcttgt gcgcacaaga tatgttccct 142560
tatctttgag catttaacga gtagaaaatt gtacaatgga aggctaacta gtattatagc 142620
tatatgctgt aagcaaatat accaatcttg cattggttta cataaaatga agtgcttgtt 142680
catatgcaga cattgaaatg ggaaattgtg gacatgggca gcttgaatgg gacatttgtg 142740
aactctcggg cagttcacca tccaaatgtt gggtccaggc actggggtga gccagctgaa 142800
ctagcagatg gtgacattat aactctagga acttcatcaa aactatctgt aagtttttta 142860
tatgctttca gcatctcttc ttgtttctct catgtttgct gaaatatttg cttaactccc 142920
attttctttc ttgcggggca taattggact agtgtactaa cttccttcat tcataggttt 142980
tatactagtc tgacatgaag cttccagaat tgttaaacag gcatgcctta tagaattcgt 143040
ctcagcaatt gtgaacccta cacatgttaa ttcctagtta tccataatct gaaaccatta 143100
gtatttcttt aagataaata aagctagtaa ctgtgctttg aatgaaaaga tatttatttt 143160
caatcattgt tcagtcttgt gtactgaaga tacttatttt catttttatc agtattccct 143220
tctgttctaa gcctgtctgc tgtcagccca ttccaagaat aatttcctta tgtttgatcc 143280
aatttaagtt gaaaaagaat gtgcttcctg aacacaactc ggataaatat ctgctaaaat 143340
ggtttggttg gagatgaggg aattgtgcaa ctttgtatca tcaatttatt accaacaaac 143400
tagttgctct attcggtaga gctacattga tttactgcac taagataagt atgcaactaa 143460

-continued

```
cacgaccaag tctccttatc ctgttaattg gttatccttg ctgactattt gattgctcca 143520
gtccctaatt taaaaattca ttcaacattc ttcctgaaaa taaaatatgc tgactcacca 143580
agacgctgct cttattttga atttcaatca aaccatgttc tggaaattag gattttggaa 143640
tactccagct atcacaaacc gtttttttctt tcctggccaa gtactctaat tcataagctg 143700
aagtttcttc attgtattgg taatcacatt catcattcaa gttgctctgc gacatatttg 143760
aagttctatg gcgcattttc tttaacctat tctttggtag cattcttatg ttccatttta 143820
taatttgcgt tgctatgtca ctgaaggtcc agatctcact gcaaaatcag cgagtccctg 143880
ctgggattgg tatggcatct gatccaatgg tgggccgtcg aagtggaaag aagcttgcaa 143940
tggaggatat aagcttttgc cagtgccctc tgcagggtgt tgaacaggtg ctgaccattt 144000
aactatgata aatttatatg cctgtttttg ataccaactg gttttgcagt ttggactctt 144060
tggaattttt gatggacatg gtggtgatgg agctgccaga gctgtcagca agttagtctt 144120
tcattcccac ctgatattca atatatatca tggatatatt ttattctaac atatgaggat 144180
tcatgtacta acttatatct aatggaactt actctttcat tagtaatctg attatttatc 144240
atcatagcca catgaaaaac tgatgtttc tccccctcct gatttctagg atttttccag 144300
aaaatgtggc aactcttttg tctcaccatg agacaaaaga aaaggttctt tcatactctg 144360
atgcttctga cgttcttaga tatgctttta ctatgacaga agctgcaatc gatcatgagt 144420
atgaggttgg ttctcctatt ctctgatctg attattttg ttgtatggct tgaaattgcc 144480
aaagtaggtt ttggtttaaa cttctttgcc cctactatgg tgatttaatt tgtactccat 144540
gggtggttca aatgcttgca ttaaatttaa agtaaatttc acaaaactac atgtactttg 144600
cccaaactat cacaaaacta cagatttaag atgatatatc acaaaactac aaatttagaa 144660
ccaaatttat caaagaacaa cagatttaag atggagtatc ataaaattac atgtttagta 144720
ataaaattat tacaaaatta catgttttgc accaagttaa gtacaaaact acaacattta 144780
taactctaac ataatagtac ttgtaggaat ttaaacttgt aaaatatatg tagttttgtg 144840
ataatttgag tattaaatct gtagttttgc gataattcga tcaaagtact tgtagttttg 144900
tgaaatttac tctttaaatg tttagctttt ttaaccatcc tttaccttta ctatcattat 144960
ttttgttgtt gttaaactgt tcactactga gatagatttg tcattaccaa cactaaaaaa 145020
attacattag ctgagacctg tttcttatca tatatctagt tccataaatg aaacagtcaa 145080
gtcctgttct gaatgaagta cagtcatgtc ctattctatg atttgagctt tgccgtgaac 145140
ttgcattagc atagtttaac taaattttct atgcttggta cgtggtaaca agaatcccga 145200
agttccaatg tggttgccta ttgcaactta gtaaattcat ttatggatgt tcctagctgt 145260
cgtccatttc aaggttctga catgtcacta gctgaatcat gaaaacagtc attacctgtg 145320
ataacttttt attaaacact ttgggggtgc ctaaaaatgg ttttgggaag catccatatg 145380
atttctgaac cactttatgt agtgccctgc tgactaaaag ttcaggtatt ccacatttta 145440
caaacagtaa ggcgaagaat aaaagatatc ctgtcccaca ctgtgcaaat catagggtctg 145500
catctagtta atttaaatcc atctttgatc ggaacaacaa tgatatgctt tagttagttc 145560
ctgctagtag ttgcaagttg catactccct ccatcccata atataaggga ttttggaggg 145620
atgtgacata tcctaggact acgaatctgg ataggcacct gtccagattt gtagtcatag 145680
gatatgtcac atccctccaa aatcccttat atcatgggac ggagggagta ctcaactagc 145740
cgttggtgag cagtatgcat aactgctaat atcatcactg attccatcca caggattcgg 145800
```

-continued atttagaaag tttttctcca aaacattaga tcttgttgcg aaagtttttc tcctgaacat 145860
ttagatctgg ttgtgaactt catctggata tggttgatac taactttatt gatttgctgc 145920
tagttgttgc agacctaggc agtcatttat agagcagtac ttttatttgc taaatctata 145980
ttttctgatc cgacccccat gatttgaatt ataagtgttt tcatccatta tagattttgt 146040
tgcaaatatt atccacaaat gtatatacta ggtacttcat tagcttacaa tgccaaaaat 146100
acttcatgag ctctttttg ggttgaaacc tagaggtagc aacaattgtt tcttttcctg 146160
ggattctgca gtctggcctg tttttcatta tcagtagctt ccacattatt gataccattt 146220
tagccatcaa tagttttgtg ccttttctct tcaattattt ttacacgata acaactgctg 146280
tggtttatga tatttgtgtg tactatttca ggggtgcaca gcaacagtcc tgctgatttg 146340
gtttgatcaa aagaaagact gttttgccca atgtgctaat ctaggtgatt cagcttgtgt 146400
tatgaggtaa aaagtacctt tttactttat tttctgaagt ttagccgttt gtctgttgac 146460
tgtaacctcc agttttttat gtataacatc tgcttttgtc agtgtcaatg gaaagatgat 146520
tgaaatgact gaagatcatc gagtagctag tgtaactgaa cgagctagga tagcaagagc 146580
tggacaggcc ctgaaagctg gcgaagtccg gattaatggt ttgctctttg cccgtttcaa 146640
gttttgagtg caagtctgag attaccataa atggtgaaag ctatattgtt attttttatt 146700
tctccaggac ttaatctcgc caggatgttc ggagataagt ttctaaaaga gcaagattca 146760
cgcttcagct cagaaccata tgtgagccaa gctgttcaca ttacaaaagc atgcacagct 146820
tttgcagtta ttgctaggta acatgatttc tcagtgctgc gaaggtaatg cttactgatg 146880
taatgtgtca atcatgacgt tccggtgatt gtttgcatgt gtgcagcgat gggctctggg 146940
atgttattag tactaaaagg gcagttcagc ttgttgttga ggtgaacgag cacgctgttt 147000
tttcgtgtta gttgcattgt tcttttaatt gttgtctcat gctggtcata tgttgcaggg 147060
tagggagaga aacagtggtg atagtgcctc ggcggacaaa gtagccaatc gtatactaag 147120
tgaagctagg aatttgcgaa ccaaggacaa tacatccgta atatttgtag attttgacat 147180
cttgagaaca gaccattgta ttgccaaatg attttgacta tttttgggac accatattcc 147240
aagaaatcat ttgcctggct gttgctcgtc gcttccataa ttttgcttca gctatggtgt 147300
caaagatgct gcaatgtcat gaagtgttgc ctacctatcc tgtgactgta aattatgtgg 147360
acttttaagt tagcttatta ttggatctga tagactgatg taaccagtgt cattgccttc 147420
atacactgcc tcatcatttg attaggtggt tatctttcag tagatttaac ttcaaatttc 147480
ttgatgaaaa ctcaagcata aagtgcatat gcttgatgtt catcagaaac cttttaccat 147540
gtcacagaat atactacagt aagccctcca aggacatcct gccaagtgaa aactgctgtg 147600
atttcccaac aactccaaag ttccaaactc catcactggt caggttgtaa atgcattgta 147660
ttgccttgca ttgtctgtct ctttcaatca tttttgcaca aaggtcaggc ttcagaagcc 147720
tccagttgtt tccctgacag aaatggaata ctgtggaatc tgccaagggc tagaatctag 147780
tggtgtaact ctgaaattct ctgtcctaat ccagcaagat gcatgaggaa ggctagtaaa 147840
tgctgtccct tttactcttc tctgcagatt tggcacaaat cattcaattc ctttctctgc 147900
tacttagggc actgcaagtt gttagagctc tttgccttaa tttgtgagct ttgtagctga 147960
aaatcttggg tgtcaaatgc tttgcatgct tctccaaaca tgcaagttgt ttctagatct 148020
gtttgacaaa actttgacta acagtagtat gtgcacaagt gactgctgaa aaggagggaa 148080
gagttatagt gtaaatattt ttccttacta atcaaaacga tataagattt gaaaattacc 148140
agtttgaatt tacgtaaagt tcaccgtccc cccctccacc ccaaaaaaga aaaaagctgc 148200

-continued tgccaaaact tcaaattatc aaatttaatt ttgaaggtag agtattttca acgttttctt 148260
tatcagcatt gtcttttgtg aataaaagct ttattcacaa attatttctt aattgctaat 148320
tagccatttt ggcttatagt tagcctagtc tttcaagtcg ctaagtgcat atgcttgatg 148380
ttcatcagaa accttttacc atgtcataga atatactaca gtaaacttca aattatttct 148440
taatcgctaa ttagtcattt tggcttatag ttagctcttg gctaaccatg catcggcata 148500
atgtaacaag ggaggtatta actactacct accttatggg tcaatttcga caacacaggc 148560
attggcatat tgtaacaagt gaggtgttaa ctactactcc taccttatgg gtcaatttgg 148620
ccaacacact atattgttga aattaattaa ataatttccc cccgctcgct ctctctcacc 148680
ctacagtctc acaaacaaga caaacagtac agaggtacta gtaagaaaat agacacaaac 148740
atgcgtatat attggacggc atcttgtttg gttcctctgt tcactcgtac agaaactcca 148800
aagctacgta cttgaataaa aacgctaatg acctactggc caatagttaa tcaacaggca 148860
ttctgcctat atacggcctc taattaagac acaccctatc tactgaccgt atatatatgc 148920
acgtacgtag tacgtataca gtatcacgca ttgcaacagc taaactaact gtctgacaat 148980
acgctcacag aagcacgttt tgatggctag ctaactacac catgctaaca ctaagatgta 149040
cacattacaa tattaattgc ttccaacaca tatggagaaa aaggatcaat atataactga 149100
gggtatatat tctgtgtaga ataaaaattc caaaccaatc aaactcggtt gagatgagaa 149160
agtgccggtg gttgttagat gcataattaa ctgcactcat cagggtttaa gttgctcggt 149220
gtttgttagt tgatcggtgt gtgcatattg atgtgcgtgc ttgttcatct tccatgtaat 149280
aagaaaacct actactccct ccgtcctata atataagaga ttttgagttt ttgcttttaa 149340
cgtttgacca cttgtcttat tcaaaatttt ttaaaattat tatttgtgac ttgctttatt 149400
atctactgta ctttaagcac aatttttcgt tttttatatt tgaaattttt ttaaaataag 149460
acgagtggtc aaacgttgca agcaaaaact aaaaatccct tatattgtgg gacggaggga 149520
gtagttgtta tgatcctctt agatacttcc tccgtcccaa aataagtgca gttttgcact 149580
attcacgctc aacgtttgac cgttcgtctt atttgaaatt tttttaattt gtatatgaac 149640
agtaaatact gatatgtttt tttaataaaa aagatcatct ttcagctttc acaacattat 149700
aattcctttt actgaaaata ctactagtct tacccagtgg ttagattata ttaaagaaaa 149760
tatttaacta ccgacgttgt aactaggtaa aaagccaaga actaagaact tcactcatca 149820
tctaaatata tgcgcagaga ataattaatt tcatttctga agcaaattcc aaaattccaa 149880
aatttatcag tttaaattta caaatatttt gtaccaacat aaaaaaagaa taaaaaccgt 149940
gctgacgtcg aaaacgacat gtatgaaccg tttttttttt cctttgtcga cacatgtgga 150000
ggccggggag tagtacgcat agtagctcct atagtccacg tgaccgacct cggcatgagc 150060
cgtcgtgtgc agccaccagt caaaccccac caccttcaaa tcaattcttc catccccaac 150120
tatcagacca tctccctacc taagctccct cactcactcg cctttactta tcgatctcga 150180
tcatccacga gctagctagc agtgctcgcc atggccggcg gcgaggcgca tgcggcgctg 150240
caggcggtgg cgcagagcct ccggtggacc tacagcctcc tctggcagct ctgccccac 150300
caagggtacc taccctacct acctacgaca cgatgcacag tgttcatcca tggccggcca 150360
tggcggatcg tcgtcgttgt cgatgatcat cgaaggaagc tagaggatat ggctcaatac 150420
tttgataata tatatactga tctctccgta caacaaaaat ataaaaattc tagctagtat 150480
cgaatgagac atatgctatg ctagtactac gaatctaaaa agatgtacat attttgattc 150540

-continued gtattattag gatatatcac gagtttttat attttgagac ggatgtaata attctgaatt 150600
tagttgtgat cgcatggcat gcaggagctc gctggtgtgg ggggaggggc actacaacgg 150660
cgccgtcaag acgcggaagt cgacggtgat gcagccgccg ccggcggagg aggaggacga 150720
cgccgaccac gcggcgcgcc accggagccg gcagctgagg gagctctacg actggctgca 150780
gcaggccggg gagaactcca gcggcggcgt gcagacgtcg tcgacgacgg cgagccggcg 150840
gccgggggcg gctctgtcgc cggaggacct gacggagacg gagtggttct tcctcatgtc 150900
ggcatcctac tccttccctc ccggcatcgg gtatataata aaaaatatag atataaatat 150960
ttaagcatgc atgcataaat taaaccacac ttcttgttac gtgttcttgg caaaatgatg 151020
aacaattacc actaattaat tggagccaga aaccctaaag atttacccac ctggttaatt 151080
aatcggtgtg ttgatccacg catgcatgca tgcagaaaat caagatcagg atagctcctt 151140
ttcttttgca ggttaattag ctagatcttc acgtataatt agctagctag attttaaaat 151200
ataatttatt caatttgatt tatgattttt attttttatt tcaaatagat acaactgtat 151260
acaaaatttt attttggtac atacctccga tccaactaca tcagaggtaa aaaaaaaatt 151320
aaaccgttgg aattgattag aacaagatcg tgcggtcaaa ttatatcata actaactttt 151380
ctgattctct aaagcataga gatgtatata tacatcgtat tattaggctc tatatttcct 151440
gattaacact agatgcatat ataattttga tagtcaaaat atacttttga taggctctaa 151500
agaaaaactt aataacatgt actccctcca tatacttttg atagtcatat ttcatcttga 151560
cacacagatc aagtataagt aattctactt atcatccatt taaacacgct actagttatt 151620
cctcataaac aagcgattca ttaatattta catttctcga tgcttgtgta gccaatattg 151680
tgtggaagaa tggaatgtca ttaagaggat aggttgttgg attgaaatat gcctatcaaa 151740
aataaatttt tagatttgaa aatatgccta tcaaaagtag atggagggag tattaattaa 151800
tgtgaatttc caatcctact gttgtgatat taggctttgt accttcttgt ccaggaggta 151860
tatatatggc tcttttaagg atgggagaaa atatcatctt taatacaact atatatggct 151920
tttgtttgat aaatacaact tttattttgt atgaatacaa atatattgat aaatatccac 151980
cattataatc ctaacccatt aggatcatat ggtgtatatt tttttaacta tttgtttttt 152040
ataaattaat attaagagat cacaataaaa atatagtatt atgaaagtac tcttaacaac 152100
atatccaatg ataaaattat tattattaca aaatatagtg gtcaaattgt atagaattca 152160
atagcctgat tttatgacgt caagtaaatt aaataaagaa tgaaggtagt gctagagtga 152220
tcaaacaata tctctcctaa aatatgtcct ataagtttta ctccataaat ccaagggtca 152280
aaagttgttg ggttattttt ttagataata acatactacc ccttttcaaa atgtatgatt 152340
ctattgactt tttgcacaac atttaaccat ttgtcatatt aaaaattagt ataaacatct 152400
aaaaatataa gttacaatta tattttattt gatgataaaa caactcacaa caaaataaat 152460
aatatttata taatcttttt ggaataaaac gaatgatcaa acattattca aaaagtcaat 152520
ggtatagtac gttttgaaat tgatagacta tgagagcaaa attttgagat aacatggaaa 152580
attatcctct tagacattgc actgtgtaat aattaataat aatgaatgaa aggctaagac 152640
ttttcttcca ccttatataa gtggttgaat atatagcaat cacatcatta catgattttg 152700
taaccaaccg tctctatagc tccgatacag tgctagtttc acatcgtaat aattaaagag 152760
tataataata aatcgaggtg tacttctcat cgatgaagtg atgtgccgct tagctaaatt 152820
aaactcgtat gcgaaaaatc agtatatgtc cggttaattt ctaagagaga gattgagaga 152880
gaataattgc gcccctccaa atccccctct tggacgttag ggagctatat agacggtatt 152940
gctaagtgcg atgtgtacat aacgtacctg tcgtaggaac atttctcatc caaattaagt 153000
agtaatgcat ggcatgaaat ccatttttgt attttgcatg gcaaagaatg acaacaagga 153060
atacactagc tagccctgcc ctttttcaat ttaatttaac atcaaactta gttattgtat 153120
ttcttttgtc agaatagcat gcattgcata ctctttaaaa ataattaatt agtgtatttt 153180
actagtctta caaaagtatc aagagagaca actaattata gttgggagac accaaacttg 153240
tttttaataa tgacaattaa aaccctacct ctacatccaa catagacgta catagtccga 153300
aggcgccaaa tatttgtaca tttagctacc agatttcagt acgagttctc acattataat 153360
tttgattttt ttattttttt tataaacaat ctggtaccct tttatgtctg gaaggaaaaa 153420
aaaaatctaa attgcaacat tttagtcggt gagaatggta ctctgtccta gctactttct 153480
acacatgaga gagagagaga gagagagaga gagagccttt aattgccctt gcccatgcat 153540
ctttctttgc acacatgtat gcttttcaca ttgtcatgag gagagaactt gttaagttgc 153600
acacatgtgt gctttgcatg tcttcaggtt acctggaagg gcatttgcaa ggagaggcca 153660
tgtatggctc actggagcaa atgaagttga cagcaaagta ttcctaagag caattcttgc 153720
caaggttcag ccatcacctt ctcttaccta tttttcactc tgaatgccaa cagtgctttg 153780
cacattgtag tctgtttgca gactgcaaat gatgaccata atcagatcag aaaataaaat 153840
aatattatat actttttgag ccagctagca agaatatgta acaataattc tccttttttt 153900
ttcttgttct tttccctgat gtggtgcata acaaataacc aaactgatga atggcagagt 153960
gctggtatcc aggtatttgc ctctaaaagt agctacacgt ttactatgaa attttgtggc 154020
ttttgttcat ctttggatgc agtggccatt atctaaaaac tatgaatttc cagactgcag 154080
tttttatcta attttgtgac tttgtacatc agacagttgt gtgcattcct gttgtcgatg 154140
gcgtcctgga aattggaact acggaaaagg tgatttcgta tattatcagc tgacaatcta 154200
attatatggg ccatataatt aagtataaat caaaatacct cataatatat tataaagtat 154260
ctaatgtgat tatgtgaata ttggctattt caatgtaatt tgatatatga aactgataat 154320
cctctgaaac tccgtaagga tcaaactaat caaaatgtat atattttcaa ggtggaggaa 154380
gatatgggcc tgattcagta tgcaaggggc atcttcatgg atcaacatgg catccacatg 154440
aagcctaccc tctcacagca ctcaacatcc aacccagtca cccactgtac tcatcagcat 154500
ccaatccagg ttcagatgca actaggtatc accagccaaa caaagtttga ttattcagat 154560
gagctcaatg cagatgagga gaatgatgac acagaagaag agggcatgtc aggttcagac 154620
actaacaaca ctgacactga aaggaattca ggccagctgc aacttcaaat gcaagaccaa 154680
ctgaacatgg tgagcaatga ccaccagaca ataccaaata atgcagtttc cagtgagcta 154740
atgcagtgtg agatgtcaga agtggtaaga gatggctgct caaataatat tttagaggat 154800
gaaatccaaa tgctgatgga ttgccaaaac agtaattgtc agttaaattt gcaagggcca 154860
gatgagcctt gtcactcttg gcattttctc tgcgaggagt tacaaaatga ttaccagcca 154920
ggtattacat ttgagaagat aatccttcaa aagcaccctt gttccaaaaa tatatatttg 154980
tactcttcac acaagcactg ccattttttt tctttttgc atacatcctc aattcttgca 155040
tttcttttcc atatatttga tacaactgtc tccatttccc ttctgtcaca gctactgaag 155100
atcaagtggc atcacctgaa aatacccatt acccaaaaac actcatgaca atcctacatt 155160
acaacacgct gcgacagcaa gagatgaaca tcaagaacta cttgccagtt tcagagaaat 155220
catcattctc cagatggact actcctgaag gaagtgatga caacaagacc atgatcagtc 155280
caggcaccac acagagaatg ctcaagagca tcctgatgat tgttcccagt agtcactgca 155340
gttacagggg agcagaaaca cctgaatcaa ggggcgggaa aggcgcaagt ggatgccatc 155400
caaggtgatt tcagtgccaa ccatgtgctg aaagagagga gaagaagaga gaagctcaat 155460
gagaagttca taattctgcg atctttggta cctttcatga caaaggtaat taagtactcc 155520
ctctatttct ataaagccgt atttgactag ttatcttatt tagaaagtat gtgcaaatat 155580
gtaaaatata agtcatactt aaagaacttt taatgttatt aaataataag tcacaccaaa 155640
aataaaacat atatattttt aataagataa atgattaaat gtatatataa aaattaatag 155700
cgtcacatat tttaaaatag aggggtattt aagtacccac aggatcatca aaattcagtt 155760
atcttttctt aagcctctaa cgaacattgg aagatcctca ctaatggcag catgaatcta 155820
gggttcacta tttcggaatg caaaatatgt tttaccgggc atccgatttt taaaaaattc 155880
agaatgaaga aaattgaatc ttttttatgg atttgaataa atcttgataa attcgaaaaa 155940
atttccgaac ttttggccag aagtgaatcc tacccgtatc caccggtaat aaacctaaat 156000
ttttgggagt aatgaattaa tgttatatat aatccatgaa ttatatagtt ccaaactact 156060
ccgtaacaaa ttttcaggag tagtgaaatt aatattatta caatctcaga aaaaaatggc 156120
agaaacaatt aatctgtttt caattattaa ttaatttgtt tttgtgtcca gatggacaag 156180
gcgtcgatac taggcgacac gatcgagtac gtgaagcagc taaggaaccg catacaagag 156240
ctcgagtcgt cgtcgtcgtc gtcacgagca gccgcccggg cgccatcggc ggcggccgcc 156300
gggaggcgga ggaagagatc cgccgccgcc gccactgcca cggcggcgga agggatgagc 156360
agcagcaatg gccgcaatgg cggcgaggcg gcggaggtgg tgcaggtgtc catcatcgag 156420
agcgacgcgc tgctggagct ccggtgcggt tgcggcggcg gcggcggcgg tgtggtgctg 156480
ctccgggtga tgcaggcgat gcaggagctc cagctggagg tcaccgccgt ccaggcctcg 156540
tgcgccggtg gcgagctgct cgccgagctg cgcgccaagg tcgtcgttat gatcctgatc 156600
tgcatgaaaa tgcaaatgca aatgcaaatg cagaattaag ctttcattct tgctcctctg 156660
aattctgaat ttatatattc acccttcttt cgatctgctc gtacgttcgt ttcgcctaaa 156720
ttatgtacaa attaactgaa tctttgaact gaaaataact gaatcttttt tgtgtgtttt 156780
tgtgtgggtg aattggttgg cgcaggtgaa ggggaggagg aggagcagca tcgctcaggt 156840
gaagagggcc atccatctcg tcctctcctc ctcatcgata tcaccctgaa ttaattaata 156900
attaatctag cttcgtgcat gaatgcatgc cacaaatata tacaaattta ccatatcaat 156960
atgtgagaga gtaataatca tataattgca atcaagcacc tgtgctgcat gcatatatat 157020
attctgattg caattcattt gcaaatgtta aaactagata tgtatgtaca tatatcatat 157080
atgtggagta cattaacatt agattaatta gaaccatcta tatatctaac catcgtggca 157140
aattggttag atcagggaag tgaaaaaact ctagtaataa taatagtaat gtaatgccat 157200
tttat 157205

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tcaattcttc catccccaac 20

-continued

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

atgccatgcg atcacaacta                                                  20


<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

ctgatctctc cgtacaacaa aa                                               22


<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

tgccaagaac acgtaacaag                                                  20


<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

gagggagctc tacgactgg                                                   19


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

ccgcacgatc ttgttctaat                                                  20


<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

caggatagct ccttttcttt tgc                                              23
```

```
<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

ggcatatttc aatccaacaa cc                                            22


<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

tcgatgcttg tgtagccaat                                               20


<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

tttgatcact ctagcactac cttca                                         25


<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

gcctgatttt atgacgtcaa gt                                            22


<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

gcactgtatc ggagctatag aga                                           23


<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

ggctaagact tttcttccac ctt                                           23


<210> SEQ ID NO 23
```

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgcaatgcat gctattctga 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttgcatggc aaagaatgac 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctgaagaca tgcaaagcac 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cttgcccatg catctttctt 20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccactgcatc caaagatgaa c 21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttccctgatg tggtgcataa 20

<210> SEQ ID NO 29
<211> LENGTH: 20

<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
gagggtaggc ttcatgtgga 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
atgggcctga ttcagtatgc 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
ggaacaaggg tgcttttgaa 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
gccttgtcac tcttggcatt 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
ggttggcact gaaatcacct 20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
caccacacag agaatgctca a 21

<210> SEQ ID NO 35
<211> LENGTH: 20
<212> TYPE: DNA

<213> ORGANISM: Artificial Sequence
<220> FEATURE:
<223> OTHER INFORMATION: Description of Artificial Sequence: Synthetic
primer

<400> SEQUENCE: 35
catgctgcca ttagtgagga 20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
agcctctaac gaacattgga a 21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
cagaggagca agaatgaaag c 21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
gcgacagcaa gagatgaaca 20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
acgggtagga ttcacttctg g 21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
tgcgatcttt ggtacctttc a 21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
gctctcgatg atggacacct 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
agcagctaag gaaccgcata 20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
ttcagggtga tatcgatgag g 21

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
tcaacgtttg accgttcatc 20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
cacatgtgtc gacaaaggaa a 21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
cgtcgaaaac gacatgtatg a 21

<210> SEQ ID NO 47
<211> LENGTH: 20
<212> TYPE: DNA
<213> ORGANISM: Artificial Sequence
<220> FEATURE:

<223> OTHER INFORMATION: Description of Artificial Sequence: Synthetic
primer

<400> SEQUENCE: 47
gttggggatg gaagaattga 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
acctacgaca cgatgcacag 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
atgccatgcg atcacaacta 20

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
ttgcaacatt ttagtcggtg ag 22

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
ccatacatgg cctctccttg 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
tacaggggag cagaaacacc 20

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
aaaggtacca aagatcgcag aa 22

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
caggtgtcca tcatcgagag 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
aggatcataa cgacgacctt 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
gccaaggtcg tcgttatgat 20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
ccaaccaatt cacccacac 19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
ggagggttgc cgatatatga 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
atgcagcggg agtttttatg 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
tatggctaca cgcctacacg 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gaagcgtggg atgtttgttt 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
tactccccca ttcctctcct 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
agccctgctc actgttcatt 20

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
aactcttagt ggggtcttag tcct 24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
caaagggagt gatacctaca catt 24

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ggagtggttc ttcgacagta aaa 23

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
ggagacgcag ttgaagatcc 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
aggggcagtt ttcagtcaga 20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ctattgcccc ctgtggtcta 20

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
atcatatctg gggtcggata gaa 23

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
gtacatgcag taccgcgaca 20

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
tgcatgctta attacgtggt c 21

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
tgggacggag ggagtagtag 20

<210> SEQ ID NO 74
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
acgcaaggct tagctg 16

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
aaatgaaagc gatgcga 17

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
caggcaccac acagagaatg 20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77

-continued

```
ctcctctctt tcagcacatg g                                                21


<210> SEQ ID NO 78
<211> LENGTH: 1987
<212> TYPE: DNA
<213> ORGANISM: Oryza sativa

<400> SEQUENCE: 78

atggccggcg gcgaggcgca tgcggcgctg caggcggtgg cgcagagcct ccggtggacc      60

tacagcctcc tctggcagct ctgcccccac caagggagct cgctggtgtg gggggagggg     120

cactacaacg gcgccgtcaa gacgcggaag tcgacggtga tgcagccgcc gccggcggag     180

gaggaggacg acgccgacca cgcggcgcgc caccggagcc ggcagctgag ggagctctac     240

gactggctgc agcaggccgg ggagaactcc agcggcggcg tgcagacgtc gtcgacgacg     300

gcgagccggc ggccgggggc ggctctgtcg ccggaggacc tgacggagac ggagtggttc     360

ttcctcatgt cggcatccta ctccttccct cccggcatcg ggttacctgg aagggcattt     420

gcaaggagag gccatgtatg gctcactgga gcaaatgaag ttgacagcaa agtattccta     480

agagcaattc ttgccaagac agttgtgtgc attcctgttg tcgatggcgt cctggaaatt     540

ggaactacgg aaaaggtgga ggaagatatg ggcctgattc agtatgcaag ggcatcttc      600

atggatcaac atggcatcca catgaagcct accctctcac agcactcaac atccaaccca     660

gtcacccact gtactcatca gcatccaatc caggttcaga tgcaactagg tatcaccagc     720

caaacaaagt ttgattattc agatgagctc aatgcagatg aggagaatga tgacacagaa     780

gaagagggca tgtcaggttc agacactaac aacactgaca ctgaaaggaa ttcaggccag     840

ctgcaacttc aaatgcaaga ccaactgaac atggtgagca atgaccacca gacaatacca     900

aataatgcag tttccagtga gctaatgcag tgtgagatgt cagaagtggt aagagatggc     960

tgctcaaata atattttaga ggatgaaatc caaatgctga tggattgcca aaacagtaat    1020

tgtcagttaa atttgcaagg gccagatgag ccttgtcact cttggcattt tctctgcgag    1080

gagttacaaa atgattacca gccagctact gaagatcaag tggcatcacc tgaaaatacc    1140

cattacccaa aaacactcat gacaatccta cattacaaca cgctgcgaca gcaagagatg    1200

aacatcaaga actacttgcc agtttcagag aaatcatcat tctccagatg gactactcct    1260

gaaggaagtg atgacaacaa gaccatgatc agtccaggca ccacacagag aatgctcaag    1320

agcatcctga tgattgttcc cagtagtcac tgcagttaca ggggagcaga aacacctgaa    1380

tcaaggggcg ggaaaggcgc aagtggatgc catccaaggt gatttcagtg ccaaccatgt    1440

gctgaaagag aggagaagaa gagagaagct caatgagaag ttcataattc tgcgatcttt    1500

ggtacctttc atgacaaaga tggacaaggc gtcgatacta ggcgacacga tcgagtacgt    1560

gaagcagcta aggaaccgca tacaagagct cgagtcgtcg tcgtcgtcgt cacgagcagc    1620

cgcccgggcg ccatcggcgg cggccgccgg gaggcggagg aagagatccg ccgccgccgc    1680

cactgccacg gcggcggaag ggatgagcag cagcaatggc cgcaatggcg gcgaggcggc    1740

ggaggtggtg caggtgtcca tcatcgagag cgacgcgctg ctggagctcc ggtgcggttg    1800

cggcggcggc ggcggcggtg tggtgctgct ccgggtgatg caggcgatgc aggagctcca    1860

gctggaggtc accgccgtcc aggcctcgtg cgccggtggc gagctgctcg ccgagctgcg    1920

cgccaaggtc gtcgttatga tcctgatctg catgaaaatg caaatgcaaa tgcaaatgca    1980

gaattaa                                                              1987
```

<210> SEQ ID NO 79
<211> LENGTH: 1987
<212> TYPE: DNA
<213> ORGANISM: Oryza sativa

<400> SEQUENCE: 79
atggccggcg gcgaggcgca tgcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggctctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatacca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca gcaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggatgc catccaaggt gatttcagtg ccaaccatgt 1440
gctgaaagag aggagaagaa gagagaagct caatgagaag ttcataattc tgcgatcttt 1500
ggtacctttc atgacaaaga tggacaaggc gtcgatacta ggcgacacga tcgagtacgt 1560
gaagcagcta aggaaccgca tacaagagct cgagtcgtcg tcgtcgtcgt cacgagcagc 1620
cgcccgggcg ccatcggcgg cggccgccgg gaggcggagg aagagatccg ccgccgccgc 1680
cactgccacg gcggcggaag ggatgagcag cagcaatggc cgcaatggcg gcgaggcggc 1740
ggaggtggtg caggtgtcca tcatcgagag cgacgcgctg ctggagctcc ggtgcggttg 1800
cggcggcggc ggcggcggtg tggtgctgct ccgggtgatg caggcgatgc aggagctcca 1860
gctggaggtc accgccgtcc aggcctcgtg cgccggtggc gagctgctcg ccgagctgcg 1920
cgccaaggtc gtcgttatga tcctgatctg catgaaaatg caaatgcaaa tgcaaatgca 1980
gaattaa 1987

<210> SEQ ID NO 80
<211> LENGTH: 1987
<212> TYPE: DNA

<213> ORGANISM: Oryza sativa

<400> SEQUENCE: 80
atggccggcg gcgaggcgca tgcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggctctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag gggcatcttc 600
atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatacca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca gcaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggatgc catccaaggt gatttcagtg ccaaccatgt 1440
gctgaaagag aggagaagaa gagagaagct caatgagaag ttcataattc tgcgatcttt 1500
ggtacctttc atgacaaaga tggacaaggc gtcgatacta ggcgacacga tcgagtacgt 1560
gaagcagcta aggaaccgca tacaagagct cgagtcgtcg tcgtcgtcgt cacgagcagc 1620
cgcccgggcg ccatcggcgg cggccgccgg gaggcggagg aagagatccg ccgccgccgc 1680
cactgccacg gcggcggaag ggatgagcag cagcaatggc cgcaatggcg gcgaggcggc 1740
ggaggtggtg caggtgtcca tcatcgagag cgacgcgctg ctggagctcc ggtgcggttg 1800
cggcggcggc ggcggcggtg tggtgctgct ccgggtgatg caggcgatgc aggagctcca 1860
gctggaggtc accgccgtcc aggcctcgtg cgccggtggc gagctgctcg ccgagctgcg 1920
cgccaaggtc gtcgttatga tcctgatctg catgaaaatg caaatgcaaa tgcaaatgca 1980
gaattaa 1987

<210> SEQ ID NO 81
<211> LENGTH: 1730
<212> TYPE: DNA
<213> ORGANISM: Oryza sativa
<220> FEATURE:
<221> NAME/KEY: modified_base
<222> LOCATION: (1717)..(1717)
<223> OTHER INFORMATION: a, c, t, g, unknown or other

<400> SEQUENCE: 81

```
atggccggcg gcgaggcgca agcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaaggt ggaggaagat atgggcctga ttcagtatgc aaggggcatc    540
ttcatggatc aacatggcat ccacatgaag cctaccctct cacagcactc aacatccaac    600
ccggtcaccc actgtactca tcagcatcca atccaggttc agatgcaact aggtatcacc    660
agccaaacaa agtttgatta ttcagatgag ctcaatgcag atgaggagaa tgatgacaca    720
gaagaagagg gcatgtcagg ttcagacact aacaacactg acactgaaag gaattcaggc    780
cagctgcaac ttcaaatgca agaccaactg aacatggtga gcaatgacca ccagacaatg    840
ccaaataatg cagtttccag tgagctaatg cagtgtgaga tgtcagaagt gggccagatg    900
agccttgtca ctcttggcat ttctctgcg aggagttaca aaatgattac cagccagaga    960
aatcatcatt ctccagatgg actactcctg aaggaagtga tgacaacaag accatgatca   1020
gtccaggcac cacacagaga atgctcaaga gcatcctgat gattgttccc agtagtcact   1080
gaagttacag gggagcagaa acacctgaat caaggggcgg gaaaggcgca agtggaacgc   1140
gaaaagtcgg tgccatccaa ggtgatttca gtgccaacca tgtgctgaaa gagaggagaa   1200
gaagagagaa gctcaatgag aagttcataa ttctgcgatc tttggtacct ttcatgacaa   1260
agatggacaa ggcgtcgata ctaggcgaca cgatcgagta cgtgaagcag ctaaggaacc   1320
gcatacaaga gctcgagtcg tcgtcgtcgt cgtcacgagc agccgcccgg gcgccatcgg   1380
cggcggccgc cgggaggcgg aggaagagat ccgccgccgc cgccactgcc acggcggcgg   1440
aagggatgag cagcagcaat ggccgcaatg gcggcgaggc ggcggaggtg gtgcaggtgt   1500
ccatcatcga gagcgacgcg ctgctggagc tccggtgcgg ttgcggcggc ggcggcggcg   1560
gcggcggtgt ggtgctgctc cgggtgatgc aggcgatgca ggagctccag ctggaggtca   1620
ccgccgtcca ggcctcgtgc gccggcggcg agctgctcgc cgagctgcgc gccaaggtcg   1680
tcgtcatgat cctgatctgc atgaaaatgc aaatgcnaat gcagaattaa               1730
```

<210> SEQ ID NO 82
<211> LENGTH: 2001
<212> TYPE: DNA
<213> ORGANISM: Oryza sativa

<400> SEQUENCE: 82

```
atggccggcg gcgaggcgca tgcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
```

```
gactggctgc agcaggccgg ggagaactcc agcggcggcg tgcagacgtc gtcgacgacg    300

gcgagccggc ggccgggggc ggctctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag ggcatcttc     600

atggatcaac atggcatcca catgaagcct accctctcac agcactcaac atccaaccca    660

gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatacca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgtcagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca gcaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggcg ggaaaggcgc aagtggaacg cgaaaagtcg gtgccatcca aggtgatttc   1440

agtgccaacc atgtgctgaa agagaggaga agaagagaga agctcaatga gaagttcata   1500

attctgcgat ctttggtacc tttcatgaca aagatggaca aggcgtcgat actaggcgac   1560

acgatcgagt acgtgaagca gctaaggaac cgcatacaag agctcgagtc gtcgtcgtcg   1620

tcgtcacgag cagccgcccg ggcgccatcg gcggcggccg ccgggaggcg gaggaagaga   1680

tccgccgccg ccgccactgc cacggcggcg gaagggatga gcagcagcaa tggccgcaat   1740

ggcggcgagg cggcggaggt ggtgcaggtg tccatcatcg agagcgacgc gctgctggag   1800

ctccggtgcg gttgcggcgg cggcggcggc ggtgtggtgc tgctccgggt gatgcaggcg   1860

atgcaggagc tccagctgga ggtcaccgcc gtccaggcct cgtgcgccgg tggcgagctg   1920

ctcgccgagc tgcgcgccaa ggtcgtcgtt atgatcctga tctgcatgaa aatgcaaatg   1980

caaatgcaaa tgcagaatta a                                             2001
```

```
<210> SEQ ID NO 83
<211> LENGTH: 2001
<212> TYPE: DNA
<213> ORGANISM: Oryza sativa

<400> SEQUENCE: 83
```

```
atggccggcg gcgaggcgca tgcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggctctgtcg ccggaggacc tgacggagac ggagtggttc    360
```

ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag gggcatcttc 600
atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatacca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca gcaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgtcgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggtgtggtgc tgctccgggt gatgcaggcg 1860
atgcaggagc tccagctgga ggtcaccgcc gtccaggcct cgtgcgccgg tggcgagctg 1920
ctcgccgagc tgcgcgccaa ggtcgtcgtt atgatcctga tctgcatgaa aatgcaaatg 1980
caaatgcaaa tgcagaatta a 2001

<210> SEQ ID NO 84
<211> LENGTH: 1987
<212> TYPE: DNA
<213> ORGANISM: Oryza sativa

<400> SEQUENCE: 84
atggccggcg gcgaggcgca tgcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggctctgtcg ccggaggacc tgacggagac ggagtggttc 360
ttcctcatgt cggcatccta ctccttccct cccggcatcg ggttacctgg aagggcattt 420

-continued

```
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatacca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca gcaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggatgc catccaaggt gatttcagtg ccaaccatgt   1440
gctgaaagag aggagaagaa gagagaagct caatgagaag ttcataattc tgcgatcttt   1500
ggtacctttc atgacaaaga tggacaaggc gtcgatacta ggcgacacga tcgagtacgt   1560
gaagcagcta aggaaccgca tacaagagct cgagtcgtcg tcgtcgtcgt cacgagcagc   1620
cgcccgggcg ccatcggcgg cggccgccgg gaggcggagg aagagatccg ccgccgccgc   1680
cactgccacg gcggcggaag ggatgagcag cagcaatggc cgcaatggcg gcgaggcggc   1740
ggaggtggtg caggtgtcca tcatcgagag cgacgcgctg ctggagctcc ggtgcggttg   1800
cggcggcggc ggcggcggtg tggtgctgct ccgggtgatg caggcgatgc aggagctcca   1860
gctggaggtc accgccgtcc aggcctcgtg cgccggtggc gagctgctcg ccgagctgcg   1920
cgccaaggtc gtcgttatga tcctgatctg catgaaaatg caaatgcaaa tgcaaatgca   1980
gaattaa                                                             1987
```

<210> SEQ ID NO 85
<211> LENGTH: 1987
<212> TYPE: DNA
<213> ORGANISM: Oryza sativa

<400> SEQUENCE: 85

```
atggccggcg gcgaggcgca tgcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgagggc ggctctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
```

ggaactacgg aaaaggtgga ggaagatatg ggcctgattc agtatgcaag ggcatcttc 600 atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatacca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca gcaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggatgc catccaaggt gatttcagtg ccaaccatgt 1440
gctgaaagag aggagaagaa gagagaagct caatgagaag ttcataattc tgcgatcttt 1500
ggtacctttc atgacaaaga tggacaaggc gtcgatacta ggcgacacga tcgagtacgt 1560
gaagcagcta aggaaccgca tacaagagct cgagtcgtcg tcgtcgtcgt cacgagcagc 1620
cgcccgggcg ccatcggcgg cggccgccgg gaggcggagg aagagatccg ccgccgccgc 1680
cactgccacg gcggcggaag ggatgagcag cagcaatggc cgcaatggcg gcgaggcggc 1740
ggaggtggtg caggtgtcca tcatcgagag cgacgcgctg ctggagctcc ggtgcggttg 1800
cggcggcggc ggcggcggtg tggtgctgct ccgggtgatg caggcgatgc aggagctcca 1860
gctggaggtc accgccgtcc aggcctcgtg cgccggtggc gagctgctcg ccgagctgcg 1920
cgccaaggtc gtcgttatga tcctgatctg catgaaaatg caaatgcaaa tgcaaatgca 1980
gaattaa 1987

<210> SEQ ID NO 86
<211> LENGTH: 2001
<212> TYPE: DNA
<213> ORGANISM: Oryza sativa

<400> SEQUENCE: 86
atggccggcg gcgaggcgca agcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggcgctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaacccg 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatgcca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca acaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgaagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgtcgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggcggcggtg tggtgctgct ccgggtgatg 1860
caggcgatgc aggagctcca gctggaggtc accgccgtcc aggcctcgtg cgccggcggc 1920
gagctgctcg ccgagctgcg cgccaaggtc gtcgtcatga tcctgatctg catgaaaatg 1980
caaatgcaaa tgcagaatta a 2001

<210> SEQ ID NO 87
<211> LENGTH: 2000
<212> TYPE: DNA
<213> ORGANISM: Oryza sativa

<400> SEQUENCE: 87
tggccggcgg cgaggcgcaa gcggcgctgc aggcggtggc gcagagcctc cggtggacct 60
acagcctcct ctggcagctc tgccccacc aagggagctc gctggtgtgg ggggaggggc 120
actacaacgg cgccgtcaag acgcggaagt cgacggtgat gcagccgccg ccggcggagg 180
aggaggacga cgccgaccac gcggcgcgcc accggagccg gcagctgagg gagctctacg 240
actggctgca gcaggccggg gagaactcca gcggcggcgt gcagacgtcg tcgacgacgg 300
cgagccggcg gccgggggcg gcgctgtcgc cggaggacct gacggagacg gagtggttct 360
tcctcatgtc ggcatcctac tccttccctc ccggcatcgg gttacctgga agggcatttg 420
caaggagagg ccatgtatgg ctcactggag caaatgaagt tgacagcaaa gtattcctaa 480
gagcaattct tgccaagaca gttgtgtgca ttcctgttgt cgatggcgtc ctggaaattg 540
gaactacgga aaaggtggag gaagatatgg gcctgattca gtatgcaagg ggcatcttca 600
tggatcaaca tggcatccac atgaagccta ccctctcaca gcactcaaca tccaacccgg 660
tcacccactg tactcatcag catccaatcc aggttcagat gcaactaggt atcaccagcc 720

-continued

```
aaacaaagtt tgattattca gatgagctca atgcagatga ggagaatgat gacacagaag    780
aagagggcat gtcaggttca gacactaaca acactgacac tgaaaggaat tcaggccagc    840
tgcaacttca aatgcaagac caactgaaca tggtgagcaa tgaccaccag acaatgccaa    900
ataatgcagt ttccagtgag ctaatgcagt gtgagatgtc agaagtggta agagatggct    960
gctcaaataa tattttagag gatgaaatcc aaatgctgat ggattgccaa aacagtaatt   1020
gtcagttaaa tttgcaaggg ccagatgagc cttgtcactc ttggcatttt ctctgcgagg   1080
agttacaaaa tgattaccag ccagctactg aagatcaagt ggcatcacct gaaaataccc   1140
attacccaaa aacactcatg acaatcctac attacaacac gctgcgacaa caagagatga   1200
acatcaagaa ctacttgcca gtttcagaga aatcatcatt ctccagatgg actactcctg   1260
aaggaagtga tgacaacaag accatgatca gtccaggcac cacacagaga atgctcaaga   1320
gcatcctgat gattgttccc agtagtcact gaagttacag gggagcagaa acacctgaat   1380
caaggggcgg gaaaggcgca agtggaacgc gaaaagtcgg tgccatccaa ggtgatttca   1440
gtgccaacca tgtgctgaaa gagaggagaa gaagagagaa gctcaatgag aagttcataa   1500
ttctgcgatc tttggtacct ttcatgacaa agatggacaa ggcgtcgata ctaggcgaca   1560
cgatcgagta cgtgaagcag ctaaggaacc gcatacaaga gctcgagtcg tcgtcgtcgt   1620
cgtcacgagc agccgcccgg gcgccatcgg cggcggccgc cgggaggcgg aggaagagat   1680
ccgccgccgc cgccactgcc acggcggcgg aagggatgag cagcagcaat ggccgcaatg   1740
gcggcgaggc ggcggaggtg gtgcaggtgt ccatcatcga gagcgacgcg ctgctggagc   1800
tccggtgcgg ttgcggcggc ggcggcggcg gcggcggtgt ggtgctgctc cgggtgatgc   1860
aggcgatgca ggagctccag ctggaggtca ccgccgtcca ggcctcgtgc gccggcggcg   1920
agctgctcgc cgagctgcgc gccaaggtcg tcgtcatgat cctgatctgc atgaaaatgc   1980
aaatgcaaat gcagaattaa                                               2000
```

<210> SEQ ID NO 88
<211> LENGTH: 2001
<212> TYPE: DNA
<213> ORGANISM: Oryza sativa

<400> SEQUENCE: 88

```
atggccggcg gcgaggcgca agcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaacccg    660
gtcacccact gtactcatca gcatccaatc caggttcaga tgcaactagg tatcaccagc    720
caaacaaagt ttgattattc agatgagctc aatgcagatg aggagaatga tgacacagaa    780
```

```
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgaagttaca ggggagcaga aacacctgaa   1380
tcaaggggcg ggaaaggcgc aagtggaacg cgaaaagtcg gtgccatcca aggtgatttc   1440
agtgccaacc atgtgctgaa agagaggaga agaagagaga agctcaatga gaagttcata   1500
attctgcgat ctttggtacc tttcatgaca aagatggaca aggcgtcgat actaggcgac   1560
acgatcgagt acgtgaagca gctaaggaac cgcatacaag agctcgagtc gtcgtcgtcg   1620
tcgtcacgag cagccgcccg ggcgccatcg gcggcggccg ccgggaggcg gaggaagaga   1680
tccgccgccg ccgccactgc cacggcggcg gaagggatga gcagcagcaa tggccgcaat   1740
ggcggcgagg cggcggaggt ggtgcaggtg tccatcatcg agagcgacgc gctgctggag   1800
ctccggtgcg gttgcggcgg cggcggcggc ggcggcggtg tggtgctgct ccgggtgatg   1860
caggcgatgc aggagctcca gctggaggtc accgccgtcc aggcctcgtg cgccggcggc   1920
gagctgctcg ccgagctgcg cgccaaggtc gtcgtcatga tcctgatctg catgaaaatg   1980
caaatgcaaa tgcagaatta a                                             2001
```

<210> SEQ ID NO 89
<211> LENGTH: 2007
<212> TYPE: DNA
<213> ORGANISM: Oryza sativa

<400> SEQUENCE: 89

```
atggccggcg gcgaggcgca agcggcgctg caggcggtgg cgcagagcct ccggtggacc     60
tacagcctcc tctggcagct ctgcccccac caaggtagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
```

```
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggaacg cgaaaagtcg gtgccatcca aggtgatttc   1440
agtgccaacc atgtgctgaa agagaggaga agaagagaga agctcaatga gaagttcata   1500
attctgcgat ctttggtacc tttcatgaca aagatggaca aggcgtcgat actaggcgac   1560
acgatcgagt acgtgaagca gctaaggaac cgcatacaag agctcgagtc gtcgtcgtcg   1620
tcgtcacgag cagccgcccg ggcgccatcg gcggcggccg ccgggaggcg gaggaagaga   1680
tccgccgccg ccgccactgc cacggcggcg gaagggatga gcagcagcaa tggccgcaat   1740
ggcggcgagg cggcggaggt ggtgcaggtg tccatcatcg agagcgacgc gctgctggag   1800
ctccggtgcg gttgcggcgg cggcggcggc ggcggcggcg gcggtgtggt gctgctccgg   1860
gtgatgcagg cgatgcagga gctccagctg gaggtcaccg ccgtccaggc ctcgtgcgcc   1920
ggcggcgagc tgctcgccga gctgcgcgcc aaggtcgtcg tcatgatcct gatctgcatg   1980
aaaatgcaaa tgcaaatgca gaattaa                                       2007
```

<210> SEQ ID NO 90
<211> LENGTH: 2007
<212> TYPE: DNA
<213> ORGANISM: Oryza rufipogon

<400> SEQUENCE: 90

```
atggccggcg gcgaggcgca agcggcgctg caggcggtgg cgcagagcct ccggtggacc     60
tacagcctcc tctggcagct ctgcccccac caaggtagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
aataatgcag tttccagtga gctaatgcag tgtgagatgt cagaagtggt aagagatggc    960
```

-continued

```
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggaacg cgaaaagtcg gtgccatcca aggtgatttc   1440
agtgccaacc atgtgctgaa agagaggaga agaagagaga agctcaatga gaagttcata   1500
attctgcgat ctttggtacc tttcatgaca aagatggaca aggcgtcgat actaggcgac   1560
acgatcgagt acgtgaagca gctaaggaac cgcatacaag agctcgagtc gtcgtcgtcg   1620
tcgtcacgag cagccgcccg ggcgccatcg gcggcggccg ccgggaggcg gaggaagaga   1680
tccgccgccg ccgccactgc cacggcggcg gaagggatga gcagcagcaa tggccgcaat   1740
ggcggcgagg cggcggaggt ggtgcaggtg tccatcatcg agagcgacgc gctgctggag   1800
ctccggtgcg gttgcggcgg cggcggcggc ggcggcggcg gcggtgtggt gctgctccgg   1860
gtgatgcagg cgatgcagga gctccagctg gaggtcaccg ccgtccaggc ctcgtgcgcc   1920
ggcggcgagc tgctcgccga gctgcgcgcc aaggtcgtcg tcatgatcct gatctgcatg   1980
aaaatgcaaa tgcaaatgca gaattaa                                       2007
```

<210> SEQ ID NO 91
<211> LENGTH: 1987
<212> TYPE: DNA
<213> ORGANISM: Oryza sativa

<400> SEQUENCE: 91

```
atggccggcg gcgaggcgca agcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggctctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatacca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
```

gagttacaaa atgattacca gccagctact gaagatcaag tggcatcacc tgaaaatacc 1140
cattacccaa aaacactcat gacaatccta cattacaaca cgctgcgaca gcaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggatgc catccaaggt gatttcagtg ccaaccatgt 1440
gctgaaagag aggagaagaa gagagaagct caatgagaag ttcataattc tgcgatcttt 1500
ggtacctttc atgacaaaga tggacaaggc gtcgatacta ggcgacacga tcgagtacgt 1560
gaagcagcta aggaaccgca tacaagagct cgagtcgtcg tcgtcgtcgt cacgagcagc 1620
cgcccgggcg ccatcggcgg cggccgccgg gaggcggagg aagagatccg ccgccgccgc 1680
cactgccacg gcggcggaag ggatgagcag cagcaatggc cgcaatggcg gcgaggcggc 1740
ggaggtggtg caggtgtcca tcatcgagag cgacgcgctg ctggagctcc ggtgcggttg 1800
cggcggcggc ggcggcggtg tggtgctgct ccgggtgatg caggcgatgc aggagctcca 1860
gctggaggtc accgccgtcc aggcctcgtg cgccggtggc gagctgctcg ccgagctgcg 1920
cgccaaggtc gtcgttatga tcctgatctg catgaaaatg caaatgcaaa tgcaaatgca 1980
gaattaa 1987

<210> SEQ ID NO 92
<211> LENGTH: 1987
<212> TYPE: DNA
<213> ORGANISM: Oryza sativa

<400> SEQUENCE: 92
atggccggcg gcgaggcgca agcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggctctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatacca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140

-continued

```
cattacccaa aaacactcat gacaatccta cattacaaca cgctgcgaca gcaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggatgc catccaaggt gatttcagtg ccaaccatgt   1440
gctgaaagag aggagaagaa gagagaagct caatgagaag ttcataattc tgcgatcttt   1500
ggtacctttc atgacaaaga tggacaaggc gtcgatacta ggcgacacga tcgagtacgt   1560
gaagcagcta aggaaccgca tacaagagct cgagtcgtcg tcgtcgtcgt cacgagcagc   1620
cgcccgggcg ccatcggcgg cggccgccgg gaggcggagg aagagatccg ccgccgccgc   1680
cactgccacg gcggcggaag ggatgagcag cagcaatggc cgcaatggcg gcgaggcggc   1740
ggaggtggtg caggtgtcca tcatcgagag cgacgcgctg ctggagctcc ggtgcggttg   1800
cggcggcggc ggcggcggtg tggtgctgct ccgggtgatg caggcgatgc aggagctcca   1860
gctggaggtc accgccgtcc aggcctcgtg cgccggtggc gagctgctcg ccgagctgcg   1920
cgccaaggtc gtcgttatga tcctgatctg catgaaaatg caaatgcaaa tgcaaatgca   1980
gaattaa                                                              1987
```

<210> SEQ ID NO 93
<211> LENGTH: 2001
<212> TYPE: DNA
<213> ORGANISM: Oryza sativa

<400> SEQUENCE: 93

```
atggccggcg gcgaggcgca agcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaacccg    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
```

gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgccgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggcggcggtg tggtgctgct ccgggtgatg 1860
caggcgatgc aggagctcca gctggaggtc accgccgtcc aggcctcgtg cgccggcggc 1920
gagctgctcg ccgagctgcg cgccaaggtc gtcgtcatga tcctgatctg catgaaaatg 1980
caaatgcaaa tgcagaatta a 2001

<210> SEQ ID NO 94
<211> LENGTH: 2001
<212> TYPE: DNA
<213> ORGANISM: Oryza sativa

<400> SEQUENCE: 94
atggccggcg gcgaggcgca agcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggcgctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaacccg 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatgcca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca acaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320

-continued

```
agcatcctga tgattgttcc cagtagtcac tgcagttaca ggggagcaga aacacctgaa   1380

tcaaggggcg ggaaaggcgc aagtggaacg cgaaaagtcg gtgccatcca aggtgatttc   1440

agtgccaacc atgtgctgaa agagaggaga agaagagaga agctcaatga gaagttcata   1500

attctgcgat ctttggtacc tttcatgaca aagatggaca aggcgtcgat actaggcgac   1560

acgatcgagt acgtgaagca gctaaggaac cgcatacaag agctcgagtc gtcgtcgtcg   1620

tcgtcacgag cagccgcccg ggcgccatcg gcggcggccg ccgggaggcg gaggaagaga   1680

tccgccgccg ccgccactgc cacggcggcg gaagggatga gcagcagcaa tggccgcaat   1740

ggcggcgagg cggcggaggt ggtgcaggtg tccatcatcg agagcgacgc gctgctggag   1800

ctccggtgcg gttgcggcgg cggcggcggc ggcggcggtg tggtgctgct ccgggtgatg   1860

caggcgatgc aggagctcca gctggaggtc accgccgtcc aggcctcgtg cgccggcggc   1920

gagctgctcg ccgagctgcg cgccaaggtc gtcgtcatga tcctgatctg catgaaaatg   1980

caaatgcaaa tgcagaatta a                                             2001
```

<210> SEQ ID NO 95
<211> LENGTH: 1995
<212> TYPE: DNA
<213> ORGANISM: Oryza rufipogon

<400> SEQUENCE: 95

```
atggccggcg gcgaggcgca agcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggcgctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag gggcatcttc    600

atggatcaac atggcatcca catgaagcct accctctcac agcactcaac atccaaccca    660

gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatgcca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgtcagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca acaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggcg ggaaaggcgc aagtggaacg cgaaaagtcg gtgccatcca aggtgatttc   1440
```

```
agtgccaacc atgtgctgaa agagaggaga agaagagaga agctcaatga gaagttcata   1500

attctgcgat ctttggtacc tttcatgaca aagatggaca aggcgtcgat actaggcgac   1560

acgatcgagt acgtgaagca gctaaggaac cgcatacaag agctcgagtc gtcgtcgtcg   1620

tcgtcacgag cagccgcccg ggcgccatcg gcggcggccg ccgggaggcg gaggaagaga   1680

tccgccgccg ccgccactgc cacggcggcg gaagggatga gcagcagcaa tggccgcaat   1740

ggcggcgagg cggcggaggt ggtgcaggtg tccatcatcg agagcgacgc gctgctggag   1800

ctccggtgcg gttgcggcgg cggcggcggc ggtgtggtgc tgctccgggt gatgcaggcg   1860

atgcaggagc tccagctgga ggtcaccgcc gtccaggcct cgtgcgccgg cggcgagctg   1920

ctcgccgagc tgcgcgccaa ggtcgtcgtc atgatcctga tctgcatgaa aatgcaaatg   1980

caaatgcaga attaa                                                    1995
```

<210> SEQ ID NO 96
<211> LENGTH: 1995
<212> TYPE: DNA
<213> ORGANISM: Oryza rufipogon

<400> SEQUENCE: 96

```
atggccggcg gcgaggcgca agcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggcgctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag ggcatcttc    600

ttggatcaac atggcatcca catgaagcct accctctcac agcactcaac atccaaccca    660

gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatgcca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgccagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca acaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggca ggaaaggcgc aagtggaacg cgaaaagtcg gtgccatcca aggtgatttc   1440

agtgccaacc atgtgctgaa agagaggaga agaagagaga agctcaatga gaagttcata   1500
```

```
attctgcgat ctttggtacc tttcatgaca aagatggaca aggcgtcgat actaggcgac   1560

acgatcgagt acgtgaagca gctaaggaac cgcatacaag agctcgagtc gtcgtcgtcg   1620

tcgtcacgag cagccgcccg ggcgccatcg gcggcggccg ccgggaggcg gaggaagaga   1680

tccgccgccg ccgccactgc cacggcggcg gaagggatga gcagcagcaa tggccgcaat   1740

ggcggcgagg cggcggaggt ggtgcaggtg tccatcatcg agagcgacgc gctgctggag   1800

ctccggtgcg gttgcggcgg cggcggcggc ggtgtggtgc tgctccgggt gatgcaggcg   1860

atgcaggagc tccagctgga ggtcaccgcc gtccaggcct cgtgcgccgg tggcgagctg   1920

ctcgccgagc tgcgcgccaa ggtcgtcgtc atgatcctga tctgcatgaa aatgcaaatg   1980

caaatgcaga attaa                                                    1995
```

<210> SEQ ID NO 97
<211> LENGTH: 1987
<212> TYPE: DNA
<213> ORGANISM: Oryza sativa

<400> SEQUENCE: 97

```
atggccggcg gcgaggcgca tgcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggctctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag ggcatcttc     600

atggatcaac atggcatcca catgaagcct accctctcac agcactcaac atccaaccca    660

gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatacca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgtcagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca gcaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggcg ggaaaggcgc aagtggatgc catccaaggt gatttcagtg ccaaccatgt   1440

gctgaaagag aggagaagaa gagagaagct caatgagaag ttcataattc tgcgatcttt   1500

ggtacctttc atgacaaaga tggacaaggc gtcgatacta ggcgacacga tcgagtacgt   1560

gaagcagcta aggaaccgca tacaagagct cgagtcgtcg tcgtcgtcgt cacgagcagc   1620
```

```
cgcccgggcg ccatcggcgg cggccgccgg gaggcggagg aagagatccg ccgccgccgc   1680

cactgccacg gcggcggaag ggatgagcag cagcaatggc cgcaatggcg gcgaggcggc   1740

ggaggtggtg caggtgtcca tcatcgagag cgacgcgctg ctggagctcc ggtgcggttg   1800

cggcggcggc ggcggcggtg tggtgctgct ccgggtgatg caggcgatgc aggagctcca   1860

gctggaggtc accgccgtcc aggcctcgtg cgccggtggc gagctgctcg ccgagctgcg   1920

cgccaaggtc gtcgttatga tcctgatctg catgaaaatg caaatgcaaa tgcaaatgca   1980

gaattaa                                                             1987
```

<210> SEQ ID NO 98
<211> LENGTH: 1987
<212> TYPE: DNA
<213> ORGANISM: Oryza sativa

<400> SEQUENCE: 98

```
atggccggcg gcgaggcgca tgcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggctctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag ggcatcttc     600

atggatcaac atggcatcca catgaagcct accctctcac agcactcaac atccaaccca    660

gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatacca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgtcagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca gcaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggcg ggaaaggcgc aagtggatgc catccaaggt gatttcagtg ccaaccatgt   1440

gctgaaagag aggagaagaa gagagaagct caatgagaag ttcataattc tgcgatcttt   1500

ggtacctttc atgacaaaga tggacaaggc gtcgatacta ggcgacacga tcgagtacgt   1560

gaagcagcta aggaaccgca tacaagagct cgagtcgtcg tcgtcgtcgt cacgagcagc   1620

cgcccgggcg ccatcggcgg cggccgccgg gaggcggagg aagagatccg ccgccgccgc   1680
```

-continued

```
cactgccacg gcggcggaag ggatgagcag cagcaatggc cgcaatggcg gcgaggcggc   1740

ggaggtggtg caggtgtcca tcatcgagag cgacgcgctg ctggagctcc ggtgcggttg   1800

cggcggcggc ggcggcggtg tggtgctgct ccgggtgatg caggcgatgc aggagctcca   1860

gctggaggtc accgccgtcc aggcctcgtg cgccggtggc gagctgctcg ccgagctgcg   1920

cgccaaggtc gtcgttatga tcctgatctg catgaaaatg caaatgcaaa tgcaaatgca   1980

gaattaa                                                             1987
```

<210> SEQ ID NO 99
<211> LENGTH: 1987
<212> TYPE: DNA
<213> ORGANISM: Oryza sativa

<400> SEQUENCE: 99

```
atggccggcg gcgaggcgca tgcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggctctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag ggcatcttc    600

atggatcaac atggcatcca catgaagcct accctctcac agcactcaac atccaaccca    660

gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatacca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgtcagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca gcaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggcg ggaaaggcgc aagtggatgc catccaaggt gatttcagtg ccaaccatgt   1440

gctgaaagag aggagaagaa gagagaagct caatgagaag ttcataattc tgcgatcttt   1500

ggtacctttc atgacaaaga tggacaaggc gtcgatacta ggcgacacga tcgagtacgt   1560

gaagcagcta aggaaccgca tacaagagct cgagtcgtcg tcgtcgtcgt cacgagcagc   1620

cgcccgggcg ccatcggcgg cggccgccgg gaggcggagg aagagatccg ccgccgccgc   1680

cactgccacg gcggcggaag ggatgagcag cagcaatggc cgcaatggcg gcgaggcggc   1740

ggaggtggtg caggtgtcca tcatcgagag cgacgcgctg ctggagctcc ggtgcggttg   1800
```

```
cggcggcggc ggcggcggtg tggtgctgct ccgggtgatg caggcgatgc aggagctcca   1860

gctggaggtc accgccgtcc aggcctcgtg cgccggtggc gagctgctcg ccgagctgcg   1920

cgccaaggtc gtcgttatga tcctgatctg catgaaaatg caaatgcaaa tgcaaatgca   1980

gaattaa                                                             1987


<210> SEQ ID NO 100
<211> LENGTH: 1730
<212> TYPE: DNA
<213> ORGANISM: Oryza sativa
<220> FEATURE:
<221> NAME/KEY: modified_base
<222> LOCATION: (1717)..(1717)
<223> OTHER INFORMATION: a, c, t, g, unknown or other

<400> SEQUENCE: 100

atggccggcg gcgaggcgca agcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggcgctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaaggt ggaggaagat atgggcctga ttcagtatgc aaggggcatc    540

ttcatggatc aacatggcat ccacatgaag cctaccctct cacagcactc aacatccaac    600

ccggtcaccc actgtactca tcagcatcca atccaggttc agatgcaact aggtatcacc    660

agccaaacaa agtttgatta ttcagatgag ctcaatgcag atgaggagaa tgatgacaca    720

gaagaagagg gcatgtcagg ttcagacact aacaacactg acactgaaag gaattcaggc    780

cagctgcaac ttcaaatgca agaccaactg aacatggtga gcaatgacca ccagacaatg    840

ccaaataatg cagtttccag tgagctaatg cagtgtgaga tgtcagaagt gggccagatg    900

agccttgtca ctcttggcat ttctctgcg aggagttaca aaatgattac cagccagaga    960

aatcatcatt ctccagatgg actactcctg aaggaagtga tgacaacaag accatgatca   1020

gtccaggcac cacacagaga atgctcaaga gcatcctgat gattgttccc agtagtcact   1080

gaagttacag gggagcagaa acacctgaat caaggggcgg gaaaggcgca agtggaacgc   1140

gaaaagtcgg tgccatccaa ggtgatttca gtgccaacca tgtgctgaaa gagaggagaa   1200

gaagagagaa gctcaatgag aagttcataa ttctgcgatc tttggtacct ttcatgacaa   1260

agatggacaa ggcgtcgata ctaggcgaca cgatcgagta cgtgaagcag ctaaggaacc   1320

gcatacaaga gctcgagtcg tcgtcgtcgt cgtcacgagc agccgcccgg gcgccatcgg   1380

cggcggccgc cgggaggcgg aggaagagat ccgccgccgc cgccactgcc acggcggcgg   1440

aagggatgag cagcagcaat ggccgcaatg gcggcgaggc ggcggaggtg gtgcaggtgt   1500

ccatcatcga gagcgacgcg ctgctggagc tccggtgcgg ttgcggcggc ggcggcggcg   1560

gcggcggtgt ggtgctgctc cgggtgatgc aggcgatgca ggagctccag ctggaggtca   1620

ccgccgtcca ggcctcgtgc gccggcggcg agctgctcgc cgagctgcgc gccaaggtcg   1680

tcgtcatgat cctgatctgc atgaaaatgc aaatgcnaat gcagaattaa               1730
```

<210> SEQ ID NO 101
<211> LENGTH: 2001
<212> TYPE: DNA
<213> ORGANISM: Oryza sativa

<400> SEQUENCE: 101
atggccggcg gcgaggcgca tgcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggctctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatacca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca gcaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgtcgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggtgtggtgc tgctccgggt gatgcaggcg 1860
atgcaggagc tccagctgga ggtcaccgcc gtccaggcct cgtgcgccgg tggcgagctg 1920
ctcgccgagc tgcgcgccaa ggtcgtcgtt atgatcctga tctgcatgaa aatgcaaatg 1980
caaatgcaaa tgcagaatta a 2001

<210> SEQ ID NO 102
<211> LENGTH: 2001

<212> TYPE: DNA
<213> ORGANISM: Oryza sativa

<400> SEQUENCE: 102
atggccggcg gcgaggcgca tgcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggctctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatacca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca gcaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgtcgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggtgtggtgc tgctccgggt gatgcaggcg 1860
atgcaggagc tccagctgga ggtcaccgcc gtccaggcct cgtgcgccgg tggcgagctg 1920
ctcgccgagc tgcgcgccaa ggtcgtcgtt atgatcctga tctgcatgaa aatgcaaatg 1980
caaatgcaaa tgcagaatta a 2001

<210> SEQ ID NO 103
<211> LENGTH: 1987
<212> TYPE: DNA
<213> ORGANISM: Oryza sativa

<400> SEQUENCE: 103

```
atggccggcg gcgaggcgca tgcggcgctg caggcggtgg cgcagagcct ccggtggacc      60
tacagcctcc tctggcagct ctgcccccac caagggagct cgctggtgtg gggggagggg     120
cactacaacg gcgccgtcaa gacgcggaag tcgacggtga tgcagccgcc gccggcggag     180
gaggaggacg acgccgacca cgcggcgcgc caccggagcc ggcagctgag ggagctctac     240
gactggctgc agcaggccgg ggagaactcc agcggcggcg tgcagacgtc gtcgacgacg     300
gcgagccggc ggccgggggc ggctctgtcg ccggaggacc tgacggagac ggagtggttc     360
ttcctcatgt cggcatccta ctccttccct cccggcatcg ggttacctgg aagggcattt     420
gcaaggagag gccatgtatg gctcactgga gcaaatgaag ttgacagcaa agtattccta     480
agagcaattc ttgccaagac agttgtgtgc attcctgttg tcgatggcgt cctggaaatt     540
ggaactacgg aaaaggtgga ggaagatatg ggcctgattc agtatgcaag ggcatcttc      600
atggatcaac atggcatcca catgaagcct accctctcac agcactcaac atccaaccca     660
gtcacccact gtactcatca gcatccaatc caggttcaga tgcaactagg tatcaccagc     720
caaacaaagt ttgattattc agatgagctc aatgcagatg aggagaatga tgacacagaa     780
gaagagggca tgtcaggttc agacactaac aacactgaca ctgaaaggaa ttcaggccag     840
ctgcaacttc aaatgcaaga ccaactgaac atggtgagca atgaccacca gacaatacca     900
aataatgcag tttccagtga gctaatgcag tgtgagatgt cagaagtggt aagagatggc     960
tgctcaaata atattttaga ggatgaaatc caaatgctga tggattgcca aaacagtaat    1020
tgtcagttaa atttgcaagg gccagatgag ccttgtcact cttggcattt tctctgcgag    1080
gagttacaaa atgattacca gccagctact gaagatcaag tggcatcacc tgaaaatacc    1140
cattacccaa aaacactcat gacaatccta cattacaaca cgctgcgaca gcaagagatg    1200
aacatcaaga actacttgcc agtttcagag aaatcatcat tctccagatg gactactcct    1260
gaaggaagtg atgacaacaa gaccatgatc agtccaggca ccacacagag aatgctcaag    1320
agcatcctga tgattgttcc cagtagtcac tgcagttaca ggggagcaga aacacctgaa    1380
tcaaggggcg ggaaaggcgc aagtggatgc catccaaggt gatttcagtg ccaaccatgt    1440
gctgaaagag aggagaagaa gagagaagct caatgagaag ttcataattc tgcgatcttt    1500
ggtacctttc atgacaaaga tggacaaggc gtcgatacta ggcgacacga tcgagtacgt    1560
gaagcagcta aggaaccgca tacaagagct cgagtcgtcg tcgtcgtcgt cacgagcagc    1620
cgcccgggcg ccatcggcgg cggccgccgg gaggcggagg aagagatccg ccgccgccgc    1680
cactgccacg gcggcggaag ggatgagcag cagcaatggc cgcaatggcg gcgaggcggc    1740
ggaggtggtg caggtgtcca tcatcgagag cgacgcgctg ctggagctcc ggtgcggttg    1800
cggcggcggc ggcggcggtg tggtgctgct ccgggtgatg caggcgatgc aggagctcca    1860
gctggaggtc accgccgtcc aggcctcgtg cgccggtggc gagctgctcg ccgagctgcg    1920
cgccaaggtc gtcgttatga tcctgatctg catgaaaatg caaatgcaaa tgcaaatgca    1980
gaattaa                                                              1987
```

<210> SEQ ID NO 104
<211> LENGTH: 1987
<212> TYPE: DNA
<213> ORGANISM: Oryza sativa

<400> SEQUENCE: 104

```
atggccggcg gcgaggcgca tgcggcgctg caggcggtgg cgcagagcct ccggtggacc      60
```

-continued

```
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgagggc ggctctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatacca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca gcaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggatgc catccaaggt gatttcagtg ccaaccatgt   1440
gctgaaagag aggagaagaa gagagaagct caatgagaag ttcataattc tgcgatcttt   1500
ggtacctttc atgacaaaga tggacaaggc gtcgatacta ggcgacacga tcgagtacgt   1560
gaagcagcta aggaaccgca tacaagagct cgagtcgtcg tcgtcgtcgt cacgagcagc   1620
cgcccgggcg ccatcggcgg cggccgccgg gaggcggagg aagagatccg ccgccgccgc   1680
cactgccacg gcggcggaag ggatgagcag cagcaatggc cgcaatggcg gcgaggcggc   1740
ggaggtggtg caggtgtcca tcatcgagag cgacgcgctg ctggagctcc ggtgcggttg   1800
cggcggcggc ggcggcggtg tggtgctgct ccgggtgatg caggcgatgc aggagctcca   1860
gctggaggtc accgccgtcc aggcctcgtg cgccggtggc gagctgctcg ccgagctgcg   1920
cgccaaggtc gtcgttatga tcctgatctg catgaaaatg caaatgcaaa tgcaaatgca   1980
gaattaa                                                             1987
```

<210> SEQ ID NO 105
<211> LENGTH: 2001
<212> TYPE: DNA
<213> ORGANISM: Oryza sativa

<400> SEQUENCE: 105

```
atggccggcg gcgaggcgca agcggcgctg caggcggtgg cgcagagcct ccggtggacc     60
tacagcctcc tctggcagct ctgcccccac caagggagct cgctggtgtg gggggagggg    120
```

-continued

```
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc    600
atggatcaac atggcatcca catgaagcct accctctcac agcactcaac atccaacccg    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgaagttaca ggggagcaga aacacctgaa   1380
tcaaggggcg ggaaaggcgc aagtggaacg cgaaaagtcg gtgccatcca aggtgatttc   1440
agtgccaacc atgtgctgaa agagaggaga agaagagaga agctcaatga gaagttcata   1500
attctgcgat ctttggtacc tttcatgaca aagatggaca aggcgtcgat actaggcgac   1560
acgatcgagt acgtgaagca gctaaggaac cgcatacaag agctcgagtc gtcgtcgtcg   1620
tcgtcacgag cagccgcccg ggcgccatcg gcggcggccg ccgggaggcg gaggaagaga   1680
tccgccgccg ccgccactgc cacggcggcg gaagggatga gcagcagcaa tggccgcaat   1740
ggcggcgagg cggcggaggt ggtgcaggtg tccatcatcg agagcgacgc gctgctggag   1800
ctccggtgcg gttgcggcgg cggcggcggc ggcggcggtg tggtgctgct ccgggtgatg   1860
caggcgatgc aggagctcca gctggaggtc accgccgtcc aggcctcgtg cgccggcggc   1920
gagctgctcg ccgagctgcg cgccaaggtc gtcgtcatga tcctgatctg catgaaaatg   1980
caaatgcaaa tgcagaatta a                                             2001
```

<210> SEQ ID NO 106
<211> LENGTH: 2000
<212> TYPE: DNA
<213> ORGANISM: Oryza sativa

<400> SEQUENCE: 106

```
tggccggcgg cgaggcgcaa gcggcgctgc aggcggtggc gcagagcctc cggtggacct     60
acagcctcct ctggcagctc tgccccccacc aagggagctc gctggtgtgg ggggaggggc    120
actacaacgg cgccgtcaag acgcggaagt cgacggtgat gcagccgccg ccggcggagg    180
aggaggacga cgccgaccac gcggcgcgcc accggagccg gcagctgagg gagctctacg    240
```

```
actggctgca gcaggccggg gagaactcca gcggcggcgt gcagacgtcg tcgacgacgg    300

cgagccggcg gccgggggcg gcgctgtcgc cggaggacct gacggagacg gagtggttct    360

tcctcatgtc ggcatcctac tccttccctc ccggcatcgg gttacctgga agggcatttg    420

caaggagagg ccatgtatgg ctcactggag caaatgaagt tgacagcaaa gtattcctaa    480

gagcaattct tgccaagaca gttgtgtgca ttcctgttgt cgatggcgtc ctggaaattg    540

gaactacgga aaaggtggag gaagatatgg gcctgattca gtatgcaagg ggcatcttca    600

tggatcaaca tggcatccac atgaagccta ccctctcaca gcactcaaca tccaacccgg    660

tcacccactg tactcatcag catccaatcc aggttcagat gcaactaggt atcaccagcc    720

aaacaaagtt tgattattca gatgagctca atgcagatga ggagaatgat gacacagaag    780

aagagggcat gtcaggttca gacactaaca acactgacac tgaaaggaat tcaggccagc    840

tgcaacttca aatgcaagac caactgaaca tggtgagcaa tgaccaccag acaatgccaa    900

ataatgcagt ttccagtgag ctaatgcagt gtgagatgtc agaagtggta agagatggct    960

gctcaaataa tattttagag gatgaaatcc aaatgctgat ggattgccaa aacagtaatt   1020

gtcagttaaa tttgcaaggg ccagatgagc cttgtcactc ttggcatttt ctctgcgagg   1080

agttacaaaa tgattaccag ccagctactg aagatcaagt ggcatcacct gaaaataccc   1140

attacccaaa aacactcatg acaatcctac attacaacac gctgcgacaa caagagatga   1200

acatcaagaa ctacttgcca gtttcagaga aatcatcatt ctccagatgg actactcctg   1260

aaggaagtga tgacaacaag accatgatca gtccaggcac cacacagaga atgctcaaga   1320

gcatcctgat gattgttccc agtagtcact gaagttacag gggagcagaa acacctgaat   1380

caaggggcgg gaaaggcgca agtggaacgc gaaaagtcgg tgccatccaa ggtgatttca   1440

gtgccaacca tgtgctgaaa gagaggagaa gaagagagaa gctcaatgag aagttcataa   1500

ttctgcgatc tttggtacct ttcatgacaa agatggacaa ggcgtcgata ctaggcgaca   1560

cgatcgagta cgtgaagcag ctaaggaacc gcatacaaga gctcgagtcg tcgtcgtcgt   1620

cgtcacgagc agccgcccgg gcgccatcgg cggcggccgc cgggaggcgg aggaagagat   1680

ccgccgccgc cgccactgcc acggcggcgg aagggatgag cagcagcaat ggccgcaatg   1740

gcggcgaggc ggcggaggtg gtgcaggtgt ccatcatcga gagcgacgcg ctgctggagc   1800

tccggtgcgg ttgcggcggc ggcggcggcg gcggcggtgt ggtgctgctc cgggtgatgc   1860

aggcgatgca ggagctccag ctggaggtca ccgccgtcca ggcctcgtgc gccggcggcg   1920

agctgctcgc cgagctgcgc gccaaggtcg tcgtcatgat cctgatctgc atgaaaatgc   1980

aaatgcaaat gcagaattaa                                               2000
```

<210> SEQ ID NO 107
<211> LENGTH: 2001
<212> TYPE: DNA
<213> ORGANISM: Oryza sativa

<400> SEQUENCE: 107

```
atggccggcg gcgaggcgca agcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300
```

```
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag gggcatcttc    600
atggatcaac atggcatcca catgaagcct accctctcac agcactcaac atccaacccg    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgaagttaca ggggagcaga aacacctgaa   1380
tcaaggggcg ggaaaggcgc aagtggaacg cgaaaagtcg gtgccatcca aggtgatttc   1440
agtgccaacc atgtgctgaa agagaggaga agaagagaga agctcaatga gaagttcata   1500
attctgcgat ctttggtacc tttcatgaca aagatggaca aggcgtcgat actaggcgac   1560
acgatcgagt acgtgaagca gctaaggaac cgcatacaag agctcgagtc gtcgtcgtcg   1620
tcgtcacgag cagccgcccg ggcgccatcg gcggcggccg ccgggaggcg gaggaagaga   1680
tccgccgccg ccgccactgc cacggcggcg gaagggatga gcagcagcaa tggccgcaat   1740
ggcggcgagg cggcggaggt ggtgcaggtg tccatcatcg agagcgacgc gctgctggag   1800
ctccggtgcg gttgcggcgg cggcggcggc ggcggcggtg tggtgctgct ccgggtgatg   1860
caggcgatgc aggagctcca gctggaggtc accgccgtcc aggcctcgtg cgccggcggc   1920
gagctgctcg ccgagctgcg cgccaaggtc gtcgtcatga tcctgatctg catgaaaatg   1980
caaatgcaaa tgcagaatta a                                             2001
```

```
<210> SEQ ID NO 108
<211> LENGTH: 2007
<212> TYPE: DNA
<213> ORGANISM: Oryza sativa

<400> SEQUENCE: 108

atggccggcg gcgaggcgca agcggcgctg caggcggtgg cgcagagcct ccggtggacc     60
tacagcctcc tctggcagct ctgcccccac caaggtagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
```

```
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggaacg cgaaaagtcg gtgccatcca aggtgatttc   1440
agtgccaacc atgtgctgaa agagaggaga agaagagaga agctcaatga gaagttcata   1500
attctgcgat ctttggtacc tttcatgaca aagatggaca aggcgtcgat actaggcgac   1560
acgatcgagt acgtgaagca gctaaggaac cgcatacaag agctcgagtc gtcgtcgtcg   1620
tcgtcacgag cagccgcccg ggcgccatcg gcggcggccg ccgggaggcg gaggaagaga   1680
tccgccgccg ccgccactgc cacggcggcg gaagggatga gcagcagcaa tggccgcaat   1740
ggcggcgagg cggcggaggt ggtgcaggtg tccatcatcg agagcgacgc gctgctggag   1800
ctccggtgcg gttgcggcgg cggcggcggc ggcggcggcg gcggtgtggt gctgctccgg   1860
gtgatgcagg cgatgcagga gctccagctg gaggtcaccg ccgtccaggc ctcgtgcgcc   1920
ggcggcgagc tgctcgccga gctgcgcgcc aaggtcgtcg tcatgatcct gatctgcatg   1980
aaaatgcaaa tgcaaatgca gaattaa                                       2007
```

<210> SEQ ID NO 109
<211> LENGTH: 2007
<212> TYPE: DNA
<213> ORGANISM: Oryza rufipogon

<400> SEQUENCE: 109

```
atggccggcg gcgaggcgca agcggcgctg caggcggtgg cgcagagcct ccggtggacc     60
tacagcctcc tctggcagct ctgcccccac caaggtagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
```

agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600 atggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatgcca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca acaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgtcgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggcggcggcg gcggtgtggt gctgctccgg 1860
gtgatgcagg cgatgcagga gctccagctg gaggtcaccg ccgtccaggc ctcgtgcgcc 1920
ggcggcgagc tgctcgccga gctgcgcgcc aaggtcgtcg tcatgatcct gatctgcatg 1980
aaaatgcaaa tgcaaatgca gaattaa 2007

<210> SEQ ID NO 110
<211> LENGTH: 1987
<212> TYPE: DNA
<213> ORGANISM: Oryza sativa

<400> SEQUENCE: 110
atggccggcg gcgaggcgca agcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggctctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600

-continued

```
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatacca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca gcaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggatgc catccaaggt gatttcagtg ccaaccatgt   1440
gctgaaagag aggagaagaa gagagaagct caatgagaag ttcataattc tgcgatcttt   1500
ggtacctttc atgacaaaga tggacaaggc gtcgatacta ggcgacacga tcgagtacgt   1560
gaagcagcta aggaaccgca tacaagagct cgagtcgtcg tcgtcgtcgt cacgagcagc   1620
cgcccgggcg ccatcggcgg cggccgccgg gaggcggagg aagagatccg ccgccgccgc   1680
cactgccacg gcggcggaag ggatgagcag cagcaatggc cgcaatggcg gcgaggcggc   1740
ggaggtggtg caggtgtcca tcatcgagag cgacgcgctg ctggagctcc ggtgcggttg   1800
cggcggcggc ggcggcggtg tggtgctgct ccgggtgatg caggcgatgc aggagctcca   1860
gctggaggtc accgccgtcc aggcctcgtg cgccggtggc gagctgctcg ccgagctgcg   1920
cgccaaggtc gtcgttatga tcctgatctg catgaaaatg caaatgcaaa tgcaaatgca   1980
gaattaa                                                             1987
```

<210> SEQ ID NO 111
<211> LENGTH: 1987
<212> TYPE: DNA
<213> ORGANISM: Oryza sativa

<400> SEQUENCE: 111

```
atggccggcg gcgaggcgca agcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggctctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
```

-continued

```
gtcacccact gtactcatca gcatccaatc caggttcaga tgcaactagg tatcaccagc    720

caaacaaagt ttgattattc agatgagctc aatgcagatg aggagaatga tgacacagaa    780

gaagagggca tgtcaggttc agacactaac aacactgaca ctgaaaggaa ttcaggccag    840

ctgcaacttc aaatgcaaga ccaactgaac atggtgagca atgaccacca gacaatacca    900

aataatgcag tttccagtga gctaatgcag tgtgagatgt cagaagtggt aagagatggc    960

tgctcaaata atattttaga ggatgaaatc caaatgctga tggattgcca aaacagtaat   1020

tgtcagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca gcaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggcg ggaaaggcgc aagtggatgc catccaaggt gatttcagtg ccaaccatgt   1440

gctgaaagag aggagaagaa gagagaagct caatgagaag ttcataattc tgcgatcttt   1500

ggtacctttc atgacaaaga tggacaaggc gtcgatacta ggcgacacga tcgagtacgt   1560

gaagcagcta aggaaccgca tacaagagct cgagtcgtcg tcgtcgtcgt cacgagcagc   1620

cgcccgggcg ccatcggcgg cggccgccgg gaggcggagg aagagatccg ccgccgccgc   1680

cactgccacg gcggcggaag ggatgagcag cagcaatggc cgcaatggcg gcgaggcggc   1740

ggaggtggtg caggtgtcca tcatcgagag cgacgcgctg ctggagctcc ggtgcggttg   1800

cggcggcggc ggcggcggtg tggtgctgct ccgggtgatg caggcgatgc aggagctcca   1860

gctggaggtc accgccgtcc aggcctcgtg cgccggtggc gagctgctcg ccgagctgcg   1920

cgccaaggtc gtcgttatga tcctgatctg catgaaaatg caaatgcaaa tgcaaatgca   1980

gaattaa                                                              1987
```

```
<210> SEQ ID NO 112
<211> LENGTH: 2001
<212> TYPE: DNA
<213> ORGANISM: Oryza sativa

<400> SEQUENCE: 112

atggccggcg gcgaggcgca agcggcgctg caggcggtgg cgcagagcct ccggtggacc     60

tacagcctcc tctggcagct ctgcccccac caagggagct cgctggtgtg gggggagggg    120

cactacaacg gcgccgtcaa gacgcggaag tcgacggtga tgcagccgcc gccggcggag    180

gaggaggacg acgccgacca cgcggcgcgc caccggagcc ggcagctgag ggagctctac    240

gactggctgc agcaggccgg ggagaactcc agcggcggcg tgcagacgtc gtcgacgacg    300

gcgagccggc ggccgggggc ggcgctgtcg ccggaggacc tgacggagac ggagtggttc    360

ttcctcatgt cggcatccta ctccttccct cccggcatcg ggttacctgg aagggcattt    420

gcaaggagag gccatgtatg gctcactgga gcaaatgaag ttgacagcaa agtattccta    480

agagcaattc ttgccaagac agttgtgtgc attcctgttg tcgatggcgt cctggaaatt    540

ggaactacgg aaaaggtgga ggaagatatg ggcctgattc agtatgcaag ggcatcttc     600

atggatcaac atggcatcca catgaagcct accctctcac agcactcaac atccaacccg    660

gtcacccact gtactcatca gcatccaatc caggttcaga tgcaactagg tatcaccagc    720

caaacaaagt ttgattattc agatgagctc aatgcagatg aggagaatga tgacacagaa    780
```

gaagagggca tgtcaggttc agacactaac aacactgaca ctgaaaggaa ttcaggccag 840
ctgcaacttc aaatgcaaga ccaactgaac atggtgagca atgaccacca gacaatgcca 900
aataatgcag tttccagtga gctaatgcag tgtgagatgt cagaagtggt aagagatggc 960
tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca acaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgccgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggcggcggtg tggtgctgct ccgggtgatg 1860
caggcgatgc aggagctcca gctggaggtc accgccgtcc aggcctcgtg cgccggcggc 1920
gagctgctcg ccgagctgcg cgccaaggtc gtcgtcatga tcctgatctg catgaaaatg 1980
caaatgcaaa tgcagaatta a 2001

<210> SEQ ID NO 113
<211> LENGTH: 2001
<212> TYPE: DNA
<213> ORGANISM: Oryza sativa

<400> SEQUENCE: 113
atggccggcg gcgaggcgca agcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggcgctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag ggcatcttc 600
atggatcaac atggcatcca catgaagcct accctctcac agcactcaac atccaacccg 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840

```
ctgcaacttc aaatgcaaga ccaactgaac atggtgagca atgaccacca gacaatgcca    900
aataatgcag tttccagtga gctaatgcag tgtgagatgt cagaagtggt aagagatggc    960
tgctcaaata atattttaga ggatgaaatc caaatgctga tggattgcca aaacagtaat   1020
tgtcagttaa atttgcaagg gccagatgag ccttgtcact cttggcattt tctctgcgag   1080
gagttacaaa atgattacca gccagctact gaagatcaag tggcatcacc tgaaaatacc   1140
cattacccaa aaacactcat gacaatccta cattacaaca cgctgcgaca acaagagatg   1200
aacatcaaga actacttgcc agtttcagag aaatcatcat tctccagatg gactactcct   1260
gaaggaagtg atgacaacaa gaccatgatc agtccaggca ccacacagag aatgctcaag   1320
agcatcctga tgattgttcc cagtagtcac tgcagttaca ggggagcaga aacacctgaa   1380
tcaaggggcg ggaaaggcgc aagtggaacg cgaaaagtcg gtgccatcca aggtgatttc   1440
agtgccaacc atgtgctgaa agagaggaga agaagagaga agctcaatga gaagttcata   1500
attctgcgat ctttggtacc tttcatgaca aagatggaca aggcgtcgat actaggcgac   1560
acgatcgagt acgtgaagca gctaaggaac cgcatacaag agctcgagtc gtcgtcgtcg   1620
tcgtcacgag cagccgcccg ggcgccatcg gcggcggccg ccgggaggcg gaggaagaga   1680
tccgccgccg ccgccactgc cacggcggcg gaagggatga gcagcagcaa tggccgcaat   1740
ggcggcgagg cggcggaggt ggtgcaggtg tccatcatcg agagcgacgc gctgctggag   1800
ctccggtgcg gttgcggcgg cggcggcggc ggcggcggtg tggtgctgct ccgggtgatg   1860
caggcgatgc aggagctcca gctggaggtc accgccgtcc aggcctcgtg cgccggcggc   1920
gagctgctcg ccgagctgcg cgccaaggtc gtcgtcatga tcctgatctg catgaaaatg   1980
caaatgcaaa tgcagaatta a                                             2001
```

<210> SEQ ID NO 114
<211> LENGTH: 1995
<212> TYPE: DNA
<213> ORGANISM: Oryza rufipogon

<400> SEQUENCE: 114

```
atggccggcg gcgaggcgca agcggcgctg caggcggtgg cgcagagcct ccggtggacc     60
tacagcctcc tctggcagct ctgcccccac caagggagct cgctggtgtg gggggagggg    120
cactacaacg gcgccgtcaa gacgcggaag tcgacggtga tgcagccgcc gccggcggag    180
gaggaggacg acgccgacca cgcggcgcgc caccggagcc ggcagctgag ggagctctac    240
gactggctgc agcaggccgg ggagaactcc agcggcggcg tgcagacgtc gtcgacgacg    300
gcgagccggc ggccgggggc ggcgctgtcg ccggaggacc tgacggagac ggagtggttc    360
ttcctcatgt cggcatccta ctccttccct cccggcatcg ggttacctgg aagggcattt    420
gcaaggagag gccatgtatg gctcactgga gcaaatgaag ttgacagcaa agtattccta    480
agagcaattc ttgccaagac agttgtgtgc attcctgttg tcgatggcgt cctggaaatt    540
ggaactacgg aaaaggtgga ggaagatatg ggcctgattc agtatgcaag ggcatcttc     600
atggatcaac atggcatcca catgaagcct accctctcac agcactcaac atccaaccca    660
gtcacccact gtactcatca gcatccaatc caggttcaga tgcaactagg tatcaccagc    720
caaacaaagt ttgattattc agatgagctc aatgcagatg aggagaatga tgacacagaa    780
gaagagggca tgtcaggttc agacactaac aacactgaca ctgaaaggaa ttcaggccag    840
ctgcaacttc aaatgcaaga ccaactgaac atggtgagca atgaccacca gacaatgcca    900
aataatgcag tttccagtga gctaatgcag tgtgagatgt cagaagtggt aagagatggc    960
```

tgctcaaata atattttaga ggatgaaatc caaatgctga tggattgcca aaacagtaat 1020
tgtcagttaa atttgcaagg gccagatgag ccttgtcact cttggcattt tctctgcgag 1080
gagttacaaa atgattacca gccagctact gaagatcaag tggcatcacc tgaaaatacc 1140
cattacccaa aaacactcat gacaatccta cattacaaca cgctgcgaca acaagagatg 1200
aacatcaaga actacttgcc agtttcagag aaatcatcat tctccagatg gactactcct 1260
gaaggaagtg atgacaacaa gaccatgatc agtccaggca ccacacagag aatgctcaag 1320
agcatcctga tgattgttcc cagtagtcac tgcagttaca ggggagcaga aacacctgaa 1380
tcaaggggcg ggaaaggcgc aagtggaacg cgaaaagtcg gtgccatcca aggtgatttc 1440
agtgccaacc atgtgctgaa agagaggaga agaagagaga agctcaatga gaagttcata 1500
attctgcgat ctttggtacc tttcatgaca aagatggaca aggcgtcgat actaggcgac 1560
acgatcgagt acgtgaagca gctaaggaac cgcatacaag agctcgagtc gtcgtcgtcg 1620
tcgtcacgag cagccgcccg ggcgccatcg gcggcggccg ccgggaggcg gaggaagaga 1680
tccgccgccg ccgccactgc cacggcggcg gaagggatga gcagcagcaa tggccgcaat 1740
ggcggcgagg cggcggaggt ggtgcaggtg tccatcatcg agagcgacgc gctgctggag 1800
ctccggtgcg gttgcggcgg cggcggcggc ggtgtggtgc tgctccgggt gatgcaggcg 1860
atgcaggagc tccagctgga ggtcaccgcc gtccaggcct cgtgcgccgg cggcgagctg 1920
ctcgccgagc tgcgcgccaa ggtcgtcgtc atgatcctga tctgcatgaa aatgcaaatg 1980
caaatgcaga attaa 1995

<210> SEQ ID NO 115
<211> LENGTH: 1995
<212> TYPE: DNA
<213> ORGANISM: Oryza rufipogon

<400> SEQUENCE: 115
atggccggcg gcgaggcgca agcggcgctg caggcggtgg cgcagagcct ccggtggacc 60
tacagcctcc tctggcagct ctgcccccac caagggagct cgctggtgtg gggggagggg 120
cactacaacg gcgccgtcaa gacgcggaag tcgacggtga tgcagccgcc gccggcggag 180
gaggaggacg acgccgacca cgcggcgcgc caccggagcc ggcagctgag ggagctctac 240
gactggctgc agcaggccgg ggagaactcc agcggcggcg tgcagacgtc gtcgacgacg 300
gcgagccggc ggccgggggc ggcgctgtcg ccggaggacc tgacggagac ggagtggttc 360
ttcctcatgt cggcatccta ctccttccct cccggcatcg ggttacctgg aagggcattt 420
gcaaggagag gccatgtatg gctcactgga gcaaatgaag ttgacagcaa agtattccta 480
agagcaattc ttgccaagac agttgtgtgc attcctgttg tcgatggcgt cctggaaatt 540
ggaactacgg aaaaggtgga ggaagatatg ggcctgattc agtatgcaag gggcatcttc 600
ttggatcaac atggcatcca catgaagcct accctctcac agcactcaac atccaaccca 660
gtcacccact gtactcatca gcatccaatc caggttcaga tgcaactagg tatcaccagc 720
caaacaaagt ttgattattc agatgagctc aatgcagatg aggagaatga tgacacagaa 780
gaagagggca tgtcaggttc agacactaac aacactgaca ctgaaaggaa ttcaggccag 840
ctgcaacttc aaatgcaaga ccaactgaac atggtgagca atgaccacca gacaatgcca 900
aataatgcag tttccagtga gctaatgcag tgtgagatgt cagaagtggt aagagatggc 960
tgctcaaata atattttaga ggatgaaatc caaatgctga tggattgcca aaacagtaat 1020

-continued

```
tgccagttaa atttgcaagg gccagatgag ccttgtcact cttggcattt tctctgcgag   1080

gagttacaaa atgattacca gccagctact gaagatcaag tggcatcacc tgaaaatacc   1140

cattacccaa aaacactcat gacaatccta cattacaaca cgctgcgaca acaagagatg   1200

aacatcaaga actacttgcc agtttcagag aaatcatcat tctccagatg gactactcct   1260

gaaggaagtg atgacaacaa gaccatgatc agtccaggca ccacacagag aatgctcaag   1320

agcatcctga tgattgttcc cagtagtcac tgcagttaca ggggagcaga aacacctgaa   1380

tcaaggggca ggaaaggcgc aagtggaacg cgaaaagtcg gtgccatcca aggtgatttc   1440

agtgccaacc atgtgctgaa agagaggaga agaagagaga agctcaatga gaagttcata   1500

attctgcgat ctttggtacc tttcatgaca aagatggaca aggcgtcgat actaggcgac   1560

acgatcgagt acgtgaagca gctaaggaac cgcatacaag agctcgagtc gtcgtcgtcg   1620

tcgtcacgag cagccgcccg ggcgccatcg gcggcggccg ccgggaggcg gaggaagaga   1680

tccgccgccg ccgccactgc cacggcggcg gaagggatga gcagcagcaa tggccgcaat   1740

ggcggcgagg cggcggaggt ggtgcaggtg tccatcatcg agagcgacgc gctgctggag   1800

ctccggtgcg gttgcggcgg cggcggcggc ggtgtggtgc tgctccgggt gatgcaggcg   1860

atgcaggagc tccagctgga ggtcaccgcc gtccaggcct cgtgcgccgg tggcgagctg   1920

ctcgccgagc tgcgcgccaa ggtcgtcgtc atgatcctga tctgcatgaa aatgcaaatg   1980

caaatgcaga attaa                                                    1995


<210> SEQ ID NO 116
<211> LENGTH: 685
<212> TYPE: PRT
<213> ORGANISM: Zea mays

<400> SEQUENCE: 116

Met Ala Ala Gly Gly Arg Gly Glu Ala Ala Gln Lys Ala Leu Gln Ser
1               5                   10                  15

Val Ala Gln Ser Thr Gly Trp Thr Tyr Ser Leu Leu Trp Arg Leu Cys
            20                  25                  30

Pro Arg Gln Gly Ala Leu Val Trp Ala Glu Gly Tyr Tyr Asn Gly Ala
        35                  40                  45

Ile Arg Thr Arg Lys Thr Thr Met Thr Thr Val Arg Gln Pro Ala Gly
    50                  55                  60

Ala Glu Asp Ala Gly Asp Glu Glu Thr Ala Pro Arg Arg Ser Arg Gln
65                  70                  75                  80

Leu Lys Glu Leu Tyr Asp Ser Leu Ala Ala Gly Glu Ala Ala Tyr Asp
                85                  90                  95

Gly Gly Gly Gly Val Gly Gly Pro Gln Gln Gln Gln Gln Ala Ala Val
            100                 105                 110

Val Pro Pro Pro Arg Arg Pro Ala Ala Ala Leu Ala Pro Glu Asp Leu
        115                 120                 125

Thr Glu Thr Glu Trp Phe Tyr Leu Met Cys Ala Ser Tyr Cys Phe Pro
    130                 135                 140

Pro Ala Val Gly Leu Pro Gly Glu Ala Phe Val Arg Arg Ala His Val
145                 150                 155                 160

Trp Leu Cys Gly Ala Asn Lys Ala Asp Ser Lys Val Phe Ser Arg Ala
                165                 170                 175

Ile Leu Ala Arg Ser Ala Gly Ile Gln Thr Val Ala Cys Ile Pro Val
            180                 185                 190

Asp Asp Gly Val Leu Glu Ile Gly Thr Thr Glu Lys Val Glu Glu Asp
```

```
        195                 200                 205

Ile Phe Leu Ile Gln His Val Arg Asn Ile Phe Val Asp Gln His Gly
    210                 215                 220

Ala His Ile Met Pro Thr Thr Leu Ser Gly Tyr Ser Thr Ser Thr Pro
225                 230                 235                 240

Thr Thr Gln Leu Asn His Gln Pro Phe Gln Thr Lys Thr Gly Ile Ser
                245                 250                 255

Leu Asn Leu Gly Asp Glu Arg Asn Ser Glu Met Glu Asp Asp Asp Asp
            260                 265                 270

Asp Gly Arg Ile Asp Leu Glu Asn Asn Thr Glu Asn Asp Ser Thr Arg
        275                 280                 285

Arg His Leu Pro Gln Asp Ala Ser Ala Gly Asn Glu Leu Glu Thr Leu
    290                 295                 300

Asn Ala Glu Ser Ser Gly Pro Met Leu Ile Ala Asn Leu Thr Ala Gln
305                 310                 315                 320

Asp Glu Tyr Gly Gln Leu His Arg Phe Leu Ser Val Asp Leu Ser Ser
                325                 330                 335

Lys Tyr Leu Gln Ser Pro Gly Ala Glu Asp Gln Ala Ala Val Ala Glu
            340                 345                 350

Asn Ala His Tyr Ile Glu Thr Val Leu Arg Ile Leu Arg Phe Asn Ala
        355                 360                 365

Cys Arg Gln Thr Gln Ala Ala Ser Ser Asn Ile Ala Lys Thr Tyr Leu
    370                 375                 380

Ala Leu Ser Lys Asn Ser Pro Phe Ser Arg Trp Asn Trp Lys Arg Lys
385                 390                 395                 400

Gly Ile Ser Ser Met Met Ile Ala Glu Gly Thr Pro Gln Arg Met Leu
                405                 410                 415

Lys Ser Val Leu Leu Gly Ala Pro Ser Ser Ser Ser His Arg Ser His
            420                 425                 430

Arg Gly Glu Val Gln Ser Ser Ser Pro Glu Pro Arg Gly Asp Asp Gly
        435                 440                 445

Glu Gly Thr Ser Arg Ser Arg Arg Gly Pro Val Pro Ser Gln Thr Glu
    450                 455                 460

Leu Ser Ala Ser His Val Leu Lys Glu Arg Arg Arg Arg Glu Lys Leu
465                 470                 475                 480

Asn Glu Gly Phe Ala Met Leu Arg Ser Leu Val Pro Phe Val Thr Lys
                485                 490                 495

Met Asp Arg Ala Ser Ile Leu Gly Asp Thr Ile Glu Tyr Val Lys Gln
            500                 505                 510

Leu Arg Arg Arg Ile Gln Glu Leu Glu Ser Arg Arg Arg Leu Val Gly
        515                 520                 525

Ser Asn Gln Lys Thr Thr Met Ala Gln Gln Pro Pro Pro Pro Ala Ala
    530                 535                 540

Ser Thr Glu Glu Arg Gly Arg Arg Gln Thr Ser Gly Gly Tyr Leu Ala
545                 550                 555                 560

Arg Ala Ala Gly Thr Gly Ser Arg Ala Ala Glu Ala Ser Gly Asn Ser
                565                 570                 575

Asn Leu Gly Glu Glu Pro Pro Ala Ala Ala Ala Ser Asp Thr Asp Thr
            580                 585                 590

Glu Val Gln Val Ser Ile Ile Gly Ser Asp Ala Leu Leu Glu Leu Arg
        595                 600                 605

Cys Pro His Arg Glu Gly Leu Leu Leu Arg Val Met Gln Ala Leu His
    610                 615                 620
```

Gln Glu Leu Arg Leu Glu Ile Thr Ser Val Gln Ala Ser Ser Ala Gly
625 630 635 640

Asp Val Leu Leu Ala Lys Leu Arg Ala Lys Val Lys Glu Val His Gly
645 650 655

Arg Arg Ser Ser Ile Thr Glu Val Lys Arg Ala Ile His Leu Ile Val
660 665 670

Ser Ser Asp Trp Ile Cys Glu Lys Asn Pro Cys Leu Ala
675 680 685

<210> SEQ ID NO 117
<211> LENGTH: 668
<212> TYPE: PRT
<213> ORGANISM: Petunia hybrida

<400> SEQUENCE: 117

Met Gln Leu Gln Thr Met Leu Arg Asn Ala Val Gln Ser Val Gln Trp
1 5 10 15

Thr Tyr Ser Leu Phe Trp Gln Leu Cys Pro Gln Gln Gly Val Leu Val
20 25 30

Trp Arg Asp Gly Tyr Tyr Asn Gly Ala Ile Lys Thr Arg Lys Thr Val
35 40 45

Gln Pro Met Glu Val Ser Ala Glu Glu Ala Ser Leu His Arg Ser Gln
50 55 60

Gln Leu Arg Glu Leu Tyr Glu Ser Leu Ser Ala Gly Glu Ser Asn Gln
65 70 75 80

Pro Thr Arg Arg Pro Ser Ala Ala Leu Ser Pro Glu Asp Leu Thr Glu
85 90 95

Ser Glu Trp Phe Tyr Leu Met Cys Val Ser Phe Ser Phe Pro Ala Gly
100 105 110

Ile Gly Leu Pro Gly Lys Ala Tyr Ser Lys Lys His His Ile Trp Ile
115 120 125

Thr Gly Ala Asn Glu Val Glu Ser Lys Val Phe Cys Arg Ala Ile Leu
130 135 140

Ala Lys Ser Ala Arg Val Gln Thr Val Val Cys Ile Pro Leu Leu Asp
145 150 155 160

Gly Val Val Glu Leu Gly Thr Thr Gln Arg Ile Gln Glu Asp Ile Gly
165 170 175

Phe Ile Asn His Val Lys Thr Phe Phe Ile Glu Gln Gln Pro Pro Leu
180 185 190

Pro Pro Lys Pro Ala Leu Ser Glu His Ser Thr Ser Asn Pro Thr Thr
195 200 205

Phe Ser Glu Leu Asn Phe Tyr Ser Ser Asn Thr Pro Pro Ser Ala Gly
210 215 220

Thr Thr Pro Ala Asp Glu His Gly Gly Val Ala Gly Asp Glu Asp Glu
225 230 235 240

Glu Asp Glu Asp Glu Glu Asp Glu Asp Glu Glu Gln Glu Asp Asp Glu
245 250 255

Glu Ala Glu Leu Asp Ser Asp Lys Ile Ala Ala Gln Val Gly Pro Ala
260 265 270

Asp Val Ile Ala Ala Ala Glu Ala Ser Glu Leu Met Gln Leu Asp Met
275 280 285

Ser Glu Ala Ile Arg Phe Gly Ser Pro Asp Asp Gly Ser Asn Thr Asn
290 295 300

Met Asp Ser Asp Phe His Met Val Gly Val Ser Gln Ala Glu Asn Pro

```
305                 310                 315                 320

Ala Asp Tyr Gln Arg Gln Ala Glu Ser Phe Lys Ala Asp Thr Ser Ile
                325                 330                 335

Ser Trp Ala His Phe Gln Asp Leu Pro His Leu Pro Gly Gly Pro Ser
            340                 345                 350

Tyr Asp Glu Leu Ser Gln Glu Asp Thr His Tyr Ser Gln Thr Val Ser
        355                 360                 365

Thr Ile Leu Glu His Leu Ser Asn Gln Ser Ser Lys Phe Ser Ser Thr
    370                 375                 380

Ile Met Gly Cys Ile Ser Gln Thr Thr Gln Ser Ala Phe Thr Arg Trp
385                 390                 395                 400

Pro Ser Pro Ser Thr Thr Val Ser Ser Pro Phe Leu Asp Gly Gly Ala
                405                 410                 415

Thr Ser Gly Gln Trp Leu Leu Lys Ser Ile Leu Phe Ser Val Pro Phe
            420                 425                 430

Leu His Thr Lys Tyr Gln Thr Ala Ala Glu Val Ser Pro Lys Ser Arg
        435                 440                 445

Asp Ala Thr Thr Val Asp Ser Ser Thr Ala Ser Arg Phe Arg Lys Gly
    450                 455                 460

Cys Ser Ile Thr Gln Glu Glu Pro Ser Gly Asn His Val Leu Ala Glu
465                 470                 475                 480

Arg Arg Arg Arg Glu Lys Leu Asn Glu Arg Phe Ile Ile Leu Arg Ser
                485                 490                 495

Leu Val Pro Phe Val Thr Lys Met Asp Lys Ala Ser Ile Leu Gly Asp
            500                 505                 510

Thr Ile Glu Tyr Val Lys Gln Leu Arg Lys Lys Val Gln Asp Leu Glu
        515                 520                 525

Ala Arg Ala Asn Gln Thr Glu Ala Thr Leu Gln Thr Lys Asp Thr Gly
    530                 535                 540

Thr Val Lys Val Leu Gln Gly Arg Gly Lys Arg Arg Met Lys Ile Val
545                 550                 555                 560

Glu Gly Ser Val Gly Gly Gly Gln Ala Lys Ile Thr Ala Ser Ser Pro
                565                 570                 575

Ser Thr Thr His Glu Glu Glu Ile Val Gln Val Glu Val Ser Ile Ile
            580                 585                 590

Glu Ser Asp Ala Leu Val Glu Leu Arg Cys Pro Tyr Lys Glu Gly Leu
        595                 600                 605

Leu Leu Asp Val Met Gln Met Leu Arg Glu Leu Lys Val Glu Val Val
    610                 615                 620

Thr Ile Gln Ser Ser Leu Asn Asn Gly Ser Phe Phe Ala Glu Leu Arg
625                 630                 635                 640

Ala Lys Val Lys Glu Asn Ile Tyr Gly Arg Lys Ala Ser Ile Leu Glu
                645                 650                 655

Val Lys Lys Ser Ile His Gln Leu Ile Pro Arg Val
            660                 665


<210> SEQ ID NO 118
<211> LENGTH: 518
<212> TYPE: PRT
<213> ORGANISM: Arabidopsis thaliana

<400> SEQUENCE: 118

Met Asp Glu Ser Ser Ile Ile Pro Ala Glu Lys Val Ala Gly Ala Glu
1               5                   10                  15
```

-continued

```
Lys Lys Glu Leu Gln Gly Leu Leu Lys Thr Ala Val Gln Ser Val Asp
            20                  25                  30

Trp Thr Tyr Ser Val Phe Trp Gln Phe Cys Pro Gln Gln Arg Val Leu
        35                  40                  45

Val Trp Gly Asn Gly Tyr Tyr Asn Gly Ala Ile Lys Thr Arg Lys Thr
    50                  55                  60

Thr Gln Pro Ala Glu Val Thr Ala Glu Glu Ala Ala Leu Glu Arg Ser
65                  70                  75                  80

Gln Gln Leu Arg Glu Leu Tyr Glu Thr Leu Leu Ala Gly Glu Ser Thr
                85                  90                  95

Ser Glu Ala Arg Ala Cys Thr Ala Leu Ser Pro Glu Asp Leu Thr Glu
            100                 105                 110

Thr Glu Trp Phe Tyr Leu Met Cys Val Ser Phe Ser Phe Pro Pro Pro
        115                 120                 125

Ser Gly Met Pro Gly Lys Ala Tyr Ala Arg Arg Lys His Val Trp Leu
    130                 135                 140

Ser Gly Ala Asn Glu Val Asp Ser Lys Thr Phe Ser Arg Ala Ile Leu
145                 150                 155                 160

Ala Lys Ser Ala Lys Ile Gln Thr Val Val Cys Ile Pro Met Leu Asp
                165                 170                 175

Gly Val Val Glu Leu Gly Thr Thr Lys Lys Val Arg Glu Asp Val Glu
            180                 185                 190

Phe Val Glu Leu Thr Lys Ser Phe Phe Tyr Asp His Cys Lys Thr Asn
        195                 200                 205

Pro Lys Pro Ala Leu Ser Glu His Ser Thr Tyr Glu Val His Glu Glu
    210                 215                 220

Ala Glu Asp Glu Glu Glu Val Glu Glu Glu Met Thr Met Ser Glu Glu
225                 230                 235                 240

Met Arg Leu Gly Ser Pro Asp Asp Glu Asp Val Ser Asn Gln Asn Leu
                245                 250                 255

His Ser Asp Leu His Ile Glu Ser Thr His Thr Leu Asp Thr His Met
            260                 265                 270

Asp Met Met Asn Leu Met Glu Glu Gly Gly Asn Tyr Ser Gln Thr Val
        275                 280                 285

Thr Thr Leu Leu Met Ser His Pro Thr Ser Leu Leu Ser Asp Ser Val
    290                 295                 300

Ser Thr Ser Ser Tyr Ile Gln Ser Ser Phe Ala Thr Trp Arg Val Glu
305                 310                 315                 320

Asn Gly Lys Glu His Gln Gln Val Lys Thr Ala Pro Ser Ser Gln Trp
                325                 330                 335

Val Leu Lys Gln Met Ile Phe Arg Val Pro Phe Leu His Asp Asn Thr
            340                 345                 350

Lys Asp Lys Arg Leu Pro Arg Glu Asp Leu Ser His Val Val Ala Glu
        355                 360                 365

Arg Arg Arg Arg Glu Lys Leu Asn Glu Lys Phe Ile Thr Leu Arg Ser
    370                 375                 380

Met Val Pro Phe Val Thr Lys Met Asp Lys Val Ser Ile Leu Gly Asp
385                 390                 395                 400

Thr Ile Ala Tyr Val Asn His Leu Arg Lys Arg Val His Glu Leu Glu
                405                 410                 415

Asn Thr His His Glu Gln Gln His Lys Arg Thr Arg Thr Cys Lys Arg
            420                 425                 430

Lys Thr Ser Glu Glu Val Glu Val Ser Ile Ile Glu Asn Asp Val Leu
```

-continued

```
        435                 440                 445

Leu Glu Met Arg Cys Glu Tyr Arg Asp Gly Leu Leu Leu Asp Ile Leu
    450                 455                 460

Gln Val Leu His Glu Leu Gly Ile Glu Thr Thr Ala Val His Thr Ser
465                 470                 475                 480

Val Asn Asp His Asp Phe Glu Ala Glu Ile Arg Ala Lys Val Arg Gly
                485                 490                 495

Lys Lys Ala Ser Ile Ala Glu Val Lys Arg Ala Ile His Gln Val Ile
            500                 505                 510

Ile His Asp Thr Asn Leu
        515


<210> SEQ ID NO 119
<211> LENGTH: 5040
<212> TYPE: DNA
<213> ORGANISM: Oryza sativa

<400> SEQUENCE: 119

ctgtactacc agctagatct ggctcgcgcg ctgcgcacgt gctgtcaaag gctgtgtgca     60

ctgtgcagca caggttgccg acttcccgtt gttttcgtga ccttgatggg ttgcatcttc    120

gtctcatggg atctggacag gtgtcaggtt tccctcgcgg agcaaaacgc aagcagaaaa    180

ctgtggtttg cttacgatca cctggatttg atatttgcgt gccatatctg ctatgttgat    240

tctcagccgt cagcacgagc tcttgagctt tcatgttatc aatggcaaat cagatttgtt    300

ttttcctttt tctgactata atcttttagc actatatatt tgtatttttt ttcctactat    360

atcaatagaa acatcgctat cttttagcac tatatatttg tatttttttc ctactatatc    420

aatagaaaca tcgctgcggg ttgtttcaaa aaaaaaattg ctaagcttgt ttcttttatg    480

atactcctat cttactactc cttaaaaaaa agaacttatc aatcattcat gggttttata    540

tgtacatctc atctatattt ctatatggaa atggaccaaa ttagtcaatg gttgcgaata    600

atagctcagg acaggggaca gcaacaacat tacaaaatca tttgtatgag cgaatgtagc    660

tgaaccattc tagtagctgg ttaacaagcc aagcatgtca ttggatacaa aaaaatgttg    720

gcaactgtat agaaatttac aagactctga aatctgaatc tagaaaagca tcaactcatt    780

tgggcataca aaaagtgcag ttcagaaaat gtgcaggact cccatgctac catgatcact    840

ccgaacttcc ttccttgaac accttgaccc aattctcagc actgtcaatt atttcaccag    900

tcttgaccag gtaccgaacc ttcgttccat cctcaaggaa tttgtgtcca accctactcg    960

ccacattctt ttcctttgag tagagcatca catttgagct gtgaatgggg ccttcaatct   1020

gatcaaagaa aacaccaaca accataggtt aacgatcagg catctgaaac tatatatacg   1080

acactagcta gaagcagcac agaaagaagt ttcaagagaa acaatgctga ccatgacgat   1140

ttcacccggt tcatcttctg ttcctttctt gtgcttggac ttcaagttca agtccttcac   1200

tattacagtg ctgttgtgct taaaaagccg cgtaacttct ccaactttac ctttctcacg   1260

gcctgcaatg acttgtactg tatcgccaat cctaacatgc atcttgtgca ggacaggaag   1320

actgtttggt ttacacttct tcctctccca tcgcttaagc tgcattggaa aaagggaaat   1380

ttcagacatt tgagtaaata gcaagctgca gaccaaaaaa gaattgaaac ttaccctcat   1440

ttgaattggg catgtcttga tcataaattt aacctgcata taaaaattta tgcatatctt   1500

gtcagagttt cttatgaaaa tgacataaaa tgtaataatc agctgctttt gagatatgac   1560

atgaatcatg ctcacgatgt ttcttaggca agaatatcta ggataatcat atgatctttt   1620
```

agtacgagtt tcttcatata agtgcagatt ttagtacagt tcatcatata agtgccatat 1680
atagctcagt cactccattc aagagcaatt attcggcctt attttctctc atcaccactt 1740
tccaggtaag taattagtcg tgagtgagtc tcattctgag gacgaagtgc agtagactat 1800
ctagaagagc taaggaacgc caaaaagaat atacaaaaga tagaacaagt tcagtctgat 1860
aagtataccg agtgtgccaa tcatttgcta caggctatcc ccgagtgaaa tgagtttcca 1920
tcattttccc atggaagtct tctgtgaaat ttctactgtt gagtaattta aagttcaaag 1980
gcaaaattgt ttctagccag cgaaatgtga tctatacagc aggttagaac aagaaatggt 2040
ctgtctcact agagggcaca tctttcagaa aaataatcct ctgcttgaaa ggctgaatat 2100
tgggtatcca tcgcttatac caccatagga aaaaaataat attcaagttt aaactgaaac 2160
ataacaggcc acatcccatg gtagacaaca caatttctaa cttctgaatt cactcagttg 2220
atatactcaa acttgagatt tcaagcattc attaattcat ataaaccctc cttatactag 2280
ccaactaggt tcaactatac cacaaaatcc ttgagacctt ttctctaaaa aaaatatacc 2340
acaaaatttt gacacaacgt tggttgttgg ctagttgagg tcctgagcct gaactcctga 2400
aggcaacaac agtacagtga ggcgatgtag acatcaccat tgcaatgcca cgctgttggt 2460
gagctctaaa atcctaaatc tcagtgcaag ctggcatttc tacttttcca gcgaatcata 2520
agagcagagc aaacataaag gaatgcgaaa aatgagaatc agggttggga gtcggcacaa 2580
accccagccg gcgcggcggc gaaggtggag agcgggtggc cccagaagct gctggtgctc 2640
gccgcccccg gcgcagagat ggagagggac gccatcgcgc cctgcaacgc cgccaccccg 2700
gccatcttcg tctcctcccc tcctcttcct ccctcgctcg ctcaaaccgc agagaagcag 2760
cagaggataa cgaacgcctt cgtgtgctcg cggacaggat aatggcgagc gcttttctac 2820
atgacaaatg ggcctctagg ccgaatggat tggcccactt gtaagactca taaaggccta 2880
atgaaaggcc tatcgtaatc cagcccaact acaacggacc ttacggccca agtcagccgc 2940
gatcccgttc aggctcaaat atagcgggcc tcacgtaagc cgcaatcccg tctcgaccca 3000
acaagaacag gtcgcaccta cacagataaa atctattgta catttctcat ctctgctcct 3060
gattgaatta cctccctcaa ccgcaaaatg gaggaaaatc ggtcttattg tttggttatg 3120
cttatattta tgagccaaaa tttgaatttg agaacttagt tttgaatttg ctttttttgtt 3180
tttttaaaat gcttatattt tacaacattt gctttaagtt attatggaca tatataaaca 3240
ttttactcat aaataaattt ttatttgcta ataaacgatt cgaataagcg aaaaccgtag 3300
cagatcaacc cttagatggt ttgtagggtg gttcctgttg acgtggcagg ctgactcgca 3360
gagaacatga gggaggcaaa atagacttac tatcacgcac gtcagcaatc cggttaaggc 3420
ccaaatgtcg tgggccgctc gtcgtccgca atcccgtttg tggtcaagta acgtgggccg 3480
aacgtcctgg gttgatatgg gccgacaccc gttttcggat aaggcccagc ccagcatacg 3540
ctcgtcgtct tcctcgttgc gttgcgtggc ttcgtctcca cacgcatcat caccacgcca 3600
cgcgccgcga gatgctgctt cggcgggggc gcccaggcgt ggcgcctccc ggattccggc 3660
ggcttcgacg tcgccggcga cgcgcgcaag ccaagcgaca gttgcggagg caagcaaccc 3720
cccaagttcc gtccctttttg cgcttttctg ggacccattt cctctctctt ttgggggggcg 3780
ctttcgcggt gacgacgctg ccgatgcgcg tacgcctgag gagttcttcc ccatcacgcc 3840
gcgtggggga tcgggacgtc gccatttccg ctgccgtttt cttctctttg gggggttgca 3900
atctcgcgtt tcatttgata gggttgggcg tgggcggtgg ggaatgggga tgggtaggta 3960
gatggcaccg atgtgaatcg gacgacttcg aatcgaagcc ttccgatcca tgtgaggagg 4020
ttgaggaacc aacctaattt cgaatcgaag aactcttggt ttctctacct aaaaccaaat 4080
agcatagtga cagtggtcgt tatactatga attccaagct ttttgaccga agatttcgaa 4140
tcatcgagca tctttggcca agctattcta acacggttga ctcagaagtc tacgtttcta 4200
tgcattgtgt atttgagtgt tagttactat atttcgtgat aaacaaaact gttgactcaa 4260
aagtctacgt ttatatgcat tgtgtatttg tgtgttactg tatttagtga taaaccttag 4320
gtgtacatgt gagggatttc atggataaca cgtgcactac attcttgcct gttccactgg 4380
tcaccatcag caaatcgctc ctgtcccttt cgtgtggcta tcactggagc tattcaattc 4440
ttgaaaggct ctgccgtgca agcaaaccgt tttctttcca atgggataag tgtgtgactg 4500
tgctataatc tcaggataaa ttcatcacta aatcgttgct atcagttttg gtttatccac 4560
tcattaaatc aatgcaacaa atgtggtgat caataattag tagtacttgt ttgttggtat 4620
gccgtgctgc caaactagtt ggataacaaa gattcctatt atattggggt taaccactgt 4680
attttcctaa tcataatttt ttaggctcct tattgtcatt atcacttagc atcattgcat 4740
aagagaaaaa aaagggggt caatactgca ggatggtatt ttaggaagga aatgtgttat 4800
cgtgatatta acacagcctt tcttccatgt tgcttgcact cctctcaaac tggtgtagct 4860
tcctaaagac tggctcagtt acacaatttt tattcttaaa tgctggaatc ctgggaaatc 4920
cttaatgcgc ctggaattgt tgcactcaag taaagcttta gtttgctaca cccgtgacac 4980
tttcagagtt ggacatgtca aagtttcctt cccttttga taaaatgtcc agtgtgatag 5040

<210> SEQ ID NO 120
<211> LENGTH: 5040
<212> TYPE: DNA
<213> ORGANISM: Oryza sativa

<400> SEQUENCE: 120
cacaccaacg agctccaatg agctcccatt gaaatcccca tccaagcact gatgagaagg 60
gaggtcctac gaaaccgaca ctagtggatt cttagcaggt gaaatgatcc cagcactagg 120
catggatgca cgtgaccact tcatcgtttc tgatgttggg atcttcatgt gattgtgtac 180
atgactgatg cgatgcgact ttttcagtag gggaaaaatg tggttctcat tgcattgtct 240
tactagtagc tccaaccttc tttctgtttc ctcgatcgat gtctgtgcta aaattgcctc 300
ttacagtata tgagtgcaga gacataaaag gcattgctag catgacaggt caacctcact 360
agttcatgtt gttacaatat ataaaaatga tttgtaatac tacttatccc atcaataatt 420
tattttaaat ctcatcttac ctctaagagg ctctaactac ctcctgcctc aagttgtttc 480
ttgttacaca aggggcacca aagtgtttcc tcctcaactt taatctttgc tatacaatct 540
agaaatcctt atattttaaa atggagagaa caattgtcta ctgtctccaa tatcaaacaa 600
caagtgtaat aatatagcca attattagtt tcaaaaagtg gcacatcatc tacagctaat 660
ctaatactct atccatacaa tacttacaca caaatatata ctacacacac cgtcttatag 720
cccgtgctac tgttagctac acatatgtaa cacacttttc ttctctatct cctctcttct 780
catctctgct taacctaccc ataaatctta tttgccatga aaatcacttt catataatta 840
tatttttaat gccagagtct cttcttctca actttaatct ccactaagaa acctagagat 900
gctcataatt taaaactgag aaagtagttg tttactacct ccgatctcaa atagcaagta 960
taatagtata gccatctatt attagcttca aaaattggca catcatctac agctaatcta 1020
atagtctatc tatataatag ttacacataa atatttacta cacacgatgt cttataactc 1080

-continued

```
atgctatagc tggctacaaa tctataacac cgctattatt ctcatcttct atcatctctc   1140
cacctaatca caaatttgat gtggcaattt ttgaagcccg ctacttcaat tattgcacta   1200
actcaaataa atagcattat agaatgcgtg cagtcaaacc ttgaatctta aatgattaat   1260
tcatgcaaaa atactaaaat ttaacatgag aaaatggtgt tggtagattt ggcatggaaa   1320
tctcttttat ataattatat ttttaatcct ttttaccgat agtagaacca atctaaatcg   1380
tatatcttat tctaatccaa tagatcatat ctatttctac taccaaccaa ctactagtag   1440
ttgtagcgcc cgttccgtcg tggcgcctag cgggaaaact atctcttaaa aactctattt   1500
gcgaaatctg tttctttgct tgttgcctag tgtccgtgcc atctcagatc tcaaatcccc   1560
gatctatcgt cgagttcaat cccgaatcca aaccttccca aatcgatccc tccgcaaaag   1620
tttatttttc ctccctcggg ttcgatgggc cgaatctctc tcggcccatc ttcccctccc   1680
tccccggcta tctctctctc tcgctctctc tctctccctc cctcttctcc gctctgcccg   1740
cgcgccgcgc gcgcgtgcgc atgagccgcg ccgagccgag ccctccctct ccgctccctc   1800
gctgctgctt cccgcgcgcc gttgttcgca tgcacgcgcc cgtgcggtcg ccgcccgtgc   1860
cgcgcctgcg ccgtctgcgc cgcgagtcag cacgcgtgcc cgagccgcgc cgctcaaatc   1920
gccgcgccgc ccgttgcttc ccgcgcgcgc gtgccgtggt ggccgaccgc ctggtcgccg   1980
ctgccgtcag cctctgccgc gcctgtccgc gcctgccgtc cgtgtcgccg ctccgctcca   2040
aaccgccccg ccgtcatcgc cgtcgtcatc aacccgaccc cgccactccg cgcgctagct   2100
tccaagggac ggaggcagag cccctcctcc ctctgccgcg tcgcccccgc tccctcctcc   2160
ttttcccaaa gaggcaaggg gcaagccccc tttctctccc tccttttccc tttttttcctc  2220
ccgccggcgt catcctccct ccgccctgtc gccgatttgg ccgctagccg gagcgccagc   2280
tcgctggctt gaccgtccaa agtcggttcc cctctcccaa accgtcattg ccatcctata   2340
aagcccaggc gccctccctc tcttctcctc tcgttgtccc atcgcctcca ctccattgtc   2400
gccgcctccc gtgctctgtt cgccgtcgcc gtttgtcgtc gcgcgtgtcg gaggagccgg   2460
cacgagcgag gacgcggaag gggactccgg gcgcgccctc ttcttcctct tccccggccc   2520
gaggccggag agatcactcc cgtgccgtcg gcccatcgtc actgcgcccc gtcccgcacg   2580
gtagcgcatc tccctattct ccctcctcgt tccatcccct tcccttagac tcgggtagta   2640
gcacgagtag cctccccgta gctagctggc gccgccccga ctgctgccgt cgctcgccgt   2700
gtgctcgccg ccgtcgccgc ccgagctcgg aagcgcctct cgtcgccggc ctccctcgat   2760
gcgttcctcc taatccggcg caagggacgg attcccgtag ccgcgtagat gctctcgccg   2820
ccgggaatcg gcccctcgtg acctcgtcgc cgtttccctc ttccctcccc gccggttgcc   2880
gccgccgcaa tccgccgccg acgcactccc tccggcgaat ccaagccgtt ggctcgtctc   2940
ccctcgtctc gtgcaaccac ccggtgtgct cgctttcgcc tgtatcgccg tggttcgctc   3000
cgccgcccgc cgctgtcgtc cgccgtccgt tccggccggc gtcgtcgtct acctcccgcc   3060
ggcccgcgtg gctgccactt aggcgccatg tcggcgccac ctcggccgcg accggatcgg   3120
ctgacccggc cagccgctcc ctccgttccc cccccgtgcg catggtccgc ggtgagccgt   3180
gaggctgcgc gtgggcccgc cgcaccgcat cttccgcgaa ccgcgcgcgt gcaccgcgtc   3240
cctcccccaa accctagcgc gcgccgcgtg cgcgttccgc acggtgaacc gtgtcaccga   3300
caagcgggtc ccacccggga ccacgcggga tggacccggc ccaccggctc tctctcccct   3360
ccccgcccgc gcgcgcgctt tgggccgcct tcttgggccg gccggcccat ttagctcggc   3420
cgagccgccc cttttctctc gggccgcgcc ctagccgccc gagggaagtc tacttcccct   3480
```

ccctcttcct tttctttttc aaaaaggatt taaataaatc ctttttcctt tagaccaaaa 3540
atccaataat cttagaaatt caatatcttc ccaaccgtaa atccgtttga ctccgttcaa 3600
cttccaaaat tcctcaaatc tcgagatcta tctaatggca cgcttagagg tcattaatag 3660
ggctttattt tcgccgtttg ttgagttgtc ccgttttgcg tgtagtttcg gagcccgaag 3720
acccgcagtg cgaggatttc gaggatcaag ctcaagatct cgagcaaggc aagccacctt 3780
tgaacatctt gagcctatat ctgaacttaa ttatgttgct tgaaaaaaat attatgcatt 3840
gataggatcg cacttaattt gcttgtcccg tctgcaaggc agattggcga acctacctaa 3900
tttgttgcat ctgatccttc ctttgttaat tgttatacca tgttcccttg taaccatcta 3960
gttgcgcctc gatattcgtg cactctatgc gagtatcgac ggtcgccttc aaacttaaaa 4020
tctgagtaac ttcttgggta aaacttgggt tttacaaaag acttggaaaa cccgacacct 4080
gggtcggtgc ttgcgaacta aatgaatttc caaaaccacg gaccggggaa cgtaccgggt 4140
gtacggtttc ccgctcttgc acttaaggac cgtttccttg gaatttcatc cgaacataag 4200
acaagtacga ccacatgggt ggaatgggac acccctggct gagtaactag tttatcaggg 4260
gagccttgat gccgagagac atgtggattc gccggggtgg tgtcggggag gacccctggg 4320
cttcctggca cagtatggtc tgggacctaa cctgttgttg gtctgggacc cctctcgtcg 4380
gcatatggta aacctgtgtc ggctttggaa atgccttgtc atgaaagctt ggagatctcc 4440
cgacgtggct gatccccacg ggttgggtga tccgggttag taatgtcgtg tgggtaaagt 4500
gtaccccctc tgcagaggtt aacaaactgt tcgaacagcc gtgcccatgg tcatgggcgg 4560
atgtgaggtg attcctagcg tagttttgtt tgactactgc cttgtgaaat tgctgttgtg 4620
aaaaggggaa tcgatgtttg gaaaatctgc agctgatggg atcagctagg cccgggtggc 4680
cgtttgaaag ttgttggccc gggtggccgt ttgaaagttg atggccaggt gccaatcttg 4740
aacaattcta aagactgata cattgcacat actccgaccg gacgagacgc actgtctcat 4800
ccgtgtcgtt tgagaagcac tcacttagtt gttttcagaa aagagttcaa ataaaatcaa 4860
ttgcaaaaac aacagccttt ccttgaagcc tgcattaaac acttatttcc catggcttgc 4920
tgagtactcc cgtactcacc cttgctctat ataaataatc ccccccagtt gctgaagaag 4980
atgaagcgga tcccgctgac gaggagttct tccaggagca aaccggctac gatgagtttt 5040

<210> SEQ ID NO 121
<211> LENGTH: 3000
<212> TYPE: DNA
<213> ORGANISM: Oryza sativa

<400> SEQUENCE: 121
tagtaacatg tatgtacaag actgaaagat gaaatataaa tgtggcttga ctctgaagtt 60
gcatgaattt cagtttgctt cacccagaga gaccacttaa cgttttttta cgaaatttga 120
gtgacttgat ttagggtaat ctatttatca caaatattat gccacatgga ttccacgtgc 180
atacttacta gctgtgcctg gcaaccttta ttgaaacgct tagcctgcac gtatttatac 240
aacaatatct atttagctta ccaatttcgt gaaaacatat tgttctttag cagtaaattg 300
ccatagttca ttcgtggtcc atgtgcatgc agtcatggtg ttgccttggt tctaagtttc 360
taacagaggg ccatggaatg atcatgacct tttgaaggta cgattaaatt tgtaagtgta 420
cccttacttt tatgcaatag ccccaacact tcaaaaaatg ctctatggag gtttacttgt 480
gacagttcta gagatgaatg ttcttcggat gctattacga aggattcttt tgtagctcac 540
actctgttta atttattttt atagcagcca ccttttgtga tggtagcagg atgaagagcg 600
gattagtaca ggtgagagat gaggatgaca cagtggtgtt ggacaagtct atatctccgt 660
atcttgcttg cggtggtcga ttgcatcaag gggaaacttc attggagggt gtcagctgtc 720
atggatgcaa acgtggtgac ccttctaatc caacggtttg agtggccaca atactggtta 780
atattgattt tggttcctaa ccatctgacg gctgacgagc cggcaagtac gagcaatgtt 840
tttaggtgtg catctttgtt acatgttgct ataatatttc tgtgtgttta agcaccattg 900
atcagcggca agaaggtgtg tatctcgttg ctccttgtct agatgtgcat atctaatctc 960
tggtagtttc aacagtctgt gttttgggca atggggagtc catccttttt tgggaggaca 1020
actggttgga gggttcctcc attcgctaca tatctccggc ggtttgggcg tctgtcccaa 1080
cacggcttcg ctgtcgcaga acggtcgcca aggcccttca agaccggaga tggattagag 1140
actgcaccgg agcgctgggt ttgcaagcta ttcttcaata tcttcaactc tggagtctcc 1200
tgaggtcgtc ggtgcggctc tctgaccacc ccgactcttt catttggaag tgggaagcat 1260
cgggagtcta ctcttaacgt tcggcatacc cgtgcactct ttctaggtag ggctcctttc 1320
cactccgaac ccatctagaa gactcccccc cctcgagatg ccggttcttt gcctggctgg 1380
tcgcaatgag gcgctgttgg acggtggacc gcctgtgttc taggggtttg cctcacccgg 1440
atggatgtgt gctctgcgac caacatgaag agactattga tcacatcttg gttgcctgtc 1500
cggagtctca tcagctttgg tgggtcctcc tttccagcac tggtttgcca tagtttctcc 1560
ccttgaatga agattccttt tatctctggg tctacaattc ctgccttaaa gtggggaggg 1620
ctagcaggcg gggatttgat acaatagcaa cccttactgc gtggacaatc tggaaggaga 1680
ggaacaatag ggtcttcaac tctcagcaaa ggccctggtc agagatagcc cgagctatga 1740
cggaagcgac tctctggcgg ttggcacacg aggtgctgcc ggtgctaacc atttaggtct 1800
tgttctaggt cgtttccttc tgatgtcgcg agaataggct taagcttttt attgttctcc 1860
tgttttcgca tccccctcct aattttcttg tttggcttcg cttgtacata ctctttattt 1920
ctcttaatac aaatatgcgt gccttgcgta ttcccaaaca aaaaaaaaac tctggtagta 1980
atatattttt ttgtcatatc ccttgtacat tctataagtt tgttgaattg tattttagga 2040
tggcaatctg tggatgataa atcaaacccg tgatatgaag cttttagttt ttccagactt 2100
tttagtacta ctatttgcta gatgattctg agtagataca attgctgatg gttttgatta 2160
atttttagac aatgtgatag ttttgtactt tttcttaaat atatttcata tatgacatgg 2220
atcaaatgga cagaatttgg gaaatttaat ttgattaaca tgaatttaat aatttattaa 2280
cacaaatttt atagtgccgt agcgttagca cggacagatt actagtagtg taaaatttta 2340
aatcttcttg taaaatttag aagcacgagg actaaaatga gaagtgccca aaagggtagg 2400
tttttttttag aggtgttgcc tcagcgccta cctgttattt gaggccattg gataggagtg 2460
ggcctatatt gttcatgccc tcgtgcgcgt acacaatcat agtttcacat agtagaaatg 2520
gtgcttaaga cttttaaact ttcgttcttc actgtccaaa tatatgctaa ttaaggttgg 2580
aaactagaaa acaatagaaa aaattcaact acaaaataag ttctacaatt taaatttcta 2640
acttgtaaaa gtcaaattct tgttatgcct tatataggct aacgagcatg caatgagttt 2700
atacatacgg atcgtatcat ctgaattaag aaacaacagg ggcattattg acagggacca 2760
atcaaccaat gttacgaacg cgcacgtgat tgatggatgg agctaaccgc gcgtgcccga 2820
caccgctggt tgttgttagc tacaaacgta acacatgcat gcaccgatcc atggatggag 2880
caaagcggcg gcagcgccgg agtataaatc tacccgcgct ctgcctgcct cgccatcacc 2940

-continued

```
ggccgccgat cgagtacgtg cgcacgcagc tcatctacta gcctacttcg ggagggcgac   3000
```

<210> SEQ ID NO 122
<211> LENGTH: 3000
<212> TYPE: DNA
<213> ORGANISM: Oryza sativa

<400> SEQUENCE: 122

```
tccataatta gagaatgttt actgtagcat cacatgagct aatcatggat taattaggct     60
cattagattc gtctcgcgaa ttagtccaag attatggatg ggttttatta atagtctatg    120
tttaacattt ataattagtg tccaaacatc cgatgtgata ggaacttaaa aattttagtc    180
ctatctaaac agggtctaag atgcaaattc tttagtccta tctaaacagg gtctaagatg    240
caaattctat cctgattttt attagcacgt atattaaact gctaaatgat tttttttca     300
aactttctac atacgttgaa actaatctaa aatatcagta aatttatttt ttaaaattta    360
caataattaa aacttaatta gttaagcgtt aatgtttttt attcgtatcc taacttcatc    420
ttttctataa aaaaaataca aacaaacacc acctaagaga cgcagtcgct gtgtgcggct    480
caaacgagca gtcttttcga tgtggaggtt tcagatagga ataagttcac atggtgacca    540
tcaagagtga ttgaaatcta atcgatgacc ctaaaccata aaaccagata ttttgacccc    600
aaaactatgg aaaccggtgc aatttgactc cttcggcggt tttggagggc ggtttcgcag    660
acgtggcggt attgaccggc aatcctttac acgtggcgct gacgtggcat ttagaattaa    720
aaaatatgtg tggggcccat ttgtcaatga cacagaaaat agattgtggg acccacgtgt    780
cccttctctc tccccttcct cagttccctc tctctcctcg ccattccctc tctctctctc    840
ccgcggcagg cggagatggc ggggcgacct gcgagcggtg gcggcaaccg ggctgagctc    900
catcgtgacg aagacggagg agaccaaagc ggcggcggcg ggaggcacac gaggcggggt    960
acggcgagct cggcccggca atgggaggac gaggggagcc ggcggcggtg cgagcggcga   1020
ctgagggacg ggggccgacg ggccagagcc ggcggcggtg gcgggagggc gggcgggtga   1080
gcacggcagc ttgtggcagg aggacgtggg gagccggcgg cggcaggagg gcgggcgggc   1140
gagggcagcg gcggctcgtg gtagagggag gacgagggga agctgcggcc gaggtatctg   1200
agttcctctt tggccgcttc gccgccgacc acgccgccat cgccatcgcc atttcaggag   1260
tcaaagtcga agtcgccgcc gcagcctgct tcttccgccc gccgccgttc ccctcatcct   1320
cccactgctt ctcccgcccg ccgctgttcc cctcgtcctc ccactgcttc tcccgcccga   1380
cgccgcccgc gggccgccgc cgctcggccg ccgccgacgt ctcaatgccg gccgctgatg   1440
acgtctcgat gccaggcgct gggtggtgtg ggtggtggtg gtgcgagagg aacggcaagc   1500
ggccgccgct tcagctccag cccacggtcg ccgccgcagc tccagccgcc gccgctcgct   1560
ccccgcggac ggctgtaggg gagagggagc aagaaagaga gaagggaggg gaggaagaag   1620
aaagggagaa gatggcgtgt ggggcccaca tgtcagtggg ccccataatt gtgtgtgtga   1680
atgacaaatg ggtcccacgt ataacatttt aattgaaatg ccacctaagc gccacatcaa   1740
cgccacgtgt aaagaagacc cggtcaatac cgccacgtcg gcgccacgtc agcgaaactg   1800
ccctccaaaa ccgccgaggg agtccaattg caccggtttc catagtttgg gggtcaaaat   1860
atccggtttt gtggtttagg gtcatggatt agatttcaat cacttttgaa ggtcaccaag   1920
tgaacttatt cctttcagat aaccttagcg agctctaaag caaaattttt cataaatata   1980
aatatataca tataaatttt tcataaaagg gagcatctat ccatttgtcg ggtgatctaa   2040
```

```
tacgtactac tccctccgtt tctccctccg tttcaaaatg tttgacaccg ttgacttttt   2100

aatacgtgtt tgaccattcg ttttattcaa atcatttaag taattattta ttcttttcat   2160

atcatttgat tcattgttaa atatattttc atgtacacat atagttttac atatttcaca   2220

atttttttg aataagatga acggtcaaat atgtgctaaa aaatcaacga tgtcgaacat   2280

tttaaaacgg aggaagtaca agtctacaac gtacacatgc accgatggat gggtgaagca   2340

aagcagcggc agcgccgggt atatgcgtgg tttgcaaggg tctatatttt gttgcaccct   2400

tttggttatg caattgctac actatttgtg tttaaacaat tgctgttaac tttagatact   2460

gtggtgatgc atgctgtgac atgctaattt gctaacggtg ctgcttaaga acccgatagc   2520

tttgtgtctc tttacttttg acaaatgtgg ctggaagttc aatgttaaat atattattcg   2580

gtatttccct attgccattt gcatattcaa caatatgtga atttgtcata tacacaacag   2640

caatcacaat gaatataaaa gcctaatatc tccacttctc taacatttgg caagtataat   2700

ctcaggcaca aattgaacca aacagcacct gaccattgta tcccctcagg cttgttttca   2760

gggcatcaac caaacacact actctcaggg agacatgcct aaccaggtaa ctttgctatc   2820

taagctcagg ctactctcag gaatgtaaaa tgctcaggca ggttgctcag gatagcaacc   2880

aaacaagcta aatctacccg cgctctgcct gcctcgccat cgccggccgg ccgccgatcg   2940

agtaattgcg cagcgcacgc agctcatcat ccactagact aattacttcg ggagggcgac   3000
```

<210> SEQ ID NO 123
<211> LENGTH: 3000
<212> TYPE: DNA
<213> ORGANISM: Oryza sativa

<400> SEQUENCE: 123

```
gggcacgtgg gggggagttg ttgcatcggc gcggcgcgtg ggtgggtaga tatgattggg     60

cgggttgggc ctggaaattg tgacattggg cctgtttaga tccatttgga ataacaaatg    120

gtaaaagttt tggtggcaaa agttttacaa ttgcaaaata ctagttggtg tttagatgca    180

tgttaaagtt ttgccatttt agcactaaag tgagagagag aaagagagag ggagtgatcc    240

caaagcactt tttggcacaa tttgctacta tggattagca aatgccaaat gccaaactgc    300

caacttttgc tactagtgtt tggatctaaa atggcaaaaa gtgctacaaa atagcaaaac    360

ttttaccatt ttgaaagatc taaacagcgt cattattggt ggacttggcg agtaggatgt    420

acacacgtac gaattttagg caagacgtag ctcgtgcagt cgtgctcgtc ctcggctgcc    480

ctttttctct agtcagttat ccatcttccc tcatcaacgg gtgtgcttag ttcacatcaa    540

aattgaaagt ttggtaaaaa ttgaaataat gtgatagaaa agttggaaat ttgtgtgtgt    600

acgaaagttt tgatgtgatg gaaaagttga aagtttgaag aaatagtttg gaactaaact    660

cggcccaact taagctttca gatcgacttg actgatgcat ataactcaat ataatattag    720

agccaaaggg tacatgtaca tagctcgtgc agttatactc gtcctcggct gcctattttt    780

ctcgtagtga ttttgccttc tgctcgcttt tttgcatata ccgtactgct gtacatcagt    840

cgattcatat tttccctttc cccaatctca gttgactgaa tgaattccgt tggttttaaa    900

tcgaacaacc aagtaattgt ttttaacctc cagctgaatg agtgtgagag atgagcagga    960

tggtatggag gactaactag ggggtgtaat ttcctcgtta ggggtaggga cccggcgggt   1020

accctacggt gacaagggca gagtagaaat tttaccccac gtatttgcca gggtaaggcc   1080

gtaactattt tcacgggtgg gggcgggggga ggaaagtgac tcgtgaatga ctcggcaacc   1140

accccgaagt gacaagaaac aacattcacc ttgatcttta gtccaggacc cattaataac   1200
```

-continued

```
ccatatgcct tgtattcctc cataaaacct atgttacaaa aacaatcaat attgttatag   1260
ctcccattaa aggtagtggc gtatgtggag tcctctttat agctcctgag atactgacgc   1320
aattgattac ctcccatacg tagctatgcc ggatgacctt gatatcctct ttggcactcc   1380
ctctagttgg atgcgacaac tgcgagtact catgtattgc tcccgctttg acctcctcgc   1440
cagtaaagcg acgcacaaac aacttccttc aatccagcga ggcggcaatt aaaactcttc   1500
caacatgaca accaacctta acctcctcct tatggacatg ccgacagctg aggttcaata   1560
ttctctccct tcaatccagt gaggtgacga tcagccctcc tccgacatat ctttcagctt   1620
tgacctcctt catttttgtt tctggtgtct cctctttctt ctcattgatg accctggatg   1680
ggatagggga cctaactcct tcctaattct aggagtagcc aacgatgata ggatggcttc   1740
ctcagagagc ccacgatgcc ggtagcacgc aaaccttagt aagcttcgcg ggatttggtt   1800
ttgggctaat gagtgttagg aggggagtag agagagatga gagcagcttt agatggaggg   1860
ccatgtggtg gaaatgggtg ggcgcgaggt ggcatcaacg ccaacggagg ttgctggaac   1920
aagagcggcc atgtgattag gagatgatgg gcaacatcgg tggatctggc gtctcgctca   1980
atcgaagact gggaaggaga ggttggtcgg ggataaagct tcggagtttg aacatagcca   2040
cataggtgac gataacatca tgaagaaaga taagagggaa aactaaaaaa ggttgtgact   2100
ggtggggctc gtcatcgtga ggatggaggt ggtgctaaga gtggcagagc cgcgtacgtt   2160
tcatgctcaa caacgcgagt ggcagcatta aaattgctta tgtatgaagt ttaaaacaat   2220
ttaaactgtc caaaaactga cttatagata atagaagaac aaaatgacca gttgataaac   2280
cctaataatt tcatactatt gggagttggg accttatctt gcacgaccat ccatagcagt   2340
acgtgcaagc acatgccgca agaaaatgtt cctcacgctt agaaatttct tcaaacagat   2400
aaggatatac gtggcgatag ttttttttt ctctcgaggg gatgtctctt cctttcatgt   2460
cttgtatgtt atccaaacaa tataaaaaaa tgataatgta gattaatacg tgagttcaat   2520
ttcgacccta cgagatataa agaaaaggac tactttgact gatatttatt agtttgatcc   2580
ctcttttatc accatgtatt gccctctttc tatcttgtaa gctaaaacaa gaaggccgga   2640
ttcatcgttc acccataaaa ttagccacga gcacaaatga acacacatgg ctagactaat   2700
caccaccaca tccaaatata ggcaacactt aataatagag gataataaaa gggagcaaaa   2760
caggttgggt cttggctttc tcccctctct ctctccctct tgtcattgcc ttcctcccct   2820
ttaggcaatg acagagtata attaagctga acaaacaaca ttgctaggag cttggaaaaa   2880
cctaacaaaa ccggcgtatc cattttagct aatctttctt taatctcccc ccattagaga   2940
gcacttagaa gatataggag tcggttggat agcgagagag agagagagag tgagagatcc   3000
```

<210> SEQ ID NO 124
<211> LENGTH: 3000
<212> TYPE: DNA
<213> ORGANISM: Oryza sativa

<400> SEQUENCE: 124

```
gatagaagca gacacagttt caattatatt tcttatccac gaaattggca tgaagtttaa     60
tttttagttg catgagaagc aagtagatat cacacaagaa gttcttcgaa taatggttgg    120
ggtgggggat caaaccttat gtgttcaata agttggcgtg cacaagctag tagtaatggc    180
tgcggtcaaa acaatatgca cattcattag atctatccat ggtctgacct tacattgaac    240
agtataataa ccttacctca tctctctttc caaaaagaac agatacattg taggttggat    300
```

-continued

```
cagaaaaaac actttcatct ttcctattaa tgaggaagaa aacatgatca gaaatactaa    360
agtggcagga aaaacagaac atagtaacaa ctacaatggt atatcatcaa taaagtgcta    420
gctgtcaact atcatctatc gtgtttaaga aataacagaa gcattatcct gtataaactg    480
taacatcatg aggtcatgag ttatgacctg acatgcactc caaaatctat gttgacagtt    540
tcctagcctt tttgcaacta gcggataaac gcaccaacat atgtatgcgg aattgtggat    600
ggatcctcac tgttctttca gaaacataag ctaaaagctg agagctaaag gtttaaaatt    660
tggataggac taatagcatg gaaagaattg tctatcctga actggcaatg cccagaataa    720
accatgctat atgtgagaat aaacaacata cctggcagct agtatggttc ccatgcatcc    780
tatttgtgtc accatcacct gtatatttta ttattaggtg agcatatttt atatgtgaaa    840
acttgtcatc caatcaaata aatatcactt gcaaggtgta actaaccata aagttatcct    900
catacttgct gataacaata tctgtcttat tgccctagaa aaccaagaag gaaaataagt    960
tagctgcacg caaagaactg aaataactaa caccaagcaa tgcaaatgtg gtttttgcaa   1020
ggactagaca attacaattt gccaaagtga taacaattga ctaaagtatg atagccaatg   1080
cagatcatgt tcgcgtccaa cgacagaaca aacttgttct tacgggcaat ggctaacgat   1140
atgcgatgac atgttgaatc gagttctaat ccaggaacag ttttaacaaa ctgtttttct   1200
aaaaggtgtt tttatcgcag tcatatgcaa tgcactaata tatgcttaac agttactgga   1260
gcaaaggctc tcacattgat atccaaagag agggacttgt gcggcacagg aaactgagca   1320
ttcggctgca cagaattcat ccccatctcc atctgcgaaa caagcatact gcgagtaatc   1380
agagagacca caaagaaggt catcgacaca ccaacacata agagaaccca aataaacttc   1440
tattcactaa gcagaagtta cagaacagcc acgcagcttc tgaatcccta aatcacagcg   1500
ttcgcttcga gaaatccccg cataattggc taaatggctg gtgcgtaaaa gatattgccc   1560
caaaccttta taaactggca ataaggaaaa atagaatggt gtcgaccgaa cttcaagaca   1620
acacatggat tacctccttc cgacaaatca cagagattga aaccatcaat gaactagttc   1680
aactaggtgg actcatatct caaattcaat tgcaattggg cactgaggat gacataattt   1740
ggacaagaaa tgaaactgga acctgcatat ccaaaagtgc ctaccttgcg caattcattg   1800
gatcatgctc taaacaagaa ttcagtcatc tttggggctc tcaagcacag ccaaaacaat   1860
aatttttagg atggttgatt ctacaccaaa aaaccctaac ggctgaaaac ctgctaatta   1920
gacattggcc ttgccactgg atttgctcgc attgcagcga agattttgaa gacaccgatc   1980
atctcttcag agactgcccc ttcacgaggc aagtatggaa cagagtttcg acaatgagag   2040
ggtctgatcc aaagccgccg tcacaaaacc tcaaaatttg ggtggatgat atcacggcca   2100
atggaagtaa aaaaaaacac aagcgagaac agcttgatct cctcgtgatg acttggtggc   2160
acatctggct acaatgaaac acaagaattt ttcagcagca accaagcacg acagcacaag   2220
tcgtaaacct aattatacaa gacatagacc tacgcgaatt agctctcaaa ccgccttgat   2280
tttctacccc atccttcttc ccccgaagtt gtaatctctt caacctgtat tcgtctaaac   2340
caccctattc ttcttttatt tacttcttct aatataatcg gcagagctcc tgccgcctta   2400
ttcttcaaaa aaagaaatcc ccgcggaaat cccaaatcaa caaaggagtt agggggcaaa   2460
gtactggggg gggggggggg ggaagaggag ggttatggcc gtcgggagct gtgaggttgg   2520
cggcgcactc gaccaatccc cctcctgcgc ggcggcggcc gaggagggga agttgtcggc   2580
ggttcacggc ggcgaagccg tcgctagaaa gagggggctg agcaggtggt cgaatcaggg   2640
agttctccga gtaaatcagg aagaagaaga ggtcataccg gcgcaatcag acggcgagct   2700
```

ctccgggcct tcgccgccgc cgccgccgtc gtcgtctccg gcggcgactc gagagagaga 2760
gcgggggtgg agcggaggag aggcggcggc gcaactcaac caatgagcgg aggacacgta 2820
tccccctccc gcgcccgtcc gatcagtagc aacccccgc gccaagattc gtgcagacca 2880
cgcgcgtgca ggtagcaacg gctcacgcac gcgccgcagc tacccagcca ctcctcgatc 2940
gtctcctccc cattataagc agcagcaagc aagcaaacca aagcaaagca tcgatctccc 3000

<210> SEQ ID NO 125
<211> LENGTH: 3000
<212> TYPE: DNA
<213> ORGANISM: Oryza sativa

<400> SEQUENCE: 125
cgcggggagg tggtggcgag gagagcgcta gttaagcact tggtttgggg ccaccgccgc 60
ggatccgcac ggcgagagag gggcggagaa gaggcagctg agggaggcga acgcggccgc 120
cctggacctc cgcgagcgct agtcagggac cggagacgag gaactgaccc gccgtgggga 180
tgtacggtgg gagggaggag acggtgcagg cgcggtcgac gaacgcggcg tgagctagcg 240
agcacccgtg cgccggtgga tgtgcacccc gctgcttgct tggtcggtga ggcctcctcg 300
ggagctaagc ttgtatgcgt gtggctcgag ggcgagggat gaggcactgc gcagtggagg 360
gaggtgtcgt gccgctatgc cttagattgt agccaaaata aaccttatca aattttgtca 420
atttggcaat attgccaagt tttgacatga tttattacgt atttactccc tgcatcccaa 480
aatataagca tttttagcat agtgacaagt cagacatttt caactttgac tattaataga 540
aaagataaaa aagatcattc atataaaatt aatgttatta gatttatcat taaacaaact 600
atcaataatg tataactctt tttatttaaa atattttact tttatagata ttattggtca 660
aaaataatat ctcgttgacc gtgtcaaagt ctaaaaatac ctatattttg gaacggaggg 720
agtactaaag tttgataaaa aaaactaaat taatgtacat atttaacaac ttaaaaaaag 780
atatgattta aaatgacatc aagctaaaca tctgaagcta aatgcatcgt tcggtgtgaa 840
cctgtatatg ttttggccac gatctagaac atggtaccta ccccttctat tagcaattta 900
gctgctcttc ttgttttttt ttccttaagt tcgtggggag cttggaactt tcggagtggt 960
aggtgtatct gaaagtctga gatgtgccac gcctcttttc ttctgtcctg tcttcatctc 1020
ctacctaacc cctgcctgca tcaaccctca tatgttgtcc ttggcgaata aaaacatttc 1080
cctactcacg ctctttcgat cttcagctcc tctctatttc tctcgtcaac aattagcgct 1140
ctctattcat cgcaaggagc aaaagcagtt tcagttccaa cctccttctg gttccattgc 1200
taagaagtaa gttaatctct ctttcttgct tccttctgat ggatccttgc tagtagtagt 1260
attactccga gcatgtttaa tttggttgct acctgagaga agcatgcctg gacttatgtc 1320
ctgtttgaat ccagggacta aatcacatag aatgtttgat attaattaga agtattaaac 1380
gtagactaat gacaaaacct attctataat cttagactaa ttcgcgagat aaatctattg 1440
agcctaatta attcatgatt agcctatgtg aagctaccgt aaaaatatgc taattatgga 1500
ttaattaggc ttataaaatt tgtatcgcaa attaactctc atttatgtaa tttgttttat 1560
tattaattta tatttaatac ttctagttag tgtcaaatat agtccttgtc acatcggatg 1620
tttagacgct aatttcgagt attaaatata gactaattag aaaactaatt gcataaatga 1680
gagctaattc acgagataaa ttttttaagc ctaattaatc tataattagc acatatttaa 1740
tgctagcatc acatagacta taatcatgga ttaattaggc ctaaaaattc gtctcatgaa 1800

-continued

```
ttaggtctta tttatgcaat tagttttgta attagtctat gtttaatact ctaaaatagc   1860

atctaaacat ctaatgtgat agggactaaa gttttaggct gtgtttagat ccaggggtga   1920

aaagttttac cgtgttacat cgaatatacg gacatacatt tgaagtatta aacgtagtct   1980

aataacaaaa caaattacag atttcgcctg taaattgcga gacgaattta ttaaacctaa   2040

ctaattcatc attagaaaat atttactgta acaccatatt attaaatcat ggagtaatta   2100

ggcttaaaag atttgtgtcg atcttgattg gttgctaccc aagactgttc tccactggcc   2160

tggcctgacg catactccag ccatagaggc gtgcaattag cgcggccgat ttctgtcgcc   2220

cgaggctcca ggcgtaaaca aatgcgtgct ttaccatcga aatctcaact gtacgaagtc   2280

atcaccgcgt gccgccatcg cacgaggctg cccctgatct gacgccactg cgtgaagccc   2340

acacctacct caatcgccac cgccggcaag cgaagccact gccgtggtcg tcgttgagcg   2400

aagtccccgc gttggtcgag tttgtacgaa gcttcgcgtg atcccctttg ccggatccag   2460

cttagagcga agcttcaatt cagctgatgc tgctgatttt gctgatcgtt attgcgactt   2520

tggggatatt tttggaaagt taggtatgta gcatatggat tttgtgagat ttttcccgag   2580

acgccaagcc gttttgtcga gatttttgtt cttcccgtct aatacttgag ttagcagtaa   2640

tcatctactc gatcaggcag cagcagcaaa ccaaacaagc aactcgtcag gtggaaccca   2700

tgagtttgtt ggagtgcaaa ttcttcaggc gtggtgctca ggtcaccaac caaacaggcc   2760

ttctgtcttt cgtccgtctt gagggatatc aagaaaagac attctcatgg ttctaaaaaa   2820

aagggatatc aagaactcaa aaagactttc tcatgaatga atgtatctaa ttccatctga   2880

aactctggtg gtagcttcat acccacttcg gactttgcac tagcttgtac atttagagaa   2940

attctgaaag tagtatgtga aggttgttga aatatgctta tatacaaaac atgaccatac   3000
```

<210> SEQ ID NO 126
<211> LENGTH: 3000
<212> TYPE: DNA
<213> ORGANISM: Oryza sativa

<400> SEQUENCE: 126

```
tgttaggacg agggatcagc gatctctgtg acgaactgct gcctccgaca aaggcgccgg     60

aaggcagacg gggacctgcg cgtaacgtat ttagttagga cgtagtcatg ttaccgagaa    120

taaatcatat atacttgaac taacctctgg gcggagcagt accgtgcgaa gaaccagctg    180

taggtcgcac aactccggta ctaggggcgc gtggacatgg tggtactgga ccaggtggag    240

gtaccgcgtc catggcgctg caacaagaga agacgcgcat gacagcgtgc atcttctctt    300

gcatccggtc gaaggtaatc ctctgctcag catcactcaa gtatagcccg gcgtccaacc    360

tcactattat cgaggtaata tcggcgttca cagctcgtgc cgtgtcggcc tattcaagac    420

ataagacagc atgtcagtag gaaaataatt gaaggaactg agtagaaact attgccagaa    480

gtgagtagaa gttcgacata cccccatgaa gtagtctcgg tcacggtgcg tggggtactc    540

gtccctgaca gtggcaagtc gcggctgtgg tgcggctgga gtgatgttgt tgcggtgatg    600

ttgcagtgat acttcttgac atcttgtaag tggcactggt gctcggtcac aatgctaact    660

ttccaataat ctttccatgt acccttatat gcatgaacac gccacggaca atcttctttc    720

acgcacctca cttcatacac ataattggtt gacttgacca ccctaaactc tctcatcaat    780

gagaccgccc aatgcttcac tgcctccttc atatcctcct tatgagcata cgtagcaccc    840

tcaattacct cgttatcctt gtattcctag ggtacatgat gttcctctga gataacaagt    900

cccgagaagt cctcatttgt ccaatcagtg ggcattacat caccttcctc gtcggatgat    960
```

```
gcatcgccct ccgcttgctc gttatccgaa tcttccctct tcatttcatc aacgattgta   1020
ctgattctct ccccctcatc tgccacgccc atggcctgca ccacccctgt gtcatttccc   1080
tcatcttccc ccgatggttc aacaaaatcc cccacatggc ttggaccctc gacatcttcg   1140
gtttccattg caatatttct atcattttca tgcaccgaca caaaaataac caagggccat   1200
gacctttcaa aagccatctc cagataccgt ttccaagcaa tagtgctatg cgcatcggca   1260
tgagttccca aaaataacct tccgttgcac gactcactac aaccgatact gacattgtgt   1320
ggacttctga gtctattcta tatccttgca tcaaccaatt ataaattgac tgaaatgatc   1380
tctcagcagg cctatcgatg cccttcgatg tcattacaaa atctgacaga tcaacaccat   1440
caggaccaaa tctaaggttg ccttcaccgt gaactatctg aaacatgacc ttacttgaca   1500
ttgtgcttga tgaaaaaata tctatgttaa ctaagttcat atcatactaa ccagatctaa   1560
ccccccattc atcaatacat actacgccct aagttaaaga tactacaaat aagttgtatg   1620
tcctatgtct caaattctaa aataggctgt gtgctacaga tctactaaag tatatggtaa   1680
aaaaactaaa atgcaacaaa aaaaatggaa acacatttca aatgaatgta ttacctgtga   1740
tggagtcagc aaaccagcag ggcttcgccg ctccccttct cttcctcctc acccctccct   1800
ctttctcttt ttctggattt tgagtgaata taatgaaaat tctgagaggg ggaaggggtt   1860
ttatactcgg aggggtaaaa atcgccctcc ctaagggcgg caagggggcc gcctgcaaaa   1920
ttccaggccg cctcgccgcc cttttgcagg cggccccccg cacagtaata aatcgccctt   1980
cgggagggcg gcaagggggc cgcctgcaaa aaaccaggcc gcccttttgc aggcggcccc   2040
ccgcaccgta gtaaaccgcc ctccgtaagg gcggcgaggg ggcctcctgc aaaatggcag   2100
ccccccctata gacggccgtt aggcgtgcgc taacggtggt cagccacgtc acgaaaatcg   2160
ccctctggga ggaaaaaatc gccctcccag aaggcggcgg gcgactactt ttgtaaaatt   2220
ttgaaacaca aaattacttt tgtaaatatt ttaataaaaa aaattaaaaa taaaaaaaat   2280
ttctccaccc gggttggttc atcggtacat gaagaagccc atcggcccag catcagttta   2340
ggcccaaatg atcaggcggc ccatcaaata tgtgcacatg tgctcttcag tggtagcata   2400
gggtatagat tatttgactg tacgattgga ggggacaact cctctttttt atattactat   2460
atagaatata gattattttg tgaagtcact cgcataaata cattaaatat tataaagcta   2520
ataaataact ttgaaaaaga agctatttaa accatgctta aaaagtttga gaaaacatac   2580
tttcggaagc gtgctaccta cattagctgt ttaaaacgcc accgaagtga tataagacga   2640
ggacgtccta acaaattcag ttttaatttc ctcgtctttg catatatgga aggaaccgaa   2700
gaacttcacc tcaaaaaaaa aaaaagaaac tctgctctta acagattaaa tcttgttaaa   2760
ctaggattag cttcggttta agctgagact gcgtttggtg aacattgcta cctacccatc   2820
cattagcaat ttaggtctca ttttttcttg agttgcagcg gtttgggact ttgggagtgg   2880
taggtgtatc tgacagtctc gaatgtgcca catctctttt cttctctcct gtctccttct   2940
ccaacctaac ccctgcctgc ctgcatcaac catatatgtt gtccttcacc aataaaacac   3000
```

```
<210> SEQ ID NO 127
<211> LENGTH: 3000
<212> TYPE: DNA
<213> ORGANISM: Oryza sativa

<400> SEQUENCE: 127

agagccatga acccacaagg atgagaatat atcttactta aataagaaaa gtaaataaca     60
```

-continued

```
aagaaaatca caaatacata tataaaagaa gcatccatcg tggtacaaga tcgtaaagag    120
tgtcaacata tccggcattc ctccggagaa aatggcgaca tctctggcac ttctctgaaa    180
ctcccctgga gagaacttca acatctccag cactcttccg gaactccccc gaagagaact    240
ttgacatcaa gggcactcct ttcggagctt cccctcactc tcttcttata ttctagttgt    300
actagagagt agtctaaaaa gtgagttgta ctccacttga tttatgtgtc ttgagagtga    360
gatgataatc tccttttata tccctcctat gatgcttact atgatggtta taagatcggt    420
tcacccacaa ccgtcatagg gaatgaatta atctgggtcg tccacgtaga aggtggaggt    480
gagagtccac aaaggcggtt tgaccgacct tagggttcgg gcgacccctt ggtcctactt    540
tccgaccgct ccttctgccg ggaaatggtt tataataacc actatctcta agttagatgt    600
tttatttcat tcgcttttat atagggattg atggtcagat ttaatactta aggaccgtca    660
aaaacaattg tttcatcttc tccggcacta gcagcacccc caaactacca tagggaccta    720
tgtattacgt tcccgggggt ggggtcaggt gggagggggt gggggagagg gaaaaggggg    780
caattctctc gctttaaagg gatggttctg ggaggcggca gcccggcggt gggtgccgga    840
tcgaacgagc ggcgagacaa cggcagcgct accgaagccg cagggtcaga agcgagtgct    900
gggccagtgt tggcgacggg gacaaagaag aaggactggt tagggggagg cgtctggtgg    960
tggcggattc cgtggcgggg agccaccgaa gaaggggaag acggcgacac gggagcagct   1020
cgccgccacc gtcttaagga gaggagaggg tgggggttgg ggagggggga acgggctcgc   1080
ttgcggcgtt gatgccttcc ggccaaccag cgaggctagg cagcggtgct ctgggatggg   1140
ttggcggtgc ggattgcagt ctcgcacgag caaacaacag cgacgtgagg gatggagtaa   1200
ggtgaaatgg aatgaggtga gggttttagg gtttggttgc cctgtacgaa ttttaaacca   1260
attagatgct ctagaatttg aaagattttc tttttccttg gggttggggg ggggggggtta   1320
ttgacagtct cttaaaaaac ctcgtgtgga tgatctcccc tagatacttt tctcattgca   1380
ggactgagaa aaaaaatact aaggcttcct ctaggtttct ctcaaagcag caagggtgac   1440
gagggggtcc ttttttaacc caaccccgaa aatccactcc tacgggggag tctaatgtca   1500
ccgtccgagt tgaatcctag aattttctga tagcaccatt tttactagct aaaaatcctt   1560
tttttttcct tcccttcagt tcatcaagat tttgaagctc tagccgcatt acgcattata   1620
gtacgccatg tacaccaatg cctgagccaa aagcaattaa gcagagatga tcatcgatct   1680
gatcgacctg aaacgatccc cgaaatatca tcatcgatcc taaccaaatc aagcaacaaa   1740
aggtacgttc tcctcaaaaa aaacaaaaaa gaaaaaagtg agagagaaag aaataaagcc   1800
gcagcagcag caacagcaac agcgtacaca cacacaagca agcgtacgca ccactgtacg   1860
cacgcgcgta tacgtgctgt ccctagcaaa tgcaccagca accagtctcc ttttcccaca   1920
acgacaccac ccagcattcc agcaactagc agtccacgcc tctccacggg cgcgcgcgcg   1980
cgcggccacc gtgagttgga ccttccatcc atcgatcgat cgatcgatcc agcaacaaac   2040
tggcatctcg cgcgcgcgcg cgagcgagcg agcgacgtcg tcgtcatatc gcatgtggcg   2100
cagacggcac gcacacgtat tactgttgtt tcgacgacga tccaggaaga aaaggggaaa   2160
gtgatttcat cccctcgtgt gcatatatac caactaaata gtcatcaaag gatttgaaaa   2220
tttttctggc aagatagatt aatataaaat atatagcact ctacaaacat gcaagttaaa   2280
aattcaactt gtacaagttg taacaaaaat agcaaacata gatgcgaatg tacgttaact   2340
attttcggtt tgatttgttc ttttttgttg taacctgtag aagtcaaatt tggtcttgta   2400
tgtttgtata gtggtgtatt tcatgttaat atatattatc atttttttca attttttttaa   2460
```

ctatttactt cctccgtttt atgttataat acattttaac tttggtcaaa attaaactgc 2520
tttaagtttg accaaattta tagagaaaag tagtaatatt ttcaacctag gataaattta 2580
ttatgaaaat atattgaatt attgatttaa tgaaactaat ttagtattat aaatatttta 2640
ctatatttat ctatatattt agtcaaactt aaaacagttt aattttgttc aaaatcaaaa 2700
cgacttataa tctaaaactg aggaagtaga tgacatataa acaaacgaga gtacattccc 2760
acggaggaat gaaaatccat ctccgaagaa aagctttagc tttggtagag cgagcgagag 2820
ctgcattggc cacgcgagcc aactaacccc tccgagtcca ggccggttgg tacacgtgtc 2880
gccgccgccg tccgtttccc acccggagcc cacgtggccg ccatccgccc gtccgcccga 2940
cctaaccacc ccccctcccc cccgcgccta tatatatcag cacgcgcccc accacgcttt 3000

<210> SEQ ID NO 128
<211> LENGTH: 3000
<212> TYPE: DNA
<213> ORGANISM: Oryza sativa

<400> SEQUENCE: 128
cggtagtggc ggggccgtcc tccgcacgga tctggtggca gcggcatcct tcctgggctt 60
gtccccgtgt gcacaacggc gaaggtggca ggaggagccc gggagaggag ggaaggggcc 120
gggtgacaac ggcaacggtg gggccatccc ttgtgcggat ccggcgacaa atccgcatct 180
agctagggtt ttgatttttg ggattttttt ttcatatttc ttttttgtgt gcggacgaca 240
taagtactcg caagcgaaaa aacagatttc cgtgtgtggg tgtgctatcc gcatgaaaaa 300
aatagcgatt ttcgtagaca ctttcgttta tactggcgac tcacccatac gaggttttgc 360
ccgtttggaa aaatgctttc ttaaagtagt atagatctgc tgtaatattc gttcaggtga 420
gaagtgaaaa aattgcaacc aaacgtgtag aaaacttatg acagattagt gtcaaaacac 480
acgtgatcat gagagcagta tgtatagatc tgctcttatg acagattagt gtcaaaacac 540
agtatagatc tataccagaa gaaaactttc aactttcaca ctgctaatta gatctgctca 600
acgattattg tgcaggtgag aagtggaaaa actgcaacca aaatcgcaag cgcacgcaga 660
gtacttgtac gttagctacc gctgctggcc aactgagcaa aggaggtctt tttagttaca 720
tatgacttac atacatatat atatatatat atatatatat atatatatat atatatatat 780
atatatatat atatatatat atatatatat atatatatat aatcatacaa ttatataaaa 840
tataatgtaa ttatagtata tgtgcaatat atataattac actacaatta catttgaaag 900
atttttataa aaaaaatgct agatatttag atactcccta ggtgtttcat ccttgtactc 960
atcaggcctt ctctagccag ggtcaatctc ggcccatcgt cttgaagtca tatctgaagt 1020
ccggcctcca caacaaggag ctaaatgcgc aatgatccaa ctaatcaagt gaagtgtagt 1080
aattttgttt gggagtagca tacgtactta aaaaatactt acaaaaaatat tactaactaa 1140 ctcccaacca tttattttaa gtatgtagtt ggaagctaga aaagctaagg cctcctttga 1200
ttaataggaa ttcatgggga aaatgtagga tttcagcctt tgatcacagg attatggcac 1260
aggaaagtta gaggaaattt tccttacaaa ctcatttcac aggaaaacat aggaaaagaa 1320
aacatccagt accctaagct ctttgttcca tctctttttt ccatcatgtg tgcgtaggat 1380
tgagataaat gacagaccta tgcatcattg ttgttctttt ggaagaaaat aagatcaaag 1440
tgacatgtat taatacactt cctgacatta tctttccagt gaaattccta taccttttca 1500
aaggcctagt aacacaactt tcctatgttt tgcaatcctc tatttttaca attactatac 1560

```
atttctacaa gaatcctacg ttttttttat tcctccattt tcgattcctg tgatttaaaa   1620
tggccctaaa ttaatcaatc ctgctggtat gcaacatcac ccttactaaa atgtttgtaa   1680
catttttttt aacttgtagg caatatgaag ctcaagcatg atcatcggat tcgtttttgt   1740
cttcatgcat tagtcctagg ttcagcaagt tgacataaag tccacggtaa caacttaact   1800
aattacagtt aaaaaaaatt ggatgagcgt actacgacag tctgacaggg atacatgtac   1860
atctcaagtt cttaaccttc aattcagtgt cctctttttt ttcgcggatg cgtaaaagta   1920
ttacacaaca atatattaat agaattacac gacgtaactg ccagaggtca cacaaggaaa   1980
agctagaggg agaaaaaaaa tataaaggga ataaggactc caaaattggc aaatgaaaaa   2040
gtgctattat cctcccaaca agactcctag atgatcagta ttggcgcttg accagttgac   2100
cacacatgac cttacagctt gaccagttga ccacacatga ccttacagct tgattgaatc   2160
gaacaccgca ggaacagacg agagagaaaa aaaacataaa aacccttgct tgagatcctt   2220
tccttccaaa attgcgagga cactagcaac acaaagaaat cgaagccctt gcggagaggc   2280
ttcgggagaa gggctctaga agtcggccac caattttaaa gtgagctgcc atgggcagga   2340
gcgagggctg aacaatcggc cagtaacaac acgtggtgcc agatctatcg agcgaacaca   2400
caatcgtttc gctgtcttaa gctcctggca cagaaggggg caaaccgagt ggctgctttc   2460
acgcctcaac ggaagatcga cggtccagta gcgctgctgg agcgcaagca aaagaaagag   2520
tttacatttg gatggtcctt tggccgacca caatagatta gcacatgcat aagagtagag   2580
gcccagaaag aaagcatggt aataggagtt tgtcgatcgc tcgtccaacg ccagacaagc   2640
cgatcctctt aacttgggtg agctggacgt gacgcacaag atcctatacc accgagaatt   2700
gccagatgac agggacagtt agagtaccgc ggatgtcgcg aaccaataat ccaaagcatg   2760
ctgatttaat tacaaactcc tgtcccaagc atgcaccaat aatccaatat agaattaaag   2820
tcgcctctgc tcgatcaact aactggccag cttgcctttt tatataaacg gttaatcaac   2880
ctggtcttag atatcgacca ataaacaaag gaattactaa tagcaagtcg ccgctacctt   2940
gcccctgctg cctcgttacc acacgaaatc acgaagggag aaggctgaag aatagcaacc   3000
```

<210> SEQ ID NO 129
<211> LENGTH: 3000
<212> TYPE: DNA
<213> ORGANISM: Oryza sativa

<400> SEQUENCE: 129

```
cacactcaag tcaccatgtg acatcctaca tactcttcta aaccgttatg tgacactcta     60
ataaattaga gaaaatctta aaaattatga gaaaaaaaaa tcaccatccg ttataactta    120
taaactggtg aatctattat ttctaaccat tagatatatc tcaaggatct gtttccaata    180
aaagaaatct cccctctata tatacatact cctcctccct ctcctatttt atactcccta    240
cattctaaaa tatttgacac cgttgacttt tttaaaaatg tttgaccgtt cgtcttattc    300
aaaaaattta agtaattatt aattcttttc ctatcatttg atttattgtt aaatatactt    360
ttatatatgt atacatatag ttttacacat ttcacaaaag taagtttttg aataagacga    420
acggtctaat atatttaaaa aagtcaacgg cgtcaaatat ttagggaatg agggagtacc    480
tagcaacccc atctaaaaaa acttaagtga tcataattgt ttctaagtta tataataaac    540
cacaacgatg cagataaatc aaaacattga ataggttttc aacgtgtgtg ctgcttgctt    600
taatttggtt atccaaatag gctaacctat tcttgctagg gattatcaat gcaattagca    660
tgaggtctgc tacaaataag ggtgtgcacg tgttttcatc ctgctaagct ctactagacg    720
```

-continued

```
atttatcttt ttactggcta aacaacaagc accctaaata atcatcaaat ttgcaaacac    780
atctaaattt agatccatgg tgtctttaaa aaacttaatg attcaaccgt ggtaaacttc    840
tacggaaaag aataatttct agggcatgtc atcctaatta ccatttaaaa ataaaaaaaa    900
tataaactaa aaaaaataca aacactccta tacttccacg tggtacgcct ataaacacta    960
ccaaaccgcc acatggtatt ataataaatt ggtaaaccat ctatttttca actattatat   1020
ttatcttttt ttccttaaaa aaatcacaat ccacatccat cgcctctctc ccaccggcac   1080
aactatcctc tccccactag cccacccttc acaccaccct acgcacgtaa gtatacatac   1140
atacactttc tccgtctcca ataattcttt ctctcacctt cctattttat aaataacaat   1200
tttaattata aaaaaaaatt atgaagaaaa caaatctaac catcaatttt caattaaatt   1260
ggcggactca taatttgatc aatttttatt taaataagtg gagttataat tttaacaatt   1320
ggatttaaag acataaataa ttcaaacaga tgaacgcatt aaatctacct caataaaaat   1380
aaaatctcat taccaaataa caacgaaaca ttgaaaaaca tgacaacgca tcttatatat   1440
tcttgaatcg ttttacatag taaagatcga ttaaacatgc tctatagtac tcttaagtca   1500
ccacagtcac cacgtatgat attttaaaac tttgaaaaaa ttgaaattca aagaaaaaat   1560
aaagtatata tatctatcca cttaatttga tgacacatta tttttaacta ttagaatacc   1620
tttctcttta taaaaaaact taagccacca catgtcatgt cttaaatatc cttagaatga   1680
gaaaacaaca aatcataggt tctcacttag attatttaca aagattaaaa aaaacaatgt   1740
accctccacc tccctctcca atcacatgca cataacacta ttgcattgcg aaccctttct   1800
catatctgat tcgagttcta tgctattcat ttctctccag tctcctccct attttcagct   1860
actaaactaa agagataaac aaatattaaa aagaccataa ttttaagcta cacttataat   1920
tttattttat atatcatcta atcgatttta gatgatggtt tctttttcat ataaggtcgc   1980
cacatgttac cccataaatc ctcctaggcc tttttaaacc gatgaaccta ttatttccaa   2040
ccattagatc tatctcatat taaaagacaa gcgtgtattc ataatacatc atcttccaaa   2100
ataatatatt gcacaactat atatcttcat ccaatattat tcacgctagg ttgcatggag   2160
tctcacacac actctacatg gaacgttcac atatggattc tcaaactaaa caataatatt   2220
aggctatatt aacccatgca tttagtggag ccacatatcc cacccaattc atccgtcaat   2280
aaacaatgac aacctatact caattaaaaa aatcttactt ttgaatttac acttaatttg   2340
ctatttgcta tacatgtttt ctaacacaaa atatgagtac ctacttttta gatgatgaag   2400
aatattataa ataattgctt gtagggatta attaaatatg gtatgttata aagataacta   2460
atagctaggt tagaacatta taaaagcaat gctaatgaaa ataatttatg gagaaatcat   2520
atattgtaga tgttcaacat agtctacgac acatgcccgc gcattcgcgc gagctatctt   2580
cctagttaaa ctaattacgt aattgaacta agtaaaactg gattagtctc cttccacgtc   2640
taaatcctag ctccgtcact aatatcgctc ctcgtgtctg aacacgtata cattgctttt   2700
tataaaaaaa aattacacag tacaacgcat atattgctta acatgactct aattccactc   2760
ctttcacatg ttaacatgtg taataccatg tgaccgtgtg atgatcgatc gatgatcacc   2820
attggcatgt gcatcagcaa aatctcgcac gcacgcacgc acgcgcattg gtgtaagcta   2880
tatatagccc ctgatcatct gtgtgcatct tacagtgcag aggagcaagc aattgcacat   2940
cactcgacag tccacacagt gcatataatc gatctctctg cgatcgaccg cggctgcgcc   3000
```

<210> SEQ ID NO 130

<211> LENGTH: 3000
<212> TYPE: DNA
<213> ORGANISM: Oryza sativa

<400> SEQUENCE: 130
tcgagatctg ctccctctaa ttcctctacg ccctctccca tcaccgatgc gcctctcagc 60
tggcaggctt cgcaaggcca tcgtcaatca tagccaacga catgatcacc gatgctgaca 120
aggctcggca ggcgctgccg attgctacgg cctcctgcgt actcaggagc ggtggattca 180
ccgcctgttg gtgggctcta ggcacccgct gacaacttca acctccagtg gacttgggag 240
tggcagatct gctgccgata gggtttgtta aacgatgacg acaattgtgg tctcctaaag 300
gctcataagc aaccggtcca ccggaggttg cctcaccctg ccttatcccc tttcttcctt 360
cgcatccacc acaccactac cacctctagc tagatccaga tcaaggtaca tggcaggagc 420
gctgagatgg aggctgatga tcaaggcagt gggagaaagg ggccaatgct gagctcgata 480
acggcaagct ttgctgcagc cttgacctat gttcacttcg cttttatttc gctatgagat 540
aaatgtgaat ttgttatgga attgcgttat atatgtgttg agcattgtta tggtgatgtg 600
gaagtttact ctcgactttg gatttgcggt gtgtctgata ttgatttgca gtggtgtgga 660
tccgtagaaa tgggacgagc aggaaatggc actgcatctg gatatttttg agctatatta 720
tttgttttca ccgaaaatca cctcccaagt tgctcggctt aacctaacca cctgcaaaaa 780
ttgattttta catgtggtta tggcaatttg gtagaggcgc aggtggctca tccgcatgta 840
cacatatttt tccgcctata agtccatcga aattttgact aattattaat cttttagaaa 900
aattattttg aaataaaccg tgtaaaaatc ttcagcaaaa ataacatgag ctcaggggcc 960
gtatggcatt gaggtccaat agctcagcat cgtccctgat cgatgccgct aaccccgtca 1020
ggcgttattc agcttagagg gcgattggag aggattaagg gggaataatt ccagactata 1080
ataggtgtga aataaatccc ctccaattcc tctctcataa ggattaaccg aataaggcct 1140
cacggtgatg cgcgagaaga tgcaatggat tgaccaccat aacgcttggc gctgacctcg 1200
tatactccaa aaagaagagt gggtacgtca tgtacatcca caagttgaca agttgtgtgg 1260
tggttacatt gttttgctat atatcttatg cacacatatc acctaagttt gaatctcacg 1320
tacgatggtt aggtggttag gttcttaatt tgaatggtta gttattacta gcgcgcgcgc 1380
acaaacactg aaaaatataa ttttttaaat tgtgagtgta tatttagtca taagaatttg 1440
attcatacca aagcaataaa tcaacttaaa ttaaacttta ttttacaatc cattattaca 1500
tacctaagta attatatata agtttagatc ctatatacct acaatcaaaa tttaacaaaa 1560
agatattcaa atttagttca aacttgtttg aactagctag taaataagtt aatgttcata 1620
actaaacatt tttttaaaaa aatcagactc attagcatta ggtacatact caatttttaa 1680
tcatgttggc cgggccccat gaagccccag ttaattttaa tatatatata tatatatata 1740
tatatataaa gttaaatttg agttgttttg ttgctaggta taggtatgaa tcgaatactt 1800
ataactagat atatagaaaa ttttgaaaaa tttagacgaa tttgtgtatt tcatattatg 1860
gtgcccgggt gcccatatat gtcctatgtg tgtgtatgta aaccggagtt gctcaaagta 1920
tatatactat aaaaagagtg tgctaaatat attcaattaa aaaagaaaca cttatcatag 1980
aaatgataat ttcataggat caactccgac acaataattt tctcatcaat ttaagattcc 2040
atggttcaat ataattatgc tttagatttt atatatgttc tgtgaggata attagaagaa 2100
aatcgcgaag tgagtatagc tcaacttgtt aggttttttt ggtagaacca acccacccgg 2160
ttttatgtcc tagactttga tacgcgggtg tttgtgatta cggctaacta ttgttgtagt 2220
agtagccaac gtacctgtct acatcgaggc acttgtggtc aatttgtaaa tcccaacata 2280
tgtcgtctca gtctttcaaa ggtgctcgta gaggtagggt agtgtgcgtg tgtgctcgta 2340
ggggtcattg tgcgcatatt atgagcgtgt gcatttgtac tgtttttctt aaaaaaatca 2400
taactcgtta ataagatagc aggttcataa tatatagaat gaaataatat gtttttttc 2460 caaaaaaggt catccacgca caaaaatgca tatgttaggc tagcaaaatt ttaagaaact 2520
ttaaataaga tgtccacgtt tgtgtgcgca tgcttccttc ctgtttagtt agattacaaa 2580
tatatttagt tcaagaatta caccaatata ttcgtatata tattaaagta ctggtttttg 2640
cagctgaaaa gaatatatct tatgagatcg aattgaaact tttgttcaaa cttcaatgaa 2700
tcttaattaa acacgttttc agaaaaaaaa atagtatcgt cacacaaatt caacggagat 2760
atattattgt taggaaaatt ggaaaagggt acaacgttct ggcagacaaa cgtgcagctc 2820
acccctataa ataacttagc tgcgaccatt tgttcgaatc agccgggctg agaggcagca 2880
gctagctagc gcacatgcat tttcgttgtg gcgaacaagc tagctgctag taccctcagt 2940
tataccaaga tatacactac attcctagct aggtacgatt agccgccggt gagtggggag 3000

<210> SEQ ID NO 131
<211> LENGTH: 4009
<212> TYPE: DNA
<213> ORGANISM: Oryza sativa

<400> SEQUENCE: 131
tgacaataaa aaaggagtgg tgggaaggtg acaatggtgt aacaaatttt tataaactat 60
aaaaatgaaa cccaaggagg accaagtttg atttttaaga atcccaatga cagtaaaaat 120
aaatgtgatt ggtgggccat aaaggagtta ggtgacagcg gttgacgata cttctaaaat 180
ctataaaagg gaaacccaag ataatcaggt ttgaatctta gaatcctaac gacattaaat 240
aggcggggtg ataggtgggt tgtaaagagt cacagtggtt gacgagactt ttaaaaacaa 300
taaaaatgga acaatgatga ccaggttcaa atttaaaaat actactaata ataaaaacga 360
tgggtggcgg gcaattggcg tggcttttaa aaacgatgat cagattcgat tttttaaata 420
ctgtaaacaa taaagaggag gaacaacggg caggccatca aggagtaggg tgatggcggt 480
tgacataact actatagatt ataaaaataa aaccccaatg ctaattagat ttgatttatt 540
ctattgaaaa aaaaaatgag tgagaggcgg accgtaggag tagagtaatg acggttaaaa 600
actataagaa cgaaacagtg atcgataatg tttgattttt aaagtaccaa gaacaattaa 660
tagaaatggt agccagccag gcaagcaacc ggaggagcga caaaggagag gggtggcgtc 720
tgatgcgact tttaaaacta taatattata aagttgataa taataatgtt aatttaaaaa 780
atatcatgtg gaaatgagtt aacctttttac aaattttcaa gaaaataaag ggtaaaaaat 840
tagatgattt tatataagat acttagccgt gcaaatatgt gggccaccct actagttttt 900
cgctgaatct gaataatttt gaacggtaaa aaaaatccgg ttcattctgt ctcctctacc 960
cccttcaaac gagaaccggc cggtgtgcac gtgcacgtag ctcacaccta cctatcaaaa 1020
cgctggtcat tctgttctag cttgttagta gtacaagtgt gtctatgaga gaatccatta 1080
tatgccaaaa aaaaaacata agcacagacg aaattatagc gttatacttc atctatcttt 1140
tatgtacaca tttacataca aaagttaatt tattttgaga cgaagggagt gattaataac 1200
aatatttatt aacaaagtag aacaatatat ttaggggaaa aattgtatac taaaacaaat 1260
cctatattat tattattatt atttattaat tgtgtaaaaa tataattgga tatgtaaaaa 1320

-continued

```
tgggagtaca catgtgtgag catctctaag tgacgaggaa aaggaatagc agaggacaag   1380
ccaagggtca agtagggtaa tggcagctag agagactttg aaaaattata aaatagaaca   1440
ctaatgatga tcacgttcga ttttttaat ttgcaatgac aataaaaaag gagtggtgga   1500
aaggtgacaa tggtgtaaca gattttgtat aaactataaa aataacccaa agaaggccaa   1560
gtttaaattt taagaatccc aattgcaata aaaatatgtg cgattggcgg gccataaagt   1620
tgttaggtga tagcggttga cgatacttcc aaaatctata aaagggaaac ctaagttaat   1680
caggtttgaa tcttaaaatc ctaacaacat taaagaggcg aggtgatagg cgggctgtaa   1740
agagtcacag tggttgacga gacttttaaa aataataaaa acggaacaac gacgaccagg   1800
ttcaaattta aaaatgctac taataataaa aacgatgggt ggcgggtgag acgtaaagga   1860
gtagagtggc ggcagttagc ggggctttta aaaacgatga tcagattgga ttttttaaat   1920
gccatcgaca ataaagagga ggagcaacag gcaagccatc aaggagtagg gtgatggtgg   1980
ttgacaggac ttctatagat tataaaaata aaaccccaat aataatcaga tttgatttat   2040
tctattgaca aaaaaaagat gagtgagaga cggaccgtaa aggagcagag taatgatggt   2100
taaaaactat aagaacgaaa cagtgatggt ttgattttta aggtaccaag aacaatcaat   2160
agaaatggtg gccagccagg caagcagctg gaggagctac aaggagaggg gtggcgccca   2220
atgcgacttt taaaactata aaattataaa gttggtaatg ataatgttaa ttttaaaaaa   2280
tatcatgtgg aaatgagttg acctttaca aattttcaag aaaataaagg gtaaaaaatt   2340
agatgatttt atatcggtgc tagatgtaca aatgcgtggg ccaacctact agtttttggc   2400
tgaatctgaa caattttgaa cggtccaaaa aaaccggttc attctgtctc ctttgcctgt   2460
cgtcacgctg tcatcacgct gcggatgcag cgtactaaac gcaccggcct ttcaaacaag   2520
aaccggccgg tgtgcaggtg cacgtagctc aaacctacct atcaaaacgc tggtcattct   2580
gtctactcca tccgacccca aaaaaaaaag acaaaccctg attttcgtgt ctaacgtttg   2640
accgtccgtc ttatttaaga aaattatgaa aaaaaattaa aaaaacaagt cacacataaa   2700
atattaatca tgttttatca tctaacaata atgaaaatac gaattataaa aaaatttcat   2760
ataagacgga cagtcaaagt tggacacgga aacctagagt aacttgttag gcagtacaag   2820
tgtgtgtagc tatactcccc ctgtcctgta ccagcttata tatataggcg agccaacgag   2880
cgagagccat caccaagtgc aaggtagcta tcatatattc tgcgaatcca acacaagcac   2940
cgcggcgtag tactactact tgcgcgcgcg tgttagattc gcgtgcgaat ccaacacaag   3000
cagatcgatc acgcacggta cgccatgggc gaggcggtga aggggccagt ggtggtgacg   3060
ggcgcgtcgg gcttcgtcgg ctcatggctc gtcatgaagc tcctccaggc cggctacacc   3120
gtccgcgcca cagtgcgcga cccctgtgag ctctctcatc gtgcactcta gctctctcct   3180
cgtagtttac tgactccaat tatatatgcc gcttgcttga ctctgacaag tgtacgtgtt   3240
gttgttgttg ttttcagcta acgttgggaa gacgaagccg ttgctggagc tggcggggta   3300
gaaggagagg ctgacgctgt ggaaggccga cctgggcgag gaaggcagct tcgacgcggc   3360
gatcaggggt tgcacgggcg tgttccacgt cgcgacgccc atggacttcg agtccgagga   3420
cccggagaac gaggtggtca agcccaccgt ggaagggatg ctgagcatca tgcgggcctg   3480
cagggacgcc ggcaccgtca agcgcatcgt cttcacctcc tccgccggga ccgtcaacat   3540
cgaggagcgg cagcgcccct cctacgacca cgacgactgg agcgacatcg acttctgccg   3600
ccgcgtcaag atgaccggat gggtatgtat cgaaaatgtt gtcgtgggtt aggaacaacg   3660
atcctccacg tacataaaac gaaacgataa gttaacatga gcatgattaa tattagtatg   3720
```

```
gtataattga tatttgttta aaaatctaaa aaatattaat atgattttta aataactatt   3780

ttatagaatt ttttttatga aaacacaagg aaacagaaat tgagaaatag tacgttcaaa   3840

ctcaccctta agcaactgaa actagcttag cacgtgaatt tggccgtgtg agtcatatga   3900

tatgaaggtc ggggatgttt tttttttttt tgcggggatg taattaacta attatgtaaa   3960

ccatttctat tgtctaaaag aagttagcaa gtgataattg tggtggcag              4009
```

<210> SEQ ID NO 132
<211> LENGTH: 3008
<212> TYPE: DNA
<213> ORGANISM: Oryza sativa

<400> SEQUENCE: 132

```
gaaatggtct gtctcactag agggcacatc tttcagaaaa ataatcctct gcttgaaagg     60

ctgaatattg ggtatccatc gcttatacca ccataggaaa aaaataatat tcaagtttaa    120

actgaaacat aacaggccac atcccatggt agacaacaca atttctaact tctgaattca    180

ctcagttgat atactcaaac ttgagatttc aagcattcat taattcatat aaaccctcct    240

tatactagcc aactaggttc aactatacca caaaatcctt gagacctttt ctctaaaaaa    300

aatataccac aaaattttga cacaacgttg gttgttggct agttgaggtc ctgagcctga    360

actcctgaag gcaacaacag tacagtgagg cgatgtagac atcaccattg caatgccacg    420

ctgttggtga gctctaaaat cctaaatctc agtgcaagct ggcatttcta cttttccagc    480

gaatcataag agcagagcaa acataaagga atgcgaaaaa tgagaatcag ggttgggagt    540

cggcacaaac cccagccggc gcggcggcga aggtggagag cgggtggccc cagaagctgc    600

tggtgctcgc cgcccccggc gcagagatgg agagggacgc catcgcgccc tgcaacgccg    660

ccaccccggc catcttcgtc tcctcccctc ctcttcctcc ctcgctcgct caaaccgcag    720

agaagcagca gaggataacg aacgccttcg tgtgctcgcg gacaggataa tggcgagcgc    780

ttttctacat gacaaatggg cctctaggcc gaatggattg gcccacttgt aagactcata    840

aaggcctaat gaaaggccta tcgtaatcca gcccaactac aacggacctt acggcccaag    900

tcagccgcga tcccgttcag gctcaaatat agcgggcctc acgtaagccg caatcccgtc    960

tcgacccaac aagaacaggt cgcacctaca cagataaaat ctattgtaca tttctcatct   1020

ctgctcctga ttgaattacc tccctcaacc gcaaaatgga ggaaaatcgg tcttattgtt   1080

tggttatgct tatatttatg agccaaaatt tgaatttgag aacttagttt tgaatttgct   1140

tttttgtttt tttaaaatgc ttatatttta caacatttgc tttaagttat tatggacata   1200

tataaacatt ttactcataa ataaattttt atttgctaat aaacgattcg aataagcgaa   1260

aaccgtagca gatcaaccct tagatggttt gtagggtggt tcctgttgac gtggcaggct   1320

gactcgcaga gaacatgagg gaggcaaaat agacttacta tcacgcacgt cagcaatccg   1380

gttaaggccc aaatgtcgtg ggccgctcgt cgtccgcaat cccgtttgtg gtcaagtaac   1440

gtgggccgaa cgtcctgggt tgatatgggc cgacacccgt tttcggataa ggcccagccc   1500

agcatacgct cgtcgtcttc ctcgttgcgt tgcgtggctt cgtctccaca cgcatcatca   1560

ccacgccacg cgccgcgaga tgctgcttcg gcgggggcgc ccaggcgtgg cgcctcccgg   1620

attccggcgg cttcgacgtc gccggcgacg cgcgcaagcc aagcgacagt tgcggaggca   1680

agcaaccccc caagttccgt cccttttgcg cttttctggg acccatttcc tctctctttt   1740

ggggggcgct ttcgcggtga cgacgctgcc gatgcgcgta cgcctgagga gttcttcccc   1800
```

atcacgccgc gtgggggatc gggacgtcgc catttccgct gccgttttct tctctttggg 1860
gggttgcaat ctcgcgtttc atttgatagg gttgggcgtg ggcggtgggg aatggggatg 1920
ggtaggtaga tggcaccgat gtgaatcgga cgacttcgaa tcgaagcctt ccgatccatg 1980
tgaggaggtt gaggaaccaa cctaatttcg aatcgaagaa ctcttggttt ctctacctaa 2040
aaccaaatag catagtgaca gtggtcgtta tactatgaat tccaagcttt ttgaccgaag 2100
atttcgaatc atcgagcatc tttggccaag ctattctaac acggttgact cagaagtcta 2160
cgtttctatg cattgtgtat ttgagtgtta gttactatat ttcgtgataa acaaaactgt 2220
tgactcaaaa gtctacgttt atatgcattg tgtatttgtg tgttactgta tttagtgata 2280
aaccttaggt gtacatgtga gggatttcat ggataacacg tgcactacat tcttgcctgt 2340
tccactggtc accatcagca aatcgctcct gtccctttcg tgtggctatc actggagcta 2400
ttcaattctt gaaaggctct gccgtgcaag caaaccgttt tctttccaat gggataagtg 2460
tgtgactgtg ctataatctc aggataaatt catcactaaa tcgttgctat cagttttggt 2520
ttatccactc attaaatcaa tgcaacaaat gtggtgatca ataattagta gtacttgttt 2580
gttggtatgc cgtgctgcca aactagttgg ataacaaaga ttcctattat attggggtta 2640
accactgtat tttcctaatc ataatttttt aggctcctta ttgtcattat cacttagcat 2700
cattgcataa gagaaaaaaa aggggggtca atactgcagg atggtatttt aggaaggaaa 2760
tgtgttatcg tgatattaac acagcctttc ttccatgttg cttgcactcc tctcaaactg 2820
gtgtagcttc ctaaagactg gctcagttac acaattttta ttcttaaatg ctggaatcct 2880
gggaaatcct taatgcgcct ggaattgttg cactcaagta aagctttagt ttgctacacc 2940
cgtgacactt tcagagttgg acatgtcaaa gtttccttcc ctttttgata aaatgtccag 3000
tgtgatag 3008

<210> SEQ ID NO 133
<211> LENGTH: 3000
<212> TYPE: DNA
<213> ORGANISM: Oryza sativa

<400> SEQUENCE: 133
gtgcccttta aggtctcatg atgtcccagt ctgcaatggg cactgcaaga aggctacaac 60
caacggtgca atttcaccca aatcagtacc agctccctct aatatggttt ctgctgttag 120
ctcaatgctc ttatcccttg gagaggatcc cttcaggaaa gaacttgtag gtactcctca 180
gcgttacgtg caatggctga tgaagttcag agcatgtaac ctagatgtga agctgaatgg 240
ctttacactc aataatttga gtgtatacca gagtccagct ggagatgctg ctgaccatcg 300
agcaatccat tctgagctgc atttgccatt ttgtgcgcag tgcgagcacc atcttctgcc 360
gttctatgga gtagtgcata ttggctacct tgacggcgga gatggtgaag tgattgatcg 420
atctcatttt caggccttgg ttcattttta tggatgcaag cttcaggttc aagagagaat 480
gacaaggcag atagctgaag cagtttattc tgtttcgcat tgtggggcca tagttgttgt 540
agaagctaac cacatttgca tgatatcaag gggaatagag aaaatcagga gtagcactgc 600
aacgattgca gttctgggtc agtttttgac ggacccttct gccaaggcac gctttctgca 660
gaacgtagta gatacaactg gtttggcagt atgaatcact tagatcatac aaactagaat 720
atcagctaag aatacatgat tcagagaagt accgcagcca ctttaatatg gttgaaagtt 780
ggtacccagt tcggtgtgtt accggcaaac attgcccatt ggttcgagac cggggctggt 840
gccacgtctc tctggaagga aaatgtccat ttgcttggtg agggaaaatt ttcgtcacat 900

```
ggaagattat attgaagctg tcactggaag caccaaaagg gtttggtttt ctctgtgttg    960
taccattttt catttgcacg gcacttgaaa tctatactgc actaattgca gatgtgccga   1020
gaaagatata tacacagaag caatgtttgt cacatcattt ttcactgtag caaattttga   1080
tgagatcaat ggctccagct cctgtgaaat gaatgtgatt gttctcttga gtgttgaccc   1140
gccaatgcac tcgctgtctt cttctctctt tttttcctga gggcatcata tgcatatttt   1200
tggctcgtgg ggtttgcacc aactggcatt ttgccctttt ggtgcttgta gattgcagat   1260
acgcggggct agcgatttac tggtattttg acgggctgtt gcgacaggtt ggtggagcac   1320
gcgacgtctc cctccccgcc gggagaacgc gcgccacggc tacccgcccg ctcaccacca   1380
atcgttcaaa gcggccgcgc gaactaagca gcgggaccgg atcttacatc actgttcact   1440
catcgcgtgc catgcagaca aacgagacgt ggtactatac tacctcattc ctaaccgatc   1500
ccagtcgaac agttgttagt tcatggtagc atgatgtgat catcccagaa gagtgtgttt   1560
ttcctcgcgt agttgcggat aatgcttctc ctcgaacgtc tgaagtaagg agaaaagtcg   1620
gacaggcagc ctctgacaca cgtacaccta ttcaagacta tatctctatc tccaaccata   1680
taacatacac ttttaacgat atttaaaacg aatttttttc ttaaattact tagctgatct   1740
acaattcgat cacaccgtta tattcgttat aattaaatct ttacaacaag atatcgcttg   1800
attatattcc gatacaaaat aatcatatgt tttaatccat taacattttt tttcttacgt   1860
gatagggaca tgtttcaata tgtgtcttca gcgtgtttca caaaattcac tcacaaaact   1920
aactgttact actctctcct ctctctctcc acctcatgca tgcatgcatg cattttaact   1980
agtttcaaaa cgatttttct cttaaactaa ttattcaacc tacgatctga tcacaccgtt   2040
gtattctttg taattaaatc tttaaaacaa gatatcgcat gattatattt tgatgaaaga   2100
aaaacatatg tttcgatcca ttaacattgg ttgttttata tgtgatagtg atatgtttca   2160
acgtgtatct tcatcatgtt tcataaactt tttaaatgtt tcagttgctg atatttttgt   2220
ttcaccatat ataacttgat gtttcacttg ttagttaact ggaacatttg actgaccgat   2280
tttttttgc atgctgcata cacaggtggt gtgatgacgt gtaaacagtc gggcgtccga   2340
tatttggtgg aatatcggac gtccgatgcg gagtcatctc ccgtagttgc ccgttgccaa   2400
tttttttcta cagtaactac aacttctctg atatggacaa aaatccaaac tatttaggtg   2460
agtttctgtt tatggaagaa gctgcagctg ttaaaaactc tcccaaacat atccaaagat   2520
atttcctacg ctcatctcta ggatatttgt aggtattgta gggctagttt agctcccata   2580
gtcccattga agcgtacgtg cacacaacca aaaatgtttg ctggagcagt ggagagcacg   2640
gaatgttaga tagcacctac ccttcaccgt caaatcggaa ctacctaagc ttatcgatcg   2700
ggtgatcagt tatgctaaag gcctgcagct agctagagaa cacaaacgca tcgatgagta   2760
gtagttggaa cgtgccactg cccactgcac gactttagtt cttcgaccct gtgtgagtag   2820
tagcgaaccc agcctctcta tgtagcgtgc tccacccgta cagtacgccc ctccctatat   2880
acggatgatc acgcagtaca cgctctccct atcgtaaaac ccgcgaaaac cacaaccgaa   2940
acgcaagggt cgatccatcc acgcctatcg cgcgcgcgtg catcgggtcg atcgatcgag   3000
```

<210> SEQ ID NO 134
<211> LENGTH: 3000
<212> TYPE: DNA
<213> ORGANISM: Oryza sativa

<400> SEQUENCE: 134

-continued

```
ttggcgtact cgttggcttt ttcaaacata agcttgactg tcctgggagg cttacgccca     60
aacttgccga ctagttcttc gtggcgaatc cctttggtga acgcggcgat gatgacgtcg    120
tcggtgatgt cggagatctt gttacgttgt tcagaaaatc gccggatgta atctcgaagg    180
gattctccgg acttctgaat gacgttgtag agatcatatt gtgtgccggg acgctcgaag    240
gtgccttgga agttggcgat gaagtggtcg cgtagttcgg cccaagatcc aattgtacca    300
cggggcaatc catggagcca agatcgggcg gaatccgcta aagccactgg taaatagttc    360
gccatggcct tgctgtctcc tcctgctgcg cggatcgcga gaccgtagac ggtaagccac    420
gattcggggt tagtggtgcc gtcgtacttc tctattccag tcggcttgaa gccggctggc    480
caatccactc gacgcaggtc gtcggtgaag gctgctactc cgtcaaggtc gtcgtcgtgg    540
ctgtccggcg agtgatggta gcctcgagct gctcggcgct gtatgattgt gtcgcgaaga    600
tcgatggggc ggcgacgagg tggtgagcga ggccgttcca ctcggcgctc cctatgaagg    660
tcgggaggtg agtgaacaga ccgctcgtcg tgacccctgc tcctgcggtt ggatcctgcg    720
ccggtgatgc tgaggcttgg atgacggtag tcatgagatc ggaagtgggg aactcggctg    780
ccagtcggcg tgtggacgct ttcggagtta actgggaccg aagccgcaat catggtcttc    840
gtctggttca agatgttgac gacgtggtcg gattgattga gctcgttttg gttgaggagg    900
gtgtcgagaa gggtgatcgc ggcaaccgca ttctgttgag gggtgcggaa aaccggtgtc    960
ccttcgacat cttgctggcc gatgagatca cgcgctcggc gccctgcttc caaagctcgc   1020
tgacgtcgat cctcagcctc cttcgcggtc cgctcacggt cctgctgctc acgccgtagc   1080
cgttcttgtt cttgtgcttg atgctcctcc tctagtcggc gacgttcttc ggtctcccgg   1140
gcttggcgtt gctcctccgt ctcattattg gccatgaaaa cgccaaagta gagaggggtg   1200
tagttgtcat ctaggcttcc gtcgaagtcg tcgaagtcgt cgaagtcgtt gtagcgagaa   1260
ctaaattcgt cgtactccac aatgtcagta ggacgtgagt cgacggtggg agagctgttg   1320
tagtcatcca gctgatccgt cgaaaccgtg ccgagtggtt ggaggatgac gccgacttcc   1380
ctgaagctag gcgaaatcgg tgttgaagcc gacttccgcc taggcctacg ggatgaagac   1440
gctgtcgtgg tggagacggc cgctaaatcg tcggggagct tcatcaggac tggtgggtaa   1500
gccccatcat cttgatctgg tgtcgttgga gaagatgcga tctcggccga gtggtttgaa   1560
gccgactcgg tcgagatggt cttgaagtag ctttcagccg cgttcgggaa tccaaacggg   1620
accgaaatcc ggttctctcc cgactggtct gattccgagt cgaggagaga aatcttgccg   1680
aagttgttgg tgacgaagtc gaggctgccg aaccgaaacg tctgcccggg tgggaagacg   1740
aggtcgtcga tgccggagat ggaacccatt gcactgatcg gcgaaaagct tgacgcttcc   1800
cctacctggc gcgccaactg tcgaaactag atttcggcaa taataaaaag gggtggcta    1860
tcaagctagg aaagtgtatg ggtttggaga caaaaagatt tatacaggtt caggccttct   1920
tataaaagaa gtaataccct actcctgtcc ggggatgaat ccgccgagtg tgttattgat   1980
tgtatgattt ggagaaaatc caacaactgc ccctagaggc gcccggaccc cccttatata   2040
taggaaggag tccgggttac aaaagataat ctatatccct aacggaatac acagatacag   2100
attaaataca gtcgtgaccg actaagtctt aagttgtttc cttgatatac aagtcaggaa   2160
acaaacccag gatacacata agatattcta tctatattcg gtatcctata ttcagtccaa   2220
atatcatcgc cgtgtagata tgggatatcc ataatctcca catgatgtga tccgtaactt   2280
tggtcacatt gccacgtaag ataacatttg atatatgaag acagttaata atgcatattt   2340
tgtatcgaat catagggtag ctcctatata tttcagctct ttggtccttt gacatctgat   2400
```

```
gctttagttt aggggaaaaa atcaagatta actataactg actaatcaat atgtcaatgt   2460

tgctaaaaaa acaaaatcaa aggaaataac ttaatttttt taatgaaatg gataagtttt   2520

ttaataacat ggatttactt aaatattacc gtagcgttag cgcggataaa ttactagtat   2580

acgtaaaaag aataacatca tgatttattt agaaagggta aaaacggatg gagtattgaa   2640

tttgttgata tccgggacaa tctcgtgtca atgatgaaat tttctttgat aaaaaaggtg   2700

aaagttgcac cactacatgc tgtgacatat tttctttact catttgaaac aagttgattt   2760

ctatgatatg tgccaagtag tcgagagcca aataaaataa aattattagt gattgcaaca   2820

ggtgggctgg ttttgcgtca tttgaccagt acacagccac acatgccatg aggagaaaag   2880

gaatcaagca aacaaccttt ggtacctgtt cggtggtagg tacgaagggt agtttgttag   2940

ctgcacagca cgcgggggta ccgtgtatat atcaactacc cagtccgcgt tttcctctct   3000
```

<210> SEQ ID NO 135
<211> LENGTH: 2982
<212> TYPE: DNA
<213> ORGANISM: Oryza sativa

<400> SEQUENCE: 135

```
gccgtcgtca tcaacccgac cccgccactc cgcgcgctag cttccaaggg acggaggcag     60

agcccctcct ccctctgccg cgtcgccccc gctccctcct ccttttccca aagaggcaag    120

gggcaagccc cctttctctc cctccttttc cctttttttcc tcccgccggc gtcatcctcc   180

ctccgccctg tcgccgattt ggccgctagc cggagcgcca gctcgctggc ttgaccgtcc    240

aaagtcggtt cccctctccc aaaccgtcat tgccatccta taaagcccag gcgccctccc    300

tctcttctcc tctcgttgtc ccatcgcctc cactccattg tcgccgcctc ccgtgctctg    360

ttcgccgtcg ccgtttgtcg tcgcgcgtgt cggaggagcc ggcacgagcg aggacgcgga    420

aggggactcc gggcgcgccc tcttcttcct cttccccggc ccgaggccgg agagatcact    480

cccgtgccgt cggcccatcg tcactgcgcc ccgtcccgca cggtagcgca tctccctatt    540

ctccctcctc gttccatccc cttcccttag actcgggtag tagcacgagt agcctccccg    600

tagctagctg gcgccgcccc gactgctgcc gtcgctcgcc gtgtgctcgc cgccgtcgcc    660

gcccgagctc ggaagcgcct ctcgtcgccg gcctccctcg atgcgttcct cctaatccgg    720

cgcaagggac ggattcccgt agccgcgtag atgctctcgc cgccgggaat cggcccctcg    780

tgacctcgtc gccgtttccc tcttccctcc ccgccggttg ccgccgccgc aatccgccgc    840

cgacgcactc cctccggcga atccaagccg ttggctcgtc tcccctcgtc tcgtgcaacc    900

acccggtgtg ctcgctttcg cctgtatcgc cgtggttcgc tccgccgccc gccgctgtcg    960

tccgccgtcc gttccggccg gcgtcgtcgt ctacctcccg ccggcccgcg tggctgccac   1020

ttaggcgcca tgtcggcgcc acctcggccg cgaccggatc ggctgacccg gccagccgct   1080

ccctccgttc cccccccgtg cgcatggtcc gcggtgagcc gtgaggctgc gcgtgggccc   1140

gccgcaccgc atcttccgcg aaccgcgcgc gtgcaccgcg tccctccccc aaaccctagc   1200

gcgcgccgcg tgcgcgttcc gcacggtgaa ccgtgtcacc gacaagcggg tcccacccgg   1260

gaccacgcgg gatggacccg gcccaccggc tctctctccc ctccccgccc gcgcgcgcgc   1320

tttgggccgc cttcttgggc cggccggccc atttagctcg gccgagccgc ccctttttctc  1380

tcgggccgcg ccctagccgc ccgagggaag tctacttccc ctccctcttc cttttctttt   1440

tcaaaaagga tttaaataaa tcctttttcc tttagaccaa aaatccaata atcttagaaa   1500
```

```
ttcaatatct tcccaaccgt aaatccgttt gactccgttc aacttccaaa attcctcaaa   1560

tctcgagatc tatctaatgg cacgcttaga ggtcattaat agggctttat tttcgccgtt   1620

tgttgagttg tcccgttttg cgtgtagttt cggagcccga agacccgcag tgcgaggatt   1680

tcgaggatca agctcaagat ctcgagcaag gcaagccacc tttgaacatc ttgagcctat   1740

atctgaactt aattatgttg cttgaaaaaa atattatgca ttgataggat cgcacttaat   1800

ttgcttgtcc cgtctgcaag gcagattggc gaacctacct aatttgttgc atctgatcct   1860

tcctttgtta attgttatac catgttccct tgtaaccatc tagttgcgcc tcgatattcg   1920

tgcactctat gcgagtatcg acggtcgcct tcaaacttaa aatctgagta acttcttggg   1980

taaaacttgg gttttacaaa agacttggaa aacccgacac ctgggtcggt gcttgcgaac   2040

taaatgaatt tccaaaacca cggaccgggg aacgtaccgg gtgtacggtt tcccgctctt   2100

gcacttaagg accgtttcct tggaatttca tccgaacata agacaagtac gaccacatgg   2160

gtggaatggg acacccctgg ctgagtaact agtttatcag gggagccttg atgccgagag   2220

acatgtggat tcgccggggt ggtgtcgggg aggacccctg ggcttcctgg cacagtatgg   2280

tctgggacct aacctgttgt tggtctggga cccctctcgt cggcatatgg taaacctgtg   2340

tcggctttgg aaatgccttg tcatgaaagc ttggagatct cccgacgtgg ctgatcccca   2400

cgggttgggt gatccgggtt agtaatgtcg tgtgggtaaa gtgtaccccc tctgcagagg   2460

ttaacaaact gttcgaacag ccgtgcccat ggtcatgggc ggatgtgagg tgattcctag   2520

cgtagttttg tttgactact gccttgtgaa attgctgttg tgaaaagggg aatcgatgtt   2580

tggaaaatct gcagctgatg ggatcagcta ggcccgggtg gccgtttgaa agttgttggc   2640

ccgggtggcc gtttgaaagt tgatggccag gtgccaatct tgaacaattc taaagactga   2700

tacattgcac atactccgac cggacgagac gcactgtctc atccgtgtcg tttgagaagc   2760

actcacttag ttgttttcag aaaagagttc aaataaaatc aattgcaaaa acaacagcct   2820

ttccttgaag cctgcattaa acacttattt cccatggctt gctgagtact cccgtactca   2880

cccttgctct atataaataa tcccccccag ttgctgaaga agatgaagcg gatcccgctg   2940

acgaggagtt cttccaggag caaaccggct acgatgagtt tt                      2982
```

<210> SEQ ID NO 136
<211> LENGTH: 3000
<212> TYPE: DNA
<213> ORGANISM: Oryza sativa

<400> SEQUENCE: 136

```
cagtgaggag gagaatgagg agtgatgaac caatttctgg tttgtgcggt caaaaggaga     60

gggaggagaa gaacagtagg ggaggggggga ggaggaggag ggagggccac aatgggtaaa   120

tcacttggga attcatgaac caaatacatg aacttttaga aataagaaca accttactca   180

gttaatgagt tgcttggttg gcctactcaa tgaaaacatt attaaaacca ctccataaga   240

tatattgtca ccaacttctt attgatagca atcaaagaaa ttgatgaata gcttctattc   300

cgataatatc aacgacatgt atataaaata aagttgttac tcccagtata ttgccagcaa   360

ccatctttct ctaagcgcac acacaccttt tctgagccta taggattgaa aagaccaaaa   420

cgttggggtt gctatttggc gctcacgtgc caacaataga gctggtgtgc gcgccatctg   480

gcgcccccca cgcacacatt ttcatttctt tttttttttg caatcttttt ccctattttg   540

gcgcccctcc cctcgcgcgt attttccttt tttcctgcgt tttttcccga ttaaaaaatc   600

gttaacacac gtgttttcga atctcgatat gaaagttttc caatctgaag aaagtttcaa   660
```

-continued

```
atctagagtt gaaagttttc aaattttgac ttgaaagttt tcaaacctga gttgaaagtt    720
tcaaatttga gttaaaagtt tttcaaattt gagataaaaa gttgaaagtt ttcaaacttt    780
aacttaaaag aattcaaatt tcgagtgaga gttttcaaag ttagagttga aagtttttaa    840
aatttaattt caaagtttaa attttgagtt gaaattttca aaatttcagt ttagagtttc    900
aagttgtaag ttgatattct taaaatttag gtatggcttt tttaagaaaa aaaatagaaa    960
gtttttttca cgtatagatt tcttctaagt ttcaaccttt agggaaaaaa aaggaaaatc   1020
ttaccttaat ttctattatt atgtaaaaca tcatcagccc tttagtacag attaaaggcc   1080
cattcctgtt tgtgggccat gaaattagta cataatcccc atccggaata agttcacttt   1140
gagttcctta aaagtgacca gaatctaatc catgacccta aaccgtaata ccggatatct   1200
cgacccctca actattaaaa tcggtacaat ttgactccct cggcagtttt ggatggtggt   1260
ttcgctaaca tggcgtctac gtggcagtat tgactaggtc ttcgtcctat gtggcgttga   1320
cgtggcgctt aagtggcatt agaattaaaa atatatatgc gggcccattt gtcattcaca   1380
aaaagaaatt gtgggcccac tgacatgtgg ggcccacata aatccctatt cctcctccct   1440
ctcttccttc tttctctttc tctccctttc tcatcggttc ttccccttcg gccggcggcg   1500
ggcggtgagg gccgaagctg cgctgggtga cgagagcgag cagctggcgg gcggcgacga   1560
atggctcgac tgcgctggcg tgcacgggag gcggcagaga gcagcgggcc agctgcaagc   1620
cgacagtgac gccggcaagc aagcaggcaa gtctgcaatt tcattatcac cagcagatag   1680
atgctactgt agctttgatg gggttactag ctcagctcgg gttcgagctc gtagaatgaa   1740
ttgacgagca cgtcgtcggc gagctccagc ctgtcgaact gcttcatcac caagtcgaag   1800
tacgccgggt acgggccggg gccgacctta atgaaccacg gcaagccctc cagctccagc   1860
gccggcaagc cgatcagcgc gatggcgccg gcctccacgg ggatgtgtac acggccgcac   1920
cacgcgtggc cgtacaccac gttgacggcg cacgactgcg tgaagaacgt gaacgccacc   1980
gccgctgcgg cgcgccacgg cgcgcgccaa gaggaggaac gcgtcgtaga ggaggacgca   2040
cacggggcgt ccacctccac cccccggcgg tggcagcggc ctcgtcccgg aggagctcgt   2100
ccaacgtcac cgcccacgct gactcgaggc gatggatgcg gagccggcga ggagatgaac   2160
cccgatggag aggtcgggga ggacgacgcc agcagtggcg aggtggaggt gccggcagtg   2220
gcgaggtgga ggcgccggcg acaggaactc atgacgccgg cgtggccgca tgggggagag   2280
agagagaagg aagagagaga gggaggatga agaagggatg acgtacgggt cccagatatc   2340
agtgggtccc gtatgtcagt ggacccacaa aattttcttc tgaataacaa atgggtccca   2400
tatgtatgtt tttaattttt aatgccaccc aaacgccatt tcaacggcag acaaggtcaa   2460
cattaccaca tggacgccac gccagcaaaa ccactcttca aaactgccga gggagtcaag   2520
ttgcaccggt tttaacagta taggggtcaa gatatctggt ttatagttca gtggtatgga   2580
ttagattcgg atcactttta agggagtcaa agtgaactta ttcctcccca tccacagatg   2640
tggtcaggca tgtattccgg cccatccaag tatccacaac gaaatcgcgg aaggaaaacc   2700
gaccgatctc gatatcacgc gccccacccc cacgccgcca aaaatatctc aggaaaacaa   2760
ctgcaaatca caccacctgt acgctgtagt cctgtaccat gtggtcatgt ctttgtcgtg   2820
cacggaggaa gaaaaaaaag gaaaaaaaaa ccggcaaact ttctcatttg ccagtttttc   2880
tcaccagcaa cagcaaacga cggcagcttc ctgcaccgaa cgatccggct tacatatctc   2940
cctccgaaag ctcactttct catttgccag tttgtttttc tccctccaca gtgcacagcc   3000
```

<210> SEQ ID NO 137
<211> LENGTH: 3000
<212> TYPE: DNA
<213> ORGANISM: Oryza sativa

<400> SEQUENCE: 137
atatatcata ttcagttcta tatattcgtt ttttatggga cggagggagt atatggtatg 60
acatgtggtg gttgatcaag agagttctac ttatggagta gtggtggttg atcaagagag 120
ttctatttat gaagtaacgt taggggttgt tcagaatgat accattttta attataccat 180
tttttaaaaa agttgttaaa aaaatgtcta cgtttagctt gttgccaatt ttggtaaatg 240
catgaaaaaa atcctatttt agtaatatgt caacttgcta aaatttaata aggtttattt 300
tgaaaacaat ttgaacatgc ccttagtaaa tttatttact aaacactagt actaatcatg 360
aactcggtcg atctatatac atatataatc acctaaagaa ctttacgtgg aattgggaat 420
caagctcgtt ggtgagtatt agtttgattg gcatactcaa atcgtcaaaa ttcaccatac 480 tttttttac taacatgtga ctaataaaat taaaagccat atattagcta gaagagagta 540
agtttacaac gagatacaaa gctcatgtaa taatgaagaa atctataaca cgtgatcaaa 600
cgataagtaa cttgatcgaa catacttaac tttatttatg gtatggtcaa tttgacacgg 660
atgttcgtat ttataataaa ttattgttta gtaaaacaga tatatttatc agtaatatat 720
atatacatat atatatattg actttgttaa tatcacgata actcctagta agaatgatag 780
agtgtatttg tcgatcaatt tcaagacacc acgaatctcg cagagatgtg ctaaactgct 840
aataagaaaa accagtgcgc atttctttt gtcttaaaga agagcagcgt ttgaccagag 900
tcacctattc acactaggtg actagagcct gtttggtgca ctaccacaat ttaccttact 960
gtaccacatc taaaatgaga catgtttgac taaattagac gttcatttag ttcgtgccat 1020
attaatgata aaatttcttc atcaggatgt gtgtcccata tattattaac acattaaagc 1080
attgcaaact tgctttctta tagtaaaagt gcggctttga ttttattagt caggcaggct 1140
agctaataag attatgggcc tgttcggggg agctttagat tctgagaaac agctgtttgg 1200
tagccagctt ctgagaatct agaaaagctc cgaaacccag cttctccagc ttttggcttc 1260
ttagttcatt ttttaaaatc tgtaactaca tattctcaga agttatgaat tgtttggggc 1320
agtttctagc agaagcggct tttgggaaaa gcccaaacag ggcctatggc ttgtttcggc 1380
aacgtgagta tgccaacctt ggctcgcgcg gacggagcaa cgagtcgaac acgtgccggg 1440
cgcgccagtg aaacggatgg cgcgcgagac gccaccagcg gccacgccac ggcaccggca 1500
cgtcggcgtc gtcgccacct gggacgaagt cgagagtcga gacatcgcac gttcgttcgc 1560
gcgctgccca gcgcgcgcca cccgcctcgc cgcgccgcgc cgcgacgcga cgcgacgcgc 1620
gccacctata ataaacacca cccgcgcgcg cgcgcgccca gcgcgtcgtc tcgtcgtctc 1680
cgctgttcgc tcgcctcaac acacgagtgc gacggcggcg aggaagaagg gggccacgat 1740
tgggaaggtg tttggttggc gcaggaagga ggggaaaaaa agaaaaagaa aagaaaagaa 1800
aagaagctgt ttttggggag tcgtgctttg gagagctgaa aaagaaggtg agtaaaaagg 1860
ttttttgatc tttggttggt tactgcttct cccgtgatct cctcctcctt cttctccagt 1920
gcggctgctc tgggctcgag ggcatcgtga atctacaacg tcaatcgcat tgtcttgatt 1980
aattcctatg ggagttcttg gggatttgtc gaggggacga gattttttac ccctaggcga 2040
tgcgattttg gttgcgattt gttcttctcg tttggatcac tggtccctga atattttctt 2100
tcctttcctc ggtgaatgaa tggtgttgac tgttgaggta gctggttgat gaacactcat 2160

```
gcatacagtt ttttttttt tttttggtct ctctcttctt ctgctgactt attaagaaga   2220

aacattgcaa tcttagactt tattaccatt ttctctcttc ttctgctgac ttatttaagt   2280

ttcttgattt tttctttcgg tgatatagtg atgtttgtgc tgggtatagt gaaatttctg   2340

tggttatctt gagcttctat agccacccga aacactagta ctaatcttgt gcagtacaag   2400

tccctatcta gtccatgttc ttcacttatt tgctctgact agtttgcttt gctgcaggtt   2460

taagctgtct gattcaacgg acggtgcaac agagattgga cagatgggtt ccctcataag   2520

ttagttgttt tctcacaatt ctctcgtgct tgacagttgc atcattgatt catcattgag   2580

ccctttcac ttttggactg tcacattttt ttttgagctt tcctattaag ggtgtgttta   2640

gatcccaaaa attttggcca aaaatatcac atcaaatgtg tcgtttggac acatgtatag   2700

agcattaaag gtggacgaaa aaaaaactaa ttgcacaatt tgcatgtaaa ttgcgagacg   2760

aatattttaa gcttaattgt gccatggttt gacaatgtga ttctacagta aatatttgct   2820

aatgacgaat taattaggct taataaattc gtctcacagt ttacatgcgg aatctgtaat   2880

ttgttttgtt taatacttca aatgtgtgtc cgtatgcttc aaaaataatt tggccaaaga   2940

actaaacacc gcctaacatt gattttttg gggggtaatg atttttcagg ttcttgggcg   3000
```

<210> SEQ ID NO 138
<211> LENGTH: 50
<212> TYPE: PRT
<213> ORGANISM: Oryza rufipogon

<400> SEQUENCE: 138

```
Val Leu Lys Glu Arg Arg Arg Arg Glu Lys Leu Asn Glu Lys Phe Ile
1               5                   10                  15

Ile Leu Arg Ser Leu Val Pro Phe Met Thr Lys Met Asp Lys Ala Ser
            20                  25                  30

Ile Leu Gly Asp Thr Ile Glu Tyr Val Lys Gln Leu Arg Asn Arg Ile
        35                  40                  45

Gln Glu
    50
```

<210> SEQ ID NO 139
<211> LENGTH: 50
<212> TYPE: PRT
<213> ORGANISM: Zea mays

<400> SEQUENCE: 139

```
Val Leu Lys Glu Arg Arg Arg Arg Glu Lys Leu Asn Glu Gly Phe Ala
1               5                   10                  15

Met Leu Arg Ser Leu Val Pro Phe Val Thr Lys Met Asp Arg Ala Ser
            20                  25                  30

Ile Leu Gly Asp Thr Ile Glu Tyr Val Lys Gln Leu Arg Arg Arg Ile
        35                  40                  45

Gln Glu
    50
```

<210> SEQ ID NO 140
<211> LENGTH: 50
<212> TYPE: PRT
<213> ORGANISM: Petunia hybrida

<400> SEQUENCE: 140

```
Val Leu Ala Glu Arg Arg Arg Arg Glu Lys Leu Asn Glu Arg Phe Ile
1               5                   10                  15
```

```
Ile Leu Arg Ser Leu Val Pro Phe Val Thr Lys Met Asp Lys Ala Ser
            20                  25                  30

Ile Leu Gly Asp Thr Ile Glu Tyr Val Lys Gln Leu Arg Lys Lys Val
        35                  40                  45

Gln Asp
    50


<210> SEQ ID NO 141
<211> LENGTH: 50
<212> TYPE: PRT
<213> ORGANISM: Arabidopsis thaliana

<400> SEQUENCE: 141

Val Val Ala Glu Arg Arg Arg Arg Glu Lys Leu Asn Glu Lys Phe Ile
1               5                   10                  15

Thr Leu Arg Ser Met Val Pro Phe Val Thr Lys Met Asp Lys Val Ser
            20                  25                  30

Ile Leu Gly Asp Thr Ile Ala Tyr Val Asn His Leu Arg Lys Arg Val
        35                  40                  45

His Glu
    50


<210> SEQ ID NO 142
<211> LENGTH: 14
<212> TYPE: DNA
<213> ORGANISM: Oryza sp.

<400> SEQUENCE: 142

acgcgaaaag tcgg                                                       14


<210> SEQ ID NO 143
<211> LENGTH: 12
<212> TYPE: DNA
<213> ORGANISM: Oryza rufipogon

<400> SEQUENCE: 143

gtagtcactg ca                                                         12


<210> SEQ ID NO 144
<211> LENGTH: 12
<212> TYPE: DNA
<213> ORGANISM: Oryza rufipogon

<400> SEQUENCE: 144

gtagtcactg aa                                                         12


<210> SEQ ID NO 145
<211> LENGTH: 16
<212> TYPE: DNA
<213> ORGANISM: Artificial Sequence
<220> FEATURE:
<223> OTHER INFORMATION: Description of Artificial Sequence: Synthetic
      anthocyanin regulatory element consensus
      oligonucloetide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 145
```

```
ttgactggng gntgcg                                                   16


<210> SEQ ID NO 146
<211> LENGTH: 1705
<212> TYPE: DNA
<213> ORGANISM: Oryza sativa

<400> SEQUENCE: 146

gcaggaagaa attcaaattt gcgaatattc tctctctctc cccggcgaag gcgacggcga     60

aggagaaggc tacggcgatc ggcggcgatc ggcggcatga agcttaagat gaacaaggcc    120

tgcgacatcg cctccatctc cgtcctccct ccccggagga ccggagggag cagcggcgcg    180

tcggcttccg gttccgtggc ggtggcggtg gcgtctcagc cgcggtcgca gccgctctcg    240

cagtcgcagc agtccttctc gcagggcgcc tccgcctcgc tcttgcactc gcagtcgcag    300

ttctcgcagg tctccctcga cgacaacctc ctcaccctcc tcccttcccc cacccgcgat    360

cagagatttg gcttgcatga tgactcatcc aagaggatgt cctctttacc agccagttca    420

gcttcttgcg cgcgagaaga gtctcagctg caactggcaa aattaccaag caacccagtg    480

caccgctgga accccctccat tgcagatact agatcaggtc aggttactaa tgaggatgtt   540

gagcgcaaat ttcagcatct ggcaagctca gtacataaga tggggatggt ggtagactca    600

gtccaaagtg acgtaatgca gttaaacaga gccatgaagg aggcatcatt agattctggt    660

agcatacggc aaaagattgc tgtccttgaa agctcacttc agcaaattct taagggacaa    720

gacgatctca aagcactctt tggaagcagc acaaaacaca atcctgatca gacaagtgtt    780

ctgaattctc taggcagcaa attgaatgag atatcctcga cccttgcaac cttgcagaca    840

caaatgcaag caagacaact gcagggtgat cagacaactg ttctgaattc taatgccagc    900

aaatcgaatg agatatcctc gactcttgca accctgcaga cacaaatgca agcagatata    960

agacaactgc ggtgtgacgt cttcagagtt tttacaaaag agatggaggg ggttgttaga   1020

gctatcaggt ctgtcaatag taggcctgct gcaatgcaaa tgatggcaga ccagagttac   1080

caagtaccag tttcaaatgg atggacccag attaaccaga caccagtagc agctggaagg   1140

tctccaatga accgagcacc agtagcagct ggaaggtccc ggatgaacca attacctgaa   1200

acaaaagtgc tttctgcaca tttggtttat cctgcaaagg tgacagatct gaagccaaag   1260

gtggagcagg gaaaggtaaa agcagctcca caaaagccgt ttgcttcgag ctactacagg   1320

gtggcaccta aacaggaaga ggtagcgatt agaaaggtca atatacaagt gccagcaaag   1380

aaggcaccag tcagcataat catcgagtcg gatgatgaca gtgaaggacg tgcgtcctgc   1440

gtgattttga agacagaaac aggtagcaag gagtggaaag tgacaaagca aggcaccgaa   1500

gagggcctgg agatcctgcg gagggcgagg aagaggagga ggagagagat gcagtccatc   1560

gtgctcgcat cctagctaat taatggtaac gccgcatgca tcgtcatcat catctcaaga   1620

ttgactgatt gttttaacat aaagccaaac aaaggaaaga gataaagatt acgacaagac   1680

gaaattaaaa ggtaaatcaa ccact                                         1705


<210> SEQ ID NO 147
<211> LENGTH: 2116
<212> TYPE: DNA
<213> ORGANISM: Oryza sativa

<400> SEQUENCE: 147

ctctcatctc gcgcgcggcg cgccgccgta gagacgaaat ggtgatggct cagaagacga     60
```

-continued

```
aggaggcgga gatcacggag caggattcgc tgcttctgac aaggaatttg ctccgcattg    120
ctatatacaa catcagctac atcagaggtc tattccctga gaagtacttc aatgataagt    180
cggttccggc actagagatg aagattaaga agctaatgcc catggatact gagtcgagga    240
ggttgattga ttggatggaa aaaggtgtct atgatgcact acagaagaaa tatctcaaga    300
cccttctctt ctgcatctgt gagaaggagg aaggcccaat gattgaggag tatgcattct    360
catttagcta ccccaacacg agcggtgatg aagttgcaat gaacttgagc cgcacaggga    420
gcaagaaaaa cagtgctaca tttaaatcaa atgcagcaga agtcactcct gatcagatga    480
ggagctctgc ttgtaagatg ataagaacac tggtttcact tatgaggacc ttggaccaaa    540
tgccagagga gaggaccatt ctaatgaagc tgctatacta cgatgatgtc acacctgaag    600
attacgagcc accctttttt aagtgttgcg ctgacaacga ggccataaat atatggaaca    660
agaacccctt gaagatggaa gttggaaatg tcaatagcaa gcatctcgtg ttagctttga    720
aggtcaagag tgtccttgac ccttgtgatg ataacaatgt caacagtgaa gatgataata    780
tgagcttgga taatgaatct gaccaagata atgatttttc tgacactgag gttcgcccat    840
ctgaagcaga gcgttacatt gttgctccaa atgatgggac ttgcaaaggt caaaatggta    900
caatctcaga agatgatact caagatcctg ttcacgagga agagctaaca gctcaagtaa    960
gagagtggat atgctcaaga gacactgaaa gtcttgaggt ttcagatgtc cttgttaatt   1020
tccccgacat atcaatggaa atggttgaag atattatgga gaggctactt aaagatggtt   1080
tactatccag agcaaaaaag gatagttatt ctgttaataa gattgctgat cctacaacac   1140
cacacataaa gaaagaggtc atcatgcaaa atgtctcacc tactgaagga actaaaaata   1200
gcaatggtga tctgatgtat atgaaggcac tgtaccatgc acttccaatg gattatgtgt   1260
cagtaggcaa acttcatggc aagctagatg gggaggccag ccagaacatg gttcgtaagt   1320
tgattgaaaa aatggtgcaa gacggatatg tcaagaattc agccaaccga agactaggca   1380
aagctgtcat tcattctgaa gtcaccaaca gaaagctcct tgagataaaa aagattctgg   1440
aagtcgatat agccgaacaa atggccattg ataccaatgc agaacctggt gagcctgagc   1500
gcaaagacca cctgagtggc catgaaatga gagatggatc gacgatgggt tgcctccagt   1560
ccgtcggatc tgacctcacc cgcacccggg agcttccgga gccgcagcag aacgtgtcca   1620
tgcagagcgg gcaggaagct tccacggtgg ataaggatcc aagcaggact cctacaagcg   1680
tgcgcgagca ggcgtccgtt tgttccctgg agagtggggt tctcgggcag aaggtcagaa   1740
agtctttggc tggtgctggc gggacgcagt gctcgcagga caagcgattc aggaaggcca   1800
gcacggtgaa ggagccgatc ctccagtacg tcaagcgcca gaagtcccaa gttcaagttc   1860
aagttcagtg agggttcgtg tcgcaagcgt caggagcaac taacatcgta gttcaggtgc   1920
agaagaccac aagtagatat atccatccta ttcctagttc cggtgctcaa gtttgtgcag   1980
atagtcagag agcactcacg cacacgtaga tatctgtcca tgccgctgtc ccaaatggca   2040
aatggagata gacgctacta tgtgctaaca cacactcaaa ttaagcattc aaaacgcaaa   2100
aaaaaaaaaa aaaaaa                                                   2116
```

<210> SEQ ID NO 148
<211> LENGTH: 4681
<212> TYPE: DNA
<213> ORGANISM: Oryza sativa

<400> SEQUENCE: 148

```
tggatgtttc atgggcttct tgatcctatc tccaggtttt taggctttac gatgagtggt     60
```

```
ttgcgtaact tctgctttta ttcttgctga tcagagagca gttcctggtt tttgttatga    120
tggtgttgtt tcttttgggg gctaagacca agataatagt attagtatat ccttgtggag    180
ttgttggagc tatagtggca actgccaaac acagcccaac cagcattgct tcgagtcctt    240
ccactagatg ttgattcaag taggataggt ttgcttgttt catgttcttg tacatttgag    300
ctgacaatcg catgaaagct gagtgttcct gttcttttct aattgttcag gatgcatttc    360
tgagagggcg taatggttca gactgcagaa ggatgtgtat tgcacagttt tatctgtcag    420
tcatctatat cctacttgaa gttacaaggc tacatcttat aagataattg ttacagtccc    480
aaaaagaata acgtggaaat ggtatccaat agtttctggc ttttcatcct gctagtgagc    540
ttcatcccca tttctgcttg ggcagaatca cgtgatataa gtactctgtt cactctgagg    600
gattcaatca ccgaaggaaa aggctttctc cgtaactggt ttgattcgga aactccccca    660
tgcagctggt caggcataac ttgcatagga cataatgttg tggcgattga tttgtcctct    720
gttccactct atgctccgtt tccattatgc attggggcat tccagtcact tgttcggctc    780
aacttcagtg gatgtgggtt ttccggagag cttccggaag ctttgggaaa tttgcagaat    840
ctccagtacc tagacttgag caataacgag cttactgggc caatacctat ctcactatat    900
aacctgaaga tgctgaagga aatggtgctt gactacaact ccttgtcagg acaacttagt    960
cctgctattg ctcagctgca gcaccttact aagctatcta tatccatgaa ttccatctcc   1020
ggaagccttc caccagatct gggcagcctg aagaacctgg agttgttgga cattaagatg   1080
aacacattca atggatctat accagcaact tttgggaacc tgtcttgtct cttgcacttt   1140
gatgctagcc agaataacct aactggatca atattccctg gaataacctc gttgacaaac   1200
ctattgacac ttgatctatc atcaaacagt tttgagggaa caattcctag ggagattggt   1260
caactggaaa atctggaatt actgattcta ggaaagaatg atctcactgg aaggattcca   1320
caagagattg gtagtctgaa gcagcttaag ttacttcatc tcgaggaatg tcagttcaca   1380
ggcaaaatac cttggtcaat cagtggactc agcagcttga cagaacttga catatcagat   1440
aacaactttg acgctgagct cccatcatcc atgggtgagc ttggcaatct aacacagctg   1500
attgcaaaga atgctgggct cagtgggaac atgccaaaag aacttgggaa ttgcaagaag   1560
cttactgtta taaacctgtc attcaatgcc cttattggac ctattcctga agaatttgca   1620
gatttagagg ctattgtctc attttttgtg gaaggaaata aactatcggg tcgtgtccca   1680
gattggattc agaaatggaa aaatgcaagg tccatcaggt tgggacagaa caaattcagt   1740
ggacctttgc cagtgctgcc attgcagcat ctgctaagtt tcgctgcaga atccaacctt   1800
ctctcaggtt ctataccttc tcacatatgc caagccaact ccttgcattc actcttattg   1860
catcataaca atctgactgg gactattgat gaggcattta aagggtgcac gaacctcact   1920
gaattgaact tgttagacaa ccatattcat ggggaggtac caggatattt agcagaatta   1980
cccctggtta ctctggagtt gtcacaaaac aaattcgcag ggatgttacc tgcggagctg   2040
tgggagtcaa aaacccttct agagatatct ctcagtaaca atgaaattac cggcccaata   2100
cctgagagta ttggtaaact ctctgtattg caaaggttgc atatagacaa taacttactc   2160
gaagggccta tccctcagtc tgttggtgat ctaaggaatc tgaccaatct atccctgcgt   2220
ggcaataggt tatctgggat cattccacta gcacttttca actgcagaaa acttgccacg   2280
ctggacttga gctataacaa tctgactggg aacattccaa gtgccatatc tcacttgaca   2340
ttgcttgata gcttgatttt gtcttccaac cagctgtctg gttctatccc tgctgagatt   2400
```

-continued

```
tgcgtgggat ttgagaatga ggctcaccct gactcagagt ttcttcagca ccatggtctt   2460
cttgatctgt catacaacca attgactggt cagatcccaa catctataaa gaactgtgca   2520
atggtgatgg tgctcaacct ccaaggcaat ttgctgaatg gcaccattcc tgtggagctt   2580
ggcgagctaa caaatcttac atccattaac ttgtcattta atgaatttgt tggaccaatg   2640
cttccatggt ctggaccttt ggttcaattg caaggcctta ttctgtccaa taaccaccta   2700
gatggctcca ttcctgctaa gataggccaa atccttccca aaattgcagt gctagacttg   2760
tcaagcaatg cactcactgg cactctacca cagtctttgc tctgcaacaa ttacctaaac   2820
catctggatg tcagcaacaa ccacctatct gggcatatcc agttctcttg ccccgatggc   2880
aaagaatact caagtacact gctcttcttc aattcaagca gcaaccattt ctcagggagc   2940
ctagatgagt ctatctcgaa cttcacacaa ttgtctactc ttgatatcca caacaatagc   3000
ctcactggaa ggttgccttc agcactttct gatctcagtt ctttgaatta tcttgatctg   3060
tcgagcaaca atctctatgg tgccataccc tgtggaatct gcaatatatt tggcctctca   3120
tttgccaact tctcaggtaa ctatattgac atgtacagct tggcagattg tgctgcagga   3180
ggcatttgtt ctactaatgg tactgatcat aaagcattgc atccatatca tcgggttcga   3240
agggcaatta ccatctgtgc ctttacattc gtcatcatca ttgttttagt gcttctggct   3300
gtttatctga gacggaagct ggttagaagc aggcctttgg cttttgaatc tgccagtaag   3360
gccaaggcta cagttgagcc tacctcaact gatgaactgc taggaaagaa gtcaagggaa   3420
cctctgagta tcaatcttgc aacatttgag catgcacttc tgagggtcac cgcggatgat   3480
attctgaaag ccacagaaaa cttcagtaag gtgcacataa taggtgatgg tggatttggc   3540
actgtctaca aggcagcgct ccctgaaggc cggagagtcg cgatcaagag gctccatggt   3600
ggccatcagt tccaaggtga ccgtgagttt ctagctgaga tggagacaat tggaaaggtg   3660
aaacatccaa acctcgtccc tctacttggc tactgtgttt gtggcgatga acgattcctg   3720
atctacgagt acatggagaa tgggagcctc gagatgtggc tgagaaaccg agcagatgca   3780
cttgaagctc ttggatggcc ggaccgtctc aagatctgcc tcggttcagc ccgtgggctc   3840
gccttcctgc atcatggctt tgtgccccat atcatccacc gggacatgaa gtcgagcaac   3900
attctactgg atgagaactt cgagccgagg gtctctgact tcggccttgc aaggatcatc   3960
agtgcctgtg agacccatgt cagcactgac attgccggta catttggata cattcctccg   4020
gagtatggcc tcacaatgaa gtccaccacg aaaggcgacg tctacagctt cggcgtcgtc   4080
atgctggagc tcctcaccgg acggccacct acaggccagg aggaggtgca agggggtgga   4140
aacctcgtcg gctgggtgcg gtggatgatc gcccgcggta agcagaacga gctgttcgat   4200
ccatgcttgc cggtttcaag cgtgtggcgg gagcagatgg cgcgcgtgct cgccatcgcc   4260
cgggactgca ccgccgacga gccgttcaag aggccgacaa tgctggaggt ggtgaagggg   4320
ctcaagatga cccacggcat ggaatgtgga cctctggtgg tgaccgtctc cagggacatg   4380
taatgctctc tgcttgatct tcctgaaact aatgtagtaa taatgtagtc agtagggagt   4440
aggctaatgg tagttaggag taactcgtag ctatagagta accgagctat ctggaggctg   4500
taatgaggga aactagagtt actcatgttc aggctgtagt tggaactagt attaagacct   4560
tttatcttgt actattgtca ctggtggttc ctgtggcaat gtgagtgctt aatgtgctgt   4620
cgtttgaata aaagtactgc ttgcctgttt ctaagtgtta aaaaaaaaaa aaaaaaaaaa   4680
a                                                                   4681
```

<210> SEQ ID NO 149
<211> LENGTH: 1302
<212> TYPE: DNA
<213> ORGANISM: Arabidopsis thaliana

<400> SEQUENCE: 149

```
cacacttaaa gctttcgtct ttacctcttc ccttctctct ctctatctaa aaagagttcc     60
gagaagaaga tcatcatcaa tggcgacttc tctcttcttc atgtcaacag atcaaaactc    120
cgtcggaaac ccaaacgatc ttctgagaaa cacccgtctt gtcgtcaata gctccggcga    180
gatccggaca gagacactga agagtcgtgg tcggaaacca ggatcgaaga caggtcagca    240
aaaacagaag aaaccaacgt tgagaggaat gggtgtagca aagctcgagc gtcagagaat    300
cgaagaagaa aagaagcaac tcgccgccgc cacagtcgga gacacgtcat cagtagcatc    360
gatctctaac aacgctaccc gtttacccgt accggtagac ccgggtgttg tgctacaagg    420
cttcccaagc tcactcggga gcaacaggat ctattgtggt ggagtcgggt cgggtcaggt    480
tatgatcgac ccggttattt ctccatgggg ttttgttgag acctcctcca ctactcatga    540
gctctcttca atctcaaatc ctcaaatgtt taacgcttct tccaataatc gctgtgacac    600
ttgcttcaag aagaaacgtt tggatggtga tcagaataat gtagttcgat ccaacggtgg    660
tggattttcg aaatacacaa tgattcctcc tccgatgaac ggctacgatc agtatcttct    720
tcaatcagat catcatcaga ggagccaagg tttcctttat gatcatagaa tcgctagagc    780
agcttcagtt tctgcttcta gtactactat taatccttat ttcaacgagg caacaaatca    840
tacgggacca atggaggaat ttgggagcta catggaagga aaccctagaa atggatcagg    900
aggtgtgaag gagtacgagt tttttccggg gaaatatggt gaaagagttt cagtggtggc    960
tacaacgtcg tcactcgtag gtgattgcag tcctaatacc attgatttgt ccttgaagct   1020
ttaaatgttt tatctttcta tattgattta aacaaaatcg tctctttaaa gaaaaaacat   1080
tttaagtaga tgaaagtaag aaacagaaga aaaaaaagag agagcctttt ttggtgtatg   1140
catctgagag ctgagtcgaa agaaagattc agcttttgga ttaccctttt ggttgtttat   1200
tatgagattc taacctaaac actcagacat atatgttctg ttctcttcct taattgttgt   1260
catgaaactt ctcaaaaaaa aaaaaaaaaa aaaaaaaaaa aa                       1302
```

<210> SEQ ID NO 150
<211> LENGTH: 1133
<212> TYPE: DNA
<213> ORGANISM: Arabidopsis thaliana

<400> SEQUENCE: 150

```
atggcgactt ctctcttctt catgtcaaca gatcaaaact ccgtcggaaa cccaaacgat     60
cttctgagaa acacccgtct tgtcgtcaat agctccggcg agatccggac agagacactg    120
aagagtcgtg gtcggaaacc aggatcgaag acaggtcagc aaaaacagaa gaaaccaacg    180
ttgagaggaa tgggtgtagc aaagctcgag cgtcagagaa tcgaagaaga aaagaagcaa    240
ctcgccgccg ccacagtcgg agacacgtca tcagtagcat cgatctctaa caacgctacc    300
cgtttacccg taccggtaga cccgggtgtt gtgctacaag gcttcccaag ctcactcggg    360
agcaacagga tctattgtgg tggagtcggg tcgggtcagg ttatgatcga cccggttatt    420
tctccatggg gttttgttga gacctcctcc actactcatg agctctcttc aatctcaaat    480
cctcaaatgt ttaacgcttc ttccaataat cgctgtgaca cttgcttcaa ggtttgtttg    540
tttttaatc gttttcatca acatgattga tatatatata gtttttgcac ttgaaaaagt    600
```

```
tttgattttt atttatgtaa aaaactgcag aagaaacgtt tggatggtga tcagaataat    660

gtagttcgat ccaacggtgg tggattttcg aaatacacaa tgattcctcc tccgatgaac    720

ggctacgatc agtatcttct tcaatcagat catcatcaga ggagccaagg tttcctttat    780

gatcatagaa tcgctagagc agcttcagtt tctgcttcta gtactactat taatccttat    840

ttcaacgagg caacaaatca tacggtacta agtatagtcc atttattaat actcatatat    900

aggtatatat gtatataact gttgatctta tttgatttaa ctggtgggtt tagggaccaa    960

tggaggaatt tgggagctac atggaaggaa accctagaaa tggatcagga ggtgtgaagg   1020

agtacgagtt ttttccgggg aaatatggtg aaagagtttc agtggtggct acaacgtcgt   1080

cactcgtagg tgattgcagt cctaatacca ttgatttgtc cttgaagctt taa          1133
```

<210> SEQ ID NO 151
<211> LENGTH: 2279
<212> TYPE: DNA
<213> ORGANISM: Oryza sativa

<400> SEQUENCE: 151

```
ctcgccgccg ccgccgccgc caccacccac catggctacg accgccgcgg ccgcggccgc     60

cgccctgtcc gccgccgcga cggccaagac cggccgtaag aaccaccagc gacaccacgt    120

ccttcccgct cgaggccggg tgggggcggc ggcggtcagg tgctcggcgg tgtccccggt    180

caccccgccg tccccggcgc cgccggccac gccgctccgg ccgtgggggc cggccgagcc    240

ccgcaagggc gcggacatcc tcgtggaggc gctggagcgg tgcggcgtca gcgacgtgtt    300

cgcctacccg ggcggcgcgt ccatggagat ccaccaggcg ctgacgcgct ccccggtcat    360

caccaaccac ctcttccgcc acgagcaggg cgaggcgttc gcggcgtccg ggtacgcgcg    420

cgcgtccggc cgcgtcgggg tctgcgtcgc cacctccggc cccggggcaa ccaacctcgt    480

gtccgcgctc gccgacgcgc tgctcgactc cgtcccgatg gtcgccatca cgggccaggt    540

cccccgccgc atgatcggca ccgacgcctt ccaggagacg cccatagtcg aggtcacccg    600

ctccatcacc aagcacaatt accttgtcct tgatgtggag gacatccccc gcgtcataca    660

ggaagccttc ttcctcgcgt cctcgggccg tcctggcccg gtgctggtcg acatccccaa    720

ggacatccag cagcagatgg ccgtgccggt ctgggacacc tcgatgaatc taccagggta    780

catcgcacgc ctgcccaagc cacccgcgac agaattgctt gagcaggtct tgcgtctggt    840

tggcgagtca cggcgcccga ttctctatgt cggtggtggc tgctctgcat ctggtgacga    900

attgcgctgg tttgttgagc tgactggtat cccagttaca accactctga tgggcctcgg    960

caatttcccc agtgacgacc cgttgtccct gcgcatgctt gggatgcatg gcacggtgta   1020

cgcaaattat gccgtggata aggctgacct gttgcttgcg tttggtgtgc ggtttgatga   1080

tcgtgtgaca gggaaaattg aggcttttgc aagcagggcc aagattgtgc acattgacat   1140

tgatccagca gagattggaa agaacaagca accacatgtg tcaatttgcg cagatgttaa   1200

gcttgcttta cagggcttga atgctctgct acaacagagc acaacaaaga caagttctga   1260

ttttagtgca tggcacaatg agttggacca gcagaagagg gagtttcctc tggggtacaa   1320

aacttttggt gaagagatcc caccgcaata tgccattcag gtgctggatg agctgacgaa   1380

aggtgaggca atcatcgcta ctggtgttgg gcagcaccag atgtgggcgg cacaatatta   1440

cacctacaag cggccacggc agtggctgtc ttcggctggt ctgggcgcaa tgggatttgg   1500

gctgcctgct gcagctggtg cttctgtggc taacccaggt gtcacagttg ttgatattga   1560

tggggatggt agcttcctca tgaacattca ggagctggca ttgatccgca ttgagaacct   1620
```

ccctgtgaag gtgatggtgt tgaacaacca acatttgggt atggtggtgc aattggagga 1680
taggttttac aaggcgaata gggcgcatac atacttgggc aacccggaat gtgagagcga 1740
gatatatcca gattttgtga ctattgctaa ggggttcaat attcctgcag tccgtgtaac 1800
aaagaagagt gaagtccgtg ccgccatcaa gaagatgctc gagactccag ggccatactt 1860
gttggatatc atcgtcccgc accaggagca tgtgctgcct atgatcccaa ttgggggcgc 1920
attcaaggac atgatcctgg atggtgatgg caggactgtg tattaatcta taatctgtat 1980
gttggcaaag caccagcccg gcctatgttt gacctgaatg acccataaag agtggtatgc 2040
ctatgatgtt tgtatgtgct ctatcaataa ctaaggtgtc aactatgaac catatgctct 2100
tctgttttac ttgtttgatg tgcttggcat ggtaatccta attagcttcc tgctgtctag 2160
gtttgtagtg tgttgttttc tgtaggcata tgcatcacaa gatatcatgt aagtttcttg 2220
tcctacatat caataataag agaataaagt acttctatgt aaaaaaaaaa aaaaaaaaa 2279

<210> SEQ ID NO 152
<211> LENGTH: 69
<212> TYPE: DNA
<213> ORGANISM: Oriza sp.

<400> SEQUENCE: 152
gcgatcgcaa ccagtcaaga cgaatggcag gcagctaagt agctaacaac aacaggcttg 60
tattgtatg 69

<210> SEQ ID NO 153
<211> LENGTH: 80
<212> TYPE: DNA
<213> ORGANISM: Zea mays

<400> SEQUENCE: 153
cctgtcctgt accagcttat atatataggc gagccaacga gcgagagcca tcaccaagtg 60
caaggtagct atcatatatt 80

<210> SEQ ID NO 154
<211> LENGTH: 76
<212> TYPE: DNA
<213> ORGANISM: Arabidopsis thaliana

<400> SEQUENCE: 154
ttcaatcgtg gttaatagaa caacaaggag acaataagag gctgacggtg cctaccaaag 60
ctcaggttat actttt 76

<210> SEQ ID NO 155
<211> LENGTH: 77
<212> TYPE: DNA
<213> ORGANISM: Arabidopsis thaliana

<400> SEQUENCE: 155
tatcgatcgg gtgatcagtt atgctaaagg cctgcagcta gctagagaac acaaacgcat 60
cgatgagtag tagttgg 77

<210> SEQ ID NO 156
<211> LENGTH: 78
<212> TYPE: DNA
<213> ORGANISM: Zea mays

<400> SEQUENCE: 156

-continued acgccaccgc ccgcgaccca ggtacgccgt acgcgcgagc tcgctcgcta gcatcgatga 60
agctcgtggc gtggtgaa 78

<210> SEQ ID NO 157
<211> LENGTH: 128
<212> TYPE: DNA
<213> ORGANISM: Zea mays

<400> SEQUENCE: 157
ttcgttgtgg cgaacaagct agctgctagt accctcagtt ataccaagat atacactaca 60
ttcctagcta ggtacgatta gccgccggtg agtggggaga tggtgacatc aacagtgaag 120
ttggagga 128

<210> SEQ ID NO 158
<211> LENGTH: 80
<212> TYPE: DNA
<213> ORGANISM: Arabidopsis thaliana

<400> SEQUENCE: 158
gccagcaaaa ccactcttca aaactgccga gggagtcaag ttgcaccggt tttaacagta 60
taggggtcaa gatatctggt 80

<210> SEQ ID NO 159
<211> LENGTH: 104
<212> TYPE: DNA
<213> ORGANISM: Zea mays

<400> SEQUENCE: 159
gctcacgcac gcgccgcagc tacccagcca ctcctcgatc gtctcctccc cattataagc 60
agcagcaagc aagcaaacca aagcaaagca tcgatctccc atgg 104

<210> SEQ ID NO 160
<211> LENGTH: 79
<212> TYPE: DNA
<213> ORGANISM: Zea mays

<400> SEQUENCE: 160
ctgctggagc gcaagcaaaa gaaagagttt acatttggat ggtcctttgg ccgaccacaa 60
tagattagca catgcataa 79

<210> SEQ ID NO 161
<211> LENGTH: 79
<212> TYPE: DNA
<213> ORGANISM: Zea mays

<400> SEQUENCE: 161
tcggcgatgt ccttggcgag gcggagcgcg gtgcagccgg cgttgcagcc gtgcatgtag 60
aggacggcgc gctgcacgg 79

<210> SEQ ID NO 162
<211> LENGTH: 76
<212> TYPE: DNA
<213> ORGANISM: Zea mays

<400> SEQUENCE: 162
tggtgtttga atgtcctgaa gatgaacatg aagatttaag tgttttacgt aaaatgaggt 60
tgtaataacg tgtgat 76

<210> SEQ ID NO 163
<211> LENGTH: 84
<212> TYPE: DNA
<213> ORGANISM: Oryza sativa

<400> SEQUENCE: 163
ctgcaaaatg gcagcccccc tatagacggc cgttaggcgt gcgctaacgg tggtcagcca 60
cgtcacgaaa atcgccctct ggga 84

<210> SEQ ID NO 164
<211> LENGTH: 79
<212> TYPE: DNA
<213> ORGANISM: Zea mays

<400> SEQUENCE: 164
cgccatcgcc ggccggccgc cgatcgagta attgcgcagc gcacgcagct catcatccac 60
tagactaatt acttcggga 79

<210> SEQ ID NO 165
<211> LENGTH: 64
<212> TYPE: DNA
<213> ORGANISM: Zea mays

<400> SEQUENCE: 165
tcgccatcac cggccgccga tcgagtacgt gcgcacgcag ctcatctact agcctacttc 60
ggga 64

<210> SEQ ID NO 166
<211> LENGTH: 78
<212> TYPE: DNA
<213> ORGANISM: Arabidopsis thaliana

<400> SEQUENCE: 166
atgatatgtg ccaagtagtc gagagccaaa taaaataaaa ttattagtga ttgcaacagg 60
tgggctggtt ttgcgtca 78

<210> SEQ ID NO 167
<211> LENGTH: 63
<212> TYPE: DNA
<213> ORGANISM: Zea mays

<400> SEQUENCE: 167
tcaccggccg ccgatcgagt acgtcgccag cgcacgcagc tcatctacta gcctacttcg 60
gga 63

<210> SEQ ID NO 168
<211> LENGTH: 79
<212> TYPE: DNA
<213> ORGANISM: Zea mays

<400> SEQUENCE: 168
cgccatcgcc ggccggccgc cgatcgagta attgcgcagc gcacgcagct catcatccac 60
tagactaatt acttcggga 79

<210> SEQ ID NO 169
<211> LENGTH: 80
<212> TYPE: DNA
<213> ORGANISM: Zea mays

<400> SEQUENCE: 169

-continued cctgtcctgt accagcttat atatataggc gagccaacga gcgagagcca tcaccaagtg 60
caaggtagct atcatatatt 80

<210> SEQ ID NO 170
<211> LENGTH: 77
<212> TYPE: DNA
<213> ORGANISM: Zea mays

<400> SEQUENCE: 170
acgccaccgc ccgcgaccca ggtacgccgt acgcgcgagc tcgctcctag catcgatgaa 60
gctcgtggcg tggtgaa 77

<210> SEQ ID NO 171
<211> LENGTH: 77
<212> TYPE: DNA
<213> ORGANISM: Arabidopsis thaliana

<400> SEQUENCE: 171
tatcgatcgg gtgatcagtt atgctaaagg cctgcagcta gctagagaac acaaacgcat 60
cgatgagtag tagttgg 77

<210> SEQ ID NO 172
<211> LENGTH: 63
<212> TYPE: DNA
<213> ORGANISM: Zea mays

<400> SEQUENCE: 172
tcaccggccg ccgatcgagt acgtcgccag cgcacgcagc tcatctacta gcctacttcg 60
gga 63

<210> SEQ ID NO 173
<211> LENGTH: 79
<212> TYPE: DNA
<213> ORGANISM: Zea mays

<400> SEQUENCE: 173
cgccatcgcc ggccggccgc cgatcgagta attgcgcagc gcacgcagct catcatccac 60
tagactaatt acttcggga 79

<210> SEQ ID NO 174
<211> LENGTH: 77
<212> TYPE: DNA
<213> ORGANISM: Zea mays

<400> SEQUENCE: 174
acgccaccgc ccgcgaccca ggtacgccgt acgcgcgagc tcgctcctag catcgatgaa 60
gctcgtggcg tggtgaa 77

<210> SEQ ID NO 175
<211> LENGTH: 77
<212> TYPE: DNA
<213> ORGANISM: Arabidopsis thaliana

<400> SEQUENCE: 175
tatcgatcgg gtgatcagtt atgctaaagg cctgcagcta gctagagaac acaaacgcat 60
cgatgagtag tagttgg 77

<210> SEQ ID NO 176
<211> LENGTH: 63

-continued

<212> TYPE: DNA
<213> ORGANISM: Zea mays

<400> SEQUENCE: 176
tcaccggccg ccgatcgagt acgtcgccag cgcacgcagc tcatctacta gcctacttcg 60
gga 63

<210> SEQ ID NO 177
<211> LENGTH: 79
<212> TYPE: DNA
<213> ORGANISM: Zea mays

<400> SEQUENCE: 177
cgccatcgcc ggccggccgc cgatcgagta attgcgcagc gcacgcagct catcatccac 60
tagactaatt acttcggga 79

<210> SEQ ID NO 178
<211> LENGTH: 77
<212> TYPE: DNA
<213> ORGANISM: Arabidopsis thaliana

<400> SEQUENCE: 178
tatcgatcgg gtgatcagtt atgctaaagg cctgcagcta gctagagaac acaaacgcat 60
cgatgagtag tagttgg 77

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 179
tagggcattt ggagagttgg 20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 180
gcagattctc cacccaggta 20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 181
gaagagggag tgggaggact 20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
cagaagacga cccaggagac 20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 183
gcccactact cgatcctgaa 20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
tcatttgacc aacgcttctg 20

<210> SEQ ID NO 185
<211> LENGTH: 3043
<212> TYPE: DNA
<213> ORGANISM: Oryza sativa

<400> SEQUENCE: 185
ataactacta tagattataa aaataaaacc ccaatgctaa ttagatttga tttattctat 60
tgaaaaaaaa aatgagtgag aggcggaccg taggagtaga gtaatgacgg ttaaaaacta 120
taagaacgaa acagtgatcg ataatgtttg atttttaaag taccaagaac aattaataga 180
aatggtagcc agccaggcaa gcaaccggag gagcgacaaa ggagaggggt ggcgtctgat 240
gcgactttta aaactataat attataaagt tgataataat aatgttaatt taaaaaatat 300
catgtggaaa tgagttaacc ttttacaaat tttcaagaaa ataaagggta aaaaattaga 360
tgattttata taagatactt agccgtgcaa atatgtgggc caccctacta gtttttcgct 420
gaatctgaat aattttgaac ggtaaaaaaa atccggttca ttctgtctcc tctacctgtc 480
gtctacactt cacgaacgac gctgtcatca cgctgcggat gcaggttaca gtttacacac 540
gtactaaatg caccggccct tcaaacgaga accggccggt gtgcacgtgc acgtagctca 600
cacctaccta tcaaaacgct ggtcattctg ttctagcttg ttagtagtac aagtgtgtct 660
atgagagaat ccattatatg ccaaaaaaaa aacataagca cagacgaaat tatagcgtta 720
tacttcatct atcttttatg tacacattta catacaaaag ttaatttatt ttgagacgaa 780
gggagtgatt aataacaata tttattaaca aagtagaaca atatatttag gggaaaaatt 840
gtatactaaa acaaatccta tattattatt attattattt attaattgtg taaaaatata 900
attggatatg taaaaatggg agtacacatg tgtgagcatc tctaagtgac gaggaaaagg 960
aatagcagag gacaagccaa gggtcaagta gggtaatggc agctagagag actttgaaaa 1020
attataaaat agaacactaa tgatgatcac gttcgatttt tttaatttgc aatgacaata 1080
aaaaaggagt ggtggaaagg tgacaatggt gtaacagatt ttgtataaac tataaaaata 1140
acccaaagaa ggccaagttt aaattttaag aatcccaatt gcaataaaaa tatgtgcgat 1200
tggcgggcca taaagttgtt aggtgatagc ggttgacgat acttccaaaa tctataaaag 1260
ggaaacctaa gttaatcagg tttgaatctt aaaatcctaa caacattaaa gaggcgaggt 1320
gataggcggg ctgtaaagag tcacagtggt tgacgagact tttaaaaata ataaaaacgg 1380
aacaacgacg accaggttca aatttaaaaa tgctactaat aataaaaacg atgggtggcg 1440
ggtgagacgt aaaggagtag agtggcggca gttagcgggg cttttaaaaa cgatgatcag 1500
attggatttt ttaaatgcca tcgacaataa agaggaggag caacaggcaa gccatcaagg 1560
agtagggtga tggtggttga caggacttct atagattata aaaataaaac cccaataata 1620
atcagatttg atttattcta ttgacaaaaa aaagatgagt gagagacgga ccgtaaagga 1680
gcagagtaat gatggttaaa aactataaga acgaaacagt gatggtttga tttttaaggt 1740
accaagaaca atcaatagaa atggtggcca gccaggcaag cagctggagg agctacaagg 1800
agaggggtgg cgcccaatgc gacttttaaa actataaaat tataaagttg gtaatgataa 1860
tgttaatttt aaaaaatatc atgtggaaat gagttgacct tttacaaatt ttcaagaaaa 1920
taaagggtaa aaaattagat gattttatat cggtgctaga tgtacaaatg cgtgggccaa 1980
cctactagtt tttggctgaa tctgaacaat tttgaacggt ccaaaaaaac cggttcattc 2040
tgtctccttt gcctgtcgtc acgctgtcat cacgctgcgg atgcagcgta ctaaacgcac 2100
cggcctttca aacaagaacc ggccggtgtg caggtgcacg tagctcaaac ctacctatca 2160
aaacgctggt cattctgtct actccatccg accccaaaaa aaaaagacaa accctgattt 2220
tcgtgtctaa cgtttgaccg tccgtcttat ttaagaaaat tatgaaaaaa aattaaaaaa 2280
acaagtcaca cataaaatat taatcatgtt ttatcatcta acaataatga aaatacgaat 2340
tataaaaaaa tttcatataa gacggacagt caaagttgga cacggaaacc tagagtaact 2400
tgttaggcag tacaagtgtg tgtagctata ctccccctgt cctgtaccag cttatatata 2460
taggcgagcc aacgagcgag agccatcacc aagtgcaagg tagctatcat atattctgcg 2520
aatccaacac aagcaccgcg gcgtagtact actacttgcg cgcgcgtgtt agattcgcgt 2580
gcgaatccaa cacaagcaga tcgatcacgc acggtacgcc atgggcgagg cggtgaaggg 2640
gccagtggtg gtgacgggcg cgtcgggctt cgtcggctca tggctcgtca tgaagctcct 2700
ccaggccggc tacaccgtcc gcgccacagt gcgcgacccc tgtgagctct ctcatcgtgc 2760
actctagctc tctcctcgta gtttactgac tccaattata tatgccgctt gcttgactct 2820
gacaagtgta cgtgttgttg ttgttgtttt cagctaacgt tgggaagacg aagccgttgc 2880
tggagctggc ggggtagaag gagaggctga cgctgtggaa ggccgacctg ggcgaggaag 2940
gcagcttcga cgcggcgatc aggggttgca cgggcgtgtt ccacgtcgcg acgcccatgg 3000
acttcgagtc cgaggacccg gagaacgagg tggtcaagcc cac 3043

<210> SEQ ID NO 186
<211> LENGTH: 16
<212> TYPE: DNA
<213> ORGANISM: Oryza sativa

<400> SEQUENCE: 186
actacttgcg cgcgcg 16

<210> SEQ ID NO 187
<211> LENGTH: 14
<212> TYPE: DNA
<213> ORGANISM: Artificial Sequence
<220> FEATURE:

<223> OTHER INFORMATION: Description of Artificial Sequence: Synthetic
maize anthocyanin regulatory element consensus
oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other

<400> SEQUENCE: 187
nnactngcgn ngcg 14

<210> SEQ ID NO 188
<211> LENGTH: 14
<212> TYPE: DNA
<213> ORGANISM: Oryza sativa

<400> SEQUENCE: 188
agattcgcgt gcga 14

<210> SEQ ID NO 189
<211> LENGTH: 14
<212> TYPE: DNA
<213> ORGANISM: Artificial Sequence
<220> FEATURE:
<223> OTHER INFORMATION: Description of Artificial Sequence: Synthetic
myb-like and bHLH-like consensus DNA binding
oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 189
ngantngcnn gngn 14

<210> SEQ ID NO 190
<211> LENGTH: 14
<212> TYPE: DNA
<213> ORGANISM: Artificial Sequence
<220> FEATURE:
<223> OTHER INFORMATION: Description of Artificial Sequence: Synthetic
Myb-like and bHLH-like consensus DNA binding
oligonucleotide
<220> FEATURE:
<221> NAME/KEY: modified_base
<222> LOCATION: (9)..(9)
<223> OTHER INFORMATION: a, c, t, g, unknown or other

<400> SEQUENCE: 190
cgactggcng gtgc 14

<210> SEQ ID NO 191
<211> LENGTH: 2996
<212> TYPE: DNA
<213> ORGANISM: Oryza sativa

<400> SEQUENCE: 191
ataactacta tagattataa aaataaaacc ccaatgctaa ttagatttga tttattctat 60
tgaaaaaaaa aatgagtgag aggcggaccg taggagtaga gtaatgacgg ttaaaaacta 120
taagaacgaa acagtgatcg ataatgtttg atttttaaag taccaagaac aattaataga 180
aatggtagcc agccaggcaa gcaaccggag gagcgacaaa ggagaggggt ggcgtctgat 240
gcgactttta aaactataat attataaagt tgataataat aatgttaatt taaaaaatat 300
catgtggaaa tgagttaacc ttttacaaat tttcaagaaa ataaagggta aaaaattaga 360
tgattttata taagatactt agccgtgcaa atatgtgggc caccctacta gtttttcgct 420
gaatctgaat aattttgaac ggtaaaaaaa atccggttca ttctgtctcc tctacctgtc 480
gtctacactt cacgaacgac gctgtcatca cgctgcggat gcaggttaca gtttacacac 540
gtactaaatg caccggccct tcaaacgaga accggccggt gtgcacgtgc acgtagctca 600
cacctaccta tcaaaacgct ggtcattctg ttctagcttg ttagtagtac aagtgtgtct 660
atgagagaat ccattatatg ccaaaaaaaa aacataagca cagacgaaat tatagcgtta 720
tacttcatct atcttttatg tacacattta catacaaaag ttaatttatt ttgagacgaa 780
gggagtgatt aataacaata tttattaaca aagtagaaca atatatttag gggaaaaatt 840
gtatactaaa acaaatccta tattattatt attattattt attaattgtg taaaaatata 900
attggatatg taaaaatggg agtacacatg tgtgagcatc tctaagtgac gaggaaaagg 960
aatagcagag gacaagccaa gggtcaagta gggtaatggc agctagagag actttgaaaa 1020
attataaaat agaacactaa tgatgatcac gttcgatttt tttaatttgc aatgacaata 1080
aaaaaggagt ggtggaaagg tgacaatggt gtaacagatt ttgtataaac tataaaaata 1140
acccaaagaa ggccaagttt aaattttaag aatcccaatt gcaataaaaa tatgtgcgat 1200
tggcgggcca taaagttgtt aggtgatagc ggttgacgat acttccaaaa tctataaaag 1260
ggaaacctaa gttaatcagg tttgaatctt aaaatcctaa caacattaaa gaggcgaggt 1320
gataggcggg ctgtaaagag tcacagtggt tgacgagact tttaaaaata ataaaaacgg 1380
aacaacgacg accaggttca aatttaaaaa tgctactaat aataaaaacg atgggtggcg 1440
ggtgagacgt aaaggagtag agtggcggca gttagcgggg cttttaaaaa cgatgatcag 1500
attggatttt ttaaatgcca tcgacaataa agaggaggag caacaggcaa gccatcaagg 1560
agtagggtga tggtggttga caggacttct atagattata aaaataaaac cccaataata 1620
atcagatttg atttattcta ttgacaaaaa aaagatgagt gagagacgga ccgtaaagga 1680
gcagagtaat gatggttaaa aactataaga acgaaacagt gatggtttga tttttaaggt 1740
accaagaaca atcaatagaa atggtggcca gccaggcaag cagctggagg agctacaagg 1800
agaggggtgg cgcccaatgc gacttttaaa actataaaat tataaagttg gtaatgataa 1860
tgttaatttt aaaaaatatc atgtggaaat gagttgacct tttacaaatt ttcaagaaaa 1920

-continued

```
taaagggtaa aaaattagat gattttatat cggtgctaga tgtacaaatg cgtgggccaa   1980

cctactagtt tttggctgaa tctgaacaat tttgaacggt ccaaaaaaac cggttcattc   2040

tgtctccttt gcctgtcgtc acgctgtcat cacgctgcgg atgcagcgta ctaaacgcac   2100

cggcctttca aacaagaacc ggccggtgtg caggtgcacg tagctcaaac ctacctatca   2160

aaacgctggt cattctgtct actccatccg accccaaaaa aaaaagacaa accctgattt   2220

tcgtgtctaa cgtttgaccg tccgtcttat ttaagaaaat tatgaaaaaa aattaaaaaa   2280

acaagtcaca cataaaatat taatcatgtt ttatcatcta acaataatga aaatacgaat   2340

tataaaaaaa tttcatataa gacggacagt caaagttgga cacggaaacc tagagtaact   2400

tgttaggcag tacaagtgtg tgtagctata ctccccctgt cctgtaccag cttatatata   2460

taggcgagcc aacgagcgag agccatcacc aagtgcaagg tagctatcat atattctgcg   2520

aatccaacac aagcaccgcg gcgtagtact actacttgcg cgcgcgtgtt agattcgcgt   2580

gcgaatccaa cacaagcaga tcgatcacgc acggtacgcc atgggcgagg cggtgaaggg   2640

gccagtggtg gtgacgggcg cgtcgggctt cgtcggctca tggctcgtca tgaagctcct   2700

ccaggccggc tacaccgtcc gcgccacagt gcgcgacccc tgtgagctct ctcatcgtgc   2760

actctagctc tctcctcgta gtttactgac tccaattata tatgccgctt gcttgactct   2820

gacaagtgta cgtgttgttg ttgttgtttt cagctaacgt tgggaagacg aagccgttgc   2880

tggagctggc ggggtagaag gagaggctga cgctgtggaa ggccgacctg ggcgaggaag   2940

gcagcttcga cgcggcgatc aggggttgca cgggcgtgtt ccacgtcgcg acgccc       2996
```

<210> SEQ ID NO 192
<211> LENGTH: 519
<212> TYPE: DNA
<213> ORGANISM: Oryza sativa

<400> SEQUENCE: 192

```
aacgggatgc cgccgagcca cgtcaccgcg ctggcgctgc tcacggggaa cgaggcccac     60

tactcgatcc tgaagcaggt gcagttcgtc cacctcgacg acctctgcga cgccgagatc    120

ttcctcttcg agagccccga ggcgcgcggc cgctacgtct gctcctccca cgacgccacc    180

atccacggcc tcgcgacgat gctcgcggac atgttcccgg agtacgacgt gccgcggagc    240

tttcccggga tcgacgccga ccacctccag ccggtgcact tctcgtcgtg gaagctcctc    300

gcccacgggt tcaggttcag gtacacgctg gaggacatgt tcgaggccgc cgtccggacg    360

tgcagggaga aggggcttct cccgccgctg ccgccaccgc cgacgacggc cgtggccgga    420

ggagacggct cggcgggtgt ggccggcgag aaggaaccga tactggggag ggggaccggg    480

acggcggttg gtgctgaaac agaagcgttg gtcaaatga                           519
```

<210> SEQ ID NO 193
<211> LENGTH: 1311
<212> TYPE: DNA
<213> ORGANISM: Oryza sativa

<400> SEQUENCE: 193

```
gtaatgatgg ttaaaaacta taagaacgaa acagtgatgg tttgattttt aaggtaccaa     60

gaacaatcaa tagaaatggt ggccagccag gcaagcagct ggaggagcta caaggagagg    120

ggtggcgccc aatgcgactt ttaaaactat aaaattataa agttggtaat gataatgtta    180

attttaaaaa atatcatgtg gaaatgagtt gaccttttac aaattttcaa gaaaataaag    240

ggtaaaaaat tagatgattt tatatcggtg ctagatgtac aaatgcgtgg gccaacctac    300
```

-continued

```
tagtttttgg ctgaatctga acaattttga acggtccaaa aaaaccggtt cattctgtct    360

cctttgcctg tcgtcacgct gtcatcacgc tgcggatgca gcgtactaaa cgcaccggcc    420

tttcaaacaa gaaccggccg gtgtgcaggt gcacgtagct caaacctacc tatcaaaacg    480

ctggtcattc tgtctactcc atccgacccc aaaaaaaaaa gacaaaccct gattttcgtg    540

tctaacgttt gaccgtccgt cttatttaag aaaattatga aaaaaaatta aaaaaacaag    600

tcacacataa aatattaatc atgttttatc atctaacaat aatgaaaata cgaattataa    660

aaaaatttca tataagacgg acagtcaaag ttggacacgg aaacctagag taacttgtta    720

ggcagtacaa gtgtgtgtag ctatactccc cctgtcctgt accagcttat atatataggc    780

gagccaacga gcgagagcca tcaccaagtg caaggtagct atcatatatt ctgcgaatcc    840

aacacaagca ccgcggcgta gtactactac ttgcgcgcgc gtgttagatt cgcgtgcgaa    900

tccaacacaa gcagatcgat cacgcacggt acgccatggg cgaggcggtg aaggggccag    960

tggtggtgac gggcgcgtcg ggcttcgtcg gctcatggct cgtcatgaag ctcctccagg   1020

ccggctacac cgtccgcgcc acagtgcgcg acccctgtga gctctctcat cgtgcactct   1080

agctctctcc tcgtagttta ctgactccaa ttatatatgc cgcttgcttg actctgacaa   1140

gtgtacgtgt tgttgttgtt gttttcagct aacgttggga agacgaagcc gttgctggag   1200

ctggcggggt cgaaggagag gctgacgctg tggaaggccg acctgggcga ggaaggcagc   1260

ttcgacgcgg cgatcagggg ttgcacgggc gtgttccacg tcgcgacgcc c            1311
```

<210> SEQ ID NO 194
<211> LENGTH: 78
<212> TYPE: DNA
<213> ORGANISM: Zea mays

<400> SEQUENCE: 194

```
gccatcgccg gccggccgcc gatcgagtaa ttgcgcagcg cacgcagctc atcatccact     60

agactaatta cttcggga                                                   78
```

<210> SEQ ID NO 195
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 195

```
caannnnatc                                                            10
```

<210> SEQ ID NO 196
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196

```
ttwtwttwtt                                                            10
```